US011674136B2

(12) United States Patent
Liu et al.

(10) Patent No.: US 11,674,136 B2
(45) Date of Patent: Jun. 13, 2023

(54) DNA-TEMPLATED MACROCYCLE LIBRARY

(71) Applicant: President and Fellows of Harvard College, Cambridge, MA (US)

(72) Inventors: David R. Liu, Cambridge, MA (US); Dmitry L. Usanov, Cambridge, MA (US); Juan Pablo Maianti, Cambridge, MA (US); Alix I. Chan, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/968,408

(22) PCT Filed: Feb. 8, 2019

(86) PCT No.: PCT/US2019/017318
§ 371 (c)(1),
(2) Date: Aug. 7, 2020

(87) PCT Pub. No.: WO2019/168654
PCT Pub. Date: Sep. 6, 2019

(65) Prior Publication Data
US 2020/0399634 A1    Dec. 24, 2020

Related U.S. Application Data

(60) Provisional application No. 62/628,715, filed on Feb. 9, 2018.

(51) Int. Cl.
| | |
|---|---|
| *C12N 15/00* | (2006.01) |
| *C12N 15/10* | (2006.01) |
| *A61K 38/12* | (2006.01) |
| *C07K 7/56* | (2006.01) |
| *A61K 38/00* | (2006.01) |

(52) U.S. Cl.
CPC .......... *C12N 15/1068* (2013.01); *A61K 38/12* (2013.01); *C07K 7/56* (2013.01); *A61K 38/00* (2013.01)

(58) Field of Classification Search
CPC ........................... C12N 15/1068; A61K 38/12
See application file for complete search history.

(56) References Cited

U.S. PATENT DOCUMENTS

| | | | |
|---|---|---|---|
| 7,070,928 B2 | 7/2006 | Liu et al. | |
| 7,223,545 B2 | 5/2007 | Liu et al. | |
| 7,442,160 B2 | 10/2008 | Liu et al. | |
| 7,442,683 B2 | 10/2008 | Kurome et al. | |
| 7,557,068 B2 | 7/2009 | Liu et al. | |
| 7,998,904 B2 | 8/2011 | Liu et al. | |
| 8,632,989 B1 | 1/2014 | Rodgers et al. | |
| 8,975,232 B2 | 3/2015 | Liu et al. | |
| 9,243,038 B2 | 1/2016 | Liu et al. | |
| 9,610,322 B2 | 4/2017 | Liu et al. | |
| 2002/0068301 A1 | 6/2002 | Lai et al. | |
| 2004/0067503 A1 | 4/2004 | Tan et al. | |
| 2005/0042669 A1 | 2/2005 | Liu et al. | |
| 2006/0025566 A1 | 2/2006 | Hoveyda et al. | |
| 2008/0139456 A1 | 6/2008 | Burke et al. | |
| 2008/0242598 A1 | 10/2008 | Fairlie et al. | |
| 2010/0003232 A1 | 1/2010 | Tang et al. | |
| 2010/0105601 A2 | 4/2010 | Brady et al. | |
| 2011/0028494 A1 | 2/2011 | Holloway et al. | |
| 2012/0165228 A1 | 6/2012 | Liu et al. | |
| 2013/0178429 A1 | 7/2013 | Liu et al. | |
| 2014/0213515 A1 | 7/2014 | Liu et al. | |
| 2016/0213744 A1 | 7/2016 | Liu et al. | |
| 2016/0282364 A1 | 9/2016 | Maianti et al. | |

FOREIGN PATENT DOCUMENTS

| | | |
|---|---|---|
| EP | 2 371 421 A1 | 10/2011 |
| WO | 2004/016767 A2 | 2/2004 |
| WO | 2007/016441 A1 | 2/2007 |
| WO | 2008/156701 A2 | 12/2008 |

(Continued)

OTHER PUBLICATIONS

*U.S. Appl. No. 13/812,431, filed Mar. 26, 2013, Liu et al..
*U.S. Appl. No. 14/643,709, filed Mar. 10, 2015, Liu et al..
*U.S. Appl. No. 14/130,336, filed Mar. 3, 2014, Liu et al..
*U.S. Appl. No. 15/004,862, filed Jan. 22, 2016, Liu et al..
*U.S. Appl. No. 15/034,731, filed May 5, 2016, Maianti et al..
*U.S. Appl. No. 15/568,930, filed Oct. 24, 2017, Maianti et al..
PCT/US2011/045966, Dec. 16, 2011, International Search Report and Written Opinion.
PCT/US2011/045966, dated Feb. 7, 2013, International Preliminary Report on Patentability.
EP 12807710.4, Jan. 5, 2015, Extended European Search Report.
PCT/US2012/044977, Dec. 6, 2012, International Search Report and Written Opinion.

(Continued)

*Primary Examiner* — Jeanette M Lieb
(74) *Attorney, Agent, or Firm* — Wolf, Greenfield & Sacks, P.C.

(57) ABSTRACT

The present invention provides nucleic acid templates (e.g., including orthogonal codon sets (e.g., codons from orthogonal codon sets depicted in Tables 5 or 7)) for DNA-templated methods of synthesizing, selecting, and amplifying compounds (e.g., polymers and/or small molecules) described herein. Also provided are novel macrocyclic compounds of Formula (I), and pharmaceutically acceptable salts, solvates, hydrates, polymorphs, co-crystals, tautomers, stereoisomers, isotopically labeled derivatives, prodrugs, libraries, and compositions thereof. Also provided are methods and kits involving the inventive compounds or compositions for treating and/or preventing a disease (e.g., a disease associated with aberrant enzyme activity (e.g., aberrant protease and/or kinase activity (e.g., aberrant IDE activity)), impaired insulin signaling, or insulin resistance in a subject (e.g., a subject having diabetes). Treatment of a subject with a proliferative disease using a compound or composition of the invention may inhibit aberrant protease activity (e.g., aberrant IDE activity).

18 Claims, 160 Drawing Sheets
Specification includes a Sequence Listing.

(56) References Cited

FOREIGN PATENT DOCUMENTS

| WO | 2012/016186 A1 | 2/2012 |
|---|---|---|
| WO | 2013/006451 A2 | 1/2013 |

OTHER PUBLICATIONS

PCT/US2012/044977, Jan. 16, 2014, International Preliminary Report on Patentability.
PCT/US2014/064322, Mar. 5, 2015, International Search Report and Written Opinion.
PCT/US2014/064322, May 19, 2016, International Preliminary Report on Patentability.
PCT/US19/17318, Jul. 29, 2019, Invitation to Pay Additional Fees.
PCT/US19/17318, Sep. 27, 2019, International Search Report and Written Opinion.
PCT/US19/17318, Aug. 11, 2020, International Preliminary Report on Patentability.
International Search Report and Written Opinion for Application No. PCT/US2011/045966, dated Dec. 16, 2011.
International Preliminary Report on Patentability for Application No. PCT/US2011/045966, dated Feb. 7, 2013.
Extended European Search Report for Application No. EP 12807710.4 dated Jan. 5, 2015.
International Search Report and Written Opinion for Application No. PCT/US2012/044977, dated Dec. 6, 2012.
International Preliminary Report on Patentability for Application No. PCT/US2012/044977, dated Jan. 16, 2014.
International Search Report and Written Opinion for Application No. PCT/US2014/064322, dated Mar. 5, 2015.
International Preliminary Report on Patentability for Application No. PCT/US2014/064322, dated May 19, 2016.
Invitation to Pay Additional Fees for Application No. PCT/US19/17318 dated Jul. 29, 2019.
International Search Report and Written Opinion for Application No. PCT/US19/17318 dated Sep. 27, 2019.
International Preliminary Report on Patentability for Application No. PCT/US19/17318 dated Aug. 11, 2020.
Abdul-Hay et al., Deletion of insulin-degrading enzyme elicits antipodal, age-dependent effects on glucose and insulin tolerance. PLoS One. 2011;6(6):e20818. doi: 10.1371/journal.pone.0020818. Epub Jun. 9, 2011.
Abdul-Hay et al., Optimization of Peptide Hydroxamate Inhibitors of Insulin-Degrading Enzyme Reveals Marked Substrate-Selectivity. J Med Chem 2013;56(6):2246-2255. doi:10.1021/jm301280p. Epub Mar. 15, 2013.
Adams et al., PHENIX: a comprehensive Python-based system for macromolecular structure solution. Acta Crystallogr D Biol Crystallogr. Feb. 2010;66(Pt 2):213-21. doi: 10.1107/S0907444909052925. Epub Jan. 22, 2010.
Adams et al., PHENIX: building new software for automated crystallographic structure determination. Acta Crystallogr D Biol Crystallogr. Nov. 2002;58(Pt 11): 1948-54. Epub Oct. 21, 2002.
Adrian et al., Allosteric inhibitors of Bcr-abl-dependent cell proliferation. Nat Chem Biol. Feb. 2006;2(2):95-102. Epub Jan. 15, 2006.
Ahmed et al., Solid-phase synthesis and CD spectroscopic investigations of novel beta-peptides from L-aspartic acid and beta-amino-L-alanine. Org Lett. Jan. 4, 2007;9(1):25-8. doi: 10.1021/ol062465l.
Ahren et al., The augmenting effect on insulin secretion by oral versus intravenous glucose is exaggerated by high-fat diet in mice. J Endocrinol. Apr. 2008;197(1):181-7. doi: 10.1677/JOE-07-0460.
Anderson et al., Discovery of selective aminothiazole aurora kinase inhibitors. ACS Chem Biol. Mar. 20, 2008;3(3):180-92. doi: 10.1021/cb700200w. Epub Feb. 29, 2008.
Andrikopoulos et al., Evaluating the glucose tolerance test in mice. Am J Physiol Endocrinol Metab. Dec. 2008;295(6):E1323-32. doi: 10.1152/ajpendo.90617.2008. Epub Sep. 23, 2008.
Authter et al., Proteolysis of glucagon within hepatic endosomes by membrane-associated cathepsins B and D. J Biol Chem. Jun. 30, 1995;270(26):15798-807.
Azam et al., Activation of tyrosine kinases by mutation of the gatekeeper threonine. Nat Struct Mol Biol. Oct. 2008;15(10):1109-18. doi: 10.1038/nsmb.1486. Epub Sep. 14, 2008.
Azam et al., Activity of dual SRC-ABL inhibitors highlights the role of BCR/ABL kinase dynamics in drug resistance. Proc Natl Acad Sci U S A. Jun. 13, 2006;103(24):9244-9. Epub Jun. 5, 2006.
Barker et al., Characterization of pp60c-src tyrosine kinase activities using a continuous assay: autoactivation of the enzyme is an intermolecular autophosphorylation process. Biochemistry. Nov. 14, 1995;34(45):14843-51.
Barnard et al., In vitro inhibition of Ras-Raf association by short peptides. Biochem Biophys Res Commun. Jun. 9, 1998;247(1):176-80.
Barouch-Bentov et al., A conserved salt bridge in the G loop of multiple protein kinases is important for catalysis and for in vivo Lyn function. Mol Cell. Jan. 16, 2009;33(1):43-52. doi: 10.1016/j.molcel.2008.12.024.
Bartl et al., Disorder-specific effects of polymorphisms at opposing ends of the Insulin Degrading Enzyme gene. BMC Med Genet. Nov. 22, 2011;12:151. doi: 10.1186/1471-2350-12-151.
Beaumont et al., Design of ester prodrugs to enhance oral absorption of poorly permeable compounds: challenges to the discovery scientist. Curr Drug Metab. Dec. 2003;4(6):461-85.
Becker et al., Insulysin and pitrilysin: insulin-degrading enzymes of mammals and bacteria. Methods Enzymol. 1995;248:693-703.
Bednarek et al., Selective high affinity peptide antagonist of alpha melanotropin action at human melanocortin recept or 4: their synthesis and biological evaluation in vitro. J Med Chem. 2001;44:3665-72.
Bennett et al., Degradation of amylin by insulin-degrading enzyme. J Biol Chem. Nov. 24, 2000;275(47):36621-5.
Bennett et al., Degradation of relaxin family peptides by insulin-degrading enzyme. Ann N Y Acad Sci. Apr. 2009;1160:38-41. doi:10.1111/j.1749-6632.2008.03782.x.
Bentley et al., Accurate whole human genome sequencing using reversible terminator chemistry. Nature. Nov. 6, 2008;456(7218):53-9.
Berge et al., Pharmaceutical salts. J Pharm Sci. Jan. 1977;66(1):1-19.
Bikker et al., Kinase domain mutations in cancer: implications for small molecule drug design strategies. J Med Chem. Mar. 26, 2009;52(6):1493-509.
Bradner et al., A robust small-molecule microarray platform for screening cell lysates. Chem Biol. May 2006;13(5):493-504.
Brenner et al., Encoded combinatorial chemistry. Proc Natl Acad Sci U S A. Jun. 15, 1992;89(12):5381-3. doi: 10.1073/pnas.89.12.5381.
Brudno et al., An in vitro translation, selection and amplification system for peptide nucleic acids. Nat Chem Biol. Feb. 2010;6(2):148-55. doi: 10.1038/nchembio.280. Epub Dec. 27, 2009.
Buller et al., D. Drug discovery with DNA-encoded chemical libraries. Bioconjug Chem. Sep. 15, 2010;21(9):1571-80. doi: 10.1021/bc1001483.
Burke et al., Development and application of fluorescence polarization assays in drug discovery. Comb Chem High Throughput Screen. May 2003;6(3):183-94. Review.
Calderone et al., Directing otherwise incompatible reactions in a single solution by using DNA-templated organic synthesis. Angew Chem Int Ed Engl. Nov. 4, 2002;41(21):4104-8. doi: 10.1002/1521-3773(Nov. 4, 2002)41:21<4104::AID-ANIE4104>3.0.CO;2-O.
Calderone et al., Small-molecule diversification from iterated branching reaction pathways enabled by DNA-templated synthesis. Angew Chem Int Ed Engl. Dec. 1, 2005;44(45):7383-6.
Capdeville et al., Glivec (STI571, imatinib), a rationally developed, targeted anticancer drug. Nat Rev Drug Discov. Jul. 2002;1(7):493-502.
Carrasquillo et al., Concordant association of insulin degrading enzyme gene (IDE) variants with IDE mRNA, Abeta, and Alzheimer's disease. PLoS One. Jan. 19, 2010;5(1):e8764.

(56) References Cited

OTHER PUBLICATIONS

Chan et al., Novel selection methods for DNA-encoded chemical libraries. Curr Opin Chem Biol. Jun. 2015;26:55-61. doi: 10.1016/j.cbpa.2015.02.010.

Cheetham et al., Crystal structure of aurora-2, an oncogenic serine/threonine kinase. J Biol Chem. Nov. 8, 2002;277(45):42419-22. Epub Sep. 16, 2002.

Chen et al., A biomolecule-compatible visible-light-induced azide reduction from a DNA-encoded reaction-discovery system. Nat Chem. Feb. 2011;3(2):146-53. doi: 10.1038/nchem.932. Epub Jan. 9, 2011.

Chene et al., A small synthetic peptide, which inhibits the p53-hdm2 interaction, stimulates the p53 pathway in tumour cell lines. J Mol Biol. May 26, 2000;299(1):245-53.

Chudakov et al., Fluorescent proteins and their applications in imaging living cells and tissues. Physiol Rev. Jul. 2010;90(3):1103-63. doi: 10.1152/physrev.00038.2009. Review.

Church, Genomes for all. Sci Am. Jan. 2006;294(1):46-54.

Ciaccio et al., Somatostatin: a novel substrate and a modulator of insulin-degrading enzyme activity. J Mol Biol. Feb. 6, 2009;385(5):1556-67. doi:10.1016/j.jmb.2008.11.025. Epub Nov. 25, 2008.

Clark et al., Design, synthesis and selection of DNA-encoded small-molecule libraries. Nat Chem Biol. Sep. 2009;5(9):647-54. doi:10.1038/nchembio.211. Epub Aug. 2, 2009. Erratum in: Nat Chem Biol. Oct. 2009;5(10):772.

Clark, Selecting chemicals: the emerging utility of DNA-encoded libraries. Curr Opin Chem Biol. Jun. 2010;14(3):396-403. doi: 10.1016/j.cbpa.2010.02.017.

Coan et al., Stoichiometry and physical chemistry of promiscuous aggregate-based inhibitors. J Am Chem Soc. Jul. 23, 2008;130(29):9606-12. doi:10.1021/ja802977h. Epub Jun. 28, 2008. Epub Jun. 28, 2008.

Cohen, Protein kinases—the major drug targets of the twenty-first century? Nat Rev Drug Discov. Apr. 2002;1(4):309-15.

Connors et al., DNA-encoded chemical libraries of macrocycles. Curr Opin Chem Biol. Jun. 2015;26:42-7. doi: 10.1016/j.cbpa.2015.02.004.

Cools et al., PKC412 overcomes resistance to imatinib in a murine model of FIP1L1-PDGFRα-induced myeloproliferative disease. Cancer Cell. May 2003;3(5):459-69.

Cowan-Jacob et al., The crystal structure of a c-Src complex in an active conformation suggests possible steps in c-Src activation. Structure. Jun. 2005;13(6):861-71.

Cronican et al., Potent delivery of functional proteins into Mammalian cells in vitro and in vivo using a supercharged protein. ACS Chem Biol. Aug. 20, 2010;5(8):747-52. doi:10.1021/cb1001153.

Cronican et al., Potent delivery of functional proteins into Mammalian cells in vitro and in vivo using a supercharged protein. ACS Chem Biol. Aug. 20, 2010;5(8):747-52. Supporting Information. 18 pages.

Crowell et al., The effects of tegaserod, a 5-HT receptor agonist, on gastric emptying in a murine model of diabetes mellitus. Neurogastroenterol Motil. Oct. 2005;17(5):738-43.

Das et al., 2-aminothiazole as a novel kinase inhibitor template. Structure-activity relationship studies toward the discovery of N-(2-chloro-6-methylphenyl)-2-[[6-[4-(2-hydroxyethyl)-1-piperazinyl)]-2-methyl-4-pyrimidinyl]amino)]-1,3-thiazole-5-carboxamide (dasatinib, BMS-354825) as a potent pan-Src kinase inhibitor. J Med Chem. Nov. 16, 2006;49(23):6819-32.

Dewey et al., New uridine derivatives for systematic evolution of RNA ligands by exponential enrichment. J. Am. Chem. Soc. Aug. 1995;117(32):8474-5.

Ditchfield et al., Aurora B couples chromosome alignment with anaphase by targeting BubR1, Mad2, and Cenp-E to kinetochores. J Cell Biol. Apr. 28, 2003;161(2):267-80.

Doyon et al., Highly sensitive in vitro selections for DNA-linked synthetic small molecules with protein binding affinity and specificity. J Am Chem Soc. Oct. 15, 2003;125(41):12372-3.

Drag et al., Emerging principles in protease-based drug discovery. Nat Rev Drug Discov. Sep. 2010;9(9):690-701. doi: 10.1038/nrd3053. Review.

Driggers et al., The exploration of macrocycles for drug discovery—an underexploited structural class. Nat Rev Drug Discov. Jul. 2008;7(7):608-24. doi: 10.1038/nrd2590.

Drucker, The biology of incretin hormones. Cell Metab. Mar. 2006;3(3):153-65. Review.

Duckworth et al., Insulin and glucagon degradation by the same enzyme. Diabetes. Jun. 1974;23(6):536-43.

Duckworth et al., Insulin degradation: progress and potential. Endocr Rev. Oct. 1998;19(5):608-24. Review.

Dumelin et al., Selection of streptavidin binders from a DNA-encoded chemical library. Bioconjug Chem. Mar.-Apr. 17, 2006;17(2):366-70.

Emsley et al., Coot: model-building tools for molecular graphics. Acta Crystallogr D Biol Crystallogr. Dec. 2004;60(Pt 12 Pt 1):2126-32. Epub Nov. 26, 2004.

Ettmayer et al., Lessons learned from marketed and investigational prodrugs. J Med Chem. May 6, 2004;47(10):2393-404.

Fancelli et al., Potent and selective Aurora inhibitors identified by the expansion of a novel scaffold for protein kinase inhibition. J Med Chem. Apr. 21, 2005;48(8):3080-4.

Farris et al., Insulin-degrading enzyme regulates the levels of insulin, amyloid beta-protein, and the beta-amyloid precursor protein intracellular domain in vivo. Proc Natl Acad Sci U S A. Apr. 1, 2003;100(7):4162-7. Epub Mar. 12, 2003.

Fontés et al., Miniglucagon (MG)-generating endopeptidase, which processes glucagon into MG, is composed of N-arginine dibasic convertase and aminopeptidase B. Endocrinology. Feb. 2005;146(2):702-12. Epub Nov. 11, 2004.

Forster et al., Programming peptidomimetic syntheses by translating genetic codes designed de novo. Proc Natl Acad Sci U S A. May 27, 2003;100(11):6353-7. Epub May 16, 2003.

Franzini et al., J. DNA-encoded chemical libraries: advancing beyond conventional small-molecule libraries. Acc Chem Res. Apr. 15, 2014;47(4):1247-55. doi: 10.1021/ar400284t. Epub Mar. 28, 2014.

Fu et al., Roles of Aurora kinases in mitosis and tumorigenesis. Mol Cancer Res. Jan. 2007;5(1):1-10. Review.

García-Echeverría et al., Discovery of potent antagonists of the interaction between human double minute 2 and tumor suppressor p53. J Med Chem. Aug. 24, 2000;43(17):3205-8.

Gartner et al. DNA-templated organic synthesis and selection of a library of macrocycles. Science. Sep. 10, 2004;305(5690): 1601-5. Epub Aug. 19, 2004.

Gartner et al., Expanding the reaction scope of DNA-templated synthesis. Angew Chem Int Ed Engl. May 17, 2002;41(10):1796-800.

Gartner et al., Multistep small-molecule synthesis programmed by DNA templates. J Am Chem Soc. Sep. 4, 2002;124(35):10304-6.

Gartner et al., The generality of DNA-templated synthesis as a basis for evolving non-natural small molecules. J Am Chem Soc. Jul. 18, 2001;123(28):6961-3.

Gazit et al., Tyrphostins I: synthesis and biological activity of protein tyrosine kinase inhibitors. J Med Chem. Oct. 1989;32(10):2344-52.

Gedulin et al., Role of endogenous amylin in glucagon secretion and gastric emptying in rats demonstrated with the selective antagonist, AC187. Regul Pept. Dec. 10, 2006;137(3):121-7. Epub Aug. 17, 2006.

Gelling et al., Lower blood glucose, hyperglucagonemia, and pancreatic alpha cell hyperplasia in glucagon receptor knockout mice. Proc Natl Acad Sci U S A. Feb. 4, 2003;100(3):1438-43. Epub Jan. 24, 2003.

Georghiou et al., Highly specific, bisubstrate-competitive Src inhibitors from DNA-templated macrocycles. Nat Chem Biol. Feb. 19, 2012;8(4):366-74. doi: 10.1038/nchembio.792.

Golas et al., SKI-606, a Src/Abl inhibitor with in vivo activity in colon tumor xenograft models. Cancer Res. Jun. 15, 2005;65(12):5358-64.

(56) References Cited

OTHER PUBLICATIONS

Gottlieb et al., NMR Chemical Shifts of Common Laboratory Solvents as Trace Impurities. J Org Chem. Oct. 17, 1997;62(21):7512-7515.
Gradinaru et al., Fluorescence anisotropy: from single molecules to live cells. Analyst. Mar. 2010;135(3):452-9. doi:10.1039/b920242k. Epub Jan. 7, 2010. Review.
Gu et al., Quantitative trait loci near the insulin-degrading enzyme (IDE) gene contribute to variation in plasma insulin levels. Diabetes. Aug. 2004;53(8):2137-42.
Guo et al., Molecular basis for the recognition and cleavages of IGF-II, TGF-alpha, and amylin by human insulin-degrading enzyme. J Mol Biol. Jan. 15, 2010;395(2):430-43. doi:10.1016/j.jmb.2009.10.072. Epub Nov. 5, 2009.
Hall, Advanced sequencing technologies and their wider impact in microbiology. J Exp Biol. May 2007;210(Pt 9):1518-25. Review.
Halpin et al., DNA display I. Sequence-encoded routing of DNA populations. PLoS Biology. Jul. 2004; 2(7):1015-21.
Halpin et al., DNA display II. Genetic manipulation of combinatorial chemistry libraries for small-molecule evolution. PLoS Biology. Jul. 2004; 2(7):1022-30.
Halpin et al., DNA display III. Solid-phase organic synthesis on unprotected DNA. PLoS Biology. Jul. 2004; 2(7):1031-8.
Hamel et al., Identification of the cleavage sites of transforming growth factor alpha by insulin-degrading enzymes. Biochim Biophys Acta. Apr. 4, 1997;1338(2):207-14.
Han et al., Targeted prodrug design to optimize drug delivery AAPS PharmSci. 2000;2(1):E6.
Hanke et al., Discovery of a novel, potent, and Src family-selective tyrosine kinase inhibitor. Study of Lek—and FynT-dependent T cell activation. J Biol Chem. Jan. 12, 1996;271(2):695-701.
Hanks et al., Protein kinase catalytic domain sequence database: identification of conserved features of primary structure and classification of family members. Methods Enzymol. 1991;200:38-62.
Hanks et al., The eukaryotic protein kinase superfamily: kinase (catalytic) domain structure and classification. FASEB J. May 1995;9(8):576-96. Review.
Hanks et al., The protein kinase family: conserved features and deduced phylogeny of the catalytic domains. Science. Jul. 1, 1988;241(4861):42-52. Review.
Hansen et al., A yoctoliter-scale DNA reactor for small-molecule evolution. J Am Chem Soc. Jan. 28, 2009;131(3):1322-7. doi:10.1021/ja808558a.
Harrington et al., VX-680, a potent and selective small-molecule inhibitor of the Aurora kinases, suppresses tumor growth in vivo. Nat Med. Mar. 2004;10(3):262-7. Epub Feb. 22, 2004. Erratum in: Nat Med. Apr. 2007;13(4):511.
Heid et al., Real time quantitative PCR. Genome Res. Oct. 1996;6(10):986-94.
Higuchi et al., Simultaneous amplification and detection of specific DNA sequences. Biotechnology (N Y). Apr. 1992;10(4):413-7.
Hill et al., A chemical genetic method for generating bivalent inhibitors of protein kinases. J Am Chem Soc. May 20, 2009;131(19):6686-8. doi:10.1021/ja900871y.
Hollander et al., Effect of pramlintide on weight in overweight and obese insulin-treated type 2 diabetes patients. Obes Res. Apr. 2004;12(4):661-8.
Holmes et al., Vascular endothelial growth factor receptor-2: structure, function, intracellular signalling and therapeutic inhibition. Cell Signal. Oct. 2007;19(10):2003-12. Epub Jun. 12, 2007. Review.
Horhota et al., Kinetic analysis of an efficient DNA-dependent TNA polymerase. J Am Chem Soc. May 25, 2005;127(20):7427-34.
Hruby et al., Synthesis of oligopeptide and peptidomimetic libraries. Curr Opin Chem Biol. Jun. 1997;1(1): 114-9.
Hubbard, Crystal structure of the activated insulin receptor tyrosine kinase in complex with peptide substrate and ATP analog. EMBO J. Sep. 15, 1997;16(18):5572-81.
Irby et al., Activating SRC mutation in a subset of advanced human colon cancers. Nat Genet. Feb. 1999;21(2):187-90.

Jameson et al., Fluorescence polarization: past, present and future. Comb Chem High Throughput Screen. May 2003;6(3):167-73. Review.
Jameson et al., Fluorescence polarization/anisotropy in diagnostics and imaging. Chem Rev. May 12, 2010;110(5):2685-708. doi:10.1021/cr900267p. Review.
Johnson et al., Development of an internally quenched fluorescent substrate selective for endothelin-converting enzyme-1. Anal Biochem. Nov. 1, 2000;286(1):112-8.
Josephson et al., Ribosomal synthesis of unnatural peptides. J Am Chem Soc. Aug. 24, 2005;127(33):11727-35.
Joyce, Directed evolution of nucleic acid enzymes. Annu Rev Biochem. 2004;73:791-836. Review.
Kanan et al., Reaction discovery enabled by DNA-templated synthesis and in vitro selection. Nature. Sep. 30, 2004;431(7008):545-9.
Kansy et al., Physicochemical high throughput screening: parallel artificial membrane permeation assay in the description of passive absorption processes. J Med Chem. Mar. 26, 1998;41(7):1007-10.
Karaman et al., A quantitative analysis of kinase inhibitor selectivity. Nat Biotechnol. Jan. 2008;26(1):127-32.
Karamohamed et al., Polymorphisms in the insulin-degrading enzyme gene are associated with type 2 diabetes in men from the NHLBI Framingham Heart Study. Diabetes. Jun. 2003;52(6):1562-7.
Kim et al., Peptidomics approach to elucidate the proteolytic regulation of bioactive peptides. Proc Natl Acad Sci U S A. May 29, 2012;109(22):8523-7. Epub May 14, 2012.
Kleiner et al., DNA-templated polymerization of side-chain-functionalized peptide nucleic acid aldehydes. J Am Chem Soc. Apr. 9, 2008;130(14):4646-59. Epub Mar. 15, 2008.
Kleiner et al., In vitro selection of a DNA-templated small-molecule library reveals a class of macrocyclic kinase inhibitors. J Am Chem Soc. Aug. 25, 2010;132(33):11779-91.
Kleiner et al., In vitro selection of a DNA-templated small-molecule library reveals a class of macrocyclic kinase inhibitors. J Am Chem Soc. Aug. 25, 2010;132(33):11779-91. Supporting Information. 36 pages.
Kleiner et al., Small-molecule discovery from DNA-encoded chemical libraries. Chem Soc Rev. Dec. 2011;40(12):5707-17. Epub Jun. 14, 2011.
Knight et al., Chemical genetics: where genetics and pharmacology meet. Cell. Feb. 9, 2007;128(3):425-30.
Knight et al., Features of selective kinase inhibitors. Chem Biol. Jun. 2005;12(6):621-37.
Kolterman et al., Reduction of postprandial hyperglycemia in subjects with IDDM by intravenous infusion of AC137, a human amylin analogue. Diabetes Care. Aug. 1995;18(8):1179-82.
Krishnamurty et al., Biochemical mechanisms of resistance to small-molecule protein kinase inhibitors. ACS Chem Biol. Jan. 15, 2010;5(1):121-38. doi: 10.1021/cb9002656. Review.
Kurochkin et al., Alzheimer's beta-amyloid peptide specifically interacts with and is degraded by insulin degrading enzyme. FEBS Lett. May 23, 1994;345(1):33-7.
Kwon et al., Quantitative comparison of the relative cell permeability of cyclic and linear peptides. Chem Biol. Jun. 2007;14(6):671-7.
Lam et al., The "One-Bead-One-Compound" Combinatorial Library Method. Chem Rev. Apr. 1, 1997;97(2):411-448.
Lang et al., DOCK 6: combining techniques to model RNA-small molecule complexes. RNA. Jun. 2009;15(6):1219-30. doi: 10.1261/rna.1563609. Epub Apr. 15, 2009.
Latham et al., The application of a modified nucleotide in aptamer selection: novel thrombin aptamers containing 5-(1-pentynyl)-2'-deoxyuridine. Nucleic Acids Res. Jul. 25, 1994;22(14):2817-22.
Lea et al., Fluorescence polarization assays in small molecule screening. Expert Opin Drug Discov. Jan. 2011;6(1):17-32. doi: 10.1517/17460441.2011.537322.
Lee et al., Enhancing the catalytic repertoire of nucleic acids: a systematic study of linker length and rigidity. Nucleic Acids Res. Apr. 1, 2001;29(7):1565-73.

(56) References Cited

OTHER PUBLICATIONS

Lee et al., Metabolic manifestations of insulin deficiency do not occur without glucagon action. Proc Natl Acad Sci U S A. Sep. 11, 2012;109(37):14972-6. doi: 10.1073/pnas.1205983109. Epub Aug. 13, 2012.
Leissring et al., Designed inhibitors of insulin-degrading enzyme regulate the catabolism and activity of insulin. PLoS One. May 7, 2010;5(5):e10504. doi: 10.1371/journal.pone.0010504.
Leslie, Recent changes to the MOSFLM package for processing film and image plate data. Joint CCP4 + ESF-EAMCB Newsletter on Protein Crystallography, 1992;26:27-33.
Levinson et al., A Src-like inactive conformation in the abl tyrosine kinase domain. PLoS Biol. May 2006;4(5):e144. Epub May 2, 2006.
Levitzki, Protein tyrosine kinase inhibitors as novel therapeutic agents. Pharmacol Ther. May-Jun. 1999;82(2-3):231-9. Review.
Li et al., DNA-templated organic synthesis: nature's strategy for controlling chemical reactivity applied to synthetic molecules. Angew Chem Int Ed Engl. Sep. 20, 2004;43(37):4848-70. Review.
Li et al., Multistep DNA-templated synthesis using a universal template. J Am Chem Soc. Nov. 27, 2013; 135(47):17727-30. doi: 10.1021/ja409936r. Epub Nov. 18, 2013.
Li et al., The C-terminal domain of human insulin degrading enzyme is required for dimerization and substrate recognition. Biochem Biophys Res Commun. May 19, 2006;343(4):1032-7. Epub Mar. 22, 2006.
Lin et al., Screening and selection methods for large-scale analysis of protein function. Angew Chem Int Ed Engl. Dec. 2, 2002;41(23):4402-25. Review.
Liu et al., Synthesis and screening of a cyclic peptide library: Discovery of small molecule ligands against human prolactin receptor. Bioord Med Chem Lett. 2009;17:1026-33. doi:10.1016/j.bmc.2008.01.015. Epub Jan. 13, 2008.
Livak et al., Oligonucleotides with fluorescent dyes at opposite ends provide a quenched probe system useful for detecting PCR product and nucleic acid hybridization. PCR Methods Appl. Jun. 1995;4(6):357-62.
Llauger-Bufi et al., Synthesis of novel fluorescent probes for the molecular chaperone Hsp90. Bioorg Med Chem Lett. Nov. 17, 2003;13(22):3975-8.
Llovera et al., The catalytic domain of insulin-degrading enzyme forms a denaturant-resistant complex with amyloid beta peptide: implications for Alzheimer disease pathogenesis. J Biol Chem. Jun. 20, 2008;283(25):17039-48. doi: 10.1074/jbc.M706316200. Epub Apr. 14, 2008.
Löber et al., Palladium-catalyzed hydroamination of 1,3-dienes: a colorimetric assay and enantioselective additions. J Am Chem Soc. May 9, 2001;123(18):4366-7.
Lombardo et al., Discovery of N-(2-chloro-6-methyl- phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays. J Med Chem. Dec. 30, 2004;47(27):6658-61.
Maianti et al., Anti-diabetic activity of insulin-degrading enzyme inhibitors mediated by multiple hormones. Nature. Jul. 3, 2014;511(7507):94-8. doi: 10.1038/nature13297. Epub May 21, 2014.
Malaisse, Pharmacology of the meglitinide analogs: new treatment options for type 2 diabetes mellitus. Treat Endocrinol. 2003;2(6):401-14. Review.
Malito et al., Amyloid beta-degrading cryptidases: insulin degrading enzyme, presequence peptidase, and neprilysin. Cell Mol Life Sci. Aug. 2008;65(16):2574-85. doi: 10.1007/s00018-008-8112-4. Review.
Malito et al., Molecular bases for the recognition of short peptide substrates and cysteine-directed modifications of human insulin-degrading enzyme. Biochemistry. Dec. 2, 2008;47(48):12822-34. doi: 10.1021/bi801192h.
Manfredi et al., Antitumor activity of MLN8054, an orally active small-molecule inhibitor of Aurora A kinase. Proc Natl Acad Sci U S A. Mar. 6, 2007;104(10):4106-11. Epub Feb. 23, 2007.

Manning et al., The protein kinase complement of the human genome. Science. Dec. 6, 2002;298(5600):1912-34. Review.
Manolopoulou et al., Molecular basis of catalytic chamber-assisted unfolding and cleavage of human insulin by human insulin-degrading enzyme. J Biol Chem. May 22, 2009;284(21):14177-88. doi:10.1074/jbc.M900068200. Epub Mar. 25, 2009.
Maresso et al., Sortase as a target of anti-infective therapy. Pharmacol Rev. Mar. 2008;60(1):128-41. Review.
Martens et al., PREPL: a putative novel oligopeptidase propelled into the limelight. Biol Chem. Jul. 2006;387(7):879-83. Review.
Matulic-Adamic et al., Functionalized nucleoside 5'-triphosphates for in vitro selection of new catalytic ribonucleic acids. Bioorg Med Chem Lett. Jun. 5, 2000;10(11):1299-302.
McCoy et al. Likelihood-enhanced fast translation functions. Acta Crystallogr D Biol Crystallogr. Apr. 2005;61(Pt 4):458-64. Epub Mar. 24, 2005.
McCoy et al., Phaser crystallographic software. J Appl Crystallogr. Aug. 1, 2007;40(Pt 4):658-674. Epub Jul. 13, 2007.
Melkko et al., Encoded self-assembling chemical libraries. Nat Biotechnol. May 2004;22(5):568-74. Epub Apr. 18, 2004.
Melkko et al., Isolation of high-affinity trypsin inhibitors from a DNA-encoded chemical library. Angew Chem Int Ed Engl. 2007;46(25):4671-4.
Miller et al., Amyloid-beta peptide levels in brain are inversely correlated with insulysin activity levels in vivo. Proc Natl Acad Sci U S A. May 13, 2003;100(10):6221-6. Epub May 5, 2003.
Mirsky et al., Effect of insulinase-inhibitor on hypoglycemic action of insulin. Science. Sep. 23 1955;122(3169):559-60.
Mirsky et al., The inactivation of insulin by tissue extracts; the distribution and properties of insulin inactivating extracts. Arch Biochem. Jan. 1949;20(1):1-9.
Misbin et al., Inhibition of insulin degradation by insulin-like growth factors. Endocrinology. Oct. 1983;113(4):1525-7.
Mol et al., Structural basis for the autoinhibition and STI-571 inhibition of c-Kit tyrosine kinase. J Biol Chem. Jul. 23, 2004;279(30):31655-63. Epub Apr. 29, 2004.
Momiyama et al., Synthesis of acyclic alpha,beta-unsaturated ketones via Pd(II)-catalyzed intermolecular reaction of alkynamides and alkenes. J Am Chem Soc. Feb. 28, 2007;129(8):2230-1. Epub Feb. 6, 2007.
Monzillo et al., Evaluation of insulin sensitivity in clinical practice and in research settings. Nutr Rev. Dec. 2003;61(12):397-412. Review.
Mooradian et al., Drug therapy of postprandial hyperglycaemia. Drugs. Jan. 1999;57(1):19-29. Review.
Moustakas et al., Development and validation of a modular, extensible docking program: DOCK 5. J Comput Aided Mol Des. Oct.-Nov. 2006;20(10-11):601-19. Epub Dec. 6, 2006.
Mullard, DNA tags help the hunt for drugs. Nature. Feb. 18 2016;530(7590):367-9. doi: 10.1038/530367a.
Müller et al., Atrial natriuretic peptide (ANP) is a high-affinity substrate for rat insulin-degrading enzyme. Eur J Biochem. Dec. 5, 1991;202(2):285-92.
Muller et al., Prodrug approaches for enhancing the bioavailability of drugs with low solubility. Chem Biodivers. Nov. 2009;6(11):2071-83. doi: 10.1002/cbdv.200900114.
Müller et al., Rat insulin-degrading enzyme: cleavage pattern of the natriuretic peptide hormones ANP, BNP, and CNP revealed by HPLC and mass spectrometry. Biochemistry. Nov. 17, 1992;31(45):11138-43.
Musich et al., Synthesis of anthopleurine, the alarm pheromone from Anthopleura elegantissima. J. Am. Chem. Soc. Jul. 1987;100(15):4865-72.
Nasir et al., Fluorescence polarization: an analytical tool for immunoassay and drug discovery. Comb Chem High Throughput Screen. Aug. 1999;2(4):177-90. Review.
Ohren et al., Structures of human MAP kinase kinase 1 (MEK1) and MEK2 describe novel noncompetitive kinase inhibition. Nat Struct Mol Biol. Dec. 2004;11(12):1192-7. Epub Nov. 14, 2004. Erratum in: Nat Struct Mol Biol. Mar. 2005;12(3):278.
Otwinowski et al., Processing of x-ray diffraction data collected in oscillation mode. Methods in Enzymology. 276 (Macromolecular Crystallography, part A):307-26.

(56) References Cited

OTHER PUBLICATIONS

Owicki, Fluorescence polarization and anisotropy in high throughput screening: perspectives and primer. J Biomol Screen. Oct. 2000;5(5):297-306. Review.

Parker et al., The regulation of Acinetobacter sp. alpha-oxoglutarate dehydrogenase complex. Biochem J. Nov. 1972;130(1):39P.

Patick et al., Protease inhibitors as antiviral agents. Clin Microbiol Rev. Oct. 1998;11(4):614-27. Review.

Perrin et al., Bridging the gap between proteins and nucleic acids: a metal-independent RNAseA mimic with two protein-like functionalities. J Am Chem Soc. Feb. 28, 2001;123(8):1556-63.

Perrin, Polarization of light of fluorescence, average life of molecules. J Phys Radium. 1926;7:390-401.

Pirrung, Spatially Addressable Combinatorial Libraries. Chem Rev. Apr. 1, 1997;97(2):473-488.

PubChem CID 46938796. Nov. 15, 2010. [Retrieved from the internet Dec. 2, 2011:http://pubchem.ncbi.nim.nih.gov/summary/summary.cgi?cid-46938796&loc=ec_res].

Qiu et al., Insulin-degrading enzyme regulates extracellular levels of amyloid beta-protein by degradation. J Biol Chem. Dec. 4, 1998;273(49):32730-8.

Riddle et al., Emerging therapies mimicking the effects of amylin and glucagon-like peptide 1. Diabetes Care. Feb. 2006;29(2):435-49. Review.

Riediger et al., The anorectic hormone amylin contributes to feeding-related changes of neuronal activity in key structures of the gut-brain axis. Am J Physiol Regul Integr Comp Physiol. Jan. 2004;286(1):R114-22. Epub Sep. 4, 2003.

Roh et al., Overexpression of the oncogenic kinase Pim-1 leads to genomic instability. Cancer Res. Dec. 1, 2003;63(23):8079-84.

Rosenbaum et al., Efficient and sequence-specific DNA-templated polymerization of peptide nucleic acid aldehydes. J Am Chem Soc. Nov. 19, 2003;125(46):13924-5.

Rozenman et al., Development and initial application of a hybridization-independent, DNA-encoded reaction discovery system compatible with organic solvents. J Am Chem Soc. Dec. 5, 2007;129(48):14933-8. Epub Nov. 10, 2007.

Ruff et al., Enhanced functional potential of nucleic acid aptamer libraries patterned to increase secondary structure. J Am Chem Soc. Jul. 14, 2010;132(27):9453-64. doi: 10.1021/ja103023m.

Ruff et al., Enhanced functional potential of nucleic acid aptamer libraries patterned to increase secondary structure. J Am Chem Soc. Jul. 14, 2010;132(27):9453-64. Supporting Information. 25 pages.

Sadry et al., Emerging combinatorial hormone therapies for the treatment of obesity and T2DM. Nat Rev Endocrinol. Jul. 2013;9(7):425-33. doi: 10.1038/nrendo.2013.47. Epub Mar. 12, 2013. Review.

Safavi et al., Identification of gamma-endorphin-generating enzyme as insulin-degrading enzyme. Biochemistry. Nov. 12, 1996;35(45):14318-25.

Saghatelian et al., Activity-based probes for the proteomic profiling of metalloproteases. Proc Natl Acad Sci U S A. Jul. 6, 2004;101(27):10000-5. Epub Jun. 25, 2004.

Sattler et al., Structure of Bcl-xL-Bak peptide complex: recognition between regulators of apoptosis. Science. Feb. 14, 1997;275(5302):983-6.

Schenker et al., Simultaneous interaction of enzymes with two modifiers: reappraisal of kinetic models and new paradigms. J Theor Biol. Nov. 21, 2009;261(2):318-29. doi: 10.1016/j.jtbi.2009.07.033. Epub Aug. 4, 2009.

Scheuermann et al., DNA-encoded chemical libraries for the discovery of MMP-3 inhibitors. Bioconjug Chem. Mar. 2008;19(3):778-85. Epub Feb. 7, 2008.

Schindler et al., Structural mechanism for STI-571 inhibition of abelson tyrosine kinase. Science. Sep. 15, 2000;289(5486):1938-42.

Schmitz et al., Amylin agonists: a novel approach in the treatment of diabetes. Diabetes. Dec. 2004;53 Suppl 3:S233-8. Review.

Seeliger et al., c-Src binds to the cancer drug imatinib with an inactive Abl/c-Kit conformation and a distributed thermodynamic penalty. Structure. Mar. 2007;15(3):299-311.

Seeliger et al., Equally potent inhibition of c-Src and Abl by compounds that recognize inactive kinase conformations. Cancer Res. Mar. 15, 2009;69(6):2384-92. Epub Mar. 10, 2009.

Seeliger et al., High yield bacterial expression of active c-Abl and c-Src tyrosine kinases. Protein Sci. Dec. 2005;14(12):3135-9. Epub Oct. 31, 2005.

Shan et al., How does a drug molecule find its target binding site? J Am Chem Soc. Jun. 22, 2011;133(24):9181-3. Epub May 13, 2011.

Sharma et al., Targeting Akt3 signaling in malignant melanoma using isoselenocyanates. Clin Cancer Res. Mar. 1, 2009;15(5):1674-85. Epub Feb. 10, 2009.

Shen et al., Structures of human insulin-degrading enzyme reveal a new substrate recognition mechanism. Nature. Oct. 19, 2006;443(7113):870-4. Epub Oct. 11, 2006.

Shoichet, Interpreting steep dose-response curves in early inhibitor discovery. J Med Chem. Dec. 14, 2006;49(25):7274-7.

Shroyer et al., Purification and characterization of a rat liver cytosol neutral thiol peptidase that degrades glucagon, insulin, and isolated insulin A and B chains. Arch Biochem Biophys. Jan. 1985;236(1):205-19.

Sicheri et al., Crystal structure of the Src family tyrosine kinase Hck. Nature. Feb. 13, 1997;385(6617):602-9.

Singh et al., Recent trends in targeted anticancer prodrug and conjugate design. Curr Med Chem. 2008;15(18):1802-26.

Sladek et al., A genome-wide association study identifies novel risk loci for type 2 diabetes. Nature. Feb. 22, 2007;445(7130):881-5. Epub Feb. 11, 2007.

Snyder et al., Effects of template sequence and secondary structure on DNA-templated reactivity. J Am Chem Soc. Jan. 30, 2008;130(4):1392-401. doi: 10.1021/ja076780u. Epub Jan. 8, 2008.

Snyder et al., Ordered multistep synthesis in a single solution directed by DNA templates. Angew Chem Int Ed Engl. Dec. 1, 2005;44(45):7379-82.

Songyang et al., Catalytic specificity of protein-tyrosine kinases is critical for selective signalling. Nature. Feb. 9, 1995;373(6514):536-9.

Songyang et al., Recognition and specificity in protein tyrosine kinase-mediated signalling. Trends Biochem Sci. Nov. 1995;20(11):470-5.

Souza-Fagundes et al., A high-throughput fluorescence polarization anisotropy assay for the 70N domain of replication protein A. Anal Biochem. Feb. 15, 2012;421(2):742-9. doi: 10.1016/j.ab.2011.11.025. Epub Dec. 1, 2011.

Stella et al., Cyclodextrins. Toxicol Pathol. Jan. 2008;36(1):30-42. doi: 10.1177/0192623307310945. Review.

Stout et al., High-throughput structural biology in drug discovery: protein kinases. Curr Pharm Des. 2004;10(10):1069-82. Review.

Sugimura et al., Mutation of the SRC gene in endometrial carcinoma. Jpn J Cancer Res. Apr. 2000;91(4):395-8.

Tan, Diversity-oriented synthesis: exploring the intersections between chemistry and biology. Nat Chem Biol. Jul. 2005;1(2):74-84. Review.

Tatton et al., The Src-selective kinase inhibitor PP1 also inhibits Kit and Bcr-Abl tyrosine kinases. J Biol Chem. Feb. 14, 2003;278(7):4847-53. Epub Dec. 9, 2002.

Taylor et al., Investigating and Engineering Enzymes by Genetic Selection. Angew Chem Int Ed Engl. Sep. 17, 2001;40(18):3310-3335.

Testa, Prodrug research: futile or fertile? Biochem Pharmacol. Dec. 1, 2004;68(11):2097-106.

Thompson et al., Attenuation of androgen receptor-dependent transcription by the serine/threonine kinase Pim-1. Lab Invest. Sep. 2003;83(9):1301-9.

Trebbien et al., Neutral endopeptidase 24.11 is important for the degradation of both endogenous and exogenous glucagon in anesthetized pigs. Am J Physiol Endocrinol Metab. Sep. 2004;287(3):E431-8. Epub May 4, 2004.

Tse et al., Translation of DNA into a library of 13,000 synthetic small-molecule macrocycles suitable for in vitro selection. J Am Chem Soc. Nov. 19, 2008;130(46):15611-26. doi: 10.1021/ja805649f. Epub Oct. 29, 2008.

(56) References Cited

OTHER PUBLICATIONS

Tse et al., Translation of DNA into a library of 13,000 synthetic small-molecule macrocycles suitable for in vitro selection. J Am Chem Soc. Nov. 19, 2008;130(46):15611-26. Epub Oct. 29, 2008, supporting information.

Unger et al., Glucagonocentric restructuring of diabetes: a pathophysiologic and therapeutic makeover. J Clin Invest. Jan. 3, 2012;122(1):4-12. doi: 10.1172/JCI60016. Epub Jan. 3, 2012. Review.

Usanov et al., Second-generation DNA-templated macrocycle libraries for the discovery of bioactive small molecules. Nat Chem. Jul. 2018;10(7):704-714. doi: 10.1038/s41557-018-0033-8. Epub Apr. 2, 2018.

Vonrhein et al., Data processing and analysis with the autoPROC toolbox. Acta Crystallogr D Biol Crystallogr. Apr. 2011;67(Pt 4):293-302. doi: 10.1107/S0907444911007773. Epub Mar. 18, 2011.

Walters et al., Designing screens: how to make your hits a hit. Nat Rev Drug Discov. Apr. 2003;2(4):259-66. Review.

Wilson et al., In vitro Selection of Functional Nucleic Acids. Ann. Rev. Biochem., 1999; 68:611-48.

Winzell et al., The high-fat diet-fed mouse: a model for studying mechanisms and treatment of impaired glucose tolerance and type 2 diabetes. Diabetes. Dec. 2004;53 Suppl 3:S215-9.

Workman et al., Probing the probes: fitness factors for small molecule tools. Chem Biol. Jun. 25, 2010;17(6):561-77. doi: 10.1016/j.chembiol.2010.05.013. Review.

Wrenn et al., Synthetic ligands discovered by in vitro selection. J Am Chem Soc. Oct. 31, 2007;129(43):13137-43. Epub Oct. 6, 2007.

Xu et al., Crystal structures of c-Src reveal features of its autoinhibitory mechanism. Mol Cell. May 1999;3(5):629-38.

Xu et al., Three-dimensional structure of the tyrosine kinase c-Src. Nature. Feb. 13, 1997;385(6617):595-602.

Young, Effects on plasma glucose and lactate. Adv Pharmacol. 2005;52:193-208. Review.

Young, Inhibition of glucagon secretion. Adv Pharmacol. 2005;52:151-71. Review.

Zeggini et al., Replication of genome-wide association signals in UK samples reveals risk loci for type 2 diabetes. Science. Jun. 1, 2007;316(5829):1336-41. Epub Apr. 26, 2007. Erratum in: Science. Aug. 24, 2007;317(5841):1035-6.

Zhang et al., In vitro degradation of insulin-like peptide 3 by insulin-degrading enzyme. Protein J. Feb. 2010;29(2):93-8. doi:10.1007/sl0930-009-9226-8.

Zhang et al., Targeting cancer with small molecule kinase inhibitors. Nat Rev Cancer. Jan. 2009;9(1):28-39. doi: 10.1038/nrc2559. Review.

Zimmermann et al., DNA-encoded chemical libraries: foundations and applications in lead discovery. Drug Discov Today. Nov. 2016;21(11):1828-1834. doi: 10.1016/j.drudis.2016.07.013.

MODEL OF DNA TEMPLATES:

☆ ~NNNNNN~ ~NNNNNN~ ~NNNNNN~ ~NNNNN~
            codon 3     codon 2     codon 1    codon 4 (scaffold)

FIG. 2C

|    | 3A-2A-1A-4A | 3B-2B-1B-4B | 3C-2C-1C-4C | 3D-2D-1D-4D | 3E-2E-1E-4E |
|----|-------------|-------------|-------------|-------------|-------------|
| 1A | 99          | 0           | 0           | 0           | 0           |
| 1B | 0           | 99          | 0           | 0           | 0           |
| 1C | 0           | 0           | 99          | 0           | 0           |
| 1D | 0           | 0           | 0           | 99          | 0           |
| 1E | 0           | 0           | 0           | 0           | 99          | ideal-case reactivity table (1) high DTS conversions for matched anticodon/template pairs only

| 2 | 3a-2a-1a-4a | 3b-2b-1b-4b | 3c-2c-1c-4c | 3d-2d-1d-4d | 3e-2e-1e-4e | 3f-2f-1f-4f | 3g-2g-1g-4g | 3h-2h-1h-4h | 3i-2i-1i-4i | 3j-2j-1j-4j | 3k-2k-1k-4k | 3l-2l-1l-4l | 3m-2m-1m-4m | 3n-2n-1n-4n | 3o-2o-1o-4o | 3p-2p-1p-4p | 3q-2q-1q-4q | 3r-2r-1r-4r | 3s-2s-1s-4s | 3t-2t-1t-4t | 3u-2u-1u-4u | 3v-2v-1v-4v | 3w-2w-1w-4w | 3x-2x-1x-4x | 3y-2y-1y-4y | 3z-2z-1z-4z | 3ww-2ww-1ww-4ww | 3xx-2xx-1xx-4xx | 3yy-2yy-1yy-4yy | 3zz-2zz-1zz-4zz |
|---|---|---|---|---|---|---|---|---|---|---|---|---|---|---|---|---|---|---|---|---|---|---|---|---|---|---|---|---|---|---|
| 2a | 99 | 1 | 7 | 1 | 0 | 0 | 2 | 0 | 2 | 0 | 0 | 0 | 1 | 0 | 7 | 1 | 0 | 0 | 7 | 0 | 0 | 0 | 2 | 5 | 0 | 0 | 18 | 0 | | |
| 2b | 3 | 97 | 7 | 1 | 0 | 2 | 0 | 7 | 0 | 0 | 1 | 0 | 0 | 35 | 10 | 0 | 10 | 1 | 0 | 0 | 0 | 0 | 57 | 11 | 1 | 3 | 0 | 0 | 0 | |
| 2c | 0 | 5 | 98 | 1 | 0 | 0 | 11 | 4 | 0 | 0 | 0 | 0 | 0 | 0 | 1 | 0 | 39 | 1 | 0 | 0 | 0 | 0 | 19 | 0 | 4 | 2 | 0 | 0 | 0 | 0 |
| 2d | 0 | 4 | 7 | 99 | 3 | 0 | 0 | 5 | 0 | 0 | 0 | 0 | 0 | 0 | 2 | 0 | 1 | 5 | 0 | 0 | 0 | 0 | 16 | 0 | 2 | 1 | 0 | 0 | 0 | 0 |
| 2e | 1 | 3 | 1 | 3 | 97 | 0 | 0 | 0 | 0 | 0 | 0 | 0 | 30 | 0 | 2 | 0 | 2 | 0 | 0 | 0 | 0 | 0 | 24 | 0 | 5 | 1 | 5 | 0 | 0 | 0 |
| 2f | 1 | 5 | 18 | 1 | 1 | 82 | 1 | 7 | 0 | 0 | 0 | 0 | 25 | 16 | 5 | 0 | 21 | 2 | 0 | 0 | 0 | 0 | 36 | 0 | 4 | 3 | 0 | 0 | 0 | 0 |
| 2g | 0 | 36 | 13 | 20 | 88 | 1 | 92 | 43 | 3 | 6 | 1 | 0 | 0 | 2 | 7 | 2 | 16 | 9 | 0 | 0 | 5 | 2 | 45 | 0 | 5 | 3 | 1 | 0 | 3 | 0 |
| 2h | 0 | 4 | 4 | 0 | 0 | 0 | 0 | 99 | 0 | 0 | 0 | 0 | 0 | 4 | 0 | 2 | 0 | 0 | 0 | 0 | 0 | 0 | 17 | 0 | 3 | 0 | 0 | 0 | 0 | 0 |
| 2i | 1 | 2 | 2 | 0 | 0 | 0 | 1 | 1 | 79 | 0 | 0 | 0 | 0 | 0 | 2 | 0 | 2 | 0 | 0 | 0 | 0 | 0 | 7 | 0 | 3 | 1 | 0 | 0 | 0 | 0 |
| 2j | 0 | 2 | 3 | 14 | 0 | 0 | 1 | 2 | 0 | 69 | 0 | 0 | 0 | 0 | 5 | 0 | 1 | 0 | 0 | 0 | 0 | 0 | 10 | 0 | 1 | 1 | 0 | 0 | 0 | 0 |
| 2k | 4 | 2 | 1 | 0 | 0 | 0 | 1 | 0 | 0 | 0 | 87 | 0 | 0 | 2 | 2 | 0 | 1 | 0 | 0 | 0 | 0 | 0 | 8 | 0 | 3 | 0 | 0 | 0 | 0 | 0 |
| 2l | 77 | 10 | 35 | 88 | 22 | 24 | 9 | 84 | 8 | 18 | 58 | 70 | 39 | 28 | 65 | 7 | 54 | 19 | 1 | 8 | 56 | 17 | 99 | 3 | 15 | 63 | 6 | 18 | 43 | 9 |
| 2m | 0 | 3 | 1 | 3 | 1 | 0 | 1 | 4 | 0 | 0 | 0 | 0 | 99 | 0 | 2 | 0 | 1 | 0 | 0 | 0 | 1 | 0 | 17 | 0 | 1 | 1 | 0 | 0 | 0 | 0 |
| 2n | 1 | 7 | 10 | 52 | 0 | 0 | 1 | 39 | 0 | 0 | 0 | 7 | 0 | 85 | 1 | 0 | 3 | 3 | 0 | 0 | 5 | 0 | 25 | 0 | 0 | 3 | 0 | 0 | 20 | 0 |
| 2o | 0 | 3 | 5 | 5 | 0 | 0 | 2 | 2 | 0 | 0 | 0 | 0 | 1 | 0 | 91 | 0 | 2 | 0 | 0 | 0 | 3 | 0 | 26 | 0 | 0 | 1 | 0 | 1 | 0 | 0 |
| 2p | 0 | 2 | 4 | 0 | 0 | 0 | 1 | 0 | 0 | 0 | 0 | 0 | 4 | 0 | 1 | 39 | 1 | 1 | 0 | 0 | 0 | 0 | 11 | 0 | 0 | 0 | 0 | 0 | 0 | 0 |
| 2q | 13 | 1 | 4 | 1 | 0 | 0 | 0 | 1 | 0 | 0 | 0 | 0 | 0 | 0 | 0 | 0 | 90 | 1 | 0 | 0 | 0 | 0 | 7 | 0 | 0 | 4 | 0 | 0 | 0 | 0 |
| 2r | 0 | 2 | 26 | 4 | 0 | 0 | 0 | 27 | 0 | 0 | 0 | 0 | 1 | 0 | 1 | 0 | 99 | 0 | 0 | 0 | 0 | 0 | 19 | 0 | 0 | 0 | 0 | 0 | 0 | 0 |
| 2s | 1 | 7 | 35 | 16 | 5 | 2 | 3 | 94 | 0 | 3 | 5 | 0 | 11 | 0 | 5 | 9 | 1 | 13 | 69 | 0 | 5 | 0 | 50 | 0 | 2 | 6 | 1 | 0 | 0 | 0 |
| 2t | 0 | 1 | 5 | 1 | 0 | 0 | 2 | 8 | 7 | 0 | 2 | 0 | 2 | 0 | 2 | 0 | 25 | 3 | 0 | 75 | 1 | 0 | 40 | 0 | 0 | 9 | 0 | 0 | 0 | 0 |
| 2u | 2 | 3 | 4 | 2 | 9 | 5 | 2 | 6 | 0 | 1 | 2 | 0 | 2 | 0 | 2 | 0 | 2 | 5 | 0 | 0 | 94 | 1 | 38 | 0 | 2 | 5 | 0 | 0 | 0 | 0 |
| 2v | 0 | 2 | 7 | 3 | 4 | 3 | 1 | 8 | 0 | 0 | 0 | 0 | 40 | 0 | 2 | 0 | 1 | 0 | 0 | 0 | 3 | 99 | 21 | 1 | 0 | 0 | 1 | 0 | 0 | 0 |
| 2w | 35 | 3 | 36 | 63 | 6 | 1 | 3 | 85 | 4 | 2 | 10 | 0 | 41 | 2 | 5 | 1 | 20 | 21 | 0 | 16 | 5 | 9 | 99 | 0 | 5 | 71 | 0 | 6 | 32 | 0 |
| 2x | 39 | 10 | 38 | 70 | 3 | 85 | 7 | 73 | 28 | 50 | 90 | 6 | 93 | 8 | 12 | 32 | 36 | 39 | 10 | 19 | 78 | 98 | 99 | 78 | 77 | 83 | 53 | 1 | 23 | 44 |
| 2y | 48 | 26 | 38 | 89 | 40 | 59 | 21 | 84 | 30 | 50 | 63 | 19 | 70 | 35 | 41 | 24 | 66 | 68 | 10 | 14 | 56 | 93 | 99 | 27 | 99 | 76 | 31 | 16 | 39 | 56 |
| 2z | 3 | 15 | 38 | 4 | 8 | 4 | 6 | 65 | 6 | 18 | 4 | 1 | 7 | 2 | 9 | 56 | 7 | 18 | 10 | 2 | 14 | 27 | 49 | 5 | 80 | 99 | 12 | 0 | 8 | 15 |
| 2ww | 4 | 23 | 58 | 17 | 38 | 49 | 16 | 97 | 22 | 38 | 29 | 8 | 19 | 6 | 19 | 33 | 10 | 33 | 8 | 16 | 39 | 77 | 75 | 10 | 99 | 46 | 64 | 0 | 7 | 70 |
| 2xx | 0 | 1 | 0 | 0 | 0 | 1 | 0 | 0 | 0 | 0 | 2 | 0 | 3 | 0 | 0 | 0 | 0 | 0 | 0 | 2 | 0 | 0 | 3 | 1 | 0 | 57 | 0 | 0 | | |
| 2yy | 0 | 2 | 2 | 12 | 1 | 0 | 0 | 0 | 0 | 5 | 0 | 3 | 0 | 1 | 0 | 0 | 0 | 0 | 0 | 4 | 9 | 0 | 2 | 1 | 0 | 0 | 58 | 0 | | |
| 2zz | 0 | 10 | 2 | 0 | 1 | 0 | 1 | 0 | 0 | 0 | 0 | 1 | 4 | 0 | 0 | 0 | 0 | 0 | 0 | 0 | 0 | 0 | 2 | 10 | 0 | 1 | 0 | 0 | 0 | 49 |

FIG. 7B

| 3 | 3a-2a-1a-4a | 3b-2b-1b-4b | 3c-2c-1c-4c | 3d-2d-1d-4d | 3e-2e-1e-4e | 3f-2f-1f-4f | 3g-2g-1g-4g | 3h-2h-1h-4h | 3i-2i-1i-4i | 3j-2j-1j-4j | 3k-2k-1k-4k | 3l-2l-1l-4l | 3m-2m-1m-4m | 3n-2n-1n-4n | 3o-2o-1o-4o | 3p-2p-1p-4p | 3q-2q-1q-4q | 3r-2r-1r-4r | 3s-2s-1s-4s | 3t-2t-1t-4t | 3u-2u-1u-4u | 3v-2v-1v-4v | 3w-2w-1w-4w | 3x-2x-1x-4x | 3y-2y-1y-4y | 3z-2z-1z-4z | 3ww-2ww-1ww-4ww | 3xx-2xx-1xx-4xx | 3yy-2yy-1yy-4yy | 3zz-2zz-1zz-4zz |
|---|---|---|---|---|---|---|---|---|---|---|---|---|---|---|---|---|---|---|---|---|---|---|---|---|---|---|---|---|---|---|
| 3a | 82 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3b | 0 | 62 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3c | 0 | 0 | 81 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3d | 0 | 0 | 0 | 51 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| 3e | 0 | 0 | 0 | 0 | 61 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3f | 0 | 0 | 0 | 0 | 0 | 88 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 |
| 3g | 0 | 0 | 0 | 0 | 0 | 0 | 63 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3h | 0 | 0 | 0 | 0 | 0 | 0 | 0 | 64 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3i | 0 | 0 | 0 | 1 | 0 | 0 | 0 | 0 | 48 | 0 | 0 | 0 | 0 | 0 | 0 | 0 | 0 | 0 | 0 | 0 | 0 | 0 | 43 | 0 | 0 | 0 | 0 | 0 | 0 | 0 |
| 3j | 0 | 0 | 0 | 0 | 0 | 0 | 0 | 0 | 0 | 34 | 0 | 0 | 0 | 0 | 0 | 0 | 0 | 0 | 0 | 0 | 0 | 1 | 0 | 0 | 0 | 0 | 0 | 0 | 0 | 0 |
| 3k | 0 | 0 | 0 | 0 | 0 | 0 | 0 | 0 | 0 | 0 | 39 | 0 | 0 | 0 | 0 | 0 | 0 | 0 | 0 | 0 | 0 | 0 | 0 | 0 | 0 | 0 | 0 | 0 | 0 | 0 |
| 3l | 0 | 0 | 0 | 0 | 0 | 0 | 0 | 0 | 0 | 0 | 0 | 24 | 1 | 0 | 0 | 0 | 0 | 0 | 0 | 0 | 0 | 0 | 0 | 0 | 0 | 0 | 0 | 0 | 0 | 0 |
| 3m | 0 | 0 | 0 | 0 | 0 | 0 | 0 | 0 | 0 | 0 | 0 | 0 | 57 | 0 | 0 | 0 | 0 | 0 | 0 | 0 | 0 | 0 | 0 | 0 | 0 | 0 | 0 | 0 | 0 | 0 |
| 3n | 0 | 0 | 0 | 0 | 0 | 0 | 0 | 0 | 0 | 0 | 0 | 0 | 0 | 63 | 0 | 0 | 0 | 0 | 0 | 0 | 0 | 0 | 0 | 0 | 0 | 0 | 0 | 0 | 0 | 0 |
| 3o | 0 | 0 | 0 | 0 | 0 | 0 | 0 | 0 | 0 | 0 | 0 | 0 | 0 | 0 | 76 | 0 | 0 | 0 | 0 | 0 | 0 | 0 | 0 | 0 | 0 | 0 | 0 | 0 | 0 | 0 |
| 3p | 0 | 1 | 0 | 0 | 0 | 0 | 0 | 0 | 0 | 0 | 0 | 0 | 0 | 0 | 0 | 31 | 0 | 0 | 0 | 1 | 2 | 0 | 0 | 0 | 0 | 0 | 0 | 0 | 0 | 0 |
| 3q | 0 | 0 | 0 | 0 | 0 | 0 | 0 | 0 | 0 | 0 | 0 | 0 | 0 | 0 | 0 | 0 | 58 | 0 | 0 | 0 | 0 | 0 | 0 | 0 | 0 | 0 | 0 | 0 | 0 | 0 |
| 3r | 0 | 0 | 0 | 0 | 0 | 0 | 0 | 0 | 0 | 0 | 0 | 0 | 0 | 0 | 0 | 1 | 0 | 32 | 0 | 0 | 0 | 0 | 0 | 0 | 0 | 0 | 0 | 0 | 0 | 0 |
| 3s | 0 | 0 | 0 | 0 | 0 | 0 | 1 | 0 | 0 | 0 | 0 | 0 | 0 | 1 | 0 | 0 | 0 | 0 | 60 | 0 | 0 | 0 | 0 | 0 | 0 | 0 | 0 | 0 | 0 | 0 |
| 3t | 0 | 0 | 0 | 0 | 0 | 0 | 0 | 0 | 0 | 0 | 0 | 0 | 0 | 0 | 0 | 0 | 0 | 0 | 0 | 47 | 0 | 0 | 0 | 0 | 9 | 0 | 0 | 0 | 0 | 0 |
| 3u | 0 | 0 | 0 | 0 | 0 | 0 | 0 | 0 | 0 | 0 | 0 | 0 | 0 | 0 | 0 | 0 | 0 | 0 | 0 | 0 | 79 | 0 | 0 | 0 | 0 | 0 | 0 | 0 | 0 | 0 |
| 3v | 0 | 0 | 0 | 0 | 0 | 0 | 0 | 0 | 0 | 0 | 0 | 0 | 0 | 0 | 0 | 0 | 0 | 0 | 0 | 0 | 4 | 79 | 0 | 0 | 0 | 0 | 0 | 0 | 0 | 0 |
| 3w | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 91 | 0 | 0 | 0 | 0 | 0 | 0 | 0 |
| 3x | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 30 | 0 | 0 | 0 | 0 | 0 | 0 |
| 3y | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 89 | 0 | 0 | 0 | 0 | 0 |
| 3z | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 39 | 0 | 0 | 0 | 0 |
| 3ww | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 30 | 0 | 0 | 0 |
| 3xx | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 0 | 0 |
| 3yy | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 32 | 0 |
| 3zz | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 15 |

| 2 | 3a-2a-1a-4a | 3b-2b-1b-4b | 3c-2c-1c-4c | 3d-2d-1d-4d | 3e-2e-1e-4e | 3f-2f-1f-4f | 3g-2g-1g-4g | 3h-2h-1h-4h | 3i-2i-1i-4i | 3j-2j-1j-4j | 3k-2k-1k-4k | 3l-2l-1l-4l | 3m-2m-1m-4m | 3n-2n-1n-4n | 3o-2o-1o-4o | 3p-2p-1p-4p | 3q-2q-1q-4q | 3r-2r-1r-4r | 3s-2s-1s-4s | 3t-2t-1t-4t | 3u-2u-1u-4u | 3v-2v-1v-4v | 3w-2w-1w-4w | 3x-2x-1x-4x | 3y-2y-1y-4y | 3z-2z-1z-4z | 3ww-2ww-1ww-4ww | 3xx-2xx-1xx-4xx | 3yy-2yy-1yy-4yy | 3zz-2zz-1zz-4zz |
|---|---|---|---|---|---|---|---|---|---|---|---|---|---|---|---|---|---|---|---|---|---|---|---|---|---|---|---|---|---|---|
| 2a | 99 | 0 | 0 | 0 | 0 | 0 | 0 | 1 | 0 | 0 | 0 | 0 | 0 | 0 | 2 | 0 | 5 | 0 | 0 | 0 | 9 | 0 | 5 | 0 | 3 | 0 | 0 | 0 | 11 | 0 |
| 2b | 0 | 93 | 0 | 0 | 0 | 0 | 0 | 0 | 0 | 0 | 0 | 0 | 39 | 5 | 0 | 10 | 0 | 0 | 0 | 0 | 0 | 0 | 38 | 21 | 1 | 0 | 0 | 0 | 0 | 0 |
| 2c | 0 | 0 | 99 | 0 | 0 | 0 | 3 | 0 | 0 | 0 | 0 | 0 | 0 | 0 | 0 | 25 | 0 | 0 | 0 | 0 | 0 | 0 | 15 | 0 | 0 | 0 | 0 | 0 | 0 | 0 |
| 2d | 0 | 0 | 0 | 84 | 0 | 0 | 0 | 0 | 0 | 0 | 0 | 0 | 0 | 0 | 0 | 2 | 1 | 0 | 0 | 0 | 0 | 0 | 8 | 0 | 0 | 0 | 0 | 0 | 0 | 0 |
| 2e | 0 | 0 | 0 | 0 | 93 | 0 | 0 | 1 | 0 | 0 | 0 | 8 | 0 | 0 | 0 | 2 | 0 | 0 | 0 | 1 | 0 | 12 | 1 | 0 | 0 | 0 | 0 | 0 | 0 | 0 |
| 2f | 0 | 0 | 3 | 0 | 1 | 92 | 0 | 2 | 0 | 0 | 0 | 0 | 5 | 17 | 1 | 0 | 17 | 0 | 0 | 0 | 0 | 0 | 17 | 0 | 0 | 0 | 0 | 0 | 0 | 0 |
| 2g | 0 | 11 | 0 | 1 | 24 | 0 | 95 | 13 | 1 | 0 | 0 | 0 | 1 | 3 | 0 | 11 | 2 | 0 | 0 | 9 | 2 | 23 | 1 | 0 | 0 | 1 | 0 | 2 | 0 |
| 2h | 0 | 0 | 1 | 0 | 0 | 0 | 0 | 97 | 0 | 0 | 0 | 0 | 0 | 0 | 0 | 3 | 1 | 0 | 0 | 0 | 0 | 6 | 0 | 0 | 0 | 0 | 0 | 0 | 0 | 0 |
| 2i | 0 | 0 | 0 | 0 | 0 | 0 | 0 | 0 | 93 | 0 | 1 | 0 | 0 | 0 | 0 | 2 | 0 | 0 | 0 | 2 | 0 | 7 | 0 | 0 | 0 | 1 | 0 | 1 | 1 |
| 2j | 0 | 0 | 0 | 2 | 0 | 0 | 0 | 1 | 0 | 64 | 0 | 0 | 0 | 1 | 0 | 2 | 1 | 0 | 0 | 0 | 0 | 9 | 0 | 0 | 0 | 1 | 0 | 0 | 1 | 1 |
| 2k | 1 | 0 | 0 | 0 | 0 | 0 | 0 | 0 | 0 | 0 | 90 | 0 | 0 | 0 | 0 | 1 | 0 | 0 | 0 | 0 | 0 | 4 | 0 | 0 | 2 | 1 | 1 | 1 | 0 |
| 2l | 40 | 2 | 6 | 34 | 1 | 4 | 2 | 52 | 4 | 7 | 20 | 75 | 13 | 30 | 60 | 5 | 49 | 10 | 1 | 8 | 68 | 22 | 99 | 7 | 16 | 34 | 5 | 19 | 40 | 8 |
| 2m | 0 | 0 | 0 | 1 | 1 | 0 | 0 | 4 | 0 | 0 | 0 | 99 | 0 | 1 | 0 | 2 | 1 | 0 | 0 | 4 | 0 | 9 | 0 | 5 | 0 | 0 | 1 | 0 |
| 2n | 1 | 0 | 2 | 16 | 0 | 0 | 0 | 17 | 0 | 0 | 1 | 3 | 0 | 99 | 0 | 3 | 3 | 0 | 0 | 6 | 0 | 14 | 0 | 0 | 6 | 1 | 0 | 18 | 1 |
| 2o | 1 | 0 | 0 | 0 | 0 | 0 | 1 | 3 | 0 | 0 | 1 | 0 | 0 | 0 | 99 | 0 | 4 | 1 | 0 | 0 | 3 | 2 | 12 | 0 | 0 | 5 | 1 | 0 | 2 | 1 |
| 2p | 1 | 0 | 1 | 0 | 0 | 0 | 0 | 1 | 0 | 0 | 0 | 0 | 0 | 0 | 3 | 31 | 2 | 1 | 0 | 0 | 3 | 0 | 7 | 0 | 0 | 4 | 0 | 0 | 1 | 0 |
| 2q | 5 | 0 | 1 | 0 | 0 | 0 | 0 | 3 | 0 | 0 | 0 | 0 | 0 | 0 | 0 | 1 | 0 | 99 | 4 | 0 | 0 | 0 | 0 | 0 | 0 | 2 | 0 | 0 | 1 | 0 |
| 2r | 1 | 0 | 8 | 2 | 0 | 0 | 0 | 13 | 0 | 0 | 0 | 0 | 0 | 0 | 0 | 2 | 99 | 0 | 0 | 1 | 0 | 0 | 1 | 2 | 0 | 0 | 0 | 0 | 1 | 1 |
| 2s | 2 | 2 | 7 | 6 | 0 | 0 | 0 | 78 | 1 | 1 | 2 | 0 | 1 | 1 | 5 | 4 | 2 | 8 | 92 | 0 | 7 | 5 | 27 | 0 | 4 | 0 | 1 | 0 | 1 | 2 |
| 2t | 1 | 0 | 1 | 0 | 0 | 0 | 0 | 3 | 3 | 0 | 0 | 0 | 0 | 2 | 0 | 15 | 3 | 0 | 97 | 4 | 0 | 15 | 0 | 0 | 0 | 0 | 0 | 0 | 1 | 0 |
| 2u | 1 | 0 | 1 | 0 | 0 | 1 | 0 | 3 | 0 | 0 | 0 | 1 | 0 | 0 | 0 | 1 | 0 | 2 | 4 | 0 | 99 | 4 | 12 | 0 | 2 | 0 | 0 | 0 | 1 | 1 |
| 2v | 0 | 1 | 2 | 0 | 0 | 0 | 3 | 0 | 0 | 0 | 0 | 11 | 0 | 0 | 0 | 2 | 1 | 0 | 0 | 5 | 99 | 10 | 2 | 2 | 1 | 0 | 0 | 1 |
| 2w | 18 | 0 | 9 | 10 | 0 | 0 | 0 | 69 | 2 | 1 | 7 | 0 | 9 | 2 | 4 | 0 | 14 | 13 | 1 | 20 | 10 | 6 | 99 | 1 | 7 | 29 | 1 | 3 | 32 | 3 |
| 2x | 23 | 0 | 8 | 11 | 4 | 52 | 2 | 43 | 21 | 36 | 97 | 0 | 67 | 5 | 10 | 28 | 27 | 22 | 18 | 29 | 93 | 99 | 88 | 99 | 79 | 53 | 56 | 1 | 21 | 53 |
| 2y | 34 | 8 | 18 | 36 | 7 | 21 | 8 | 71 | 18 | 41 | 49 | 11 | 33 | 32 | 58 | 23 | 68 | 63 | 16 | 26 | 75 | 96 | 99 | 45 | 99 | 41 | 30 | 18 | 46 | 61 |
| 2z | 0 | 1 | 19 | 0 | 1 | 1 | 2 | 49 | 3 | 8 | 0 | 0 | 0 | 8 | 38 | 1 | 11 | 6 | 1 | 2 | 19 | 33 | 2 | 64 | 99 | 3 | 0 | 1 | 8 |
| 2ww | 0 | 4 | 27 | 3 | 3 | 9 | 4 | 96 | 9 | 23 | 9 | 2 | 2 | 3 | 18 | 27 | 3 | 21 | 13 | 23 | 49 | 63 | 61 | 15 | 99 | 8 | 99 | 0 | 5 | 89 |
| 2xx | 0 | 0 | 0 | 0 | 0 | 0 | 0 | 0 | 0 | 0 | 0 | 0 | 2 | 0 | 0 | 1 | 0 | 0 | 0 | 0 | 1 | 4 | 0 | 2 | 0 | 0 | 88 | 0 | 0 |
| 2yy | 0 | 0 | 0 | 2 | 0 | 0 | 0 | 0 | 3 | 0 | 0 | 0 | 0 | 0 | 0 | 3 | 0 | 0 | 0 | 0 | 4 | 6 | 0 | 0 | 0 | 0 | 0 | 96 | 0 |
| 2zz | 0 | 2 | 0 | 0 | 0 | 0 | 1 | 0 | 0 | 0 | 0 | 0 | 1 | 1 | 0 | 0 | 0 | 0 | 0 | 0 | 3 | 9 | 0 | 0 | 0 | 0 | 0 | 1 | 76 |

|     | 1a | 1b | 1c | 1d | 1e | 1f | 1g | 1h | 1i | 1j | 1k | 1l | 1m | 1n | 1o |
|-----|----|----|----|----|----|----|----|----|----|----|----|----|----|----|----|
| 1a  | 91 | 0  | 1  | 0  | 0  | 0  | 0  | 2  | 1  | 0  | 0  | 0  | 2  | 0  | 5  |
| 1b  | 0  | 87 | 0  | 0  | 0  | 1  | 0  | 0  | 0  | 1  | 0  | 0  | 0  | 0  | 5  |
| 1c  | 0  | 1  | 99 | 0  | 0  | 1  | 0  | 6  | 1  | 0  | 0  | 0  | 0  | 0  | 1  |
| 1d  | 0  | 0  | 0  | 57 | 0  | 1  | 0  | 0  | 0  | 5  | 0  | 0  | 0  | 0  | 2  |
| 1e  | 0  | 0  | 0  | 0  | 90 | 0  | 0  | 0  | 0  | 0  | 0  | 0  | 0  | 0  | 2  |
| 1f  | 0  | 2  | 0  | 0  | 0  | 82 | 0  | 0  | 0  | 0  | 0  | 0  | 0  | 1  | 2  |
| 1g  | 0  | 4  | 3  | 3  | 0  | 0  | 98 | 9  | 13 | 2  | 0  | 4  | 6  | 3  | 0  |
| 1h  | 85 | 3  | 1  | 3  | 4  | 3  | 2  | 99 | 14 | 2  | 96 | 2  | 2  | 7  | 10 |
| 1i  | 2  | 0  | 3  | 1  | 0  | 1  | 1  | 5  | 92 | 1  | 3  | 0  | 1  | 4  | 6  |
| 1j  | 0  | 0  | 0  | 1  | 0  | 0  | 1  | 0  | 0  | 75 | 0  | 0  | 0  | 0  | 1  |
| 1k  | 0  | 1  | 1  | 7  | 1  | 0  | 0  | 0  | 0  | 2  | 82 | 0  | 0  | 0  | 1  |
| 1l  | 1  | 1  | 2  | 0  | 1  | 0  | 0  | 0  | 0  | 0  | 0  | 83 | 0  | 0  | 3  |
| 1m  | 0  | 0  | 2  | 0  | 6  | 0  | 0  | 0  | 1  | 0  | 0  | 0  | 99 | 7  | 3  |
| 1n  | 0  | 0  | 0  | 0  | 0  | 1  | 0  | 1  | 0  | 0  | 0  | 0  | 3  | 99 | 1  |
| 1o  | 4  | 2  | 4  | 3  | 0  | 1  | 1  | 6  | 4  | 0  | 7  | 1  | 0  | 7  | 33 |
| 1p  | 0  | 0  | 3  | 0  | 1  | 6  | 0  | 1  | 0  | 0  | 6  | 0  | 0  | 0  | 3  |
| 1q  | 0  | 0  | 0  | 0  | 0  | 1  | 0  | 1  | 0  | 0  | 1  | 0  | 4  | 1  | 1  |
| 1r  | 0  | 0  | 0  | 0  | 0  | 23 | 0  | 1  | 4  | 0  | 2  | 4  | 1  | 2  | 3  |
| 1s  | 1  | 1  | 3  | 2  | 0  | 0  | 1  | 7  | 0  | 0  | 0  | 0  | 7  | 0  | 2  |
| 1t  | 0  | 0  | 0  | 3  | 7  | 0  | 0  | 0  | 0  | 0  | 0  | 0  | 0  | 1  | 4  |
| 1u  | 0  | 0  | 0  | 4  | 0  | 0  | 3  | 36 | 0  | 0  | 2  | 82 | 6  | 2  | 67 |
| 1v  | 1  | 7  | 0  | 0  | 2  | 1  | 0  | 2  | 2  | 0  | 2  | 3  | 1  | 2  | 1  |
| 1w  | 18 | 35 | 34 | 52 | 39 | 6  | 9  | 78 | 59 | 23 | 43 | 69 | 24 | 53 | 38 |
| 1x  | 0  | 0  | 3  | 0  | 0  | 0  | 0  | 4  | 2  | 4  | 8  | 0  | 0  | 3  | 6  |
| 1y  | 55 | 87 | 89 | 74 | 85 | 39 | 59 | 87 | 90 | 61 | 80 | 75 | 70 | 81 | 98 |
| 1z  | 3  | 5  | 6  | 0  | 0  | 0  | 2  | 3  | 0  | 0  | 2  | 0  | 0  | 0  | 2  |
| 1ww | 0  | 0  | 2  | 0  | 0  | 0  | 0  | 0  | 0  | 0  | 0  | 0  | 0  | 0  | 0  |
| 1xx | 0  | 0  | 2  | 0  | 0  | 0  | 1  | 0  | 0  | 0  | 0  | 0  | 0  | 0  | 4  |
| 1yy | 0  | 0  | 0  | 0  | 4  | 0  | 0  | 0  | 0  | 0  | 0  | 0  | 1  | 0  | 2  |
| 1zz | 23 | 98 | 87 | 21 | 74 | 13 | 45 | 79 | 85 | 89 | 47 | 16 | 33 | 44 | 27 |
| 2a  | 0  | 0  | 0  | 0  | 0  | 0  | 0  | 1  | 0  | 0  | 0  | 0  | 0  | 0  | 2  |
| 2b  | 0  | 0  | 0  | 0  | 0  | 0  | 0  | 0  | 0  | 0  | 0  | 0  | 0  | 0  | 4  |
| 2c  | 0  | 0  | 0  | 0  | 0  | 0  | 3  | 0  | 0  | 0  | 0  | 0  | 0  | 0  | 0  |
| 2d  | 0  | 0  | 0  | 0  | 0  | 0  | 0  | 0  | 0  | 0  | 0  | 0  | 0  | 0  | 0  |
| 2e  | 0  | 0  | 0  | 0  | 0  | 0  | 0  | 1  | 0  | 0  | 0  | 0  | 0  | 0  | 0  |
| 2f  | 0  | 0  | 3  | 0  | 1  | 0  | 0  | 2  | 0  | 0  | 0  | 0  | 5  | 0  | 1  |
| 2g  | 0  | 1  | 0  | 0  | 0  | 0  | 0  | 0  | 0  | 0  | 0  | 0  | 0  | 1  | 0  |
| 2h  | 0  | 0  | 1  | 0  | 0  | 0  | 0  | 0  | 0  | 0  | 0  | 0  | 0  | 0  | 0  |
| 2i  | 0  | 0  | 0  | 0  | 0  | 0  | 0  | 0  | 0  | 0  | 1  | 0  | 0  | 0  | 0  |
| 2j  | 0  | 0  | 0  | 2  | 0  | 0  | 0  | 0  | 0  | 0  | 0  | 0  | 0  | 0  | 1  |
| 2k  | 1  | 0  | 0  | 0  | 0  | 0  | 0  | 0  | 0  | 0  | 0  | 0  | 0  | 1  | 0  |
| 2l  | 3  | 2  | 3  | 2  | 1  | 1  | 0  | 6  | 4  | 1  | 20 | 27 | 13 | 5  | 60 |
| 2m  | 0  | 0  | 0  | 1  | 1  | 0  | 0  | 4  | 0  | 0  | 0  | 0  | 0  | 0  | 1  |
| 2n  | 1  | 0  | 1  | 0  | 0  | 0  | 0  | 0  | 0  | 1  | 3  | 0  | 0  | 0  | 0  |
| 2o  | 1  | 0  | 0  | 0  | 0  | 0  | 1  | 3  | 0  | 0  | 1  | 0  | 0  | 0  | 0  |
| 2p  | 1  | 0  | 1  | 0  | 0  | 0  | 0  | 1  | 0  | 0  | 0  | 0  | 0  | 0  | 3  |
| 2q  | 5  | 0  | 1  | 0  | 0  | 0  | 0  | 3  | 0  | 0  | 0  | 0  | 0  | 0  | 0  |

FIG. 13

|    | 1p | 1q | 1r | 1s | 1t | 1u | 1v | 1w | 1x | 1y | 1z | 1ww | 1xx | 1yy | 1zz | 2a |
|----|----|----|----|----|----|----|----|----|----|----|----|-----|-----|-----|-----|----|
| 1a | 0  | 0  | 4  | 0  | 0  | 0  | 1  | 4  | 0  | 0  | 0  | 0   | 0   | 0   | 0   | 0  |
| 1b | 0  | 0  | 4  | 0  | 0  | 1  | 0  | 0  | 0  | 0  | 0  | 0   | 0   | 1   | 0   | 0  |
| 1c | 0  | 2  | 1  | 1  | 0  | 1  | 1  | 46 | 0  | 3  | 0  | 0   | 0   | 0   | 0   | 0  |
| 1d | 0  | 0  | 4  | 0  | 0  | 0  | 0  | 0  | 0  | 0  | 0  | 0   | 0   | 1   | 0   | 0  |
| 1e | 0  | 0  | 3  | 0  | 0  | 0  | 0  | 3  | 0  | 1  | 0  | 0   | 0   | 0   | 0   | 0  |
| 1f | 2  | 0  | 4  | 0  | 0  | 0  | 0  | 5  | 0  | 3  | 1  | 0   | 0   | 3   | 0   | 0  |
| 1g | 2  | 5  | 7  | 63 | 21 | 60 | 1  | 35 | 60 | 30 | 0  | 12  | 0   | 4   | 8   | 0  |
| 1h | 10 | 34 | 9  | 19 | 8  | 38 | 4  | 94 | 14 | 96 | 93 | 32  | 12  | 35  | 55  | 85 |
| 1i | 0  | 0  | 2  | 2  | 0  | 4  | 3  | 72 | 0  | 8  | 1  | 0   | 0   | 4   | 1   | 2  |
| 1j | 0  | 0  | 2  | 0  | 0  | 1  | 0  | 7  | 0  | 6  | 0  | 0   | 0   | 1   | 0   | 0  |
| 1k | 0  | 0  | 3  | 0  | 1  | 0  | 0  | 66 | 0  | 1  | 0  | 0   | 0   | 1   | 0   | 0  |
| 1l | 0  | 0  | 2  | 0  | 0  | 1  | 5  | 5  | 0  | 0  | 1  | 0   | 0   | 0   | 0   | 0  |
| 1m | 0  | 1  | 6  | 1  | 0  | 4  | 0  | 12 | 0  | 3  | 0  | 0   | 0   | 0   | 0   | 0  |
| 1n | 0  | 1  | 2  | 0  | 0  | 0  | 0  | 8  | 0  | 1  | 0  | 1   | 0   | 1   | 0   | 0  |
| 1o | 4  | 2  | 4  | 4  | 1  | 15 | 2  | 89 | 2  | 10 | 1  | 2   | 0   | 6   | 1   | 4  |
| 1p | 70 | 1  | 0  | 0  | 0  | 0  | 2  | 38 | 0  | 0  | 5  | 4   | 0   | 7   | 0   | 0  |
| 1q | 2  | 99 | 0  | 0  | 0  | 0  | 2  | 2  | 0  | 3  | 1  | 4   | 0   | 0   | 0   | 0  |
| 1r | 0  | 5  | 99 | 0  | 0  | 2  | 5  | 21 | 0  | 2  | 0  | 0   | 0   | 3   | 0   | 0  |
| 1s | 0  | 2  | 1  | 95 | 0  | 2  | 2  | 56 | 0  | 3  | 0  | 0   | 0   | 1   | 0   | 1  |
| 1t | 0  | 1  | 0  | 0  | 99 | 12 | 5  | 16 | 1  | 0  | 5  | 0   | 0   | 0   | 0   | 0  |
| 1u | 2  | 14 | 8  | 3  | 1  | 99 | 29 | 99 | 14 | 14 | 0  | 3   | 0   | 0   | 5   | 0  |
| 1v | 0  | 5  | 3  | 1  | 0  | 4  | 99 | 0  | 0  | 4  | 1  | 0   | 0   | 0   | 0   | 1  |
| 1w | 20 | 26 | 39 | 81 | 59 | 40 | 35 | 99 | 29 | 59 | 72 | 8   | 22  | 28  | 50  | 18 |
| 1x | 12 | 4  | 5  | 9  | 16 | 75 | 76 | 97 | 91 | 46 | 51 | 34  | 0   | 0   | 18  | 0  |
| 1y | 60 | 81 | 91 | 97 | 66 | 90 | 96 | 99 | 60 | 99 | 51 | 38  | 44  | 84  | 88  | 55 |
| 1z | 0  | 1  | 1  | 0  | 0  | 1  | 0  | 45 | 1  | 1  | 87 | 0   | 0   | 0   | 0   | 3  |
| 1ww| 0  | 0  | 1  | 0  | 0  | 0  | 0  | 0  | 0  | 0  | 0  | 1   | 19  | 0   | 0   | 0  |
| 1xx| 0  | 0  | 0  | 0  | 0  | 0  | 1  | 0  | 0  | 1  | 0  | 0   | 81  | 0   | 0   | 0  |
| 1yy| 0  | 3  | 1  | 7  | 0  | 21 | 3  | 23 | 23 | 2  | 3  | 1   | 0   | 31  | 0   | 0  |
| 1zz| 43 | 72 | 98 | 90 | 14 | 51 | 63 | 97 | 17 | 49 | 86 | 27  | 6   | 24  | 64  | 23 |
| 2a | 0  | 5  | 0  | 0  | 0  | 0  | 0  | 5  | 0  | 3  | 0  | 0   | 0   | 0   | 0   | 99 |
| 2b | 0  | 0  | 0  | 0  | 0  | 0  | 0  | 38 | 20 | 1  | 0  | 0   | 0   | 0   | 0   | 0  |
| 2c | 0  | 0  | 0  | 0  | 0  | 0  | 0  | 15 | 0  | 0  | 0  | 0   | 0   | 0   | 0   | 0  |
| 2d | 0  | 2  | 1  | 0  | 0  | 0  | 0  | 8  | 0  | 0  | 0  | 0   | 0   | 0   | 0   | 0  |
| 2e | 0  | 2  | 0  | 0  | 0  | 1  | 0  | 12 | 0  | 0  | 0  | 0   | 0   | 0   | 0   | 0  |
| 2f | 0  | 0  | 0  | 0  | 0  | 0  | 0  | 17 | 1  | 0  | 0  | 0   | 0   | 0   | 0   | 0  |
| 2g | 0  | 0  | 2  | 0  | 0  | 9  | 2  | 23 | 1  | 0  | 0  | 1   | 0   | 2   | 0   | 0  |
| 2h | 0  | 3  | 1  | 0  | 0  | 0  | 0  | 6  | 0  | 0  | 0  | 0   | 0   | 0   | 0   | 0  |
| 2i | 0  | 2  | 0  | 0  | 0  | 2  | 0  | 7  | 0  | 0  | 0  | 1   | 0   | 1   | 1   | 0  |
| 2j | 0  | 2  | 1  | 0  | 0  | 0  | 0  | 9  | 0  | 0  | 1  | 0   | 0   | 1   | 1   | 0  |
| 2k | 0  | 1  | 0  | 0  | 0  | 0  | 0  | 4  | 0  | 0  | 2  | 1   | 1   | 1   | 0   | 1  |
| 2l | 5  | 8  | 10 | 1  | 2  | 68 | 21 | 99 | 7  | 16 | 34 | 5   | 19  | 6   | 8   | 40 |
| 2m | 0  | 2  | 1  | 0  | 0  | 4  | 0  | 9  | 0  | 0  | 5  | 0   | 0   | 1   | 0   | 0  |
| 2n | 0  | 3  | 3  | 0  | 0  | 6  | 0  | 14 | 0  | 0  | 6  | 1   | 0   | 0   | 1   | 0  |
| 2o | 0  | 4  | 1  | 0  | 0  | 3  | 0  | 12 | 0  | 0  | 5  | 1   | 0   | 2   | 1   | 1  |
| 2p | 0  | 0  | 1  | 0  | 0  | 3  | 0  | 7  | 0  | 0  | 4  | 0   | 0   | 1   | 0   | 1  |
| 2q | 0  | 0  | 0  | 0  | 0  | 0  | 0  | 0  | 0  | 0  | 2  | 0   | 1   | 0   | 0   | 5  |

FIG. 13
(Continued)

|     | 2b | 2c | 2d | 2e | 2f | 2g | 2h | 2i | 2j | 2k | 2l | 2m | 2n | 2o | 2p | 2q |
|-----|----|----|----|----|----|----|----|----|----|----|----|----|----|----|----|----|
| 1a  | 1  | 0  | 0  | 0  | 0  | 0  | 2  | 1  | 0  | 0  | 0  | 2  | 0  | 5  | 0  | 0  |
| 1b  | 0  | 3  | 0  | 0  | 1  | 0  | 0  | 0  | 1  | 0  | 0  | 0  | 0  | 5  | 0  | 0  |
| 1c  | 0  | 1  | 0  | 0  | 1  | 0  | 1  | 0  | 0  | 0  | 0  | 0  | 0  | 1  | 0  | 2  |
| 1d  | 0  | 0  | 0  | 1  | 0  | 0  | 0  | 0  | 5  | 0  | 0  | 0  | 0  | 1  | 0  | 0  |
| 1e  | 0  | 0  | 0  | 0  | 1  | 0  | 0  | 0  | 0  | 0  | 0  | 0  | 0  | 2  | 0  | 0  |
| 1f  | 2  | 0  | 3  | 0  | 0  | 3  | 0  | 0  | 0  | 0  | 0  | 0  | 1  | 2  | 2  | 0  |
| 1g  | 0  | 3  | 1  | 4  | 10 | 0  | 9  | 13 | 77 | 1  | 0  | 0  | 13 | 7  | 57 | 2  |
| 1h  | 3  | 18 | 1  | 4  | 7  | 2  | 6  | 14 | 36 | 96 | 2  | 40 | 2  | 10 | 10 | 34 |
| 1i  | 0  | 3  | 1  | 0  | 1  | 1  | 3  | 6  | 2  | 0  | 0  | 1  | 1  | 7  | 0  | 0  |
| 1j  | 0  | 0  | 1  | 0  | 0  | 1  | 0  | 0  | 0  | 0  | 0  | 0  | 0  | 1  | 0  | 0  |
| 1k  | 1  | 1  | 7  | 1  | 1  | 0  | 0  | 0  | 1  | 3  | 0  | 0  | 0  | 1  | 0  | 0  |
| 1l  | 1  | 2  | 0  | 1  | 0  | 0  | 0  | 0  | 0  | 0  | 0  | 0  | 0  | 3  | 0  | 0  |
| 1m  | 0  | 0  | 0  | 0  | 1  | 0  | 0  | 0  | 0  | 0  | 0  | 0  | 7  | 3  | 0  | 1  |
| 1n  | 0  | 0  | 0  | 0  | 1  | 0  | 1  | 0  | 0  | 0  | 0  | 0  | 3  | 5  | 0  | 0  |
| 1o  | 2  | 4  | 2  | 0  | 3  | 1  | 4  | 6  | 0  | 6  | 1  | 1  | 3  | 1  | 4  | 5  |
| 1p  | 0  | 0  | 0  | 1  | 6  | 0  | 1  | 0  | 0  | 6  | 0  | 4  | 0  | 3  | 3  | 1  |
| 1q  | 0  | 0  | 0  | 0  | 1  | 0  | 1  | 0  | 0  | 1  | 0  | 6  | 1  | 1  | 1  | 3  |
| 1r  | 3  | 0  | 0  | 0  | 1  | 2  | 0  | 4  | 0  | 2  | 4  | 1  | 2  | 3  | 0  | 5  |
| 1s  | 1  | 3  | 2  | 0  | 0  | 1  | 7  | 0  | 0  | 1  | 0  | 0  | 0  | 2  | 0  | 0  |
| 1t  | 0  | 0  | 3  | 7  | 1  | 0  | 0  | 0  | 0  | 0  | 0  | 2  | 1  | 4  | 0  | 1  |
| 1u  | 0  | 0  | 0  | 0  | 4  | 0  | 6  | 33 | 4  | 2  | 3  | 6  | 27 | 67 | 2  | 87 |
| 1v  | 7  | 0  | 0  | 0  | 1  | 0  | 2  | 2  | 0  | 2  | 3  | 3  | 1  | 2  | 0  | 5  |
| 1w  | 35 | 34 | 52 | 39 | 6  | 9  | 78 | 59 | 23 | 43 | 69 | 24 | 53 | 38 | 20 | 26 |
| 1x  | 0  | 3  | 0  | 2  | 0  | 0  | 0  | 2  | 3  | 8  | 27 | 2  | 32 | 6  | 15 | 0  |
| 1y  | 87 | 89 | 74 | 85 | 39 | 59 | 87 | 90 | 61 | 80 | 75 | 70 | 81 | 98 | 60 | 81 |
| 1z  | 5  | 6  | 0  | 0  | 0  | 2  | 3  | 0  | 0  | 2  | 0  | 0  | 0  | 2  | 0  | 1  |
| 1ww | 0  | 2  | 0  | 0  | 0  | 0  | 0  | 0  | 0  | 0  | 0  | 0  | 0  | 3  | 0  | 0  |
| 1xx | 0  | 2  | 0  | 0  | 0  | 1  | 0  | 0  | 0  | 0  | 0  | 0  | 0  | 4  | 0  | 0  |
| 1yy | 0  | 0  | 0  | 0  | 0  | 0  | 1  | 0  | 1  | 0  | 0  | 0  | 0  | 2  | 0  | 0  |
| 1zz | 71 | 87 | 21 | 74 | 13 | 45 | 79 | 85 | 89 | 47 | 16 | 33 | 44 | 27 | 43 | 72 |
| 2a  | 0  | 0  | 0  | 0  | 0  | 0  | 1  | 0  | 0  | 0  | 0  | 0  | 0  | 2  | 0  | 1  |
| 2b  | 93 | 0  | 0  | 0  | 0  | 0  | 0  | 0  | 0  | 0  | 0  | 0  | 0  | 5  | 0  | 0  |
| 2c  | 0  | 99 | 0  | 0  | 0  | 3  | 0  | 0  | 0  | 0  | 0  | 0  | 0  | 0  | 0  | 0  |
| 2d  | 0  | 0  | 84 | 0  | 0  | 0  | 0  | 0  | 0  | 0  | 0  | 0  | 0  | 0  | 0  | 2  |
| 2e  | 0  | 0  | 0  | 93 | 0  | 0  | 1  | 0  | 0  | 0  | 0  | 1  | 0  | 0  | 0  | 2  |
| 2f  | 0  | 3  | 0  | 0  | 92 | 0  | 0  | 0  | 0  | 0  | 0  | 5  | 0  | 1  | 0  | 0  |
| 2g  | 0  | 0  | 1  | 0  | 0  | 95 | 0  | 0  | 0  | 0  | 0  | 0  | 1  | 3  | 0  | 0  |
| 2h  | 0  | 1  | 0  | 0  | 0  | 0  | 97 | 0  | 0  | 0  | 0  | 0  | 0  | 0  | 0  | 3  |
| 2i  | 0  | 0  | 0  | 0  | 0  | 0  | 0  | 91 | 0  | 0  | 0  | 0  | 0  | 0  | 0  | 2  |
| 2j  | 0  | 0  | 2  | 0  | 0  | 0  | 1  | 0  | 64 | 0  | 0  | 0  | 0  | 1  | 0  | 2  |
| 2k  | 0  | 0  | 0  | 0  | 0  | 0  | 0  | 0  | 0  | 90 | 0  | 0  | 1  | 0  | 0  | 1  |
| 2l  | 2  | 6  | 3  | 1  | 1  | 2  | 0  | 4  | 1  | 20 | 75 | 13 | 22 | 1  | 5  | 49 |
| 2m  | 0  | 0  | 1  | 1  | 0  | 0  | 4  | 0  | 0  | 0  | 0  | 97 | 0  | 0  | 0  | 2  |
| 2n  | 0  | 1  | 8  | 0  | 0  | 0  | 0  | 0  | 0  | 1  | 3  | 0  | 99 | 0  | 0  | 3  |
| 2o  | 0  | 0  | 0  | 0  | 0  | 1  | 3  | 0  | 0  | 1  | 0  | 0  | 0  | 99 | 0  | 0  |
| 2p  | 0  | 1  | 0  | 0  | 0  | 0  | 1  | 0  | 0  | 0  | 0  | 0  | 0  | 0  | 31 | 0  |
| 2q  | 0  | 1  | 0  | 0  | 0  | 0  | 3  | 0  | 0  | 0  | 0  | 0  | 0  | 1  | 0  | 99 |

FIG. 13
(Continued)

|     | 2r | 2s | 2t | 2u | 2v | 2w | 2x | 2y | 2z | 2ww | 2xx | 2yy | 2zz | 3a | 3b | 3c |
|-----|----|----|----|----|----|----|----|----|----|-----|-----|-----|-----|-----|----|----|
| 1a  | 4  | 0  | 0  | 0  | 1  | 4  | 0  | 0  | 0  | 0   | 0   | 1   | 0   | 0  | 0  | 1  |
| 1b  | 4  | 0  | 0  | 1  | 0  | 0  | 0  | 0  | 0  | 0   | 0   | 1   | 0   | 6  | 0  | 0  |
| 1c  | 6  | 1  | 0  | 0  | 4  | 1  | 0  | 1  | 0  | 0   | 0   | 0   | 0   | 0  | 2  | 0  |
| 1d  | 4  | 0  | 0  | 0  | 0  | 0  | 0  | 0  | 0  | 0   | 0   | 1   | 0   | 0  | 0  | 0  |
| 1e  | 3  | 0  | 0  | 0  | 0  | 3  | 0  | 1  | 0  | 0   | 0   | 1   | 0   | 0  | 0  | 0  |
| 1f  | 4  | 0  | 0  | 0  | 0  | 5  | 0  | 3  | 1  | 0   | 0   | 3   | 0   | 0  | 2  | 0  |
| 1g  | 7  | 6  | 3  | 17 | 70 | 35 | 60 | 30 | 2  | 0   | 0   | 33  | 4   | 0  | 65 | 0  |
| 1h  | 23 | 19 | 8  | 14 | 44 | 94 | 14 | 96 | 93 | 32  | 2   | 35  | 55  | 35 | 3  | 18 |
| 1i  | 5  | 2  | 0  | 4  | 5  | 3  | 0  | 8  | 1  | 1   | 0   | 4   | 1   | 2  | 0  | 3  |
| 1j  | 2  | 0  | 0  | 1  | 0  | 7  | 0  | 6  | 0  | 0   | 0   | 1   | 0   | 0  | 0  | 0  |
| 1k  | 3  | 0  | 1  | 0  | 0  | 1  | 0  | 0  | 0  | 0   | 0   | 1   | 0   | 0  | 1  | 1  |
| 1l  | 2  | 0  | 0  | 1  | 5  | 5  | 0  | 0  | 1  | 0   | 0   | 2   | 0   | 0  | 0  | 2  |
| 1m  | 6  | 1  | 0  | 4  | 3  | 1  | 0  | 0  | 0  | 0   | 0   | 1   | 0   | 0  | 59 | 0  |
| 1n  | 2  | 0  | 0  | 0  | 0  | 0  | 0  | 0  | 0  | 1   | 0   | 1   | 0   | 0  | 6  | 0  |
| 1o  | 2  | 2  | 1  | 0  | 1  | 6  | 2  | 10 | 1  | 2   | 0   | 6   | 1   | 4  | 1  | 4  |
| 1p  | 1  | 0  | 0  | 0  | 5  | 2  | 0  | 0  | 5  | 4   | 0   | 7   | 0   | 43 | 0  | 0  |
| 1q  | 5  | 0  | 0  | 0  | 2  | 2  | 0  | 3  | 1  | 4   | 0   | 0   | 0   | 0  | 3  | 0  |
| 1r  | 5  | 0  | 0  | 2  | 5  | 0  | 3  | 0  | 0  | 0   | 0   | 3   | 0   | 0  | 3  | 26 |
| 1s  | 2  | 1  | 0  | 2  | 4  | 2  | 0  | 3  | 1  | 0   | 0   | 1   | 0   | 1  | 1  | 3  |
| 1t  | 1  | 0  | 0  | 0  | 4  | 5  | 1  | 0  | 5  | 0   | 0   | 0   | 0   | 0  | 0  | 0  |
| 1u  | 3  | 3  | 1  | 2  | 29 | 35 | 14 | 14 | 22 | 0   | 0   | 2   | 0   | 0  | 26 | 0  |
| 1v  | 3  | 1  | 0  | 0  | 0  | 0  | 0  | 2  | 1  | 0   | 0   | 0   | 0   | 0  | 5  | 0  |
| 1w  | 39 | 81 | 59 | 40 | 61 | 85 | 29 | 49 | 72 | 8   | 22  | 28  | 50  | 18 | 35 | 34 |
| 1x  | 5  | 9  | 16 | 75 | 89 | 76 | 91 | 46 | 51 | 34  | 0   | 3   | 0   | 0  | 1  | 0  |
| 1y  | 91 | 97 | 66 | 90 | 96 | 99 | 60 | 82 | 88 | 36  | 44  | 84  | 88  | 55 | 87 | 89 |
| 1z  | 1  | 0  | 0  | 1  | 1  | 0  | 1  | 1  | 24 | 0   | 0   | 0   | 0   | 3  | 5  | 6  |
| 1ww | 1  | 0  | 0  | 0  | 0  | 0  | 0  | 0  | 0  | 1   | 1   | 0   | 0   | 0  | 0  | 2  |
| 1xx | 1  | 0  | 0  | 0  | 1  | 0  | 0  | 1  | 1  | 0   | 0   | 0   | 0   | 0  | 0  | 2  |
| 1yy | 0  | 1  | 0  | 0  | 4  | 3  | 23 | 2  | 3  | 1   | 0   | 0   | 0   | 2  | 0  | 0  |
| 1zz | 98 | 90 | 14 | 51 | 63 | 97 | 17 | 49 | 86 | 27  | 6   | 9   | 24  | 23 | 98 | 71 |
| 2a  | 0  | 0  | 0  | 0  | 0  | 5  | 0  | 3  | 0  | 0   | 0   | 0   | 0   | 0  | 0  | 0  |
| 2b  | 0  | 0  | 0  | 0  | 0  | 0  | 20 | 1  | 0  | 0   | 0   | 0   | 0   | 0  | 0  | 0  |
| 2c  | 0  | 0  | 0  | 0  | 0  | 0  | 0  | 0  | 0  | 0   | 0   | 0   | 0   | 0  | 0  | 0  |
| 2d  | 1  | 0  | 0  | 0  | 0  | 1  | 0  | 0  | 0  | 0   | 0   | 0   | 0   | 0  | 0  | 0  |
| 2e  | 0  | 0  | 0  | 1  | 0  | 0  | 1  | 0  | 0  | 0   | 0   | 0   | 0   | 0  | 0  | 0  |
| 2f  | 0  | 0  | 0  | 0  | 0  | 4  | 2  | 0  | 0  | 0   | 0   | 0   | 0   | 0  | 0  | 3  |
| 2g  | 2  | 0  | 0  | 0  | 2  | 5  | 1  | 0  | 0  | 1   | 0   | 2   | 0   | 0  | 3  | 0  |
| 2h  | 1  | 0  | 0  | 0  | 0  | 6  | 0  | 0  | 0  | 0   | 0   | 0   | 0   | 0  | 0  | 1  |
| 2i  | 0  | 0  | 0  | 2  | 0  | 7  | 0  | 0  | 0  | 1   | 0   | 1   | 1   | 0  | 0  | 0  |
| 2j  | 1  | 0  | 0  | 0  | 0  | 1  | 0  | 0  | 1  | 0   | 0   | 1   | 1   | 0  | 0  | 0  |
| 2k  | 0  | 0  | 0  | 0  | 0  | 4  | 0  | 0  | 2  | 1   | 1   | 1   | 0   | 1  | 0  | 0  |
| 2l  | 8  | 1  | 8  | 1  | 22 | 99 | 7  | 16 | 34 | 5   | 1   | 40  | 8   | 40 | 1  | 3  |
| 2m  | 1  | 0  | 0  | 4  | 0  | 0  | 0  | 0  | 5  | 0   | 0   | 1   | 0   | 0  | 0  | 0  |
| 2n  | 3  | 0  | 0  | 6  | 0  | 0  | 0  | 0  | 6  | 1   | 0   | 0   | 0   | 0  | 0  | 0  |
| 2o  | 1  | 0  | 0  | 3  | 2  | 0  | 0  | 0  | 5  | 1   | 0   | 2   | 1   | 1  | 0  | 0  |
| 2p  | 0  | 0  | 0  | 3  | 0  | 7  | 0  | 0  | 4  | 0   | 0   | 1   | 0   | 1  | 0  | 1  |
| 2q  | 0  | 0  | 0  | 0  | 0  | 0  | 0  | 0  | 2  | 0   | 0   | 1   | 0   | 5  | 0  | 1  |

FIG. 13
(Continued)

|     | 3d | 3e | 3f | 3g | 3h | 3i | 3j | 3k | 3l | 3m | 3n | 3o | 3p | 3q | 3r | 3s |
|-----|----|----|----|----|----|----|----|----|----|----|----|----|----|----|----|----|
| 1a  | 0  | 0  | 0  | 0  | 2  | 1  | 0  | 0  | 0  | 2  | 0  | 5  | 0  | 0  | 4  | 0  |
| 1b  | 0  | 0  | 1  | 0  | 0  | 0  | 1  | 0  | 0  | 0  | 0  | 5  | 0  | 0  | 4  | 0  |
| 1c  | 0  | 6  | 0  | 0  | 6  | 1  | 2  | 0  | 0  | 0  | 0  | 4  | 0  | 1  | 2  | 1  |
| 1d  | 0  | 0  | 1  | 0  | 0  | 0  | 5  | 0  | 0  | 0  | 0  | 2  | 0  | 0  | 4  | 0  |
| 1e  | 0  | 0  | 0  | 0  | 0  | 0  | 0  | 0  | 0  | 0  | 0  | 2  | 0  | 0  | 3  | 0  |
| 1f  | 3  | 0  | 0  | 0  | 5  | 0  | 0  | 0  | 0  | 0  | 1  | 2  | 2  | 0  | 4  | 0  |
| 1g  | 3  | 11 | 4  | 14 | 0  | 13 | 14 | 0  | 3  | 0  | 17 | 7  | 57 | 3  | 2  | 63 |
| 1h  | 3  | 1  | 7  | 2  | 3  | 6  | 36 | 89 | 2  | 40 | 7  | 2  | 10 | 34 | 23 | 19 |
| 1i  | 1  | 0  | 1  | 1  | 5  | 3  | 0  | 3  | 0  | 3  | 3  | 1  | 0  | 6  | 0  | 2  |
| 1j  | 1  | 0  | 0  | 1  | 0  | 0  | 3  | 0  | 0  | 0  | 0  | 1  | 0  | 0  | 2  | 0  |
| 1k  | 7  | 1  | 1  | 12 | 0  | 0  | 1  | 1  | 0  | 0  | 0  | 1  | 0  | 0  | 3  | 0  |
| 1l  | 0  | 1  | 0  | 0  | 0  | 0  | 0  | 0  | 5  | 0  | 0  | 3  | 0  | 0  | 2  | 0  |
| 1m  | 0  | 4  | 0  | 7  | 0  | 0  | 0  | 0  | 0  | 0  | 7  | 3  | 0  | 1  | 4  | 0  |
| 1n  | 0  | 0  | 1  | 0  | 1  | 0  | 0  | 0  | 0  | 3  | 4  | 5  | 0  | 1  | 0  | 0  |
| 1o  | 3  | 0  | 3  | 0  | 2  | 4  | 6  | 4  | 1  | 5  | 7  | 3  | 4  | 15 | 5  | 4  |
| 1p  | 0  | 1  | 6  | 0  | 1  | 0  | 0  | 6  | 0  | 4  | 0  | 3  | 5  | 3  | 1  | 0  |
| 1q  | 0  | 0  | 1  | 0  | 1  | 0  | 0  | 1  | 0  | 6  | 1  | 1  | 2  | 1  | 3  | 0  |
| 1r  | 0  | 0  | 0  | 1  | 1  | 0  | 0  | 2  | 4  | 1  | 2  | 3  | 0  | 5  | 27 | 0  |
| 1s  | 2  | 0  | 0  | 0  | 7  | 0  | 0  | 7  | 0  | 0  | 0  | 2  | 0  | 24 | 22 | 2  |
| 1t  | 3  | 7  | 1  | 0  | 0  | 0  | 0  | 0  | 2  | 1  | 4  | 0  | 0  | 1  | 1  | 0  |
| 1u  | 0  | 0  | 4  | 3  | 0  | 33 | 4  | 0  | 82 | 3  | 27 | 18 | 2  | 59 | 2  | 0  |
| 1v  | 8  | 0  | 0  | 0  | 2  | 2  | 0  | 2  | 3  | 3  | 8  | 1  | 0  | 1  | 3  | 1  |
| 1w  | 52 | 39 | 6  | 9  | 78 | 59 | 23 | 43 | 69 | 24 | 53 | 38 | 20 | 26 | 39 | 81 |
| 1x  | 0  | 2  | 21 | 0  | 0  | 0  | 19 | 0  | 27 | 2  | 32 | 6  | 15 | 4  | 0  | 7  |
| 1y  | 74 | 85 | 39 | 59 | 87 | 90 | 61 | 80 | 75 | 70 | 61 | 98 | 60 | 81 | 91 | 97 |
| 1z  | 0  | 0  | 0  | 2  | 3  | 0  | 0  | 2  | 0  | 0  | 0  | 2  | 0  | 1  | 1  | 0  |
| 1ww | 0  | 0  | 0  | 0  | 0  | 0  | 0  | 0  | 0  | 0  | 0  | 3  | 0  | 0  | 0  | 0  |
| 1xx | 0  | 0  | 0  | 1  | 0  | 0  | 0  | 0  | 0  | 0  | 0  | 4  | 0  | 0  | 10 | 0  |
| 1yy | 0  | 0  | 0  | 0  | 0  | 1  | 1  | 0  | 0  | 0  | 0  | 0  | 0  | 3  | 0  | 7  |
| 1zz | 21 | 74 | 13 | 45 | 79 | 85 | 89 | 47 | 16 | 33 | 44 | 27 | 43 | 72 | 98 | 90 |
| 2a  | 0  | 0  | 0  | 0  | 0  | 1  | 0  | 0  | 0  | 0  | 0  | 2  | 0  | 5  | 0  | 0  |
| 2b  | 0  | 0  | 0  | 0  | 0  | 0  | 0  | 0  | 0  | 0  | 0  | 39 | 5  | 0  | 4  | 0  |
| 2c  | 0  | 0  | 0  | 1  | 0  | 0  | 0  | 0  | 0  | 0  | 0  | 0  | 0  | 15 | 0  | 0  |
| 2d  | 0  | 0  | 0  | 0  | 0  | 0  | 0  | 0  | 0  | 0  | 0  | 0  | 0  | 2  | 1  | 0  |
| 2e  | 0  | 0  | 0  | 0  | 0  | 0  | 0  | 0  | 0  | 0  | 0  | 0  | 0  | 2  | 0  | 0  |
| 2f  | 0  | 0  | 0  | 0  | 0  | 0  | 0  | 0  | 0  | 5  | 15 | 1  | 0  | 9  | 0  | 0  |
| 2g  | 1  | 23 | 0  | 7  | 3  | 0  | 0  | 0  | 0  | 0  | 1  | 3  | 0  | 6  | 0  | 0  |
| 2h  | 0  | 0  | 0  | 0  | 0  | 0  | 0  | 0  | 0  | 0  | 0  | 0  | 0  | 3  | 0  | 0  |
| 2i  | 0  | 0  | 0  | 0  | 0  | 0  | 0  | 0  | 0  | 0  | 0  | 0  | 0  | 2  | 0  | 0  |
| 2j  | 2  | 0  | 0  | 0  | 1  | 0  | 0  | 0  | 0  | 0  | 0  | 1  | 0  | 2  | 1  | 0  |
| 2k  | 0  | 0  | 0  | 0  | 0  | 0  | 0  | 0  | 0  | 0  | 0  | 0  | 0  | 1  | 0  | 0  |
| 2l  | 34 | 1  | 2  | 1  | 5  | 0  | 6  | 16 | 25 | 13 | 27 | 27 | 5  | 31 | 10 | 1  |
| 2m  | 1  | 1  | 0  | 0  | 4  | 0  | 0  | 0  | 0  | 0  | 0  | 0  | 0  | 2  | 1  | 0  |
| 2n  | 1  | 0  | 0  | 0  | 0  | 0  | 0  | 1  | 3  | 0  | 18 | 0  | 0  | 0  | 3  | 0  |
| 2o  | 0  | 0  | 0  | 1  | 3  | 0  | 0  | 1  | 0  | 0  | 0  | 0  | 0  | 0  | 0  | 0  |
| 2p  | 0  | 0  | 0  | 0  | 1  | 0  | 0  | 0  | 0  | 0  | 0  | 3  | 0  | 2  | 0  | 0  |
| 2q  | 0  | 0  | 0  | 0  | 3  | 0  | 0  | 0  | 0  | 0  | 0  | 1  | 0  | 0  | 4  | 0  |

FIG. 13
(Continued)

|  | 3t | 3u | 3v | 3w | 3x | 3y | 3z | 3ww | 3xx | 3yy | 3zz | 4a | 4b | 4c | 4d | 4e |
|---|---|---|---|---|---|---|---|---|---|---|---|---|---|---|---|---|
| 1a | 0 | 0 | 1 | 4 | 0 | 0 | 0 | 0 | 0 | 1 | 0 | 0 | 1 | 1 | 0 | 0 |
| 1b | 0 | 1 | 0 | 0 | 0 | 0 | 0 | 0 | 0 | 1 | 0 | 6 | 0 | 3 | 0 | 0 |
| 1c | 1 | 0 | 0 | 33 | 0 | 1 | 0 | 0 | 0 | 1 | 0 | 0 | 2 | 0 | 0 | 1 |
| 1d | 0 | 0 | 0 | 0 | 0 | 0 | 0 | 0 | 0 | 1 | 0 | 0 | 0 | 1 | 0 | 1 |
| 1e | 0 | 0 | 0 | 3 | 0 | 1 | 0 | 0 | 0 | 1 | 0 | 0 | 0 | 0 | 0 | 0 |
| 1f | 0 | 0 | 0 | 5 | 0 | 3 | 1 | 0 | 0 | 3 | 0 | 0 | 2 | 0 | 0 | 0 |
| 1g | 21 | 2 | 3 | 35 | 60 | 30 | 2 | 15 | 0 | 9 | 8 | 2 | 0 | 3 | 3 | 0 |
| 1h | 8 | 38 | 44 | 94 | 14 | 96 | 93 | 32 | 12 | 35 | 55 | 85 | 1 | 18 | 3 | 3 |
| 1i | 0 | 4 | 5 | 59 | 0 | 4 | 6 | 1 | 0 | 0 | 1 | 2 | 0 | 3 | 1 | 0 |
| 1j | 0 | 1 | 0 | 7 | 0 | 6 | 0 | 0 | 0 | 1 | 0 | 0 | 0 | 0 | 1 | 0 |
| 1k | 1 | 0 | 0 | 49 | 0 | 1 | 0 | 0 | 0 | 1 | 0 | 0 | 1 | 1 | 7 | 0 |
| 1l | 0 | 1 | 5 | 5 | 0 | 0 | 1 | 0 | 0 | 5 | 0 | 1 | 1 | 2 | 0 | 1 |
| 1m | 0 | 0 | 3 | 10 | 0 | 3 | 0 | 0 | 0 | 7 | 0 | 0 | 4 | 0 | 0 | 0 |
| 1n | 0 | 0 | 0 | 2 | 0 | 0 | 0 | 1 | 0 | 1 | 0 | 0 | 0 | 1 | 0 | 0 |
| 1o | 1 | 6 | 4 | 76 | 2 | 10 | 10 | 2 | 0 | 0 | 1 | 4 | 2 | 1 | 3 | 0 |
| 1p | 0 | 0 | 0 | 33 | 0 | 0 | 5 | 4 | 0 | 0 | 0 | 0 | 0 | 3 | 0 | 1 |
| 1q | 0 | 0 | 2 | 2 | 0 | 3 | 1 | 4 | 0 | 4 | 0 | 0 | 0 | 1 | 0 | 0 |
| 1r | 0 | 2 | 5 | 8 | 3 | 2 | 0 | 0 | 0 | 3 | 0 | 0 | 0 | 0 | 0 | 0 |
| 1s | 0 | 2 | 0 | 28 | 0 | 0 | 11 | 0 | 0 | 0 | 0 | 1 | 1 | 3 | 2 | 0 |
| 1t | 0 | 0 | 1 | 12 | 1 | 0 | 5 | 0 | 0 | 3 | 0 | 0 | 0 | 0 | 3 | 0 |
| 1u | 1 | 0 | 0 | 99 | 14 | 14 | 22 | 3 | 0 | 18 | 2 | 0 | 0 | 2 | 4 | 0 |
| 1v | 0 | 4 | 0 | 21 | 0 | 0 | 1 | 0 | 0 | 47 | 0 | 1 | 0 | 0 | 2 | 5 |
| 1w | 59 | 40 | 61 | 91 | 29 | 59 | 49 | 8 | 22 | 28 | 50 | 18 | 35 | 34 | 52 | 39 |
| 1x | 16 | 75 | 89 | 99 | 50 | 46 | 51 | 34 | 0 | 0 | 18 | 0 | 1 | 3 | 0 | 0 |
| 1y | 66 | 90 | 96 | 99 | 60 | 99 | 82 | 38 | 44 | 84 | 88 | 55 | 87 | 89 | 74 | 85 |
| 1z | 0 | 1 | 1 | 27 | 0 | 1 | 7 | 0 | 0 | 0 | 0 | 3 | 5 | 6 | 0 | 0 |
| 1ww | 0 | 0 | 0 | 0 | 0 | 0 | 2 | 0 | 1 | 0 | 0 | 0 | 0 | 2 | 0 | 0 |
| 1xx | 0 | 0 | 1 | 0 | 0 | 1 | 1 | 0 | 0 | 0 | 0 | 0 | 0 | 2 | 0 | 0 |
| 1yy | 0 | 3 | 0 | 23 | 3 | 2 | 3 | 1 | 0 | 2 | 0 | 0 | 0 | 0 | 0 | 4 |
| 1zz | 14 | 51 | 63 | 97 | 17 | 49 | 86 | 27 | 6 | 59 | 9 | 23 | 98 | 87 | 21 | 74 |
| 2a | 0 | 0 | 0 | 0 | 0 | 1 | 0 | 0 | 0 | 3 | 0 | 0 | 0 | 0 | 0 | 0 |
| 2b | 0 | 0 | 0 | 21 | 15 | 1 | 0 | 0 | 0 | 0 | 0 | 0 | 0 | 0 | 0 | 0 |
| 2c | 0 | 0 | 0 | 2 | 0 | 0 | 0 | 0 | 0 | 0 | 0 | 0 | 0 | 0 | 0 | 0 |
| 2d | 0 | 0 | 0 | 2 | 0 | 0 | 0 | 0 | 0 | 0 | 0 | 0 | 0 | 0 | 0 | 0 |
| 2e | 0 | 0 | 0 | 3 | 0 | 0 | 0 | 0 | 0 | 0 | 0 | 0 | 0 | 0 | 0 | 0 |
| 2f | 0 | 0 | 0 | 10 | 1 | 0 | 0 | 0 | 0 | 0 | 0 | 0 | 0 | 0 | 0 | 0 |
| 2g | 0 | 2 | 0 | 10 | 1 | 0 | 0 | 1 | 0 | 2 | 0 | 0 | 0 | 0 | 1 | 10 |
| 2h | 0 | 0 | 0 | 6 | 0 | 0 | 0 | 0 | 0 | 0 | 0 | 0 | 0 | 1 | 0 | 0 |
| 2i | 0 | 2 | 0 | 7 | 0 | 0 | 0 | 1 | 0 | 1 | 1 | 0 | 0 | 0 | 0 | 0 |
| 2j | 0 | 0 | 0 | 4 | 0 | 0 | 0 | 0 | 0 | 1 | 1 | 0 | 0 | 0 | 2 | 0 |
| 2k | 0 | 0 | 0 | 4 | 0 | 0 | 2 | 1 | 1 | 0 | 1 | 0 | 0 | 0 | 0 | 0 |
| 2l | 8 | 53 | 2 | 99 | 6 | 16 | 34 | 5 | 19 | 40 | 8 | 40 | 2 | 1 | 1 | 1 |
| 2m | 0 | 4 | 0 | 5 | 0 | 0 | 0 | 0 | 0 | 1 | 0 | 0 | 0 | 0 | 1 | 1 |
| 2n | 0 | 6 | 0 | 9 | 0 | 0 | 0 | 1 | 0 | 2 | 0 | 1 | 0 | 0 | 0 | 0 |
| 2o | 0 | 3 | 2 | 8 | 0 | 0 | 0 | 1 | 0 | 2 | 1 | 1 | 0 | 0 | 0 | 0 |
| 2p | 0 | 3 | 0 | 7 | 0 | 0 | 4 | 0 | 0 | 1 | 0 | 1 | 0 | 1 | 0 | 0 |
| 2q | 0 | 0 | 0 | 0 | 0 | 0 | 2 | 0 | 0 | 1 | 0 | 5 | 0 | 1 | 0 | 0 |

FIG. 13
(Continued)

|     | 4f | 4g | 4h | 4i | 4j | 4k | 4l | 4m | 4n | 4o | 4p | 4q | 4r | 4s | 4t | 4u |
|-----|----|----|----|----|----|----|----|----|----|----|----|----|----|----|----|----|
| 1a  | 0  | 0  | 2  | 1  | 0  | 0  | 0  | 2  | 0  | 5  | 0  | 0  | 4  | 0  | 0  | 0  |
| 1b  | 1  | 0  | 0  | 0  | 1  | 0  | 0  | 0  | 0  | 5  | 0  | 0  | 4  | 0  | 0  | 1  |
| 1c  | 1  | 0  | 6  | 0  | 0  | 0  | 0  | 0  | 0  | 2  | 0  | 0  | 1  | 0  | 0  | 1  |
| 1d  | 1  | 0  | 0  | 0  | 5  | 0  | 0  | 0  | 0  | 2  | 0  | 0  | 4  | 0  | 0  | 0  |
| 1e  | 1  | 0  | 0  | 0  | 0  | 0  | 0  | 0  | 0  | 2  | 0  | 0  | 3  | 0  | 0  | 0  |
| 1f  | 0  | 0  | 0  | 0  | 0  | 0  | 0  | 0  | 1  | 2  | 2  | 0  | 4  | 0  | 0  | 0  |
| 1g  | 10 | 3  | 9  | 0  | 0  | 1  | 1  | 2  | 4  | 2  | 57 | 5  | 3  | 3  | 21 | 60 |
| 1h  | 6  | 2  | 26 | 14 | 36 | 96 | 2  | 40 | 7  | 9  | 10 | 34 | 23 | 19 | 2  | 38 |
| 1i  | 1  | 1  | 5  | 7  | 2  | 3  | 0  | 3  | 1  | 0  | 0  | 2  | 5  | 2  | 0  | 3  |
| 1j  | 0  | 1  | 0  | 0  | 0  | 0  | 0  | 0  | 0  | 1  | 0  | 0  | 2  | 0  | 0  | 1  |
| 1k  | 0  | 1  | 0  | 0  | 2  | 4  | 0  | 0  | 0  | 1  | 0  | 0  | 3  | 0  | 1  | 0  |
| 1l  | 0  | 0  | 0  | 0  | 0  | 0  | 5  | 0  | 0  | 3  | 0  | 0  | 2  | 0  | 0  | 1  |
| 1m  | 0  | 0  | 3  | 1  | 0  | 0  | 0  | 0  | 4  | 3  | 0  | 1  | 6  | 1  | 0  | 1  |
| 1n  | 1  | 0  | 1  | 0  | 0  | 0  | 0  | 3  | 1  | 0  | 0  | 1  | 2  | 0  | 0  | 0  |
| 1o  | 3  | 1  | 4  | 6  | 6  | 2  | 1  | 5  | 7  | 5  | 0  | 0  | 6  | 4  | 1  | 6  |
| 1p  | 6  | 0  | 1  | 0  | 0  | 6  | 0  | 4  | 0  | 3  | 1  | 0  | 4  | 0  | 0  | 0  |
| 1q  | 1  | 0  | 1  | 0  | 0  | 1  | 0  | 6  | 1  | 1  | 2  | 0  | 5  | 0  | 0  | 0  |
| 1r  | 0  | 2  | 1  | 4  | 0  | 2  | 4  | 1  | 2  | 3  | 0  | 5  | 4  | 0  | 0  | 2  |
| 1s  | 0  | 1  | 7  | 0  | 0  | 0  | 0  | 7  | 0  | 2  | 0  | 0  | 0  | 6  | 0  | 0  |
| 1t  | 0  | 0  | 0  | 1  | 0  | 0  | 0  | 2  | 1  | 0  | 0  | 0  | 0  | 0  | 0  | 5  |
| 1u  | 4  | 3  | 36 | 0  | 3  | 2  | 82 | 0  | 27 | 67 | 2  | 4  | 0  | 2  | 1  | 35 |
| 1v  | 1  | 0  | 2  | 2  | 0  | 2  | 1  | 2  | 1  | 6  | 0  | 5  | 3  | 0  | 0  | 4  |
| 1w  | 6  | 9  | 78 | 59 | 23 | 43 | 69 | 24 | 53 | 38 | 20 | 26 | 39 | 81 | 59 | 35 |
| 1x  | 0  | 0  | 4  | 2  | 15 | 3  | 27 | 2  | 0  | 6  | 15 | 3  | 5  | 9  | 16 | 75 |
| 1y  | 39 | 59 | 87 | 90 | 61 | 80 | 75 | 70 | 81 | 98 | 60 | 81 | 91 | 97 | 66 | 90 |
| 1z  | 0  | 2  | 3  | 0  | 2  | 0  | 0  | 0  | 0  | 2  | 0  | 1  | 1  | 0  | 0  | 0  |
| 1ww | 0  | 0  | 0  | 0  | 0  | 0  | 0  | 0  | 0  | 0  | 0  | 0  | 1  | 0  | 0  | 0  |
| 1xx | 0  | 1  | 0  | 0  | 0  | 0  | 0  | 0  | 0  | 4  | 0  | 0  | 0  | 0  | 0  | 0  |
| 1yy | 0  | 0  | 0  | 1  | 0  | 0  | 0  | 2  | 0  | 0  | 0  | 1  | 7  | 0  | 0  | 3  |
| 1zz | 13 | 45 | 79 | 85 | 89 | 47 | 16 | 33 | 44 | 27 | 43 | 72 | 98 | 90 | 14 | 51 |
| 2a  | 0  | 0  | 1  | 0  | 0  | 0  | 0  | 0  | 0  | 2  | 0  | 5  | 0  | 0  | 0  | 1  |
| 2b  | 0  | 0  | 0  | 0  | 0  | 0  | 0  | 0  | 0  | 5  | 0  | 2  | 0  | 0  | 0  | 0  |
| 2c  | 0  | 3  | 0  | 0  | 0  | 0  | 0  | 0  | 0  | 0  | 0  | 0  | 0  | 0  | 0  | 0  |
| 2d  | 0  | 0  | 0  | 0  | 0  | 0  | 0  | 0  | 0  | 0  | 0  | 0  | 2  | 1  | 0  | 0  |
| 2e  | 0  | 0  | 1  | 0  | 0  | 0  | 0  | 0  | 0  | 0  | 0  | 0  | 2  | 0  | 0  | 0  |
| 2f  | 0  | 0  | 2  | 0  | 0  | 0  | 0  | 5  | 0  | 0  | 1  | 0  | 1  | 0  | 0  | 0  |
| 2g  | 0  | 0  | 0  | 0  | 0  | 0  | 0  | 0  | 1  | 0  | 0  | 0  | 2  | 2  | 0  | 1  |
| 2h  | 0  | 0  | 0  | 0  | 0  | 0  | 0  | 0  | 0  | 0  | 0  | 0  | 3  | 1  | 0  | 0  |
| 2i  | 0  | 0  | 0  | 0  | 0  | 1  | 0  | 0  | 0  | 0  | 0  | 0  | 2  | 0  | 0  | 2  |
| 2j  | 0  | 0  | 1  | 0  | 0  | 0  | 0  | 0  | 0  | 1  | 0  | 2  | 1  | 0  | 0  | 0  |
| 2k  | 0  | 0  | 0  | 0  | 0  | 0  | 0  | 0  | 1  | 0  | 0  | 0  | 1  | 0  | 0  | 0  |
| 2l  | 0  | 2  | 11 | 4  | 7  | 20 | 36 | 13 | 30 | 60 | 1  | 1  | 10 | 1  | 1  | 68 |
| 2m  | 0  | 0  | 4  | 0  | 0  | 0  | 0  | 0  | 0  | 1  | 0  | 2  | 1  | 0  | 0  | 4  |
| 2n  | 0  | 0  | 3  | 0  | 0  | 0  | 3  | 0  | 0  | 0  | 0  | 3  | 3  | 0  | 0  | 0  |
| 2o  | 0  | 1  | 3  | 0  | 0  | 1  | 0  | 0  | 0  | 0  | 0  | 4  | 1  | 0  | 0  | 0  |
| 2p  | 0  | 0  | 1  | 0  | 0  | 0  | 0  | 0  | 0  | 0  | 0  | 0  | 2  | 1  | 0  | 3  |
| 2q  | 0  | 0  | 3  | 0  | 0  | 0  | 0  | 0  | 0  | 1  | 0  | 0  | 4  | 0  | 0  | 0  |

FIG. 13
(Continued)

|     | 4v | 4w | 4x | 4y | 4z | 4ww | 4xx | 4yy | 4zz |
|-----|----|----|----|----|----|----|----|----|----|
| 1a  | 1  | 4  | 0  | 0  | 0  | 0  | 0  | 0  | 0  |
| 1b  | 0  | 0  | 0  | 0  | 0  | 0  | 0  | 0  | 0  |
| 1c  | 4  | 1  | 0  | 3  | 0  | 0  | 0  | 1  | 0  |
| 1d  | 0  | 0  | 0  | 0  | 0  | 0  | 0  | 1  | 0  |
| 1e  | 0  | 3  | 0  | 1  | 0  | 0  | 0  | 1  | 0  |
| 1f  | 0  | 5  | 0  | 3  | 1  | 0  | 0  | 3  | 0  |
| 1g  | 9  | 35 | 15 | 0  | 2  | 15 | 0  | 4  | 0  |
| 1h  | 44 | 94 | 14 | 96 | 93 | 32 | 12 | 35 | 9  |
| 1i  | 5  | 1  | 0  | 2  | 0  | 1  | 0  | 4  | 1  |
| 1j  | 0  | 7  | 0  | 6  | 0  | 0  | 0  | 1  | 0  |
| 1k  | 0  | 0  | 0  | 1  | 0  | 0  | 0  | 1  | 0  |
| 1l  | 5  | 5  | 0  | 0  | 1  | 0  | 0  | 0  | 0  |
| 1m  | 3  | 0  | 0  | 3  | 0  | 0  | 0  | 2  | 0  |
| 1n  | 0  | 0  | 0  | 1  | 0  | 1  | 0  | 1  | 0  |
| 1o  | 0  | 1  | 2  | 6  | 2  | 2  | 0  | 1  | 1  |
| 1p  | 0  | 0  | 0  | 0  | 5  | 4  | 0  | 0  | 0  |
| 1q  | 2  | 2  | 0  | 3  | 1  | 0  | 0  | 1  | 0  |
| 1r  | 5  | 0  | 3  | 2  | 0  | 0  | 0  | 3  | 0  |
| 1s  | 4  | 0  | 0  | 0  | 0  | 0  | 0  | 1  | 0  |
| 1t  | 7  | 0  | 1  | 0  | 3  | 0  | 0  | 0  | 0  |
| 1u  | 29 | 99 | 0  | 0  | 22 | 2  | 0  | 18 | 0  |
| 1v  | 0  | 2  | 0  | 4  | 1  | 0  | 0  | 0  | 0  |
| 1w  | 61 | 49 | 29 | 59 | 72 | 8  | 22 | 28 | 50 |
| 1x  | 0  | 99 | 7  | 46 | 51 | 34 | 0  | 0  | 0  |
| 1y  | 96 | 82 | 60 | 51 | 88 | 38 | 44 | 84 | 88 |
| 1z  | 1  | 7  | 1  | 1  | 0  | 0  | 0  | 0  | 0  |
| 1ww | 0  | 0  | 0  | 0  | 2  | 0  | 1  | 0  | 0  |
| 1xx | 1  | 0  | 0  | 0  | 0  | 0  | 0  | 0  | 0  |
| 1yy | 4  | 0  | 0  | 2  | 2  | 0  | 0  | 0  | 0  |
| 1zz | 63 | 97 | 17 | 49 | 86 | 9  | 6  | 59 | 64 |
| 2a  | 0  | 5  | 0  | 3  | 0  | 0  | 0  | 0  | 0  |
| 2b  | 0  | 0  | 0  | 1  | 0  | 0  | 0  | 0  | 0  |
| 2c  | 0  | 0  | 0  | 0  | 0  | 0  | 0  | 0  | 0  |
| 2d  | 0  | 0  | 0  | 0  | 0  | 0  | 0  | 0  | 0  |
| 2e  | 0  | 0  | 1  | 0  | 0  | 0  | 0  | 0  | 0  |
| 2f  | 0  | 1  | 2  | 0  | 0  | 0  | 0  | 0  | 0  |
| 2g  | 2  | 1  | 1  | 0  | 0  | 1  | 0  | 2  | 0  |
| 2h  | 0  | 6  | 0  | 0  | 0  | 0  | 0  | 0  | 0  |
| 2i  | 0  | 7  | 0  | 0  | 0  | 1  | 0  | 1  | 1  |
| 2j  | 0  | 0  | 0  | 0  | 1  | 0  | 0  | 1  | 1  |
| 2k  | 0  | 4  | 0  | 0  | 2  | 1  | 1  | 1  | 0  |
| 2l  | 22 | 99 | 7  | 16 | 34 | 5  | 19 | 40 | 3  |
| 2m  | 0  | 0  | 0  | 0  | 5  | 0  | 0  | 1  | 0  |
| 2n  | 0  | 0  | 0  | 0  | 6  | 0  | 0  | 0  | 0  |
| 2o  | 2  | 0  | 0  | 0  | 5  | 1  | 0  | 2  | 1  |
| 2p  | 0  | 7  | 0  | 0  | 4  | 0  | 0  | 1  | 0  |
| 2q  | 0  | 0  | 0  | 0  | 2  | 0  | 0  | 1  | 0  |

FIG. 13
(Continued)

|     | 1a | 1b | 1c | 1d | 1e | 1f | 1g | 1h | 1i | 1j | 1k | 1l | 1m | 1n | 1o |
|-----|----|----|----|----|----|----|----|----|----|----|----|----|----|----|----|
| 2r  | 1  | 0  | 1  | 0  | 0  | 0  | 0  | 1  | 0  | 0  | 0  | 0  | 0  | 0  | 0  |
| 2s  | 2  | 2  | 7  | 4  | 0  | 0  | 0  | 1  | 0  | 0  | 2  | 0  | 1  | 1  | 5  |
| 2t  | 1  | 0  | 1  | 0  | 0  | 0  | 0  | 3  | 3  | 0  | 0  | 0  | 0  | 0  | 2  |
| 2u  | 1  | 0  | 1  | 0  | 0  | 1  | 0  | 3  | 0  | 0  | 1  | 0  | 0  | 0  | 1  |
| 2v  | 1  | 0  | 2  | 0  | 0  | 0  | 0  | 3  | 0  | 0  | 0  | 0  | 0  | 0  | 0  |
| 2w  | 0  | 0  | 1  | 0  | 0  | 0  | 0  | 9  | 2  | 0  | 0  | 0  | 0  | 1  | 1  |
| 2x  | 23 | 0  | 8  | 11 | 4  | 52 | 2  | 43 | 21 | 36 | 97 | 0  | 67 | 5  | 10 |
| 2y  | 34 | 8  | 18 | 36 | 7  | 21 | 8  | 71 | 18 | 41 | 49 | 11 | 33 | 32 | 58 |
| 2z  | 0  | 1  | 1  | 0  | 0  | 1  | 2  | 7  | 1  | 0  | 0  | 0  | 0  | 0  | 0  |
| 2ww | 0  | 2  | 3  | 3  | 2  | 6  | 4  | 31 | 6  | 23 | 3  | 2  | 0  | 3  | 1  |
| 2xx | 0  | 0  | 0  | 0  | 0  | 0  | 0  | 0  | 0  | 0  | 0  | 0  | 0  | 0  | 2  |
| 2yy | 0  | 0  | 0  | 2  | 0  | 0  | 0  | 3  | 0  | 0  | 0  | 0  | 0  | 0  | 0  |
| 2zz | 0  | 2  | 0  | 0  | 0  | 0  | 1  | 0  | 0  | 0  | 0  | 0  | 0  | 1  | 1  |
| 3a  | 0  | 0  | 0  | 0  | 0  | 0  | 0  | 0  | 0  | 0  | 2  | 0  | 0  | 2  | 3  |
| 3b  | 0  | 0  | 0  | 0  | 4  | 0  | 1  | 2  | 0  | 0  | 0  | 0  | 0  | 5  | 6  |
| 3c  | 0  | 0  | 0  | 0  | 0  | 0  | 2  | 1  | 0  | 0  | 0  | 0  | 0  | 1  | 1  |
| 3d  | 0  | 0  | 0  | 0  | 0  | 0  | 0  | 0  | 0  | 0  | 0  | 0  | 0  | 1  | 0  |
| 3e  | 0  | 0  | 0  | 0  | 6  | 0  | 16 | 0  | 0  | 0  | 0  | 0  | 0  | 1  | 0  |
| 3f  | 0  | 0  | 0  | 0  | 0  | 0  | 0  | 0  | 0  | 0  | 0  | 0  | 0  | 1  | 2  |
| 3g  | 0  | 0  | 2  | 0  | 0  | 0  | 0  | 0  | 0  | 0  | 0  | 0  | 0  | 1  | 3  |
| 3h  | 0  | 0  | 2  | 0  | 0  | 0  | 0  | 1  | 0  | 0  | 0  | 0  | 0  | 1  | 3  |
| 3i  | 0  | 5  | 0  | 0  | 0  | 0  | 0  | 0  | 1  | 0  | 1  | 0  | 0  | 0  | 5  |
| 3j  | 0  | 0  | 2  | 0  | 0  | 0  | 0  | 0  | 0  | 0  | 0  | 0  | 0  | 1  | 1  |
| 3k  | 0  | 0  | 2  | 0  | 0  | 0  | 0  | 0  | 0  | 0  | 0  | 0  | 0  | 1  | 3  |
| 3l  | 0  | 0  | 1  | 0  | 0  | 0  | 0  | 1  | 0  | 0  | 0  | 1  | 2  | 2  | 4  |
| 3m  | 0  | 0  | 1  | 0  | 0  | 0  | 1  | 1  | 0  | 0  | 0  | 0  | 0  | 2  | 3  |
| 3n  | 0  | 0  | 0  | 0  | 0  | 0  | 0  | 1  | 0  | 0  | 0  | 0  | 0  | 1  | 0  |
| 3o  | 0  | 0  | 0  | 0  | 0  | 0  | 2  | 1  | 0  | 0  | 0  | 0  | 0  | 0  | 0  |
| 3p  | 0  | 0  | 8  | 0  | 1  | 0  | 0  | 0  | 0  | 0  | 0  | 0  | 0  | 2  | 1  |
| 3q  | 0  | 0  | 2  | 0  | 0  | 0  | 1  | 3  | 0  | 0  | 0  | 0  | 0  | 2  | 4  |
| 3r  | 0  | 0  | 5  | 0  | 1  | 0  | 0  | 1  | 0  | 0  | 0  | 0  | 0  | 1  | 1  |
| 3s  | 1  | 1  | 2  | 1  | 1  | 0  | 1  | 0  | 2  | 0  | 5  | 6  | 0  | 7  | 5  |
| 3t  | 0  | 0  | 0  | 0  | 0  | 0  | 0  | 0  | 0  | 0  | 0  | 0  | 0  | 3  | 2  |
| 3u  | 0  | 0  | 1  | 0  | 1  | 0  | 0  | 0  | 0  | 0  | 0  | 0  | 0  | 2  | 2  |
| 3v  | 0  | 0  | 0  | 0  | 1  | 0  | 1  | 0  | 2  | 0  | 0  | 0  | 0  | 2  | 4  |
| 3w  | 0  | 0  | 0  | 0  | 0  | 0  | 0  | 1  | 0  | 0  | 0  | 0  | 0  | 6  | 3  |
| 3x  | 0  | 0  | 0  | 0  | 0  | 0  | 0  | 1  | 0  | 0  | 0  | 0  | 0  | 1  | 1  |
| 3y  | 0  | 0  | 0  | 0  | 0  | 1  | 0  | 0  | 0  | 1  | 0  | 0  | 0  | 0  | 2  |
| 3z  | 0  | 0  | 0  | 0  | 0  | 0  | 0  | 0  | 0  | 0  | 0  | 0  | 0  | 0  | 1  |
| 3ww | 0  | 0  | 0  | 0  | 0  | 0  | 0  | 0  | 0  | 0  | 0  | 0  | 0  | 0  | 0  |
| 3xx | 0  | 0  | 0  | 0  | 0  | 0  | 0  | 0  | 0  | 0  | 0  | 0  | 0  | 0  | 0  |
| 3yy | 0  | 0  | 0  | 0  | 0  | 0  | 0  | 0  | 0  | 0  | 0  | 0  | 0  | 0  | 1  |
| 3zz | 0  | 0  | 0  | 0  | 0  | 0  | 0  | 0  | 0  | 0  | 0  | 0  | 0  | 0  | 0  |

FIG. 13
(Continued)

|     | 1p | 1q | 1r | 1s | 1t | 1u | 1v | 1w | 1x | 1y | 1z | 1ww | 1xx | 1yy | 1zz | 2a |
|-----|----|----|----|----|----|----|----|----|----|----|----|-----|-----|-----|-----|----|
| 2r  | 0  | 2  | 2  | 0  | 0  | 1  | 0  | 0  | 1  | 2  | 0  | 0   | 0   | 1   | 1   | 1  |
| 2s  | 1  | 2  | 0  | 0  | 0  | 7  | 3  | 22 | 0  | 4  | 0  | 1   | 0   | 1   | 2   | 2  |
| 2t  | 0  | 0  | 3  | 0  | 0  | 4  | 0  | 15 | 0  | 0  | 0  | 0   | 0   | 1   | 0   | 1  |
| 2u  | 0  | 2  | 4  | 0  | 0  | 9  | 1  | 12 | 0  | 2  | 0  | 0   | 0   | 1   | 1   | 1  |
| 2v  | 0  | 2  | 1  | 0  | 0  | 5  | 0  | 10 | 1  | 2  | 0  | 1   | 0   | 0   | 1   | 1  |
| 2w  | 0  | 2  | 0  | 1  | 0  | 10 | 3  | 99 | 1  | 7  | 0  | 1   | 2   | 0   | 3   | 3  |
| 2x  | 28 | 27 | 22 | 18 | 29 | 93 | 82 | 88 | 85 | 79 | 53 | 56  | 1   | 21  | 53  | 23 |
| 2y  | 23 | 68 | 63 | 16 | 26 | 75 | 96 | 99 | 45 | 94 | 41 | 30  | 18  | 46  | 61  | 34 |
| 2z  | 4  | 0  | 0  | 4  | 1  | 2  | 4  | 33 | 2  | 64 | 7  | 0   | 0   | 1   | 8   | 0  |
| 2ww | 18 | 1  | 21 | 13 | 23 | 49 | 63 | 61 | 15 | 89 | 1  | 0   | 0   | 5   | 89  | 0  |
| 2xx | 0  | 0  | 1  | 0  | 0  | 0  | 1  | 4  | 0  | 2  | 0  | 0   | 0   | 0   | 0   | 0  |
| 2yy | 0  | 0  | 3  | 0  | 0  | 0  | 4  | 6  | 0  | 0  | 0  | 0   | 0   | 0   | 0   | 0  |
| 2zz | 0  | 0  | 0  | 0  | 0  | 0  | 3  | 9  | 0  | 0  | 0  | 0   | 0   | 1   | 1   | 0  |
| 3a  | 1  | 0  | 1  | 0  | 0  | 2  | 0  | 0  | 0  | 0  | 0  | 0   | 0   | 0   | 0   | 0  |
| 3b  | 0  | 0  | 0  | 0  | 0  | 0  | 0  | 18 | 0  | 0  | 0  | 0   | 0   | 0   | 0   | 1  |
| 3c  | 0  | 0  | 0  | 0  | 0  | 0  | 0  | 11 | 3  | 0  | 0  | 0   | 0   | 0   | 0   | 0  |
| 3d  | 0  | 0  | 0  | 0  | 0  | 0  | 0  | 5  | 0  | 0  | 0  | 0   | 0   | 0   | 0   | 0  |
| 3e  | 2  | 0  | 2  | 0  | 0  | 0  | 0  | 4  | 0  | 0  | 1  | 0   | 0   | 0   | 0   | 0  |
| 3f  | 0  | 0  | 0  | 0  | 0  | 5  | 0  | 0  | 0  | 0  | 0  | 0   | 0   | 0   | 0   | 0  |
| 3g  | 0  | 0  | 0  | 0  | 0  | 0  | 0  | 40 | 0  | 0  | 0  | 0   | 0   | 0   | 0   | 0  |
| 3h  | 0  | 0  | 2  | 0  | 0  | 3  | 2  | 0  | 0  | 0  | 1  | 0   | 0   | 0   | 0   | 0  |
| 3i  | 0  | 0  | 2  | 0  | 0  | 7  | 0  | 43 | 0  | 0  | 1  | 0   | 0   | 6   | 0   | 0  |
| 3j  | 0  | 0  | 0  | 0  | 0  | 3  | 2  | 1  | 0  | 0  | 1  | 0   | 0   | 0   | 0   | 0  |
| 3k  | 0  | 0  | 1  | 0  | 0  | 0  | 2  | 7  | 0  | 0  | 0  | 0   | 0   | 0   | 0   | 0  |
| 3l  | 0  | 2  | 0  | 0  | 0  | 2  | 3  | 0  | 0  | 0  | 0  | 0   | 0   | 0   | 0   | 0  |
| 3m  | 0  | 2  | 1  | 0  | 0  | 0  | 3  | 1  | 0  | 0  | 0  | 0   | 0   | 0   | 0   | 0  |
| 3n  | 0  | 0  | 0  | 0  | 0  | 0  | 2  | 0  | 0  | 0  | 0  | 0   | 0   | 0   | 0   | 0  |
| 3o  | 0  | 0  | 0  | 1  | 0  | 0  | 2  | 4  | 0  | 0  | 0  | 0   | 0   | 0   | 0   | 0  |
| 3p  | 0  | 1  | 0  | 1  | 0  | 9  | 0  | 0  | 0  | 0  | 0  | 0   | 0   | 0   | 0   | 1  |
| 3q  | 0  | 0  | 1  | 0  | 0  | 0  | 0  | 0  | 0  | 0  | 0  | 0   | 0   | 0   | 0   | 0  |
| 3r  | 0  | 0  | 1  | 0  | 0  | 0  | 0  | 18 | 0  | 0  | 0  | 0   | 6   | 0   | 0   | 0  |
| 3s  | 0  | 0  | 3  | 0  | 0  | 21 | 0  | 63 | 0  | 0  | 5  | 0   | 0   | 4   | 0   | 0  |
| 3t  | 0  | 0  | 0  | 0  | 0  | 2  | 2  | 7  | 0  | 0  | 0  | 0   | 0   | 0   | 0   | 0  |
| 3u  | 0  | 2  | 1  | 0  | 0  | 5  | 0  | 3  | 0  | 0  | 0  | 0   | 0   | 0   | 0   | 0  |
| 3v  | 0  | 0  | 0  | 0  | 0  | 2  | 0  | 0  | 0  | 0  | 0  | 0   | 0   | 0   | 0   | 0  |
| 3w  | 0  | 0  | 3  | 0  | 0  | 1  | 0  | 0  | 1  | 0  | 0  | 0   | 0   | 0   | 0   | 0  |
| 3x  | 0  | 0  | 0  | 0  | 0  | 0  | 0  | 0  | 1  | 0  | 0  | 0   | 0   | 0   | 0   | 0  |
| 3y  | 0  | 0  | 0  | 0  | 0  | 1  | 0  | 0  | 3  | 8  | 0  | 1   | 0   | 0   | 1   | 0  |
| 3z  | 0  | 0  | 0  | 0  | 0  | 3  | 1  | 0  | 0  | 0  | 0  | 0   | 0   | 0   | 0   | 0  |
| 3ww | 0  | 0  | 0  | 0  | 0  | 0  | 0  | 0  | 0  | 0  | 1  | 0   | 0   | 0   | 0   | 0  |
| 3xx | 0  | 0  | 0  | 0  | 0  | 0  | 0  | 0  | 0  | 0  | 2  | 1   | 0   | 0   | 0   | 0  |
| 3yy | 0  | 0  | 0  | 0  | 0  | 0  | 0  | 0  | 0  | 0  | 2  | 0   | 0   | 0   | 0   | 0  |
| 3zz | 0  | 0  | 0  | 0  | 0  | 7  | 5  | 0  | 0  | 1  | 0  | 0   | 0   | 0   | 0   | 0  |

FIG. 13
(Continued)

|     | 2b | 2c | 2d | 2e | 2f | 2g | 2h | 2i | 2j | 2k | 2l | 2m | 2n | 2o | 2p | 2q |
|-----|----|----|----|----|----|----|----|----|----|----|----|----|----|----|----|----|
| 2r  | 99 | 0  | 0  | 1  | 0  | 0  | 1  | 2  | 0  | 0  | 0  | 1  | 1  | 1  | 0  | 0  |
| 2s  | 3  | 92 | 0  | 0  | 5  | 3  | 0  | 0  | 0  | 1  | 0  | 1  | 2  | 2  | 2  | 4  |
| 2t  | 3  | 0  | 97 | 0  | 0  | 0  | 0  | 0  | 0  | 0  | 0  | 0  | 1  | 0  | 1  | 0  | 1 |
| 2u  | 4  | 0  | 0  | 99 | 4  | 1  | 0  | 1  | 0  | 0  | 0  | 1  | 1  | 1  | 0  | 1  |
| 2v  | 1  | 0  | 0  | 0  | 99 | 3  | 2  | 1  | 0  | 1  | 0  | 0  | 1  | 1  | 0  | 2  |
| 2w  | 1  | 1  | 9  | 0  | 6  | 99 | 1  | 5  | 2  | 1  | 0  | 2  | 3  | 1  | 0  | 0  |
| 2x  | 22 | 18 | 29 | 93 | 99 | 82 | 96 | 79 | 53 | 56 | 1  | 21 | 53 | 23 | 0  | 8  |
| 2y  | 63 | 15 | 26 | 75 | 96 | 99 | 45 | 99 | 41 | 30 | 18 | 46 | 61 | 34 | 8  | 18 |
| 2z  | 6  | 6  | 1  | 1  | 6  | 7  | 2  | 2  | 99 | 3  | 0  | 1  | 5  | 0  | 1  | 13 |
| 2ww | 16 | 5  | 23 | 49 | 63 | 61 | 15 | 99 | 8  | 94 | 0  | 5  | 6  | 0  | 4  | 27 |
| 2xx | 1  | 0  | 0  | 0  | 1  | 4  | 0  | 2  | 0  | 0  | 86 | 0  | 0  | 0  | 0  | 0  |
| 2yy | 3  | 0  | 0  | 0  | 4  | 6  | 0  | 0  | 0  | 0  | 0  | 93 | 0  | 0  | 0  | 0  |
| 2zz | 0  | 0  | 0  | 0  | 3  | 0  | 0  | 0  | 0  | 0  | 0  | 0  | 75 | 0  | 1  | 0  |
| 3a  | 1  | 0  | 0  | 0  | 0  | 0  | 0  | 0  | 0  | 0  | 0  | 0  | 0  | 95 | 0  | 0  |
| 3b  | 0  | 0  | 0  | 0  | 0  | 2  | 0  | 0  | 0  | 0  | 0  | 0  | 0  | 1  | 92 | 0  |
| 3c  | 0  | 0  | 0  | 0  | 0  | 11 | 8  | 0  | 0  | 0  | 0  | 0  | 0  | 0  | 1  | 97 |
| 3d  | 0  | 0  | 0  | 0  | 0  | 5  | 0  | 0  | 0  | 0  | 0  | 0  | 0  | 0  | 0  | 0  |
| 3e  | 2  | 0  | 0  | 0  | 5  | 0  | 0  | 0  | 1  | 0  | 0  | 0  | 0  | 0  | 4  | 0  |
| 3f  | 0  | 0  | 0  | 5  | 0  | 0  | 0  | 0  | 0  | 0  | 0  | 0  | 0  | 0  | 0  | 0  |
| 3g  | 0  | 0  | 0  | 0  | 0  | 1  | 0  | 0  | 0  | 0  | 0  | 0  | 0  | 0  | 0  | 2  |
| 3h  | 2  | 0  | 0  | 3  | 2  | 0  | 0  | 0  | 1  | 0  | 0  | 0  | 0  | 0  | 0  | 2  |
| 3i  | 2  | 3  | 0  | 7  | 3  | 0  | 0  | 0  | 1  | 0  | 0  | 6  | 0  | 2  | 1  | 0  |
| 3j  | 1  | 0  | 0  | 0  | 3  | 1  | 0  | 0  | 1  | 1  | 0  | 0  | 0  | 0  | 0  | 2  |
| 3k  | 1  | 0  | 0  | 0  | 2  | 7  | 0  | 0  | 0  | 0  | 0  | 0  | 0  | 0  | 0  | 2  |
| 3l  | 0  | 0  | 0  | 2  | 3  | 0  | 0  | 0  | 0  | 0  | 0  | 0  | 0  | 0  | 0  | 1  |
| 3m  | 1  | 0  | 0  | 0  | 3  | 1  | 0  | 0  | 0  | 0  | 0  | 0  | 0  | 0  | 0  | 1  |
| 3n  | 0  | 0  | 0  | 0  | 2  | 0  | 0  | 0  | 0  | 0  | 0  | 0  | 0  | 0  | 0  | 0  |
| 3o  | 0  | 0  | 1  | 0  | 2  | 4  | 0  | 0  | 0  | 0  | 0  | 0  | 0  | 0  | 0  | 0  |
| 3p  | 0  | 1  | 0  | 0  | 0  | 0  | 0  | 0  | 0  | 0  | 0  | 0  | 0  | 4  | 20 | 10 |
| 3q  | 0  | 0  | 0  | 0  | 0  | 0  | 0  | 0  | 0  | 0  | 0  | 0  | 0  | 0  | 0  | 2  |
| 3r  | 0  | 0  | 0  | 0  | 0  | 0  | 0  | 0  | 0  | 0  | 0  | 0  | 0  | 0  | 0  | 5  |
| 3s  | 6  | 3  | 0  | 0  | 0  | 1  | 0  | 0  | 1  | 0  | 0  | 0  | 0  | 0  | 4  | 2  |
| 3t  | 0  | 0  | 0  | 0  | 2  | 7  | 0  | 0  | 0  | 0  | 0  | 0  | 0  | 0  | 0  | 0  |
| 3u  | 1  | 0  | 0  | 0  | 5  | 0  | 0  | 0  | 0  | 0  | 0  | 0  | 0  | 0  | 0  | 1  |
| 3v  | 0  | 0  | 0  | 2  | 3  | 0  | 0  | 0  | 0  | 0  | 0  | 0  | 0  | 0  | 0  | 0  |
| 3w  | 3  | 0  | 0  | 1  | 1  | 0  | 0  | 0  | 0  | 0  | 0  | 0  | 0  | 0  | 0  | 0  |
| 3x  | 0  | 0  | 0  | 0  | 0  | 0  | 0  | 0  | 0  | 0  | 0  | 0  | 0  | 0  | 0  | 0  |
| 3y  | 0  | 0  | 0  | 0  | 4  | 0  | 3  | 4  | 1  | 0  | 0  | 0  | 1  | 0  | 0  | 0  |
| 3z  | 0  | 0  | 0  | 3  | 1  | 0  | 0  | 11 | 0  | 0  | 0  | 0  | 0  | 0  | 0  | 0  |
| 3ww | 0  | 0  | 0  | 0  | 0  | 0  | 0  | 1  | 0  | 0  | 0  | 0  | 0  | 0  | 0  | 0  |
| 3xx | 0  | 0  | 0  | 0  | 0  | 0  | 0  | 2  | 1  | 0  | 0  | 0  | 0  | 0  | 0  | 0  |
| 3yy | 0  | 0  | 0  | 0  | 0  | 0  | 0  | 2  | 0  | 0  | 0  | 0  | 0  | 0  | 0  | 0  |
| 3zz | 0  | 0  | 0  | 7  | 5  | 0  | 0  | 1  | 0  | 0  | 0  | 4  | 0  | 0  | 0  | 0  |

FIG. 13
(Continued)

|     | 2r | 2s | 2t | 2u | 2v | 2w | 2x | 2y | 2z | 2ww | 2xx | 2yy | 2zz | 3a | 3b | 3c |
|-----|----|----|----|----|----|----|----|----|----|-----|-----|-----|-----|----|----|----|
| 2r  | 0  | 0  | 2  | 0  | 0  | 0  | 0  | 0  | 0  | 0   | 0   | 0   | 0   | 1  | 0  | 0  |
| 2s  | 2  | 7  | 6  | 0  | 0  | 0  | 0  | 1  | 1  | 2   | 0   | 1   | 1   | 5  | 4  | 1  |
| 2t  | 0  | 1  | 0  | 0  | 0  | 0  | 3  | 3  | 0  | 0   | 0   | 0   | 0   | 2  | 0  | 0  |
| 2u  | 0  | 1  | 0  | 0  | 1  | 0  | 3  | 0  | 0  | 1   | 0   | 0   | 0   | 1  | 0  | 2  |
| 2v  | 0  | 2  | 0  | 0  | 0  | 0  | 3  | 0  | 0  | 0   | 0   | 1   | 0   | 0  | 0  | 2  |
| 2w  | 0  | 1  | 1  | 0  | 0  | 0  | 0  | 0  | 0  | 7   | 0   | 0   | 1   | 0  | 0  | 6  |
| 2x  | 0  | 8  | 11 | 4  | 52 | 2  | 43 | 21 | 36 | 97  | 0   | 67  | 5   | 10 | 28 | 27 |
| 2y  | 8  | 18 | 36 | 7  | 21 | 8  | 71 | 18 | 41 | 49  | 11  | 33  | 32  | 58 | 23 | 68 |
| 2z  | 1  | 1  | 0  | 1  | 1  | 2  | 3  | 3  | 0  | 0   | 0   | 0   | 0   | 1  | 38 | 1  |
| 2ww | 4  | 2  | 3  | 3  | 3  | 4  | 13 | 9  | 2  | 1   | 2   | 1   | 3   | 6  | 27 | 3  |
| 2xx | 0  | 0  | 0  | 0  | 0  | 0  | 0  | 0  | 0  | 0   | 0   | 0   | 0   | 2  | 0  | 0  |
| 2yy | 0  | 0  | 2  | 0  | 0  | 0  | 3  | 0  | 0  | 0   | 0   | 0   | 0   | 0  | 0  | 0  |
| 2zz | 0  | 0  | 0  | 0  | 0  | 1  | 0  | 0  | 0  | 0   | 0   | 0   | 1   | 1  | 0  | 0  |
| 3a  | 0  | 0  | 0  | 0  | 0  | 0  | 0  | 0  | 0  | 2   | 0   | 0   | 2   | 3  | 1  | 0  |
| 3b  | 0  | 0  | 0  | 4  | 0  | 1  | 2  | 0  | 0  | 0   | 0   | 0   | 5   | 6  | 0  | 0  |
| 3c  | 1  | 0  | 0  | 0  | 0  | 2  | 1  | 0  | 0  | 0   | 0   | 0   | 0   | 1  | 1  | 0  |
| 3d  | 0  | 0  | 0  | 0  | 0  | 0  | 0  | 0  | 0  | 0   | 0   | 0   | 0   | 2  | 1  | 0  |
| 3e  | 0  | 0  | 0  | 0  | 0  | 0  | 3  | 0  | 0  | 0   | 0   | 0   | 0   | 1  | 4  | 2  |
| 3f  | 0  | 0  | 0  | 0  | 0  | 0  | 0  | 0  | 0  | 0   | 0   | 0   | 0   | 1  | 2  | 0  |
| 3g  | 0  | 2  | 0  | 0  | 0  | 0  | 0  | 0  | 0  | 0   | 0   | 0   | 0   | 2  | 3  | 0  |
| 3h  | 0  | 2  | 0  | 0  | 0  | 0  | 0  | 0  | 0  | 0   | 0   | 0   | 1   | 1  | 3  | 0  |
| 3i  | 0  | 0  | 0  | 0  | 0  | 0  | 0  | 3  | 0  | 0   | 0   | 0   | 1   | 0  | 1  | 0  |
| 3j  | 0  | 2  | 0  | 0  | 0  | 0  | 0  | 0  | 0  | 0   | 0   | 0   | 0   | 1  | 1  | 0  |
| 3k  | 0  | 2  | 0  | 0  | 0  | 0  | 0  | 0  | 0  | 0   | 0   | 0   | 0   | 1  | 3  | 0  |
| 3l  | 0  | 1  | 0  | 0  | 0  | 1  | 0  | 0  | 0  | 0   | 0   | 0   | 0   | 1  | 4  | 0  | 2 |
| 3m  | 0  | 1  | 0  | 0  | 0  | 1  | 1  | 0  | 0  | 0   | 0   | 0   | 1   | 2  | 2  | 0  | 2 |
| 3n  | 0  | 0  | 0  | 0  | 0  | 0  | 1  | 0  | 0  | 0   | 0   | 0   | 0   | 1  | 1  | 0  | 0 |
| 3o  | 0  | 0  | 0  | 0  | 0  | 2  | 1  | 0  | 0  | 0   | 0   | 0   | 0   | 1  | 0  | 0  |
| 3p  | 0  | 0  | 0  | 0  | 0  | 0  | 0  | 0  | 0  | 0   | 0   | 0   | 0   | 2  | 2  | 1  | 0 |
| 3q  | 0  | 2  | 0  | 0  | 0  | 1  | 3  | 0  | 0  | 0   | 0   | 0   | 0   | 2  | 4  | 0  | 0 |
| 3r  | 0  | 5  | 0  | 1  | 0  | 1  | 0  | 0  | 0  | 0   | 0   | 0   | 0   | 1  | 1  | 0  | 1 |
| 3s  | 2  | 1  | 0  | 1  | 0  | 1  | 0  | 4  | 1  | 0   | 5   | 3   | 6   | 0  | 9  | 0  |
| 3t  | 0  | 0  | 0  | 0  | 0  | 0  | 0  | 0  | 0  | 0   | 0   | 0   | 0   | 3  | 2  | 0  | 0 |
| 3u  | 0  | 1  | 0  | 1  | 0  | 0  | 0  | 0  | 0  | 0   | 0   | 0   | 0   | 2  | 2  | 0  | 2 |
| 3v  | 0  | 0  | 0  | 1  | 0  | 1  | 0  | 2  | 0  | 0   | 0   | 0   | 0   | 2  | 4  | 0  | 0 |
| 3w  | 0  | 0  | 0  | 0  | 0  | 0  | 1  | 0  | 0  | 0   | 0   | 0   | 0   | 6  | 3  | 0  | 0 |
| 3x  | 0  | 0  | 0  | 0  | 0  | 0  | 1  | 0  | 0  | 0   | 0   | 0   | 0   | 1  | 1  | 0  | 0 |
| 3y  | 0  | 0  | 0  | 0  | 1  | 0  | 0  | 0  | 1  | 0   | 0   | 0   | 0   | 0  | 2  | 10 | 0 |
| 3z  | 0  | 0  | 0  | 0  | 0  | 0  | 0  | 0  | 0  | 0   | 0   | 0   | 0   | 0  | 1  | 0  | 0 |
| 3ww | 0  | 0  | 0  | 0  | 0  | 0  | 0  | 0  | 0  | 0   | 0   | 0   | 0   | 0  | 0  | 0  | 0 |
| 3xx | 0  | 0  | 0  | 0  | 0  | 0  | 0  | 0  | 0  | 0   | 0   | 0   | 0   | 0  | 0  | 0  | 0 |
| 3yy | 0  | 0  | 0  | 0  | 0  | 0  | 0  | 0  | 0  | 0   | 0   | 0   | 0   | 0  | 1  | 0  | 0 |
| 3zz | 0  | 0  | 0  | 0  | 0  | 0  | 0  | 0  | 0  | 0   | 0   | 0   | 0   | 0  | 0  | 0  | 0 |

FIG. 13
(Continued)

|     | 3d | 3e | 3f | 3g | 3h | 3i | 3j | 3k | 3l | 3m | 3n | 3o | 3p | 3q | 3r | 3s |
|-----|----|----|----|----|----|----|----|----|----|----|----|----|----|----|----|----|
| 2r  | 0  | 0  | 0  | 0  | 0  | 0  | 0  | 0  | 0  | 0  | 0  | 1  | 0  | 0  | 2  | 0  | 0 |
| 2s  | 6  | 0  | 0  | 0  | 19 | 0  | 1  | 2  | 0  | 1  | 0  | 5  | 4  | 2  | 1  | 0  |
| 2t  | 0  | 0  | 0  | 0  | 3  | 3  | 0  | 0  | 0  | 0  | 0  | 2  | 0  | 11 | 3  | 0  |
| 2u  | 0  | 0  | 1  | 0  | 3  | 0  | 0  | 1  | 0  | 0  | 0  | 1  | 0  | 2  | 4  | 0  |
| 2v  | 0  | 0  | 0  | 0  | 3  | 0  | 0  | 0  | 0  | 0  | 0  | 0  | 0  | 2  | 1  | 0  |
| 2w  | 9  | 0  | 0  | 0  | 7  | 0  | 1  | 0  | 0  | 0  | 0  | 1  | 0  | 7  | 4  | 1  |
| 2x  | 11 | 4  | 52 | 2  | 43 | 21 | 36 | 97 | 0  | 67 | 5  | 10 | 28 | 27 | 22 | 18 |
| 2y  | 36 | 7  | 21 | 8  | 71 | 18 | 41 | 49 | 11 | 33 | 32 | 58 | 23 | 68 | 63 | 16 |
| 2z  | 0  | 1  | 1  | 0  | 49 | 3  | 0  | 0  | 0  | 0  | 0  | 0  | 38 | 1  | 4  | 6  |
| 2ww | 2  | 3  | 8  | 2  | 54 | 9  | 1  | 3  | 1  | 2  | 3  | 9  | 27 | 3  | 12 | 13 |
| 2xx | 0  | 0  | 0  | 0  | 0  | 0  | 0  | 0  | 0  | 0  | 0  | 2  | 0  | 0  | 1  | 0  |
| 2yy | 2  | 0  | 0  | 0  | 3  | 0  | 0  | 0  | 0  | 0  | 0  | 0  | 0  | 0  | 3  | 0  |
| 2zz | 0  | 0  | 0  | 1  | 0  | 0  | 0  | 0  | 0  | 0  | 1  | 1  | 0  | 0  | 0  | 0  |
| 3a  | 0  | 10 | 0  | 0  | 0  | 0  | 0  | 2  | 0  | 0  | 2  | 3  | 1  | 0  | 1  | 0  |
| 3b  | 0  | 4  | 0  | 1  | 2  | 0  | 0  | 0  | 0  | 0  | 0  | 5  | 6  | 0  | 0  | 0  |
| 3c  | 0  | 0  | 0  | 2  | 1  | 0  | 0  | 0  | 0  | 0  | 0  | 1  | 1  | 0  | 0  | 0  |
| 3d  | 86 | 0  | 0  | 0  | 0  | 0  | 0  | 0  | 0  | 0  | 0  | 2  | 2  | 0  | 0  | 0  |
| 3e  | 0  | 76 | 0  | 6  | 0  | 0  | 0  | 0  | 0  | 0  | 1  | 1  | 4  | 2  | 0  | 2  | 0 |
| 3f  | 0  | 0  | 89 | 0  | 0  | 0  | 0  | 0  | 0  | 0  | 0  | 1  | 2  | 0  | 0  | 0  |
| 3g  | 0  | 0  | 0  | 96 | 0  | 0  | 0  | 0  | 0  | 0  | 0  | 2  | 3  | 0  | 0  | 0  |
| 3h  | 0  | 0  | 0  | 0  | 99 | 0  | 0  | 0  | 0  | 0  | 1  | 1  | 3  | 0  | 2  | 0  |
| 3i  | 17 | 0  | 0  | 0  | 0  | 80 | 0  | 1  | 0  | 1  | 16 | 2  | 0  | 5  | 0  | 7  |
| 3j  | 0  | 0  | 0  | 0  | 0  | 0  | 83 | 0  | 0  | 0  | 0  | 1  | 0  | 0  | 3  | 0  |
| 3k  | 0  | 0  | 0  | 0  | 0  | 0  | 0  | 95 | 0  | 0  | 0  | 3  | 0  | 0  | 1  | 0  |
| 3l  | 0  | 0  | 0  | 0  | 1  | 0  | 0  | 0  | 84 | 0  | 1  | 1  | 0  | 2  | 0  | 0  |
| 3m  | 0  | 0  | 0  | 1  | 1  | 0  | 0  | 0  | 0  | 90 | 1  | 2  | 0  | 2  | 1  | 0  |
| 3n  | 0  | 0  | 0  | 0  | 1  | 0  | 0  | 0  | 0  | 0  | 93 | 1  | 0  | 0  | 0  | 0  |
| 3o  | 0  | 0  | 0  | 2  | 1  | 0  | 0  | 0  | 0  | 0  | 1  | 97 | 0  | 0  | 0  | 1  |
| 3p  | 0  | 8  | 0  | 3  | 0  | 0  | 0  | 0  | 0  | 0  | 0  | 2  | 78 | 1  | 0  | 1  |
| 3q  | 0  | 0  | 0  | 1  | 3  | 0  | 0  | 0  | 0  | 0  | 2  | 4  | 0  | 99 | 0  | 0  |
| 3r  | 0  | 1  | 0  | 2  | 4  | 0  | 0  | 15 | 0  | 0  | 1  | 1  | 0  | 1  | 99 | 0  |
| 3s  | 1  | 1  | 0  | 1  | 0  | 12 | 0  | 2  | 8  | 3  | 6  | 1  | 19 | 9  | 0  | 91 |
| 3t  | 0  | 0  | 0  | 0  | 0  | 0  | 0  | 0  | 0  | 0  | 0  | 3  | 2  | 0  | 0  | 0  |
| 3u  | 0  | 1  | 0  | 0  | 0  | 0  | 0  | 0  | 0  | 0  | 0  | 2  | 2  | 0  | 2  | 1  | 0 |
| 3v  | 0  | 1  | 0  | 1  | 0  | 2  | 0  | 0  | 0  | 0  | 0  | 2  | 4  | 0  | 0  | 0  |
| 3w  | 0  | 0  | 0  | 0  | 1  | 0  | 0  | 0  | 0  | 0  | 0  | 6  | 3  | 0  | 3  | 0  |
| 3x  | 0  | 0  | 0  | 0  | 1  | 0  | 0  | 0  | 0  | 0  | 0  | 1  | 1  | 0  | 0  | 0  |
| 3y  | 0  | 0  | 1  | 0  | 0  | 0  | 1  | 0  | 0  | 0  | 0  | 2  | 10 | 0  | 0  | 0  |
| 3z  | 0  | 0  | 0  | 0  | 0  | 0  | 0  | 0  | 0  | 0  | 0  | 1  | 0  | 0  | 0  | 0  |
| 3ww | 0  | 0  | 0  | 0  | 0  | 0  | 0  | 0  | 0  | 0  | 0  | 0  | 0  | 0  | 0  | 0  |
| 3xx | 0  | 0  | 0  | 0  | 0  | 0  | 0  | 0  | 0  | 0  | 0  | 0  | 0  | 0  | 20 | 0  |
| 3yy | 0  | 0  | 0  | 0  | 0  | 0  | 0  | 0  | 0  | 0  | 0  | 1  | 0  | 0  | 0  | 0  |
| 3zz | 0  | 0  | 0  | 0  | 0  | 0  | 0  | 0  | 0  | 0  | 0  | 0  | 0  | 0  | 0  | 0  |

FIG. 13
(Continued)

|     | 3t | 3u | 3v | 3w | 3x | 3y | 3z | 3ww | 3xx | 3yy | 3zz | 4a | 4b | 4c | 4d | 4e |
|-----|----|----|----|----|----|----|----|----|----|----|----|----|----|----|----|----|
| 2r  | 0  | 0  | 0  | 0  | 1  | 2  | 0  | 0  | 0  | 1  | 1  | 0  | 0  | 0  | 2  | 0  |
| 2s  | 0  | 2  | 0  | 14 | 0  | 4  | 0  | 1  | 0  | 1  | 2  | 2  | 2  | 7  | 2  | 0  |
| 2t  | 11 | 4  | 0  | 10 | 0  | 0  | 0  | 0  | 0  | 1  | 0  | 1  | 0  | 1  | 0  | 0  |
| 2u  | 0  | 0  | 4  | 9  | 0  | 2  | 0  | 0  | 0  | 1  | 1  | 1  | 0  | 1  | 0  | 0  |
| 2v  | 0  | 0  | 0  | 10 | 2  | 2  | 0  | 1  | 0  | 0  | 1  | 1  | 0  | 2  | 0  | 0  |
| 2w  | 3  | 2  | 0  | 17 | 0  | 6  | 1  | 1  | 3  | 2  | 1  | 16 | 0  | 0  | 0  | 0  |
| 2x  | 29 | 93 | 99 | 88 | 82 | 79 | 53 | 56 | 1  | 21 | 53 | 23 | 0  | 8  | 11 | 4  |
| 2y  | 26 | 75 | 96 | 99 | 45 | 99 | 41 | 30 | 18 | 46 | 61 | 34 | 8  | 18 | 36 | 7  |
| 2z  | 1  | 0  | 6  | 16 | 2  | 64 | 2  | 3  | 0  | 0  | 6  | 0  | 0  | 1  | 0  | 1  |
| 2ww | 23 | 12 | 63 | 61 | 13 | 99 | 8  | 82 | 0  | 0  | 86 | 0  | 1  | 6  | 3  | 3  |
| 2xx | 0  | 0  | 1  | 4  | 0  | 2  | 0  | 0  | 0  | 0  | 0  | 0  | 0  | 0  | 0  | 0  |
| 2yy | 0  | 0  | 4  | 6  | 0  | 0  | 0  | 0  | 0  | 0  | 0  | 0  | 0  | 0  | 2  | 0  |
| 2zz | 0  | 0  | 3  | 4  | 0  | 0  | 0  | 0  | 0  | 1  | 0  | 0  | 2  | 0  | 0  | 0  |
| 3a  | 0  | 2  | 0  | 1  | 0  | 0  | 0  | 0  | 0  | 0  | 0  | 0  | 1  | 0  | 0  | 0  |
| 3b  | 0  | 0  | 0  | 0  | 0  | 0  | 0  | 0  | 0  | 0  | 0  | 0  | 5  | 0  | 0  | 4  |
| 3c  | 0  | 0  | 0  | 11 | 3  | 0  | 0  | 0  | 0  | 0  | 0  | 0  | 0  | 0  | 0  | 0  |
| 3d  | 0  | 0  | 0  | 5  | 0  | 0  | 0  | 0  | 0  | 0  | 0  | 0  | 0  | 0  | 0  | 0  |
| 3e  | 0  | 0  | 0  | 5  | 0  | 0  | 1  | 0  | 0  | 0  | 0  | 0  | 0  | 0  | 0  | 0  |
| 3f  | 0  | 5  | 0  | 0  | 0  | 0  | 0  | 0  | 0  | 0  | 0  | 0  | 0  | 0  | 0  | 0  |
| 3g  | 0  | 0  | 0  | 9  | 0  | 0  | 0  | 0  | 0  | 0  | 0  | 0  | 0  | 2  | 0  | 0  |
| 3h  | 0  | 3  | 2  | 0  | 0  | 0  | 1  | 0  | 0  | 0  | 0  | 0  | 0  | 2  | 0  | 0  |
| 3i  | 0  | 7  | 24 | 43 | 0  | 0  | 1  | 0  | 0  | 0  | 0  | 0  | 2  | 2  | 0  | 0  |
| 3j  | 0  | 3  | 0  | 1  | 0  | 0  | 5  | 1  | 0  | 0  | 0  | 0  | 0  | 2  | 0  | 0  |
| 3k  | 0  | 0  | 2  | 7  | 0  | 0  | 0  | 0  | 0  | 0  | 0  | 0  | 0  | 2  | 0  | 0  |
| 3l  | 0  | 2  | 3  | 0  | 0  | 0  | 0  | 0  | 0  | 0  | 0  | 0  | 0  | 1  | 0  | 0  |
| 3m  | 0  | 0  | 3  | 1  | 0  | 0  | 0  | 0  | 0  | 0  | 0  | 0  | 0  | 1  | 0  | 0  |
| 3n  | 0  | 0  | 2  | 0  | 0  | 0  | 0  | 0  | 0  | 0  | 0  | 0  | 0  | 0  | 0  | 0  |
| 3o  | 0  | 0  | 2  | 4  | 0  | 0  | 0  | 0  | 0  | 0  | 0  | 0  | 0  | 0  | 0  | 0  |
| 3p  | 0  | 0  | 2  | 0  | 0  | 0  | 0  | 9  | 0  | 0  | 0  | 0  | 8  | 0  | 0  | 0  |
| 3q  | 0  | 0  | 0  | 0  | 0  | 0  | 0  | 0  | 0  | 0  | 0  | 0  | 0  | 2  | 0  | 0  |
| 3r  | 0  | 0  | 0  | 2  | 0  | 0  | 0  | 0  | 6  | 0  | 0  | 0  | 0  | 5  | 0  | 1  |
| 3s  | 0  | 0  | 0  | 63 | 0  | 0  | 10 | 0  | 0  | 0  | 0  | 4  | 2  | 0  | 1  | 1  |
| 3t  | 90 | 0  | 0  | 2  | 0  | 0  | 0  | 0  | 0  | 0  | 0  | 0  | 0  | 0  | 0  | 0  |
| 3u  | 0  | 99 | 0  | 3  | 0  | 0  | 0  | 0  | 0  | 0  | 0  | 0  | 0  | 1  | 0  | 1  |
| 3v  | 0  | 2  | 99 | 0  | 0  | 0  | 0  | 0  | 0  | 0  | 0  | 0  | 0  | 0  | 0  | 1  |
| 3w  | 0  | 1  | 1  | 99 | 0  | 0  | 0  | 0  | 0  | 0  | 0  | 0  | 0  | 0  | 0  | 0  |
| 3x  | 0  | 0  | 0  | 0  | 89 | 0  | 0  | 0  | 0  | 0  | 0  | 0  | 0  | 0  | 0  | 0  |
| 3y  | 0  | 1  | 0  | 0  | 3  | 96 | 1  | 1  | 0  | 0  | 1  | 0  | 0  | 0  | 0  | 0  |
| 3z  | 0  | 3  | 1  | 0  | 0  | 1  | 93 | 0  | 0  | 0  | 0  | 0  | 0  | 0  | 0  | 0  |
| 3ww | 0  | 0  | 0  | 0  | 0  | 1  | 0  | 89 | 0  | 0  | 0  | 0  | 0  | 0  | 0  | 0  |
| 3xx | 0  | 0  | 0  | 0  | 0  | 2  | 1  | 0  | 75 | 0  | 0  | 0  | 0  | 0  | 0  | 0  |
| 3yy | 0  | 0  | 0  | 0  | 0  | 2  | 0  | 0  | 0  | 94 | 0  | 0  | 0  | 0  | 0  | 0  |
| 3zz | 0  | 7  | 5  | 0  | 0  | 1  | 0  | 0  | 0  | 4  | 74 | 0  | 0  | 0  | 0  | 0  |

FIG. 13
(Continued)

|     | 4f | 4g | 4h | 4i | 4j | 4k | 4l | 4m | 4n | 4o | 4p | 4q | 4r | 4s | 4t | 4u |
|-----|----|----|----|----|----|----|----|----|----|----|----|----|----|----|----|----|
| 2r  | 0  | 0  | 0  | 0  | 0  | 0  | 0  | 0  | 1  | 0  | 0  | 2  | 0  | 0  | 0  | 1  |
| 2s  | 0  | 0  | 4  | 1  | 1  | 2  | 0  | 1  | 1  | 0  | 4  | 0  | 0  | 0  | 0  | 3  |
| 2t  | 0  | 0  | 3  | 3  | 0  | 0  | 0  | 0  | 0  | 2  | 0  | 0  | 3  | 0  | 0  | 0  |
| 2u  | 1  | 0  | 3  | 0  | 0  | 1  | 0  | 0  | 0  | 1  | 0  | 2  | 0  | 0  | 0  | 1  |
| 2v  | 0  | 0  | 3  | 0  | 0  | 0  | 0  | 0  | 0  | 0  | 0  | 2  | 1  | 0  | 0  | 3  |
| 2w  | 0  | 0  | 3  | 2  | 0  | 2  | 0  | 0  | 2  | 0  | 0  | 0  | 0  | 0  | 0  | 6  |
| 2x  | 52 | 2  | 43 | 21 | 36 | 97 | 0  | 67 | 5  | 10 | 28 | 27 | 22 | 18 | 29 | 82 |
| 2y  | 21 | 8  | 71 | 18 | 41 | 49 | 11 | 33 | 32 | 58 | 23 | 68 | 63 | 16 | 26 | 75 |
| 2z  | 1  | 2  | 1  | 3  | 0  | 0  | 0  | 0  | 0  | 0  | 1  | 0  | 4  | 6  | 1  | 2  |
| 2ww | 9  | 1  | 6  | 3  | 3  | 5  | 2  | 2  | 3  | 18 | 27 | 2  | 21 | 13 | 23 | 49 |
| 2xx | 0  | 0  | 0  | 0  | 0  | 0  | 0  | 0  | 0  | 2  | 0  | 0  | 1  | 0  | 0  | 0  |
| 2yy | 0  | 0  | 3  | 0  | 0  | 0  | 0  | 0  | 0  | 0  | 0  | 0  | 3  | 0  | 0  | 0  |
| 2zz | 0  | 1  | 0  | 0  | 0  | 0  | 0  | 0  | 1  | 1  | 0  | 0  | 0  | 0  | 0  | 0  |
| 3a  | 0  | 0  | 0  | 0  | 0  | 2  | 0  | 0  | 2  | 3  | 1  | 0  | 1  | 0  | 0  | 0  |
| 3b  | 0  | 1  | 2  | 0  | 0  | 0  | 0  | 0  | 5  | 6  | 0  | 0  | 0  | 0  | 0  | 0  |
| 3c  | 0  | 2  | 1  | 0  | 0  | 0  | 0  | 0  | 1  | 1  | 0  | 0  | 0  | 0  | 0  | 0  |
| 3d  | 0  | 0  | 0  | 0  | 0  | 0  | 0  | 0  | 0  | 0  | 0  | 0  | 0  | 0  | 0  | 0  |
| 3e  | 0  | 0  | 3  | 0  | 0  | 0  | 0  | 1  | 1  | 4  | 2  | 0  | 2  | 0  | 0  | 0  |
| 3f  | 0  | 0  | 0  | 0  | 0  | 0  | 0  | 0  | 1  | 2  | 0  | 0  | 0  | 0  | 0  | 5  |
| 3g  | 0  | 0  | 1  | 0  | 0  | 0  | 0  | 0  | 2  | 3  | 0  | 0  | 0  | 0  | 0  | 0  |
| 3h  | 0  | 0  | 0  | 0  | 0  | 0  | 0  | 1  | 1  | 3  | 0  | 0  | 2  | 0  | 0  | 3  |
| 3i  | 0  | 0  | 0  | 6  | 0  | 0  | 0  | 1  | 5  | 0  | 0  | 0  | 2  | 0  | 0  | 0  |
| 3j  | 0  | 0  | 0  | 0  | 0  | 0  | 0  | 0  | 1  | 0  | 0  | 0  | 3  | 0  | 0  | 2  |
| 3k  | 0  | 0  | 0  | 0  | 0  | 0  | 0  | 1  | 3  | 0  | 0  | 0  | 1  | 0  | 0  | 0  |
| 3l  | 0  | 0  | 1  | 0  | 0  | 0  | 1  | 0  | 2  | 4  | 0  | 2  | 0  | 0  | 0  | 2  |
| 3m  | 0  | 1  | 1  | 0  | 0  | 0  | 0  | 2  | 2  | 3  | 0  | 2  | 1  | 0  | 0  | 0  |
| 3n  | 0  | 0  | 1  | 0  | 0  | 0  | 0  | 0  | 0  | 1  | 0  | 0  | 0  | 0  | 0  | 0  |
| 3o  | 0  | 2  | 1  | 0  | 0  | 0  | 0  | 0  | 0  | 0  | 0  | 0  | 0  | 1  | 0  | 0  |
| 3p  | 0  | 0  | 1  | 0  | 0  | 0  | 0  | 0  | 0  | 0  | 3  | 1  | 0  | 1  | 0  | 0  |
| 3q  | 0  | 1  | 3  | 0  | 0  | 0  | 0  | 0  | 2  | 0  | 0  | 1  | 1  | 0  | 0  | 0  |
| 3r  | 0  | 1  | 1  | 0  | 0  | 0  | 0  | 0  | 1  | 1  | 0  | 1  | 1  | 0  | 0  | 0  |
| 3s  | 0  | 1  | 0  | 0  | 1  | 5  | 0  | 3  | 1  | 0  | 1  | 0  | 6  | 0  | 0  | 1  |
| 3t  | 0  | 0  | 0  | 0  | 0  | 0  | 0  | 0  | 3  | 2  | 0  | 0  | 0  | 0  | 2  | 2  |
| 3u  | 0  | 0  | 0  | 0  | 0  | 0  | 0  | 0  | 2  | 2  | 0  | 2  | 1  | 0  | 0  | 0  |
| 3v  | 0  | 1  | 0  | 2  | 0  | 0  | 0  | 0  | 2  | 4  | 0  | 0  | 0  | 0  | 0  | 0  |
| 3w  | 0  | 0  | 1  | 0  | 0  | 0  | 0  | 0  | 6  | 3  | 0  | 0  | 3  | 0  | 0  | 0  |
| 3x  | 0  | 0  | 1  | 0  | 0  | 0  | 0  | 0  | 1  | 1  | 0  | 0  | 0  | 0  | 0  | 0  |
| 3y  | 1  | 0  | 0  | 0  | 1  | 0  | 0  | 0  | 0  | 0  | 5  | 0  | 0  | 0  | 0  | 0  |
| 3z  | 0  | 0  | 0  | 0  | 0  | 0  | 0  | 0  | 1  | 0  | 0  | 0  | 0  | 0  | 0  | 1  |
| 3ww | 0  | 0  | 0  | 0  | 0  | 0  | 0  | 0  | 0  | 0  | 0  | 0  | 0  | 0  | 0  | 0  |
| 3xx | 0  | 0  | 0  | 0  | 0  | 0  | 0  | 0  | 0  | 0  | 0  | 0  | 0  | 0  | 0  | 0  |
| 3yy | 0  | 0  | 0  | 0  | 0  | 0  | 0  | 0  | 0  | 1  | 0  | 0  | 0  | 0  | 0  | 2  |
| 3zz | 0  | 0  | 0  | 0  | 0  | 0  | 0  | 0  | 0  | 0  | 0  | 0  | 0  | 0  | 0  | 7  |

FIG. 13
(Continued)

|     | 4v | 4w | 4x | 4y | 4z | 4ww | 4xx | 4yy | 4zz |
|-----|----|----|----|----|----|----|----|----|----|
| 2r  | 0  | 0  | 1  | 2  | 0  | 0  | 0  | 1  | 0  |
| 2s  | 5  | 0  | 0  | 4  | 0  | 1  | 0  | 1  | 2  |
| 2t  | 0  | 0  | 0  | 0  | 0  | 0  | 0  | 1  | 0  |
| 2u  | 4  | 1  | 0  | 2  | 0  | 0  | 0  | 1  | 1  |
| 2v  | 0  | 1  | 2  | 2  | 0  | 1  | 0  | 0  | 0  |
| 2w  | 2  | 5  | 1  | 7  | 21 | 1  | 3  | 0  | 0  |
| 2x  | 99 | 85 | 96 | 79 | 53 | 56 | 1  | 21 | 53 |
| 2y  | 96 | 99 | 45 | 48 | 41 | 30 | 18 | 46 | 61 |
| 2z  | 1  | 2  | 2  | 7  | 0  | 3  | 0  | 1  | 3  |
| 2ww | 2  | 61 | 15 | 99 | 0  | 86 | 0  | 4  | 89 |
| 2xx | 1  | 4  | 0  | 0  | 0  | 0  | 0  | 0  | 0  |
| 2yy | 4  | 6  | 0  | 0  | 0  | 0  | 0  | 0  | 0  |
| 2zz | 3  | 0  | 0  | 0  | 0  | 0  | 0  | 1  | 0  |
| 3a  | 0  | 1  | 0  | 0  | 0  | 0  | 0  | 0  | 0  |
| 3b  | 0  | 1  | 0  | 0  | 0  | 0  | 0  | 0  | 0  |
| 3c  | 0  | 3  | 0  | 0  | 0  | 0  | 0  | 0  | 0  |
| 3d  | 0  | 5  | 0  | 0  | 0  | 0  | 0  | 0  | 0  |
| 3e  | 4  | 2  | 0  | 0  | 1  | 0  | 0  | 0  | 0  |
| 3f  | 0  | 0  | 0  | 0  | 0  | 0  | 0  | 0  | 0  |
| 3g  | 0  | 7  | 0  | 0  | 0  | 0  | 0  | 0  | 0  |
| 3h  | 2  | 0  | 0  | 0  | 1  | 0  | 0  | 0  | 0  |
| 3i  | 0  | 2  | 0  | 0  | 1  | 0  | 0  | 3  | 0  |
| 3j  | 0  | 1  | 0  | 0  | 0  | 1  | 0  | 0  | 0  |
| 3k  | 2  | 7  | 0  | 0  | 0  | 0  | 0  | 0  | 0  |
| 3l  | 3  | 0  | 0  | 0  | 0  | 0  | 0  | 0  | 0  |
| 3m  | 3  | 1  | 0  | 0  | 0  | 0  | 0  | 0  | 0  |
| 3n  | 2  | 0  | 0  | 0  | 0  | 0  | 0  | 0  | 0  |
| 3o  | 2  | 4  | 0  | 0  | 0  | 0  | 0  | 0  | 0  |
| 3p  | 0  | 0  | 0  | 0  | 0  | 0  | 0  | 0  | 0  |
| 3q  | 0  | 0  | 0  | 0  | 0  | 0  | 0  | 0  | 0  |
| 3r  | 0  | 0  | 0  | 0  | 0  | 0  | 6  | 0  | 0  |
| 3s  | 0  | 0  | 0  | 0  | 1  | 0  | 0  | 0  | 0  |
| 3t  | 2  | 7  | 0  | 0  | 0  | 0  | 0  | 0  | 0  |
| 3u  | 0  | 3  | 0  | 0  | 0  | 0  | 0  | 0  | 0  |
| 3v  | 0  | 0  | 0  | 0  | 0  | 0  | 0  | 0  | 0  |
| 3w  | 0  | 4  | 1  | 0  | 0  | 0  | 0  | 0  | 0  |
| 3x  | 0  | 0  | 0  | 0  | 0  | 0  | 0  | 0  | 0  |
| 3y  | 0  | 0  | 3  | 0  | 1  | 1  | 0  | 0  | 1  |
| 3z  | 1  | 0  | 0  | 0  | 0  | 0  | 0  | 0  | 0  |
| 3ww | 0  | 0  | 0  | 0  | 0  | 0  | 0  | 0  | 0  |
| 3xx | 0  | 0  | 0  | 2  | 0  | 0  | 0  | 0  | 0  |
| 3yy | 0  | 0  | 0  | 2  | 0  | 0  | 0  | 0  | 0  |
| 3zz | 5  | 0  | 0  | 1  | 0  | 0  | 0  | 0  | 0  |

FIG. 13
(Continued)

|    | 1a | 1b | 1c | 1d | 1e | 1f | 1i | 1j | 1k | 1l | 1m | 1n | 1o | 1p | 1q | 1r | 1s | 1t | 1v | 1z | 1ww | 1xx | 1yy | 2a |
|----|----|----|----|----|----|----|----|----|----|----|----|----|----|----|----|----|----|----|----|----|-----|-----|-----|----|
| 1a | 91 | 0 | 1 | 0 | 0 | 0 | 1 | 0 | 0 | 0 | 2 | 0 | 5 | 0 | 0 | 4 | 0 | 0 | 1 | 0 | 0 | 0 | 0 | 0 |
| 1b | 0 | 87 | 0 | 0 | 0 | 1 | 0 | 1 | 0 | 0 | 0 | 0 | 5 | 0 | 0 | 4 | 0 | 0 | 0 | 0 | 0 | 0 | 1 | 0 |
| 1c | 0 | 1 | 99 | 0 | 0 | 1 | 1 | 0 | 0 | 0 | 0 | 0 | 1 | 0 | 2 | 1 | 1 | 0 | 1 | 0 | 0 | 0 | 0 | 0 |
| 1d | 0 | 0 | 0 | 57 | 0 | 1 | 0 | 5 | 0 | 0 | 0 | 0 | 2 | 0 | 0 | 4 | 0 | 0 | 0 | 0 | 0 | 0 | 1 | 0 |
| 1e | 0 | 0 | 0 | 0 | 90 | 0 | 0 | 0 | 0 | 0 | 0 | 0 | 2 | 0 | 0 | 3 | 0 | 0 | 0 | 0 | 0 | 0 | 1 | 0 |
| 1f | 0 | 2 | 0 | 0 | 0 | 82 | 0 | 0 | 0 | 0 | 0 | 0 | 1 | 2 | 0 | 4 | 0 | 0 | 1 | 0 | 0 | 0 | 3 | 0 |
| 1i | 2 | 0 | 3 | 1 | 0 | 1 | 92 | 1 | 3 | 0 | 1 | 4 | 6 | 0 | 0 | 2 | 2 | 0 | 3 | 1 | 0 | 0 | 4 | 2 |
| 1j | 0 | 0 | 0 | 1 | 0 | 0 | 0 | 75 | 0 | 0 | 0 | 0 | 1 | 0 | 0 | 2 | 0 | 0 | 0 | 0 | 0 | 0 | 1 | 0 |
| 1k | 0 | 1 | 1 | 7 | 1 | 0 | 0 | 2 | 82 | 0 | 0 | 0 | 1 | 0 | 0 | 3 | 0 | 1 | 0 | 0 | 0 | 0 | 1 | 0 |
| 1l | 1 | 1 | 2 | 0 | 1 | 0 | 0 | 0 | 0 | 83 | 0 | 0 | 3 | 0 | 0 | 2 | 0 | 0 | 5 | 1 | 0 | 0 | 0 | 0 |
| 1m | 0 | 0 | 2 | 0 | 6 | 0 | 1 | 0 | 0 | 0 | 99 | 7 | 3 | 0 | 1 | 6 | 1 | 0 | 0 | 0 | 0 | 0 | 0 | 0 |
| 1n | 0 | 0 | 0 | 0 | 0 | 1 | 0 | 0 | 0 | 0 | 3 | 99 | 1 | 0 | 1 | 2 | 0 | 0 | 0 | 0 | 1 | 0 | 1 | 0 |
| 1o | 4 | 2 | 4 | 3 | 0 | 1 | 4 | 0 | 7 | 1 | 0 | 7 | 33 | 4 | 2 | 4 | 4 | 1 | 2 | 1 | 2 | 0 | 6 | 4 |
| 1p | 0 | 0 | 3 | 0 | 1 | 6 | 0 | 0 | 6 | 0 | 0 | 0 | 3 | 70 | 1 | 0 | 0 | 0 | 2 | 5 | 4 | 0 | 7 | 0 |
| 1q | 0 | 0 | 0 | 0 | 0 | 1 | 0 | 0 | 1 | 0 | 4 | 1 | 1 | 2 | 99 | 0 | 0 | 0 | 2 | 1 | 4 | 0 | 0 | 0 |
| 1r | 0 | 0 | 0 | 0 | 0 | 23 | 4 | 0 | 2 | 4 | 1 | 2 | 3 | 0 | 5 | 99 | 0 | 0 | 5 | 0 | 0 | 0 | 3 | 0 |
| 1s | 1 | 1 | 3 | 2 | 0 | 0 | 0 | 0 | 0 | 0 | 7 | 0 | 2 | 0 | 2 | 1 | 95 | 0 | 2 | 0 | 0 | 0 | 1 | 1 |
| 1t | 0 | 0 | 0 | 3 | 7 | 0 | 0 | 0 | 0 | 0 | 0 | 1 | 4 | 0 | 1 | 0 | 0 | 99 | 5 | 5 | 0 | 0 | 0 | 0 |
| 1v | 1 | 7 | 0 | 0 | 2 | 1 | 2 | 0 | 2 | 3 | 1 | 2 | 1 | 0 | 5 | 3 | 1 | 0 | 99 | 1 | 0 | 0 | 0 | 1 |
| 1z | 3 | 5 | 6 | 0 | 0 | 0 | 0 | 0 | 2 | 0 | 0 | 0 | 2 | 0 | 1 | 1 | 0 | 0 | 0 | 87 | 0 | 0 | 0 | 3 |
| 1ww | 0 | 0 | 2 | 0 | 0 | 0 | 0 | 0 | 0 | 0 | 0 | 0 | 0 | 0 | 0 | 1 | 0 | 0 | 0 | 1 | 19 | 0 | 0 | 0 |
| 1xx | 0 | 0 | 2 | 0 | 0 | 0 | 0 | 0 | 0 | 0 | 0 | 4 | 0 | 0 | 0 | 0 | 1 | 0 | 0 | 0 | 0 | 81 | 0 | 0 |
| 1yy | 0 | 0 | 0 | 0 | 4 | 0 | 0 | 0 | 0 | 0 | 1 | 0 | 2 | 0 | 3 | 1 | 7 | 0 | 3 | 3 | 1 | 0 | 31 | 0 |
| 2a | 0 | 0 | 0 | 0 | 0 | 0 | 0 | 0 | 0 | 0 | 0 | 0 | 2 | 0 | 5 | 0 | 0 | 0 | 0 | 0 | 0 | 0 | 0 | 99 |
| 2b | 0 | 0 | 0 | 0 | 0 | 0 | 0 | 0 | 0 | 0 | 0 | 0 | 4 | 0 | 0 | 0 | 0 | 0 | 0 | 0 | 0 | 0 | 0 | 0 |
| 2c | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 2d | 0 | 0 | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| 2e | 0 | 0 | 0 | 0 | 0 | 0 | 0 | 0 | 0 | 0 | 0 | 0 | 2 | 0 | 0 | 0 | 0 | 0 | 0 | 0 | 0 | 0 | 0 | 0 |
| 2f | 0 | 0 | 3 | 0 | 1 | 0 | 0 | 0 | 0 | 0 | 0 | 0 | 5 | 0 | 1 | 0 | 0 | 0 | 0 | 0 | 0 | 0 | 0 | 0 |
| 2g | 0 | 1 | 0 | 0 | 0 | 0 | 0 | 0 | 0 | 0 | 0 | 1 | 0 | 0 | 0 | 2 | 0 | 0 | 2 | 0 | 1 | 0 | 2 | 0 |
| 2h | 0 | 0 | 1 | 0 | 0 | 0 | 0 | 0 | 0 | 0 | 0 | 0 | 0 | 0 | 0 | 3 | 1 | 0 | 0 | 0 | 0 | 0 | 0 | 0 |
| 2i | 0 | 0 | 0 | 0 | 0 | 0 | 0 | 0 | 1 | 0 | 0 | 0 | 0 | 0 | 2 | 0 | 0 | 0 | 0 | 0 | 1 | 0 | 1 | 0 |
| 2j | 0 | 0 | 0 | 2 | 0 | 0 | 0 | 0 | 0 | 0 | 0 | 1 | 0 | 2 | 1 | 0 | 0 | 0 | 1 | 0 | 0 | 0 | 1 | 0 |
| 2k | 1 | 0 | 0 | 0 | 0 | 0 | 0 | 0 | 0 | 0 | 0 | 0 | 1 | 0 | 0 | 1 | 0 | 0 | 0 | 0 | 2 | 1 | 1 | 1 |
| 2m | 0 | 0 | 0 | 1 | 1 | 0 | 0 | 0 | 0 | 0 | 0 | 1 | 0 | 2 | 1 | 0 | 0 | 0 | 5 | 0 | 0 | 0 | 1 | 0 |
| 2n | 1 | 0 | 1 | 0 | 0 | 0 | 0 | 0 | 1 | 3 | 0 | 0 | 0 | 0 | 3 | 3 | 0 | 0 | 0 | 6 | 1 | 0 | 0 | 0 |
| 2o | 1 | 0 | 0 | 0 | 0 | 0 | 0 | 0 | 0 | 1 | 0 | 0 | 0 | 0 | 4 | 1 | 0 | 0 | 0 | 5 | 1 | 0 | 2 | 1 |
| 2q | 5 | 0 | 1 | 0 | 0 | 0 | 0 | 0 | 0 | 0 | 0 | 0 | 0 | 0 | 0 | 0 | 0 | 0 | 0 | 0 | 2 | 0 | 1 | 5 |
| 2r | 1 | 0 | 1 | 0 | 0 | 0 | 0 | 0 | 0 | 0 | 0 | 0 | 0 | 0 | 2 | 2 | 0 | 0 | 0 | 0 | 0 | 0 | 1 | 1 |

FIG. 14

| | 2b | 2c | 2d | 2e | 2f | 2g | 2h | 2i | 2j | 2k | 2m | 2n | 2o | 2q | 2r | 2s | 2t | 2u | 2v | 2w | 2z | 2xx | 2yy | 2zz |
|---|---|---|---|---|---|---|---|---|---|---|---|---|---|---|---|---|---|---|---|---|---|---|---|---|
| 1a | 1 | 0 | 0 | 0 | 0 | 0 | 2 | 1 | 0 | 0 | 2 | 0 | 5 | 0 | 4 | 0 | 0 | 0 | 1 | 4 | 0 | 0 | 1 | 0 |
| 1b | 0 | 3 | 0 | 0 | 1 | 0 | 0 | 0 | 1 | 0 | 0 | 0 | 5 | 0 | 4 | 0 | 0 | 1 | 0 | 0 | 0 | 0 | 1 | 0 |
| 1c | 0 | 1 | 0 | 0 | 1 | 0 | 1 | 0 | 0 | 0 | 0 | 0 | 1 | 2 | 6 | 1 | 0 | 0 | 4 | 1 | 0 | 0 | 0 | 0 |
| 1d | 0 | 0 | 0 | 1 | 0 | 0 | 0 | 0 | 5 | 0 | 0 | 0 | 1 | 0 | 4 | 0 | 0 | 0 | 0 | 0 | 0 | 0 | 1 | 0 |
| 1e | 0 | 0 | 0 | 0 | 1 | 0 | 0 | 0 | 0 | 0 | 0 | 0 | 2 | 0 | 3 | 0 | 0 | 0 | 0 | 3 | 0 | 0 | 1 | 0 |
| 1f | 2 | 0 | 3 | 0 | 0 | 3 | 0 | 0 | 0 | 0 | 0 | 1 | 2 | 0 | 4 | 0 | 0 | 0 | 0 | 5 | 1 | 0 | 3 | 0 |
| 1i | 0 | 3 | 1 | 0 | 1 | 1 | 3 | 6 | 2 | 0 | 1 | 1 | 7 | 0 | 5 | 2 | 0 | 4 | 5 | 3 | 1 | 0 | 4 | 1 |
| 1j | 0 | 0 | 1 | 0 | 0 | 1 | 0 | 0 | 0 | 0 | 0 | 0 | 1 | 0 | 2 | 0 | 0 | 1 | 0 | 7 | 0 | 0 | 1 | 0 |
| 1k | 1 | 1 | 7 | 1 | 1 | 0 | 0 | 0 | 1 | 3 | 0 | 1 | 0 | 3 | 0 | 1 | 0 | 0 | 1 | 0 | 0 | 0 | 1 | 0 |
| 1l | 1 | 2 | 0 | 1 | 0 | 0 | 0 | 0 | 0 | 0 | 0 | 0 | 3 | 0 | 2 | 0 | 0 | 1 | 5 | 5 | 1 | 0 | 2 | 0 |
| 1m | 0 | 0 | 0 | 0 | 1 | 0 | 0 | 0 | 0 | 0 | 0 | 7 | 3 | 1 | 6 | 1 | 0 | 4 | 3 | 1 | 0 | 0 | 1 | 0 |
| 1n | 0 | 0 | 0 | 0 | 1 | 0 | 1 | 0 | 0 | 0 | 3 | 5 | 0 | 0 | 2 | 0 | 0 | 0 | 0 | 0 | 0 | 0 | 1 | 0 |
| 1o | 2 | 4 | 2 | 0 | 3 | 1 | 4 | 6 | 0 | 6 | 1 | 3 | 1 | 5 | 2 | 2 | 1 | 0 | 1 | 6 | 1 | 0 | 6 | 1 |
| 1p | 0 | 0 | 0 | 1 | 6 | 0 | 1 | 0 | 0 | 6 | 4 | 0 | 3 | 1 | 1 | 0 | 0 | 0 | 5 | 2 | 5 | 0 | 7 | 0 |
| 1q | 0 | 0 | 0 | 0 | 1 | 0 | 1 | 0 | 0 | 1 | 6 | 1 | 1 | 3 | 5 | 0 | 0 | 0 | 2 | 2 | 1 | 0 | 0 | 0 |
| 1r | 3 | 0 | 0 | 0 | 1 | 2 | 0 | 4 | 0 | 2 | 1 | 2 | 3 | 5 | 5 | 0 | 0 | 2 | 5 | 0 | 0 | 0 | 3 | 0 |
| 1s | 1 | 3 | 2 | 0 | 0 | 1 | 7 | 0 | 0 | 1 | 0 | 0 | 2 | 0 | 2 | 1 | 0 | 2 | 4 | 2 | 1 | 0 | 1 | 0 |
| 1t | 0 | 0 | 3 | 7 | 1 | 0 | 0 | 0 | 0 | 0 | 2 | 1 | 4 | 1 | 1 | 0 | 0 | 0 | 4 | 5 | 5 | 0 | 0 | 0 |
| 1v | 7 | 0 | 0 | 0 | 1 | 0 | 2 | 2 | 0 | 2 | 3 | 1 | 2 | 5 | 3 | 1 | 0 | 0 | 0 | 0 | 1 | 0 | 0 | 0 |
| 1z | 5 | 6 | 0 | 0 | 0 | 2 | 3 | 0 | 0 | 2 | 0 | 0 | 2 | 1 | 1 | 0 | 0 | 1 | 1 | 0 | 24 | 0 | 0 | 0 |
| 1ww | 0 | 2 | 0 | 0 | 0 | 0 | 0 | 0 | 0 | 0 | 0 | 0 | 3 | 0 | 1 | 0 | 0 | 0 | 0 | 0 | 0 | 0 | 1 | 0 |
| 1xx | 0 | 2 | 0 | 0 | 0 | 1 | 0 | 0 | 0 | 0 | 0 | 0 | 4 | 0 | 1 | 0 | 0 | 0 | 1 | 0 | 1 | 0 | 0 | 0 |
| 1yy | 0 | 0 | 0 | 0 | 0 | 0 | 0 | 1 | 0 | 1 | 0 | 0 | 2 | 0 | 0 | 1 | 0 | 0 | 4 | 3 | 3 | 0 | 0 | 0 |
| 2a | 0 | 0 | 0 | 0 | 0 | 0 | 1 | 0 | 0 | 0 | 0 | 0 | 2 | 0 | 0 | 0 | 0 | 0 | 0 | 5 | 0 | 0 | 0 | 0 |
| 2b | 93 | 0 | 0 | 0 | 0 | 0 | 0 | 0 | 0 | 0 | 0 | 0 | 5 | 0 | 0 | 0 | 0 | 0 | 0 | 0 | 0 | 0 | 0 | 0 |
| 2c | 0 | 99 | 0 | 0 | 0 | 3 | 0 | 0 | 0 | 0 | 0 | 0 | 0 | 0 | 0 | 0 | 0 | 0 | 0 | 0 | 0 | 0 | 0 | 0 |
| 2d | 0 | 0 | 84 | 0 | 0 | 0 | 0 | 0 | 0 | 0 | 0 | 0 | 0 | 0 | 2 | 1 | 0 | 0 | 0 | 0 | 1 | 0 | 0 | 0 |
| 2e | 0 | 0 | 0 | 93 | 0 | 0 | 1 | 0 | 0 | 0 | 1 | 0 | 0 | 0 | 2 | 0 | 0 | 0 | 1 | 0 | 0 | 0 | 0 | 0 |
| 2f | 0 | 3 | 0 | 0 | 92 | 0 | 0 | 0 | 0 | 0 | 5 | 0 | 1 | 0 | 0 | 0 | 0 | 0 | 0 | 4 | 0 | 0 | 0 | 0 |
| 2g | 0 | 0 | 1 | 0 | 0 | 95 | 0 | 0 | 0 | 0 | 0 | 1 | 3 | 0 | 2 | 0 | 0 | 0 | 2 | 5 | 0 | 0 | 2 | 0 |
| 2h | 0 | 1 | 0 | 0 | 0 | 0 | 97 | 0 | 0 | 0 | 0 | 0 | 3 | 1 | 0 | 0 | 0 | 6 | 0 | 0 | 0 | 0 | 0 | 0 |
| 2i | 0 | 0 | 0 | 0 | 0 | 0 | 0 | 91 | 0 | 0 | 0 | 0 | 2 | 0 | 0 | 0 | 2 | 0 | 7 | 0 | 0 | 1 | 1 |  |
| 2j | 0 | 0 | 2 | 0 | 0 | 0 | 1 | 0 | 64 | 0 | 0 | 0 | 1 | 2 | 1 | 0 | 0 | 0 | 0 | 1 | 0 | 0 | 1 | 1 |
| 2k | 0 | 0 | 0 | 0 | 0 | 0 | 0 | 0 | 0 | 90 | 0 | 1 | 0 | 1 | 0 | 0 | 0 | 0 | 0 | 4 | 2 | 1 | 1 | 0 |
| 2m | 0 | 0 | 1 | 1 | 0 | 0 | 4 | 0 | 0 | 0 | 97 | 0 | 0 | 2 | 1 | 0 | 0 | 4 | 0 | 0 | 5 | 0 | 1 | 0 |
| 2n | 0 | 1 | 8 | 0 | 0 | 0 | 0 | 0 | 0 | 1 | 0 | 99 | 0 | 3 | 3 | 0 | 0 | 6 | 0 | 0 | 6 | 0 | 0 | 0 |
| 2o | 0 | 0 | 0 | 0 | 0 | 1 | 3 | 0 | 0 | 1 | 0 | 0 | 99 | 0 | 1 | 0 | 0 | 3 | 2 | 0 | 2 | 0 | 2 | 1 |
| 2q | 0 | 1 | 0 | 0 | 0 | 0 | 3 | 0 | 0 | 0 | 0 | 0 | 1 | 99 | 0 | 0 | 0 | 0 | 0 | 0 | 0 | 0 | 1 | 0 |
| 2r | 0 | 0 | 2 | 0 | 0 | 0 | 0 | 0 | 0 | 0 | 0 | 1 | 0 | 0 | 99 | 0 | 0 | 1 | 0 | 0 | 0 | 0 | 1 | 1 |

FIG. 14
(Continued)

|     | 3a | 3b | 3c | 3d | 3e | 3f | 3g | 3h | 3i | 3j | 3k | 3l | 3m | 3n | 3o | 3p | 3q | 3r | 3s | 3t | 3u | 3v | 3x | 3y |
|-----|----|----|----|----|----|----|----|----|----|----|----|----|----|----|----|----|----|----|----|----|----|----|----|----|
| 1a  | 0  | 0  | 1  | 0  | 0  | 0  | 0  | 2  | 1  | 0  | 0  | 0  | 2  | 0  | 5  | 0  | 0  | 4  | 0  | 0  | 0  | 1  | 0  | 0  |
| 1b  | 6  | 0  | 0  | 0  | 0  | 1  | 0  | 0  | 0  | 1  | 0  | 0  | 0  | 0  | 5  | 0  | 0  | 4  | 0  | 0  | 1  | 0  | 0  | 0  |
| 1c  | 0  | 2  | 0  | 0  | 6  | 0  | 0  | 6  | 1  | 2  | 0  | 0  | 0  | 0  | 4  | 0  | 1  | 2  | 1  | 1  | 0  | 0  | 0  | 1  |
| 1d  | 0  | 0  | 0  | 0  | 0  | 1  | 0  | 0  | 0  | 5  | 0  | 0  | 0  | 0  | 2  | 0  | 0  | 4  | 0  | 0  | 0  | 0  | 0  | 0  |
| 1e  | 0  | 0  | 0  | 0  | 0  | 0  | 0  | 0  | 0  | 0  | 0  | 0  | 0  | 0  | 2  | 0  | 0  | 3  | 0  | 0  | 0  | 0  | 0  | 1  |
| 1f  | 0  | 2  | 0  | 3  | 0  | 0  | 0  | 5  | 0  | 0  | 0  | 0  | 0  | 1  | 2  | 2  | 0  | 4  | 0  | 0  | 0  | 0  | 0  | 3  |
| 1i  | 2  | 0  | 3  | 1  | 0  | 1  | 1  | 5  | 3  | 0  | 3  | 0  | 3  | 3  | 1  | 0  | 6  | 0  | 2  | 0  | 4  | 5  | 0  | 4  |
| 1j  | 0  | 0  | 0  | 1  | 0  | 0  | 1  | 0  | 0  | 3  | 0  | 0  | 0  | 0  | 1  | 0  | 0  | 2  | 0  | 0  | 1  | 0  | 0  | 6  |
| 1k  | 0  | 1  | 1  | 7  | 1  | 1  | 12 | 0  | 0  | 1  | 1  | 0  | 0  | 0  | 1  | 0  | 0  | 3  | 0  | 1  | 0  | 0  | 0  | 1  |
| 1l  | 0  | 0  | 2  | 0  | 1  | 0  | 0  | 0  | 0  | 0  | 5  | 0  | 0  | 3  | 0  | 0  | 2  | 0  | 0  | 1  | 5  | 0  | 0  |    |
| 1m  | 0  | 59 | 0  | 0  | 4  | 0  | 7  | 0  | 0  | 0  | 0  | 0  | 0  | 7  | 3  | 0  | 1  | 4  | 0  | 0  | 0  | 3  | 0  | 3  |
| 1n  | 0  | 6  | 0  | 0  | 0  | 1  | 0  | 1  | 0  | 0  | 0  | 0  | 3  | 4  | 5  | 0  | 1  | 0  | 0  | 0  | 0  | 0  | 0  | 0  |
| 1o  | 4  | 1  | 4  | 3  | 0  | 3  | 0  | 2  | 4  | 6  | 4  | 1  | 5  | 7  | 3  | 4  | 15 | 5  | 4  | 1  | 6  | 4  | 2  | 10 |
| 1p  | 43 | 0  | 0  | 0  | 1  | 6  | 0  | 1  | 0  | 0  | 6  | 0  | 4  | 0  | 3  | 5  | 3  | 1  | 0  | 0  | 0  | 0  | 0  | 0  |
| 1q  | 0  | 3  | 0  | 0  | 0  | 1  | 0  | 1  | 0  | 0  | 1  | 0  | 6  | 1  | 1  | 2  | 1  | 3  | 0  | 0  | 0  | 2  | 0  | 3  |
| 1r  | 0  | 3  | 26 | 0  | 0  | 0  | 1  | 1  | 0  | 0  | 2  | 4  | 1  | 2  | 3  | 0  | 5  | 27 | 0  | 0  | 2  | 5  | 3  | 2  |
| 1s  | 1  | 1  | 3  | 2  | 0  | 0  | 0  | 7  | 0  | 0  | 7  | 0  | 0  | 0  | 2  | 0  | 24 | 22 | 2  | 0  | 2  | 0  | 0  | 0  |
| 1t  | 0  | 0  | 0  | 3  | 7  | 1  | 0  | 0  | 0  | 0  | 0  | 0  | 2  | 1  | 4  | 0  | 1  | 1  | 0  | 0  | 0  | 1  | 1  | 0  |
| 1v  | 0  | 5  | 0  | 8  | 0  | 0  | 0  | 2  | 2  | 0  | 2  | 3  | 3  | 8  | 1  | 0  | 1  | 3  | 1  | 0  | 4  | 0  | 0  | 0  |
| 1z  | 3  | 5  | 6  | 0  | 0  | 0  | 2  | 3  | 0  | 3  | 0  | 2  | 0  | 0  | 0  | 2  | 0  | 1  | 1  | 0  | 0  | 1  | 1  | 0  |
| 1ww | 0  | 0  | 2  | 0  | 0  | 0  | 0  | 0  | 0  | 0  | 0  | 0  | 0  | 0  | 3  | 0  | 0  | 0  | 0  | 0  | 0  | 0  | 0  | 0  |
| 1xx | 0  | 0  | 2  | 0  | 0  | 0  | 1  | 0  | 0  | 0  | 0  | 0  | 0  | 0  | 4  | 0  | 0  | 10 | 0  | 0  | 0  | 1  | 0  | 1  |
| 1yy | 2  | 0  | 0  | 0  | 0  | 0  | 0  | 0  | 1  | 1  | 0  | 0  | 0  | 0  | 0  | 0  | 3  | 0  | 7  | 0  | 3  | 0  | 3  | 2  |
| 2a  | 0  | 0  | 0  | 0  | 0  | 0  | 0  | 1  | 0  | 0  | 0  | 0  | 0  | 0  | 2  | 0  | 5  | 0  | 0  | 0  | 0  | 0  | 0  | 1  |
| 2b  | 0  | 0  | 0  | 0  | 0  | 0  | 0  | 0  | 0  | 0  | 0  | 0  | 0  | 39 | 5  | 0  | 4  | 0  | 0  | 0  | 0  | 0  | 15 | 1  |
| 2c  | 0  | 0  | 0  | 0  | 0  | 0  | 1  | 0  | 0  | 0  | 0  | 0  | 0  | 0  | 0  | 0  | 15 | 0  | 0  | 0  | 0  | 0  | 0  | 0  |
| 2d  | 0  | 0  | 0  | 0  | 0  | 0  | 0  | 0  | 0  | 0  | 0  | 0  | 0  | 0  | 0  | 0  | 2  | 1  | 0  | 0  | 0  | 0  | 0  | 0  |
| 2e  | 0  | 0  | 0  | 0  | 0  | 0  | 0  | 0  | 0  | 0  | 0  | 0  | 0  | 0  | 0  | 0  | 0  | 2  | 0  | 0  | 0  | 0  | 0  | 0  |
| 2f  | 0  | 0  | 3  | 0  | 0  | 0  | 0  | 0  | 0  | 0  | 0  | 5  | 15 | 1  | 0  | 9  | 0  | 0  | 0  | 0  | 0  | 1  | 0  |    |
| 2g  | 0  | 3  | 0  | 1  | 23 | 0  | 7  | 3  | 0  | 0  | 0  | 0  | 0  | 1  | 3  | 0  | 6  | 0  | 0  | 0  | 2  | 0  | 1  | 0  |
| 2h  | 0  | 0  | 1  | 0  | 0  | 0  | 0  | 0  | 0  | 0  | 0  | 0  | 0  | 0  | 3  | 1  | 0  | 0  | 0  | 0  | 0  | 0  | 0  | 0  |
| 2i  | 0  | 0  | 0  | 0  | 0  | 0  | 0  | 0  | 0  | 0  | 0  | 0  | 0  | 0  | 0  | 0  | 2  | 0  | 0  | 0  | 2  | 0  | 0  | 0  |
| 2j  | 0  | 0  | 0  | 2  | 0  | 0  | 0  | 1  | 0  | 0  | 0  | 0  | 0  | 1  | 0  | 2  | 1  | 0  | 0  | 0  | 1  | 0  | 0  |    |
| 2k  | 1  | 0  | 0  | 0  | 0  | 0  | 0  | 0  | 0  | 0  | 0  | 0  | 0  | 0  | 0  | 0  | 1  | 0  | 0  | 0  | 0  | 0  | 0  | 0  |
| 2m  | 0  | 0  | 0  | 1  | 1  | 0  | 0  | 4  | 0  | 0  | 0  | 0  | 0  | 0  | 0  | 2  | 1  | 0  | 4  | 0  | 0  | 0  |    |    |
| 2n  | 0  | 0  | 0  | 1  | 0  | 0  | 0  | 0  | 0  | 0  | 1  | 3  | 0  | 18 | 0  | 0  | 0  | 3  | 0  | 0  | 6  | 0  | 0  | 0  |
| 2o  | 1  | 0  | 0  | 0  | 0  | 0  | 1  | 3  | 0  | 0  | 1  | 0  | 0  | 0  | 0  | 0  | 0  | 0  | 0  | 0  | 3  | 2  | 0  | 0  |
| 2q  | 5  | 0  | 1  | 0  | 0  | 0  | 0  | 3  | 0  | 0  | 0  | 0  | 0  | 0  | 1  | 0  | 4  | 0  | 0  | 0  | 0  | 0  | 0  |    |
| 2r  | 1  | 0  | 0  | 0  | 0  | 0  | 0  | 0  | 0  | 0  | 0  | 0  | 1  | 0  | 0  | 2  | 0  | 0  | 0  | 0  | 1  | 2  |    |    |

FIG. 14
(Continued)

| | 3z | 3ww | 3xx | 3yy | 3zz | 4a | 4b | 4c | 4d | 4e | 4f | 4g | 4h | 4i | 4j | 4k | 4l | 4m | 4n | 4o | 4p | 4q | 4r | 4s |
|---|---|---|---|---|---|---|---|---|---|---|---|---|---|---|---|---|---|---|---|---|---|---|---|---|
| 1a | 0 | 0 | 0 | 1 | 0 | 0 | 1 | 1 | 0 | 0 | 0 | 0 | 2 | 1 | 0 | 0 | 0 | 2 | 0 | 5 | 0 | 0 | 4 | 0 |
| 1b | 0 | 0 | 0 | 1 | 0 | 6 | 0 | 3 | 0 | 0 | 1 | 0 | 0 | 0 | 1 | 0 | 0 | 0 | 0 | 5 | 0 | 0 | 4 | 0 |
| 1c | 0 | 0 | 0 | 1 | 0 | 0 | 2 | 0 | 0 | 1 | 1 | 0 | 6 | 0 | 0 | 0 | 0 | 0 | 0 | 2 | 0 | 0 | 1 | 0 |
| 1d | 0 | 0 | 0 | 1 | 0 | 0 | 0 | 1 | 0 | 1 | 1 | 0 | 0 | 0 | 5 | 0 | 0 | 0 | 0 | 2 | 0 | 0 | 4 | 0 |
| 1e | 0 | 0 | 0 | 1 | 0 | 0 | 0 | 0 | 0 | 0 | 1 | 0 | 0 | 0 | 0 | 0 | 0 | 0 | 0 | 2 | 0 | 0 | 3 | 0 |
| 1f | 1 | 0 | 0 | 3 | 0 | 0 | 2 | 0 | 0 | 0 | 0 | 0 | 0 | 0 | 0 | 0 | 0 | 0 | 1 | 2 | 2 | 0 | 4 | 0 |
| 1i | 6 | 1 | 0 | 0 | 1 | 2 | 0 | 3 | 1 | 0 | 1 | 1 | 5 | 7 | 2 | 3 | 0 | 3 | 1 | 0 | 0 | 2 | 5 | 2 |
| 1j | 0 | 0 | 0 | 1 | 0 | 0 | 0 | 0 | 1 | 0 | 0 | 1 | 0 | 0 | 0 | 0 | 0 | 0 | 0 | 1 | 0 | 0 | 2 | 0 |
| 1k | 0 | 0 | 0 | 1 | 0 | 0 | 1 | 1 | 7 | 0 | 0 | 1 | 0 | 0 | 2 | 4 | 0 | 0 | 0 | 1 | 0 | 0 | 3 | 0 |
| 1l | 1 | 0 | 0 | 5 | 0 | 1 | 1 | 2 | 0 | 1 | 0 | 0 | 0 | 0 | 0 | 0 | 5 | 0 | 0 | 3 | 0 | 0 | 2 | 0 |
| 1m | 0 | 0 | 0 | 7 | 0 | 0 | 4 | 0 | 0 | 0 | 0 | 0 | 3 | 1 | 0 | 0 | 0 | 0 | 4 | 3 | 0 | 1 | 6 | 1 |
| 1n | 0 | 1 | 0 | 1 | 0 | 0 | 0 | 1 | 0 | 0 | 1 | 0 | 1 | 0 | 0 | 0 | 0 | 3 | 1 | 0 | 0 | 1 | 2 | 0 |
| 1o | 10 | 2 | 0 | 0 | 1 | 4 | 2 | 1 | 3 | 0 | 3 | 1 | 4 | 6 | 6 | 2 | 1 | 5 | 7 | 5 | 0 | 0 | 6 | 4 |
| 1p | 5 | 4 | 0 | 0 | 0 | 0 | 0 | 3 | 0 | 1 | 6 | 0 | 1 | 0 | 0 | 0 | 6 | 0 | 4 | 0 | 3 | 1 | 0 | 4 |
| 1q | 1 | 4 | 0 | 4 | 0 | 0 | 0 | 1 | 0 | 0 | 1 | 0 | 1 | 0 | 0 | 1 | 0 | 6 | 1 | 1 | 2 | 0 | 5 | 0 |
| 1r | 0 | 0 | 0 | 3 | 0 | 0 | 0 | 0 | 0 | 0 | 0 | 2 | 1 | 4 | 0 | 2 | 4 | 1 | 2 | 3 | 0 | 5 | 4 | 0 |
| 1s | 11 | 0 | 0 | 0 | 0 | 1 | 1 | 3 | 2 | 0 | 0 | 1 | 7 | 0 | 0 | 0 | 0 | 7 | 0 | 2 | 0 | 0 | 0 | 6 |
| 1t | 5 | 0 | 0 | 3 | 0 | 0 | 0 | 3 | 0 | 0 | 0 | 0 | 1 | 0 | 0 | 0 | 2 | 1 | 0 | 0 | 0 | 0 | 0 |
| 1v | 1 | 0 | 0 | 47 | 0 | 1 | 0 | 0 | 2 | 5 | 1 | 0 | 2 | 2 | 0 | 2 | 1 | 2 | 1 | 6 | 0 | 5 | 3 | 0 |
| 1z | 7 | 0 | 0 | 0 | 0 | 3 | 5 | 6 | 0 | 0 | 0 | 2 | 3 | 0 | 0 | 2 | 0 | 0 | 0 | 2 | 0 | 1 | 1 | 0 |
| 1ww | 2 | 0 | 1 | 0 | 0 | 0 | 0 | 2 | 0 | 0 | 0 | 0 | 0 | 0 | 0 | 0 | 0 | 0 | 0 | 0 | 0 | 0 | 1 | 0 |
| 1xx | 1 | 0 | 0 | 0 | 0 | 0 | 0 | 2 | 0 | 0 | 1 | 0 | 0 | 0 | 0 | 0 | 0 | 0 | 0 | 0 | 4 | 0 | 0 | 0 |
| 1yy | 3 | 1 | 0 | 2 | 0 | 0 | 0 | 0 | 4 | 0 | 0 | 0 | 1 | 1 | 0 | 0 | 2 | 0 | 0 | 0 | 1 | 7 | 0 |
| 2a | 0 | 0 | 0 | 3 | 0 | 0 | 0 | 0 | 0 | 0 | 0 | 1 | 0 | 0 | 0 | 0 | 0 | 0 | 0 | 2 | 0 | 5 | 0 | 0 |
| 2b | 0 | 0 | 0 | 0 | 0 | 0 | 0 | 0 | 0 | 0 | 0 | 0 | 0 | 0 | 0 | 0 | 0 | 0 | 0 | 0 | 5 | 0 | 2 | 0 | 0 |
| 2c | 0 | 0 | 0 | 0 | 0 | 0 | 0 | 0 | 0 | 0 | 0 | 3 | 0 | 0 | 0 | 0 | 0 | 0 | 0 | 0 | 0 | 0 | 0 | 0 |
| 2d | 0 | 0 | 0 | 0 | 0 | 0 | 0 | 0 | 0 | 0 | 0 | 0 | 0 | 0 | 0 | 0 | 0 | 0 | 0 | 0 | 0 | 2 | 1 | 0 |
| 2e | 0 | 0 | 0 | 0 | 0 | 0 | 0 | 0 | 0 | 0 | 0 | 1 | 0 | 0 | 0 | 0 | 0 | 0 | 0 | 0 | 0 | 2 | 0 | 0 |
| 2f | 0 | 0 | 0 | 0 | 0 | 0 | 0 | 0 | 0 | 0 | 0 | 2 | 0 | 0 | 0 | 0 | 5 | 0 | 1 | 0 | 1 | 0 | 0 |
| 2g | 0 | 1 | 0 | 2 | 0 | 0 | 0 | 1 | 10 | 0 | 0 | 0 | 0 | 0 | 0 | 0 | 1 | 0 | 0 | 2 | 2 | 0 |
| 2h | 0 | 0 | 0 | 0 | 0 | 0 | 1 | 0 | 1 | 0 | 0 | 0 | 0 | 0 | 0 | 0 | 0 | 0 | 0 | 0 | 3 | 1 | 0 |
| 2i | 0 | 1 | 0 | 1 | 1 | 0 | 0 | 0 | 0 | 0 | 0 | 0 | 0 | 0 | 1 | 0 | 0 | 0 | 0 | 0 | 2 | 0 | 0 |
| 2j | 0 | 0 | 0 | 1 | 1 | 0 | 0 | 0 | 2 | 0 | 0 | 0 | 1 | 0 | 0 | 0 | 0 | 0 | 1 | 0 | 2 | 1 | 0 |
| 2k | 2 | 1 | 1 | 1 | 0 | 1 | 0 | 0 | 0 | 0 | 0 | 0 | 0 | 0 | 0 | 0 | 0 | 0 | 1 | 0 | 0 | 1 | 0 | 0 |
| 2m | 0 | 0 | 0 | 1 | 0 | 0 | 0 | 0 | 1 | 1 | 0 | 0 | 4 | 0 | 0 | 0 | 0 | 0 | 0 | 1 | 0 | 2 | 1 | 0 |
| 2n | 0 | 1 | 0 | 2 | 0 | 1 | 0 | 0 | 0 | 0 | 0 | 0 | 3 | 0 | 0 | 0 | 3 | 0 | 0 | 0 | 0 | 3 | 3 | 0 |
| 2o | 0 | 1 | 0 | 2 | 1 | 1 | 0 | 0 | 0 | 0 | 0 | 1 | 3 | 0 | 0 | 1 | 0 | 0 | 0 | 0 | 0 | 4 | 1 | 0 |
| 2q | 2 | 0 | 0 | 1 | 0 | 5 | 0 | 1 | 0 | 0 | 0 | 0 | 3 | 0 | 0 | 0 | 0 | 0 | 0 | 1 | 0 | 0 | 4 | 0 |
| 2r | 0 | 0 | 0 | 1 | 1 | 0 | 0 | 0 | 2 | 0 | 0 | 0 | 0 | 0 | 0 | 0 | 0 | 0 | 1 | 0 | 0 | 2 | 0 | 0 |

FIG. 14
(Continued)

|  | 4t | 4u | 4v | 4w | 4x | 4y | 4z | 4ww | 4xx | 4yy | 4zz |
|---|---|---|---|---|---|---|---|---|---|---|---|
| 1a | 0 | 0 | 1 | 4 | 0 | 0 | 0 | 0 | 0 | 0 | 0 |
| 1b | 0 | 1 | 0 | 0 | 0 | 0 | 0 | 0 | 0 | 0 | 0 |
| 1c | 0 | 1 | 4 | 1 | 0 | 3 | 0 | 0 | 0 | 1 | 0 |
| 1d | 0 | 0 | 0 | 0 | 0 | 0 | 0 | 0 | 0 | 1 | 0 |
| 1e | 0 | 0 | 0 | 3 | 0 | 1 | 0 | 0 | 0 | 1 | 0 |
| 1f | 0 | 0 | 0 | 5 | 0 | 3 | 1 | 0 | 0 | 3 | 0 |
| 1i | 0 | 3 | 5 | 1 | 0 | 2 | 0 | 1 | 0 | 4 | 1 |
| 1j | 0 | 1 | 0 | 7 | 0 | 6 | 0 | 0 | 0 | 1 | 0 |
| 1k | 1 | 0 | 0 | 0 | 0 | 1 | 0 | 0 | 0 | 1 | 0 |
| 1l | 0 | 1 | 5 | 5 | 0 | 0 | 1 | 0 | 0 | 0 | 0 |
| 1m | 0 | 1 | 3 | 0 | 0 | 3 | 0 | 0 | 0 | 2 | 0 |
| 1n | 0 | 0 | 0 | 0 | 0 | 1 | 0 | 1 | 0 | 1 | 0 |
| 1o | 1 | 6 | 0 | 1 | 2 | 6 | 2 | 2 | 0 | 1 | 1 |
| 1p | 0 | 0 | 0 | 0 | 0 | 0 | 5 | 4 | 0 | 0 | 0 |
| 1q | 0 | 0 | 2 | 2 | 0 | 3 | 1 | 0 | 0 | 1 | 0 |
| 1r | 0 | 2 | 5 | 0 | 3 | 2 | 0 | 0 | 0 | 3 | 0 |
| 1s | 0 | 0 | 4 | 0 | 0 | 0 | 0 | 0 | 0 | 1 | 0 |
| 1t | 0 | 5 | 7 | 0 | 1 | 0 | 3 | 0 | 0 | 0 | 0 |
| 1v | 0 | 4 | 0 | 2 | 0 | 4 | 1 | 0 | 0 | 0 | 0 |
| 1z | 0 | 0 | 1 | 7 | 1 | 1 | 0 | 0 | 0 | 0 | 0 |
| 1ww | 0 | 0 | 0 | 0 | 0 | 0 | 2 | 0 | 1 | 0 | 0 |
| 1xx | 0 | 0 | 1 | 0 | 0 | 0 | 0 | 0 | 0 | 0 | 0 |
| 1yy | 0 | 3 | 4 | 0 | 0 | 2 | 2 | 0 | 0 | 0 | 0 |
| 2a | 0 | 1 | 0 | 5 | 0 | 3 | 0 | 0 | 0 | 0 | 0 |
| 2b | 0 | 0 | 0 | 0 | 0 | 1 | 0 | 0 | 0 | 0 | 0 |
| 2c | 0 | 0 | 0 | 0 | 0 | 0 | 0 | 0 | 0 | 0 | 0 |
| 2d | 0 | 0 | 0 | 0 | 0 | 0 | 0 | 0 | 0 | 0 | 0 |
| 2e | 0 | 0 | 0 | 0 | 1 | 0 | 0 | 0 | 0 | 0 | 0 |
| 2f | 0 | 0 | 0 | 1 | 2 | 0 | 0 | 0 | 0 | 0 | 0 |
| 2g | 0 | 1 | 2 | 1 | 1 | 0 | 0 | 0 | 0 | 2 | 0 |
| 2h | 0 | 0 | 0 | 6 | 0 | 0 | 0 | 0 | 0 | 0 | 0 |
| 2i | 0 | 2 | 0 | 7 | 0 | 0 | 0 | 1 | 0 | 1 | 1 |
| 2j | 0 | 0 | 0 | 0 | 0 | 0 | 1 | 0 | 0 | 1 | 1 |
| 2k | 0 | 0 | 0 | 4 | 0 | 0 | 2 | 1 | 1 | 1 | 0 |
| 2m | 0 | 4 | 0 | 0 | 0 | 0 | 5 | 0 | 0 | 1 | 0 |
| 2n | 0 | 0 | 0 | 0 | 0 | 0 | 6 | 0 | 0 | 0 | 0 |
| 2o | 0 | 0 | 2 | 0 | 0 | 0 | 5 | 1 | 0 | 2 | 1 |
| 2q | 0 | 0 | 0 | 0 | 0 | 0 | 2 | 0 | 0 | 1 | 0 |
| 2r | 0 | 1 | 0 | 0 | 1 | 2 | 0 | 0 | 0 | 1 | 0 |

FIG. 14
(Continued)

|     | 1a | 1b | 1c | 1d | 1e | 1f | 1i | 1j | 1k | 1l | 1m | 1n | 1o | 1p | 1q | 1r | 1s | 1t | 1v | 1z | 1ww | 1xx | 1yy | 2a |
|-----|----|----|----|----|----|----|----|----|----|----|----|----|----|----|----|----|----|----|----|----|-----|-----|-----|----|
| 2s  | 2  | 2  | 7  | 4  | 0  | 0  | 0  | 0  | 2  | 0  | 1  | 1  | 5  | 1  | 2  | 0  | 0  | 0  | 3  | 0  | 1   | 0   | 1   | 2  |
| 2t  | 1  | 0  | 1  | 0  | 0  | 0  | 3  | 0  | 0  | 0  | 0  | 0  | 2  | 0  | 0  | 3  | 0  | 0  | 0  | 0  | 0   | 0   | 1   | 1  |
| 2u  | 1  | 0  | 1  | 0  | 0  | 1  | 0  | 0  | 1  | 0  | 0  | 0  | 1  | 0  | 2  | 4  | 0  | 0  | 1  | 0  | 0   | 0   | 1   | 1  |
| 2v  | 1  | 0  | 2  | 0  | 0  | 0  | 0  | 0  | 0  | 0  | 0  | 0  | 0  | 0  | 2  | 1  | 0  | 0  | 0  | 0  | 0   | 2   | 0   | 1  |
| 2w  | 0  | 0  | 1  | 0  | 0  | 0  | 2  | 0  | 0  | 0  | 1  | 0  | 1  | 0  | 2  | 0  | 1  | 0  | 3  | 0  | 0   | 0   | 0   | 3  |
| 2z  | 0  | 1  | 1  | 0  | 0  | 1  | 1  | 0  | 0  | 0  | 0  | 0  | 0  | 4  | 0  | 0  | 4  | 1  | 4  | 7  | 0   | 0   | 1   | 0  |
| 2xx | 0  | 0  | 0  | 0  | 0  | 0  | 0  | 0  | 0  | 0  | 0  | 0  | 2  | 0  | 0  | 1  | 0  | 0  | 1  | 0  | 0   | 0   | 0   | 0  |
| 2yy | 0  | 0  | 0  | 2  | 0  | 0  | 0  | 0  | 0  | 0  | 0  | 0  | 0  | 0  | 0  | 3  | 0  | 0  | 4  | 0  | 0   | 0   | 0   | 0  |
| 2zz | 0  | 2  | 0  | 0  | 0  | 0  | 0  | 0  | 0  | 0  | 1  | 1  | 0  | 0  | 0  | 0  | 0  | 0  | 3  | 0  | 0   | 0   | 1   | 0  |
| 3a  | 0  | 0  | 0  | 0  | 0  | 0  | 0  | 0  | 0  | 0  | 0  | 2  | 3  | 1  | 0  | 1  | 0  | 0  | 0  | 0  | 0   | 0   | 0   | 0  |
| 3b  | 0  | 0  | 0  | 0  | 4  | 0  | 0  | 0  | 0  | 0  | 0  | 5  | 6  | 0  | 0  | 0  | 0  | 0  | 0  | 0  | 0   | 0   | 0   | 1  |
| 3c  | 0  | 0  | 0  | 0  | 0  | 0  | 0  | 0  | 0  | 0  | 0  | 1  | 1  | 0  | 0  | 0  | 0  | 0  | 0  | 0  | 0   | 0   | 0   | 0  |
| 3d  | 0  | 0  | 0  | 0  | 0  | 0  | 0  | 0  | 0  | 0  | 0  | 0  | 0  | 0  | 0  | 0  | 0  | 0  | 0  | 0  | 0   | 0   | 0   | 0  |
| 3e  | 0  | 0  | 0  | 0  | 6  | 0  | 0  | 0  | 0  | 0  | 0  | 1  | 1  | 0  | 2  | 0  | 2  | 0  | 0  | 0  | 1   | 0   | 0   | 0  |
| 3f  | 0  | 0  | 0  | 0  | 0  | 0  | 0  | 0  | 0  | 0  | 0  | 1  | 2  | 0  | 0  | 0  | 0  | 0  | 0  | 0  | 0   | 0   | 0   | 0  |
| 3g  | 0  | 0  | 2  | 0  | 0  | 0  | 0  | 0  | 0  | 0  | 0  | 2  | 3  | 0  | 0  | 0  | 0  | 0  | 0  | 0  | 0   | 0   | 0   | 0  |
| 3h  | 0  | 0  | 2  | 0  | 0  | 0  | 0  | 0  | 0  | 0  | 1  | 1  | 3  | 0  | 0  | 2  | 0  | 0  | 2  | 1  | 0   | 0   | 0   | 0  |
| 3i  | 0  | 5  | 0  | 0  | 0  | 0  | 1  | 0  | 1  | 0  | 0  | 0  | 5  | 0  | 0  | 2  | 0  | 0  | 0  | 1  | 0   | 0   | 6   | 0  |
| 3j  | 0  | 0  | 2  | 0  | 0  | 0  | 0  | 0  | 0  | 0  | 0  | 1  | 1  | 10 | 0  | 0  | 0  | 0  | 2  | 1  | 0   | 0   | 0   | 0  |
| 3k  | 0  | 0  | 2  | 0  | 0  | 0  | 0  | 0  | 0  | 0  | 0  | 1  | 3  | 0  | 0  | 1  | 0  | 0  | 2  | 0  | 0   | 0   | 0   | 0  |
| 3l  | 0  | 0  | 1  | 0  | 0  | 0  | 0  | 0  | 0  | 1  | 0  | 2  | 4  | 0  | 2  | 0  | 0  | 0  | 3  | 0  | 0   | 0   | 0   | 0  |
| 3m  | 0  | 0  | 1  | 0  | 0  | 0  | 0  | 0  | 0  | 0  | 2  | 2  | 3  | 0  | 2  | 1  | 0  | 0  | 3  | 0  | 0   | 0   | 0   | 0  |
| 3n  | 0  | 0  | 0  | 0  | 0  | 0  | 0  | 0  | 0  | 0  | 0  | 1  | 0  | 0  | 0  | 0  | 0  | 0  | 2  | 0  | 0   | 0   | 0   | 0  |
| 3o  | 0  | 0  | 0  | 0  | 0  | 0  | 0  | 0  | 0  | 0  | 0  | 0  | 0  | 0  | 0  | 0  | 1  | 0  | 2  | 0  | 0   | 0   | 0   | 0  |
| 3p  | 0  | 0  | 8  | 0  | 1  | 0  | 0  | 0  | 0  | 0  | 0  | 2  | 1  | 0  | 1  | 0  | 1  | 0  | 0  | 0  | 0   | 0   | 0   | 1  |
| 3q  | 0  | 0  | 2  | 0  | 0  | 0  | 0  | 0  | 0  | 0  | 0  | 2  | 4  | 0  | 0  | 1  | 0  | 0  | 0  | 0  | 0   | 0   | 0   | 0  |
| 3r  | 0  | 0  | 5  | 0  | 1  | 0  | 0  | 0  | 0  | 0  | 0  | 1  | 4  | 0  | 0  | 1  | 0  | 0  | 0  | 0  | 0   | 0   | 6   | 0  |
| 3s  | 1  | 1  | 2  | 1  | 1  | 0  | 2  | 0  | 5  | 6  | 0  | 7  | 5  | 0  | 0  | 3  | 7  | 0  | 0  | 5  | 0   | 0   | 4   | 0  |
| 3t  | 0  | 0  | 0  | 0  | 0  | 0  | 0  | 0  | 0  | 0  | 0  | 3  | 2  | 0  | 0  | 0  | 0  | 0  | 2  | 0  | 0   | 0   | 0   | 0  |
| 3u  | 0  | 0  | 1  | 0  | 1  | 0  | 0  | 0  | 0  | 0  | 0  | 2  | 4  | 0  | 2  | 1  | 0  | 0  | 0  | 0  | 0   | 0   | 0   | 0  |
| 3v  | 0  | 0  | 0  | 0  | 0  | 1  | 0  | 2  | 0  | 0  | 0  | 0  | 0  | 0  | 0  | 0  | 0  | 0  | 0  | 0  | 0   | 0   | 0   | 0  |
| 3x  | 0  | 0  | 0  | 0  | 0  | 0  | 0  | 0  | 0  | 0  | 0  | 1  | 1  | 0  | 0  | 0  | 0  | 0  | 0  | 0  | 0   | 0   | 0   | 0  |
| 3y  | 0  | 0  | 0  | 0  | 0  | 1  | 0  | 1  | 0  | 0  | 0  | 2  | 1  | 0  | 0  | 0  | 0  | 0  | 0  | 0  | 1   | 0   | 0   | 0  |
| 3z  | 0  | 0  | 3  | 0  | 0  | 0  | 0  | 0  | 0  | 0  | 0  | 0  | 0  | 0  | 0  | 0  | 0  | 0  | 1  | 0  | 0   | 0   | 0   | 0  |
| 3ww | 0  | 0  | 0  | 0  | 0  | 0  | 0  | 0  | 0  | 0  | 0  | 0  | 0  | 0  | 0  | 0  | 0  | 0  | 0  | 0  | 0   | 0   | 0   | 0  |
| 3xx | 0  | 0  | 0  | 0  | 0  | 0  | 0  | 0  | 0  | 0  | 0  | 0  | 0  | 0  | 0  | 0  | 0  | 0  | 1  | 0  | 0   | 0   | 0   | 0  |
| 3yy | 0  | 0  | 0  | 0  | 0  | 0  | 0  | 0  | 0  | 0  | 0  | 1  | 0  | 0  | 0  | 0  | 0  | 0  | 0  | 0  | 0   | 0   | 0   | 0  |
| 3zz | 0  | 0  | 0  | 0  | 0  | 0  | 0  | 0  | 0  | 0  | 0  | 0  | 0  | 0  | 0  | 0  | 0  | 5  | 0  | 0  | 0   | 0   | 0   | 0  |

FIG. 14
(Continued)

|  | 2b | 2c | 2d | 2e | 2f | 2g | 2h | 2i | 2j | 2k | 2m | 2n | 2o | 2q | 2r | 2s | 2t | 2u | 2v | 2w | 2z | 2xx | 2yy | 2zz |
|---|---|---|---|---|---|---|---|---|---|---|---|---|---|---|---|---|---|---|---|---|---|---|---|---|
| 2s | 2 | 7 | 6 | 0 | 0 | 0 | 0 | 1 | 1 | 2 | 1 | 1 | 5 | 1 | 3 | 92 | 0 | 0 | 5 | 3 | 0 | 0 | 1 | 2 |
| 2t | 0 | 1 | 0 | 0 | 0 | 0 | 3 | 3 | 0 | 0 | 0 | 0 | 2 | 0 | 3 | 0 | 97 | 0 | 0 | 0 | 0 | 0 | 1 | 0 |
| 2u | 0 | 1 | 0 | 0 | 1 | 0 | 3 | 0 | 0 | 1 | 0 | 0 | 1 | 2 | 4 | 0 | 0 | 99 | 4 | 1 | 0 | 0 | 1 | 1 |
| 2v | 0 | 2 | 0 | 0 | 0 | 0 | 3 | 0 | 0 | 0 | 1 | 0 | 0 | 2 | 1 | 0 | 0 | 0 | 99 | 3 | 0 | 0 | 0 | 1 |
| 2w | 0 | 1 | 1 | 0 | 0 | 0 | 0 | 0 | 0 | 7 | 0 | 1 | 0 | 6 | 1 | 1 | 9 | 0 | 6 | 99 | 2 | 0 | 2 | 3 |
| 2z | 1 | 1 | 0 | 1 | 1 | 2 | 3 | 3 | 0 | 0 | 0 | 1 | 1 | 6 | 6 | 1 | 1 | 6 | 7 | 0 | 99 | 0 | 1 | 5 |
| 2xx | 0 | 0 | 0 | 0 | 0 | 0 | 0 | 0 | 0 | 0 | 0 | 0 | 2 | 0 | 1 | 0 | 0 | 0 | 1 | 4 | 0 | 86 | 0 | 0 |
| 2yy | 0 | 0 | 2 | 0 | 0 | 0 | 3 | 0 | 0 | 0 | 0 | 0 | 0 | 0 | 3 | 0 | 0 | 0 | 4 | 6 | 0 | 0 | 93 | 0 |
| 2zz | 0 | 0 | 0 | 0 | 0 | 1 | 0 | 0 | 0 | 0 | 0 | 1 | 1 | 0 | 0 | 0 | 0 | 0 | 3 | 0 | 0 | 0 | 0 | 75 |
| 3a | 0 | 0 | 0 | 0 | 0 | 0 | 0 | 0 | 0 | 0 | 2 | 0 | 2 | 3 | 0 | 1 | 0 | 0 | 0 | 0 | 0 | 0 | 0 | 0 |
| 3b | 0 | 0 | 0 | 4 | 0 | 1 | 2 | 0 | 0 | 0 | 0 | 5 | 6 | 0 | 0 | 0 | 0 | 0 | 0 | 2 | 0 | 0 | 0 | 0 |
| 3c | 1 | 0 | 0 | 0 | 0 | 2 | 1 | 0 | 0 | 0 | 0 | 1 | 1 | 0 | 0 | 0 | 0 | 0 | 0 | 11 | 0 | 0 | 0 | 0 |
| 3d | 0 | 0 | 0 | 0 | 0 | 0 | 0 | 0 | 0 | 0 | 0 | 2 | 1 | 0 | 0 | 0 | 0 | 0 | 0 | 5 | 0 | 0 | 0 | 0 |
| 3e | 0 | 0 | 0 | 0 | 0 | 0 | 3 | 0 | 0 | 0 | 0 | 1 | 4 | 0 | 2 | 0 | 0 | 0 | 5 | 0 | 1 | 0 | 0 | 0 |
| 3f | 0 | 0 | 0 | 0 | 0 | 0 | 0 | 0 | 0 | 0 | 0 | 1 | 2 | 0 | 0 | 0 | 0 | 0 | 5 | 0 | 0 | 0 | 0 | 0 |
| 3g | 0 | 2 | 0 | 0 | 0 | 0 | 0 | 0 | 0 | 0 | 0 | 2 | 3 | 0 | 0 | 0 | 0 | 0 | 0 | 1 | 0 | 0 | 0 | 0 |
| 3h | 0 | 2 | 0 | 0 | 0 | 0 | 0 | 0 | 0 | 0 | 1 | 1 | 3 | 0 | 2 | 0 | 0 | 3 | 2 | 0 | 1 | 0 | 0 | 0 |
| 3i | 0 | 0 | 0 | 0 | 0 | 0 | 0 | 3 | 0 | 0 | 1 | 0 | 1 | 0 | 2 | 3 | 0 | 7 | 3 | 0 | 1 | 0 | 6 | 0 |
| 3j | 0 | 2 | 0 | 0 | 0 | 0 | 0 | 0 | 0 | 0 | 0 | 1 | 1 | 0 | 1 | 0 | 0 | 0 | 3 | 1 | 1 | 0 | 0 | 0 |
| 3k | 0 | 2 | 0 | 0 | 0 | 0 | 0 | 0 | 0 | 0 | 0 | 1 | 3 | 0 | 1 | 0 | 0 | 0 | 2 | 7 | 0 | 0 | 0 | 0 |
| 3l | 0 | 1 | 0 | 0 | 0 | 0 | 1 | 0 | 0 | 0 | 0 | 1 | 4 | 2 | 0 | 0 | 0 | 0 | 2 | 3 | 0 | 0 | 0 | 0 |
| 3m | 0 | 1 | 0 | 0 | 1 | 1 | 0 | 0 | 0 | 1 | 2 | 2 | 2 | 1 | 0 | 0 | 0 | 0 | 3 | 1 | 0 | 0 | 0 | 0 |
| 3n | 0 | 0 | 0 | 0 | 0 | 0 | 1 | 0 | 0 | 0 | 0 | 1 | 1 | 0 | 0 | 0 | 0 | 0 | 2 | 0 | 0 | 0 | 0 | 0 |
| 3o | 0 | 0 | 0 | 0 | 0 | 2 | 1 | 0 | 0 | 0 | 1 | 0 | 0 | 0 | 1 | 0 | 0 | 0 | 2 | 4 | 0 | 0 | 0 | 0 |
| 3p | 0 | 0 | 0 | 0 | 0 | 0 | 0 | 0 | 0 | 0 | 2 | 2 | 0 | 0 | 1 | 0 | 0 | 0 | 0 | 0 | 0 | 0 | 0 | 0 |
| 3q | 0 | 2 | 0 | 0 | 0 | 1 | 3 | 0 | 0 | 0 | 0 | 2 | 4 | 0 | 0 | 0 | 0 | 0 | 0 | 0 | 0 | 0 | 0 | 0 |
| 3r | 0 | 5 | 0 | 1 | 0 | 1 | 0 | 0 | 0 | 0 | 0 | 0 | 1 | 1 | 1 | 0 | 0 | 0 | 0 | 0 | 0 | 0 | 0 | 0 |
| 3s | 2 | 1 | 0 | 1 | 0 | 1 | 0 | 4 | 1 | 0 | 3 | 6 | 0 | 0 | 6 | 3 | 0 | 0 | 0 | 1 | 1 | 0 | 0 | 0 |
| 3t | 0 | 0 | 0 | 0 | 0 | 0 | 0 | 0 | 0 | 0 | 0 | 3 | 2 | 0 | 0 | 0 | 0 | 0 | 2 | 7 | 0 | 0 | 0 | 0 |
| 3u | 0 | 1 | 0 | 1 | 0 | 0 | 0 | 0 | 0 | 0 | 0 | 2 | 2 | 2 | 1 | 0 | 0 | 0 | 5 | 0 | 0 | 0 | 0 | 0 |
| 3v | 0 | 0 | 0 | 1 | 0 | 1 | 0 | 2 | 0 | 0 | 0 | 2 | 4 | 0 | 0 | 0 | 0 | 0 | 2 | 3 | 0 | 0 | 0 | 0 |
| 3x | 0 | 0 | 0 | 0 | 0 | 0 | 1 | 0 | 0 | 0 | 0 | 1 | 1 | 0 | 0 | 0 | 0 | 0 | 0 | 0 | 0 | 0 | 0 | 0 |
| 3y | 0 | 0 | 0 | 0 | 1 | 0 | 0 | 1 | 0 | 0 | 0 | 2 | 0 | 0 | 0 | 0 | 0 | 0 | 4 | 0 | 1 | 0 | 0 | 1 |
| 3z | 0 | 0 | 0 | 0 | 0 | 0 | 0 | 0 | 0 | 0 | 0 | 0 | 1 | 0 | 0 | 0 | 0 | 0 | 3 | 1 | 0 | 0 | 0 | 0 |
| 3ww | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3xx | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 |
| 3yy | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 |
| 3zz | 0 | 0 | 0 | 0 | 0 | 0 | 0 | 0 | 0 | 0 | 0 | 0 | 0 | 0 | 0 | 0 | 0 | 0 | 7 | 5 | 0 | 0 | 4 | 0 |

FIG. 14
(Continued)

|     | 3a | 3b | 3c | 3d | 3e | 3f | 3g | 3h | 3i | 3j | 3k | 3l | 3m | 3n | 3o | 3p | 3q | 3r | 3s | 3t | 3u | 3v | 3x | 3y |
|-----|----|----|----|----|----|----|----|----|----|----|----|----|----|----|----|----|----|----|----|----|----|----|----|----|
| 2s  | 2  | 2  | 4  | 6  | 0  | 0  | 0  | 19 | 0  | 1  | 2  | 0  | 1  | 0  | 5  | 4  | 2  | 1  | 0  | 0  | 2  | 0  | 0  | 4  |
| 2t  | 1  | 0  | 1  | 0  | 0  | 0  | 0  | 3  | 3  | 0  | 0  | 0  | 0  | 0  | 0  | 2  | 0  | 11 | 3  | 0  | 11 | 4  | 0  | 0  |
| 2u  | 1  | 0  | 1  | 0  | 0  | 1  | 0  | 3  | 0  | 0  | 1  | 0  | 0  | 0  | 0  | 1  | 1  | 2  | 4  | 0  | 0  | 4  | 0  | 2  |
| 2v  | 1  | 0  | 2  | 0  | 0  | 0  | 0  | 3  | 0  | 0  | 0  | 0  | 0  | 0  | 0  | 0  | 1  | 2  | 1  | 0  | 0  | 0  | 2  | 2  |
| 2w  | 1  | 0  | 0  | 9  | 0  | 0  | 0  | 7  | 0  | 1  | 0  | 0  | 0  | 0  | 0  | 1  | 0  | 7  | 4  | 1  | 3  | 2  | 0  | 6  |
| 2z  | 0  | 1  | 13 | 0  | 1  | 1  | 0  | 49 | 3  | 0  | 0  | 0  | 0  | 0  | 0  | 38 | 1  | 4  | 6  | 1  | 0  | 6  | 2  | 64 |
| 2xx | 0  | 0  | 0  | 0  | 0  | 0  | 0  | 0  | 0  | 0  | 0  | 0  | 0  | 0  | 2  | 0  | 0  | 1  | 0  | 0  | 0  | 1  | 0  | 2  |
| 2yy | 0  | 0  | 0  | 2  | 0  | 0  | 0  | 3  | 0  | 0  | 0  | 0  | 0  | 0  | 0  | 0  | 0  | 3  | 0  | 0  | 0  | 4  | 0  | 0  |
| 2zz | 0  | 1  | 0  | 0  | 0  | 0  | 1  | 0  | 0  | 0  | 0  | 0  | 0  | 1  | 1  | 0  | 0  | 0  | 0  | 0  | 0  | 3  | 0  | 0  |
| 3a  | 95 | 0  | 0  | 0  | 10 | 0  | 0  | 0  | 0  | 0  | 0  | 2  | 0  | 0  | 2  | 3  | 1  | 0  | 1  | 0  | 0  | 2  | 0  | 0  |
| 3b  | 1  | 92 | 0  | 0  | 4  | 0  | 1  | 2  | 0  | 0  | 0  | 0  | 0  | 5  | 6  | 0  | 0  | 0  | 0  | 0  | 0  | 0  | 0  | 0  |
| 3c  | 0  | 1  | 97 | 0  | 0  | 0  | 2  | 1  | 0  | 0  | 0  | 0  | 0  | 1  | 1  | 0  | 0  | 0  | 0  | 0  | 0  | 0  | 3  | 0  |
| 3d  | 0  | 0  | 0  | 86 | 0  | 0  | 0  | 0  | 0  | 0  | 0  | 0  | 0  | 2  | 2  | 0  | 0  | 0  | 0  | 0  | 0  | 0  | 0  | 0  |
| 3e  | 0  | 4  | 0  | 0  | 76 | 0  | 6  | 0  | 0  | 0  | 0  | 0  | 1  | 1  | 4  | 2  | 0  | 2  | 0  | 0  | 0  | 0  | 0  | 0  |
| 3f  | 0  | 0  | 0  | 0  | 0  | 89 | 0  | 0  | 0  | 0  | 0  | 0  | 0  | 1  | 2  | 0  | 0  | 0  | 0  | 0  | 0  | 5  | 0  | 0  |
| 3g  | 0  | 0  | 2  | 0  | 0  | 0  | 96 | 0  | 0  | 0  | 0  | 0  | 0  | 2  | 3  | 0  | 0  | 0  | 0  | 0  | 0  | 0  | 0  | 0  |
| 3h  | 0  | 0  | 2  | 0  | 0  | 0  | 0  | 99 | 0  | 0  | 0  | 0  | 1  | 1  | 3  | 0  | 0  | 2  | 0  | 0  | 3  | 2  | 0  | 0  |
| 3i  | 2  | 1  | 0  | 17 | 0  | 0  | 0  | 0  | 80 | 0  | 1  | 0  | 1  | 16 | 2  | 0  | 5  | 0  | 7  | 0  | 7  | 24 | 0  | 0  |
| 3j  | 0  | 0  | 2  | 0  | 0  | 0  | 0  | 0  | 0  | 83 | 0  | 0  | 0  | 0  | 1  | 0  | 3  | 0  | 0  | 3  | 0  | 0  | 0  | 0  |
| 3k  | 0  | 0  | 2  | 0  | 0  | 0  | 0  | 0  | 0  | 0  | 95 | 0  | 0  | 0  | 3  | 0  | 0  | 1  | 0  | 0  | 0  | 2  | 0  | 0  |
| 3l  | 0  | 0  | 1  | 0  | 0  | 0  | 0  | 1  | 0  | 0  | 0  | 84 | 0  | 1  | 1  | 0  | 2  | 0  | 0  | 0  | 2  | 3  | 0  | 0  |
| 3m  | 0  | 0  | 1  | 0  | 0  | 0  | 1  | 1  | 0  | 0  | 0  | 0  | 90 | 1  | 2  | 0  | 2  | 1  | 0  | 0  | 0  | 3  | 0  | 0  |
| 3n  | 0  | 0  | 0  | 0  | 0  | 0  | 0  | 0  | 1  | 0  | 0  | 0  | 0  | 93 | 1  | 0  | 0  | 0  | 0  | 0  | 0  | 2  | 0  | 0  |
| 3o  | 0  | 0  | 0  | 0  | 0  | 0  | 2  | 1  | 0  | 0  | 0  | 0  | 0  | 1  | 97 | 0  | 0  | 0  | 1  | 0  | 0  | 2  | 0  | 0  |
| 3p  | 4  | 20 | 10 | 0  | 8  | 0  | 3  | 0  | 0  | 0  | 0  | 0  | 0  | 2  | 0  | 78 | 1  | 0  | 1  | 0  | 0  | 2  | 0  | 0  |
| 3q  | 0  | 0  | 2  | 0  | 0  | 0  | 1  | 3  | 0  | 0  | 0  | 0  | 0  | 2  | 4  | 0  | 99 | 0  | 0  | 0  | 0  | 0  | 0  | 0  |
| 3r  | 0  | 0  | 5  | 0  | 1  | 0  | 2  | 4  | 0  | 0  | 15 | 0  | 0  | 1  | 1  | 0  | 1  | 99 | 0  | 0  | 0  | 0  | 0  | 0  |
| 3s  | 4  | 0  | 2  | 1  | 1  | 0  | 1  | 0  | 12 | 0  | 2  | 8  | 3  | 6  | 1  | 19 | 9  | 0  | 91 | 0  | 0  | 0  | 0  | 0  |
| 3t  | 0  | 0  | 0  | 0  | 0  | 0  | 0  | 0  | 0  | 0  | 0  | 0  | 0  | 3  | 2  | 0  | 0  | 0  | 0  | 90 | 0  | 0  | 0  | 0  |
| 3u  | 0  | 0  | 1  | 0  | 1  | 0  | 0  | 0  | 0  | 0  | 0  | 0  | 0  | 2  | 2  | 0  | 2  | 1  | 0  | 0  | 99 | 0  | 0  | 0  |
| 3v  | 0  | 0  | 0  | 0  | 1  | 0  | 1  | 0  | 2  | 0  | 0  | 0  | 0  | 2  | 4  | 0  | 0  | 0  | 0  | 0  | 2  | 99 | 0  | 0  |
| 3x  | 0  | 0  | 0  | 0  | 0  | 0  | 0  | 1  | 0  | 0  | 0  | 0  | 0  | 1  | 1  | 0  | 0  | 0  | 0  | 0  | 0  | 0  | 89 | 0  |
| 3y  | 0  | 0  | 0  | 0  | 0  | 1  | 0  | 0  | 0  | 1  | 0  | 0  | 0  | 0  | 2  | 10 | 0  | 0  | 0  | 0  | 1  | 0  | 3  | 96 |
| 3z  | 0  | 0  | 0  | 0  | 0  | 0  | 0  | 0  | 0  | 0  | 0  | 0  | 0  | 0  | 1  | 0  | 0  | 0  | 0  | 0  | 3  | 1  | 0  | 1  |
| 3ww | 0  | 0  | 0  | 0  | 0  | 0  | 0  | 0  | 0  | 0  | 0  | 0  | 0  | 0  | 0  | 0  | 0  | 0  | 0  | 0  | 0  | 0  | 0  | 1  |
| 3xx | 0  | 0  | 0  | 0  | 0  | 0  | 0  | 0  | 0  | 0  | 0  | 0  | 0  | 0  | 0  | 0  | 0  | 20 | 0  | 0  | 0  | 0  | 0  | 2  |
| 3yy | 0  | 0  | 0  | 0  | 0  | 0  | 0  | 0  | 0  | 0  | 0  | 0  | 0  | 0  | 1  | 0  | 0  | 0  | 0  | 0  | 0  | 0  | 0  | 2  |
| 3zz | 0  | 0  | 0  | 0  | 0  | 0  | 0  | 0  | 0  | 0  | 0  | 0  | 0  | 0  | 0  | 0  | 0  | 0  | 0  | 0  | 7  | 5  | 0  | 1  |

FIG. 14
(Continued)

|  | 3z | 3ww | 3xx | 3yy | 3zz | 4a | 4b | 4c | 4d | 4e | 4f | 4g | 4h | 4i | 4k | 4k | 4l | 4m | 4n | 4o | 4p | 4q | 4r | 4s |
|---|---|---|---|---|---|---|---|---|---|---|---|---|---|---|---|---|---|---|---|---|---|---|---|---|
| 2s | 0 | 1 | 0 | 1 | 2 | 2 | 2 | 7 | 2 | 0 | 0 | 0 | 4 | 1 | 1 | 2 | 0 | 1 | 1 | 0 | 4 | 0 | 0 | 0 |
| 2t | 0 | 0 | 0 | 1 | 0 | 1 | 0 | 1 | 0 | 0 | 0 | 0 | 3 | 3 | 0 | 0 | 0 | 0 | 0 | 2 | 0 | 0 | 3 | 0 |
| 2u | 0 | 0 | 0 | 1 | 1 | 1 | 0 | 1 | 0 | 0 | 1 | 0 | 3 | 0 | 0 | 1 | 0 | 0 | 0 | 1 | 0 | 2 | 0 | 0 |
| 2v | 0 | 1 | 0 | 0 | 1 | 1 | 0 | 2 | 0 | 0 | 0 | 0 | 3 | 0 | 0 | 0 | 0 | 0 | 0 | 0 | 0 | 2 | 1 | 0 |
| 2w | 1 | 1 | 3 | 2 | 1 | 16 | 0 | 0 | 0 | 0 | 0 | 0 | 3 | 2 | 0 | 2 | 0 | 0 | 2 | 0 | 0 | 0 | 0 | 0 |
| 2z | 2 | 3 | 0 | 0 | 6 | 0 | 0 | 1 | 0 | 1 | 1 | 2 | 1 | 3 | 0 | 0 | 0 | 0 | 0 | 0 | 1 | 0 | 4 | 6 |
| 2xx | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 1 | 0 |
| 2yy | 0 | 0 | 0 | 0 | 0 | 0 | 0 | 0 | 2 | 0 | 0 | 0 | 3 | 0 | 0 | 0 | 0 | 0 | 0 | 0 | 0 | 0 | 3 | 0 |
| 2zz | 0 | 0 | 0 | 1 | 0 | 0 | 2 | 0 | 0 | 0 | 0 | 1 | 0 | 0 | 0 | 0 | 0 | 0 | 1 | 1 | 0 | 0 | 0 | 0 |
| 3a | 0 | 0 | 0 | 0 | 0 | 0 | 1 | 0 | 0 | 0 | 0 | 0 | 0 | 0 | 0 | 0 | 2 | 0 | 0 | 2 | 3 | 1 | 0 | 1 |
| 3b | 0 | 0 | 0 | 0 | 0 | 5 | 0 | 0 | 4 | 0 | 1 | 2 | 0 | 0 | 0 | 0 | 0 | 5 | 6 | 0 | 0 | 0 | 0 | 0 |
| 3c | 0 | 0 | 0 | 0 | 0 | 0 | 0 | 0 | 0 | 0 | 0 | 2 | 1 | 0 | 0 | 0 | 0 | 0 | 1 | 1 | 0 | 0 | 0 | 0 |
| 3d | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3e | 1 | 0 | 0 | 0 | 0 | 0 | 0 | 0 | 0 | 0 | 0 | 0 | 3 | 0 | 0 | 0 | 0 | 0 | 1 | 1 | 4 | 2 | 0 | 2 |
| 3f | 0 | 0 | 0 | 0 | 0 | 0 | 0 | 0 | 0 | 0 | 0 | 0 | 0 | 0 | 0 | 0 | 0 | 0 | 0 | 1 | 2 | 0 | 0 | 0 |
| 3g | 0 | 0 | 0 | 0 | 0 | 0 | 0 | 2 | 0 | 0 | 0 | 0 | 1 | 0 | 0 | 0 | 0 | 0 | 0 | 2 | 3 | 0 | 0 | 0 |
| 3h | 1 | 0 | 0 | 0 | 0 | 0 | 0 | 2 | 0 | 0 | 0 | 0 | 0 | 0 | 0 | 0 | 0 | 0 | 1 | 1 | 3 | 0 | 0 | 2 |
| 3i | 1 | 0 | 0 | 0 | 0 | 2 | 2 | 0 | 0 | 0 | 0 | 0 | 0 | 0 | 0 | 0 | 0 | 0 | 1 | 5 | 0 | 0 | 0 | 2 |
| 3j | 5 | 1 | 0 | 0 | 0 | 0 | 0 | 2 | 0 | 0 | 0 | 0 | 0 | 0 | 0 | 0 | 0 | 0 | 0 | 1 | 0 | 0 | 3 | 0 |
| 3k | 0 | 0 | 0 | 0 | 0 | 0 | 0 | 2 | 0 | 0 | 0 | 0 | 0 | 0 | 0 | 0 | 0 | 0 | 1 | 3 | 0 | 0 | 1 | 0 |
| 3l | 0 | 0 | 0 | 0 | 0 | 0 | 0 | 1 | 0 | 0 | 0 | 0 | 1 | 0 | 0 | 0 | 1 | 0 | 2 | 4 | 0 | 2 | 0 | 0 |
| 3m | 0 | 0 | 0 | 0 | 0 | 0 | 0 | 1 | 0 | 0 | 1 | 1 | 0 | 0 | 0 | 0 | 0 | 2 | 2 | 3 | 0 | 2 | 1 | 0 |
| 3n | 0 | 0 | 0 | 0 | 0 | 0 | 0 | 0 | 0 | 0 | 0 | 0 | 1 | 0 | 0 | 0 | 0 | 0 | 0 | 1 | 0 | 0 | 0 | 0 |
| 3o | 0 | 0 | 0 | 0 | 0 | 0 | 0 | 0 | 0 | 0 | 0 | 2 | 1 | 0 | 0 | 0 | 0 | 0 | 0 | 0 | 0 | 0 | 0 | 1 |
| 3p | 0 | 9 | 0 | 0 | 0 | 0 | 8 | 0 | 0 | 0 | 0 | 0 | 1 | 0 | 0 | 0 | 0 | 0 | 0 | 0 | 0 | 3 | 1 | 0 |
| 3q | 0 | 0 | 0 | 0 | 0 | 0 | 0 | 2 | 0 | 0 | 0 | 1 | 3 | 0 | 0 | 0 | 0 | 0 | 2 | 0 | 0 | 1 | 1 | 0 |
| 3r | 0 | 0 | 6 | 0 | 0 | 0 | 0 | 5 | 0 | 1 | 0 | 1 | 1 | 0 | 0 | 0 | 0 | 0 | 1 | 1 | 0 | 1 | 1 | 0 |
| 3s | 10 | 0 | 0 | 0 | 0 | 4 | 2 | 0 | 1 | 1 | 0 | 1 | 0 | 0 | 1 | 5 | 0 | 3 | 1 | 0 | 1 | 0 | 6 | 0 |
| 3t | 0 | 0 | 0 | 0 | 0 | 0 | 0 | 0 | 0 | 0 | 0 | 0 | 0 | 0 | 0 | 0 | 0 | 0 | 3 | 2 | 0 | 0 | 0 | 0 |
| 3u | 0 | 0 | 0 | 0 | 0 | 0 | 0 | 1 | 0 | 1 | 0 | 0 | 0 | 0 | 0 | 0 | 0 | 0 | 2 | 2 | 0 | 2 | 1 | 0 |
| 3v | 0 | 0 | 0 | 0 | 0 | 0 | 0 | 1 | 0 | 0 | 1 | 0 | 2 | 0 | 0 | 0 | 0 | 0 | 2 | 4 | 0 | 0 | 0 | 0 |
| 3x | 0 | 0 | 0 | 0 | 0 | 0 | 0 | 0 | 0 | 0 | 0 | 1 | 0 | 0 | 0 | 0 | 0 | 0 | 1 | 1 | 0 | 0 | 0 | 0 |
| 3y | 1 | 1 | 0 | 0 | 1 | 0 | 0 | 0 | 0 | 1 | 0 | 0 | 0 | 1 | 0 | 0 | 0 | 0 | 0 | 0 | 5 | 0 | 0 | 0 |
| 3z | 93 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 |
| 3ww | 0 | 89 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3xx | 1 | 0 | 75 | 0 | 0 | 0 | 0 | 0 | 0 | 0 | 0 | 0 | 0 | 0 | 0 | 0 | 0 | 0 | 0 | 0 | 0 | 0 | 0 | 0 |
| 3yy | 0 | 0 | 0 | 94 | 0 | 0 | 0 | 0 | 0 | 0 | 0 | 0 | 0 | 0 | 0 | 0 | 0 | 0 | 0 | 1 | 0 | 0 | 0 | 0 |
| 3zz | 0 | 0 | 0 | 4 | 74 | 0 | 0 | 0 | 0 | 0 | 0 | 0 | 0 | 0 | 0 | 0 | 0 | 0 | 0 | 0 | 0 | 0 | 0 | 0 |

FIG. 14
(Continued)

|  | 4t | 4u | 4v | 4w | 4x | 4y | 4z | 4ww | 4xx | 4yy | 4zz |
|---|---|---|---|---|---|---|---|---|---|---|---|
| 2s | 0 | 3 | 5 | 0 | 0 | 4 | 0 | 1 | 0 | 1 | 2 |
| 2t | 0 | 0 | 0 | 0 | 0 | 0 | 0 | 0 | 0 | 1 | 0 |
| 2u | 0 | 1 | 4 | 1 | 0 | 2 | 0 | 0 | 0 | 1 | 1 |
| 2v | 0 | 3 | 0 | 1 | 2 | 2 | 0 | 1 | 0 | 0 | 0 |
| 2w | 0 | 6 | 2 | 5 | 1 | 7 | 21 | 1 | 3 | 0 | 0 |
| 2z | 1 | 2 | 1 | 2 | 2 | 7 | 0 | 3 | 0 | 1 | 3 |
| 2xx | 0 | 0 | 1 | 4 | 0 | 0 | 0 | 0 | 0 | 0 | 0 |
| 2yy | 0 | 0 | 4 | 6 | 0 | 0 | 0 | 0 | 0 | 0 | 0 |
| 2zz | 0 | 0 | 3 | 0 | 0 | 0 | 0 | 0 | 0 | 1 | 0 |
| 3a | 0 | 0 | 0 | 1 | 0 | 0 | 0 | 0 | 0 | 0 | 0 |
| 3b | 0 | 0 | 0 | 1 | 0 | 0 | 0 | 0 | 0 | 0 | 0 |
| 3c | 0 | 0 | 0 | 3 | 0 | 0 | 0 | 0 | 0 | 0 | 0 |
| 3d | 0 | 0 | 0 | 5 | 0 | 0 | 0 | 0 | 0 | 0 | 0 |
| 3e | 0 | 0 | 4 | 2 | 0 | 0 | 1 | 0 | 0 | 0 | 0 |
| 3F | 0 | 5 | 0 | 0 | 0 | 0 | 0 | 0 | 0 | 0 | 0 |
| 3G | 0 | 0 | 0 | 7 | 0 | 0 | 0 | 0 | 0 | 0 | 0 |
| 3H | 0 | 3 | 2 | 0 | 0 | 0 | 1 | 0 | 0 | 0 | 0 |
| 3I | 0 | 0 | 0 | 2 | 0 | 0 | 1 | 0 | 0 | 3 | 0 |
| 3j | 0 | 2 | 0 | 1 | 0 | 0 | 0 | 1 | 0 | 0 | 0 |
| 3k | 0 | 0 | 2 | 7 | 0 | 0 | 0 | 0 | 0 | 0 | 0 |
| 3l | 0 | 2 | 3 | 0 | 0 | 0 | 0 | 0 | 0 | 0 | 0 |
| 3m | 0 | 0 | 3 | 1 | 0 | 0 | 0 | 0 | 0 | 0 | 0 |
| 3n | 0 | 0 | 2 | 0 | 0 | 0 | 0 | 0 | 0 | 0 | 0 |
| 3o | 0 | 0 | 2 | 4 | 0 | 0 | 0 | 0 | 0 | 0 | 0 |
| 3p | 0 | 0 | 0 | 0 | 0 | 0 | 0 | 0 | 0 | 0 | 0 |
| 3q | 0 | 0 | 0 | 0 | 0 | 0 | 0 | 0 | 0 | 0 | 0 |
| 3r | 0 | 0 | 0 | 0 | 0 | 0 | 0 | 0 | 6 | 0 | 0 |
| 3s | 0 | 1 | 0 | 0 | 0 | 0 | 1 | 0 | 0 | 0 | 0 |
| 3t | 2 | 2 | 2 | 7 | 0 | 0 | 0 | 0 | 0 | 0 | 0 |
| 3u | 0 | 0 | 0 | 3 | 0 | 0 | 0 | 0 | 0 | 0 | 0 |
| 3v | 0 | 0 | 0 | 0 | 0 | 0 | 0 | 0 | 0 | 0 | 0 |
| 3x | 0 | 0 | 0 | 0 | 0 | 0 | 0 | 0 | 0 | 0 | 0 |
| 3y | 0 | 1 | 0 | 0 | 3 | 0 | 1 | 1 | 0 | 0 | 1 |
| 3z | 0 | 1 | 1 | 0 | 0 | 0 | 0 | 0 | 0 | 0 | 0 |
| 3ww | 0 | 0 | 0 | 0 | 0 | 0 | 0 | 0 | 0 | 0 | 0 |
| 3xx | 0 | 0 | 0 | 0 | 0 | 2 | 0 | 0 | 0 | 0 | 0 |
| 3yy | 0 | 0 | 0 | 0 | 0 | 2 | 0 | 0 | 0 | 0 | 0 |
| 3zz | 0 | 7 | 5 | 0 | 0 | 1 | 0 | 0 | 0 | 0 | 0 |

FIG. 14
(Continued)

|     | 1c | 1f | 1k | 1m | 1o | 1p | 1r | 1s | 1v | 1z | 1xx | 2b | 2c | 2d | 2f |
|-----|----|----|----|----|----|----|----|----|----|----|-----|----|----|----|----|
| 1c  | 99 | 1  | 0  | 0  | 1  | 0  | 1  | 1  | 1  | 0  | 0   | 0  | 1  | 0  | 1  |
| 1f  | 0  | 82 | 0  | 0  | 2  | 2  | 4  | 0  | 0  | 1  | 0   | 2  | 0  | 3  | 0  |
| 1k  | 1  | 0  | 82 | 0  | 1  | 0  | 3  | 0  | 0  | 0  | 0   | 1  | 1  | 7  | 1  |
| 1m  | 2  | 0  | 0  | 99 | 3  | 0  | 6  | 1  | 0  | 0  | 0   | 0  | 0  | 0  | 1  |
| 1o  | 4  | 1  | 7  | 0  | 33 | 4  | 4  | 4  | 2  | 1  | 0   | 2  | 4  | 2  | 3  |
| 1p  | 3  | 6  | 6  | 0  | 3  | 70 | 0  | 0  | 2  | 5  | 0   | 0  | 0  | 0  | 6  |
| 1r  | 0  | 23 | 2  | 1  | 3  | 0  | 99 | 0  | 5  | 0  | 0   | 3  | 0  | 0  | 1  |
| 1s  | 3  | 0  | 0  | 7  | 2  | 0  | 1  | 95 | 2  | 0  | 0   | 1  | 3  | 2  | 0  |
| 1v  | 0  | 1  | 2  | 1  | 1  | 0  | 3  | 1  | 99 | 1  | 0   | 7  | 0  | 0  | 1  |
| 1z  | 6  | 0  | 2  | 0  | 2  | 0  | 1  | 0  | 0  | 87 | 0   | 5  | 6  | 0  | 0  |
| 1xx | 2  | 0  | 0  | 0  | 4  | 0  | 0  | 0  | 0  | 1  | 81  | 0  | 2  | 0  | 0  |
| 2b  | 0  | 0  | 0  | 0  | 4  | 0  | 0  | 0  | 0  | 0  | 0   | 93 | 0  | 0  | 0  |
| 2c  | 0  | 0  | 0  | 0  | 0  | 0  | 0  | 0  | 0  | 0  | 0   | 0  | 99 | 0  | 0  |
| 2d  | 0  | 0  | 0  | 0  | 0  | 0  | 1  | 0  | 0  | 0  | 0   | 0  | 0  | 84 | 0  |
| 2f  | 3  | 0  | 0  | 5  | 1  | 0  | 0  | 0  | 0  | 0  | 0   | 0  | 3  | 0  | 92 |
| 2g  | 0  | 0  | 0  | 0  | 0  | 0  | 2  | 0  | 2  | 0  | 0   | 0  | 0  | 1  | 0  |
| 2n  | 1  | 0  | 1  | 0  | 0  | 0  | 3  | 0  | 0  | 6  | 0   | 0  | 1  | 8  | 0  |
| 2s  | 7  | 0  | 2  | 1  | 5  | 1  | 0  | 0  | 3  | 0  | 0   | 2  | 7  | 6  | 0  |
| 2t  | 1  | 0  | 0  | 0  | 2  | 0  | 3  | 0  | 0  | 0  | 0   | 1  | 0  | 0  | 0  |
| 2w  | 1  | 0  | 0  | 1  | 1  | 0  | 0  | 1  | 3  | 0  | 2   | 0  | 1  | 1  | 0  |
| 2z  | 1  | 1  | 0  | 0  | 0  | 4  | 0  | 4  | 4  | 7  | 0   | 1  | 1  | 0  | 1  |
| 3a  | 0  | 0  | 2  | 0  | 3  | 1  | 1  | 0  | 0  | 0  | 0   | 0  | 0  | 0  | 0  |
| 3b  | 0  | 0  | 0  | 0  | 6  | 0  | 0  | 0  | 0  | 0  | 0   | 0  | 0  | 0  | 0  |
| 3c  | 0  | 0  | 0  | 0  | 1  | 0  | 0  | 0  | 0  | 0  | 0   | 1  | 0  | 0  | 0  |
| 3d  | 0  | 0  | 0  | 0  | 0  | 0  | 0  | 0  | 0  | 0  | 0   | 0  | 0  | 0  | 0  |
| 3e  | 0  | 0  | 0  | 1  | 0  | 2  | 2  | 0  | 0  | 1  | 0   | 0  | 0  | 0  | 0  |
| 3g  | 2  | 0  | 0  | 0  | 3  | 0  | 0  | 0  | 0  | 0  | 0   | 0  | 2  | 0  | 0  |
| 3h  | 2  | 0  | 0  | 1  | 3  | 0  | 2  | 0  | 2  | 1  | 0   | 0  | 2  | 0  | 0  |
| 3i  | 0  | 0  | 1  | 0  | 5  | 0  | 2  | 0  | 0  | 1  | 0   | 0  | 0  | 0  | 0  |
| 3k  | 2  | 0  | 0  | 0  | 3  | 0  | 1  | 0  | 2  | 0  | 0   | 0  | 2  | 0  | 0  |
| 3l  | 1  | 0  | 0  | 0  | 4  | 0  | 0  | 0  | 3  | 0  | 0   | 0  | 1  | 0  | 0  |
| 3n  | 0  | 0  | 0  | 0  | 0  | 0  | 0  | 0  | 2  | 0  | 0   | 0  | 0  | 0  | 0  |
| 3p  | 8  | 0  | 0  | 0  | 1  | 0  | 0  | 1  | 0  | 0  | 0   | 0  | 0  | 0  | 0  |
| 3q  | 2  | 0  | 0  | 0  | 4  | 0  | 1  | 0  | 0  | 0  | 0   | 0  | 2  | 0  | 0  |
| 3r  | 5  | 0  | 0  | 0  | 1  | 0  | 1  | 0  | 0  | 0  | 6   | 0  | 5  | 0  | 0  |
| 3s  | 2  | 0  | 5  | 0  | 5  | 0  | 3  | 0  | 0  | 5  | 0   | 2  | 1  | 0  | 0  |
| 3t  | 0  | 0  | 0  | 0  | 2  | 0  | 0  | 0  | 2  | 0  | 0   | 0  | 0  | 0  | 0  |
| 3v  | 0  | 0  | 0  | 0  | 4  | 0  | 0  | 0  | 0  | 0  | 0   | 0  | 0  | 0  | 0  |
| 3x  | 0  | 0  | 0  | 0  | 1  | 0  | 0  | 0  | 0  | 0  | 0   | 0  | 0  | 0  | 0  |
| 3y  | 0  | 1  | 0  | 0  | 2  | 0  | 0  | 0  | 0  | 0  | 0   | 0  | 0  | 0  | 1  |
| 3z  | 0  | 0  | 0  | 0  | 1  | 0  | 0  | 0  | 1  | 0  | 0   | 0  | 0  | 0  | 0  |
| 3ww | 0  | 0  | 0  | 0  | 0  | 0  | 0  | 0  | 0  | 0  | 0   | 0  | 0  | 0  | 0  |
| 3xx | 0  | 0  | 0  | 0  | 0  | 0  | 0  | 0  | 0  | 0  | 1   | 0  | 0  | 0  | 0  |
| 3yy | 0  | 0  | 0  | 0  | 1  | 0  | 0  | 0  | 0  | 0  | 0   | 0  | 0  | 0  | 0  |

FIG. 15

|     | 2g | 2n | 2s | 2t | 2w | 2z | 3a | 3b | 3c | 3d | 3e | 3g | 3h | 3i | 3k |
|-----|----|----|----|----|----|----|----|----|----|----|----|----|----|----|----|
| 1c  | 0  | 0  | 1  | 0  | 1  | 0  | 0  | 2  | 0  | 0  | 6  | 0  | 6  | 1  | 0  |
| 1f  | 3  | 1  | 0  | 0  | 5  | 1  | 0  | 2  | 0  | 3  | 0  | 0  | 5  | 0  | 0  |
| 1k  | 0  | 0  | 0  | 1  | 1  | 0  | 0  | 1  | 1  | 7  | 1  | 12 | 0  | 0  | 1  |
| 1m  | 0  | 7  | 1  | 0  | 1  | 0  | 0  | 59 | 0  | 0  | 4  | 7  | 0  | 0  | 0  |
| 1o  | 1  | 3  | 2  | 1  | 6  | 1  | 4  | 1  | 4  | 3  | 0  | 0  | 2  | 4  | 4  |
| 1p  | 0  | 0  | 0  | 0  | 2  | 5  | 43 | 0  | 0  | 0  | 1  | 0  | 1  | 0  | 6  |
| 1r  | 2  | 2  | 0  | 0  | 0  | 0  | 0  | 3  | 26 | 0  | 0  | 1  | 1  | 0  | 2  |
| 1s  | 1  | 0  | 1  | 0  | 2  | 1  | 1  | 1  | 3  | 2  | 0  | 0  | 7  | 0  | 7  |
| 1v  | 0  | 1  | 1  | 0  | 0  | 1  | 0  | 5  | 0  | 8  | 0  | 0  | 2  | 2  | 2  |
| 1z  | 2  | 0  | 0  | 0  | 0  | 24 | 3  | 5  | 6  | 0  | 0  | 0  | 2  | 3  | 2  |
| 1xx | 1  | 0  | 0  | 0  | 0  | 1  | 0  | 0  | 2  | 0  | 0  | 1  | 0  | 0  | 0  |
| 2b  | 0  | 0  | 0  | 0  | 0  | 0  | 0  | 0  | 0  | 0  | 0  | 0  | 0  | 0  | 0  |
| 2c  | 3  | 0  | 0  | 0  | 0  | 0  | 0  | 0  | 0  | 0  | 0  | 1  | 0  | 0  | 0  |
| 2d  | 0  | 0  | 0  | 0  | 1  | 0  | 0  | 0  | 0  | 0  | 0  | 0  | 0  | 0  | 0  |
| 2f  | 0  | 0  | 0  | 0  | 4  | 0  | 0  | 0  | 3  | 0  | 0  | 0  | 0  | 0  | 0  |
| 2g  | 95 | 1  | 0  | 0  | 5  | 0  | 0  | 0  | 0  | 1  | 0  | 23 | 7  | 3  | 0  |
| 2n  | 0  | 99 | 0  | 0  | 0  | 6  | 0  | 0  | 0  | 1  | 0  | 0  | 0  | 0  | 1  |
| 2s  | 0  | 1  | 92 | 0  | 3  | 0  | 2  | 2  | 4  | 6  | 0  | 0  | 19 | 0  | 2  |
| 2t  | 0  | 0  | 0  | 97 | 0  | 0  | 1  | 0  | 1  | 0  | 0  | 0  | 3  | 3  | 0  |
| 2w  | 0  | 1  | 1  | 9  | 99 | 2  | 1  | 0  | 0  | 9  | 0  | 0  | 7  | 0  | 0  |
| 2z  | 2  | 0  | 6  | 1  | 7  | 99 | 0  | 1  | 13 | 0  | 1  | 0  | 49 | 3  | 0  |
| 3a  | 0  | 2  | 0  | 0  | 0  | 0  | 95 | 0  | 0  | 0  | 10 | 0  | 0  | 0  | 2  |
| 3b  | 1  | 5  | 0  | 0  | 2  | 0  | 1  | 92 | 0  | 0  | 4  | 1  | 2  | 0  | 0  |
| 3c  | 2  | 1  | 0  | 0  | 11 | 0  | 0  | 1  | 97 | 0  | 0  | 2  | 1  | 0  | 0  |
| 3d  | 0  | 2  | 0  | 0  | 5  | 0  | 0  | 0  | 0  | 86 | 0  | 0  | 0  | 0  | 0  |
| 3e  | 0  | 1  | 0  | 0  | 0  | 1  | 0  | 4  | 0  | 0  | 76 | 6  | 0  | 0  | 0  |
| 3g  | 0  | 2  | 0  | 0  | 1  | 0  | 0  | 0  | 2  | 0  | 0  | 96 | 0  | 0  | 0  |
| 3h  | 0  | 1  | 0  | 0  | 0  | 1  | 0  | 0  | 2  | 0  | 0  | 0  | 99 | 0  | 0  |
| 3i  | 0  | 0  | 3  | 0  | 0  | 1  | 2  | 1  | 0  | 17 | 0  | 0  | 0  | 80 | 1  |
| 3k  | 0  | 1  | 0  | 0  | 7  | 0  | 0  | 0  | 2  | 0  | 0  | 0  | 0  | 0  | 95 |
| 3l  | 0  | 1  | 0  | 0  | 0  | 0  | 0  | 0  | 1  | 0  | 0  | 0  | 1  | 0  | 0  |
| 3n  | 0  | 1  | 0  | 0  | 0  | 0  | 0  | 0  | 0  | 0  | 0  | 0  | 1  | 0  | 0  |
| 3p  | 0  | 2  | 1  | 0  | 0  | 0  | 4  | 20 | 10 | 0  | 8  | 3  | 0  | 0  | 0  |
| 3q  | 1  | 2  | 0  | 0  | 0  | 0  | 0  | 0  | 2  | 0  | 0  | 1  | 3  | 0  | 0  |
| 3r  | 1  | 1  | 0  | 0  | 0  | 0  | 0  | 0  | 5  | 0  | 1  | 2  | 4  | 0  | 15 |
| 3s  | 1  | 6  | 3  | 0  | 1  | 1  | 4  | 0  | 2  | 1  | 1  | 1  | 0  | 12 | 2  |
| 3t  | 0  | 3  | 0  | 0  | 7  | 0  | 0  | 0  | 0  | 0  | 0  | 0  | 0  | 0  | 0  |
| 3v  | 1  | 2  | 0  | 0  | 0  | 0  | 0  | 0  | 0  | 0  | 1  | 1  | 0  | 2  | 0  |
| 3x  | 0  | 1  | 0  | 0  | 0  | 0  | 0  | 0  | 0  | 0  | 0  | 0  | 1  | 0  | 0  |
| 3y  | 0  | 0  | 0  | 0  | 0  | 1  | 0  | 0  | 0  | 0  | 0  | 0  | 0  | 0  | 0  |
| 3z  | 0  | 0  | 0  | 0  | 0  | 0  | 0  | 0  | 0  | 0  | 0  | 0  | 0  | 0  | 0  |
| 3ww | 0  | 0  | 0  | 0  | 0  | 0  | 0  | 0  | 0  | 0  | 0  | 0  | 0  | 0  | 0  |
| 3xx | 0  | 0  | 0  | 0  | 0  | 1  | 0  | 0  | 0  | 0  | 0  | 0  | 0  | 0  | 0  |
| 3yy | 0  | 0  | 0  | 0  | 0  | 0  | 0  | 0  | 0  | 0  | 0  | 0  | 0  | 0  | 0  |

FIG. 15
(Continued)

|      | 3l | 3n | 3p | 3q | 3r | 3s | 3t | 3v | 3x | 3y | 3z | 3ww | 3xx | 3yy |
|------|----|----|----|----|----|----|----|----|----|----|----|-----|-----|-----|
| 1c   | 0  | 0  | 0  | 1  | 2  | 1  | 1  | 0  | 0  | 1  | 0  | 0   | 0   | 1   |
| 1f   | 0  | 1  | 2  | 0  | 4  | 0  | 0  | 0  | 0  | 3  | 1  | 0   | 0   | 3   |
| 1k   | 0  | 0  | 0  | 0  | 3  | 0  | 1  | 0  | 0  | 1  | 0  | 0   | 0   | 1   |
| 1m   | 0  | 7  | 0  | 1  | 4  | 0  | 0  | 3  | 0  | 3  | 0  | 0   | 0   | 7   |
| 1o   | 1  | 7  | 4  | 15 | 5  | 4  | 1  | 4  | 2  | 10 | 10 | 2   | 0   | 0   |
| 1p   | 0  | 0  | 5  | 3  | 1  | 0  | 0  | 0  | 0  | 0  | 5  | 4   | 0   | 0   |
| 1r   | 4  | 2  | 0  | 5  | 27 | 0  | 0  | 5  | 3  | 2  | 0  | 0   | 0   | 3   |
| 1s   | 0  | 0  | 0  | 24 | 22 | 2  | 0  | 0  | 0  | 0  | 11 | 0   | 0   | 0   |
| 1v   | 3  | 8  | 0  | 1  | 3  | 1  | 0  | 0  | 0  | 0  | 1  | 0   | 0   | 47  |
| 1z   | 0  | 0  | 0  | 1  | 1  | 0  | 0  | 1  | 0  | 1  | 7  | 0   | 0   | 0   |
| 1xx  | 0  | 0  | 0  | 0  | 10 | 0  | 0  | 1  | 0  | 1  | 1  | 0   | 0   | 0   |
| 2b   | 0  | 39 | 0  | 4  | 0  | 0  | 0  | 0  | 15 | 1  | 0  | 0   | 0   | 0   |
| 2c   | 0  | 0  | 0  | 15 | 0  | 0  | 0  | 0  | 0  | 0  | 0  | 0   | 0   | 0   |
| 2d   | 0  | 0  | 0  | 2  | 1  | 0  | 0  | 0  | 0  | 0  | 0  | 0   | 0   | 0   |
| 2f   | 0  | 15 | 0  | 9  | 0  | 0  | 0  | 0  | 0  | 1  | 0  | 0   | 0   | 0   |
| 2g   | 0  | 1  | 0  | 6  | 0  | 0  | 0  | 0  | 1  | 0  | 0  | 1   | 0   | 2   |
| 2n   | 1  | 18 | 0  | 0  | 3  | 0  | 0  | 0  | 0  | 0  | 0  | 1   | 0   | 2   |
| 2s   | 0  | 0  | 4  | 2  | 1  | 0  | 0  | 0  | 0  | 4  | 0  | 1   | 0   | 1   |
| 2t   | 0  | 0  | 0  | 11 | 3  | 0  | 11 | 0  | 0  | 0  | 0  | 0   | 0   | 1   |
| 2w   | 0  | 0  | 0  | 7  | 4  | 1  | 3  | 0  | 0  | 6  | 1  | 1   | 3   | 2   |
| 2z   | 0  | 0  | 38 | 1  | 4  | 6  | 1  | 6  | 2  | 64 | 2  | 3   | 0   | 0   |
| 3a   | 0  | 2  | 1  | 0  | 1  | 0  | 0  | 0  | 0  | 0  | 0  | 0   | 0   | 0   |
| 3b   | 0  | 5  | 0  | 0  | 0  | 0  | 0  | 0  | 0  | 0  | 0  | 0   | 0   | 0   |
| 3c   | 0  | 1  | 0  | 0  | 0  | 0  | 0  | 0  | 3  | 0  | 0  | 0   | 0   | 0   |
| 3d   | 0  | 2  | 0  | 0  | 0  | 0  | 0  | 0  | 0  | 0  | 0  | 0   | 0   | 0   |
| 3e   | 0  | 1  | 2  | 0  | 2  | 0  | 0  | 0  | 0  | 0  | 1  | 0   | 0   | 0   |
| 3g   | 0  | 2  | 0  | 0  | 0  | 0  | 0  | 0  | 0  | 0  | 0  | 0   | 0   | 0   |
| 3h   | 0  | 1  | 0  | 0  | 2  | 0  | 0  | 2  | 0  | 0  | 1  | 0   | 0   | 0   |
| 3i   | 0  | 16 | 0  | 5  | 0  | 7  | 0  | 24 | 0  | 0  | 1  | 0   | 0   | 0   |
| 3k   | 0  | 0  | 0  | 0  | 1  | 0  | 0  | 2  | 0  | 0  | 0  | 0   | 0   | 0   |
| 3l   | 84 | 1  | 0  | 2  | 0  | 0  | 0  | 3  | 0  | 0  | 0  | 0   | 0   | 0   |
| 3n   | 0  | 93 | 0  | 0  | 0  | 0  | 0  | 2  | 0  | 0  | 0  | 0   | 0   | 0   |
| 3p   | 0  | 2  | 78 | 1  | 0  | 1  | 0  | 2  | 0  | 0  | 0  | 9   | 0   | 0   |
| 3q   | 0  | 2  | 0  | 99 | 0  | 0  | 0  | 0  | 0  | 0  | 0  | 0   | 0   | 0   |
| 3r   | 0  | 1  | 0  | 1  | 99 | 0  | 0  | 0  | 0  | 0  | 0  | 0   | 6   | 0   |
| 3s   | 8  | 6  | 19 | 9  | 0  | 91 | 0  | 0  | 0  | 0  | 10 | 0   | 0   | 0   |
| 3t   | 0  | 3  | 0  | 0  | 0  | 0  | 90 | 0  | 0  | 0  | 0  | 0   | 0   | 0   |
| 3v   | 0  | 2  | 0  | 0  | 0  | 0  | 0  | 99 | 0  | 0  | 0  | 0   | 0   | 0   |
| 3x   | 0  | 1  | 0  | 0  | 0  | 0  | 0  | 0  | 89 | 0  | 0  | 0   | 0   | 0   |
| 3y   | 0  | 0  | 10 | 0  | 0  | 0  | 0  | 0  | 3  | 96 | 1  | 1   | 0   | 0   |
| 3z   | 0  | 0  | 0  | 0  | 0  | 0  | 0  | 1  | 0  | 1  | 93 | 0   | 0   | 0   |
| 3ww  | 0  | 0  | 0  | 0  | 0  | 0  | 0  | 0  | 0  | 1  | 0  | 89  | 0   | 0   |
| 3xx  | 0  | 0  | 0  | 0  | 20 | 0  | 0  | 0  | 0  | 2  | 1  | 0   | 75  | 0   |
| 3yy  | 0  | 0  | 0  | 0  | 0  | 0  | 0  | 0  | 0  | 2  | 0  | 0   | 0   | 94  |

FIG. 15
(Continued)

Only combinations of ≥ 19 codons per group were considered
The cut-off was increased from 7% to 15%

0000111111111
0001011111111
⋮
1111101111
(306 solutions)

000011111111
000101111111
⋮
111111111111
(386 solutions) → Combined with group 2

0000000011101011111111
0000000011101111111101
⋮
1111110111011111111101
(304821 solutions)

↓ Combined groups 1 and 3 increased the cut-off to ≥ 21

001111111001110110001111111110
001111111001110111001111111110
⋮
111111010110011101111100011111111
(1670 solutions)

11111100110111001100111001101011111100
11111100110111001100111001101011111100
⋮
1111110101101101011010011001101001111111
(2321 solutions)

Calculated the number of >7% yield problems for each solution, identified the one with least number

| codons 1 | codons 2 | codons 3 | sum of yields | max yield | # problems |
|---|---|---|---|---|---|
| 21 | 21 | 21 | 64 | 15 | 6 |
| 21 | 21 | 21 | 77 | 15 | 7 |
| 21 | 21 | 21 | 73 | 15 | 7 |
| 111110101110101000111101011110001111110111 | | | | | |
| 111110101111101010100011110101111000111110111 | | | | | |
| 111110101111101010100011110101111000111110111 | | | | | |

|     | 1z | 1ww | 1xx | 1yy | 2a | 2c | 2d | 2e | 2f | 2h | 2i | 2j | 2k | 2m | 2n | 2o |
|-----|----|----|----|----|----|----|----|----|----|----|----|----|----|----|----|----|
| 1a  | 0 | 0 | 0 | 0 | 0 | 0 | 0 | 0 | 0 | 2 | 1 | 0 | 0 | 2 | 0 | 5 |
| 1b  | 0 | 0 | 0 | 1 | 0 | 3 | 0 | 0 | 1 | 0 | 0 | 1 | 0 | 0 | 0 | 5 |
| 1c  | 0 | 0 | 0 | 0 | 0 | 1 | 0 | 0 | 1 | 1 | 0 | 0 | 0 | 0 | 0 | 0 |
| 1d  | 0 | 0 | 0 | 1 | 0 | 0 | 0 | 1 | 0 | 0 | 0 | 5 | 0 | 0 | 0 | 1 |
| 1e  | 0 | 0 | 0 | 1 | 0 | 0 | 0 | 0 | 1 | 0 | 0 | 0 | 0 | 0 | 0 | 2 |
| 1f  | 1 | 0 | 0 | 3 | 0 | 0 | 3 | 0 | 0 | 0 | 0 | 0 | 0 | 0 | 1 | 2 |
| 1i  | 1 | 0 | 0 | 4 | 2 | 3 | 1 | 0 | 1 | 3 | 6 | 2 | 0 | 1 | 1 | 7 |
| 1j  | 0 | 0 | 0 | 1 | 0 | 0 | 1 | 0 | 0 | 0 | 0 | 0 | 0 | 0 | 0 | 1 |
| 1l  | 1 | 0 | 0 | 0 | 0 | 2 | 0 | 1 | 0 | 0 | 0 | 0 | 0 | 0 | 0 | 3 |
| 1m  | 0 | 0 | 0 | 0 | 0 | 0 | 0 | 0 | 1 | 0 | 0 | 0 | 0 | 0 | 7 | 3 |
| 1n  | 0 | 1 | 0 | 1 | 0 | 0 | 0 | 0 | 0 | 1 | 0 | 0 | 0 | 3 | 5 | 0 |
| 1o  | 1 | 2 | 0 | 6 | 4 | 4 | 2 | 0 | 3 | 4 | 6 | 0 | 6 | 1 | 3 | 1 |
| 1p  | 5 | 4 | 0 | 7 | 0 | 0 | 0 | 1 | 6 | 1 | 0 | 0 | 6 | 4 | 0 | 3 |
| 1q  | 1 | 4 | 0 | 0 | 0 | 0 | 0 | 0 | 1 | 1 | 0 | 0 | 1 | 6 | 1 | 1 |
| 1s  | 0 | 0 | 0 | 1 | 1 | 3 | 2 | 0 | 0 | 7 | 0 | 0 | 1 | 0 | 0 | 2 |
| 1t  | 5 | 0 | 0 | 0 | 0 | 0 | 3 | 7 | 1 | 0 | 0 | 0 | 0 | 2 | 1 | 4 |
| 1z  | 87 | 0 | 0 | 0 | 3 | 6 | 0 | 0 | 0 | 3 | 0 | 0 | 0 | 0 | 0 | 2 |
| 1ww | 1 | 19 | 0 | 0 | 0 | 2 | 0 | 0 | 0 | 0 | 0 | 0 | 0 | 0 | 0 | 3 |
| 1xx | 0 | 0 | 81 | 0 | 0 | 2 | 0 | 0 | 0 | 0 | 0 | 0 | 0 | 0 | 0 | 4 |
| 1yy | 3 | 1 | 0 | 81 | 0 | 0 | 0 | 0 | 0 | 0 | 1 | 0 | 1 | 0 | 0 | 2 |
| 2a  | 0 | 0 | 0 | 0 | 99 | 0 | 0 | 0 | 0 | 1 | 0 | 0 | 0 | 0 | 0 | 2 |
| 2c  | 0 | 0 | 0 | 0 | 0 | 99 | 0 | 0 | 0 | 0 | 0 | 0 | 0 | 0 | 0 | 0 |
| 2d  | 0 | 0 | 0 | 0 | 0 | 0 | 84 | 0 | 0 | 0 | 0 | 0 | 0 | 0 | 0 | 0 |
| 2e  | 0 | 0 | 0 | 0 | 0 | 0 | 0 | 93 | 0 | 1 | 0 | 0 | 0 | 1 | 0 | 0 |
| 2f  | 0 | 0 | 0 | 0 | 0 | 3 | 0 | 0 | 92 | 0 | 0 | 0 | 0 | 5 | 0 | 0 |
| 2h  | 0 | 0 | 0 | 0 | 0 | 0 | 0 | 0 | 0 | 97 | 0 | 0 | 0 | 0 | 0 | 0 |
| 2i  | 0 | 1 | 0 | 1 | 0 | 0 | 0 | 0 | 0 | 0 | 91 | 0 | 0 | 0 | 0 | 0 |
| 2j  | 1 | 0 | 0 | 1 | 0 | 0 | 2 | 0 | 0 | 1 | 0 | 84 | 0 | 0 | 0 | 1 |
| 2k  | 2 | 1 | 1 | 1 | 1 | 0 | 0 | 0 | 0 | 0 | 0 | 0 | 90 | 0 | 1 | 0 |
| 2m  | 5 | 0 | 0 | 1 | 0 | 0 | 1 | 0 | 0 | 4 | 0 | 0 | 1 | 97 | 0 | 0 |
| 2n  | 6 | 1 | 0 | 0 | 0 | 8 | 0 | 0 | 0 | 0 | 0 | 0 | 1 | 0 | 99 | 0 |
| 2o  | 5 | 1 | 0 | 2 | 1 | 0 | 0 | 0 | 0 | 3 | 0 | 0 | 1 | 0 | 0 | 99 |
| 2q  | 2 | 0 | 0 | 1 | 5 | 0 | 0 | 0 | 0 | 3 | 0 | 0 | 0 | 0 | 1 | 0 |
| 2r  | 0 | 0 | 0 | 1 | 1 | 0 | 2 | 0 | 0 | 0 | 0 | 0 | 0 | 0 | 1 | 0 |
| 2t  | 0 | 0 | 0 | 1 | 1 | 1 | 0 | 0 | 0 | 3 | 3 | 0 | 0 | 0 | 0 | 2 |
| 2u  | 0 | 0 | 0 | 1 | 0 | 0 | 1 | 0 | 0 | 1 | 3 | 0 | 1 | 0 | 0 | 1 |
| 2v  | 0 | 1 | 0 | 0 | 0 | 0 | 0 | 0 | 0 | 3 | 0 | 0 | 0 | 1 | 0 | 0 |
| 2xx | 0 | 0 | 0 | 0 | 0 | 0 | 0 | 0 | 0 | 0 | 0 | 0 | 0 | 0 | 0 | 2 |
| 2yy | 0 | 0 | 0 | 0 | 0 | 0 | 2 | 0 | 0 | 3 | 0 | 0 | 0 | 0 | 0 | 0 |
| 2zz | 0 | 0 | 0 | 1 | 0 | 0 | 0 | 0 | 0 | 0 | 0 | 0 | 0 | 0 | 1 | 1 |
| 3c  | 0 | 0 | 0 | 0 | 0 | 0 | 0 | 0 | 0 | 0 | 1 | 0 | 0 | 0 | 1 | 1 |
| 3d  | 0 | 0 | 0 | 0 | 0 | 0 | 0 | 0 | 0 | 0 | 0 | 0 | 0 | 0 | 2 | 1 |
| 3e  | 1 | 0 | 0 | 0 | 0 | 0 | 0 | 0 | 0 | 3 | 0 | 0 | 0 | 0 | 1 | 4 |
| 3f  | 0 | 0 | 0 | 0 | 0 | 0 | 0 | 0 | 0 | 0 | 0 | 0 | 0 | 0 | 1 | 2 |
| 3g  | 0 | 0 | 0 | 0 | 0 | 2 | 0 | 0 | 0 | 0 | 0 | 0 | 0 | 0 | 2 | 3 |
| 3h  | 1 | 0 | 0 | 0 | 0 | 0 | 2 | 0 | 0 | 0 | 0 | 0 | 0 | 0 | 1 | 3 |
| 3i  | 1 | 0 | 0 | 0 | 0 | 0 | 2 | 0 | 0 | 0 | 0 | 0 | 0 | 0 | 1 | 1 |
| 3k  | 0 | 0 | 0 | 0 | 0 | 0 | 2 | 0 | 0 | 0 | 0 | 0 | 0 | 0 | 1 | 3 |
| 3l  | 0 | 0 | 0 | 0 | 0 | 0 | 0 | 0 | 0 | 1 | 0 | 0 | 0 | 0 | 0 | 4 |
| 3m  | 0 | 0 | 0 | 0 | 0 | 0 | 0 | 0 | 0 | 1 | 0 | 0 | 0 | 1 | 2 | 2 |
| 3o  | 0 | 0 | 0 | 0 | 0 | 0 | 0 | 0 | 0 | 0 | 0 | 0 | 0 | 0 | 1 | 0 |
| 3s  | 5 | 0 | 0 | 4 | 0 | 1 | 0 | 0 | 0 | 0 | 0 | 4 | 1 | 3 | 6 | 0 |
| 3u  | 0 | 0 | 0 | 0 | 0 | 0 | 0 | 0 | 1 | 0 | 0 | 0 | 0 | 0 | 2 | 2 |
| 3v  | 0 | 0 | 0 | 0 | 0 | 0 | 0 | 0 | 1 | 0 | 0 | 2 | 0 | 0 | 2 | 4 |
| 3x  | 0 | 0 | 0 | 0 | 0 | 0 | 0 | 0 | 0 | 0 | 0 | 0 | 0 | 0 | 1 | 1 |
| 3y  | 0 | 1 | 0 | 0 | 0 | 0 | 0 | 0 | 1 | 0 | 0 | 1 | 0 | 0 | 0 | 2 |
| 3ww | 0 | 0 | 0 | 0 | 0 | 0 | 0 | 0 | 0 | 0 | 0 | 0 | 0 | 0 | 0 | 0 |
| 3xx | 1 | 0 | 0 | 0 | 0 | 0 | 0 | 0 | 0 | 0 | 0 | 0 | 0 | 0 | 0 | 0 |
| 3yy | 0 | 0 | 0 | 0 | 0 | 0 | 0 | 0 | 0 | 0 | 0 | 0 | 0 | 0 | 0 | 1 |
| 3zz | 0 | 0 | 0 | 0 | 0 | 0 | 0 | 0 | 0 | 0 | 0 | 0 | 0 | 0 | 0 | 0 |

FIG. 18 (Continued)

|  | 2q | 2r | 2t | 2u | 2v | 2xx | 2yy | 2zz | 3c | 3d | 3e | 3f | 3g | 3h | 3j | 3k |
|---|---|---|---|---|---|---|---|---|---|---|---|---|---|---|---|---|
| 1a | 0 | 4 | 0 | 0 | 1 | 0 | 1 | 0 | 1 | 0 | 0 | 0 | 0 | 2 | 0 | 0 |
| 1b | 0 | 4 | 0 | 1 | 0 | 0 | 1 | 0 | 0 | 0 | 0 | 0 | 1 | 0 | 1 | 0 |
| 1c | 2 | 6 | 0 | 0 | 4 | 0 | 0 | 0 | 0 | 0 | 0 | 6 | 0 | 6 | 2 | 0 |
| 1d | 0 | 4 | 0 | 0 | 0 | 0 | 1 | 0 | 0 | 0 | 0 | 1 | 0 | 0 | 5 | 0 |
| 1e | 0 | 3 | 0 | 0 | 0 | 0 | 1 | 0 | 0 | 0 | 0 | 0 | 0 | 0 | 0 | 0 |
| 1f | 0 | 4 | 0 | 0 | 0 | 0 | 0 | 3 | 0 | 3 | 0 | 0 | 0 | 5 | 0 | 0 |
| 1i | 0 | 5 | 0 | 4 | 5 | 0 | 4 | 1 | 3 | 1 | 0 | 1 | 1 | 5 | 0 | 3 |
| 1j | 0 | 2 | 0 | 1 | 0 | 0 | 1 | 0 | 0 | 1 | 0 | 0 | 1 | 0 | 3 | 0 |
| 1l | 0 | 2 | 0 | 1 | 5 | 0 | 2 | 0 | 2 | 0 | 1 | 0 | 0 | 0 | 0 | 0 |
| 1m | 1 | 6 | 0 | 4 | 3 | 0 | 1 | 0 | 0 | 0 | 4 | 0 | 7 | 0 | 0 | 0 |
| 1n | 0 | 2 | 0 | 0 | 0 | 0 | 0 | 0 | 0 | 0 | 0 | 1 | 0 | 1 | 0 | 0 |
| 1o | 5 | 2 | 1 | 0 | 1 | 0 | 6 | 1 | 4 | 3 | 0 | 3 | 0 | 2 | 6 | 4 |
| 1p | 1 | 1 | 0 | 0 | 5 | 0 | 7 | 0 | 0 | 0 | 1 | 6 | 0 | 1 | 0 | 6 |
| 1q | 3 | 5 | 0 | 0 | 2 | 0 | 0 | 0 | 0 | 0 | 0 | 1 | 0 | 1 | 0 | 1 |
| 1s | 0 | 2 | 0 | 2 | 4 | 0 | 1 | 0 | 3 | 2 | 0 | 0 | 0 | 7 | 0 | 7 |
| 1t | 1 | 1 | 0 | 0 | 4 | 0 | 0 | 0 | 0 | 3 | 7 | 1 | 0 | 0 | 0 | 0 |
| 1z | 1 | 1 | 0 | 1 | 1 | 0 | 1 | 0 | 6 | 0 | 0 | 0 | 2 | 3 | 0 | 2 |
| 1ww | 0 | 1 | 0 | 0 | 0 | 1 | 0 | 0 | 2 | 0 | 0 | 0 | 0 | 0 | 0 | 0 |
| 1xx | 0 | 1 | 0 | 0 | 1 | 0 | 0 | 0 | 2 | 0 | 0 | 0 | 1 | 0 | 0 | 0 |
| 1yy | 0 | 0 | 0 | 0 | 4 | 0 | 0 | 0 | 0 | 0 | 0 | 0 | 0 | 0 | 1 | 0 |
| 2a | 1 | 0 | 0 | 0 | 0 | 0 | 0 | 0 | 0 | 0 | 0 | 0 | 0 | 1 | 0 | 0 |
| 2c | 0 | 0 | 0 | 0 | 0 | 0 | 0 | 0 | 0 | 0 | 0 | 0 | 1 | 0 | 0 | 0 |
| 2d | 2 | 1 | 0 | 0 | 0 | 0 | 0 | 0 | 0 | 0 | 0 | 0 | 0 | 0 | 0 | 0 |
| 2e | 2 | 0 | 0 | 1 | 0 | 0 | 0 | 0 | 0 | 0 | 0 | 0 | 0 | 0 | 0 | 0 |
| 2f | 2 | 0 | 0 | 0 | 0 | 0 | 0 | 3 | 0 | 0 | 0 | 0 | 0 | 0 | 0 | 0 |
| 2h | 3 | 0 | 0 | 0 | 0 | 0 | 0 | 0 | 0 | 0 | 0 | 0 | 0 | 0 | 0 | 0 |
| 2i | 2 | 0 | 0 | 2 | 0 | 0 | 1 | 0 | 1 | 0 | 0 | 0 | 0 | 0 | 0 | 0 |
| 2j | 2 | 1 | 0 | 0 | 0 | 0 | 0 | 1 | 0 | 2 | 0 | 0 | 0 | 1 | 0 | 0 |
| 2k | 1 | 0 | 0 | 0 | 0 | 0 | 1 | 0 | 0 | 0 | 0 | 0 | 0 | 0 | 0 | 0 |
| 2m | 2 | 1 | 0 | 4 | 0 | 0 | 1 | 0 | 0 | 1 | 0 | 0 | 0 | 4 | 0 | 0 |
| 2n | 3 | 3 | 0 | 6 | 0 | 0 | 0 | 0 | 0 | 0 | 1 | 0 | 0 | 0 | 0 | 1 |
| 2o | 0 | 1 | 0 | 3 | 2 | 0 | 2 | 1 | 0 | 0 | 0 | 0 | 0 | 1 | 3 | 0 | 1 |
| 2q | 99 | 0 | 0 | 0 | 0 | 0 | 1 | 0 | 1 | 0 | 0 | 0 | 0 | 3 | 0 | 0 |
| 2r | 0 | 99 | 0 | 1 | 0 | 0 | 1 | 1 | 0 | 1 | 0 | 0 | 0 | 0 | 0 | 0 |
| 2t | 0 | 3 | 97 | 0 | 0 | 0 | 1 | 0 | 1 | 0 | 0 | 0 | 0 | 3 | 0 | 0 |
| 2u | 2 | 4 | 0 | 99 | 4 | 0 | 1 | 0 | 1 | 0 | 0 | 0 | 1 | 3 | 0 | 1 |
| 2v | 2 | 1 | 0 | 0 | 99 | 0 | 0 | 1 | 2 | 0 | 0 | 0 | 0 | 3 | 0 | 0 |
| 2xx | 0 | 1 | 0 | 0 | 1 | 86 | 0 | 0 | 0 | 0 | 0 | 0 | 0 | 0 | 0 | 0 |
| 2yy | 0 | 3 | 0 | 0 | 4 | 0 | 93 | 0 | 0 | 2 | 0 | 0 | 0 | 3 | 0 | 0 |
| 2zz | 0 | 0 | 0 | 0 | 3 | 0 | 0 | 75 | 0 | 0 | 0 | 0 | 1 | 0 | 0 | 0 |
| 3c | 0 | 0 | 0 | 0 | 0 | 0 | 0 | 0 | 97 | 0 | 0 | 0 | 2 | 1 | 0 | 0 |
| 3d | 0 | 0 | 0 | 0 | 0 | 0 | 0 | 0 | 0 | 86 | 0 | 0 | 0 | 0 | 0 | 0 |
| 3e | 0 | 2 | 0 | 0 | 5 | 0 | 0 | 0 | 0 | 0 | 76 | 0 | 0 | 0 | 0 | 0 |
| 3f | 0 | 0 | 0 | 5 | 0 | 0 | 0 | 0 | 0 | 0 | 0 | 89 | 0 | 0 | 0 | 0 |
| 3g | 0 | 0 | 0 | 0 | 0 | 0 | 0 | 0 | 2 | 0 | 0 | 0 | 96 | 0 | 0 | 0 |
| 3h | 0 | 2 | 0 | 3 | 2 | 0 | 0 | 0 | 2 | 0 | 0 | 0 | 0 | 99 | 0 | 0 |
| 3j | 0 | 1 | 0 | 0 | 3 | 0 | 0 | 0 | 2 | 0 | 0 | 0 | 0 | 0 | 83 | 0 |
| 3k | 0 | 1 | 0 | 0 | 0 | 0 | 0 | 0 | 2 | 0 | 0 | 0 | 0 | 0 | 0 | 95 |
| 3l | 2 | 0 | 0 | 2 | 3 | 0 | 0 | 0 | 1 | 0 | 0 | 0 | 0 | 1 | 0 | 0 |
| 3m | 2 | 0 | 0 | 0 | 3 | 0 | 0 | 0 | 0 | 0 | 0 | 0 | 1 | 0 | 0 | 0 |
| 3o | 0 | 0 | 0 | 0 | 2 | 0 | 0 | 0 | 0 | 0 | 0 | 0 | 2 | 0 | 0 | 0 |
| 3s | 0 | 6 | 0 | 0 | 0 | 0 | 0 | 0 | 2 | 1 | 1 | 0 | 1 | 0 | 0 | 2 |
| 3u | 2 | 1 | 0 | 0 | 5 | 0 | 0 | 0 | 1 | 0 | 1 | 0 | 0 | 1 | 0 | 0 |
| 3v | 0 | 0 | 0 | 2 | 3 | 0 | 0 | 0 | 0 | 0 | 1 | 0 | 1 | 0 | 0 | 0 |
| 3x | 0 | 0 | 0 | 0 | 0 | 0 | 0 | 0 | 0 | 0 | 0 | 0 | 0 | 1 | 0 | 0 |
| 3y | 0 | 0 | 0 | 0 | 4 | 0 | 0 | 1 | 0 | 0 | 0 | 1 | 0 | 0 | 1 | 0 |
| 3ww | 0 | 0 | 0 | 0 | 0 | 0 | 0 | 0 | 0 | 0 | 0 | 0 | 0 | 0 | 0 | 0 |
| 3xx | 0 | 0 | 0 | 0 | 0 | 0 | 0 | 0 | 0 | 0 | 0 | 0 | 0 | 0 | 0 | 0 |
| 3yy | 0 | 0 | 0 | 0 | 0 | 0 | 0 | 0 | 0 | 0 | 0 | 0 | 0 | 0 | 0 | 0 |
| 3zz | 0 | 0 | 0 | 7 | 5 | 0 | 4 | 0 | 0 | 0 | 0 | 0 | 0 | 0 | 0 | 0 |

FIG. 18 (Continued)

|     | 3l | 3m | 3o | 3s | 3u | 3v | 3x | 3y | 3ww | 3xx | 3yy | 3zz | 4a | 4b | 4c | 4d |
|-----|----|----|----|----|----|----|----|----|-----|-----|-----|-----|----|----|----|----|
| 1a  | 0 | 2 | 5 | 0 | 0 | 1 | 0 | 0 | 0 | 0 | 0 | 0 | 0 | 1 | 1 | 0 |
| 1b  | 0 | 0 | 5 | 0 | 1 | 0 | 0 | 0 | 0 | 0 | 1 | 0 | 6 | 0 | 3 | 0 |
| 1c  | 0 | 0 | 4 | 1 | 0 | 0 | 0 | 1 | 0 | 0 | 1 | 0 | 0 | 2 | 0 | 0 |
| 1d  | 0 | 0 | 2 | 0 | 0 | 0 | 0 | 0 | 0 | 0 | 1 | 0 | 0 | 0 | 1 | 0 |
| 1e  | 0 | 0 | 2 | 0 | 0 | 0 | 0 | 0 | 0 | 0 | 1 | 0 | 0 | 0 | 0 | 0 |
| 1f  | 0 | 0 | 2 | 0 | 0 | 0 | 0 | 3 | 0 | 0 | 3 | 0 | 0 | 2 | 0 | 0 |
| 1i  | 0 | 3 | 1 | 2 | 4 | 5 | 0 | 4 | 1 | 0 | 0 | 1 | 2 | 0 | 3 | 1 |
| 1j  | 0 | 0 | 1 | 0 | 1 | 0 | 0 | 6 | 0 | 0 | 1 | 0 | 0 | 0 | 0 | 1 |
| 1l  | 5 | 0 | 3 | 0 | 1 | 5 | 0 | 0 | 0 | 0 | 5 | 0 | 0 | 1 | 2 | 0 |
| 1m  | 0 | 0 | 3 | 0 | 0 | 3 | 0 | 3 | 0 | 0 | 7 | 0 | 0 | 4 | 0 | 0 |
| 1n  | 0 | 3 | 5 | 0 | 0 | 0 | 0 | 0 | 1 | 0 | 1 | 0 | 0 | 0 | 1 | 0 |
| 1o  | 1 | 5 | 3 | 4 | 6 | 4 | 2 | 10 | 2 | 0 | 0 | 1 | 4 | 2 | 1 | 3 |
| 1p  | 0 | 4 | 3 | 0 | 0 | 0 | 0 | 0 | 4 | 0 | 0 | 0 | 0 | 0 | 3 | 0 |
| 1q  | 0 | 6 | 1 | 0 | 0 | 2 | 0 | 3 | 4 | 0 | 4 | 0 | 0 | 0 | 1 | 0 |
| 1s  | 0 | 0 | 2 | 2 | 2 | 0 | 0 | 0 | 0 | 0 | 0 | 0 | 1 | 1 | 3 | 2 |
| 1t  | 0 | 2 | 4 | 0 | 0 | 1 | 1 | 0 | 0 | 0 | 3 | 0 | 0 | 0 | 0 | 3 |
| 1z  | 0 | 0 | 2 | 0 | 1 | 0 | 0 | 1 | 0 | 0 | 0 | 0 | 3 | 5 | 6 | 0 |
| 1ww | 0 | 0 | 3 | 0 | 0 | 0 | 0 | 0 | 0 | 0 | 1 | 0 | 0 | 0 | 2 | 0 |
| 1xx | 0 | 0 | 4 | 0 | 0 | 1 | 0 | 1 | 0 | 0 | 0 | 0 | 0 | 0 | 2 | 0 |
| 1yy | 0 | 0 | 0 | 7 | 3 | 0 | 3 | 2 | 1 | 0 | 2 | 0 | 0 | 0 | 0 | 0 |
| 2a  | 0 | 0 | 2 | 0 | 0 | 0 | 0 | 1 | 0 | 0 | 0 | 3 | 0 | 0 | 0 | 0 |
| 2c  | 0 | 0 | 0 | 0 | 0 | 0 | 0 | 0 | 0 | 0 | 0 | 0 | 0 | 0 | 0 | 0 |
| 2d  | 0 | 0 | 0 | 0 | 0 | 0 | 0 | 0 | 0 | 0 | 0 | 0 | 0 | 0 | 0 | 0 |
| 2e  | 0 | 0 | 0 | 0 | 0 | 0 | 0 | 0 | 0 | 0 | 0 | 0 | 0 | 0 | 0 | 0 |
| 2f  | 0 | 5 | 1 | 0 | 0 | 0 | 1 | 0 | 0 | 0 | 0 | 0 | 0 | 0 | 1 | 0 |
| 2h  | 0 | 0 | 0 | 0 | 0 | 0 | 0 | 0 | 0 | 0 | 0 | 0 | 0 | 0 | 0 | 0 |
| 2i  | 0 | 0 | 0 | 0 | 0 | 2 | 0 | 0 | 0 | 0 | 1 | 1 | 0 | 0 | 0 | 0 |
| 2j  | 0 | 0 | 1 | 0 | 0 | 0 | 0 | 0 | 0 | 0 | 1 | 1 | 0 | 0 | 0 | 2 |
| 2k  | 0 | 0 | 0 | 0 | 0 | 0 | 0 | 0 | 0 | 0 | 1 | 1 | 0 | 0 | 0 | 0 |
| 2m  | 0 | 0 | 0 | 0 | 4 | 0 | 0 | 0 | 0 | 0 | 0 | 0 | 0 | 1 | 0 | 1 |
| 2n  | 3 | 0 | 0 | 0 | 6 | 0 | 0 | 0 | 0 | 0 | 2 | 0 | 0 | 1 | 0 | 0 |
| 2o  | 0 | 0 | 0 | 0 | 3 | 2 | 0 | 0 | 0 | 0 | 2 | 1 | 1 | 0 | 0 | 0 |
| 2q  | 0 | 0 | 1 | 0 | 0 | 0 | 0 | 0 | 0 | 0 | 1 | 0 | 5 | 0 | 1 | 0 |
| 2r  | 0 | 0 | 0 | 0 | 0 | 0 | 1 | 2 | 0 | 0 | 1 | 0 | 0 | 0 | 0 | 2 |
| 2t  | 0 | 0 | 2 | 0 | 4 | 0 | 0 | 0 | 0 | 0 | 1 | 0 | 1 | 0 | 1 | 0 |
| 2u  | 0 | 0 | 1 | 0 | 0 | 4 | 0 | 2 | 0 | 0 | 1 | 1 | 1 | 0 | 1 | 0 |
| 2v  | 0 | 0 | 0 | 0 | 0 | 0 | 2 | 2 | 0 | 0 | 0 | 0 | 1 | 0 | 2 | 0 |
| 2xx | 0 | 0 | 2 | 0 | 0 | 1 | 0 | 2 | 0 | 0 | 0 | 0 | 0 | 0 | 0 | 0 |
| 2yy | 0 | 0 | 0 | 0 | 0 | 4 | 0 | 0 | 0 | 0 | 0 | 0 | 0 | 0 | 0 | 2 |
| 2zz | 0 | 0 | 1 | 0 | 0 | 3 | 0 | 0 | 0 | 0 | 1 | 0 | 0 | 2 | 0 | 0 |
| 3c  | 0 | 0 | 1 | 0 | 0 | 0 | 3 | 0 | 0 | 0 | 0 | 0 | 0 | 0 | 1 | 0 |
| 3d  | 0 | 0 | 2 | 0 | 0 | 0 | 0 | 0 | 0 | 0 | 0 | 0 | 0 | 0 | 0 | 0 |
| 3e  | 0 | 1 | 4 | 0 | 0 | 0 | 0 | 0 | 0 | 0 | 0 | 0 | 0 | 0 | 3 | 0 |
| 3f  | 0 | 0 | 2 | 0 | 5 | 0 | 0 | 0 | 0 | 0 | 0 | 0 | 0 | 0 | 0 | 0 |
| 3g  | 0 | 0 | 3 | 0 | 0 | 0 | 0 | 0 | 0 | 0 | 0 | 0 | 0 | 0 | 2 | 0 |
| 3h  | 0 | 1 | 3 | 0 | 3 | 2 | 0 | 0 | 0 | 0 | 0 | 0 | 0 | 0 | 2 | 0 |
| 3i  | 0 | 0 | 1 | 0 | 3 | 0 | 0 | 0 | 1 | 0 | 0 | 0 | 0 | 0 | 2 | 0 |
| 3k  | 0 | 0 | 3 | 0 | 0 | 2 | 0 | 0 | 0 | 0 | 0 | 0 | 0 | 0 | 2 | 0 |
| 3l  | 84 | 0 | 0 | 1 | 0 | 2 | 3 | 0 | 0 | 0 | 0 | 0 | 0 | 0 | 1 | 0 |
| 3m  | 0 | 90 | 2 | 0 | 0 | 3 | 0 | 0 | 0 | 0 | 0 | 0 | 0 | 0 | 1 | 0 |
| 3o  | 0 | 0 | 97 | 1 | 0 | 2 | 0 | 0 | 0 | 0 | 0 | 0 | 0 | 0 | 0 | 0 |
| 3s  | 8 | 3 | 1 | 91 | 0 | 0 | 0 | 0 | 0 | 0 | 0 | 0 | 4 | 2 | 0 | 1 |
| 3u  | 0 | 0 | 2 | 0 | 99 | 0 | 0 | 0 | 0 | 0 | 0 | 0 | 0 | 0 | 1 | 0 |
| 3v  | 0 | 0 | 4 | 0 | 2 | 99 | 0 | 0 | 0 | 0 | 0 | 0 | 0 | 0 | 0 | 0 |
| 3x  | 0 | 0 | 1 | 0 | 0 | 0 | 89 | 0 | 0 | 0 | 0 | 0 | 0 | 0 | 0 | 0 |
| 3y  | 0 | 0 | 2 | 0 | 1 | 0 | 3 | 96 | 1 | 0 | 0 | 1 | 0 | 0 | 0 | 0 |
| 3ww | 0 | 0 | 0 | 0 | 0 | 0 | 0 | 1 | 89 | 0 | 0 | 0 | 0 | 0 | 0 | 0 |
| 3xx | 0 | 0 | 0 | 0 | 0 | 0 | 0 | 2 | 0 | 75 | 0 | 0 | 0 | 0 | 0 | 0 |
| 3yy | 0 | 0 | 1 | 0 | 0 | 0 | 0 | 2 | 0 | 0 | 94 | 0 | 0 | 0 | 0 | 0 |
| 3zz | 0 | 0 | 0 | 0 | 7 | 5 | 0 | 1 | 0 | 0 | 4 | 74 | 0 | 0 | 0 | 0 |

FIG. 18 (Continued)

|  | 4e | 4f | 4g | 4h | 4i | 4j | 4k | 4l | 4m | 4n | 4o | 4p | 4q | 4r | 4s | 4t |
|---|---|---|---|---|---|---|---|---|---|---|---|---|---|---|---|---|
| 1a | 0 | 0 | 0 | 2 | 1 | 0 | 0 | 0 | 2 | 0 | 5 | 0 | 0 | 4 | 0 | 0 |
| 1b | 0 | 1 | 0 | 0 | 0 | 0 | 1 | 0 | 0 | 0 | 5 | 0 | 0 | 4 | 0 | 0 |
| 1c | 1 | 1 | 0 | 6 | 0 | 0 | 0 | 0 | 0 | 0 | 2 | 0 | 0 | 1 | 0 | 0 |
| 1d | 1 | 1 | 0 | 0 | 0 | 5 | 0 | 0 | 0 | 0 | 2 | 0 | 0 | 4 | 0 | 0 |
| 1e | 0 | 1 | 0 | 0 | 0 | 0 | 0 | 0 | 0 | 0 | 2 | 0 | 0 | 3 | 0 | 0 |
| 1f | 0 | 0 | 0 | 0 | 0 | 0 | 0 | 0 | 0 | 1 | 2 | 2 | 0 | 4 | 0 | 0 |
| 1i | 0 | 1 | 1 | 5 | 7 | 2 | 3 | 0 | 3 | 1 | 0 | 0 | 2 | 5 | 2 | 0 |
| 1j | 0 | 0 | 1 | 0 | 0 | 0 | 0 | 0 | 0 | 0 | 1 | 0 | 0 | 2 | 0 | 0 |
| 1l | 1 | 0 | 0 | 0 | 0 | 0 | 0 | 5 | 0 | 0 | 3 | 0 | 0 | 2 | 0 | 0 |
| 1m | 0 | 0 | 0 | 3 | 1 | 0 | 0 | 0 | 0 | 4 | 3 | 0 | 1 | 6 | 1 | 0 |
| 1n | 0 | 1 | 0 | 0 | 1 | 0 | 0 | 0 | 0 | 3 | 1 | 0 | 0 | 2 | 0 | 0 |
| 1o | 0 | 3 | 1 | 4 | 6 | 6 | 2 | 1 | 5 | 7 | 5 | 0 | 0 | 6 | 4 | 1 |
| 1p | 1 | 6 | 0 | 1 | 0 | 0 | 6 | 0 | 4 | 0 | 3 | 1 | 0 | 4 | 0 | 0 |
| 1q | 0 | 1 | 0 | 1 | 0 | 0 | 1 | 0 | 6 | 1 | 1 | 2 | 0 | 5 | 0 | 0 |
| 1s | 0 | 0 | 1 | 7 | 0 | 0 | 0 | 0 | 7 | 0 | 2 | 0 | 0 | 0 | 6 | 0 |
| 1t | 0 | 0 | 0 | 0 | 0 | 1 | 0 | 0 | 0 | 2 | 1 | 0 | 0 | 0 | 0 | 0 |
| 1z | 0 | 0 | 2 | 3 | 0 | 0 | 2 | 0 | 0 | 0 | 2 | 0 | 0 | 1 | 1 | 0 |
| 1ww | 0 | 0 | 0 | 0 | 0 | 0 | 0 | 0 | 0 | 0 | 0 | 0 | 0 | 1 | 0 | 0 |
| 1xx | 0 | 0 | 1 | 0 | 0 | 0 | 0 | 0 | 0 | 0 | 4 | 0 | 0 | 0 | 0 | 0 |
| 1yy | 4 | 0 | 0 | 0 | 1 | 0 | 0 | 0 | 2 | 0 | 0 | 0 | 1 | 7 | 0 | 0 |
| 2a | 0 | 0 | 0 | 1 | 0 | 0 | 0 | 0 | 0 | 0 | 2 | 0 | 5 | 0 | 0 | 0 |
| 2c | 0 | 0 | 3 | 0 | 0 | 0 | 0 | 0 | 0 | 0 | 0 | 0 | 0 | 0 | 0 | 0 |
| 2d | 0 | 0 | 0 | 0 | 0 | 0 | 0 | 0 | 0 | 0 | 0 | 0 | 2 | 1 | 0 | 0 |
| 2e | 0 | 0 | 0 | 1 | 0 | 0 | 0 | 0 | 0 | 0 | 0 | 0 | 0 | 2 | 0 | 0 |
| 2f | 0 | 0 | 0 | 2 | 0 | 0 | 0 | 0 | 5 | 0 | 1 | 0 | 1 | 0 | 0 | 0 |
| 2h | 0 | 0 | 0 | 0 | 0 | 0 | 0 | 0 | 0 | 0 | 0 | 0 | 3 | 1 | 0 | 0 |
| 2i | 0 | 0 | 0 | 0 | 0 | 0 | 0 | 0 | 0 | 0 | 0 | 0 | 2 | 0 | 0 | 0 |
| 2j | 0 | 0 | 0 | 1 | 0 | 0 | 0 | 0 | 0 | 0 | 1 | 0 | 1 | 1 | 0 | 0 |
| 2k | 0 | 0 | 0 | 0 | 0 | 0 | 0 | 0 | 0 | 0 | 0 | 0 | 1 | 0 | 0 | 0 |
| 2m | 1 | 0 | 0 | 4 | 0 | 0 | 0 | 0 | 0 | 0 | 1 | 0 | 2 | 1 | 0 | 0 |
| 2n | 0 | 0 | 0 | 3 | 0 | 0 | 0 | 3 | 0 | 0 | 0 | 0 | 3 | 3 | 0 | 0 |
| 2o | 0 | 0 | 1 | 3 | 0 | 0 | 1 | 0 | 0 | 0 | 0 | 0 | 4 | 1 | 0 | 0 |
| 2q | 0 | 0 | 0 | 3 | 0 | 0 | 0 | 0 | 0 | 0 | 1 | 0 | 0 | 4 | 0 | 0 |
| 2r | 0 | 0 | 0 | 0 | 0 | 0 | 0 | 0 | 0 | 0 | 1 | 0 | 2 | 0 | 0 | 0 |
| 2t | 0 | 0 | 0 | 3 | 3 | 0 | 0 | 0 | 0 | 0 | 2 | 0 | 1 | 3 | 0 | 0 |
| 2u | 0 | 1 | 0 | 3 | 0 | 0 | 1 | 0 | 0 | 0 | 1 | 0 | 2 | 0 | 0 | 0 |
| 2v | 0 | 0 | 0 | 3 | 0 | 0 | 0 | 0 | 0 | 0 | 0 | 0 | 2 | 1 | 0 | 0 |
| 2xx | 0 | 0 | 0 | 0 | 0 | 0 | 0 | 0 | 0 | 0 | 2 | 0 | 0 | 1 | 0 | 0 |
| 2yy | 0 | 0 | 0 | 3 | 0 | 0 | 0 | 0 | 0 | 0 | 0 | 0 | 0 | 3 | 0 | 0 |
| 2zz | 0 | 0 | 1 | 0 | 0 | 0 | 0 | 0 | 0 | 0 | 1 | 1 | 0 | 0 | 0 | 0 |
| 3c | 0 | 0 | 2 | 1 | 0 | 0 | 0 | 0 | 2 | 0 | 1 | 0 | 0 | 0 | 0 | 0 |
| 3d | 0 | 0 | 0 | 0 | 0 | 0 | 0 | 0 | 0 | 0 | 0 | 0 | 0 | 0 | 0 | 0 |
| 3e | 0 | 0 | 0 | 3 | 0 | 0 | 0 | 0 | 0 | 1 | 1 | 4 | 2 | 0 | 2 | 0 |
| 3f | 0 | 0 | 0 | 0 | 0 | 0 | 0 | 0 | 0 | 1 | 2 | 0 | 0 | 0 | 0 | 0 |
| 3g | 0 | 0 | 0 | 1 | 0 | 0 | 0 | 0 | 0 | 2 | 3 | 0 | 0 | 0 | 0 | 0 |
| 3h | 0 | 0 | 0 | 0 | 0 | 0 | 0 | 0 | 1 | 1 | 3 | 0 | 0 | 2 | 0 | 0 |
| 3i | 0 | 0 | 0 | 0 | 0 | 0 | 0 | 0 | 0 | 1 | 0 | 0 | 0 | 3 | 0 | 0 |
| 3k | 0 | 0 | 0 | 0 | 0 | 0 | 0 | 0 | 0 | 0 | 1 | 3 | 0 | 1 | 0 | 0 |
| 3l | 0 | 0 | 0 | 1 | 0 | 0 | 0 | 0 | 1 | 0 | 2 | 4 | 0 | 2 | 0 | 0 |
| 3m | 0 | 0 | 1 | 1 | 0 | 0 | 0 | 0 | 2 | 2 | 3 | 0 | 2 | 1 | 0 | 0 |
| 3o | 0 | 0 | 2 | 1 | 0 | 0 | 0 | 0 | 0 | 0 | 0 | 0 | 0 | 0 | 1 | 0 |
| 3s | 1 | 0 | 1 | 0 | 0 | 0 | 5 | 0 | 3 | 1 | 0 | 1 | 0 | 6 | 0 | 0 |
| 3u | 1 | 0 | 0 | 0 | 0 | 0 | 0 | 0 | 0 | 2 | 2 | 0 | 2 | 0 | 0 | 0 |
| 3v | 1 | 0 | 1 | 0 | 2 | 0 | 0 | 0 | 0 | 2 | 4 | 0 | 0 | 0 | 0 | 0 |
| 3x | 0 | 0 | 0 | 1 | 0 | 0 | 0 | 0 | 0 | 1 | 1 | 0 | 0 | 0 | 0 | 0 |
| 3y | 0 | 1 | 0 | 0 | 0 | 1 | 0 | 0 | 0 | 0 | 0 | 5 | 0 | 0 | 0 | 0 |
| 3ww | 0 | 0 | 0 | 0 | 0 | 0 | 0 | 0 | 0 | 0 | 0 | 0 | 0 | 0 | 0 | 0 |
| 3xx | 0 | 0 | 0 | 0 | 0 | 0 | 0 | 0 | 0 | 0 | 0 | 0 | 0 | 0 | 0 | 0 |
| 3yy | 0 | 0 | 0 | 0 | 0 | 0 | 0 | 0 | 0 | 0 | 0 | 1 | 0 | 0 | 0 | 0 |
| 3zz | 0 | 0 | 0 | 0 | 0 | 0 | 0 | 0 | 0 | 0 | 0 | 0 | 0 | 0 | 0 | 0 |

FIG. 18 (Continued)

|     | 4u | 4v | 4w | 4x | 4y | 4z | 4uu | 4vv | 4ww | 4xx | 4yy | 4zz |
|-----|----|----|----|----|----|----|-----|-----|-----|-----|-----|-----|
| 1a  | 0  | 1  | 4  | 0  | 0  | 0  | 0   | 0   | 0   | 0   | 0   | 0   |
| 1b  | 1  | 0  | 0  | 0  | 0  | 0  | 0   | 0   | 0   | 0   | 0   | 0   |
| 1c  | 1  | 4  | 1  | 0  | 3  | 0  | 0   | 0   | 0   | 0   | 1   | 0   |
| 1d  | 0  | 0  | 0  | 0  | 0  | 0  | 0   | 0   | 0   | 0   | 1   | 0   |
| 1e  | 0  | 0  | 3  | 0  | 1  | 0  | 0   | 0   | 0   | 0   | 1   | 0   |
| 1f  | 0  | 0  | 5  | 0  | 3  | 1  | 0   | 1   | 0   | 0   | 3   | 0   |
| 1i  | 3  | 5  | 1  | 0  | 2  | 0  | 0   | 1   | 1   | 0   | 4   | 1   |
| 1j  | 1  | 0  | 7  | 0  | 6  | 0  | 0   | 0   | 0   | 0   | 1   | 0   |
| 1l  | 1  | 5  | 5  | 0  | 0  | 1  | 0   | 0   | 0   | 0   | 0   | 0   |
| 1m  | 1  | 0  | 0  | 0  | 3  | 0  | 0   | 0   | 0   | 0   | 2   | 0   |
| 1n  | 0  | 0  | 0  | 0  | 1  | 0  | 0   | 0   | 1   | 0   | 1   | 0   |
| 1o  | 6  | 0  | 1  | 2  | 6  | 2  | 0   | 0   | 2   | 0   | 1   | 1   |
| 1p  | 0  | 0  | 0  | 0  | 0  | 5  | 0   | 0   | 4   | 0   | 0   | 0   |
| 1q  | 0  | 2  | 2  | 0  | 3  | 1  | 0   | 0   | 0   | 0   | 1   | 0   |
| 1s  | 0  | 4  | 0  | 0  | 0  | 0  | 0   | 0   | 0   | 0   | 1   | 0   |
| 1t  | 5  | 7  | 0  | 1  | 0  | 3  | 0   | 0   | 0   | 0   | 0   | 0   |
| 1z  | 0  | 1  | 7  | 1  | 1  | 0  | 0   | 0   | 0   | 0   | 0   | 0   |
| 1ww | 0  | 0  | 0  | 0  | 0  | 2  | 0   | 0   | 0   | 1   | 0   | 0   |
| 1xx | 0  | 1  | 0  | 0  | 0  | 0  | 0   | 0   | 0   | 0   | 0   | 0   |
| 1yy | 3  | 4  | 0  | 0  | 2  | 2  | 0   | 0   | 0   | 0   | 0   | 0   |
| 2a  | 1  | 0  | 5  | 0  | 3  | 0  | 0   | 0   | 0   | 0   | 0   | 0   |
| 2c  | 0  | 0  | 0  | 0  | 0  | 0  | 0   | 0   | 0   | 0   | 0   | 0   |
| 2d  | 0  | 0  | 0  | 0  | 0  | 0  | 0   | 0   | 0   | 0   | 0   | 0   |
| 2e  | 0  | 0  | 0  | 1  | 0  | 0  | 0   | 0   | 0   | 0   | 0   | 0   |
| 2f  | 0  | 0  | 1  | 2  | 0  | 0  | 0   | 0   | 0   | 0   | 0   | 0   |
| 2h  | 0  | 0  | 6  | 0  | 0  | 0  | 0   | 0   | 0   | 0   | 0   | 0   |
| 2i  | 2  | 0  | 7  | 0  | 0  | 0  | 0   | 0   | 1   | 0   | 0   | 0   |
| 2j  | 0  | 0  | 0  | 0  | 0  | 0  | 0   | 0   | 0   | 0   | 1   | 1   |
| 2k  | 0  | 0  | 4  | 0  | 0  | 2  | 0   | 0   | 1   | 1   | 1   | 0   |
| 2m  | 4  | 0  | 0  | 0  | 0  | 5  | 0   | 0   | 0   | 0   | 1   | 0   |
| 2n  | 0  | 0  | 0  | 0  | 0  | 6  | 0   | 0   | 0   | 0   | 0   | 0   |
| 2o  | 0  | 2  | 0  | 0  | 0  | 5  | 0   | 0   | 1   | 0   | 2   | 1   |
| 2q  | 0  | 0  | 0  | 0  | 0  | 2  | 0   | 0   | 0   | 0   | 1   | 0   |
| 2r  | 1  | 0  | 0  | 1  | 2  | 0  | 0   | 0   | 0   | 0   | 1   | 0   |
| 2t  | 0  | 0  | 0  | 0  | 0  | 0  | 0   | 0   | 0   | 0   | 1   | 0   |
| 2u  | 1  | 4  | 1  | 0  | 2  | 0  | 0   | 0   | 0   | 0   | 1   | 1   |
| 2v  | 0  | 0  | 1  | 2  | 2  | 0  | 0   | 0   | 1   | 0   | 0   | 0   |
| 2xx | 0  | 1  | 4  | 0  | 0  | 0  | 0   | 0   | 0   | 0   | 0   | 0   |
| 2yy | 0  | 4  | 6  | 0  | 0  | 0  | 0   | 0   | 0   | 0   | 0   | 0   |
| 2zz | 0  | 3  | 0  | 0  | 0  | 0  | 0   | 11  | 0   | 0   | 1   | 0   |
| 3c  | 0  | 0  | 3  | 0  | 0  | 0  | 0   | 0   | 0   | 0   | 0   | 0   |
| 3d  | 0  | 0  | 5  | 0  | 0  | 0  | 0   | 0   | 0   | 0   | 0   | 0   |
| 3e  | 0  | 4  | 2  | 0  | 0  | 0  | 0   | 0   | 0   | 0   | 0   | 0   |
| 3f  | 5  | 0  | 0  | 0  | 0  | 0  | 0   | 0   | 0   | 0   | 0   | 0   |
| 3g  | 0  | 0  | 7  | 0  | 0  | 0  | 0   | 0   | 0   | 0   | 0   | 0   |
| 3h  | 3  | 2  | 0  | 0  | 0  | 1  | 0   | 0   | 0   | 0   | 0   | 0   |
| 3j  | 2  | 0  | 1  | 0  | 0  | 0  | 0   | 0   | 1   | 0   | 0   | 0   |
| 3k  | 0  | 2  | 7  | 0  | 0  | 0  | 0   | 0   | 0   | 0   | 0   | 0   |
| 3l  | 2  | 3  | 0  | 0  | 0  | 0  | 0   | 0   | 0   | 0   | 0   | 0   |
| 3m  | 0  | 3  | 1  | 0  | 0  | 0  | 0   | 0   | 0   | 0   | 0   | 0   |
| 3o  | 0  | 2  | 4  | 0  | 0  | 0  | 0   | 0   | 0   | 0   | 0   | 0   |
| 3s  | 1  | 0  | 0  | 0  | 0  | 0  | 0   | 0   | 1   | 0   | 0   | 0   |
| 3u  | 0  | 0  | 3  | 0  | 0  | 0  | 0   | 0   | 1   | 0   | 0   | 0   |
| 3v  | 0  | 0  | 0  | 0  | 0  | 0  | 0   | 0   | 2   | 0   | 0   | 0   |
| 3x  | 0  | 0  | 0  | 0  | 0  | 0  | 0   | 0   | 1   | 0   | 0   | 0   |
| 3y  | 1  | 0  | 0  | 3  | 0  | 1  | 0   | 2   | 1   | 0   | 0   | 1   |
| 3ww | 0  | 0  | 0  | 0  | 0  | 0  | 0   | 0   | 0   | 0   | 0   | 0   |
| 3xx | 0  | 0  | 0  | 0  | 2  | 0  | 0   | 0   | 0   | 0   | 0   | 0   |
| 3yy | 0  | 0  | 0  | 0  | 2  | 0  | 0   | 0   | 0   | 0   | 0   | 0   |
| 3zz | 7  | 5  | 0  | 0  | 1  | 0  | 0   | 0   | 0   | 0   | 0   | 0   |

FIG. 18 (Continued)

METHOD B

→ oligonucleotide synthesis universal template mix: CCCTGTACACNNNNNNATGATNNNNNNCTATTTTCATCCCACTC 3' (SEQ ID NO: 232)
GATNNNNNGTAGGGTGAG-PEG₆-(A)₂₅Cy3(A)₅ (SEQ ID NO: 245)

⇩ preparative primer extension
klenow (exo-)

CCCTGTACACNNNNNNAAGTTNNNNNNATGATNNNNNNCTANNNNNCATCCCACTC 3' (SEQ ID NO: 234)
3' GGGAGGGACATGTGNNNNNNTTCAANNNNNNTACTANNNNNNGATNNNNNGTAGGGTGAG-PEG₆-(A)₂₅Cy3(A)₅ (SEQ ID NO: 245)
(SEQ ID NO: 235)

⇩ PAGE

3' GGGAGGGACATGTGNNNNNNTTCAANNNNNNTACTANNNNNNGATNNNNNGTAGGGTGAG (SEQ ID NO: 236)

⇩ preparative primer extension
vent

CCCTGTACAC — CCCTGTACACNNNNNNAAGTTNNNNNNATGATNNNNNCTANNNNNCATCCCACTC 3' (SEQ ID NO: 237)
(SEQ ID NO: 2)    3' GGGAGGGACATGTGNNNNNNTTCAANNNNNNTACTANNNNNNGATNNNNNGTAGGGTGAG-PEG₆-(A)₂₅Cy3(A)₅ (SEQ ID NO: 245)
(SEQ ID NO: 238)

⇩ PAGE

CCCTGTACACNNNNNNAAGTTNNNNNNATGATNNNNNNCTANNNNNCATCCCACTC 3' (SEQ ID NO: 231)

FIG. 23B

METHOD C oligonucleotide synthesis ⟶

To be made via split-pool:

3'- GGGACATGTGNNNNNTTCAANNNNNTACTANNNNNGTAGGTGAG -PEG$_6$-(A)$_{25}$CY3(A)$_5$
(SEQ ID NO: 240) (SEQ ID NO: 245)

+ Ph-SCAFFOLD-N-H ... CCCTGTACAC  Vent ⇩ preparative primer extension
(SEQ ID NO: 2)

Ph-SCAFFOLD-N-H ... CCCTGTACACNNNNNAAGTTNNNNNATGATNNNNNCATCCACTC 3' (SEQ ID NO: 237)
3' GGGAGGACATGTGNNNNNTTCAANNNNNTACTANNNNNGTAGGTGAG-PEG$_6$-(A)$_{25}$CY3(A)$_5$
(SEQ ID NO: 238) (SEQ ID NO: 231)

⇩ PAGE

Ph-SCAFFOLD-N-H ... CCCTGTACACNNNNNAAGTTNNNNNATGATNNNNNCATCCACTC 3' (SEQ ID NO: 231)

FIG. 23C

Reagents 1, 25°C (template # - apparent conversion)

| | | | | | | | | | | | | | | |
|---|---|---|---|---|---|---|---|---|---|---|---|---|---|---|
| 1 | 1a | 86 | 3 | 1a | 0 | 5 | 1a | 0 | 7 | 1a | 0 | 9 | 1a | 0 | 11 | 1a | 0 | 13 | 1a | 1 |
| 1 | 1b | 17 | 3 | 1b | 0 | 5 | 1b | 0 | 7 | 1b | 0 | 9 | 1b | 0 | 11 | 1b | 0 | 13 | 1b | 0 |
| 1 | 1c | 0 | 3 | 1c | 93 | 5 | 1c | 14 | 7 | 1c | 1 | 9 | 1c | 33 | 11 | 1c | 1 | 13 | 1c | 5 |
| 1 | 1d | 0 | 3 | 1d | 1 | 5 | 1d | 0 | 7 | 1d | 0 | 9 | 1d | 0 | 11 | 1d | 0 | 13 | 1d | 0 |
| 1 | 1e | 0 | 3 | 1e | 0 | 5 | 1e | 80 | 7 | 1e | 0 | 9 | 1e | 0 | 11 | 1e | 0 | 13 | 1e | 0 |
| 1 | 1f | 0 | 3 | 1f | 0 | 5 | 1f | 0 | 7 | 1f | 0 | 9 | 1f | 0 | 11 | 1f | 0 | 13 | 1f | 0 |
| 1 | 1g | 1 | 3 | 1g | 8 | 5 | 1g | 23 | 7 | 1g | 89 | 9 | 1g | 22 | 11 | 1g | 5 | 13 | 1g | 10 |
| 1 | 1h | 83 | 3 | 1h | 23 | 5 | 1h | 9 | 7 | 1h | 6 | 9 | 1h | 28 | 11 | 1h | 89 | 13 | 1h | 77 |
| 1 | 1i | 4 | 3 | 1i | 4 | 5 | 1i | 1 | 7 | 1i | 1 | 9 | 1i | 82 | 11 | 1i | 9 | 13 | 1i | 14 |
| 1 | 1j | 0 | 3 | 1j | 0 | 5 | 1j | 0 | 7 | 1j | 0 | 9 | 1j | 1 | 11 | 1j | 0 | 13 | 1j | 0 |
| 1 | 1k | 0 | 3 | 1k | 2 | 5 | 1k | 1 | 7 | 1k | 42 | 9 | 1k | 0 | 11 | 1k | 71 | 13 | 1k | 1 |
| 1 | 1l | 1 | 3 | 1l | 2 | 5 | 1l | 0 | 7 | 1l | 0 | 9 | 1l | 1 | 11 | 1l | 0 | 13 | 1l | 1 |
| 1 | 1m | 1 | 3 | 1m | 3 | 5 | 1m | 12 | 7 | 1m | 19 | 9 | 1m | 4 | 11 | 1m | 1 | 13 | 1m | 88 |
| 1 | 1n | 0 | 3 | 1n | 0 | 5 | 1n | 0 | 7 | 1n | 0 | 9 | 1n | 0 | 11 | 1n | 2 | 13 | 1n | 19 |
| 1 | 1o | 6 | 3 | 1o | 4 | 5 | 1o | 1 | 7 | 1o | 2 | 9 | 1o | 30 | 11 | 1o | 24 | 13 | 1o | 22 |
| 1 | 1p | 46 | 3 | 1p | 4 | 5 | 1p | 2 | 7 | 1p | 1 | 9 | 1p | 0 | 11 | 1p | 15 | 13 | 1p | 17 |
| 1 | 1q | 1 | 3 | 1q | 2 | 5 | 1q | 1 | 7 | 1q | 0 | 9 | 1q | 0 | 11 | 1q | 4 | 13 | 1q | 28 |
| 1 | 1r | 2 | 3 | 1r | 42 | 5 | 1r | 1 | 7 | 1r | 2 | 9 | 1r | 8 | 11 | 1r | 8 | 13 | 1r | 0 |
| 1 | 1s | 2 | 3 | 1s | 1 | 5 | 1s | 1 | 7 | 1s | 0 | 9 | 1s | 0 | 11 | 1s | 37 | 13 | 1s | 0 |
| 1 | 1t | 1 | 3 | 1t | 2 | 5 | 1t | 15 | 7 | 1t | 0 | 9 | 1t | 0 | 11 | 1t | 0 | 13 | 1t | 2 |
| 1 | 1u | 1 | 3 | 1u | 3 | 5 | 1u | 3 | 7 | 1u | 3 | 9 | 1u | 47 | 11 | 1u | 6 | 13 | 1u | 18 |
| 1 | 1v | 1 | 3 | 1v | 2 | 5 | 1v | 5 | 7 | 1v | 0 | 9 | 1v | 1 | 11 | 1v | 8 | 13 | 1v | 12 |
| 1 | 1w | 23 | 3 | 1w | 43 | 5 | 1w | 50 | 7 | 1w | 16 | 9 | 1w | 71 | 11 | 1w | 58 | 13 | 1w | 59 |
| 1 | 1x | 1 | 3 | 1x | 4 | 5 | 1x | 5 | 7 | 1x | 1 | 9 | 1x | 4 | 11 | 1x | 23 | 13 | 1x | 5 |
| 1 | 1y | 62 | 3 | 1y | 75 | 5 | 1y | 81 | 7 | 1y | 65 | 9 | 1y | 89 | 11 | 1y | 79 | 13 | 1y | 87 |
| 1 | 1z | 0 | 3 | 1z | 2 | 5 | 1z | 2 | 7 | 1z | 1 | 9 | 1z | 0 | 11 | 1z | 0 | 13 | 1z | 1 |
| 1 | 1ww | 0 | 3 | 1ww | 5 | 5 | 1ww | 1 | 7 | 1ww | 0 | 9 | 1ww | 0 | 11 | 1ww | 0 | 13 | 1ww | 0 |
| 1 | 1xx | 0 | 3 | 1xx | 2 | 5 | 1xx | 1 | 7 | 1xx | 0 | 9 | 1xx | 0 | 11 | 1xx | 1 | 13 | 1xx | 0 |
| 1 | 1yy | 8 | 3 | 1yy | 39 | 5 | 1yy | 2 | 7 | 1yy | 0 | 9 | 1yy | 16 | 11 | 1yy | 1 | 13 | 1yy | 7 |
| 1 | 1zz | 16 | 3 | 1zz | 81 | 5 | 1zz | 75 | 7 | 1zz | 58 | 9 | 1zz | 80 | 11 | 1zz | 57 | 13 | 1zz | 66 |
| 2 | 1a | 0 | 4 | 1a | 0 | 6 | 1a | 0 | 8 | 1a | 0 | 10 | 1a | 0 | 12 | 1a | 0 | 14 | 1a | 0 |
| 2 | 1b | 69 | 4 | 1b | 0 | 6 | 1b | 0 | 8 | 1b | 0 | 10 | 1b | 0 | 12 | 1b | 0 | 14 | 1b | 1 |
| 2 | 1c | 4 | 4 | 1c | 2 | 6 | 1c | 0 | 8 | 1c | 11 | 10 | 1c | 45 | 12 | 1c | 0 | 14 | 1c | 0 |
| 2 | 1d | 0 | 4 | 1d | 62 | 6 | 1d | 0 | 8 | 1d | 0 | 10 | 1d | 14 | 12 | 1d | 0 | 14 | 1d | 0 |

FIG. 36

| | | | | | | | | | | | | | | | |
|---|---|---|---|---|---|---|---|---|---|---|---|---|---|---|---|
| 2 | 1e | 0 | 4 | 1e | 0 | 6 | 1e | 0 | 8 | 1e | 1 | 10 | 1e | 0 | 12 | 1e | 0 | 14 | 1e | 0 |
| 2 | 1f | 3 | 4 | 1f | 8 | 6 | 1f | 68 | 8 | 1f | 22 | 10 | 1f | 0 | 12 | 1f | 0 | 14 | 1f | 1 |
| 2 | 1g | 78 | 4 | 1g | 8 | 6 | 1g | 13 | 8 | 1g | 9 | 10 | 1g | 76 | 12 | 1g | 14 | 14 | 1g | 23 |
| 2 | 1h | 1 | 4 | 1h | 8 | 6 | 1h | 12 | 8 | 1h | 95 | 10 | 1h | 50 | 12 | 1h | 11 | 14 | 1h | 12 |
| 2 | 1i | 0 | 4 | 1i | 3 | 6 | 1i | 1 | 8 | 1i | 3 | 10 | 1i | 6 | 12 | 1i | 2 | 14 | 1i | 5 |
| 2 | 1j | 0 | 4 | 1j | 3 | 6 | 1j | 0 | 8 | 1j | 2 | 10 | 1j | 65 | 12 | 1j | 0 | 14 | 1j | 0 |
| 2 | 1k | 0 | 4 | 1k | 12 | 6 | 1k | 0 | 8 | 1k | 0 | 10 | 1k | 0 | 12 | 1k | 0 | 14 | 1k | 0 |
| 2 | 1l | 0 | 4 | 1l | 3 | 6 | 1l | 0 | 8 | 1l | 5 | 10 | 1l | 0 | 12 | 1l | 77 | 14 | 1l | 0 |
| 2 | 1m | 72 | 4 | 1m | 14 | 6 | 1m | 0 | 8 | 1m | 3 | 10 | 1m | 1 | 12 | 1m | 7 | 14 | 1m | 11 |
| 2 | 1n | 18 | 4 | 1n | 0 | 6 | 1n | 0 | 8 | 1n | 0 | 10 | 1n | 0 | 12 | 1n | 0 | 14 | 1n | 87 |
| 2 | 1o | 2 | 4 | 1o | 6 | 6 | 1o | 2 | 8 | 1o | 10 | 10 | 1o | 13 | 12 | 1o | 7 | 14 | 1o | 12 |
| 2 | 1p | 0 | 4 | 1p | 0 | 6 | 1p | 8 | 8 | 1p | 1 | 10 | 1p | 0 | 12 | 1p | 1 | 14 | 1p | 0 |
| 2 | 1q | 15 | 4 | 1q | 1 | 6 | 1q | 0 | 8 | 1q | 8 | 10 | 1q | 0 | 12 | 1q | 3 | 14 | 1q | 2 |
| 2 | 1r | 4 | 4 | 1r | 0 | 6 | 1r | 36 | 8 | 1r | 1 | 10 | 1r | 0 | 12 | 1r | 15 | 14 | 1r | 2 |
| 2 | 1s | 0 | 4 | 1s | 3 | 6 | 1s | 0 | 8 | 1s | 27 | 10 | 1s | 1 | 12 | 1s | 2 | 14 | 1s | 0 |
| 2 | 1t | 0 | 4 | 1t | 4 | 6 | 1t | 0 | 8 | 1t | 32 | 10 | 1t | 0 | 12 | 1t | 0 | 14 | 1t | 0 |
| 2 | 1u | 22 | 4 | 1u | 4 | 6 | 1u | 3 | 8 | 1u | 6 | 10 | 1u | 5 | 12 | 1u | 80 | 14 | 1u | 32 |
| 2 | 1v | 5 | 4 | 1v | 27 | 6 | 1v | 0 | 8 | 1v | 2 | 10 | 1v | 0 | 12 | 1v | 11 | 14 | 1v | 7 |
| 2 | 1w | 16 | 4 | 1w | 48 | 6 | 1w | 8 | 8 | 1w | 69 | 10 | 1w | 29 | 12 | 1w | 74 | 14 | 1w | 56 |
| 2 | 1x | 0 | 4 | 1x | 0 | 6 | 1x | 31 | 8 | 1x | 5 | 10 | 1x | 27 | 12 | 1x | 49 | 14 | 1x | 31 |
| 2 | 1y | 21 | 4 | 1y | 59 | 6 | 1y | 44 | 8 | 1y | 86 | 10 | 1y | 63 | 12 | 1y | 75 | 14 | 1y | 70 |
| 2 | 1z | 0 | 4 | 1z | 0 | 6 | 1z | 0 | 8 | 1z | 0 | 10 | 1z | 0 | 12 | 1z | 0 | 14 | 1z | 0 |
| 2 | 1ww | 0 | 4 | 1ww | 0 | 6 | 1ww | 0 | 8 | 1ww | 0 | 10 | 1ww | 0 | 12 | 1ww | 0 | 14 | 1ww | 0 |
| 2 | 1xx | 0 | 4 | 1xx | 1 | 6 | 1xx | 0 | 8 | 1xx | 0 | 10 | 1xx | 0 | 12 | 1xx | 0 | 14 | 1xx | 0 |
| 2 | 1yy | 0 | 4 | 1yy | 0 | 6 | 1yy | 0 | 8 | 1yy | 3 | 10 | 1yy | 0 | 12 | 1yy | 1 | 14 | 1yy | 0 |
| 2 | 1zz | 67 | 4 | 1zz | 18 | 6 | 1zz | 12 | 8 | 1zz | 83 | 10 | 1zz | 77 | 12 | 1zz | 34 | 14 | 1zz | 39 |

| 16 | 1h | 22 | 18 | 1h | 35 | 20 | 1h | 15 | 22 | 1h | 84 | 24 | 1h | 18 | 26 | 1h | 94 | 28 | 1h | 21 | 30 | 1h | 63 |
|---|---|---|---|---|---|---|---|---|---|---|---|---|---|---|---|---|---|---|---|---|---|---|---|
| 16 | 1i | 6 | 18 | 1i | 4 | 20 | 1i | 1 | 22 | 1i | 32 | 24 | 1i | 0 | 26 | 1i | 25 | 28 | 1i | 0 | 30 | 1i | 2 |
| 16 | 1j | 0 | 18 | 1j | 0 | 20 | 1j | 0 | 22 | 1j | 2 | 24 | 1j | 0 | 26 | 1j | 0 | 28 | 1j | 0 | 30 | 1j | 0 |
| 16 | 1k | 0 | 18 | 1k | 0 | 20 | 1k | 2 | 22 | 1k | 9 | 24 | 1k | 0 | 26 | 1k | 1 | 28 | 1k | 0 | 30 | 1k | 0 |
| 16 | 1l | 0 | 18 | 1l | 0 | 20 | 1l | 0 | 22 | 1l | 20 | 24 | 1l | 0 | 26 | 1l | 0 | 28 | 1l | 0 | 30 | 1l | 0 |
| 16 | 1m | 4 | 18 | 1m | 6 | 20 | 1m | 0 | 22 | 1m | 19 | 24 | 1m | 0 | 26 | 1m | 1 | 28 | 1m | 0 | 30 | 1m | 0 |
| 16 | 1n | 0 | 18 | 1n | 0 | 20 | 1n | 0 | 22 | 1n | 0 | 24 | 1n | 0 | 26 | 1n | 1 | 28 | 1n | 0 | 30 | 1n | 0 |
| 16 | 1o | 5 | 18 | 1o | 8 | 20 | 1o | 3 | 22 | 1o | 44 | 24 | 1o | 0 | 26 | 1o | 31 | 28 | 1o | 1 | 30 | 1o | 3 |
| 16 | 1p | 57 | 18 | 1p | 0 | 20 | 1p | 0 | 22 | 1p | 77 | 24 | 1p | 0 | 26 | 1p | 14 | 28 | 1p | 0 | 30 | 1p | 0 |
| 16 | 1q | 2 | 18 | 1q | 0 | 20 | 1q | 0 | 22 | 1q | 1 | 24 | 1q | 0 | 26 | 1q | 0 | 28 | 1q | 0 | 30 | 1q | 0 |
| 16 | 1r | 0 | 18 | 1r | 71 | 20 | 1r | 0 | 22 | 1r | 2 | 24 | 1r | 3 | 26 | 1r | 1 | 28 | 1r | 0 | 30 | 1r | 0 |
| 16 | 1s | 0 | 18 | 1s | 45 | 20 | 1s | 0 | 22 | 1s | 7 | 24 | 1s | 0 | 26 | 1s | 20 | 28 | 1s | 0 | 30 | 1s | 0 |
| 16 | 1t | 0 | 18 | 1t | 0 | 20 | 1t | 91 | 22 | 1t | 25 | 24 | 1t | 1 | 26 | 1t | 15 | 28 | 1t | 0 | 30 | 1t | 0 |
| 16 | 1u | 5 | 18 | 1u | 3 | 20 | 1u | 5 | 22 | 1u | 49 | 24 | 1u | 13 | 26 | 1u | 40 | 28 | 1u | 0 | 30 | 1u | 10 |
| 16 | 1v | 0 | 18 | 1v | 0 | 20 | 1v | 0 | 22 | 1v | 98 | 24 | 1v | 0 | 26 | 1v | 2 | 28 | 1v | 0 | 30 | 1v | 0 |
| 16 | 1w | 31 | 18 | 1w | 20 | 20 | 1w | 58 | 22 | 1w | 81 | 24 | 1w | 32 | 26 | 1w | 37 | 28 | 1w | 34 | 30 | 1w | 56 |
| 16 | 1x | 23 | 18 | 1x | 1 | 20 | 1x | 21 | 22 | 1x | 94 | 24 | 1x | 72 | 26 | 1x | 66 | 28 | 1x | 0 | 30 | 1x | 24 |
| 16 | 1y | 59 | 18 | 1y | 64 | 20 | 1y | 73 | 22 | 1y | 97 | 24 | 1y | 71 | 26 | 1y | 72 | 28 | 1y | 48 | 30 | 1y | 79 |
| 16 | 1z | 0 | 18 | 1z | 0 | 20 | 1z | 0 | 22 | 1z | 1 | 24 | 1z | 2 | 26 | 1z | 67 | 28 | 1z | 0 | 30 | 1z | 0 |
| 16 | 1ww | 1 | 18 | 1ww | 0 | 20 | 1ww | 0 | 22 | 1ww | 0 | 24 | 1ww | 0 | 26 | 1ww | 0 | 28 | 1ww | 0 | 30 | 1ww | 0 |
| 16 | 1xx | 0 | 18 | 1xx | 30 | 20 | 1xx | 0 | 22 | 1xx | 0 | 24 | 1xx | 0 | 26 | 1xx | 0 | 28 | 1xx | 67 | 30 | 1xx | 0 |
| 16 | 1yy | 0 | 18 | 1yy | 0 | 20 | 1yy | 0 | 22 | 1yy | 2 | 24 | 1yy | 27 | 26 | 1yy | 2 | 28 | 1yy | 0 | 30 | 1yy | 0 |
| 16 | 1zz | 48 | 18 | 1zz | 76 | 20 | 1zz | 20 | 22 | 1zz | 80 | 24 | 1zz | 26 | 26 | 1zz | 87 | 28 | 1zz | 14 | 30 | 1zz | 54 |

FIG. 36
(Continued)

Reagents 1, 30° C (template # - codon # - apparent conversion)

| | | | | | | | | | | | | | | | | | | | | |
|---|---|---|---|---|---|---|---|---|---|---|---|---|---|---|---|---|---|---|---|---|
| 1 | 1a | 91 | 3 | 1a | 1 | 5 | 1a | 0 | 7 | 1a | 0 | 9 | 1a | 1 | 11 | 1a | 0 | 13 | 1a | 2 |
| 1 | 1b | 6 | 3 | 1b | 3 | 5 | 1b | 0 | 7 | 1b | 0 | 9 | 1b | 0 | 11 | 1b | 0 | 13 | 1b | 0 |
| 1 | 1c | 0 | 3 | 1c | 99 | 5 | 1c | 6 | 7 | 1c | 0 | 9 | 1c | 15 | 11 | 1c | 0 | 13 | 1c | 0 |
| 1 | 1d | 0 | 3 | 1d | 10 | 5 | 1d | 1 | 7 | 1d | 0 | 9 | 1d | 0 | 11 | 1d | 0 | 13 | 1d | 0 |
| 1 | 1e | 0 | 3 | 1e | 0 | 5 | 1e | 90 | 7 | 1e | 0 | 9 | 1e | 0 | 11 | 1e | 0 | 13 | 1e | 0 |
| 1 | 1f | 0 | 3 | 1f | 0 | 5 | 1f | 0 | 7 | 1f | 3 | 9 | 1f | 0 | 11 | 1f | 0 | 13 | 1f | 0 |
| 1 | 1g | 2 | 3 | 1g | 3 | 5 | 1g | 11 | 7 | 1g | 98 | 9 | 1g | 13 | 11 | 1g | 1 | 13 | 1g | 6 |
| 1 | 1h | 85 | 3 | 1h | 18 | 5 | 1h | 4 | 7 | 1h | 2 | 9 | 1h | 14 | 11 | 1h | 96 | 13 | 1h | 40 |
| 1 | 1i | 2 | 3 | 1i | 3 | 5 | 1i | 0 | 7 | 1i | 1 | 9 | 1i | 92 | 11 | 1i | 3 | 13 | 1i | 3 |
| 1 | 1j | 0 | 3 | 1j | 0 | 5 | 1j | 0 | 7 | 1j | 1 | 9 | 1j | 0 | 11 | 1j | 0 | 13 | 1j | 0 |
| 1 | 1k | 0 | 3 | 1k | 1 | 5 | 1k | 1 | 7 | 1k | 35 | 9 | 1k | 0 | 11 | 1k | 82 | 13 | 1k | 0 |
| 1 | 1l | 1 | 3 | 1l | 2 | 5 | 1l | 1 | 7 | 1l | 0 | 9 | 1l | 0 | 11 | 1l | 0 | 13 | 1l | 0 |
| 1 | 1m | 0 | 3 | 1m | 2 | 5 | 1m | 6 | 7 | 1m | 11 | 9 | 1m | 1 | 11 | 1m | 0 | 13 | 1m | 99 |
| 1 | 1n | 0 | 3 | 1n | 1 | 5 | 1n | 0 | 7 | 1n | 0 | 9 | 1n | 0 | 11 | 1n | 0 | 13 | 1n | 3 |
| 1 | 1o | 4 | 3 | 1o | 4 | 5 | 1o | 0 | 7 | 1o | 1 | 9 | 1o | 18 | 11 | 1o | 7 | 13 | 1o | 5 |
| 1 | 1p | 43 | 3 | 1p | 3 | 5 | 1p | 1 | 7 | 1p | 0 | 9 | 1p | 0 | 11 | 1p | 6 | 13 | 1p | 4 |
| 1 | 1q | 0 | 3 | 1q | 1 | 5 | 1q | 0 | 7 | 1q | 0 | 9 | 1q | 0 | 11 | 1q | 1 | 13 | 1q | 6 |
| 1 | 1r | 0 | 3 | 1r | 34 | 5 | 1r | 0 | 7 | 1r | 2 | 9 | 1r | 4 | 11 | 1r | 2 | 13 | 1r | 1 |
| 1 | 1s | 1 | 3 | 1s | 3 | 5 | 1s | 0 | 7 | 1s | 1 | 9 | 1s | 0 | 11 | 1s | 15 | 13 | 1s | 7 |
| 1 | 1t | 0 | 3 | 1t | 0 | 5 | 1t | 7 | 7 | 1t | 0 | 9 | 1t | 1 | 11 | 1t | 0 | 13 | 1t | 2 |
| 1 | 1u | 0 | 3 | 1u | 2 | 5 | 1u | 0 | 7 | 1u | 3 | 9 | 1u | 33 | 11 | 1u | 2 | 13 | 1u | 6 |
| 1 | 1v | 1 | 3 | 1v | 0 | 5 | 1v | 5 | 7 | 1v | 0 | 9 | 1v | 2 | 11 | 1v | 2 | 13 | 1v | 3 |
| 1 | 1w | 18 | 3 | 1w | 34 | 5 | 1w | 39 | 7 | 1w | 9 | 9 | 1w | 59 | 11 | 1w | 43 | 13 | 1w | 24 |
| 1 | 1x | 0 | 3 | 1x | 3 | 5 | 1x | 2 | 7 | 1x | 0 | 9 | 1x | 2 | 11 | 1x | 8 | 13 | 1x | 2 |
| 1 | 1y | 55 | 3 | 1y | 89 | 5 | 1y | 85 | 7 | 1y | 59 | 9 | 1y | 90 | 11 | 1y | 80 | 13 | 1y | 70 |
| 1 | 1z | 3 | 3 | 1z | 6 | 5 | 1z | 0 | 7 | 1z | 2 | 9 | 1z | 0 | 11 | 1z | 2 | 13 | 1z | 0 |
| 1 | 1ww | 0 | 3 | 1ww | 2 | 5 | 1ww | 0 | 7 | 1ww | 0 | 9 | 1ww | 0 | 11 | 1ww | 0 | 13 | 1ww | 0 |
| 1 | 1xx | 0 | 3 | 1xx | 2 | 5 | 1xx | 0 | 7 | 1xx | 1 | 9 | 1xx | 0 | 11 | 1xx | 0 | 13 | 1xx | 0 |
| 1 | 1yy | 10 | 3 | 1yy | 37 | 5 | 1yy | 4 | 7 | 1yy | 0 | 9 | 1yy | 10 | 11 | 1yy | 2 | 13 | 1yy | 16 |
| 1 | 1zz | 23 | 3 | 1zz | 87 | 5 | 1zz | 74 | 7 | 1zz | 45 | 9 | 1zz | 85 | 11 | 1zz | 47 | 13 | 1zz | 33 |
| 2 | 1a | 1 | 4 | 1a | 0 | 6 | 1a | 0 | 8 | 1a | 2 | 10 | 1a | 0 | 12 | 1a | 0 | 14 | 1a | 0 |
| 2 | 1b | 87 | 4 | 1b | 0 | 6 | 1b | 1 | 8 | 1b | 0 | 10 | 1b | 1 | 12 | 1b | 0 | 14 | 1b | 0 |
| 2 | 1c | 2 | 4 | 1c | 0 | 6 | 1c | 1 | 8 | 1c | 6 | 10 | 1c | 29 | 12 | 1c | 0 | 14 | 1c | 0 |
| 2 | 1d | 0 | 4 | 1d | 68 | 6 | 1d | 1 | 8 | 1d | 0 | 10 | 1d | 5 | 12 | 1d | 0 | 14 | 1d | 0 |

| 16 | 1a | 0 | 18 | 1a | 4 | 20 | 1a | 0 | 22 | 1a | 1 | 23 | 1a | 4 | 25 | 1a | 0 | 27 | 1a | 0 |
|---|---|---|---|---|---|---|---|---|---|---|---|---|---|---|---|---|---|---|---|---|
| 16 | 1b | 0 | 18 | 1b | 4 | 20 | 1b | 0 | 22 | 1b | 0 | 23 | 1b | 0 | 25 | 1b | 0 | 27 | 1b | 0 |
| 16 | 1c | 0 | 18 | 1c | 11 | 20 | 1c | 18 | 22 | 1c | 4 | 23 | 1c | 46 | 25 | 1c | 3 | 27 | 1c | 0 |
| 16 | 1d | 0 | 18 | 1d | 4 | 20 | 1d | 0 | 22 | 1d | 0 | 23 | 1d | 0 | 25 | 1d | 0 | 27 | 1d | 0 |
| 16 | 1e | 0 | 18 | 1e | 3 | 20 | 1e | 0 | 22 | 1e | 0 | 23 | 1e | 3 | 25 | 1e | 1 | 27 | 1e | 0 |
| 16 | 1f | 2 | 18 | 1f | 4 | 20 | 1f | 0 | 22 | 1f | 0 | 23 | 1f | 5 | 25 | 1f | 3 | 27 | 1f | 0 |
| 16 | 1g | 57 | 18 | 1g | 7 | 20 | 1g | 21 | 22 | 1g | 70 | 23 | 1g | 35 | 25 | 1g | 30 | 27 | 1g | 15 |
| 16 | 1h | 10 | 18 | 1h | 23 | 20 | 1h | 8 | 22 | 1h | 44 | 23 | 1h | 94 | 25 | 1h | 96 | 27 | 1h | 32 |
| 16 | 1i | 0 | 18 | 1i | 5 | 20 | 1i | 0 | 22 | 1i | 5 | 23 | 1i | 72 | 25 | 1i | 8 | 27 | 1i | 1 |
| 16 | 1j | 0 | 18 | 1j | 2 | 20 | 1j | 0 | 22 | 1j | 0 | 23 | 1j | 7 | 25 | 1j | 6 | 27 | 1j | 0 |
| 16 | 1k | 0 | 18 | 1k | 3 | 20 | 1k | 1 | 22 | 1k | 0 | 23 | 1k | 66 | 25 | 1k | 1 | 27 | 1k | 0 |
| 16 | 1l | 0 | 18 | 1l | 2 | 20 | 1l | 0 | 22 | 1l | 5 | 23 | 1l | 5 | 25 | 1l | 0 | 27 | 1l | 0 |
| 16 | 1m | 0 | 18 | 1m | 6 | 20 | 1m | 0 | 22 | 1m | 3 | 23 | 1m | 12 | 25 | 1m | 3 | 27 | 1m | 0 |
| 16 | 1n | 0 | 18 | 1n | 2 | 20 | 1n | 0 | 22 | 1n | 0 | 23 | 1n | 8 | 25 | 1n | 1 | 27 | 1n | 1 |
| 16 | 1o | 4 | 18 | 1o | 9 | 20 | 1o | 1 | 22 | 1o | 15 | 23 | 1o | 89 | 25 | 1o | 10 | 27 | 1o | 2 |
| 16 | 1p | 73 | 18 | 1p | 4 | 20 | 1p | 0 | 22 | 1p | 52 | 23 | 1p | 38 | 25 | 1p | 0 | 27 | 1p | 4 |
| 16 | 1q | 2 | 18 | 1q | 5 | 20 | 1q | 0 | 22 | 1q | 2 | 23 | 1q | 2 | 25 | 1q | 3 | 27 | 1q | 4 |
| 16 | 1r | 0 | 18 | 1r | 99 | 20 | 1r | 0 | 22 | 1r | 5 | 23 | 1r | 21 | 25 | 1r | 2 | 27 | 1r | 0 |
| 16 | 1s | 0 | 18 | 1s | 37 | 20 | 1s | 0 | 22 | 1s | 4 | 23 | 1s | 56 | 25 | 1s | 3 | 27 | 1s | 0 |
| 16 | 1t | 0 | 18 | 1t | 1 | 20 | 1t | 99 | 22 | 1t | 16 | 23 | 1t | 16 | 25 | 1t | 0 | 27 | 1t | 0 |
| 16 | 1u | 2 | 18 | 1u | 8 | 20 | 1u | 1 | 22 | 1u | 29 | 23 | 1u | 99 | 25 | 1u | 14 | 27 | 1u | 3 |
| 16 | 1v | 0 | 18 | 1v | 3 | 20 | 1v | 0 | 22 | 1v | 99 | 23 | 1v | 30 | 25 | 1v | 4 | 27 | 1v | 0 |
| 16 | 1w | 20 | 18 | 1w | 39 | 20 | 1w | 59 | 22 | 1w | 61 | 23 | 1w | 99 | 25 | 1w | 59 | 27 | 1w | 8 |
| 16 | 1x | 15 | 18 | 1x | 5 | 20 | 1x | 16 | 22 | 1x | 89 | 23 | 1x | 99 | 25 | 1x | 46 | 27 | 1x | 34 |
| 27 | 1y | 38 | 29 | 1y | 84 | 35 | 1yy | 4 | 48 | 1l | 0 | 52 | 1r | 0 | 57 | 1m | 0 | 62 | 1yy | 1 |
| 27 | 1z | 0 | 29 | 1z | 0 | 35 | 1u | 66 | 48 | 1m | 0 | 52 | 1v | 0 | 57 | 1o | 6 | 62 | 1g | 13 |
| 27 | 1ww | 29 | 29 | 1ww | 0 | 35 | 1x | 88 | 48 | 1p | 50 | 52 | 1yy | 0 | 57 | 1yy | 1 | 62 | 1h | 2 |
| 27 | 1xx | 0 | 29 | 1xx | 0 | 35 | 1o | 55 | 48 | 1q | 0 | 52 | 1h | 1 | 57 | 1f | 0 | 62 | 1p | 9 |
| 27 | 1yy | 1 | 29 | 1yy | 98 | 35 | 1s | 40 | 48 | 1t | 0 | 52 | 1u | 0 | 57 | 1t | 0 | 26 | 1o | 21 |
| 27 | 1zz | 27 | 29 | 1zz | 59 | 35 | 1yy | 0 | 48 | 1v | 0 | 52 | 1g | 11 | 57 | 1x | 19 | 26 | 1m | 15 |
| 28 | 1a | 0 | 30 | 1a | 0 | 36 | 1u | 18 | 48 | 1yy | 31 | 53 | 1f | 0 | 58 | 1k | 1 | 26 | 1p | 9 |
| 28 | 1b | 0 | 30 | 1b | 0 | 37 | 1c | 1 | 48 | 1g | 4 | 53 | 1e | 0 | 58 | 1j | 0 | 26 | 1o | 21 |
| 28 | 1c | 0 | 30 | 1c | 0 | 37 | 1yy | 9 | 48 | 1u | 0 | 53 | 1c | 0 | 58 | 1h | 89 | 26 | 1m | 15 |
| 28 | 1d | 0 | 30 | 1d | 0 | 37 | 1u | 0 | 48 | 1x | 0 | 53 | 1f | 0 | 58 | 1k | 1 | 26 | 1c | 3 |
| 28 | 1e | 0 | 30 | 1e | 0 | 37 | 1x | 7 | 49 | 1b | 0 | 53 | 1e | 0 | 58 | 1j | 0 | 26 | 1i | 7 |
| 28 | 1f | 0 | 30 | 1f | 0 | 37 | 1c | 2 | 49 | 1a | 0 | 53 | 1c | 0 | 58 | 1h | 89 | 26 | 1m | 10 |
| 28 | 1g | 0 | 30 | 1g | 8 | 37 | 1i | 0 | 49 | 1yy | 0 | 53 | 1d | 57 | 58 | 1f | 0 | 26 | 1n | 99 |

FIG. 36
(Continued)

| 28 | 1h | 12 | 30 | 1h | 55 | 37 | 1g | 14 | 49 | 1l | 0 | 53 | 1m | 0 | 58 | 1o | 4 | 26 | 1o | 12 |
| --- | --- | --- | --- | --- | --- | --- | --- | --- | --- | --- | --- | --- | --- | --- | --- | --- | --- | --- | --- | --- |
| 28 | 1i | 0 | 30 | 1i | 1 | 37 | 1o | 2 | 49 | 1m | 87 | 53 | 1r | 0 | 58 | 1s | 7 | 26 | 1p | 5 |
| 28 | 1j | 0 | 30 | 1j | 0 | 37 | 1f | 5 | 49 | 1n | 17 | 53 | 1v | 0 | 58 | 1t | 0 | 26 | 1v | 2 |
| 28 | 1k | 0 | 30 | 1k | 0 | 37 | 1f | 6 | 49 | 1p | 0 | 53 | 1yy | 0 | 58 | 1yy | 0 | 26 | 1ww | 3 |
| 28 | 1l | 0 | 30 | 1l | 0 | 37 | 1m | 0 | 49 | 1q | 10 | 53 | 1g | 4 | 58 | 1l | 5 | 26 | 1yy | 2 |
| 28 | 1m | 0 | 30 | 1m | 0 | 39 | 1g | 1 | 49 | 1t | 0 | 53 | 1g | 4 | 59 | 1k | 3 | 64 | 1q | 1 |
| 28 | 1n | 0 | 30 | 1n | 0 | 39 | 1h | 4 | 49 | 1v | 5 | 53 | 1h | 18 | 59 | 1i | 7 | 64 | 1p | 3 |
| 28 | 1o | 0 | 30 | 1o | 1 | 40 | 1c | 1 | 50 | 1c | 0 | 53 | 1x | 21 | 59 | 1l | 5 | 64 | 1n | 1 |
| 28 | 1p | 0 | 30 | 1p | 0 | 40 | 1i | 14 | 50 | 1b | 0 | 54 | 1g | 14 | 59 | 1k | 3 | 64 | 1p | 1 |
| 28 | 1q | 0 | 30 | 1q | 0 | 40 | 1n | 2 | 50 | 1zz | 71 | 54 | 1f | 0 | 59 | 1i | 7 | 64 | 1p | 3 |
| 28 | 1r | 0 | 30 | 1r | 0 | 40 | 1n | 0 | 50 | 1c | 0 | 54 | 1d | 0 | 59 | 1c | 0 | 64 | 1n | 1 |
| 28 | 1s | 0 | 30 | 1s | 0 | 40 | 1o | 23 | 50 | 1b | 0 | 54 | 1k | 29 | 59 | 1o | 6 | 64 | 1c | 1 |
| 28 | 1t | 0 | 30 | 1t | 0 | 37 | 1o | 25 | 50 | 1zz | 71 | 54 | 1m | 8 | 59 | 1s | 1 | 64 | 1i | 6 |
| 28 | 1u | 0 | 30 | 1u | 5 | 37 | 1g | 66 | 50 | 1d | 0 | 54 | 1r | 1 | 59 | 1yy | 1 | 64 | 1o | 33 |
| 28 | 1v | 0 | 30 | 1v | 0 | 37 | 1h | 99 | 50 | 1m | 0 | 54 | 1v | 2 | 60 | 1m | 0 | 64 | 1s | 24 |
| 28 | 1w | 22 | 30 | 1w | 50 | 41 | 1yy | 1 | 50 | 1n | 0 | 54 | 1x | 0 | 60 | 1l | 0 | 64 | 1v | 1 |
| 28 | 1x | 0 | 30 | 1x | 18 | 41 | 1r | 46 | 50 | 1p | 0 | 55 | 1h | 3 | 60 | 1j | 0 | 64 | 1ww | 0 |
| 28 | 1y | 44 | 30 | 1y | 88 | 41 | 1u | 6 | 50 | 1q | 0 | 55 | 1g | 0 | 60 | 1m | 0 | 65 | 1r | 39 |
| 28 | 1z | 0 | 30 | 1z | 0 | 41 | 1x | 15 | 50 | 1r | 26 | 55 | 1e | 0 | 60 | 1l | 0 | 65 | 1q | 3 |
| 28 | 1ww | 1 | 30 | 1ww | 0 | 42 | 1c | 0 | 50 | 1yy | 0 | 55 | 1f | 82 | 60 | 1j | 0 | 65 | 1o | 5 |
| 28 | 1xx | 81 | 30 | 1xx | 0 | 42 | 1m | 7 | 50 | 1g | 0 | 55 | 1k | 0 | 60 | 1c | 0 | 65 | 1r | 39 |
| 28 | 1yy | 0 | 30 | 1yy | 0 | 42 | 1o | 0 | 50 | 1u | 0 | 55 | 1m | 0 | 60 | 1s | 0 | 65 | 1q | 3 |
| 28 | 1zz | 6 | 30 | 1zz | 64 | 42 | 1s | 0 | 50 | 1x | 0 | 55 | 1r | 23 | 60 | 1yy | 0 | 65 | 1o | 5 |
| 29 | 1a | 1 | 31 | 1m | 2 | 42 | 1k | 27 | 51 | 1d | 0 | 55 | 1t | 0 | 60 | 1g | 0 | 65 | 1c | 2 |
| 29 | 1b | 1 | 31 | 1q | 1 | 42 | 1k | 27 | 51 | 1c | 1 | 55 | 1u | 0 | 60 | 1u | 3 | 65 | 1n | 0 |
| 29 | 1c | 1 | 31 | 1v | 13 | 42 | 1u | 4 | 51 | 1a | 0 | 55 | 1x | 0 | 61 | 1n | 4 | 65 | 1p | 70 |
| 29 | 1d | 1 | 31 | 1x | 0 | 42 | 1x | 3 | 51 | 1d | 0 | 56 | 1i | 3 | 61 | 1m | 16 | 65 | 1r | 27 |
| 29 | 1e | 1 | 31 | 1g | 4 | 43 | 1u | 2 | 51 | 1c | 1 | 56 | 1h | 6 | 61 | 1k | 4 | 65 | 1s | 22 |
| 29 | 1f | 3 | 32 | 1c | 6 | 43 | 1x | 3 | 51 | 1a | 0 | 56 | 1f | 0 | 61 | 1n | 4 | 65 | 1ww | 0 |
| 29 | 1g | 33 | 32 | 1i | 1 | 44 | 1c | 0 | 51 | 1m | 0 | 56 | 1i | 3 | 61 | 1m | 16 | 65 | 1xx | 10 |
| 29 | 1h | 35 | 32 | 1m | 4 | 44 | 1yy | 3 | 51 | 1n | 0 | 56 | 1h | 6 | 61 | 1k | 4 | 65 | 1yy | 0 |
| 29 | 1i | 4 | 32 | 1p | 1 | 44 | 1ww | 19 | 51 | 1p | 0 | 56 | 1f | 0 | 61 | 1m | 9 | 65 | 1i | 0 |
| 29 | 1j | 1 | 32 | 1p | 2 | 45 | 1c | 0 | 51 | 1q | 0 | 56 | 1t | 0 | 61 | 1s | 0 | 65 | 1g | 2 |
| 29 | 1k | 1 | 32 | 1s | 39 | 45 | 1x | 50 | 51 | 1r | 0 | 56 | 1c | 1 | 61 | 1v | 10 | 66 | 1s | 2 |
| 29 | 1l | 34 | 32 | 1x | 0 | 45 | 1yy | 42 | 51 | 1v | 26 | 56 | 1o | 4 | 61 | 1yy | 0 | 66 | 1r | 5 |
| 29 | 1m | 17 | 32 | 1g | 4 | 46 | 1t | 1 | 51 | 1yy | 0 | 56 | 1r | 0 | 61 | 1g | 20 | 66 | 1p | 1 |
| 29 | 1n | 1 | 33 | 1i | 1 | 46 | 1o | 4 | 51 | 1g | 4 | 56 | 1yy | 1 | 62 | 1o | 9 | 66 | 1s | 2 |

| | | | | | | | | | | | | | | | | | | | | |
|---|---|---|---|---|---|---|---|---|---|---|---|---|---|---|---|---|---|---|---|---|
| 29 | 1o | 6 | 33 | 1o | 1 | 47 | 1c | 12 | 51 | 1u | 0 | 56 | 1k | 0 | 62 | 1n | 5 | 66 | 1r | 5 |
| 29 | 1p | 7 | 33 | 1m | 1 | 47 | 1o | 35 | 52 | 1e | 0 | 56 | 1m | 0 | 62 | 1l | 5 | 66 | 1p | 1 |
| 29 | 1q | 49 | 33 | 1m | 0 | 47 | 1o | 39 | 52 | 1d | 0 | 56 | 1x | 0 | 62 | 1o | 9 | 66 | 1c | 6 |
| 29 | 1r | 3 | 33 | 1g | 3 | 47 | 1t | 7 | 52 | 1b | 0 | 57 | 1j | 3 | 62 | 1n | 5 | 66 | 1i | 8 |
| 29 | 1s | 1 | 34 | 1i | 24 | 48 | 1a | 0 | 52 | 1e | 0 | 57 | 1i | 6 | 62 | 1l | 5 | 66 | 1o | 13 |
| 29 | 1t | 12 | 34 | 1t | 0 | 48 | 1zz | 24 | 52 | 1d | 0 | 57 | 1g | 79 | 62 | 1c | 4 | 66 | 1xx | 1 |
| 29 | 1u | 18 | 34 | 1o | 18 | 48 | 1xx | 0 | 52 | 1b | 0 | 57 | 1j | 3 | 62 | 1i | 1 | 66 | 1yy | 28 |
| 29 | 1v | 90 | 34 | 1g | 17 | 48 | 1a | 0 | 52 | 1m | 4 | 57 | 1i | 6 | 62 | 1o | 3 | 66 | 1u | 14 |
| 29 | 1w | 28 | 35 | 1i | 34 | 48 | 1zz | 24 | 52 | 1n | 0 | 57 | 1g | 79 | 62 | 1v | 1 | 67 | 1t | 8 |
| 29 | 1x | 3 | 35 | 1yy | 3 | 48 | 1xx | 0 | 52 | 1q | 0 | 57 | 1k | 1 | 62 | 1ww | 3 | 67 | 1s | 9 |

| | | | | | | | | | | | | | | | | | |
|---|---|---|---|---|---|---|---|---|---|---|---|---|---|---|---|---|---|
| 67 | 1g | 9 | 71 | 1i | 3 | 77 | 1g | 0 | 97 | 1m | 0 | 109 | 1c | 0 | | | |
| 67 | 1t | 8 | 71 | 1k | 1 | 77 | 1t | 0 | 97 | 1x | 12 | 109 | 1d | 0 | | | |
| 67 | 1s | 9 | 71 | 1m | 1 | 77 | 1v | 0 | 97 | 1x | 12 | 109 | 1e | 0 | | | |
| 67 | 1q | 9 | 71 | 1r | 13 | 77 | 1u | 2 | 97 | 1h | 24 | 109 | 1f | 1 | | | |
| 67 | 1c | 1 | 71 | 1s | 2 | 78 | 1r | 33 | 98 | 1s | 0 | 109 | 1i | 1 | | | |
| 67 | 1i | 2 | 71 | 1z | 0 | 78 | 1g | 3 | 98 | 1u | 0 | 109 | 1j | 76 | | | |
| 67 | 1o | 4 | 72 | 1y | 99 | 79 | 1v | 8 | 98 | 1g | 3 | 109 | 1l | 0 | | | |
| 67 | 1p | 0 | 72 | 1y | 99 | 79 | 1c | 0 | 100 | 1i | 4 | 109 | 1m | 0 | | | |
| 67 | 1q | 0 | 72 | 1x | 97 | 79 | 1g | 3 | 100 | 1o | 10 | 109 | 1n | 0 | | | |
| 67 | 1t | 0 | 72 | 1v | 0 | 79 | 1h | 9 | 100 | 1s | 0 | 109 | 1o | 0 | | | |
| 67 | 1xx | 0 | 72 | 1i | 78 | 80 | 1c | 0 | 101 | 1i | 5 | 109 | 1p | 0 | | | |
| 67 | 1yy | 1 | 72 | 1p | 94 | 80 | 1k | 12 | 101 | 1o | 0 | 109 | 1q | 0 | | | |
| 67 | 1s | 1 | 73 | 1z | 7 | 80 | 1t | 0 | 101 | 1p | 0 | 109 | 1s | 0 | | | |
| 68 | 1u | 17 | 73 | 1y | 82 | 80 | 1h | 2 | 101 | 1q | 4 | 109 | 1t | 0 | | | |
| 68 | 1t | 1 | 73 | 1w | 49 | 82 | 1g | 60 | 101 | 1v | 47 | 109 | 1z | 0 | | | |
| 68 | 1r | 4 | 73 | 1z | 7 | 83 | 1o | 15 | 101 | 1x | 0 | 109 | 1ww | 0 | | | |
| 68 | 1u | 17 | 73 | 1y | 82 | 83 | 1s | 29 | 101 | 1g | 9 | 109 | 1xx | 0 | | | |
| 68 | 1t | 11 | 73 | 1w | 49 | 83 | 1g | 3 | 102 | 1o | 2 | 109 | 1yy | 0 | | | |
| 68 | 1r | 4 | 73 | 1i | 21 | 83 | 1u | 59 | 102 | 1yy | 0 | 110 | 1j | 0 | | | |
| 68 | 1c | 1 | 73 | 1o | 35 | 84 | 1g | 54 | 102 | 1u | 3 | 110 | 1p | 69 | | | |
| 68 | 1o | 6 | 73 | 1s | 24 | 85 | 1m | 0 | 102 | 1g | 15 | 111 | 1j | 0 | | | |
| 68 | 1s | 98 | 73 | 1c | 1 | 85 | 1u | 0 | 103 | 1o | 1 | 111 | 1z | 39 | | | |
| 68 | 1t | 0 | 73 | 1k | 0 | 85 | 1g | 2 | 103 | 1p | 5 | 109 | 1c | 0 | | | |
| 68 | 1xx | 0 | 73 | 1m | 0 | 85 | 1i | 17 | 103 | 1t | 4 | 109 | 1d | 0 | | | |
| 68 | 1yy | 7 | 73 | 1n | 0 | 86 | 1o | 31 | 103 | 1v | 0 | | | | | | |
| 69 | 1v | 0 | 73 | 1p | 12 | 86 | 1s | 21 | 104 | 1n | 0 | | | | | | |

FIG. 36
(Continued)

| | | | | | | | | | | | |
|---|---|---|---|---|---|---|---|---|---|---|---|
|69|1u|2|73|1r|0|87|1u|29|104|1r|0|
|69|1s|6|73|1t|13|88|1p|53|104|1v|0|
|69|1c|0|73|1v|2|88|1yy|2|105|1i|1|
|69|1p|0|74|1ww|0|88|1g|0|105|1o|1|
|69|1yy|0|74|1z|24|88|1o|99|105|1s|1|
|70|1w|91|74|1x|99|89|1d|1|106|1i|1|
|70|1v|31|75|1xx|0|89|1m|59|106|1o|1|
|70|1t|25|75|1ww|1|89|1n|6|106|1p|0|
|70|1w|91|75|1yy|51|89|1o|1|106|1s|0|
|70|1v|31|75|1i|2|89|1q|3|106|1t|0|
|70|1t|25|75|1o|6|89|1r|68|10y|1yy|0|
|70|1c|33|75|1s|0|89|1g|65|106|1i|6|
|70|1o|76|75|1g|0|89|1h|23|10y|1o|10|
|70|1p|33|75|1u|0|90|1o|0|107|1ww|94|
|70|1t|12|76|1yy|2|90|1h|14|108|1a|0|
|70|1v|21|76|1xx|0|91|1h|5|108|1b|0|
|70|1i|59|76|1z|0|92|1x|4|108|1c|0|
|70|1k|49|76|1yy|2|92|1g|27|108|1d|0|
|70|1m|10|76|1xx|0|92|1h|26|108|1e|0|
|70|1n|2|76|1z|0|93|1g|0|108|1f|0|
|70|1r|8|76|1i|0|93|1g|0|108|1i|0|
|70|1s|28|76|1l|19|93|1u|0|108|1j|67|
|70|1z|27|76|1m|7|93|1x|2|108|1l|0|
|71|1x|76|76|1o|2|94|1o|2|106|1m|0|
|71|1w|35|76|1q|22|94|1g|6|108|1n|0|
|71|1u|35|76|1s|0|95|1v|8|108|1o|0|
|71|1x|76|76|1t|3|95|1i|3|108|1p|0|
|71|1w|35|76|1v|70|95|1x|35|108|1q|0|
|71|1u|35|76|1g|12|95|1h|9|108|1s|0|
|71|1o|6|76|1zz|9|95|1r|34|108|1t|0|
|71|1p|2|76|1yy|0|95|1s|28|108|1z|0|
|71|1t|5|76|1ww|0|95|1xx|14|108|1ww|0|
|71|1yy|3|76|1l|2|95|1u|2|108|1xx|0|
|71|1c|1|76|1m|1|95|1g|3|108|1yy|0|

| 25 | 2x | 77 | 27 | 2x | 53 | 29 | 2x | 23 | 38 | 2g | 0 | 52 | 2e | 1 | 60 | 2e | 0 | 67 | 2g | 37 | 86 | 2n | 82 |
|---|---|---|---|---|---|---|---|---|---|---|---|---|---|---|---|---|---|---|---|---|---|---|---|
| 25 | 2y | 99 | 27 | 2y | 31 | 29 | 2y | 39 | 38 | 2b | 0 | 52 | 2c | 1 | 60 | 2f | 0 | 68 | 2u | 2 | 86 | 2t | 28 |
| 25 | 2z | 80 | 27 | 2z | 12 | 29 | 2z | 8 | 38 | 2f | 0 | 52 | 2b | 0 | 60 | 2s | 0 | 68 | 2s | 11 | 88 | 2b | 0 |
| 25 | 2ww | 99 | 27 | 2ww | 64 | 29 | 2ww | 7 | 39 | 2g | 10 | 52 | 2f | 0 | 60 | 2v | 0 | 68 | 2r | 0 | 88 | 2g | 1 |
| 25 | 2xx | 3 | 27 | 2xx | 0 | 29 | 2xx | 0 | 39 | 2s | 47 | 52 | 2g | 47 | 61 | 2n | 37 | 68 | 2g | 26 | 89 | 2g | 9 |
| 25 | 2yy | 2 | 27 | 2yy | 0 | 29 | 2yy | 58 | 39 | 2j | 1 | 52 | 2n | 44 | 61 | 2l | 52 | 68 | 2s | 30 | 89 | 2b | 0 |
| 25 | 2zz | 1 | 27 | 2zz | 0 | 29 | 2zz | 0 | 39 | 2n | 18 | 52 | 2r | 2 | 61 | 2k | 4 | 69 | 2v | 2 | 90 | 2g | 16 |
| 26 | 2a | 5 | 28 | 2a | 0 | 30 | 2a | 0 | 39 | 2r | 5 | 52 | 2s | 1 | 61 | 2b | 66 | 69 | 2t | 0 | 90 | 2s | 1 |
| 26 | 2b | 3 | 28 | 2b | 0 | 30 | 2b | 0 | 39 | 2u | 4 | 52 | 2zz | 0 | 61 | 2e | 3 | 69 | 2s | 2 | 91 | 2g | 8 |
| 26 | 2c | 2 | 28 | 2c | 0 | 30 | 2c | 0 | 39 | 2yy | 2 | 53 | 2f | 1 | 61 | 2f | 32 | 70 | 2w | 35 | 91 | 2s | 53 |
| 26 | 2d | 1 | 28 | 2d | 0 | 30 | 2d | 0 | 41 | 2g | 8 | 53 | 2d | 1 | 61 | 2n | 38 | 70 | 2u | 19 | 93 | 2g | 0 |
| 26 | 2e | 1 | 28 | 2e | 0 | 30 | 2e | 0 | 41 | 2n | 0 | 53 | 2c | 1 | 61 | 2s | 1 | 70 | 2t | 25 | 95 | 2b | 74 |
| 26 | 2f | 3 | 28 | 2f | 0 | 30 | 2f | 0 | 41 | 2s | 24 | 53 | 2g | 1 | 61 | 2v | 5 | 70 | 2t | 36 | 95 | 2f | 38 |
| 26 | 2g | 3 | 28 | 2g | 0 | 30 | 2g | 0 | 41 | 2f | 5 | 53 | 2n | 0 | 62 | 2o | 5 | 71 | 2x | 95 | 95 | 2g | 4 |
| 26 | 2h | 0 | 28 | 2h | 0 | 30 | 2h | 0 | 41 | 2j | 2 | 53 | 2r | 0 | 62 | 2m | 4 | 71 | 2v | 10 | 95 | 2n | 41 |
| 26 | 2i | 1 | 28 | 2i | 0 | 30 | 2i | 0 | 41 | 2r | 4 | 53 | 2s | 0 | 62 | 2l | 56 | 71 | 2u | 6 | 95 | 2s | 0 |
| 26 | 2j | 1 | 28 | 2j | 0 | 30 | 2j | 0 | 41 | 2u | 4 | 53 | 2g | 28 | 62 | 2b | 7 | 71 | 2b | 80 | 96 | 2g | 7 |
| 26 | 2k | 0 | 28 | 2k | 0 | 30 | 2k | 0 | 41 | 2yy | 3 | 54 | 2e | 0 | 62 | 2e | 1 | 71 | 2v | 14 | 97 | 2g | 1 |
| 26 | 2l | 63 | 28 | 2l | 18 | 30 | 2l | 9 | 42 | 2g | 28 | 54 | 2d | 0 | 62 | 2f | 4 | 72 | 2y | 99 | 98 | 2g | 0 |
| 26 | 2m | 1 | 28 | 2m | 0 | 30 | 2m | 0 | 42 | 2b | 1 | 54 | 2c | 9 | 62 | 2s | 9 | 72 | 2w | 96 | 98 | 2s | 0 |
| 26 | 2n | 3 | 28 | 2n | 0 | 30 | 2n | 0 | 42 | 2c | 19 | 54 | 2g | 36 | 62 | 2v | 1 | 72 | 2v | 73 | 99 | 2b | 32 |
| 26 | 2o | 1 | 28 | 2o | 0 | 30 | 2o | 0 | 42 | 2f | 0 | 54 | 2j | 1 | 63 | 2p | 3 | 72 | 2v | 71 | 99 | 2c | 0 |
| 26 | 2p | 0 | 28 | 2p | 0 | 30 | 2p | 0 | 42 | 2t | 3 | 54 | 2n | 0 | 63 | 2n | 18 | 73 | 2z | 11 | 99 | 2g | 6 |
| 26 | 2q | 4 | 28 | 2q | 0 | 30 | 2q | 0 | 42 | 2u | 0 | 54 | 2s | 2 | 63 | 2m | 0 | 73 | 2x | 99 | 99 | 2s | 2 |
| 26 | 2r | 0 | 28 | 2r | 0 | 30 | 2r | 0 | 43 | 2g | 77 | 54 | 2yy | 0 | 63 | 2b | 4 | 73 | 2w | 18 | 100 | 2g | 4 |
| 26 | 2s | 6 | 28 | 2s | 0 | 30 | 2s | 0 | 43 | 2b | 0 | 55 | 2h | 0 | 63 | 2e | 0 | 73 | 2t | 27 | 101 | 2a | 9 |
| 26 | 2t | 9 | 28 | 2t | 0 | 30 | 2t | 0 | 43 | 2f | 1 | 55 | 2f | 0 | 63 | 2s | 85 | 74 | 2ww | 99 | 101 | 2n | 6 |
| 26 | 2u | 5 | 28 | 2u | 0 | 30 | 2u | 0 | 43 | 2n | 2 | 55 | 2e | 0 | 63 | 2f | 2 | 74 | 2y | 99 | 101 | 2s | 0 |
| 26 | 2v | 0 | 28 | 2v | 0 | 30 | 2v | 0 | 43 | 2q | 0 | 55 | 2c | 0 | 63 | 2s | 67 | 74 | 2x | 99 | 101 | 2v | 0 |
| 26 | 2w | 71 | 28 | 2w | 6 | 30 | 2w | 0 | 43 | 2u | 4 | 55 | 2n | 3 | 63 | 2v | 5 | 75 | 2xx | 1 | 102 | 2g | 1 |
| 26 | 2x | 83 | 28 | 2x | 1 | 30 | 2x | 44 | 44 | 2a | 6 | 55 | 2s | 40 | 64 | 2q | 0 | 75 | 2z | 25 | 102 | 2s | 8 |
| 26 | 2y | 76 | 28 | 2y | 16 | 30 | 2y | 56 | 45 | 2b | 27 | 55 | 2t | 0 | 64 | 2o | 1 | 75 | 2yy | 2 | | | |

FIG. 36
(Continued)

| 26 | 2z | 99 | 28 | 2z | 0 | 30 | 2z | 15 | 48 | 2a | 1 | 55 | 2u | 0 | 64 | 2n | 1 | 75 | 2t | 1 |
|---|---|---|---|---|---|---|---|---|---|---|---|---|---|---|---|---|---|---|---|---|
| 26 | 2ww | 46 | 28 | 2ww | 0 | 30 | 2ww | 70 | 48 | 2yy | 0 | 55 | 2v | 0 | 64 | 2b | 13 | 76 | 2yy | 0 |
| 26 | 2xx | 1 | 28 | 2xx | 57 | 30 | 2xx | 0 | 48 | 2xx | 0 | 56 | 2i | 2 | 64 | 2c | 43 | 76 | 2ww | 5 |
| 26 | 2yy | 1 | 28 | 2yy | 0 | 30 | 2yy | 0 | 48 | 2n | 1 | 56 | 2g | 5 | 64 | 2f | 30 | 76 | 2z | 0 |
| 26 | 2zz | 0 | 28 | 2zz | 0 | 30 | 2zz | 49 | 48 | 2q | 0 | 56 | 2f | 2 | 64 | 2g | 17 | 76 | 2a | 19 |
| 27 | 2a | 0 | 28 | 2a | 18 | 31 | 2g | 0 | 49 | 2b | 0 | 56 | 2n | 1 | 64 | 2t | 31 | 76 | 2n | 12 |
| 27 | 2b | 0 | 28 | 2b | 0 | 31 | 2a | 4 | 49 | 2zz | 3 | 56 | 2s | 4 | 65 | 2r | 0 | 76 | 2t | 0 |
| 27 | 2c | 0 | 29 | 2c | 0 | 32 | 2g | 8 | 49 | 2yy | 0 | 56 | 2t | 1 | 65 | 2p | 0 | 77 | 2zz | 1 |
| 27 | 2d | 0 | 29 | 2d | 0 | 32 | 2s | 9 | 49 | 2g | 25 | 56 | 2v | 0 | 65 | 2o | 0 | 77 | 2xx | 1 |
| 27 | 2e | 5 | 29 | 2e | 0 | 32 | 2b | 2 | 49 | 2n | 1 | 57 | 2j | 5 | 65 | 2b | 4 | 77 | 2ww | 94 |
| 27 | 2f | 0 | 29 | 2f | 0 | 32 | 2c | 4 | 50 | 2c | 0 | 57 | 2h | 5 | 65 | 2g | 9 | 77 | 2n | 1 |
| 27 | 2g | 1 | 29 | 2g | 3 | 32 | 2f | 6 | 50 | 2a | 0 | 57 | 2g | 13 | 65 | 2s | 6 | 78 | 2n | 2 |
| 27 | 2h | 0 | 29 | 2h | 0 | 33 | 2t | 5 | 50 | 2zz | 0 | 57 | 2g | 9 | 66 | 2s | 12 | 79 | 2j | 2 |
| 27 | 2i | 0 | 29 | 2i | 0 | 33 | 2f | 2 | 50 | 2g | 2 | 58 | 2k | 1 | 66 | 2q | 0 | 79 | 2yy | 5 |
| 27 | 2j | 0 | 29 | 2j | 0 | 33 | 2c | 0 | 50 | 2n | 0 | 58 | 2i | 1 | 66 | 2p | 0 | 80 | 2c | 4 |
| 27 | 2k | 0 | 29 | 2k | 0 | 34 | 2f | 1 | 50 | 2q | 2 | 58 | 2h | 0 | 66 | 2b | 8 | 80 | 2g | 16 |
| 27 | 2l | 6 | 29 | 2l | 43 | 35 | 2g | 9 | 50 | 2s | 6 | 58 | 2g | 0 | 66 | 2c | 7 | 80 | 2t | 1 |
| 27 | 2m | 0 | 29 | 2m | 0 | 35 | 2s | 23 | 51 | 2d | 1 | 58 | 2n | 0 | 66 | 2f | 13 | 82 | 2g | 3 |
| 27 | 2n | 0 | 29 | 2n | 20 | 35 | 2q | 9 | 51 | 2b | 2 | 58 | 2r | 1 | 66 | 2s | 29 | 82 | 2n | 2 |
| 27 | 2o | 0 | 29 | 2o | 0 | 35 | 2t | 46 | 51 | 2a | 2 | 58 | 2s | 2 | 66 | 2t | 6 | 83 | 2b | 12 |
| 27 | 2p | 0 | 29 | 2p | 0 | 36 | 2b | 1 | 51 | 2f | 0 | 58 | 2t | 2 | 66 | 2g | 5 | 83 | 2c | 39 |
| 27 | 2q | 0 | 29 | 2q | 0 | 36 | 2g | 1 | 51 | 2g | 7 | 58 | 2v | 0 | 67 | 2t | 33 | 83 | 2f | 27 |
| 27 | 2r | 0 | 29 | 2r | 0 | 36 | 2n | 1 | 51 | 2j | 10 | 59 | 2l | 50 | 67 | 2r | 33 | 83 | 2g | 15 |
| 27 | 2s | 1 | 29 | 2s | 0 | 36 | 2s | 3 | 51 | 2n | 3 | 59 | 2j | 0 | 67 | 2q | 0 | 83 | 2t | 30 |
| 27 | 2t | 0 | 29 | 2t | 0 | 37 | 2g | 3 | 51 | 2r | 0 | 59 | 2i | 0 | 67 | 2c | 37 | 84 | 2t | 31 |
| 27 | 2u | 0 | 29 | 2u | 0 | 37 | 2s | 2 | 51 | 2s | 1 | 60 | 2m | 0 | 67 | 2s | 99 | 84 | 2v | 3 |
| 27 | 2v | 1 | 29 | 2v | 0 | 37 | 2b | 2 | 51 | 2yy | 18 | 60 | 2k | 0 | 67 | 2t | 48 | 85 | 2f | 0 |
| 27 | 2w | 0 | 29 | 2w | 32 | 37 | 2u | 12 | 51 | 2zz | 0 | 60 | 2j | 0 | 67 | 2g | 32 | 86 | 2g | 7 |

FIG. 36
(Continued)

Reagents 2, 30 °C (template # - codon # - apparent conversion)

FIG. 36
(Continued)

| | | | | | | | | | | | | | | | | | | | | |
|---|---|---|---|---|---|---|---|---|---|---|---|---|---|---|---|---|---|---|---|---|
| 2 | 2a | 0 | 3 | 2yy | 0 | 5 | 2w | 0 | 7 | 2u | 0 | 9 | 2s | 1 | 11 | 2q | 0 | 13 | 2o | 0 |
| 2 | 2b | 93 | 3 | 2zz | 0 | 5 | 2x | 4 | 7 | 2v | 0 | 9 | 2t | 3 | 11 | 2r | 0 | 13 | 2p | 0 |
| 2 | 2c | 0 | 3 | 2c | 99 | 5 | 2y | 7 | 7 | 2w | 0 | 9 | 2u | 0 | 11 | 2s | 2 | 13 | 2q | 0 |
| 2 | 2d | 0 | 3 | 2g | 2 | 5 | 2z | 1 | 7 | 2x | 2 | 9 | 2v | 0 | 11 | 2i | 0 | 13 | 2r | 0 |
| 2 | 2e | 0 | 3 | 2n | 1 | 5 | 2ww | 3 | 7 | 2y | 8 | 9 | 2w | 2 | 11 | 2u | 1 | 13 | 2s | 1 |
| 2 | 2f | 0 | 4 | 2a | 0 | 5 | 2xx | 0 | 7 | 2z | 2 | 9 | 2x | 21 | 11 | 2v | 0 | 13 | 2t | 0 |
| 2 | 2g | 11 | 4 | 2b | 0 | 5 | 2yy | 0 | 7 | 2ww | 4 | 9 | 2y | 18 | 11 | 2w | 7 | 13 | 2u | 0 |
| 2 | 2h | 0 | 4 | 2c | 0 | 5 | 2zz | 0 | 7 | 2xx | 0 | 9 | 2z | 3 | 11 | 2x | 97 | 13 | 2v | 11 |
| 2 | 2i | 0 | 4 | 2d | 84 | 5 | 2e | 99 | 7 | 2yy | 0 | 9 | 2ww | 9 | 11 | 2y | 49 | 13 | 2w | 9 |
| 2 | 2j | 0 | 4 | 2e | 0 | 6 | 2a | 0 | 7 | 2zz | 1 | 9 | 2xx | 0 | 11 | 2z | 0 | 13 | 2x | 67 |
| 2 | 2k | 0 | 4 | 2f | 0 | 6 | 2b | 0 | 8 | 2g | 96 | 9 | 2yy | 0 | 11 | 2ww | 9 | 13 | 2y | 33 |
| 2 | 2l | 2 | 4 | 2g | 1 | 6 | 2c | 0 | 8 | 2a | 1 | 9 | 2zz | 0 | 11 | 2xx | 0 | 13 | 2z | 0 |
| 2 | 2m | 0 | 4 | 2h | 0 | 6 | 2d | 0 | 8 | 2b | 0 | 9 | 2i | 91 | 11 | 2yy | 0 | 13 | 2ww | 2 |
| 2 | 2n | 0 | 4 | 2i | 0 | 6 | 2e | 0 | 8 | 2c | 0 | 10 | 2a | 0 | 11 | 2zz | 0 | 13 | 2xx | 0 |
| 2 | 2o | 0 | 4 | 2j | 2 | 6 | 2f | 92 | 8 | 2d | 0 | 10 | 2b | 0 | 11 | 2k | 94 | 13 | 2yy | 0 |
| 2 | 2p | 0 | 4 | 2k | 0 | 6 | 2g | 0 | 8 | 2e | 1 | 10 | 2c | 0 | 12 | 2a | 0 | 13 | 2zz | 0 |
| 2 | 2q | 0 | 4 | 2l | 34 | 6 | 2h | 0 | 8 | 2f | 2 | 10 | 2d | 0 | 12 | 2b | 0 | 13 | 2f | 8 |
| 2 | 2r | 0 | 4 | 2m | 1 | 6 | 2i | 0 | 8 | 2g | 13 | 10 | 2e | 0 | 12 | 2c | 0 | 13 | 2m | 97 |
| 2 | 2s | 2 | 4 | 2n | 16 | 6 | 2j | 0 | 8 | 2h | 97 | 10 | 2f | 0 | 12 | 2d | 0 | 13 | 2s | 3 |
| 2 | 2t | 0 | 4 | 2o | 0 | 6 | 2k | 0 | 8 | 2i | 0 | 10 | 2g | 0 | 12 | 2e | 0 | 13 | 2v | 15 |
| 2 | 2u | 0 | 4 | 2p | 0 | 6 | 2l | 4 | 8 | 2j | 1 | 10 | 2h | 0 | 12 | 2f | 0 | 14 | 2a | 0 |
| 2 | 2v | 0 | 4 | 2q | 0 | 6 | 2m | 0 | 8 | 2k | 0 | 10 | 2i | 0 | 12 | 2g | 0 | 14 | 2b | 39 |
| 2 | 2w | 0 | 4 | 2r | 2 | 6 | 2n | 0 | 8 | 2l | 52 | 10 | 2j | 64 | 12 | 2h | 0 | 14 | 2c | 0 |
| 2 | 2x | 0 | 4 | 2s | 6 | 6 | 2o | 0 | 8 | 2m | 4 | 10 | 2k | 0 | 12 | 2i | 0 | 14 | 2d | 0 |
| 2 | 2y | 8 | 4 | 2t | 0 | 6 | 2p | 0 | 8 | 2n | 17 | 10 | 2l | 7 | 12 | 2j | 0 | 14 | 2e | 0 |
| 2 | 2z | 1 | 4 | 2u | 0 | 6 | 2q | 0 | 8 | 2o | 3 | 10 | 2m | 0 | 12 | 2k | 0 | 14 | 2f | 17 |
| 2 | 2ww | 4 | 4 | 2v | 0 | 6 | 2r | 0 | 8 | 2p | 1 | 10 | 2n | 0 | 12 | 2l | 75 | 14 | 2g | 1 |
| 2 | 2xx | 0 | 4 | 2w | 10 | 6 | 2s | 0 | 8 | 2q | 3 | 10 | 1o | 0 | 12 | 2m | 0 | 14 | 2h | 0 |
| 2 | 2yy | 0 | 4 | 2x | 11 | 6 | 2t | 0 | 8 | 2r | 13 | 10 | 1p | 0 | 12 | 2n | 3 | 14 | 2i | 0 |

FIG. 36
(Continued)

| 14 | 2j | 0 | 16 | 2e | 0 | 17 | 2f | 18 | 19 | 2v | 0 | 21 | 2t | 4 | 23 | 2r | 0 | 25 | 2o | 0 |
|---|---|---|---|---|---|---|---|---|---|---|---|---|---|---|---|---|---|---|---|---|
| 14 | 2k | 1 | 16 | 2f | 0 | 17 | 2g | 14 | 19 | 2w | 1 | 21 | 2u | 99 | 23 | 2s | 22 | 25 | 2p | 0 |
| 14 | 2l | 30 | 16 | 2g | 0 | 17 | 2q | 99 | 19 | 2x | 18 | 21 | 2v | 5 | 23 | 2t | 15 | 25 | 2q | 0 |
| 14 | 2m | 0 | 16 | 2h | 0 | 17 | 2t | 24 | 19 | 2y | 16 | 21 | 2w | 10 | 23 | 2u | 12 | 25 | 2r | 2 |
| 14 | 2n | 99 | 16 | 2i | 0 | 18 | 2a | 0 | 19 | 2z | 6 | 21 | 2x | 93 | 23 | 2v | 10 | 25 | 2s | 4 |
| 14 | 2o | 0 | 16 | 2j | 0 | 18 | 2b | 0 | 19 | 2ww | 13 | 21 | 2y | 75 | 23 | 2w | 99 | 25 | 2t | 0 |
| 14 | 2p | 0 | 16 | 2k | 0 | 18 | 2c | 0 | 19 | 2xx | 0 | 21 | 2z | 2 | 23 | 2x | 88 | 25 | 2u | 2 |
| 14 | 2q | 0 | 16 | 2l | 5 | 18 | 2d | 1 | 19 | 2yy | 0 | 21 | 2ww | 49 | 23 | 2y | 99 | 25 | 2v | 2 |
| 14 | 2r | 1 | 16 | 2m | 0 | 18 | 2e | 0 | 20 | 2zz | 0 | 21 | 2xx | 0 | 23 | 2z | 33 | 25 | 2w | 7 |
| 14 | 2s | 1 | 16 | 2n | 0 | 18 | 2f | 0 | 20 | 2s | 94 | 21 | 2yy | 0 | 23 | 2ww | 61 | 25 | 2x | 79 |
| 14 | 2t | 0 | 16 | 2o | 0 | 18 | 2g | 2 | 20 | 2a | 0 | 21 | 2zz | 0 | 23 | 2xx | 4 | 25 | 2y | 99 |
| 14 | 2u | 0 | 16 | 2p | 31 | 18 | 2h | 1 | 20 | 2b | 0 | 21 | 2u | 99 | 23 | 2yy | 6 | 25 | 2z | 64 |
| 14 | 2v | 0 | 16 | 2q | 0 | 18 | 2i | 0 | 20 | 2c | 0 | 22 | 2a | 0 | 23 | 2zz | 9 | 25 | 2ww | 99 |
| 14 | 2w | 2 | 16 | 2r | 0 | 18 | 2j | 1 | 20 | 2d | 0 | 22 | 2b | 0 | 23 | 2w | 99 | 25 | 2xx | 2 |
| 14 | 2x | 5 | 16 | 2s | 4 | 18 | 2k | 0 | 20 | 2e | 0 | 22 | 2c | 0 | 24 | 2a | 0 | 25 | 2yy | 0 |
| 14 | 2y | 32 | 16 | 2t | 0 | 18 | 2l | 10 | 20 | 2f | 0 | 22 | 2d | 0 | 24 | 2b | 21 | 25 | 2zz | 0 |
| 14 | 2z | 0 | 16 | 2u | 0 | 18 | 2m | 1 | 20 | 2g | 0 | 22 | 2e | 0 | 24 | 2c | 0 | 25 | 2y | 99 |
| 14 | 2ww | 3 | 16 | 2v | 0 | 18 | 2n | 3 | 20 | 2h | 0 | 22 | 2f | 0 | 24 | 2d | 0 | 26 | 2a | 0 |
| 14 | 2xx | 0 | 16 | 2w | 0 | 18 | 2o | 1 | 20 | 2i | 0 | 22 | 2g | 2 | 24 | 2e | 1 | 26 | 2b | 0 |
| 14 | 2yy | 0 | 16 | 2x | 28 | 18 | 2p | 1 | 20 | 2j | 0 | 22 | 2h | 2 | 24 | 2f | 2 | 26 | 2c | 0 |
| 14 | 2zz | 1 | 16 | 2y | 23 | 18 | 2q | 4 | 20 | 2k | 0 | 22 | 2i | 0 | 24 | 2g | 1 | 26 | 2d | 0 |
| 14 | 2b | 40 | 16 | 2z | 38 | 18 | 2r | 99 | 20 | 2l | 8 | 22 | 2j | 0 | 24 | 2h | 0 | 26 | 2e | 0 |
| 14 | 2f | 19 | 16 | 2ww | 27 | 18 | 2s | 8 | 20 | 2m | 0 | 22 | 2k | 0 | 24 | 2i | 0 | 26 | 2f | 0 |
| 14 | 2n | 99 | 16 | 2xx | 0 | 18 | 2t | 3 | 20 | 2n | 0 | 22 | 2l | 22 | 24 | 2j | 0 | 26 | 2g | 0 |
| 15 | 2a | 2 | 16 | 2yy | 0 | 18 | 2u | 4 | 20 | 2o | 0 | 22 | 2m | 0 | 24 | 2k | 0 | 26 | 2h | 0 |
| 15 | 2b | 5 | 16 | 2zz | 0 | 18 | 2v | 1 | 20 | 2p | 0 | 22 | 2n | 0 | 24 | 2l | 7 | 26 | 2i | 0 |
| 15 | 2c | 0 | 16 | 2p | 36 | 18 | 2w | 13 | 20 | 2q | 0 | 22 | 2o | 2 | 24 | 2m | 0 | 26 | 2j | 1 |
| 15 | 2d | 0 | 16 | 2s | 7 | 18 | 2x | 22 | 20 | 2r | 0 | 22 | 2p | 0 | 24 | 2n | 0 | 26 | 2k | 2 |
| 15 | 2e | 0 | 17 | 2a | 5 | 18 | 2y | 63 | 20 | 2s | 0 | 22 | 2q | 0 | 24 | 2o | 0 | 26 | 2l | 34 |
| 15 | 2f | 1 | 17 | 2b | 10 | 18 | 2z | 11 | 20 | 2t | 97 | 22 | 2r | 0 | 24 | 2p | 0 | 26 | 2m | 5 |
| 15 | 2g | 3 | 17 | 2c | 25 | 18 | 2ww | 21 | 20 | 2u | 0 | 22 | 2s | 5 | 24 | 2q | 0 | 26 | 2n | 6 |
| 15 | 2h | 0 | 17 | 2d | 2 | 18 | 2xx | 1 | 20 | 2v | 0 | 22 | 2t | 0 | 24 | 2r | 1 | 26 | 2o | 5 |

FIG. 36
(Continued)

| | | | | | | | | | | | | | | | | | | | | |
|---|---|---|---|---|---|---|---|---|---|---|---|---|---|---|---|---|---|---|---|---|
| 15 | 2i | 0 | 17 | 2e | 2 | 18 | 2yy | 3 | 20 | 2w | 20 | 22 | 2u | 4 | 24 | 2s | 0 | 26 | 2p | 4 |
| 15 | 2j | 1 | 17 | 2f | 17 | 18 | 2zz | 0 | 20 | 2x | 29 | 22 | 2v | 99 | 24 | 2t | 0 | 26 | 2q | 2 |
| 15 | 2k | 0 | 17 | 2g | 11 | 18 | 2g | 11 | 20 | 2y | 26 | 22 | 2w | 6 | 24 | 2u | 0 | 26 | 2r | 0 |
| 15 | 2l | 60 | 17 | 2h | 3 | 18 | 2s | 19 | 20 | 2z | 1 | 22 | 2x | 99 | 24 | 2v | 2 | 26 | 2s | 0 |
| 15 | 2m | 1 | 17 | 2i | 2 | 18 | 2g | 10 | 20 | 2ww | 23 | 22 | 2y | 96 | 24 | 2w | 1 | 26 | 2t | 0 |
| 15 | 2n | 0 | 17 | 2j | 2 | 18 | 2r | 99 | 20 | 2xx | 0 | 22 | 2z | 19 | 24 | 2x | 99 | 26 | 2u | 0 |
| 15 | 2o | 99 | 17 | 2k | 1 | 18 | 2s | 12 | 20 | 2yy | 0 | 22 | 2ww | 63 | 24 | 2y | 45 | 26 | 2v | 0 |
| 15 | 2p | 3 | 17 | 2l | 49 | 19 | 2a | 0 | 20 | 2zz | 0 | 22 | 2xx | 1 | 24 | 2z | 2 | 26 | 2w | 29 |
| 15 | 2q | 1 | 17 | 2m | 2 | 19 | 2b | 0 | 20 | 2t | 97 | 22 | 2yy | 4 | 24 | 2ww | 15 | 26 | 2x | 53 |
| 15 | 2r | 0 | 17 | 2n | 3 | 19 | 2c | 0 | 21 | 2a | 9 | 22 | 2zz | 3 | 24 | 2xx | 0 | 26 | 2y | 41 |
| 15 | 2s | 5 | 17 | 2o | 4 | 19 | 2d | 0 | 21 | 2b | 0 | 22 | 2v | 99 | 24 | 2yy | 0 | 26 | 2z | 99 |
| 15 | 2t | 2 | 17 | 2p | 2 | 19 | 2e | 0 | 21 | 2c | 0 | 23 | 2a | 5 | 24 | 2zz | 0 | 26 | 2ww | 8 |
| 15 | 2u | 1 | 17 | 2q | 99 | 19 | 2f | 0 | 21 | 2d | 0 | 23 | 2b | 38 | 24 | 2b | 20 | 26 | 2xx | 0 |
| 15 | 2v | 0 | 17 | 2r | 2 | 19 | 2g | 0 | 21 | 2e | 1 | 23 | 2c | 15 | 24 | 2x | 96 | 26 | 2yy | 0 |
| 15 | 2w | 4 | 17 | 2s | 2 | 19 | 2h | 0 | 21 | 2f | 0 | 23 | 2d | 8 | 25 | 2a | 3 | 26 | 2zz | 0 |
| 15 | 2x | 10 | 17 | 2t | 15 | 19 | 2i | 0 | 21 | 2g | 9 | 23 | 2e | 12 | 25 | 2b | 1 | 26 | 2t | 15 |
| 15 | 2y | 58 | 17 | 2u | 2 | 19 | 2j | 0 | 21 | 2h | 0 | 23 | 2f | 17 | 25 | 2c | 0 | 26 | 2z | 99 |
| 15 | 2z | 8 | 17 | 2v | 2 | 19 | 2k | 0 | 21 | 2i | 2 | 23 | 2g | 23 | 25 | 2d | 0 | 27 | 2a | 0 |
| 15 | 2ww | 18 | 17 | 2w | 14 | 19 | 2l | 1 | 21 | 2j | 0 | 23 | 2h | 6 | 25 | 2e | 0 | 27 | 2b | 0 |
| 15 | 2xx | 2 | 17 | 2x | 27 | 19 | 2m | 0 | 21 | 2k | 0 | 23 | 2i | 7 | 25 | 2f | 0 | 27 | 2c | 0 |
| 15 | 2yy | 0 | 17 | 2y | 68 | 19 | 2n | 0 | 21 | 2l | 68 | 23 | 2j | 9 | 25 | 2g | 0 | 27 | 2d | 0 |
| 15 | 2zz | 1 | 17 | 2z | 1 | 19 | 2o | 0 | 21 | 2m | 4 | 23 | 2k | 4 | 25 | 2h | 0 | 27 | 2e | 0 |
| 15 | 2b | 15 | 17 | 2ww | 3 | 19 | 2p | 0 | 21 | 2n | 6 | 23 | 2l | 99 | 25 | 2i | 0 | 27 | 2f | 0 |
| 15 | 2o | 99 | 17 | 2xx | 0 | 19 | 2q | 0 | 21 | 2o | 3 | 23 | 2m | 9 | 25 | 2j | 0 | 27 | 2g | 1 |
| 16 | 2a | 0 | 17 | 2yy | 0 | 19 | 2r | 0 | 21 | 2p | 3 | 23 | 2n | 14 | 25 | 2k | 0 | 27 | 2h | 0 |
| 16 | 2b | 0 | 17 | 2zz | 0 | 19 | 2s | 92 | 21 | 2q | 0 | 23 | 2o | 12 | 25 | 2l | 16 | 27 | 2i | 1 |
| 16 | 2c | 0 | 17 | 2b | 11 | 19 | 2t | 0 | 21 | 2r | 1 | 23 | 2p | 7 | 25 | 2m | 0 | 27 | 2j | 0 |
| 16 | 2d | 0 | 17 | 2c | 31 | 19 | 2u | 0 | 21 | 2s | 7 | 23 | 2q | 0 | 25 | 2n | 0 | 27 | 2k | 1 |

FIG. 36
(Continued)

| 27 | 2l | 5 | 29 | 2j | 1 | 33 | 2g | 0 | 50 | 2l | 3 | 57 | 2n | 0 | 65 | 2g | 1 | 71 | 2g | 5 |
|---|---|---|---|---|---|---|---|---|---|---|---|---|---|---|---|---|---|---|---|---|
| 27 | 2m | 0 | 29 | 2k | 1 | 33 | 2w | 0 | 50 | 2w | 0 | 57 | 2r | 1 | 65 | 2s | 1 | 71 | 2n | 0 |
| 27 | 2n | 1 | 29 | 2l | 40 | 33 | 2ww | 1 | 50 | 2z | 13 | 57 | 2s | 1 | 65 | 2c | 0 | 71 | 2o | 0 |
| 27 | 2o | 1 | 29 | 2m | 1 | 34 | 2z | 3 | 51 | 2j | 3 | 57 | 2w | 9 | 65 | 2g | 0 | 71 | 2s | 3 |
| 27 | 2p | 0 | 29 | 2n | 18 | 35 | 2g | 6 | 51 | 2a | 0 | 57 | 2z | 7 | 65 | 2o | 0 | 71 | 2t | 0 |
| 27 | 2q | 0 | 29 | 2o | 2 | 35 | 2t | 15 | 51 | 2b | 0 | 57 | 2ww | 31 | 65 | 2p | 0 | 71 | 2z | 7 |
| 27 | 2r | 0 | 29 | 2p | 1 | 35 | 2ww | 10 | 51 | 2d | 0 | 58 | 2g | 0 | 65 | 2r | 0 | 71 | 2y | 99 |
| 27 | 2s | 1 | 29 | 2q | 1 | 35 | 2z | 6 | 51 | 2g | 1 | 58 | 2h | 0 | 65 | 2z | 4 | 72 | 2w | 5 |
| 27 | 2t | 0 | 29 | 2r | 1 | 36 | 2w | 1 | 51 | 2r | 0 | 58 | 2i | 0 | 66 | 2b | 1 | 73 | 2x | 85 |
| 27 | 2u | 0 | 29 | 2s | 1 | 37 | 2s | 0 | 51 | 2ww | 2 | 58 | 2k | 0 | 66 | 2f | 2 | 73 | 2z | 2 |
| 27 | 2v | 1 | 29 | 2t | 1 | 38 | 2b | 0 | 51 | 2z | 1 | 58 | 2z | 1 | 66 | 2g | 3 | 73 | 2c | 0 |
| 27 | 2w | 1 | 29 | 2u | 1 | 38 | 2f | 0 | 51 | 2w | 17 | 58 | 2l | 16 | 66 | 2p | 0 | 73 | 2d | 0 |
| 27 | 2x | 56 | 29 | 2v | 0 | 38 | 2ww | 1 | 51 | 2w | 16 | 58 | 2ww | 6 | 66 | 2q | 0 | 73 | 2e | 0 |
| 27 | 2y | 30 | 29 | 2w | 32 | 38 | 2z | 0 | 52 | 2g | 23 | 59 | 2i | 0 | 66 | 2s | 4 | 73 | 2f | 1 |
| 27 | 2z | 3 | 29 | 2x | 21 | 39 | 2g | 4 | 52 | 2n | 17 | 59 | 2j | 0 | 66 | 2l | 8 | 73 | 2g | 1 |
| 27 | 2ww | 99 | 29 | 2y | 46 | 39 | 2n | 8 | 52 | 2b | 0 | 59 | 2l | 25 | 67 | 2g | 12 | 73 | 2j | 0 |
| 27 | 2xx | 0 | 29 | 2z | 1 | 39 | 2g | 3 | 52 | 2c | 0 | 60 | 2e | 0 | 67 | 2t | 15 | 73 | 2m | 0 |
| 27 | 2yy | 0 | 29 | 2ww | 5 | 40 | 2g | 10 | 52 | 2e | 0 | 60 | 2j | 0 | 67 | 2b | 2 | 73 | 2n | 0 |
| 27 | 2zz | 0 | 29 | 2xx | 0 | 40 | 2l | 43 | 52 | 2l | 3 | 60 | 2k | 0 | 67 | 2q | 0 | 73 | 2o | 0 |
| 27 | 2ww | 94 | 29 | 2yy | 96 | 41 | 2g | 0 | 52 | 2ww | 3 | 60 | 2m | 0 | 67 | 2r | 2 | 73 | 2s | 0 |
| 28 | 2a | 0 | 29 | 2zz | 1 | 41 | 2n | 0 | 53 | 2z | 1 | 60 | 2v | 0 | 67 | 2t | 12 | 73 | 2t | 9 |
| 28 | 2b | 0 | 29 | 2yy | 93 | 41 | 2r | 0 | 53 | 2c | 0 | 60 | 2w | 0 | 67 | 2l | 29 | 73 | 2u | 1 |
| 28 | 2c | 0 | 30 | 2a | 0 | 41 | 2s | 4 | 53 | 2d | 0 | 60 | 2ww | 3 | 68 | 2s | 8 | 73 | 2v | 1 |
| 28 | 2d | 0 | 30 | 2b | 0 | 41 | 2z | 24 | 53 | 2f | 0 | 60 | 2z | 0 | 68 | 2g | 2 | 73 | 2zz | 0 |
| 28 | 2e | 0 | 30 | 2c | 0 | 42 | 2c | 6 | 53 | 2g | 0 | 61 | 2n | 35 | 68 | 2r | 0 | 74 | 2ww | 89 |
| 28 | 2f | 0 | 30 | 2d | 0 | 42 | 2g | 11 | 53 | 2n | 0 | 61 | 2e | 1 | 68 | 2s | 22 | 74 | 2x | 99 |
| 28 | 2g | 0 | 30 | 2e | 0 | 42 | 2l | 1 | 53 | 2l | 2 | 61 | 2f | 15 | 68 | 2u | 0 | 74 | 2y | 94 |
| 28 | 2h | 0 | 30 | 2f | 0 | 42 | 2w | 0 | 53 | 2w | 0 | 61 | 2k | 0 | 68 | 2z | 4 | 75 | 2xx | 0 |

FIG. 36
(Continued)

| | | | | | | | | | | | | | | | | | | | | |
|---|---|---|---|---|---|---|---|---|---|---|---|---|---|---|---|---|---|---|---|---|
| 28 | 2i | 0 | 30 | 2g | 0 | 42 | 2ww | 2 | 53 | 2ww | 8 | 61 | 2l | 27 | 68 | 2l | 53 | 75 | 2y | 48 |
| 28 | 2j | 0 | 30 | 2h | 0 | 42 | 2z | 0 | 53 | 2z | 1 | 61 | 2n | 18 | 69 | 2g | 0 | 75 | 2z | 7 |
| 28 | 2k | 1 | 30 | 2i | 1 | 43 | 2n | 0 | 54 | 2c | 1 | 61 | 2v | 1 | 69 | 2s | 0 | 76 | 2ww | 0 |
| 28 | 2l | 19 | 30 | 2j | 1 | 43 | 2b | 0 | 54 | 2g | 15 | 61 | 2w | 2 | 69 | 2t | 0 | 76 | 2yy | 0 |
| 28 | 2m | 0 | 30 | 2k | 0 | 43 | 2f | 0 | 54 | 2d | 0 | 62 | 2s | 6 | 69 | 2v | 0 | 76 | 2z | 0 |
| 28 | 2n | 0 | 30 | 2l | 8 | 43 | 2g | 40 | 54 | 2e | 0 | 62 | 2l | 36 | 69 | 2w | 0 | 76 | 2w | 21 |
| 28 | 2o | 0 | 30 | 2m | 0 | 43 | 2ww | 6 | 54 | 2g | 13 | 62 | 2m | 0 | 69 | 2z | 6 | 77 | 2a | 0 |
| 28 | 2p | 0 | 30 | 2n | 1 | 43 | 2ww | 12 | 54 | 2l | 1 | 62 | 2o | 0 | 69 | 2i | 2 | 77 | 2n | 0 |
| 28 | 2q | 0 | 30 | 2o | 1 | 44 | 2b | 15 | 54 | 2w | 0 | 62 | 2v | 0 | 70 | 2t | 10 | 77 | 2ww | 86 |
| 28 | 2r | 0 | 30 | 2p | 0 | 45 | 2l | 6 | 54 | 2ww | 3 | 62 | 2w | 1 | 70 | 2u | 9 | 77 | 2xx | 0 |
| 28 | 2s | 0 | 30 | 2q | 0 | 45 | 2w | 0 | 55 | 2s | 19 | 62 | 2ww | 9 | 70 | 2w | 17 | 77 | 2zz | 0 |
| 28 | 2t | 0 | 30 | 2r | 1 | 45 | 2ww | 19 | 55 | 2e | 0 | 62 | 2z | 0 | 70 | 2a | 0 | 77 | 2w | 2 |
| 28 | 2u | 0 | 30 | 2s | 2 | 47 | 2w | 27 | 55 | 2f | 0 | 63 | 2f | 93 | 70 | 2b | 21 | 77 | 2z | 7 |
| 28 | 2v | 0 | 30 | 2t | 0 | 47 | 2ww | 82 | 55 | 2h | 0 | 63 | 2n | 16 | 70 | 2c | 2 | 78 | 2n | 0 |
| 28 | 2w | 3 | 30 | 2u | 1 | 47 | 2z | 24 | 55 | 2n | 0 | 63 | 2s | 62 | 70 | 2d | 2 | 78 | 2r | 0 |
| 28 | 2x | 1 | 30 | 2v | 1 | 47 | 2l | 65 | 55 | 2r | 0 | 63 | 2v | 0 | 70 | 2e | 3 | 78 | 2w | 2 |
| 28 | 2y | 18 | 30 | 2w | 3 | 48 | 2a | 0 | 55 | 2l | 5 | 63 | 2m | 0 | 70 | 2f | 10 | 78 | 2z | 13 |
| 28 | 2z | 0 | 30 | 2x | 53 | 48 | 2n | 0 | 55 | 2w | 7 | 63 | 2n | 7 | 70 | 2g | 10 | 78 | 2i | 5 |
| 28 | 2ww | 0 | 30 | 2y | 61 | 48 | 2xx | 0 | 56 | 2f | 0 | 63 | 2p | 0 | 70 | 2j | 4 | 79 | 2n | 1 |
| 28 | 2xx | 88 | 30 | 2z | 8 | 48 | 2yy | 0 | 56 | 2g | 0 | 63 | 2v | 1 | 70 | 2m | 5 | 79 | 2w | 9 |
| 28 | 2yy | 0 | 30 | 2ww | 89 | 48 | 2zz | 76 | 56 | 2i | 0 | 63 | 2w | 0 | 70 | 2n | 9 | 80 | 2g | 7 |
| 28 | 2zz | 0 | 30 | 2xx | 0 | 48 | 2ww | 6 | 56 | 2r | 0 | 63 | 2z | 75 | 70 | 2o | 8 | 80 | 2t | 0 |
| 28 | 2xx | 86 | 30 | 2yy | 0 | 48 | 2z | 5 | 56 | 2s | 0 | 64 | 2b | 4 | 70 | 2s | 14 | 80 | 2i | 1 |
| 29 | 2a | 11 | 30 | 2zz | 76 | 49 | 2g | 9 | 56 | 2l | 0 | 64 | 2c | 17 | 70 | 2z | 16 | 80 | 2w | 0 |
| 29 | 2b | 0 | 30 | 2zz | 75 | 49 | 2b | 0 | 56 | 2w | 0 | 64 | 2f | 9 | 70 | 2zz | 4 | 81 | 2l | 27 |
| 29 | 2c | 0 | 31 | 2w | 0 | 49 | 2g | 9 | 56 | 2z | 3 | 64 | 2g | 6 | 71 | 2v | 3 | 82 | 2r | 1 |
| 29 | 2d | 0 | 31 | 2ww | 4 | 49 | 2yy | 0 | 56 | 2ww | 0 | 64 | 2t | 11 | 71 | 2u | 1 | 82 | 2w | 1 |
| 29 | 2e | 0 | 32 | 2g | 5 | 49 | 2zz | 0 | 57 | 2g | 0 | 64 | 2c | 15 | 71 | 2v | 3 | 83 | 2b | 5 |
| 29 | 2f | 0 | 32 | 2b | 0 | 50 | 2a | 0 | 57 | 2g | 0 | 64 | 2n | 0 | 71 | 2x | 82 | 83 | 2c | 17 |
| 29 | 2g | 2 | 32 | 2f | 0 | 50 | 2c | 2 | 57 | 2h | 2 | 64 | 2o | 0 | 71 | 2c | 0 | 83 | 2f | 11 |
| 29 | 2h | 0 | 32 | 2ww | 12 | 50 | 2g | 0 | 57 | 2j | 0 | 64 | 2q | 0 | 71 | 2e | 0 | 83 | 2g | 6 |
| 29 | 2i | 1 | 32 | 2z | 7 | 50 | 2zz | 1 | 57 | 2i | 1 | 64 | 2w | 7 | 71 | 2f | 4 | 83 | 2t | 11 |

FIG. 36
(Continued)

| | | | | | | | | | |
|---|---|---|---|---|---|---|---|---|---|
| 83 | 2z | 3 | 97 | 2z | 10 | 109 | 2a | 0 |
| 83 | 2l | 31 | 98 | 2s | 0 | 109 | 2c | 0 |
| 84 | 2t | 11 | 98 | 2w | 0 | 109 | 2d | 0 |
| 84 | 2v | 0 | 99 | 2b | 17 | 109 | 2e | 0 |
| 84 | 2w | 3 | 99 | 2c | 0 | 109 | 2f | 0 |
| 84 | 2z | 4 | 99 | 2f | 11 | 109 | 2h | 0 |
| 84 | 2l | 21 | 99 | 2g | 2 | 109 | 2i | 0 |
| 85 | 2a | 0 | 99 | 2s | 0 | 109 | 2j | 0 |
| 85 | 2e | 0 | 99 | 2t | 0 | 109 | 2k | 0 |
| 85 | 2v | 0 | 99 | 2ww | 14 | 109 | 2m | 0 |
| 85 | 2w | 2 | 99 | 2ww | 13 | 109 | 2n | 0 |
| 85 | 2z | 0 | 100 | 2a | 1 | 109 | 2o | 0 |
| 86 | 2n | 62 | 100 | 2b | 1 | 109 | 2q | 0 |
| 86 | 2w | 1 | 100 | 2c | 1 | 109 | 2r | 0 |
| 86 | 2l | 50 | 100 | 2f | 1 | 109 | 2t | 0 |
| 87 | 2b | 0 | 100 | 2g | 1 | 109 | 2u | 0 |
| 87 | 2f | 0 | 100 | 2t | 0 | 109 | 2v | 0 |
| 87 | 2l | 22 | 100 | 2w | 6 | 109 | 2xx | 49 |
| 88 | 2g | 0 | 100 | 2z | 68 | 109 | 2yy | 0 |
| 88 | 2w | 1 | 101 | 2a | 3 | 109 | 2zz | 1 |
| 88 | 2ww | 1 | 101 | 2e | 0 | 110 | 2xx | 0 |
| 88 | 2z | 0 | 101 | 2n | 2 | 110 | 2a | 82 |
| 89 | 2r | 0 | 101 | 2v | 0 | 111 | 2xx | 0 |
| 89 | 2l | 1 | 101 | 2w | 2 | 111 | 2c | 79 |
| 89 | 2w | 0 | 101 | 2ww | 2 | | | |
| 89 | 2ww | 6 | 101 | 2z | 1 | | | |
| 89 | 2g | 3 | 102 | 2b | 0 | | | |
| 89 | 2z | 1 | 102 | 2s | 3 | | | |
| 90 | 2a | 0 | 102 | 2w | 1 | | | |
| 90 | 2l | 1 | 103 | 2a | 0 | | | |
| 90 | 2w | 0 | 103 | 2n | 0 | | | |
| 90 | 2z | 1 | 103 | 2z | 6 | | | |
| 91 | 2s | 24 | 104 | 2b | 0 | | | |

FIG. 36
(Continued)

| | | | | | |
|---|---|---|---|---|---|
| 91 | 2ww | 54 | 104 | 2d | 1 |
| 92 | 2n | 3 | 104 | 2j | 1 |
| 92 | 2r | 0 | 104 | 2m | 0 |
| 92 | 2s | 4 | 104 | 2zz | 0 |
| 92 | 2l | 11 | 105 | 2w | 2 |
| 92 | 2w | 3 | 106 | 2b | 0 |
| 93 | 2g | 0 | 106 | 2t | 0 |
| 93 | 2w | 3 | 108 | 2a | 0 |
| 93 | 2ww | 3 | 108 | 2c | 0 |
| 94 | 2b | 0 | 108 | 2d | 0 |
| 94 | 2c | 0 | 108 | 2e | 0 |
| 94 | 2f | 0 | 108 | 2f | 0 |
| 94 | 2g | 0 | 108 | 2h | 0 |
| 94 | 2t | 0 | 108 | 2i | 0 |
| 94 | 2w | 2 | 108 | 2j | 0 |
| 94 | 2ww | 5 | 108 | 2k | 0 |
| 95 | 2b | 49 | 108 | 2m | 0 |
| 95 | 2f | 20 | 108 | 2n | 0 |
| 95 | 2n | 19 | 108 | 2o | 0 |
| 95 | 2s | 0 | 108 | 2q | 0 |
| 95 | 2w | 0 | 108 | 2r | 0 |
| 95 | 2z | 0 | 108 | 2t | 0 |
| 96 | 2s | 2 | 108 | 2u | 0 |
| 96 | 2w | 4 | 108 | 2v | 0 |
| 97 | 2n | 0 | 108 | 2xx | 59 |
| 97 | 2s | 2 | 108 | 2yy | 0 |
| 97 | 2ww | 18 | 108 | 2zz | 0 |

FIG. 36
(Continued)

Reagents 3, 43°C (template # - apparent conversion)

| | | | | | | | | | | | | | | | | | | | | |
|---|---|---|---|---|---|---|---|---|---|---|---|---|---|---|---|---|---|---|---|---|
|1|3a|82|3|3a|0|5|3a|2|7|3a|0|9|3a|0|11|3a|0|13|3a|0|
|1|3b|0|3|3b|0|5|3b|1|7|3b|0|9|3b|0|11|3b|0|13|3b|0|
|1|3c|0|3|3c|81|5|3c|0|7|3c|0|9|3c|0|11|3c|0|13|3c|0|
|1|3d|0|3|3d|0|5|3d|0|7|3d|0|9|3d|0|11|3d|0|13|3d|0|
|1|3e|0|3|3e|0|5|3e|61|7|3e|0|9|3e|0|11|3e|0|13|3e|0|
|1|3f|0|3|3f|0|5|3f|0|7|3f|0|9|3f|0|11|3f|0|13|3f|1|
|1|3g|0|3|3g|0|5|3g|0|7|3g|63|9|3g|0|11|3g|0|13|3g|0|
|1|3h|0|3|3h|0|5|3h|0|7|3h|0|9|3h|0|11|3h|0|13|3h|0|
|1|3i|0|3|3i|0|5|3i|0|7|3i|0|9|3i|48|11|3i|0|13|3i|0|
|1|3j|0|3|3j|0|5|3j|0|7|3j|0|9|3j|0|11|3j|0|13|3j|0|
|1|3k|0|3|3k|0|5|3k|0|7|3k|0|9|3k|0|11|3k|39|13|3k|0|
|1|3l|0|3|3l|0|5|3l|0|7|3l|0|9|3l|0|11|3l|0|13|3l|1|
|1|3m|0|3|3m|0|5|3m|0|7|3m|0|9|3m|0|11|3m|0|13|3m|57|
|1|3n|0|3|3n|0|5|3n|0|7|3n|0|9|3n|0|11|3n|0|13|3n|0|
|1|3o|0|3|3o|0|5|3o|0|7|3o|0|9|3o|0|11|3o|0|13|3o|0|
|1|3p|0|3|3p|0|5|3p|0|7|3p|0|9|3p|0|11|3p|0|13|3p|0|
|1|3q|0|3|3q|0|5|3q|0|7|3q|0|9|3q|0|11|3q|0|13|3q|0|
|1|3r|0|3|3r|0|5|3r|0|7|3r|0|9|3r|0|11|3r|0|13|3r|1|
|1|3s|0|3|3s|0|5|3s|0|7|3s|0|9|3s|1|11|3s|0|13|3s|0|
|1|3t|0|3|3t|0|5|3t|0|7|3t|0|9|3t|0|11|3t|0|13|3t|0|
|1|3u|0|3|3u|0|5|3u|0|7|3u|0|9|3u|0|11|3u|0|13|3u|0|
|1|3v|0|3|3v|0|5|3v|0|7|3v|0|9|3v|0|11|3v|0|13|3v|0|
|1|3w|0|3|3w|0|5|3w|0|7|3w|0|9|3w|0|11|3w|0|13|3w|0|
|1|3x|0|3|3x|0|5|3x|0|7|3x|0|9|3x|0|11|3x|0|13|3x|0|
|1|3y|0|3|3y|0|5|3y|0|7|3y|0|9|3y|0|11|3y|0|13|3y|0|
|1|3z|0|3|3z|0|5|3z|0|7|3z|0|9|3z|0|11|3z|0|13|3z|0|
|1|3ww|0|3|3ww|0|5|3ww|0|7|3ww|0|9|3ww|0|11|3ww|0|13|3ww|0|
|1|3xx|0|3|3xx|0|5|3xx|0|7|3xx|0|9|3xx|0|11|3xx|0|13|3xx|0|
|1|3yy|0|3|3yy|0|5|3yy|0|7|3yy|0|9|3yy|0|11|3yy|0|13|3yy|0|
|1|3zz|0|3|3zz|0|5|3zz|0|7|3zz|0|9|3zz|0|11|3zz|0|13|3zz|0|
|2|3a|0|4|3a|0|6|3a|0|8|3a|0|10|3a|0|12|3a|0|14|3a|0|
|2|3b|6|4|3b|0|6|3b|0|8|3b|0|10|3b|0|12|3b|0|14|3b|0|

FIG. 36
(Continued)

| 2 | 3c | 0 | 4 | 3c | 0 | 6 | 3c | 0 | 8 | 3c | 0 | 10 | 3c | 0 | 12 | 3c | 0 | 14 | 3c | 0 |
|---|---|---|---|---|---|---|---|---|---|---|---|---|---|---|---|---|---|---|---|---|
| 2 | 3d | 0 | 4 | 3d | 51 | 6 | 3d | 0 | 8 | 3d | 0 | 10 | 3d | 0 | 12 | 3d | 0 | 14 | 3d | 0 |
| 2 | 3e | 0 | 4 | 3e | 0 | 6 | 3e | 0 | 8 | 3e | 0 | 10 | 3e | 0 | 12 | 3e | 0 | 14 | 3e | 0 |
| 2 | 3f | 0 | 4 | 3f | 0 | 6 | 3f | 38 | 8 | 3f | 0 | 10 | 3f | 0 | 12 | 3f | 0 | 14 | 3f | 0 |
| 2 | 3g | 0 | 4 | 3g | 0 | 6 | 3g | 0 | 8 | 3g | 0 | 10 | 3g | 0 | 12 | 3g | 0 | 14 | 3g | 0 |
| 2 | 3h | 0 | 4 | 3h | 0 | 6 | 3h | 0 | 8 | 3h | 64 | 10 | 3h | 0 | 12 | 3h | 0 | 14 | 3h | 0 |
| 2 | 3i | 0 | 4 | 3i | 1 | 6 | 3i | 0 | 8 | 3i | 0 | 10 | 3i | 0 | 12 | 3i | 0 | 14 | 3i | 0 |
| 2 | 3j | 0 | 4 | 3j | 0 | 6 | 3j | 0 | 8 | 3j | 0 | 10 | 3j | 34 | 12 | 3j | 0 | 14 | 3j | 0 |
| 2 | 3k | 0 | 4 | 3k | 0 | 6 | 3k | 0 | 8 | 3k | 0 | 10 | 3k | 0 | 12 | 3k | 0 | 14 | 3k | 0 |
| 2 | 3l | 0 | 4 | 3l | 0 | 6 | 3l | 0 | 8 | 3l | 0 | 10 | 3l | 0 | 12 | 3l | 24 | 14 | 3l | 0 |
| 2 | 3m | 0 | 4 | 3m | 0 | 6 | 3m | 0 | 8 | 3m | 0 | 10 | 3m | 0 | 12 | 3m | 0 | 14 | 3m | 0 |
| 2 | 3n | 0 | 4 | 3n | 0 | 6 | 3n | 0 | 8 | 3n | 0 | 10 | 3n | 0 | 12 | 3n | 0 | 14 | 3n | 63 |
| 2 | 3o | 0 | 4 | 3o | 0 | 6 | 3o | 0 | 8 | 3o | 0 | 10 | 3o | 0 | 12 | 3o | 0 | 14 | 3o | 0 |
| 2 | 3p | 1 | 4 | 3p | 0 | 6 | 3p | 0 | 8 | 3p | 0 | 10 | 3p | 0 | 12 | 3p | 0 | 14 | 3p | 0 |
| 2 | 3q | 0 | 4 | 3q | 0 | 6 | 3q | 0 | 8 | 3q | 0 | 10 | 3q | 0 | 12 | 3q | 0 | 14 | 3q | 0 |
| 2 | 3r | 0 | 4 | 3r | 0 | 6 | 3r | 0 | 8 | 3r | 0 | 10 | 3r | 0 | 12 | 3r | 0 | 14 | 3r | 0 |
| 2 | 3s | 0 | 4 | 3s | 0 | 6 | 3s | 0 | 8 | 3s | 0 | 10 | 3s | 0 | 12 | 3s | 0 | 14 | 3s | 0 |
| 2 | 3t | 0 | 4 | 3t | 0 | 6 | 3t | 0 | 8 | 3t | 0 | 10 | 3t | 0 | 12 | 3t | 0 | 14 | 3t | 0 |
| 2 | 3u | 0 | 4 | 3u | 0 | 6 | 3u | 0 | 8 | 3u | 0 | 10 | 3u | 0 | 12 | 3u | 0 | 14 | 3u | 0 |
| 2 | 3v | 0 | 4 | 3v | 0 | 6 | 3v | 0 | 8 | 3v | 0 | 10 | 3v | 0 | 12 | 3v | 0 | 14 | 3v | 0 |
| 2 | 3w | 0 | 4 | 3w | 0 | 6 | 3w | 0 | 8 | 3w | 0 | 10 | 3w | 0 | 12 | 3w | 0 | 14 | 3w | 0 |
| 2 | 3x | 0 | 4 | 3x | 0 | 6 | 3x | 0 | 8 | 3x | 0 | 10 | 3x | 0 | 12 | 3x | 0 | 14 | 3x | 0 |
| 2 | 3y | 0 | 4 | 3y | 0 | 6 | 3y | 0 | 8 | 3y | 0 | 10 | 3y | 0 | 12 | 3y | 0 | 14 | 3y | 0 |
| 2 | 3z | 0 | 4 | 3z | 0 | 6 | 3z | 0 | 8 | 3z | 0 | 10 | 3z | 0 | 12 | 3z | 0 | 14 | 3z | 0 |
| 2 | 3ww | 0 | 4 | 3ww | 0 | 6 | 3ww | 0 | 8 | 3ww | 0 | 10 | 3ww | 0 | 12 | 3ww | 0 | 14 | 3ww | 0 |
| 2 | 3xx | 0 | 4 | 3xx | 0 | 6 | 3xx | 0 | 8 | 3xx | 0 | 10 | 3xx | 0 | 12 | 3xx | 0 | 14 | 3xx | 0 |
| 2 | 3yy | 0 | 4 | 3yy | 0 | 6 | 3yy | 0 | 8 | 3yy | 0 | 10 | 3yy | 0 | 12 | 3yy | 0 | 14 | 3yy | 0 |
| 2 | 3zz | 0 | 4 | 3zz | 0 | 6 | 3zz | 0 | 8 | 3zz | 1 | 10 | 3zz | 0 | 12 | 3zz | 0 | 14 | 3zz | 0 |

FIG. 36
(Continued)

| 15 | 3a | 0 | 17 | 3a | 0 | 19 | 3a | 0 | 21 | 3a | 0 | 23 | 3a | 0 | 25 | 3a | 0 | 27 | 3a | 0 | 29 | 3a | 0 |
|---|---|---|---|---|---|---|---|---|---|---|---|---|---|---|---|---|---|---|---|---|---|---|---|
| 15 | 3b | 0 | 17 | 3b | 0 | 19 | 3b | 0 | 21 | 3b | 0 | 23 | 3b | 0 | 25 | 3b | 0 | 27 | 3b | 0 | 29 | 3b | 0 |
| 15 | 3c | 0 | 17 | 3c | 0 | 19 | 3c | 0 | 21 | 3c | 0 | 23 | 3c | 0 | 25 | 3c | 0 | 27 | 3c | 0 | 29 | 3c | 0 |
| 15 | 3d | 1 | 17 | 3d | 0 | 19 | 3d | 0 | 21 | 3d | 0 | 23 | 3d | 0 | 25 | 3d | 0 | 27 | 3d | 0 | 29 | 3d | 0 |
| 15 | 3e | 0 | 17 | 3e | 0 | 19 | 3e | 0 | 21 | 3e | 0 | 23 | 3e | 0 | 25 | 3e | 0 | 27 | 3e | 0 | 29 | 3e | 0 |
| 15 | 3f | 0 | 17 | 3f | 0 | 19 | 3f | 0 | 21 | 3f | 0 | 23 | 3f | 0 | 25 | 3f | 0 | 27 | 3f | 0 | 29 | 3f | 0 |
| 15 | 3g | 0 | 17 | 3g | 0 | 19 | 3g | 0 | 21 | 3g | 0 | 23 | 3g | 0 | 25 | 3g | 0 | 27 | 3g | 0 | 29 | 3g | 0 |
| 15 | 3h | 0 | 17 | 3h | 0 | 19 | 3h | 0 | 21 | 3h | 0 | 23 | 3h | 0 | 25 | 3h | 0 | 27 | 3h | 0 | 29 | 3h | 0 |
| 15 | 3i | 0 | 17 | 3i | 0 | 19 | 3i | 0 | 21 | 3i | 0 | 23 | 3i | 0 | 25 | 3i | 0 | 27 | 3i | 0 | 29 | 3i | 0 |
| 15 | 3j | 0 | 17 | 3j | 0 | 19 | 3j | 0 | 21 | 3j | 1 | 23 | 3j | 0 | 25 | 3j | 0 | 27 | 3j | 0 | 29 | 3j | 0 |
| 15 | 3k | 0 | 17 | 3k | 0 | 19 | 3k | 0 | 21 | 3k | 0 | 23 | 3k | 0 | 25 | 3k | 0 | 27 | 3k | 0 | 29 | 3k | 0 |
| 15 | 3l | 0 | 17 | 3l | 0 | 19 | 3l | 0 | 21 | 3l | 0 | 23 | 3l | 0 | 25 | 3l | 0 | 27 | 3l | 0 | 29 | 3l | 0 |
| 15 | 3m | 0 | 17 | 3m | 0 | 19 | 3m | 0 | 21 | 3m | 0 | 23 | 3m | 0 | 25 | 3m | 0 | 27 | 3m | 0 | 29 | 3m | 0 |
| 15 | 3n | 0 | 17 | 3n | 0 | 19 | 3n | 0 | 21 | 3n | 0 | 23 | 3n | 0 | 25 | 3n | 0 | 27 | 3n | 0 | 29 | 3n | 0 |
| 15 | 3o | 76 | 17 | 3o | 0 | 19 | 3o | 0 | 21 | 3o | 0 | 23 | 3o | 0 | 25 | 3o | 0 | 27 | 3o | 0 | 29 | 3o | 0 |
| 15 | 3p | 0 | 17 | 3p | 0 | 19 | 3p | 0 | 21 | 3p | 1 | 23 | 3p | 0 | 25 | 3p | 0 | 27 | 3p | 0 | 29 | 3p | 0 |
| 15 | 3q | 0 | 17 | 3q | 58 | 19 | 3q | 0 | 21 | 3q | 0 | 23 | 3q | 0 | 25 | 3q | 0 | 27 | 3q | 0 | 29 | 3q | 0 |
| 15 | 3r | 0 | 17 | 3r | 0 | 19 | 3r | 0 | 21 | 3r | 0 | 23 | 3r | 0 | 25 | 3r | 0 | 27 | 3r | 0 | 29 | 3r | 0 |
| 15 | 3s | 1 | 17 | 3s | 0 | 19 | 3s | 60 | 21 | 3s | 0 | 23 | 3s | 0 | 25 | 3s | 0 | 27 | 3s | 0 | 29 | 3s | 0 |
| 15 | 3t | 0 | 17 | 3t | 0 | 19 | 3t | 0 | 21 | 3t | 0 | 23 | 3t | 0 | 25 | 3t | 0 | 27 | 3t | 0 | 29 | 3t | 0 |
| 15 | 3u | 0 | 17 | 3u | 0 | 19 | 3u | 0 | 21 | 3u | 79 | 23 | 3u | 0 | 25 | 3u | 0 | 27 | 3u | 0 | 29 | 3u | 0 |
| 15 | 3v | 0 | 17 | 3v | 0 | 19 | 3v | 0 | 21 | 3v | 4 | 23 | 3v | 0 | 25 | 3v | 0 | 27 | 3v | 0 | 29 | 3v | 0 |
| 15 | 3w | 0 | 17 | 3w | 0 | 19 | 3w | 0 | 21 | 3w | 0 | 23 | 3w | 91 | 25 | 3w | 0 | 27 | 3w | 0 | 29 | 3w | 0 |
| 15 | 3x | 0 | 17 | 3x | 0 | 19 | 3x | 0 | 21 | 3x | 0 | 23 | 3x | 0 | 25 | 3x | 0 | 27 | 3x | 0 | 29 | 3x | 0 |
| 15 | 3y | 0 | 17 | 3y | 0 | 19 | 3y | 0 | 21 | 3y | 0 | 23 | 3y | 0 | 25 | 3y | 89 | 27 | 3y | 0 | 29 | 3y | 0 |
| 15 | 3z | 0 | 17 | 3z | 0 | 19 | 3z | 0 | 21 | 3z | 0 | 23 | 3z | 0 | 25 | 3z | 0 | 27 | 3z | 0 | 29 | 3z | 0 |
| 15 | 3ww | 0 | 17 | 3ww | 0 | 19 | 3ww | 0 | 21 | 3ww | 0 | 23 | 3ww | 0 | 25 | 3ww | 0 | 27 | 3ww | 30 | 29 | 3ww | 0 |
| 15 | 3xx | 0 | 17 | 3xx | 0 | 19 | 3xx | 0 | 21 | 3xx | 0 | 23 | 3xx | 0 | 25 | 3xx | 0 | 27 | 3xx | 0 | 29 | 3xx | 0 |
| 15 | 3yy | 0 | 17 | 3yy | 0 | 19 | 3yy | 0 | 21 | 3yy | 1 | 23 | 3yy | 0 | 25 | 3yy | 0 | 27 | 3yy | 0 | 29 | 3yy | 32 |
| 15 | 3zz | 0 | 17 | 3zz | 0 | 19 | 3zz | 0 | 21 | 3zz | 0 | 23 | 3zz | 0 | 25 | 3zz | 0 | 27 | 3zz | 0 | 29 | 3zz | 0 |
| 16 | 3a | 0 | 18 | 3a | 0 | 20 | 3a | 0 | 22 | 3a | 0 | 24 | 3a | 0 | 26 | 3a | 0 | 28 | 3a | 0 | 30 | 3a | 0 |
| 16 | 3b | 0 | 18 | 3b | 0 | 20 | 3b | 0 | 22 | 3b | 0 | 24 | 3b | 0 | 26 | 3b | 0 | 28 | 3b | 0 | 30 | 3b | 0 |
| 16 | 3c | 0 | 18 | 3c | 0 | 20 | 3c | 0 | 22 | 3c | 0 | 24 | 3c | 0 | 26 | 3c | 0 | 28 | 3c | 0 | 30 | 3c | 0 |

Reagents 3, 37°C (template # - codon # - apparent conversion)

| | | | | | | | | | | | | | | | | | | | | |
|---|---|---|---|---|---|---|---|---|---|---|---|---|---|---|---|---|---|---|---|---|
| 1 | 3a | 95 | 3 | 3a | 0 | 5 | 3a | 10 | 7 | 3a | 0 | 9 | 3a | 0 | 11 | 3a | 2 | 13 | 3a | 0 |
| 1 | 3b | 1 | 3 | 3b | 0 | 5 | 3b | 4 | 7 | 3b | 1 | 9 | 3b | 0 | 11 | 3b | 0 | 13 | 3b | 0 |
| 1 | 3c | 0 | 3 | 3c | 97 | 5 | 3c | 0 | 7 | 3c | 2 | 9 | 3c | 0 | 11 | 3c | 0 | 13 | 3c | 0 |
| 1 | 3d | 0 | 3 | 3d | 0 | 5 | 3d | 0 | 7 | 3d | 0 | 9 | 3d | 0 | 11 | 3d | 0 | 13 | 3d | 0 |
| 1 | 3e | 0 | 3 | 3e | 0 | 5 | 3e | 95 | 7 | 3e | 16 | 9 | 3e | 0 | 11 | 3e | 0 | 13 | 3e | 1 |
| 1 | 3f | 0 | 3 | 3f | 0 | 5 | 3f | 0 | 7 | 3f | 0 | 9 | 3f | 0 | 11 | 3f | 0 | 13 | 3f | 0 |
| 1 | 3g | 0 | 3 | 3g | 2 | 5 | 3g | 0 | 7 | 3g | 96 | 9 | 3g | 0 | 11 | 3g | 0 | 13 | 3g | 0 |
| 1 | 3h | 0 | 3 | 3h | 2 | 5 | 3h | 0 | 7 | 3h | 0 | 9 | 3h | 0 | 11 | 3h | 0 | 13 | 3h | 1 |
| 1 | 3i | 2 | 3 | 3i | 0 | 5 | 3i | 0 | 7 | 3i | 0 | 9 | 3i | 88 | 11 | 3i | 1 | 13 | 3i | 1 |
| 1 | 3j | 0 | 3 | 3j | 2 | 5 | 3j | 0 | 7 | 3j | 0 | 9 | 3j | 0 | 11 | 3j | 0 | 13 | 3j | 0 |
| 1 | 3k | 0 | 3 | 3k | 2 | 5 | 3k | 0 | 7 | 3k | 0 | 9 | 3k | 0 | 11 | 3k | 95 | 13 | 3k | 0 |
| 1 | 3l | 0 | 3 | 3l | 1 | 5 | 3l | 0 | 7 | 3l | 0 | 9 | 3l | 0 | 11 | 3l | 0 | 13 | 3l | 0 |
| 1 | 3m | 0 | 3 | 3m | 1 | 5 | 3m | 0 | 7 | 3m | 1 | 9 | 3m | 0 | 11 | 3m | 0 | 13 | 3m | 90 |
| 1 | 3n | 0 | 3 | 3n | 0 | 5 | 3n | 0 | 7 | 3n | 0 | 9 | 3n | 0 | 11 | 3n | 0 | 13 | 3n | 0 |
| 1 | 3o | 0 | 3 | 3o | 0 | 5 | 3o | 0 | 7 | 3o | 2 | 9 | 3o | 0 | 11 | 3o | 0 | 13 | 3o | 0 |
| 1 | 3p | 8 | 3 | 3p | 13 | 5 | 3p | 13 | 7 | 3p | 11 | 9 | 3p | 0 | 11 | 3p | 0 | 13 | 3p | 0 |
| 1 | 3q | 0 | 3 | 3q | 2 | 5 | 3q | 0 | 7 | 3q | 1 | 9 | 3q | 0 | 11 | 3q | 0 | 13 | 3q | 0 |
| 1 | 3r | 0 | 3 | 3r | 5 | 5 | 3r | 1 | 7 | 3r | 2 | 9 | 3r | 0 | 11 | 3r | 24 | 13 | 3r | 0 |
| 1 | 3s | 4 | 3 | 3s | 2 | 5 | 3s | 1 | 7 | 3s | 1 | 9 | 3s | 35 | 11 | 3s | 5 | 13 | 3s | 3 |
| 1 | 3t | 0 | 3 | 3t | 0 | 5 | 3t | 0 | 7 | 3t | 0 | 9 | 3t | 0 | 11 | 3t | 0 | 13 | 3t | 0 |
| 1 | 3u | 0 | 3 | 3u | 1 | 5 | 3u | 1 | 7 | 3u | 0 | 9 | 3u | 0 | 11 | 3u | 0 | 13 | 3u | 0 |
| 1 | 3v | 0 | 3 | 3v | 0 | 5 | 3v | 1 | 7 | 3v | 1 | 9 | 3v | 2 | 11 | 3v | 0 | 13 | 3v | 0 |
| 1 | 3w | 0 | 3 | 3w | 0 | 5 | 3w | 0 | 7 | 3w | 0 | 9 | 3w | 0 | 11 | 3w | 0 | 13 | 3w | 0 |
| 1 | 3x | 0 | 3 | 3x | 0 | 5 | 3x | 0 | 7 | 3x | 0 | 9 | 3x | 0 | 11 | 3x | 0 | 13 | 3x | 0 |
| 1 | 3y | 0 | 3 | 3y | 0 | 5 | 3y | 0 | 7 | 3y | 0 | 9 | 3y | 0 | 11 | 3y | 0 | 13 | 3y | 0 |
| 1 | 3z | 0 | 3 | 3z | 0 | 5 | 3z | 0 | 7 | 3z | 0 | 9 | 3z | 0 | 11 | 3z | 0 | 13 | 3z | 0 |
| 1 | 3ww | 0 | 3 | 3ww | 0 | 5 | 3ww | 0 | 7 | 3ww | 0 | 9 | 3ww | 0 | 11 | 3ww | 0 | 13 | 3ww | 0 |
| 1 | 3xx | 0 | 3 | 3xx | 0 | 5 | 3xx | 0 | 7 | 3xx | 0 | 9 | 3xx | 0 | 11 | 3xx | 0 | 13 | 3xx | 0 |
| 1 | 3yy | 0 | 3 | 3yy | 0 | 5 | 3yy | 0 | 7 | 3yy | 0 | 9 | 3yy | 0 | 11 | 3yy | 0 | 13 | 3yy | 0 |
| 1 | 3zz | 0 | 3 | 3zz | 0 | 5 | 3zz | 0 | 7 | 3zz | 0 | 9 | 3zz | 0 | 11 | 3zz | 0 | 13 | 3zz | 0 |

| 14 | 3zz | 0 | 16 | 3zz | 0 | 18 | 3zz | 0 | 20 | 3zz | 0 | 22 | 3zz | 5 | 23 | 3zz | 0 | 25 | 3zz | 1 |
|---|---|---|---|---|---|---|---|---|---|---|---|---|---|---|---|---|---|---|---|---|
| 15 | 3a | 3 | 17 | 3a | 0 | 19 | 3a | 0 | 21 | 3a | 2 | 23 | 3a | 1 | 24 | 3a | 0 | 26 | 3a | 0 |
| 15 | 3b | 6 | 17 | 3b | 0 | 19 | 3b | 0 | 21 | 3b | 0 | 23 | 3b | 18 | 24 | 3b | 0 | 26 | 3b | 0 |
| 15 | 3c | 1 | 17 | 3c | 0 | 19 | 3c | 0 | 21 | 3c | 0 | 23 | 3c | 11 | 24 | 3c | 8 | 26 | 3c | 0 |
| 15 | 3d | 35 | 17 | 3d | 0 | 19 | 3d | 0 | 21 | 3d | 0 | 23 | 3d | 5 | 24 | 3d | 0 | 26 | 3d | 0 |
| 15 | 3e | 4 | 17 | 3e | 0 | 19 | 3e | 0 | 21 | 3e | 0 | 23 | 3e | 10 | 24 | 3e | 0 | 26 | 3e | 1 |
| 15 | 3f | 2 | 17 | 3f | 0 | 19 | 3f | 0 | 21 | 3f | 5 | 23 | 3f | 0 | 24 | 3f | 0 | 26 | 3f | 0 |
| 15 | 3g | 3 | 17 | 3g | 0 | 19 | 3g | 0 | 21 | 3g | 0 | 23 | 3g | 40 | 24 | 3g | 0 | 26 | 3g | 0 |
| 15 | 3h | 3 | 17 | 3h | 0 | 19 | 3h | 0 | 21 | 3h | 3 | 23 | 3h | 0 | 24 | 3h | 0 | 26 | 3h | 1 |
| 15 | 3i | 16 | 17 | 3i | 18 | 19 | 3i | 8 | 21 | 3i | 7 | 23 | 3i | 43 | 24 | 3i | 0 | 26 | 3i | 1 |
| 15 | 3j | 1 | 17 | 3j | 0 | 19 | 3j | 0 | 21 | 3j | 4 | 23 | 3j | 1 | 24 | 3j | 0 | 26 | 3j | 8 |
| 15 | 3k | 3 | 17 | 3k | 0 | 19 | 3k | 0 | 21 | 3k | 0 | 23 | 3k | 7 | 24 | 3k | 0 | 26 | 3k | 0 |
| 15 | 3l | 4 | 17 | 3l | 2 | 19 | 3l | 0 | 21 | 3l | 2 | 23 | 3l | 0 | 24 | 3l | 0 | 26 | 3l | 0 |
| 15 | 3m | 3 | 17 | 3m | 2 | 19 | 3m | 0 | 21 | 3m | 0 | 23 | 3m | 1 | 24 | 3m | 0 | 26 | 3m | 0 |
| 15 | 3n | 1 | 17 | 3n | 0 | 19 | 3n | 0 | 21 | 3n | 0 | 23 | 3n | 0 | 24 | 3n | 0 | 26 | 3n | 0 |
| 15 | 3o | 97 | 17 | 3o | 0 | 19 | 3o | 1 | 21 | 3o | 0 | 23 | 3o | 4 | 24 | 3o | 0 | 26 | 3o | 0 |
| 15 | 3p | 2 | 17 | 3p | 1 | 19 | 3p | 1 | 21 | 3p | 16 | 23 | 3p | 0 | 24 | 3p | 0 | 26 | 3p | 0 |
| 15 | 3q | 4 | 17 | 3q | 99 | 19 | 3q | 0 | 21 | 3q | 0 | 23 | 3q | 0 | 24 | 3q | 0 | 26 | 3q | 0 |
| 15 | 3r | 1 | 17 | 3r | 1 | 19 | 3r | 0 | 21 | 3r | 0 | 23 | 3r | 18 | 24 | 3r | 0 | 26 | 3r | 0 |
| 15 | 3s | 12 | 17 | 3s | 39 | 19 | 3s | 94 | 21 | 3s | 21 | 23 | 3s | 63 | 24 | 3s | 0 | 26 | 3s | 10 |
| 15 | 3t | 2 | 17 | 3t | 0 | 19 | 3t | 0 | 21 | 3t | 2 | 23 | 3t | 7 | 24 | 3t | 0 | 26 | 3t | 0 |
| 15 | 3u | 2 | 17 | 3u | 2 | 19 | 3u | 0 | 21 | 3u | 99 | 23 | 3u | 3 | 24 | 3u | 0 | 26 | 3u | 0 |
| 15 | 3v | 4 | 17 | 3v | 0 | 19 | 3v | 0 | 21 | 3v | 2 | 23 | 3v | 0 | 24 | 3v | 0 | 26 | 3v | 0 |
| 15 | 3w | 3 | 17 | 3w | 0 | 19 | 3w | 0 | 21 | 3w | 1 | 23 | 3w | 99 | 24 | 3w | 1 | 26 | 3w | 0 |
| 15 | 3x | 1 | 17 | 3x | 0 | 19 | 3x | 0 | 21 | 3x | 0 | 23 | 3x | 0 | 24 | 3x | 89 | 26 | 3x | 0 |
| 15 | 3y | 2 | 17 | 3y | 0 | 19 | 3y | 0 | 21 | 3y | 1 | 23 | 3y | 0 | 24 | 3y | 3 | 26 | 3y | 1 |
| 15 | 3z | 1 | 17 | 3z | 0 | 19 | 3z | 0 | 21 | 3z | 3 | 23 | 3z | 0 | 24 | 3z | 0 | 26 | 3z | 93 |
| 15 | 3ww | 0 | 17 | 3ww | 0 | 19 | 3ww | 0 | 21 | 3ww | 0 | 23 | 3ww | 0 | 24 | 3ww | 0 | 26 | 3ww | 0 |
| 15 | 3xx | 0 | 17 | 3xx | 0 | 19 | 3xx | 0 | 21 | 3xx | 0 | 23 | 3xx | 0 | 24 | 3xx | 0 | 26 | 3xx | 1 |
| 15 | 3yy | 1 | 17 | 3yy | 0 | 19 | 3yy | 0 | 21 | 3yy | 0 | 23 | 3yy | 0 | 24 | 3yy | 0 | 26 | 3yy | 0 |
| 15 | 3zz | 0 | 17 | 3zz | 0 | 19 | 3zz | 0 | 21 | 3zz | 7 | 23 | 3zz | 0 | 24 | 3zz | 0 | 26 | 3zz | 0 |

FIG. 36
(Continued)

| 16 | 3a | 1 | 18 | 3a | 1 | 20 | 3a | 0 | 22 | 3a | 9 | 23 | 3a | 1 | 25 | 3a | 0 | 27 | 3a | 0 |
|---|---|---|---|---|---|---|---|---|---|---|---|---|---|---|---|---|---|---|---|---|
| 16 | 3b | 0 | 18 | 3b | 0 | 20 | 3b | 0 | 22 | 3b | 0 | 23 | 3b | 16 | 25 | 3b | 0 | 27 | 3b | 0 |
| 16 | 3c | 0 | 18 | 3c | 0 | 20 | 3c | 0 | 22 | 3c | 0 | 23 | 3c | 1 | 25 | 3c | 0 | 27 | 3c | 0 |
| 16 | 3d | 0 | 18 | 3d | 0 | 20 | 3d | 0 | 22 | 3d | 0 | 23 | 3d | 55 | 25 | 3d | 0 | 27 | 3d | 0 |
| 16 | 3e | 2 | 18 | 3e | 2 | 20 | 3e | 0 | 22 | 3e | 19 | 23 | 3e | 10 | 25 | 3e | 0 | 27 | 3e | 0 |
| 16 | 3f | 0 | 18 | 3f | 0 | 20 | 3f | 0 | 22 | 3f | 0 | 23 | 3f | 0 | 25 | 3f | 0 | 27 | 3f | 0 |
| 16 | 3g | 0 | 18 | 3g | 0 | 20 | 3g | 0 | 22 | 3g | 0 | 23 | 3g | 40 | 25 | 3g | 0 | 27 | 3g | 0 |
| 16 | 3h | 0 | 18 | 3h | 2 | 20 | 3h | 0 | 22 | 3h | 2 | 23 | 3h | 0 | 25 | 3h | 0 | 27 | 3h | 0 |
| 16 | 3i | 0 | 18 | 3i | 2 | 20 | 3i | 0 | 22 | 3i | 99 | 23 | 3i | 43 | 25 | 3i | 0 | 27 | 3i | 0 |
| 16 | 3j | 0 | 18 | 3j | 13 | 20 | 3j | 0 | 22 | 3j | 18 | 23 | 3j | 1 | 25 | 3j | 0 | 27 | 3j | 1 |
| 16 | 3k | 0 | 18 | 3k | 1 | 20 | 3k | 0 | 22 | 3k | 2 | 23 | 3k | 7 | 25 | 3k | 0 | 27 | 3k | 0 |
| 16 | 3l | 0 | 18 | 3l | 0 | 20 | 3l | 0 | 22 | 3l | 3 | 23 | 3l | 0 | 25 | 3l | 0 | 27 | 3l | 0 |
| 16 | 3m | 0 | 18 | 3m | 1 | 20 | 3m | 0 | 22 | 3m | 3 | 23 | 3m | 1 | 25 | 3m | 0 | 27 | 3m | 0 |
| 16 | 3n | 0 | 18 | 3n | 0 | 20 | 3n | 0 | 22 | 3n | 2 | 23 | 3n | 0 | 25 | 3n | 0 | 27 | 3n | 0 |
| 16 | 3o | 0 | 18 | 3o | 0 | 20 | 3o | 0 | 22 | 3o | 2 | 23 | 3o | 4 | 25 | 3o | 0 | 27 | 3o | 0 |
| 16 | 3p | 78 | 18 | 3p | 0 | 20 | 3p | 0 | 22 | 3p | 41 | 23 | 3p | 0 | 25 | 3p | 0 | 27 | 3p | 9 |
| 16 | 3q | 0 | 18 | 3q | 1 | 20 | 3q | 0 | 22 | 3q | 0 | 23 | 3q | 0 | 25 | 3q | 0 | 27 | 3q | 0 |
| 16 | 3r | 0 | 18 | 3r | 99 | 20 | 3r | 0 | 22 | 3r | 0 | 23 | 3r | 18 | 25 | 3r | 0 | 27 | 3r | 0 |
| 16 | 3s | 19 | 18 | 3s | 6 | 20 | 3s | 0 | 22 | 3s | 67 | 23 | 3s | 63 | 25 | 3s | 0 | 27 | 3s | 0 |
| 16 | 3t | 0 | 18 | 3t | 0 | 20 | 3t | 90 | 22 | 3t | 2 | 23 | 3t | 7 | 25 | 3t | 0 | 27 | 3t | 0 |
| 16 | 3u | 0 | 18 | 3u | 1 | 20 | 3u | 0 | 22 | 3u | 36 | 23 | 3u | 3 | 25 | 3u | 0 | 27 | 3u | 0 |
| 16 | 3v | 0 | 18 | 3v | 0 | 20 | 3v | 0 | 22 | 3v | 99 | 23 | 3v | 0 | 25 | 3v | 0 | 27 | 3v | 0 |
| 16 | 3w | 0 | 18 | 3w | 3 | 20 | 3w | 0 | 22 | 3w | 1 | 23 | 3w | 99 | 25 | 3w | 0 | 27 | 3w | 0 |
| 16 | 3x | 0 | 18 | 3x | 0 | 20 | 3x | 0 | 22 | 3x | 0 | 23 | 3x | 0 | 25 | 3x | 0 | 27 | 3x | 0 |
| 16 | 3y | 10 | 18 | 3y | 0 | 20 | 3y | 0 | 22 | 3y | 10 | 23 | 3y | 0 | 25 | 3y | 97 | 27 | 3y | 1 |
| 16 | 3z | 0 | 18 | 3z | 0 | 20 | 3z | 0 | 22 | 3z | 1 | 23 | 3z | 0 | 25 | 3z | 11 | 27 | 3z | 0 |
| 16 | 3ww | 0 | 18 | 3ww | 0 | 20 | 3ww | 0 | 22 | 3ww | 0 | 23 | 3ww | 0 | 25 | 3ww | 1 | 27 | 3ww | 89 |
| 16 | 3xx | 0 | 18 | 3xx | 39 | 20 | 3xx | 0 | 22 | 3xx | 0 | 23 | 3xx | 0 | 25 | 3xx | 2 | 27 | 3xx | 0 |
| 16 | 3YY | 0 | 18 | 3YY | 0 | 20 | 3YY | 0 | 22 | 3YY | 0 | 23 | 3YY | 0 | 25 | 3YY | 2 | 27 | 3YY | 0 |

DNA-TEMPLATED MACROCYCLE LIBRARY

RELATED APPLICATIONS

This application is a national stage filing under 35 U.S.C. § 371 of international PCT application, PCT/US2019/017318, filed Feb. 8, 2019, which claims priority under 35 U.S.C. § 119(e) to U.S. Provisional Application, U.S. Ser. No. 62/628,715, filed Feb. 9, 2018, each of which is incorporated herein by reference.

GOVERNMENT SUPPORT

This invention was made with government support under grant number R35 GM118062 awarded by the National Institutes of Health and grant number HR0011-17-2-0049 awarded by the Defense Advanced Research Projects Agency. The government has certain rights in the invention.

BACKGROUND OF THE INVENTION

The discovery of new bioactive small-molecule ligands remains a central endeavor of the life-sciences research community. Common small-molecule discovery approaches rely on screening large collections (libraries) of chemical compounds.[1] In a typical screening campaign, library members are individually assayed in separate locations for a desired biological activity, and therefore the time, effort, and expense associated with screening is proportional to the library size. While chemical library screening has yielded many important successes,[2] the development, maintenance, and high-throughput screening of large chemical libraries require infrastructure, resources, and logistics that are unavailable to most research groups.[3] Moreover, the discrete nature of screening assays can require prohibitively large quantities of unstable biological materials that need to be scaled up to match the size of the screened library. In contrast, selection methods evaluate an entire library in a single experiment, typically requiring an amount of biological material less than that of a single plate of a microtiter assay. Moreover, selections do not require infrastructure to separate, assay, or manipulate individual library members, and consume resources in a manner that is largely independent of library size.

DNA-encoded chemical libraries (DELs), mixtures of synthetic molecules that are each encoded by a covalently attached DNA tag, were developed to bring the advantages of selections and DNA sequencing to bear on biomedical targets that are best suited to synthetic small-molecule ligands. DNA encoding of chemical libraries was first proposed as a theoretical solid-phase peptide synthesis encoding strategy in 1992.[4] The use of DNA encoding for general solution-phase small-molecule libraries suitable for in vitro selection was conceived and developed over the next decade.[5,6] Since then, the field of selectable DNA-encoded libraries has greatly expanded to include a wide variety of small-molecule and synthetic polymer structures, as well as a number of different strategies to ensure the correspondence between a library member's structure and the attached DNA barcode sequence, including DNA-templated synthesis, DNA routing, DNA tagging (ligation of DNA barcodes after each synthesis step), and variants and combinations of these concepts[7-16]. Selections using DELs are typically conducted by incubating an immobilized or epitope-tagged target with the library, washing unbound library members away from library members with target affinity, and isolating the latter by eluting or denaturing the target, or by adding an excess of a known ligand or free target[15-17]. The DNA sequences encoding enriched library members are typically amplified by PCR and analyzed by high-throughput DNA sequencing to identify the inferred structures of the active library members. DELs therefore enable rapid and inexpensive simultaneous testing of an entire library in one solution for binding to a target of interest and require only small amounts of biological material (~5-50 µg of a typical target protein per selection).

Despite these advantages, the vast majority of DNA-encoded libraries remain confined to pharmaceutical companies, and much of the research progress surrounding their development and use in industry remains undisclosed[8]. A number of original strategies to synthesize DNA-encoded libraries have been reported[18-22]. In some cases, these approaches enable the construction of libraries with vast theoretical sizes exceeding millions or even billions of compounds, with the trade-off that as library size increases, the fraction of the library components that can be confirmed to undergo anticipated reaction pathways decreases. Importantly, the quality of a DNA-encoded library is determined by the proportion of correctly synthesized molecules that are correctly encoded by their DNA tags, and model studies demonstrated that library quality directly affects the reliability of selections results[23,24]. In most cases, purification of products after each chemical coupling step is not viable, which results in truncated byproducts linked to DNA tags that contaminate or even dominate the finished library[9]. This limitation can become especially problematic when challenging chemical transformations such as macrocyclizations or coupling reactions using inefficient building blocks are part of the library design. As a result, the use of conventional approaches to generate high-quality DNA-encoded libraries of macrocycles can be a particular challenge, unless the bulk of the scaffold is pre-formed and combinatorial variation is limited to the introduction of substituents, a strategy that substantially limits library structural diversity.

The development of approaches that yield highly diverse libraries of DNA-encoded macrocycles[25] represents a challenging goal that can potentially provide access to underexplored chemical space. The potential of such libraries is further highlighted by the favorable biomedical properties of macrocyclic molecules[26-30]. Macrocycles are generally known to display better stability in vivo than their linear counterparts[27,30], and to offer a balance between flexibility and pre-organization that allows macrocycles to interact across extended protein binding sites with entropic penalties that are lower than corresponding linear molecules. The latter feature renders them promising in targeting surfaces or protein-protein interactions, which can be difficult to target with conventional small-molecules libraries[31,32]. Indeed, approximately 70 macrocyclic drugs have already been approved for human use and more than 35 macrocycles are in various stages of clinical development[33].

DNA-templated synthesis (DTS) was developed as a strategy to bring the substantial strengths of reactivity programming, in vitro selection, PCR amplification, and DNA sequence analysis to the synthesis and evaluation of synthetic molecules[5,34,35]. DNA-templated synthesis is based on the principle that highly diluted DNA-tagged reactants experience a greatly increased effective molarity upon DNA hybridization[36]. This phenomenon allows many independently DNA-programmed reactions to take place simultaneously in the same solution in a highly selective fashion[37], so that products are formed only between reactants linked to complimentary DNA sequences. Our group has applied this concept to create libraries of DNA-templated small molecules[6], in which the DNA tags not only function as barcodes, but also as templates that orchestrate the synthesis of each library member.

The first discovery-oriented DNA-templated small-molecule library contained up to 13,824 macrocyclic molecules (FIG. 1)[38]. This DNA-templated macrocycle library was notable for the use of DNA hybridization to assist macrocyclization, the development of a final DNA-templated reaction step that simultaneously results in a one-pot purification of the library, thereby eliminating truncated and uncyclized byproducts, and compatibility with macrocycles of variable sizes and structures. Despite its modest size compared with subsequent industrial DNA-encoded libraries[9,11,39], this initial library was of sufficient quality and diversity to serve as a source of potent and selective inhibitors of proteins including kinases and insulin-degrading enzyme (IDE) protease, ultimately leading to biological discoveries and the validation in vivo of new targets for therapeutic intervention.[40-43]

Even though IDE and its involvement in insulin catabolism is known, the development of small-molecule inhibitors of IDE has been difficult. As a result, there is need for the development of clinically useful enzyme inhibitors (e.g., protease (e.g., IDE) and/or kinase inhibitors), and DNA-plated library technology to identify such protease and/or kinase inhibitors.

SUMMARY OF THE INVENTION

In the present disclosure, virtually every aspect of DNA-templated library technology was substantially improved and streamlined, and the resulting advances were featured to generate a larger, more diverse, and more drug-like 256,000-membered DNA-templated macrocycle library. As a test of the ability of this second-generation DNA-templated library to enable the discovery of bioactive macrocycles, in vitro selection of the library yielded potent and structurally unique macrocyclic inhibitors of insulin-degrading enzyme (IDE). These methodological advances collectively represent the state-of-the-art in DNA-templated library synthesis and provide improved access to a rich set of diverse, drug-like molecules. The present invention provides nucleic acid templates (e.g., including orthogonal codon sets) for DNA-templated methods of synthesizing, selecting, and amplifying compounds (e.g., polymers and/or small molecules) described herein. The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. In certain embodiments, compounds of Formula (I) are part of a DNA-templated compound library. In certain embodiments, compounds of Formula (I) are enzyme inhibitors (e.g., macrocyclic enzyme inhibitors). In certain embodiments, compounds of Formula (I) are IDE inhibitors (e.g., macrocyclic IDE inhibitors). In certain embodiments, compounds of Formula (I) are kinase inhibitors (e.g., macrocyclic kinase inhibitors).

In one aspect, the present invention provides compounds of Formula (I):

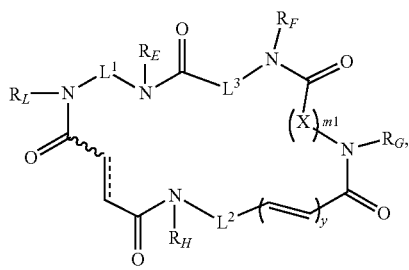

and pharmaceutically acceptable salts, solvates, hydrates, polymorphs, co-crystals, tautomers, stereoisomers, isotopically labeled derivatives, and prodrugs thereof, wherein $L^1$, $L^2$, $L^3$, X, $R_E$, $R_F$, $R_G$, $R_H$, $R_L$, m1, and y are as defined herein.

The compounds (e.g., macrocyclic IDE inhibitors) provided herein are useful for treating various diseases as well as for basic research applications. The compounds (e.g., macrocyclic IDE inhibitors) as provided herein are useful for inhibiting IDE activity in vitro or in vivo, for example, in order to increase the stability of insulin in a cell culture or in a subject, e.g., to increase the half-life of insulin in a cell culture or subject. Inhibitors of IDE as provided herein can be used to increase insulin signaling in a subject. For example, IDE inhibitors as provided herein are useful for inhibiting IDE activity in a subject having impaired insulin signaling or exhibiting insulin resistance, for example, a subject having diabetes. IDE inhibitors provided herein are also useful for inhibiting IDE activity in a subject having an aberrant (e.g., lower than normal) level of an IDE substrate other than or in addition to insulin, e.g., of glucagon, amylin, calcitonin-gene related peptide (CGRP), amyloid beta-peptide, TGF-alpha, β-endorphin, somatostatin, or atrial natriuric peptide. According to some aspects of this invention, the IDE inhibitory compounds and methods of their use are for inhibiting IDE-mediated insulin catabolism in a subject, for example, in order to ameliorate one or more symptoms of diabetes in a subject. According to some aspects of this invention, the IDE inhibitory compounds and methods of their use are for inhibiting IDE-mediated insulin, glucagon, amylin, calcitonin-gene related peptide (CGRP), amyloid beta-peptide, TGF-alpha, β-endorphin, somatostatin, and/or atrial natriuric peptide catabolism in a subject, for example, in order to ameliorate one or more symptoms of a disease or disorder associated with an underabundance of one or more of these IDE substrates.

This disclosure provides in vivo and in vitro methods of inhibiting IDE using the inhibitors described herein. For example, some aspects of the invention provide therapeutic methods using IDE inhibitors in the clinic, e.g., in the context of inhibiting IDE activity in patients having impaired insulin signaling or diabetes. In some embodiments, therapeutic methods using IDE inhibitors in patients having a disease or disorder caused by or associated with an aberrant half-life of a substrate of IDE, or treatable by modulation of the half-life of a substrate of IDE are provided. For example, in some embodiments, the present invention provides therapeutic methods of using IDE inhibitors in patients having an elevated blood pressure or hypertension related to an aberrant level of calcitonin-gene related peptide (CGRP), a potent vasodilator and IDE substrate (see PNAS 2012, 109(22), 8523-7, the entire contents of which are incorporated herein by reference). Accordingly, the IDE inhibitors provided herein are useful for treating cardiovascular disease and metabolic disease (e.g., by modulating blood pressure and/or treating hypertension.

Provided herein are methods and compositions for the DNA template-directed synthesis, amplification, selection, and evolution of molecules, based on templates (e.g., codons from orthogonal codon sets depicted in Tables 5 and/or 7) described herein. In general, these methods use an evolvable nucleic acid template to direct the synthesis of a chemical compound or library of chemical compounds (e.g., the template actually encodes the synthesis of a chemical compound). Based on a library encoded and synthesized using a template such as a nucleic acid, methods are provided for amplifying, evolving, and screening the library. In certain embodiments, the chemical compounds are compounds that are not, or do not resemble, nucleic acids or analogs thereof. In certain embodiments, the chemical compounds are small molecules. In certain embodiments, the chemical compounds of these template-encoded combinatorial libraries are polymers and more preferably are unnatural polymers (e.g., excluding natural peptides, proteins, and polynucleotides).

In certain embodiments, the method of synthesizing a compound or library of compounds comprises first providing one or more nucleic acid templates described herein (e.g., codons from orthogonal codon sets depicted in Tables 5 and/or 7), which one or more nucleic acid templates optionally have a reactive unit associated therewith. The nucleic acid template is then contacted with one or more transfer units designed to have a first moiety, an anti-codon (e.g., anti-codons depicted in Table 6), which hybridizes to a sequence of the nucleic acid, and is associated with a second moiety, a reactive unit, which includes a building block of the compound to be synthesized. Once these transfer units have hybridized to the nucleic acid template in a sequence-specific manner, the synthesis of the chemical compound can take place due to the interaction of reactive moieties present on the transfer units and/or the nucleic acid template. The sequence of the nucleic acid can later be determined to decode the synthetic history of the attached compound and thereby its structure. The method described herein may be used to synthesize one molecule at a time or may be used to synthesize hundreds to thousands to millions of compounds using combinatorial methods.

This disclosure provides templates for DNA-templated synthesis of compounds comprising: multiple-residue primer-binding sites; at least one building block codon that determines the identity of a compound building block; and at least a one building block codon that identifies a scaffold at the 5' end of the template. Provided herein are templates for DNA-templated synthesis of compounds comprising: multiple-residue primer-binding sites; at least one building block codon that determines the identity of a compound building block; and at least a one building block codon that identifies a scaffold at the 5' end of the template, wherein the template comprises codons from the orthogonal codon sets depicted in FIG. 5 or 7. In certain embodiments, the templates are for DNA-templated synthesis of small molecules. In certain embodiments, the templates are for DNA-templated synthesis of macrocyclic compounds described herein. In certain embodiments, the templates are for DNA-templated synthesis of polymers.

In certain embodiments, the template comprises codons from the orthogonal codon sets depicted in FIG. 5 or 7. In certain embodiments, the template comprises codons from the orthogonal codon sets depicted in FIG. 5 or 7, and/or anticodons depicted in Table 6. In certain embodiments, the template comprises a combination of orthogonal codons (e.g., codons from the orthogonal codon sets depicted in Tables 5 and/or 7) interspaced by constant regions comprising: multiple-residue primer-binding sites; at least three building block codons that determine the identity of three compound building blocks; and at least a fourth building block codon that identifies a scaffold (e.g., a bis-amino acid scaffold) at the 5' end of the template. In orthogonal codons, a DNA-templated synthesis reagent's anticodon efficiently anneals only with the corresponding complimentary codon of the template. In certain embodiments, the building block codons determine the identity of small molecule building blocks. In certain embodiments, the building block codons determine the identity of macrocycle building blocks. In certain embodiments, the building block codons determine the identity of polymer building blocks (e.g., monomers).

In certain embodiments, the template is an orthogonal codon set comprising: a codon selected from the group consisting of 4A-4ZZ depicted in Table 5; a codon selected from the group consisting of 1A-1T depicted in Table 5; a codon selected from the group consisting of 2A-2T depicted in Table 5; and a codon selected from the group consisting of 3A-3T depicted in Table 5. In certain embodiments, the template is an orthogonal codon set comprising: a codon selected from the group consisting of $4A_2$ through $4P_4$ depicted in Table 7. In certain embodiments, the template is an orthogonal codon set comprising: at least one codon selected from the group consisting of 1A-1T, 2A-2T, 3A-3T, 4A-4ZZ, and $4A_2$ through $4P_4$ depicted in Table 5 or 7. In certain embodiments, each of the first building block codon, second building block codon, third building block codon, or fourth building block codon, is a codon selected from the group consisting of 1A-1T, 2A-1T, 3A-1T, 4A through 4ZZ, and $4A_2$ through $4P_4$ depicted in Tables 5 or 7.

In certain embodiments, provided herein are nucleic acid templates for DNA-templated synthesis of compounds (e.g., codons from orthogonal codon sets depicted in Tables 5 and/or 7), comprising orthogonal codons interspaced by constant regions comprising: multiple-residue primer-binding sites; at least three building block codons that determine the identity of three compound building blocks; and at least a fourth building block codon that identifies a bis-amino acid scaffold at the 5' end of the template.

In certain embodiments, provided herein are methods of DNA-templated synthesis of compounds, templates for DNA-templated synthesis of compounds, anti-codons attached to functional groups and/or chemical moieties, and/or final compound products attached to templates as described herein using the orthogonal codon set described herein (e.g., codons from codon sets described in Tables 5 and 7).

Some aspects of this invention provide pharmaceutical compositions comprising a macrocyclic IDE inhibitor described herein, or a pharmaceutically acceptable salt, solvate, hydrate, stereoisomer, polymorph, tautomer, isotopically enriched form, or prodrug thereof, in an amount effective to inhibit IDE in a subject. In some embodiments, the composition further comprises a pharmaceutically acceptable carrier.

Some embodiments provide an in vitro method of inhibiting the activity of an insulin degrading enzyme (IDE) comprising contacting an IDE with a macrocyclic IDE inhibitor described herein, or a pharmaceutically acceptable salt, solvate, hydrate, stereoisomer, polymorph, tautomer, isotopically enriched form, or prodrug thereof. Some embodiments provide an in vivo method of inhibiting the activity of an insulin degrading enzyme (IDE) comprising contacting an IDE with a macrocyclic IDE inhibitor described herein, or a pharmaceutically acceptable salt, solvate, hydrate, stereoisomer, polymorph, tautomer, isotopically enriched form, or prodrug thereof. In some embodiments, the contacting results in the inhibition of the IDE activity to less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the activity in the absence of the macrocyclic IDE inhibitor or the composition. The in vivo methods of inhibiting the activity of IDE typically include contacting the IDE with the macrocyclic IDE inhibitor, the pharmaceutically acceptable salt, solvate, hydrate, stereoisomer, polymorph, tautomer, isotopically enriched form, or prodrug thereof, or the composition in a subject. In some embodiments, the subject exhibits impaired insulin signaling or insulin resistance. In some embodiments, the subject has diabetes. In some embodiments, the subject has a disease or disorder that is caused by or associated with an aberrant half-life of a substrate of IDE (e.g., insulin, glucagon, amylin, calcitonin-gene related peptide (CGRP), amyloid beta-peptide, TGF-alpha, β-endorphin, somatostatin, and/or atrial natriuric peptide), or that is treatable by modulation of the half-life of a substrate of IDE. In some embodiments, the contacting comprises administering the compound or the composition to the subject. In some embodiments, the macrocyclic IDE inhibitor or composition is administered in an amount effective to reduce an IDE activity in the subject to less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the IDE activity in the absence of the compound, the salt thereof, or the composition. In some embodiments, the IDE activity is plasma IDE activity and/or pancreas IDE activity. In some embodiments, the IDE activity is liver IDE activity and/or kidney IDE activity. In some embodiments, the IDE activity is IDE activity in a tissue where IDE is expressed. In some embodiments, the IDE activity is IDE activity in a tissue where catabolism of an IDE substrate takes place. In some embodiments, the IDE activity is IDE activity in a tissue that is reactive to an IDE substrate, e.g., an insulin-reactive tissue, a glucagon-reactive tissue, and so on. In some embodiments, the subject is a mammal. In some embodiments, the subject is a human.

Some aspects of this invention provide a method of treating a disease (e.g., a disease associated with aberrant enzyme activity (e.g., aberrant protease and/or kinase activity) (e.g., aberrant IDE activity)), impaired insulin signaling, or insulin resistance. In some embodiments, the method comprises administering a therapeutically effective amount of a macrocyclic IDE inhibitor described herein, or a pharmaceutically acceptable salt, solvate, hydrate, stereoisomer, polymorph, tautomer, isotopically enriched form, or prodrug thereof, or a pharmaceutical composition comprising the IDE inhibitor. In some embodiments, the subject exhibits an undesirable IDE activity, an undesirable level of IDE activity, or an undesirable level of a product of a reaction mediated by IDE catalytic activity. In some embodiments, the subject exhibits impaired insulin signaling or insulin resistance. In some embodiments, the macrocyclic IDE inhibitor, or the pharmaceutically acceptable salt, solvate, hydrate, stereoisomer, polymorph, tautomer, isotopically enriched form, or prodrug thereof, or the pharmaceutical composition, is administered to the subject based on the subject exhibiting an undesirable level of IDE activity or an undesirable level of a product of a reaction mediated by IDE catalytic activity. In some embodiments, the macrocyclic IDE inhibitor, or the pharmaceutically acceptable salt, solvate, hydrate, stereoisomer, polymorph, tautomer, isotopically enriched form, or prodrug thereof, or the pharmaceutical composition is administered to the subject based on the subject exhibiting impaired insulin signaling or insulin resistance. In some embodiments, the aberrant IDE activity, or the impaired insulin signaling, is a pathological level of IDE activity, a pathological level of insulin signaling impairment, respectively. In some embodiments, the subject exhibits or has been diagnosed with diabetes. In some embodiments, the subject exhibits or has been diagnosed with metabolic syndrome. In some embodiments, the subject exhibits, has been diagnosed with, or is at risk of developing a neurological disease (e.g., Alzheimer's Disease).

In another aspect, the present invention provides methods of synthesizing a DNA-templated compound library, wherein each compound is encoded by a covalently associated DNA tag, comprising: creating a template of a combination of orthogonal codons interspaced by constant regions wherein the template is based on codons from the orthogonal codon sets depicted in FIG. 5 or 7; and running templated coupling reactions to assemble a compound based on the orthogonal codons. In certain embodiments, the method further comprises capping unreacted templates (e.g., by acetylation). In certain embodiments, the method further comprises purifying the unreacted templates from the reacted templates. In certain embodiments, the purifying comprises capturing reacted templates with beads linked to a biotin-binder (e.g., streptavidin-linked beads). In certain embodiments, the method further comprises macrocyclizing DNA-templated products from the reacted templates. In another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a disease associated with aberrant enzyme activity (e.g., aberrant kinase activity (e.g., aberrant IDE activity)) in a subject. In yet another aspect, the present invention provides compounds of Formula (I), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a disease associated with aberrant enzyme activity (e.g., aberrant protease and/or kinase activity) (e.g., aberrant IDE activity)) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The present application refers to various issued patents, published patent applications, journal articles, and other publications, all of which are incorporated herein by reference. The details of one or more embodiments of the disclosure are set forth herein. Other features, objects, and advantages of the disclosure will be apparent from the Detailed Description, the Examples, and the Claims.

Definitions

Chemical Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The entire contents of each references cited in this paragraph are incorporated by reference.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions*, p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer and may also be referred to as "optically enriched." "Optically enriched," as used herein, means that the compound is made up of a significantly greater proportion of one enantiomer. In certain embodiments, the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); Wilen, *Tables of Resolving Agents and Optical Resolutions*, p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic." as used herein, includes both saturated and unsaturated, straight chain (i.e., unbranched), branched, acyclic, and cyclic (i.e., carbocyclic) hydrocarbons, which are optionally substituted with one or more functional groups. It is understood from the above description that the term "aliphatic," whether preceded by the terms substituted or unsubstituted, and unless otherwise specified, encompasses "cyclic or acyclic" and "branched or unbranched" groups. As will be appreciated by one of ordinary skill in the art, "aliphatic" is intended herein to include, but is not limited to, alkyl, alkenyl, alkynyl, and carbocyclyl (cycloalkyl, cycloalkenyl, and cycloalkynyl) moieties. In certain embodiments, as used herein, "aliphatic" is used to indicate those aliphatic groups (cyclic, acyclic, substituted, unsubstituted, branched or unbranched) having 1-20 carbon atoms. Unless otherwise specified, each instance of an aliphatic group is independently unsubstituted or substituted with one or more substituents, as valency permits, and which results in a stable compound. Exemplary Substituents are further described herein.

The term "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), and the like, which may bear one or more substituents. Additional examples of alkyl groups include n-heptyl ($C_7$), n-octyl ($C_8$) and the like, which may bear one or more substituents. Unless otherwise specified, each instance of an alkyl group is independently unsubstituted or substituted with one or more substituents, as valency permits, and which results in a stable compound. Exemplary substituents are further described herein.

The term "perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

The term "alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like, which may bear one or more substituents. Examples of $C_{2-6}$ alkenyl groups include the aforementioned $C_{2-4}$ alkenyl groups as well as pentenyl ($C_5$), pentadienyl ($C_5$), hexenyl (C), and the like, which may bear one or more substituents. Additional examples of alkenyl include heptenyl ($C_7$), octenyl ($C_8$), octatrienyl ($C_8$), and the like, which may bear one or more substituents. Unless otherwise specified, each instance of an alkenyl group is independently unsubstituted or substituted with one or more substituents, as valency permits, and which results in a stable compound. Exemplary substituents are further described herein.

The term "alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like, which may bear one or more substituents. Examples of $C_{2-6}$ alkenyl groups include the aforementioned $C_{2-4}$ alkynyl groups as well as pentynyl ($C_5$), hexynyl ($C_6$), and the like, which may bear one or more substituents. Additional examples of alkynyl include heptynyl ($C_7$), octynyl ($C_8$), and the like, which may bear one or more substituents. Unless otherwise specified, each instance of an alkynyl group is independently unsubstituted or substituted with one or more substituents, as valency permits, and which results in a stable compound. Exemplary substituents are further described herein.

The term "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined herein, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted or substituted with one or more substituents, as valency permits, and which results in a stable compound. Exemplary substituents are further described herein.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted or substituted with one or more substituents, as valency permits, and which results in a stable compound. Exemplary substituents are further described herein.

The term "heteroaliphatic," as used herein, refers to an aliphatic moiety, as defined herein, which includes both saturated and unsaturated, nonaromatic, straight chain (i.e., unbranched), branched, acyclic or cyclic (i.e., heterocyclic)

groups which are optionally substituted with one or more substituents, and which contain one or more oxygen, sulfur, nitrogen, phosphorus, or silicon atoms, e.g., in place of carbon atoms. It is understood from the above description that the term "heteroaliphatic," whether preceded by the terms substituted or unsubstituted, and unless otherwise specified, encompasses "cyclic or acyclic" and "branched or unbranched" groups. It is also understood, similar to aliphatic, that "heteroaliphatic" is intended to encompass heteroalkyl, heteroalkenyl, heteroalkynyl, and heterocyclic (heterocycloalkyl, heterocycloalkenyl, and heterocycloalkynyl) moieties. The terms "heteroalkyl," "heteroalkenyl," and "heteroalkynyl" are defined similarly, i.e., respectively refer to an alkyl, alkenyl, and alkynyl group, as defined herein, which are optionally substituted with one or more substituents, and which contain one or more oxygen, sulfur, nitrogen, phosphorus, or silicon atoms, e.g., in place of carbon atoms. Unless otherwise specified, each instance of a heteroaliphatic group is independently unsubstituted or substituted with one or more substituents, as valency permits, and which results in a stable compound. Exemplary substituents are further described herein.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to four heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. In the instance of ring fusion, it is understood that "heterocyclyl" refers to a ring system wherein the heterocyclyl ring, as defined herein, is fused with one or more carbocyclyl groups wherein the point of attachment is either on the carbocyclyl or heterocyclyl ring, or ring systems wherein the heterocyclyl ring, as defined herein, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of a heterocyclyl group is independently unsubstituted or substituted with one or more substituents, as valency permits, and which results in a stable compound. Exemplary substituents are further described herein.

In some embodiments, a heterocyclyl group is a 5- to 10-membered non-aromatic ring system having ring carbon atoms and 1-4 ring heteroatoms, wherein each heteroatom is independently selected from nitrogen, oxygen, and sulfur ("5- to 10-membered heterocyclyl"). In some embodiments, a heterocyclyl group is a 5- to 8-membered non-aromatic ring system having ring carbon atoms and 1-4 ring heteroatoms, wherein each heteroatom is independently selected from nitrogen, oxygen, and sulfur ("5- to 8-membered heterocyclyl"). In some embodiments, a heterocyclyl group is a 5- to 6-membered non-aromatic ring system having ring carbon atoms and 1-4 ring heteroatoms, wherein each heteroatom is independently selected from nitrogen, oxygen, and sulfur ("5- to 6-membered heterocyclyl"). In some embodiments, the 5-6 membered heterocyclyl has 1-3 ring heteroatoms selected from nitrogen, oxygen, and sulfur. In some embodiments, the 5- to 6-membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined herein, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted or substituted with one or more substituents, as valency permits, and which results in a stable compound. Exemplary substituents are further described herein.

The term "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined herein, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined herein, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted or substituted with one or more substituents, as valency permits, and which results in a stable compound. Exemplary substituents are further described herein.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

The term "acyl," as used herein, refers to a group having the general formula —C(=O)$R^{X5}$, —C(=O)O$R^{X5}$, —C(=O)S$R^{X5}$, —C(=O)N($R^{X6}$)$_2$, —C(=N$R^{X6}$)$R^{X1}$, —C(=N$R^{X6}$)O$R^{X5}$, —C(=N$R^{X6}$)S$R^{X5}$, —C(=N$R^{X6}$)N($R^{X6}$)$_2$, —C(=S)$R^{X5}$, —C(=S)O$R^{X5}$, —C(=S)S$R^{X5}$, and —C(=S)N($R^{X6}$)$_2$, wherein each occurrence of $R^{X5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{X6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{X6}$ groups are joined to form an substituted or unsubstituted heterocyclic ring.

The term "oxo," as used herein, refers to a group of the formula (=O).

The term "thiooxo," as used herein, refers to a group of the formula (=S).

Aliphatic (alkyl, alkenyl, alkynyl, carbocyclyl), heteroaliphatic (heteroalkyl, heteroalkenyl, heteroalkynyl, heterocyclyl), aryl, and heteroaryl groups, as defined herein, are optionally substituted. "Optionally substituted" refers to a group which may be substituted or unsubstituted. In general, the term "substituted" means that at least one hydrogen present on a group (e.g., a carbon or nitrogen atom) is replaced with a permissible substituent, e.g., a substituent which upon substitution results in a stable moiety or compound, e.g., a compound which does not spontaneously undergo transformation such as by a rearrangement, cyclization, elimination, or other reaction, and preferably possess stability sufficient to allow manufacture, and which maintains its integrity for a sufficient period of time to be useful for the purposes detailed herein. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms may have hydrogen substituents and/or any substituent as described herein which satisfy the valencies of the heteroatom and results in the formation of a stable moiety.

Exemplary substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, and combinations thereof, e.g., aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Other exemplary substituents are further described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —NH$_4$, —NH(R$^{bb}$), —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —SCN, —NCS, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —Si(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$alkyl, C$_{1-10}$ perhaloalkyl, C$_{2-10}$alkenyl, C$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$alkenyl, C$_{2-10}$alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR, —OSO$_2$R$^{ee}$, —S(=O)R$^{ee}$, —Si(R$^{cc}$)$_3$, —OSi(R$^{ee}$)$_3$, —C(=S)N(R$^{ff}$)$_2$, —C(=O)SR$^{ee}$, —C(=S)SR$^{cc}$, —SC(=S)SR$^{cc}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ (alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, succinate, maleate, fumarate, and the like), and trifluoroacetate.

"Halo" or "halogen" refers to fluorine (fluoro, —F), chlorine (chloro, —Cl), bromine (bromo, —Br), or iodine (iodo, —I).

As used herein, the term "unsubstituted hydroxyl" or "unsubstituted hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "unsubstituted thiol" or "unsubstituted thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term "unsubstituted amino" or "amino" refers to the group —NH$_2$. The term "substituted amino," by extension, refers to a monosubstituted, disubstituted, or trisubstituted amino group.

As used herein, the term "monosubstituted amino" refers to an amino group wherein the nitrogen atom directly attached to the parent molecule is substituted with one hydrogen and one group other than hydrogen. Exemplary monosubstituted amino groups include, but are not limited to, —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen. Exemplary disubstituted amino groups include, but are not limited to, —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups. Exemplary trisubstituted amino groups include, but are not limited to, —N(R$^{bb}$)$_3$ and —N(R$^{bb}$)$_3^+$X$^-$, wherein R$^{bb}$ and X$^-$ are as defined herein, with the proviso that R$^{bb}$ is not H.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein.

The term "protecting group" as used herein, refers to a chemical modification of a functional group of a compound that prevents the functional group to take part in an undesired chemical reaction. Protecting groups play an important role in multi-step organic compound synthesis, and suitable protecting groups for various functional groups and chemical environments are well known in the art. Examples of protecting groups are nitrogen protecting groups, oxygen protecting groups, sulfur protecting groups, and carboxylic acid protecting groups are described in more detail herein.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting*

Groups in Organic Synthesis, T. W. Greene and P. G. M. Wuts, 3rd edition, John Wiley & Sons, 1999, incorporated herein by reference.

Exemplary amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Exemplary carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Exemplary sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other exemplary nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxymethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, l-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, brosylate, and tosylate (Ts).

In certain embodiments, the substituent present on a sulfur atom is a sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "carboxylic acid protecting group" or "protected carboxylic acid," as used herein, are well known in the art and include those described in detail in Greene (1999). Examples of protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

These and other exemplary substituents and protecting groups are described in more detail in the Detailed Description, Examples, Figures, and Claims. The invention is not intended to be limited in any manner by the above exemplary listing of substituents and protecting groups.

Other Definitions

As used herein, the term "pharmaceutically acceptable salt" refers to those salts which are, within the scope of sound medical judgment, suitable for use in humans and other animals without undue toxicity, irritation, immunological response, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, and the like. Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

The terms "administer," "administering," or "administration," as used herein, refer to implanting, absorbing, ingesting, injecting, or inhaling a substance, for example, a compound or composition as described herein.

As used herein the term "inhibit" or "inhibition" in the context of enzymes, for example, in the context of IDE, refers to a reduction in the activity of the enzyme. In some embodiments, the term refers to a reduction of the level of enzyme activity, e.g., IDE activity, to a level that is statistically significantly lower than an initial level, which may, for example, be a baseline level of enzyme activity. In some embodiments, the term refers to a reduction of the level of enzyme activity, e.g., IDE activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein, the term "insulin degrading enzyme" or "IDE" refers to an insulin-degrading enzyme. IDE enzymes (also referred to herein as IDE proteins) and their respective encoding RNA and DNA sequences according to some aspects of this invention include human IDE protein and encoding sequences, as well as, in some embodiments, IDE proteins and encoding sequences from other species, for example, from other mammals (e.g., IDE proteins and encoding sequences from mouse, rat, cat, dog, cattle, goat, sheep, pig, or primate), from other vertebrates, and from insects. In some embodiments, an IDE inhibitor provided herein is specific for an IDE from a species, e.g., for human IDE, mouse IDE, rat IDE, and so on. In some embodiment, an IDE provided herein inhibits IDEs from more than one species, e.g., human IDE and mouse IDE. In some embodiments, an IDE provided herein exhibits equipotent inhibition of IDEs from more than one species, e.g., equipotent inhibition of human and mouse IDEs. The term IDE further includes, in some embodiments, sequence variants and mutations (e.g., naturally occurring or synthetic IDE sequence variants or mutations), and different IDE isoforms. In some embodiments, the term IDE includes protein or encoding sequences that are homologous to an IDE protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with an IDE sequence, for example, with an IDE sequence provided herein. In some embodiments, the term IDE refers to a protein exhibiting IDE activity, for example, a protein exhibiting insulin-targeted protease activity, or a nucleic acid sequence encoding such a protein. In some embodiments, the term IDE included proteins that exhibit at least 50%, at least 60%, at least 70%, at least 80%, at least 90%, at least 95%, or at least 100% insulin-targeting protease activity as compared to a known IDE protein or encoding sequence, for example, as compared to an IDE sequence provided herein. IDE protein and encoding gene sequences are well known to those of skill in the art, and exemplary protein sequences include, but are not limited to, the following sequences. Additional IDE sequences will be apparent to those of skill in the art, and the invention is not limited to the exemplary sequences provided herein.

As used herein, the term "template" refers to a molecular mold for specifying the structure or synthesis of a molecule. In certain embodiments, one or more templates are utilized in DNA-templated synthesis and hybridize to the transfer units to direct the synthesis of the chemical compound. In certain embodiments, the template can vary greatly in the number of bases. For example, in certain embodiments, the template may be 10 to 10,000 bases long, preferably between 10 and 1,000 bases long. The length of the template will depend on the length of the codons, complexity of the library, length of the unnatural polymer to be synthesized, complexity of the small molecule to be synthesized, use of constant regions, etc. The nucleic acid sequence may be prepared using any method known in the art to prepare nucleic acid sequences. These methods include both in vivo and in vitro methods including PCR, plasmid preparation, endonuclease digestion, solid phase synthesis, in vitro transcription, strand separation, etc. In certain embodiments, the nucleic acid template is synthesized using an automated DNA synthesizer. Templates which can be mutated and thereby evolved can be used to guide the synthesis of another chemical compound or library of chemical compounds as described in the present invention. As described in more detail herein, the evolvable template encodes the synthesis of a chemical compound and can be used later to decode the synthetic history of the chemical compound, to indirectly amplify the chemical compound, and/or to evolve (i.e., diversify, select, and amplify) the chemical compound. The evolvable template is, in certain embodiments, a nucleic acid. In certain embodiments of the present invention, the template is based on a nucleic acid.

The nucleic acid templates used in the present invention are made of DNA, RNA, a hybrid of DNA and RNA, or a derivative of DNA and RNA, and may be single- or double-stranded. The sequence of the template is used in the inventive method to encode the synthesis of a chemical compound, preferably a compound that is not, or does not resemble, a nucleic acid or nucleic acid analog (e.g., an unnatural polymer or a small molecule). In the case of certain unnatural polymers, the nucleic acid template is used to align the monomer units in the sequence they will appear in the polymer and to bring them in close proximity with adjacent monomer units along the template so that they will react and become joined by a covalent bond. In the case of a small molecule, the template is used to bring particular reactants within proximity of the small molecule scaffold in order that they may modify the scaffold in a particular way.

As used herein, the term "codon" refers to a variable part of a nucleic acid template which participates in DNA-templated synthesis and encode the building blocks of a compound (e.g., a small molecule).

As used herein, the term "anti-codon" refers to a DNA sequence in a DNA-tagged reagent, which is complimentary to and anneals with the corresponding codon of a nucleic acid template.

As used herein, the terms "treatment," "treat," and "treating" refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. In some embodiments, the disease or disorder being treated is associated with aberrant IDE activity, or can be treated by inhibiting IDE activity. In some embodiments, the disease is a proliferative disease, neurological disease, painful condition, psychiatric disorder, or metabolic disorder. In some embodiments, the disease is metabolic syndrome or diabetes. In some embodiments, the disease is metabolic syndrome, obesity, abdominal obesity, atherogenic dyslipidemia, elevated blood pressure, type II diabetes, insulin resistance, or related disorders characterized by negatively altered metabolism or fat accumulation. In some embodiments, the disease is diabetes or metabolic syndrome in a subject with a neurological disease (e.g., Alzheimer's Disease) or at risk of developing a neurological disease (e.g., Alzheimer's Disease).

The terms "effective amount" and "therapeutically effective amount," as used herein, refer to the amount or concentration of an inventive compound, that, when administered to a subject, is effective to at least partially treat a condition from which the subject is suffering. In some embodiments, an effective amount of an IDE inhibitor is an amount the administration of which results in inhibition of at least about 50%, at least about 60%, at least about 70%, at least about 75%, at least about 80%, at least about 90%, at least about 95%, at least about 98%, at least about 99%, at least about 99.5%, or about 100% of IDE activity as compared to a baseline level, for example, a level of IDE activity in the absence of the inhibitor.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive develop-mental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the Diagnostic and Statistical Manual of Mental Disorders-Fourth Edition (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

BRIEF DESCRIPTION OF THE DRAWINGS

FIGS. 2A to 2E. Identification of an orthogonal codon set for second-generation DNA-templated libraries. FIG. 2A, General architecture of second-generation template libraries. Consecutive Ns do not represent randomized sequences but indicate the location of individual codons. FIG. 2B, The coding system for the second-generation library. FIG. 2C, Proposed model of DNA templates used to calculate an orthogonal codon set. FIG. 2D, The ideal outcome of DNA-templated synthesis codon reactivity tables (1). Numbers represent apparent conversions of reactions between the corresponding DNA templates (horizontal) and DNA-linked reagents (vertical). Light gray fields (with a zero inside each field) and dark gray fields (with a zero inside each field) represent apparent conversions and annealing factors, respectively, that are acceptable because they correspond to mismatched reactivity below the 7% threshold. FIG. 2E, Deconvolution approach based on the model of additive annealing factors (7): experimentally obtained reactivity tables (3) are converted into anticipated affinity tables (4), which are refined with additional DTS reactions (5). Geometrical shapes represent various codons and anticodons; equations 2 and 5 denote apparent conversions of the corresponding DTS reactions ($\alpha$, $\beta$, $\gamma$). See the Supplementary Information for details of the deconvolution process leading to the final codon set.

FIG. 3A, Synthetic routes enabling incorporation of new scaffold structures into DNA templates, exemplified with scaffolds 4I and 4L. FIG. 3B, Scaffolds validated and used in the second-generation library of macrocycles. Spheres without and with interior dotted lines represent connectivity with building blocks 1 and 3, respectively. Scaffolds 4A-4H (dashed boxes) were used in the first-generation library. FIG. 3C, Iteratively selected building blocks maximizing overlap of the library with Kihlberg's parameter space for orally bioavailable molecules.[52,54]

FIG. 5A, Assembly of the first-generation library of DNA templates. For each scaffold codon, a sub-library of templates was previously assembled via splint ligation of phosphorylated 33- or 34-mers (generated on a DNA synthesizer in a split-pool manner) and 21-mers chemically modified with the scaffold amino acid. FIG. 5B, Modified version of the splint ligation assembly for the second-generation DTS library. Increasing the number of ligated fragments from two to three reduces the number of required oligonucleotide syntheses. FIG. 5C, Template library assembly strategy via preparative enzymatic primer extensions. An 8,000-membered library of templates with four deoxyinosines at the scaffold codon is prepared by split-pool oligonucleotide synthesis. Each primer extension with one of 32 poly-dA-tagged primers followed by strand separation via PAGE yields a heavy strand sub-library with an individual scaffold codon sequence. Another round of primer extensions with the corresponding chemically modified primers followed by strand separation results in 32 sub-libraries of templates, which are combined to obtain a 256,000-membered template library. A shortened method involves direct preparation of the heavy strands by split-pool oligonucleotide synthesis. Methods for template assembly are described in detail in FIGS. 23A to 23C.

FIGS. 6A, 6B, Results of the selection against IDE before (FIG. 6A) and after (FIG. 6B) computational filtering of nine promiscuous hydrophobic building blocks. (1J, 1L, 1M, 1N, 1T, 3E, 3H, 3L, 3R) that were unusually represented among hits across multiple unrelated selections. Removal of the substantial non-specific noise revealed an enriched DJP* series of macrocycles. Compounds trans-DJPM and cis-DJIR were chemically synthesized in a DNA-free form and were found to be equipotent to the structurally similar trans-6bK and trans-6bA macrocycles developed from the first-generation DNA-templated library.[45] The identified hits also included unrelated CODVV macrocycles of a new structural family. R=(CH$_2$)$_2$O(CH$_2$)$_2$NH$_2$ FIG. 6C, 6D, Concentration-dependent IDE inhibition profiles of macrocyclic hits determined by fluorogenic decapeptide cleavage assay (see the Supplementary Information). Error bars reflect to standard error of the mean. The plots for a cis- and a trans-isomer of each hit are of the same color and marker shape, with filled markers for trans-isomers, and empty markers for cis-isomers). Whereas DJPM trans isomers were more potent than cis isomers), the opposite trend was observed for other tested hits.

FIGS. 7A to 7C. Initial reactivity maps for DTS reactions with Reagents 1 (FIG. 7A), 2 (FIG. 7B) and 3 (FIG. 7C), conducted at 25, 25, and 43° C. respectively.

FIGS. 8A to 8C. Reactivity maps for DTS reactions with Reagents 1 (FIG. 8A), 2 (FIG. 8B) and 3 (FIG. 8C), conducted at 30, 30, and 37° C. respectively.

FIG. 9. The expanded affinity map of annealing factors after the initial 2×2,700 DTS reactions (at the improved temperature regime, 30, 30, 37° C. for reagents 1, 2 and 3 respectively).

FIG. 11. The expanded affinity map after the addition of "hidden" interactions.

FIG. 13. The expanded affinity map after carrying out all the DTS reactions.

FIG. 14. The expanded affinity map after removal of the most promiscuous codons 1g, 1h, 1u, 1w, 1x, 1y, 1zz, 2l, 2p, 2x, 2y, 2ww, 3w.

FIG. 15. The set of problematic codons for brute-force deconvolution.

FIG. 18. Affinity map of the computationally identified orthogonal set of codons.

FIGS. 23A to 23C. Different approaches to the assembly of the second-generation library of DNA templates. FIG. 23A. 8,000-membered universal template library as starting material; preparative PCR and primer extension. FIG. 23B. 8,000-membered universal template library as starting material; two preparative primer extensions. FIG. 23C. Heavy strand as starting material; single preparative primer extension.

Figure 36:
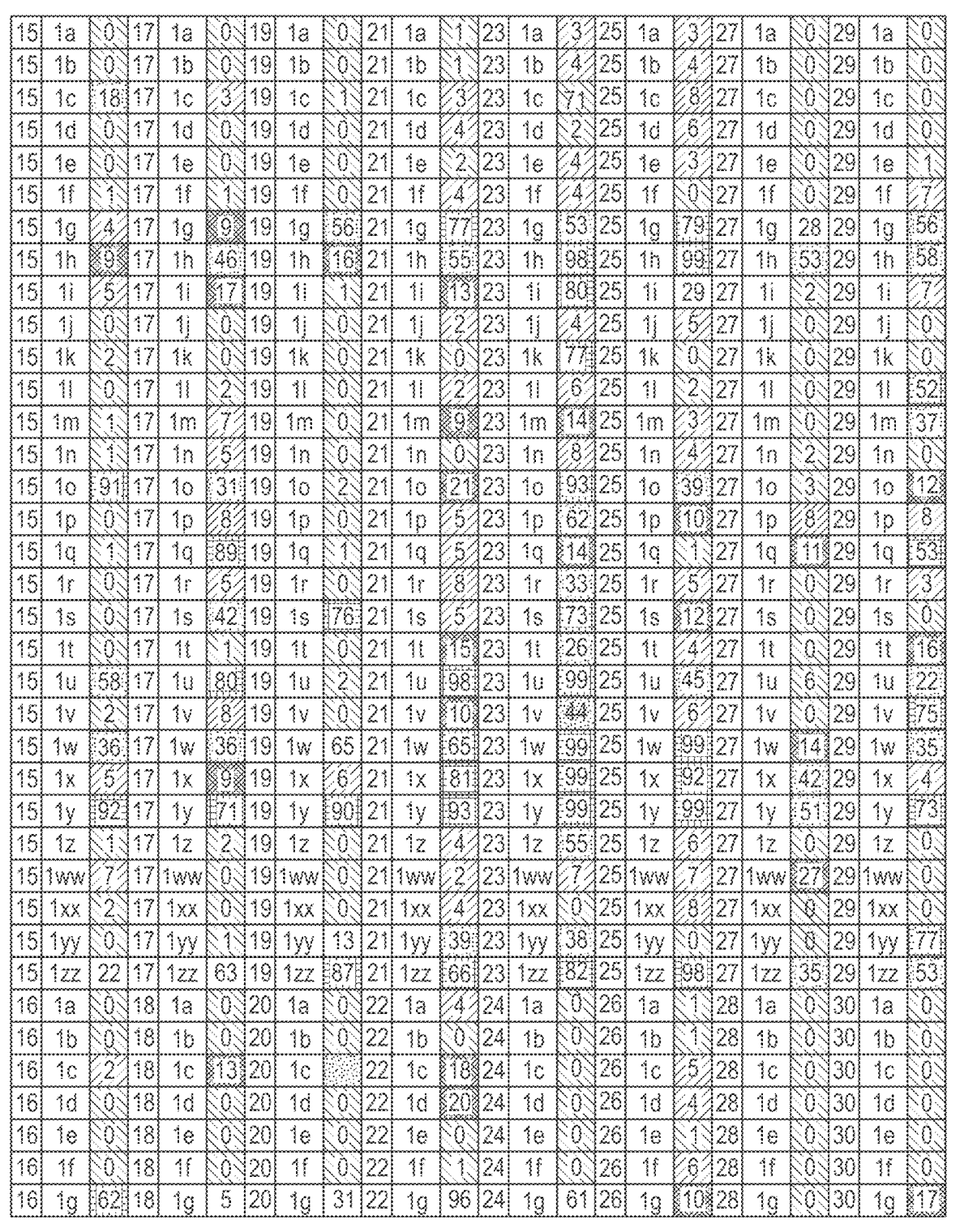
Figure 36:
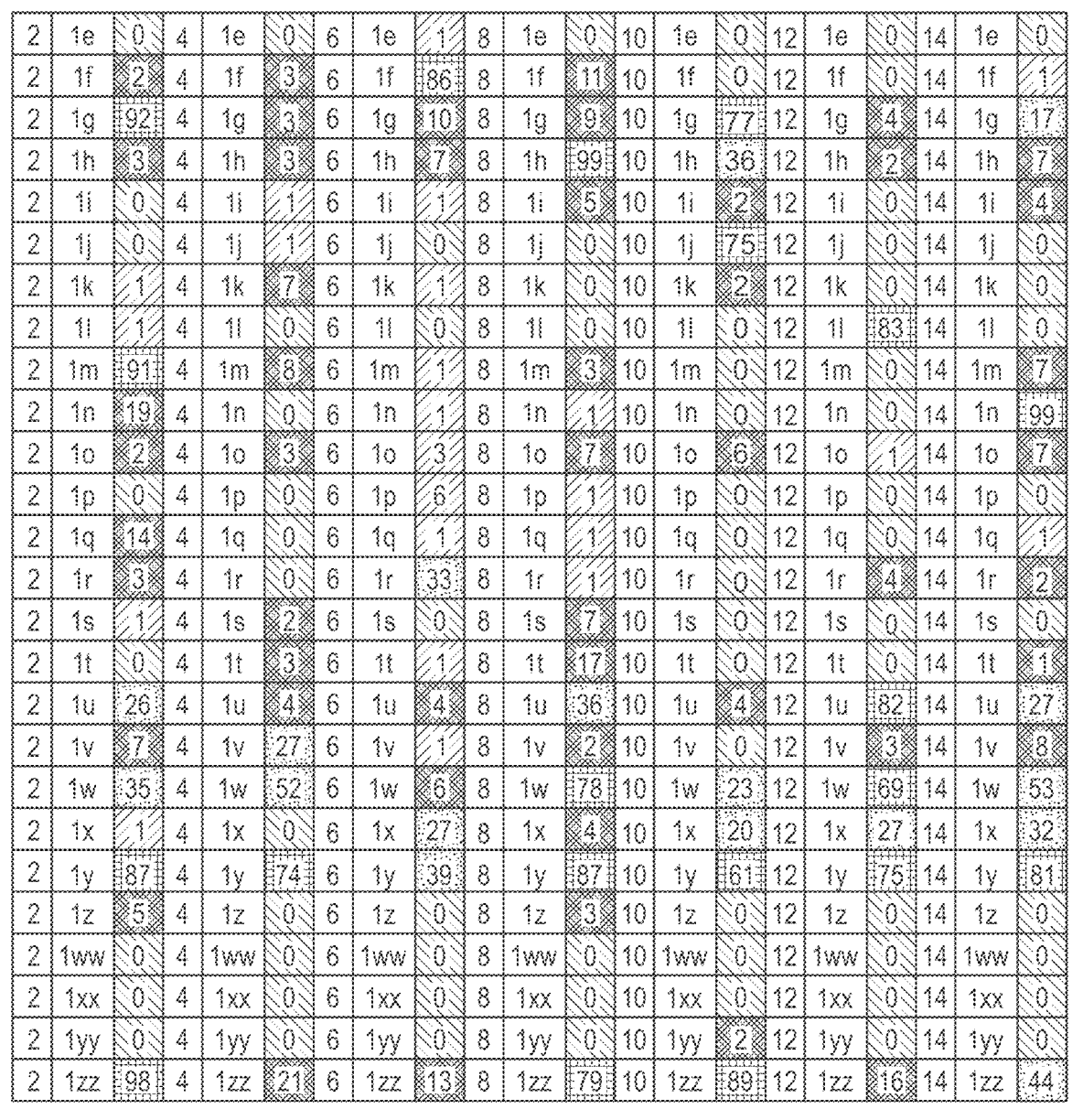
Figure 36:
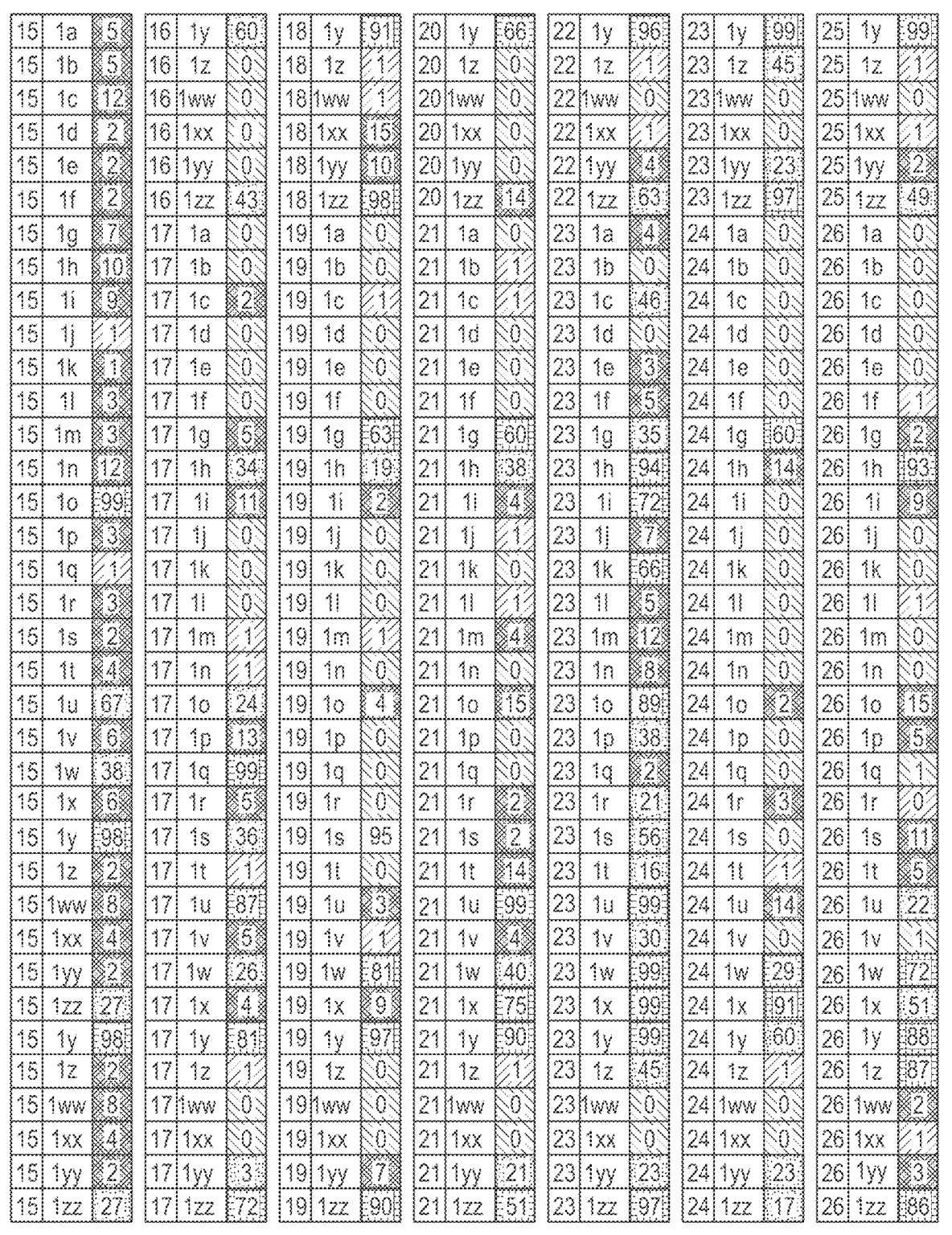
Figure 36:
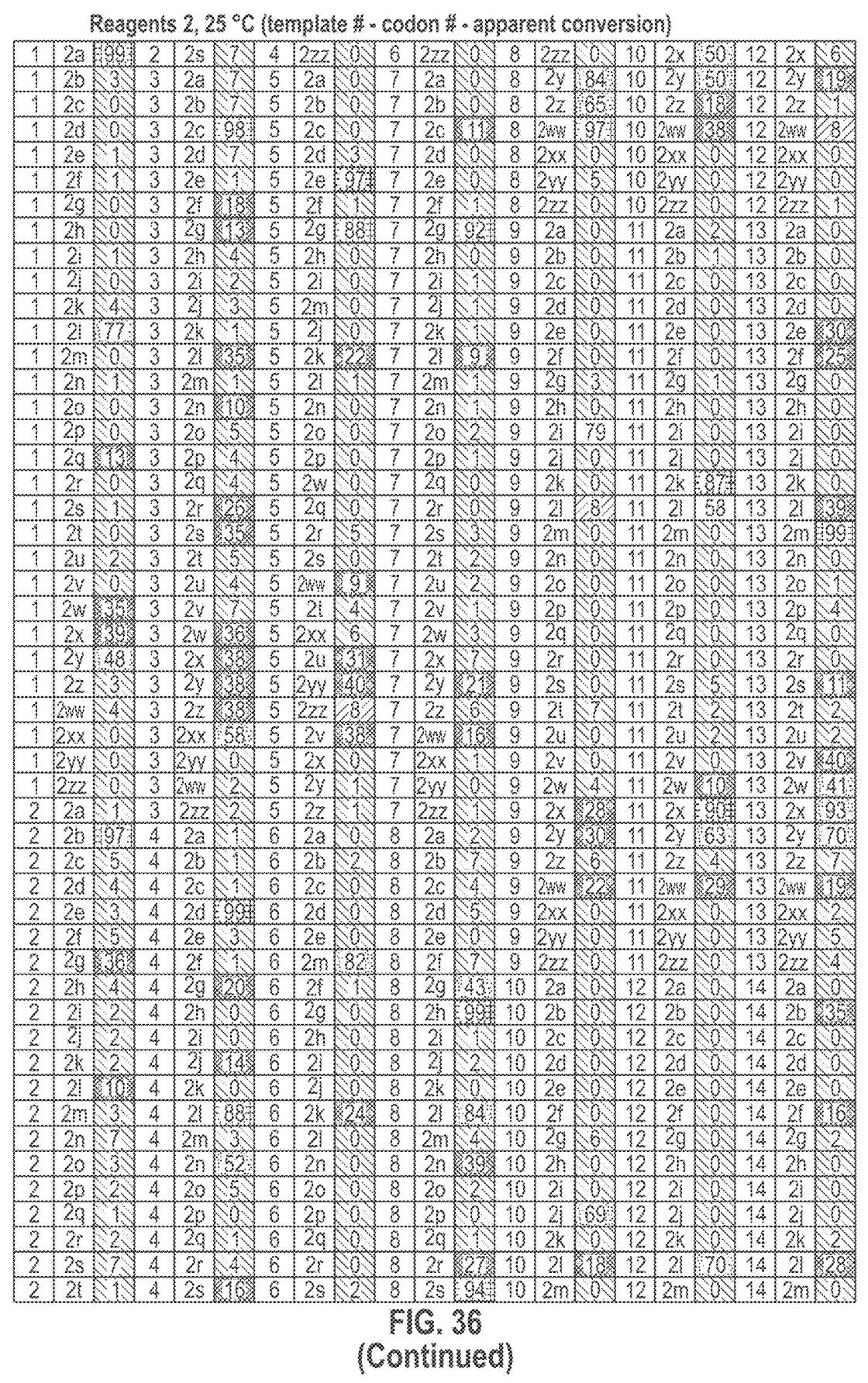
Figure 36:
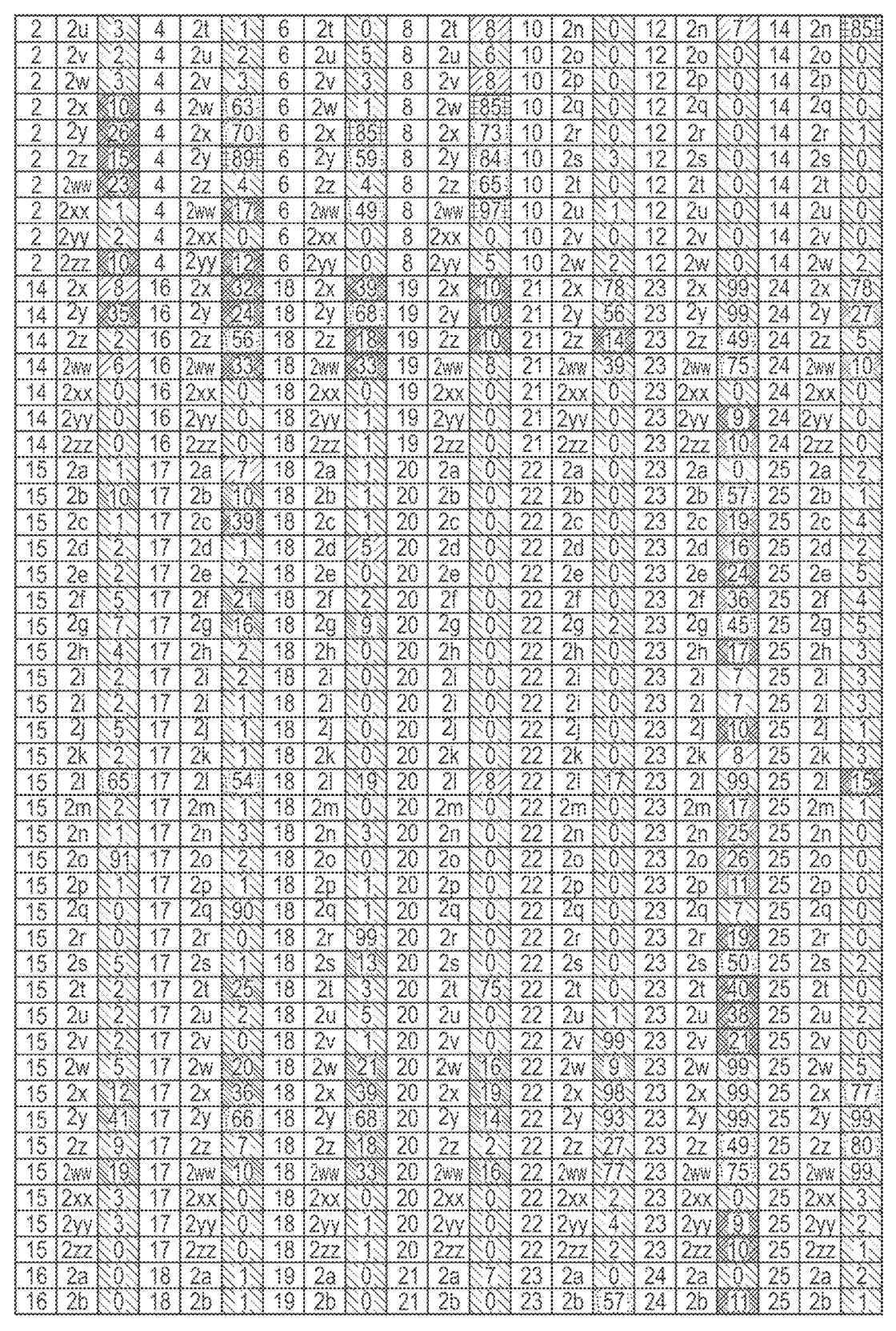
Figure 36:
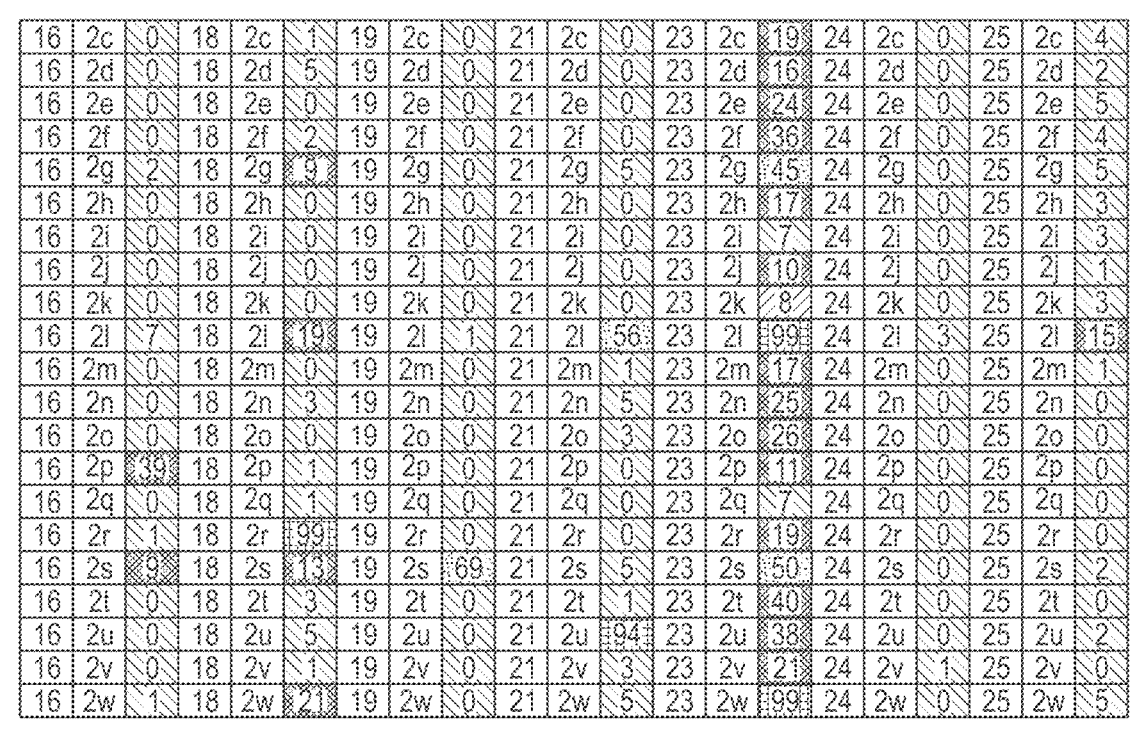
Figure 36:
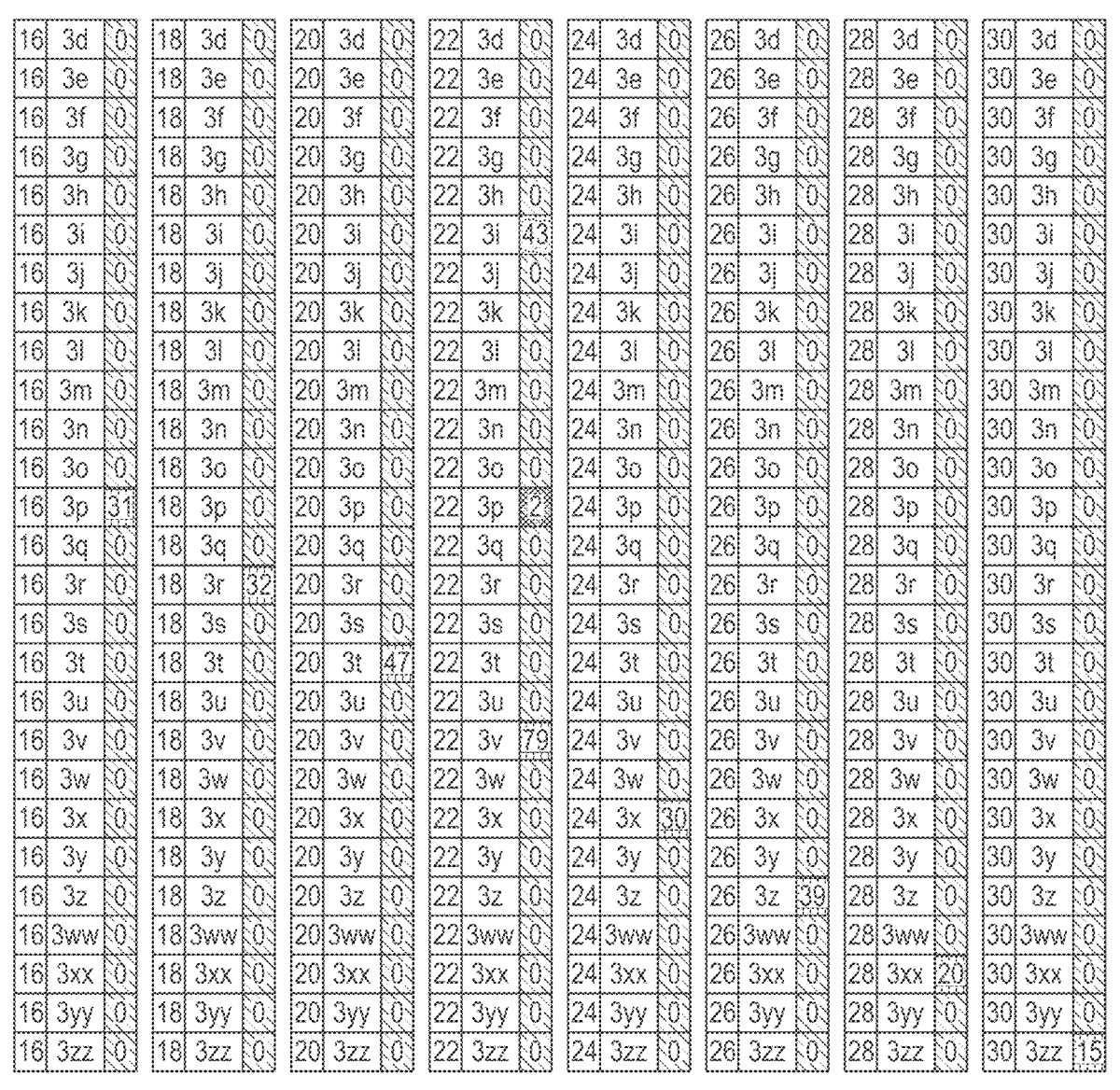
Figure 36:
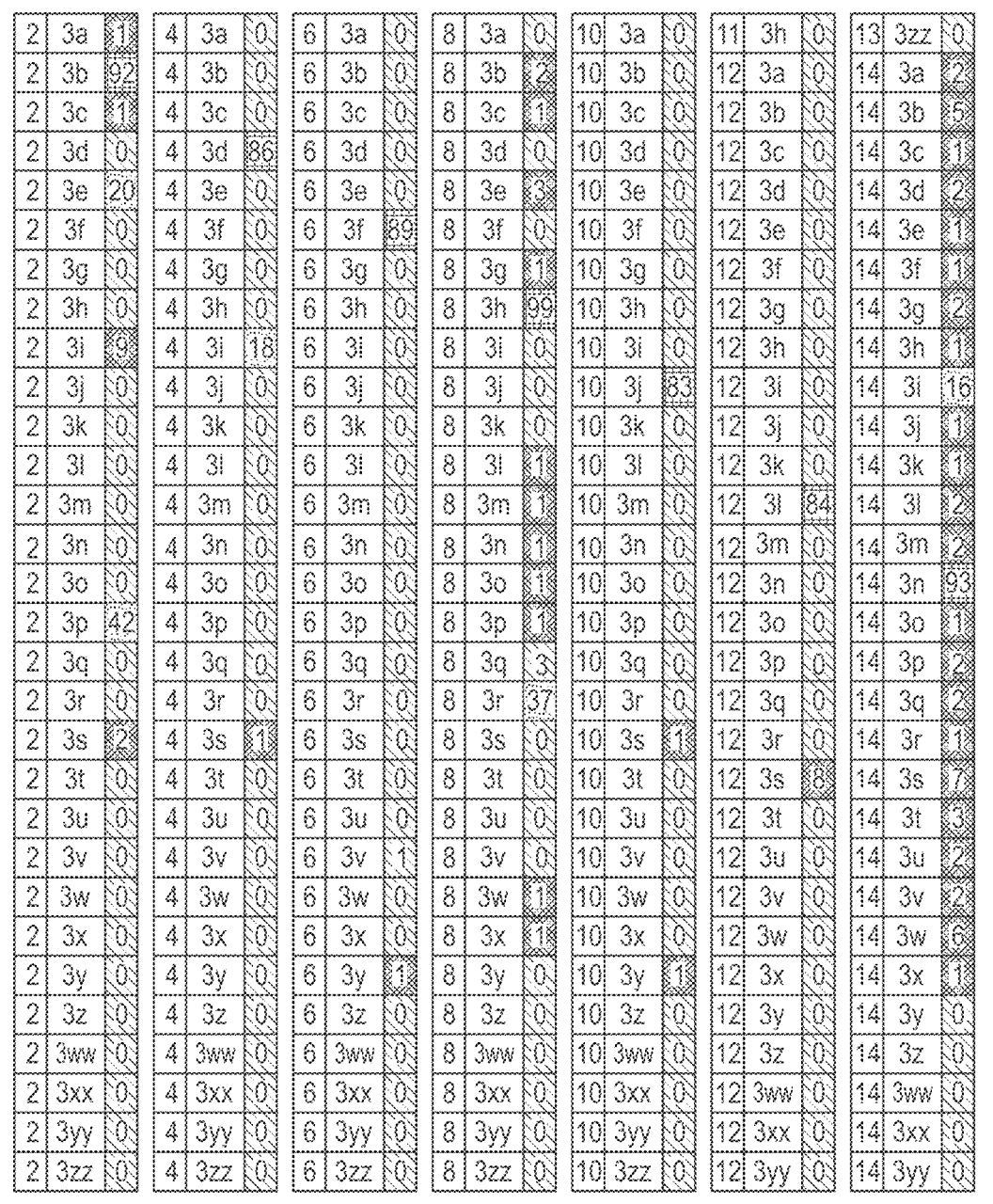
Figure 36:
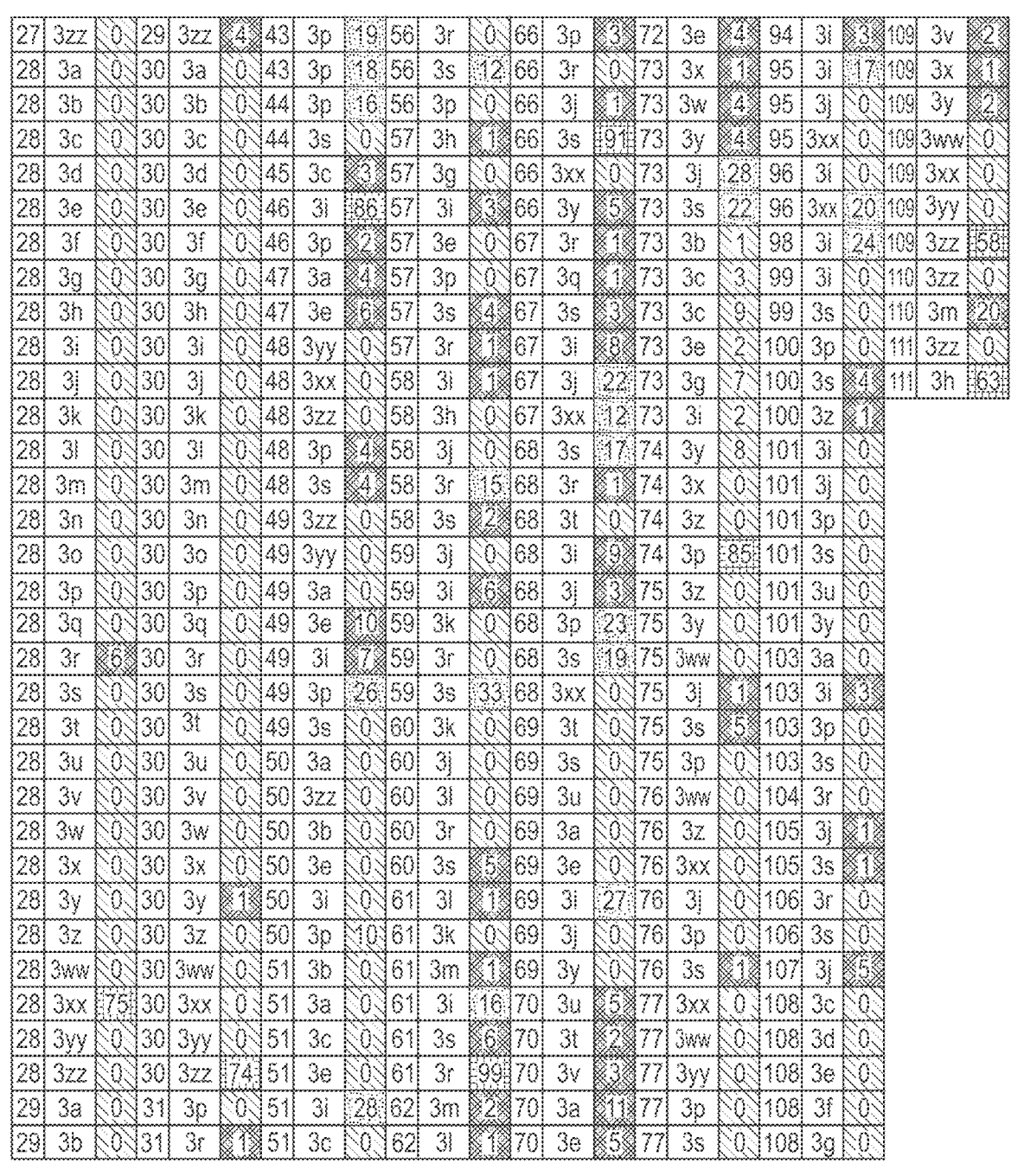
Figure 36:
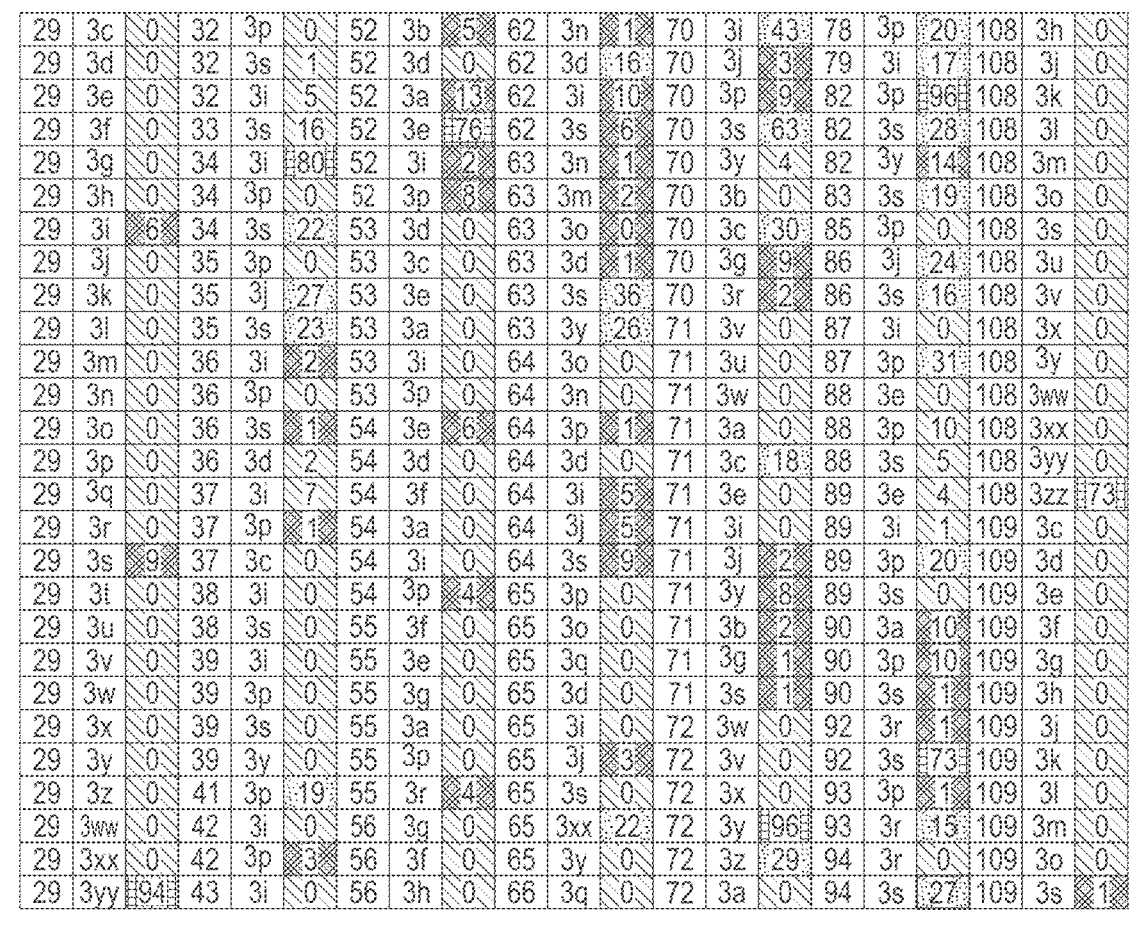

FIG. 36. Reactions conducted for the generation of affinity tables.

FIG. 38. Computationally removed promiscuous building blocks containing macrocycle-fused aromatic rings (bolded).

DETAILED DESCRIPTION OF CERTAIN EMBODIMENTS OF THE INVENTION

Figure 1:
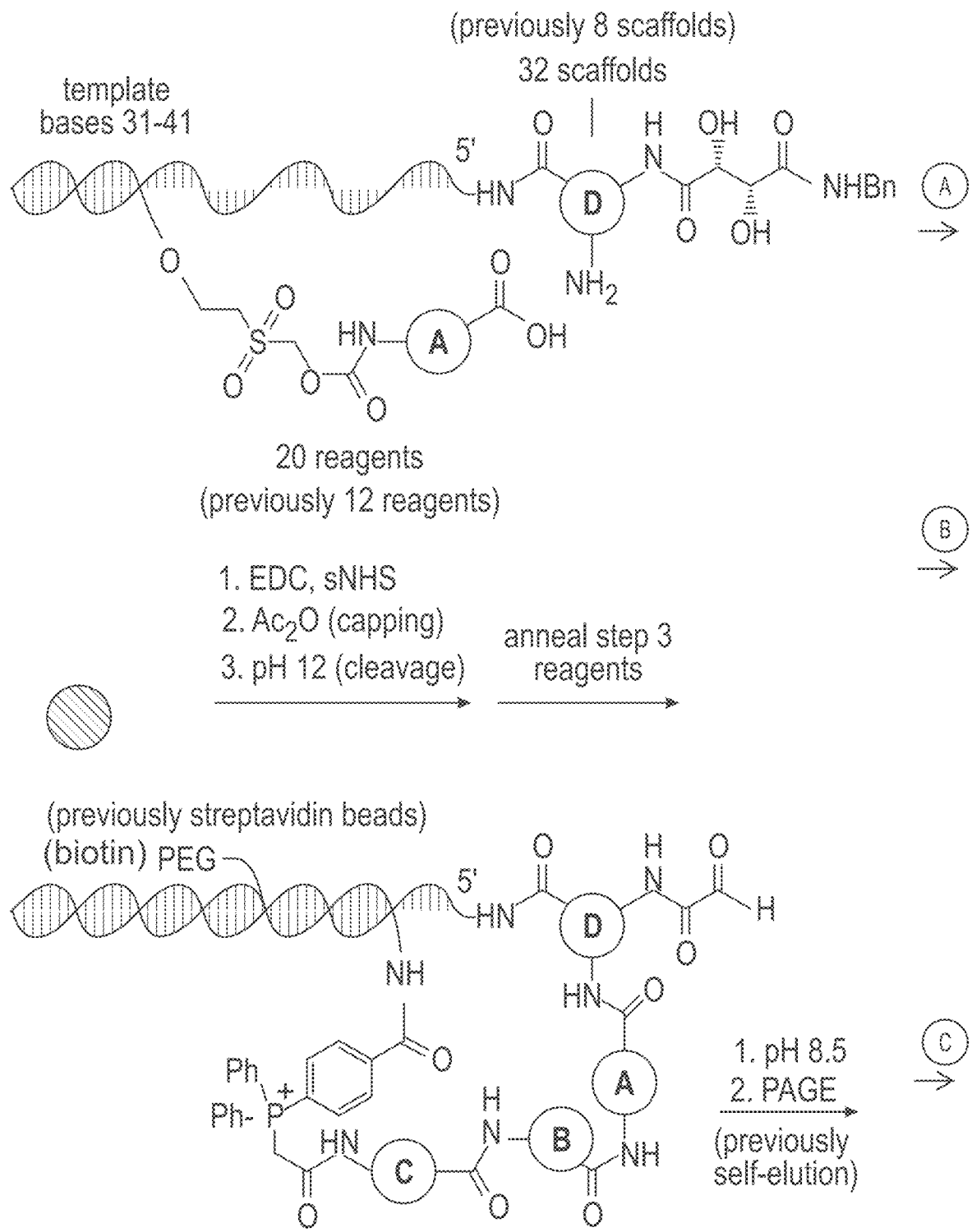
FIG. 1. DNA-templated macrocycle library synthesis scheme. Key aspects of the previously described first-generation (grey) and second-generation (black, color) library syntheses are shown. In the first step, scaffold building block D attached to 5' end of the template undergoes coupling with building block A, which is initially attached to the corresponding "anticodon" DNA via a cleavable bis(2-(succinimidooxycarbonyloxy)ethyl) sulfone (BSOCOES) linker. Unreacted templates are capped with acetic anhydride. The linker is cleaved at high pH, liberating the amino group of building block A, which subsequently undergoes the step 2 coupling with building block B followed by capping and linker cleavage. After coupling to biotin- or PEG-labeled Wittig reagent building block C, pulldown with streptavidin-tagged beads (first-generation procedure) or gel purification (second-generation procedure) enables isolation of those templates that successfully reacted at all three steps. Periodate treatment cleaves the diol fragment of the tartaramide moiety to furnish a glyoxyloyl group, which undergoes Wittig cyclization under mildly basic conditions. Successfully cyclized products are eluted off the beads on cyclization (first-generation procedure) or are purified on a polyacrylamide gel (second-generation procedure).
Figure 1:
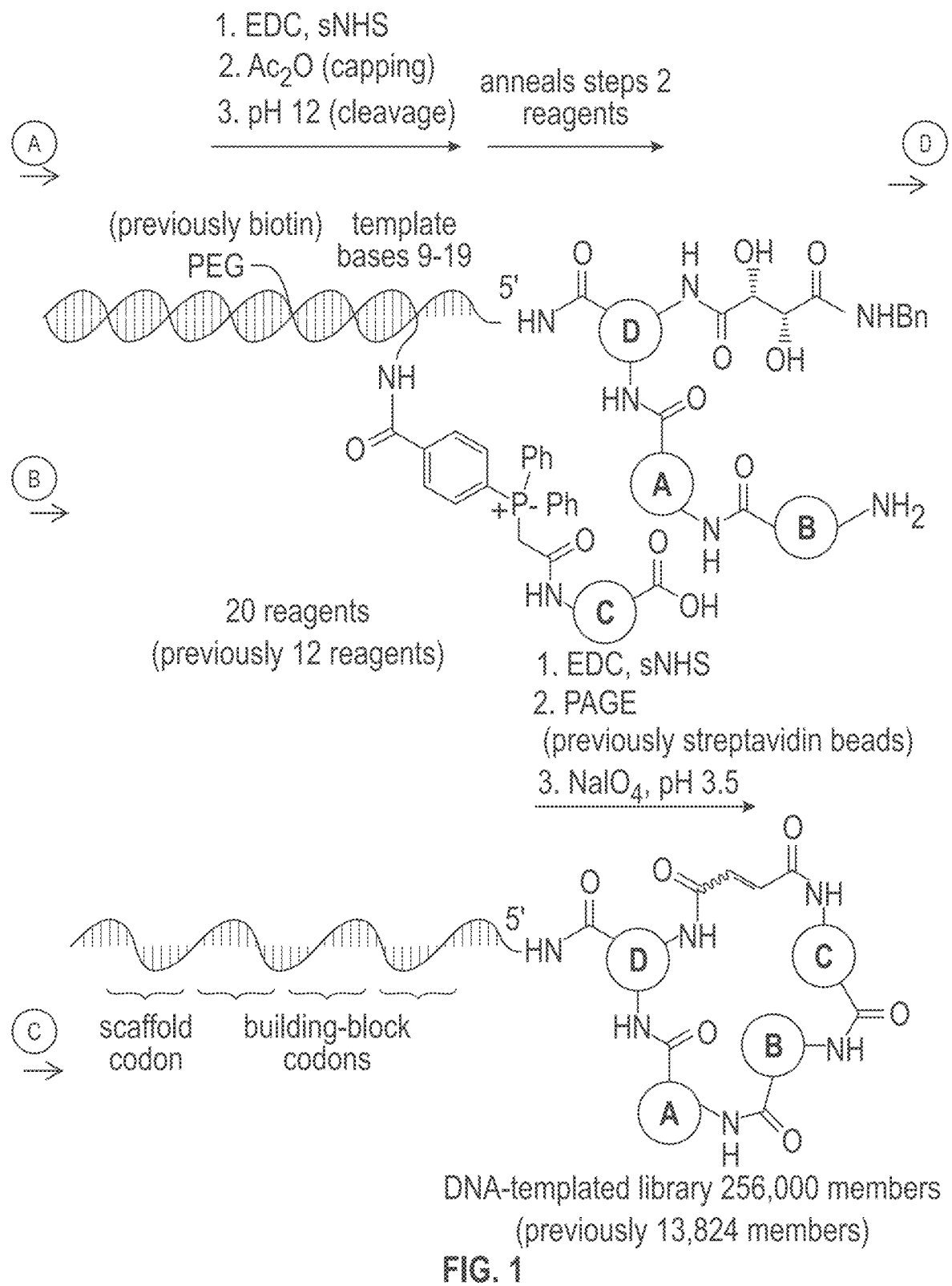
Figure 1:
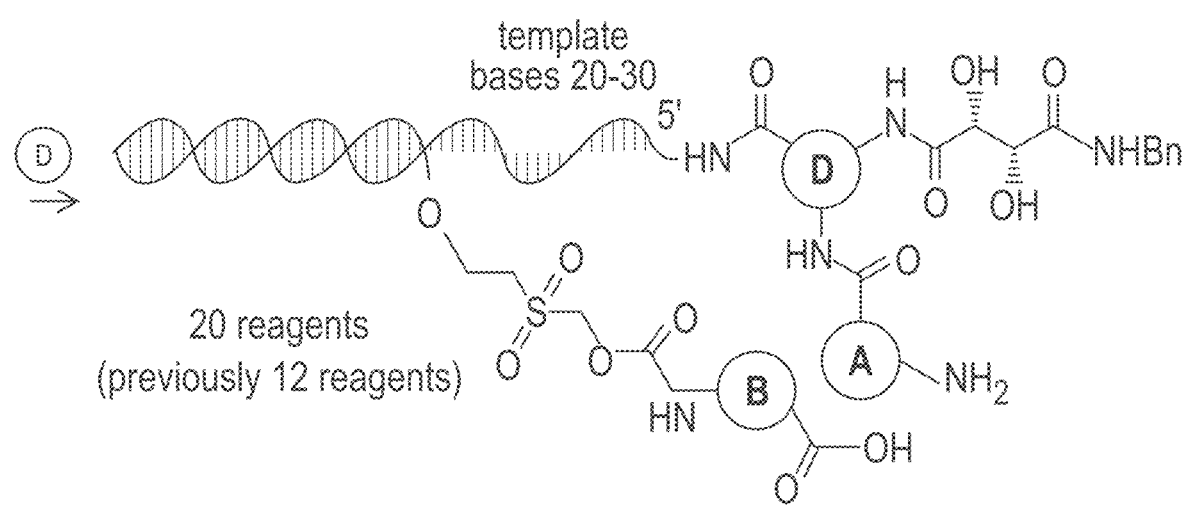

The present invention provides compounds of Formula (I). In certain embodiments, the compounds of Formula (I) are useful for the prevention and/or treatment of a disease in a subject and/or for use in research. In certain embodiments, provided herein are compounds of Formula (I), which inhibit the activity of a protease, for the prevention and/or treatment of a disease (e.g., a disease associated with aberrant enzyme activity (e.g., aberrant protease and/or kinase activity)(e.g., IDE activity)) in a subject. In certain embodiments, compounds of Formula (I) are prepared by DNA-templated synthesis and are part of a DNA-templated compound library. In certain embodiments, the DNA-templated synthesis methods, compounds, systems, kits, and compositions described herein are based on the DNA-templated synthesis methods, compounds, systems, kits, and compositions described in U.S. patent application U.S. Ser. No. 10/101,030, filed Mar. 19, 2002; U.S. Ser. No. 10/744,605, filed Dec. 23, 2003; U.S. Ser. No. 10/949,162, filed Sep. 24, 2004; U.S. Ser. No. 10/949,163, filed Sep. 24, 2004; U.S. Ser. No. 11/141,164, filed May 31, 2005; U.S. Ser. No. 11/141,542, filed May 31, 2005; U.S. Ser. No. 11/351,908, filed Feb. 10, 2006; U.S. Ser. No. 11/586,851, filed Oct. 24, 2006; U.S. Ser. No. 13/173,593, filed Jun. 30, 2011; and U.S. Ser. No. 14/497,976, filed Sep. 26, 2014; each of which is incorporated herein by reference.

In certain embodiments, compounds of Formula (I) are macrocyclic IDE inhibitors. In another aspect, the present invention provides methods of synthesizing a DNA-templated compound library, and templates for synthesizing a DNA-templated compound library which also act as an associated (e.g., covalently bound) DNA tag to encode each compound in the library. Also provided by the present disclosure are pharmaceutical compositions, kits, methods, and uses of a compound of Formula (I) as described herein.

Compounds

In certain embodiments, a compound described herein is a compound of any one of Formula (I), or a pharmaceutically acceptable salt, solvate, hydrate, polymorph, co-crystal, tautomer, stereoisomer, isotopically labeled derivative, or prodrug thereof.

In one aspect of the present invention, provided are compounds of Formula (I):

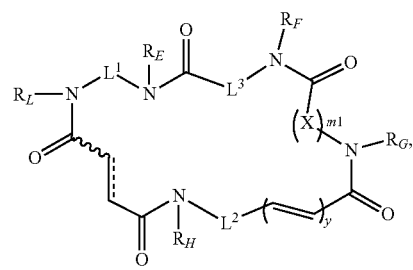

or a pharmaceutically acceptable salt, solvate, hydrate, stereoisomer, polymorph, tautomer, isotopically enriched form, or prodrug thereof, wherein:

------ is a single or double C—C bond, wherein when ------ is a double C—C bond, then ⁓ indicates that the adjacent C—C double bond is in a cis or trans configuration;

$L^1$ is substituted or unsubstituted aliphatic, substituted or unsubstituted heteroaliphatic, substituted or unsubstituted carbocyclylene, substituted or unsubstituted arylene, or substituted or unsubstituted heterocyclylene;

$L^2$ is substituted or unsubstituted aliphatic, substituted or unsubstituted heteroaliphatic, substituted or unsubstituted carbocyclylene, substituted or unsubstituted arylene, or substituted or unsubstituted heterocyclylene;

$L^3$ is substituted or unsubstituted aliphatic, substituted or unsubstituted heteroaliphatic, substituted or unsubstituted carbocyclylene, substituted or unsubstituted arylene, or substituted or unsubstituted heterocyclylene;

X is $-O-C((R^{3A})(R^{3B}))_s-$, $-C((R^{3A})(R^{3B}))_s-$, optionally substituted carbocyclylene, optionally substituted heterocyclylene, or optionally substituted arylene;

$R^{3A}$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl;

$R^{3B}$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; or optionally $R^{3A}$ and $R^{3B}$ are joined together to form optionally substituted carbocyclyl or

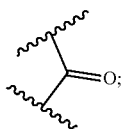 [SMILES: *C(*)=O]

each instance of $R_E$, $R_F$, $R_G$, $R_H$, and $R_L$ is independently hydrogen; halogen; substituted or unsubstituted acyl; a nitrogen protecting group; substituted or unsubstituted aliphatic; substituted or unsubstituted heteroaliphatic; substituted or unsubstituted aryl; substituted or unsubstituted heteroaryl; substituted or unsubstituted hydroxyl; substituted or unsubstituted thiol; substituted or unsubstituted amino; or optionally $R_G$ and one instance of $R^{3A}$ or $R^{3B}$ are joined together with the intervening atoms to form optionally substituted heterocyclyl;

m1 is 0, 1, or 2;
s is 0, 1, 2, 3, or 4; and
y is 0 or 1.

Compounds of Formula (I) include linker $L^1$. In certain embodiments, $L^1$ is substituted or unsubstituted aliphatic, substituted or unsubstituted heteroaliphatic, substituted or unsubstituted carbocyclene, substituted or unsubstituted arylene, or substituted or unsubstituted heterocyclylene. In certain embodiments, $L^1$ is substituted or unsubstituted $C_{1-6}$ aliphatic, substituted or unsubstituted arylene, or substituted or unsubstituted heterocyclylene.

Compounds of Formula (I) include linker $L^2$. In certain embodiments, $L^2$ is substituted or unsubstituted aliphatic, substituted or unsubstituted heteroaliphatic, substituted or unsubstituted carbocyclene, substituted or unsubstituted arylene, or substituted or unsubstituted heterocyclylene. In certain embodiments, $L^2$ is of the formula:

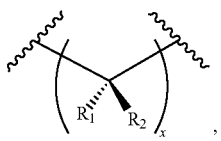

wherein: $R_1$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —$OR_A$; —$N(R_A)_2$; —$SR_A$; =O; —CN; —$NO_2$; —SCN; —$SOR_A$; or —$SO_2R_A$; wherein each occurrence of $R_A$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; $R_2$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —ORB; —$N(R_B)_2$; —$SR_B$; =O; —CN; —$NO_2$; —SCN; —SORB; or —$SO_2R_B$; wherein each occurrence of $R_B$ independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; or optionally $R_1$ and $R_2$ are joined together to form a spiro-linked, optionally substituted carbocyclyl, or optionally $R_H$ and one instance of $R^1$ or $R^2$ are joined together with the intervening atoms to form optionally substituted heterocyclyl; and x is 0, 1, 2, or 3. In certain embodiments, x is 0. In certain embodiments, x is 1. In certain embodiments, x is 2. In certain embodiments, x is 3. In certain embodiments, $R_1$ and $R_2$ are joined together to form a spiro-linked, optionally substituted carbocyclyl. In certain embodiments, $R_1$ and $R_2$ are joined together to form a spiro-linked, optionally substituted, 5-to 7-membered carbocyclyl. In certain embodiments, $R_1$ is substituted or unsubstituted aryl (e.g., substituted or unsubstituted benzyl or substituted or unsubstituted phenyl). In certain embodiments, $R_2$ is substituted or unsubstituted aryl (e.g., substituted or unsubstituted benzyl or substituted or unsubstituted phenyl).

In certain embodiments, $L^2$ is of the formula:

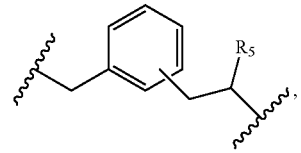

wherein $R_5$ is substituted or unsubstituted aliphatic; substituted or unsubstituted heteroaliphatic; substituted or unsubstituted aryl; substituted or unsubstituted heteroaryl; substituted or unsubstituted amino; —C(=O)—$N(R_J)_2$; —C(=O)—$OR_J$; or —C(=O)—$SR_J$, or —$CH_2$—C(=O)$N(R_J)_2$, wherein each occurrence of $R_J$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; or two $R_J$ groups are joined to form a substituted or unsubstituted heterocyclic group; optionally wherein $R_5$ further comprises a label, resin, or therapeutic agent attached thereto.

In certain embodiments, $L^2$ is of the formula:

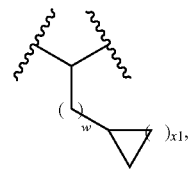

wherein w is 0, 1, or 2; and x1 is 1 or 2. In certain embodiments, w is 0. In certain embodiments, w is 1. In certain embodiments, w is 2. In certain embodiments, x1 is 1. In certain embodiments, x1 is 2. In certain embodiments, $L^2$ is of the formula:

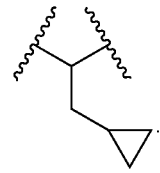 [SMILES: *C(*)CC1CC1]

In certain embodiments, $L^2$ is substituted or unsubstituted 5- to 7-membered carbocyclene, substituted or unsubstituted arylene, or substituted or unsubstituted, 4- to 10-membered heterocyclylene. In certain embodiments, $L^2$ is substituted or unsubstituted carbocyclene (e.g., substituted or unsubstituted 5- to 7-membered carbocyclene). In certain embodiments, $L^2$ is substituted or unsubstituted arylene (e.g., substituted or unsubstituted phenylene or substituted or unsubstituted benzylene). In certain embodiments, $L^2$ is substituted or unsubstituted heterocyclylene (e.g., substituted or unsubstituted, 5- to 10-membered monocyclic or bicyclic heterocyclylene, wherein one or two atoms in the heterocyclic ring are independently nitrogen, oxygen, or sulfur). In certain embodiments, $L^2$ is substituted or unsubstituted, 4- to 10-membered monocyclic or bicyclic heterocyclylene, wherein one or two atoms in the heterocyclic ring are independently nitrogen, oxygen, or sulfur.

In certain embodiments, y is 0. In certain embodiments, y is 1.

Compounds of Formula (I) include linker $L^3$. In certain embodiments, $L^3$ is substituted or unsubstituted aliphatic, substituted or unsubstituted heteroaliphatic, substituted or unsubstituted carbocyclyene, substituted or unsubstituted arylene, or substituted or unsubstituted heterocyclylene. In certain embodiments, $L^3$ is substituted or unsubstituted $C_{1-6}$ aliphatic. In certain embodiments, $L^3$ is of the formula:

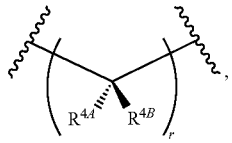

wherein $R^{4A}$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; $R^{4B}$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; or optionally $R_F$ and one instance of $R^{4A}$ or $R^{4B}$ are joined together with the intervening atoms to form optionally substituted heterocyclyl, and r is 0, 1, or 2. In certain embodiments, $R^{4A}$ is hydrogen, substituted or unsubstituted $C_{1-6}$ aliphatic, substituted or unsubstituted aryl, substituted or unsubstituted heterocyclyl, or substituted or unsubstituted heteroaryl. In certain embodiments, $R^{4A}$ is hydrogen. In certain embodiments, $R^{4A}$ is substituted or unsubstituted $C_{1-6}$ aliphatic. In certain embodiments, $R^{4A}$ is substituted or unsubstituted aryl. In certain embodiments, $R^{4A}$ is substituted or unsubstituted heterocyclyl. In certain embodiments, $R^{4A}$ is substituted or unsubstituted heteroaryl.

In certain embodiments, $R^{4B}$ is hydrogen, substituted or unsubstituted $C_{1-6}$ aliphatic, substituted or unsubstituted aryl, substituted or unsubstituted heterocyclyl, or substituted or unsubstituted heteroaryl. In certain embodiments, $R^{4B}$ is hydrogen. In certain embodiments, $R^{4B}$ is substituted or unsubstituted $C_{1-6}$ aliphatic. In certain embodiments, $R^{4B}$ is substituted or unsubstituted aryl. In certain embodiments, $R^{4B}$ is substituted or unsubstituted heterocyclyl. In certain embodiments, $R^{4B}$ is substituted or unsubstituted heteroaryl. In certain embodiments, $R^{4A}$ and $R^{4B}$ are joined together with the intervening atoms to form optionally substituted carbocyclyl, or optionally substituted heterocyclyl. In certain embodiments, $R^{4A}$ and $R^{4B}$ are joined together with the intervening atoms to form optionally substituted carbocyclyl. In certain embodiments, $R^{4A}$ and $R^{4B}$ are joined together with the intervening atoms to form optionally substituted heterocyclyl. In certain embodiments, RF and one instance of $R^{4A}$ are joined together with the intervening atoms to form optionally substituted heterocyclyl (e.g., substituted or unsubstituted, 5- to 10-membered monocyclic or bicyclic heterocyclyl ring, wherein one or two atoms in the heterocyclic ring are independently nitrogen, oxygen, or sulfur). In certain embodiments, $R_F$ and one instance of $R^{4B}$ are joined together with the intervening atoms to form optionally substituted heterocyclyl (e.g., substituted or unsubstituted, 5- to 10-membered monocyclic or bicyclic heterocyclyl ring, wherein one or two atoms in the heterocyclic ring are independently nitrogen, oxygen, or sulfur).

In certain embodiments, $L^3$ is substituted or unsubstituted carbocyclyene (e.g., substituted or unsubstituted 5- to 7-membered carbocyclyene). In certain embodiments, $L^3$ is substituted or unsubstituted arylene (e.g., substituted or unsubstituted phenylene or substituted or unsubstituted benzylene). In certain embodiments, $L^3$ is substituted or unsubstituted heterocyclylene (e.g., substituted or unsubstituted, 5- to 10-membered monocyclic or bicyclic heterocyclylene, wherein one or two atoms in the heterocyclic ring are independently nitrogen, oxygen, or sulfur).

Compounds of Formula (I) include linker X. In certain embodiments, X is —O—(CH$_2$)$_2$—. In certain embodiments, X is —C(($R^{3A}$)($R^{3B}$))$_s$—, wherein s is 0, 1, 2, 3, or 4. In certain embodiments, X is optionally substituted carbocyclyene (e.g., substituted or unsubstituted 5-to 7-membered carbocyclyene). In certain embodiments, X is optionally substituted heterocyclylene (e.g., substituted or unsubstituted, 5- to 10-membered monocyclic or bicyclic heterocyclylene, wherein one or two atoms in the heterocyclic ring are independently nitrogen, oxygen, or sulfur). In certain embodiments, X is optionally substituted arylene (e.g., substituted or unsubstituted phenylene or substituted or unsubstituted benzylene). In certain embodiments, s is 0, 1, 2, 3, or 4. In certain embodiments, $R^{3A}$ is hydrogen. In certain embodiments, $R^{3A}$ is substituted or unsubstituted $C_{1-6}$ aliphatic. In certain embodiments, $R^{3A}$ is substituted or unsubstituted heteroaliphatic. In certain embodiments, $R^{3A}$ is substituted or unsubstituted aryl (e.g., substituted or unsubstituted phenyl or substituted or unsubstituted benzyl). In certain embodiments, $R^{3A}$ is substituted or unsubstituted acyl (e.g., —C(=O)Me). In certain embodiments, $R^{3B}$ is hydrogen. In certain embodiments, $R^{3B}$ is substituted or unsubstituted $C_{1-6}$ aliphatic. In certain embodiments, $R^{3B}$ is substituted or unsubstituted heteroaliphatic. In certain embodiments, $R^{3B}$ is substituted or unsubstituted aryl (e.g., substituted or unsubstituted phenyl or substituted or unsubstituted benzyl). In certain embodiments, $R^{3B}$ is substituted or unsubstituted acyl (e.g., —C(=O)Me). In certain embodiments, $R^{3A}$ and $R^{3B}$ are joined together to form optionally substituted carbocyclyl (e.g., substituted or unsubstituted 5- to 7-membered carbocyclyl). In certain embodiments, $R^{3A}$ and $R^{3B}$ are joined together to form

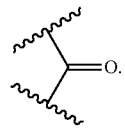 [SMILES: *C(*)=O]

In certain embodiments, $R_G$ and one instance of $R^{3A}$ or $R^{3B}$ are joined together with the intervening atoms to form optionally substituted heterocyclyl.

Exemplary compounds of Formula (I) include, but are not limited to:

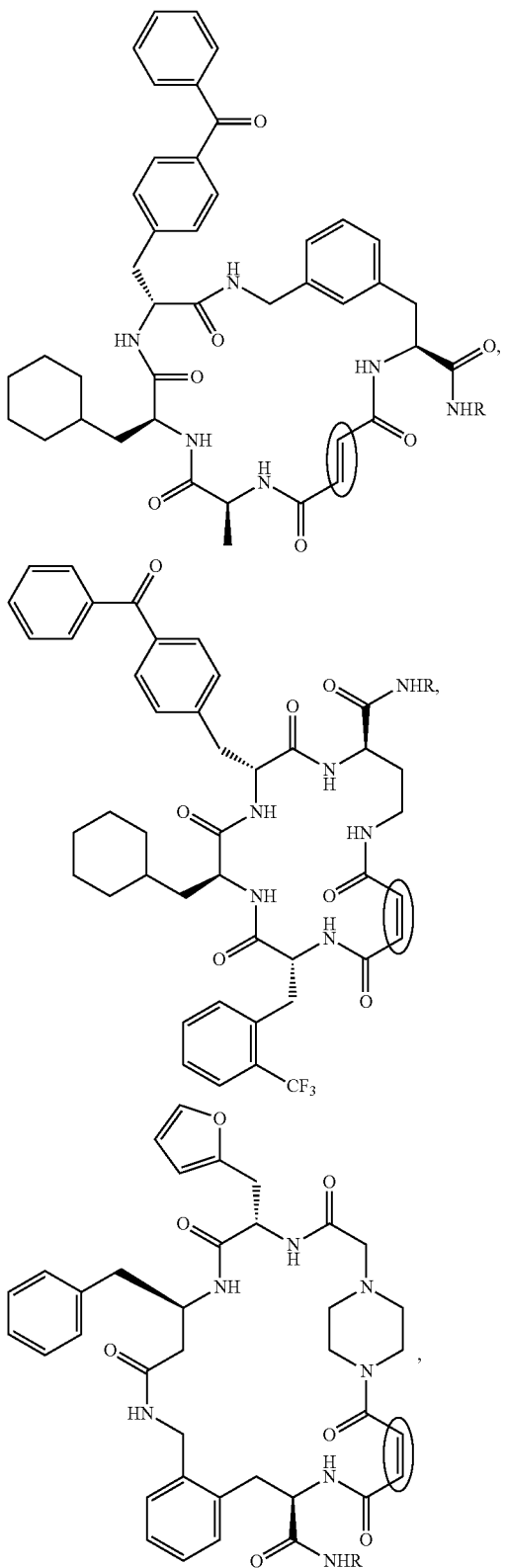

and pharmaceutically acceptable salts, solvates, hydrates, polymorphs, co-crystals, tautomers, stereoisomers, isotopically labeled derivatives, and prodrugs thereof, wherein R is —(CH$_2$)$_2$O(CH$_2$)$_2$NH$_2$.

Figure 3A:
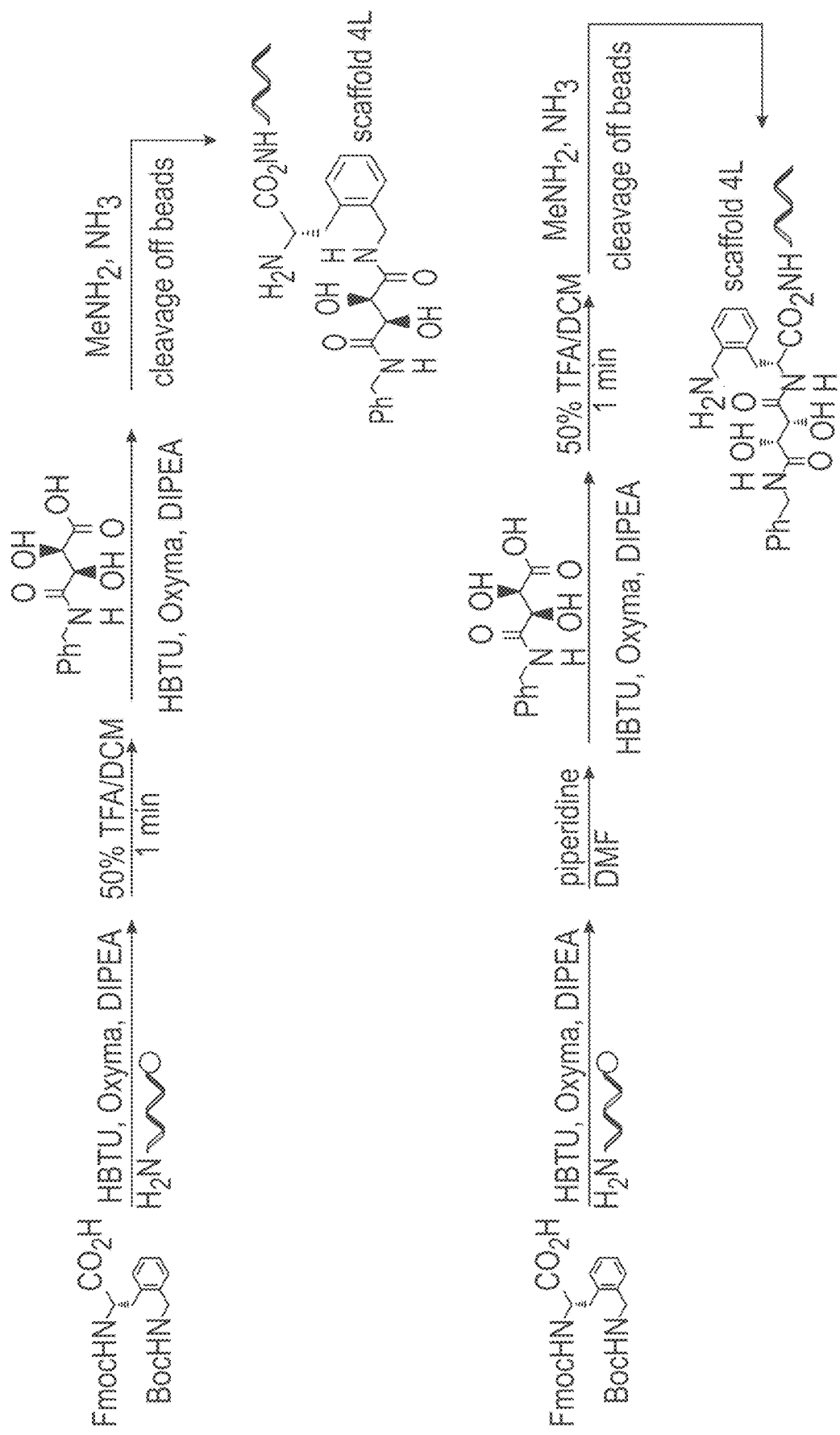
FIGS. 3A to 3C. Building blocks for the second-generation DNA-templated macrocycle library.
Figure 3B:
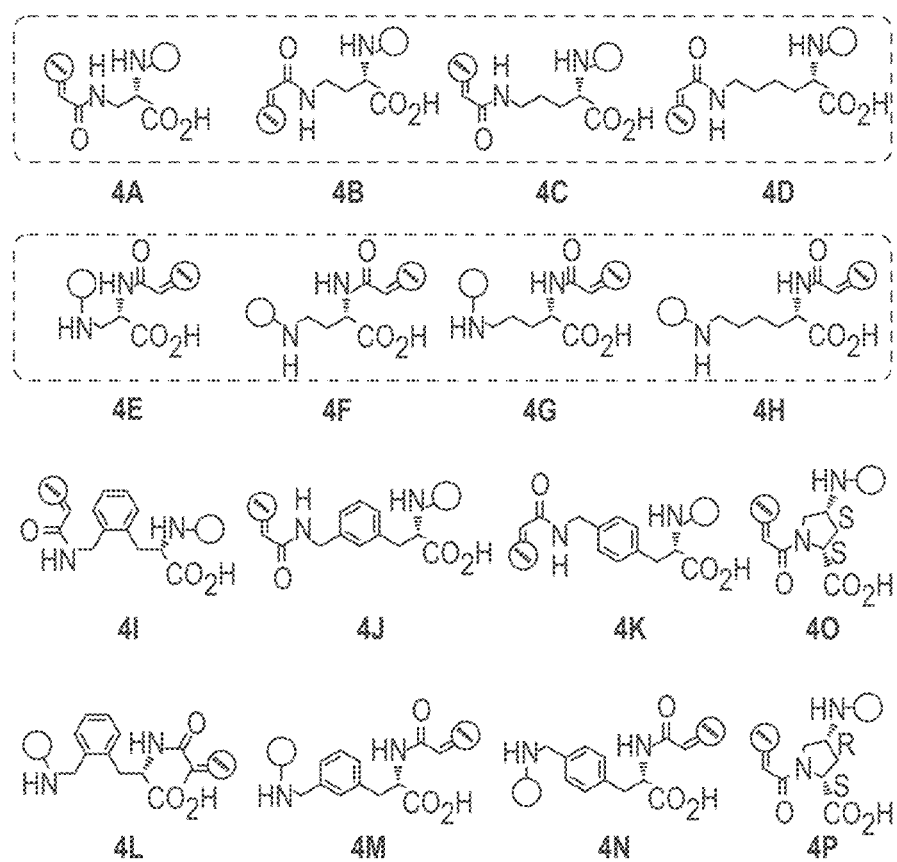
Figure 3B:
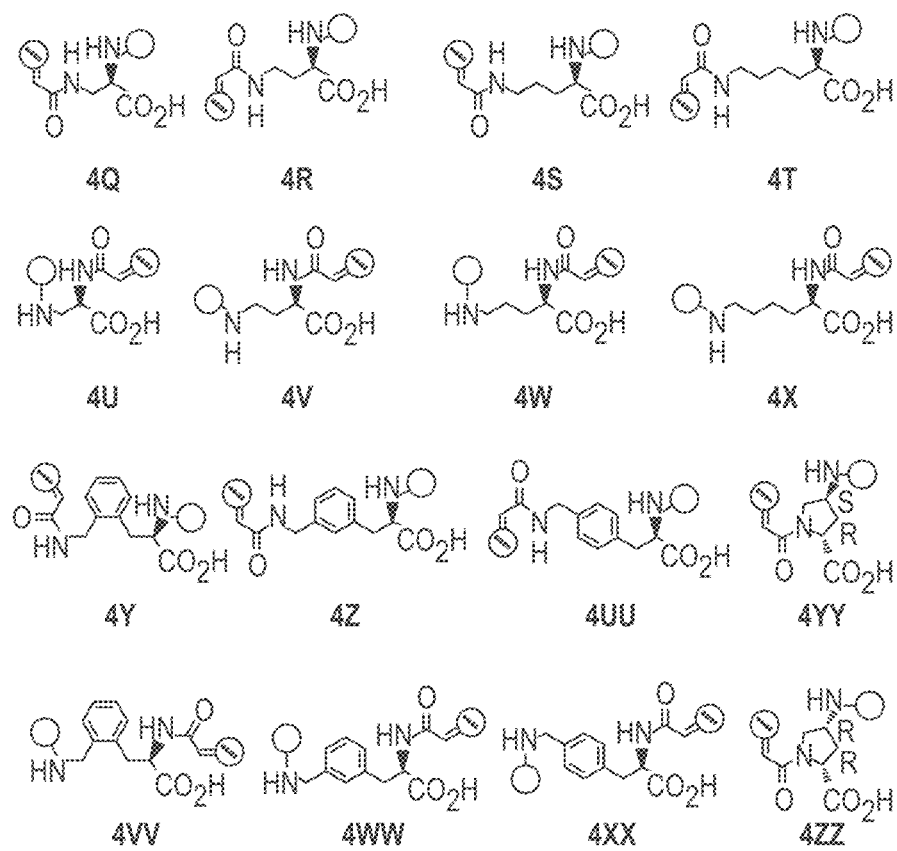
Figure 3C:
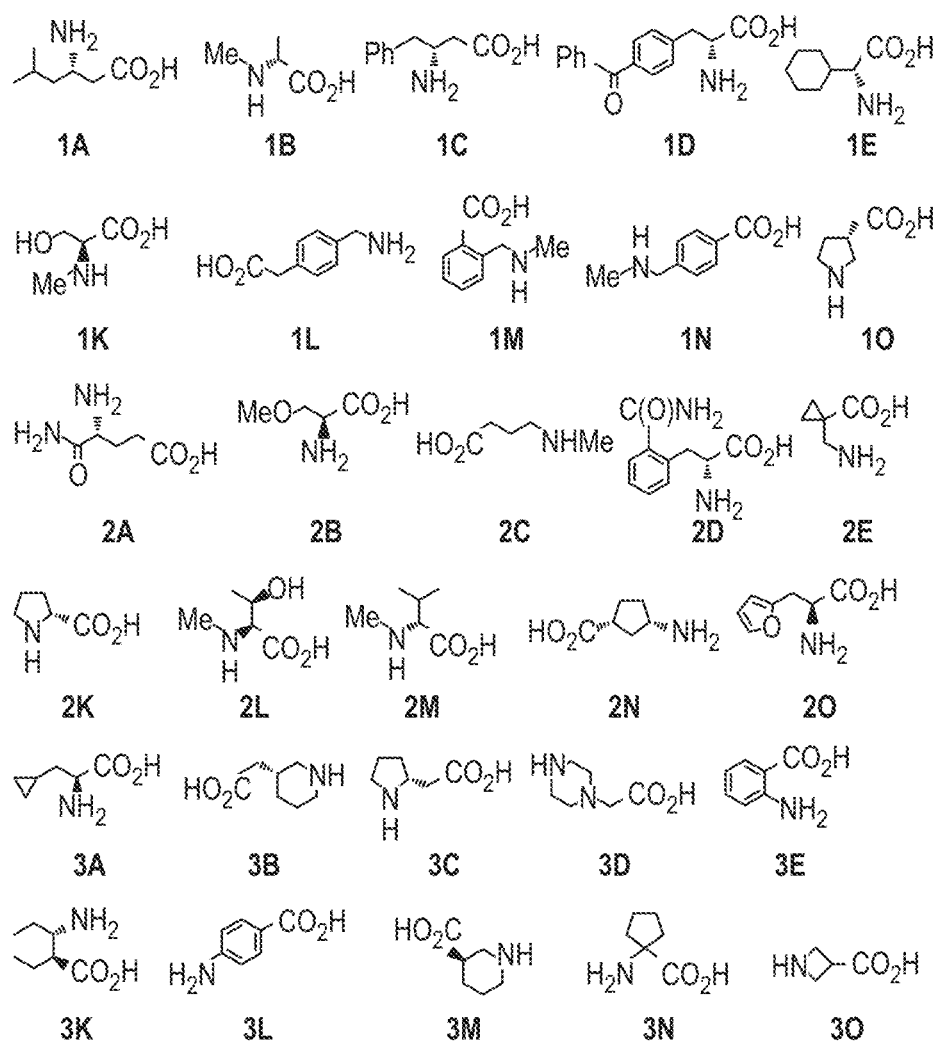
Figure 3C:
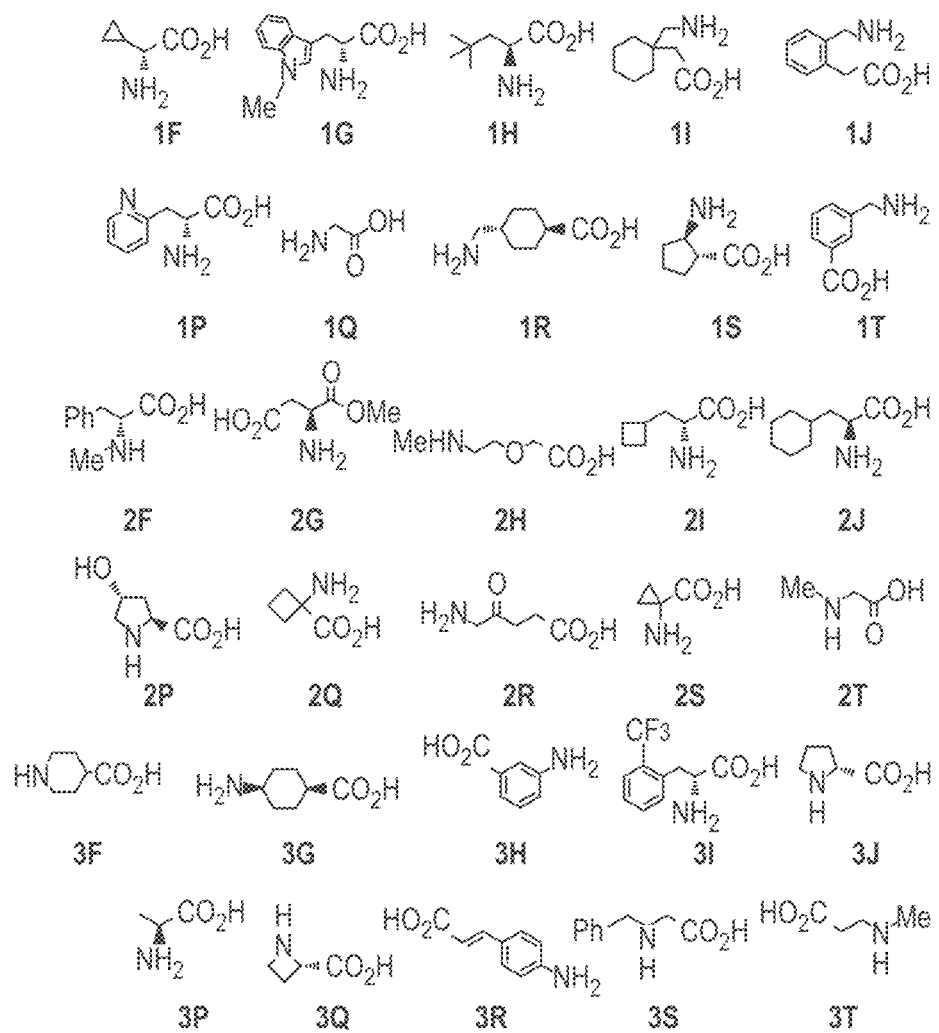
Figure 6A:
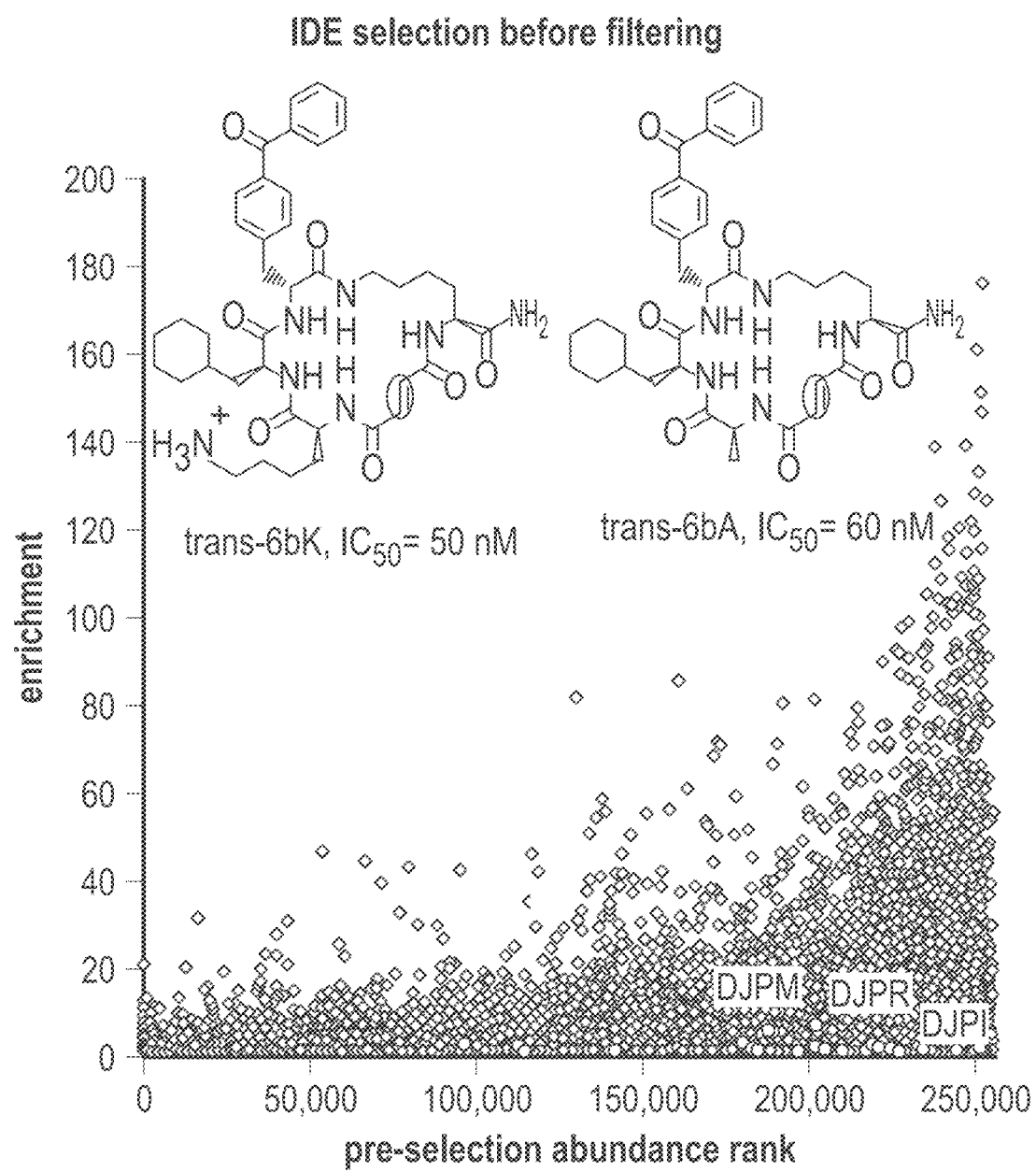
FIGS. 6A to 6D. In vitro selection of the 256,000-membered DNA-templated macrocycle library for binding to insulin-degrading enzyme (IDE).

In certain embodiments, a compound of Formula (I) is a product synthesized using the scaffold and method depicted in FIG. 1 and the building blocks depicted in FIGS. 3B and 3C. In certain embodiments, a compound of Formula (I) is a product synthesized using the scaffold depicted in FIG. 1 and the building blocks depicted in FIGS. 3B and 3C. In certain embodiments, a compound of Formula (I) is one of the compounds depicted in FIG. 6B. In certain embodiments, a compound of Formula (I) is one of the compounds disclosed in Table 28. In certain embodiments, a compound of Formula (I) is not one of the compounds depicted in FIG. 6A. In certain embodiments, a compound of Formula (I) is synthesized using DNA-templates described herein. In certain embodiments, a compound of Formula (I) is synthesized using DNA-template synthesis methods described herein. In certain embodiments, a compound of Formula (I) is synthesized using a template based on one or more codons from the orthogonal codon sets depicted in Tables 5 and/or 7. In certain embodiments, a compound of Formula (I) is synthesized using a template based on codons from an orthogonal codon set depicted in Table 5. In certain embodiments, a compound of Formula (I) is synthesized using a template based on an orthogonal codon set depicted in Table 5. In certain embodiments, a compound of Formula (I) is synthesized using a template based on an orthogonal codon set including one or more codons depicted in Table 7. In certain embodiments, a compound of Formula (I) is synthesized using a template based on codons from an orthogonal codon set depicted in Tables 5 and/or 7 and anticodons and/or reagents depicted in Table 6. In certain embodiments, a compound of Formula (I) is synthesized using a template with one or more anticodons and/or reagents depicted in Table 6.

In some embodiments, the macrocyclic IDE inhibitors provided herein include a C═C double bond in the macrocycle backbone. The position of this double bond is provided as ------ in Formula (I). In some embodiments, the macrocycle backbone C═C double bond is in the cis-configuration. The respective macrocycles are also referred to herein as cis-olefins. In some embodiments, the macrocycle backbone C═C double bond is in the trans-olefin configuration. The respective macrocycles are also referred to herein as trans-olefins. In some embodiments, a macrocyclic IDE inhibitor described herein is provided as a cis-olefin, without any significant or any detectable amount of the respective trans-olefin isomer. In some embodiments, an IDE inhibitor described herein is provided as a trans-olefin, without any significant or any detectable amount of the respective cis-olefin isomer. In some embodiments, an IDE inhibitor described herein is provided as a mixture of cis-olefin and trans-olefin isomers.

In some embodiments, a macrocyclic IDE inhibitor as described herein comprises a tag or label. In some embodiments, the tag is a fluorescent tag, for example, a fluorescent molecule or moiety that is conjugated, for example, covalently via a linker, to the macrocycle. In some embodiments, the fluorescent tag is a fluorescent protein tag, for example, a GFP tag, a YFP tag, an RFP tag, a BFP tag, or a tag comprising an enhanced fluorescent protein, such as eGFP. Other fluorescent proteins and protein tags are well known to those of skill in the art. In some embodiments, the tag is a cyane dye, or CyDye tag, for example, a Cy3 or C5 tag. In some embodiments, the tag is a fluorescein tag. In some embodiments, the tag is conjugated to the macrocycle structure via a linker. Additional suitable fluorescent tags are known to those of skill in the art and the invention is not limited in this respect. In some embodiments, the tag comprises a binding agent. In some embodiments, the binding agent is an antibody or an antigen-binding antibody fragment, a nanobody, an ScFv, an aptamer, or an adnectin. In some embodiments, the binding agent is a ligand, for example, biotin, polyhistidine, or FK506. Other binding agents are known to those of skill in the art and the invention is not limited in this respect. In some embodiments, the binding agent specifically binds an antigen, for example, an antigen immobilized on a solid surface or a cellular antigen, e.g., a cell-surface antigen. In some embodiments, the tag comprising a binding agent specifically binds to a particular cell or cell type, for example, to a pancreatic cell. In some embodiments, such binding-agent-tagged macrocycles target a specific site characterized by expression of the antigen bound by the binding agent, for example, after administration to a subject harboring such a target site. Antigens useful for targeting specific cells, cell types, tissues, or organs, for example, malignant cells, cell types, tissues, or organs, are well known to those of skill in the art and the invention is not limited in this respect.

The disclosure also embraces pharmaceutically acceptable salts of the macrocyclic IDE inhibitor disclosed herein, whether conjugated to a tag or not, as well as pharmaceutical compositions comprising the IDE inhibitors disclosed herein, or a pharmaceutically acceptable salt thereof. The disclosure also embraces tagged forms of the IDE inhibitors described herein, for example, IDE inhibitors that are covalently associated (e.g., covalently linked) to a DNA tag.

Methods for Preparing and/or Identifying Compounds of Formula (I)

Figure 26:
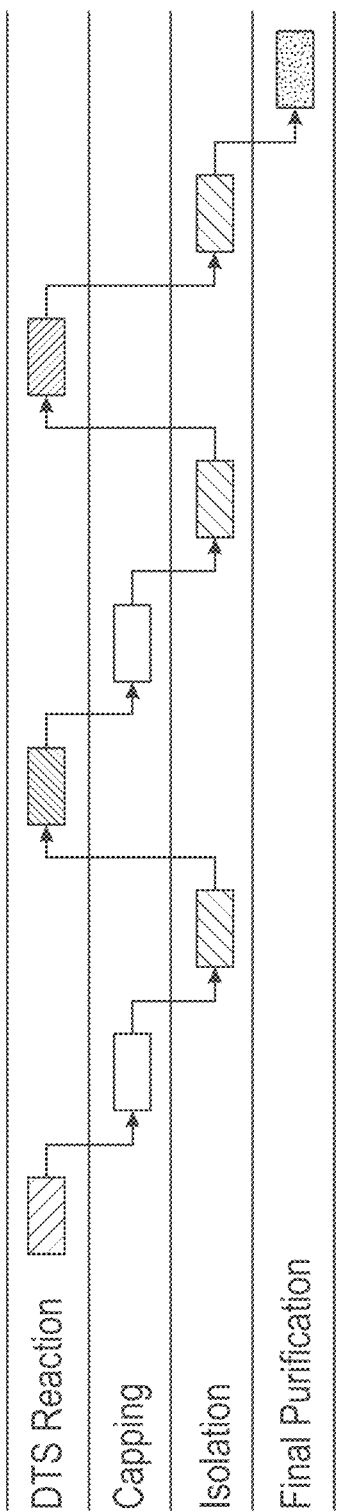
FIG. 26. Fundamental experimental improvements of the assembly of DNA-templated libraries of macrocycles.
Figure 26:
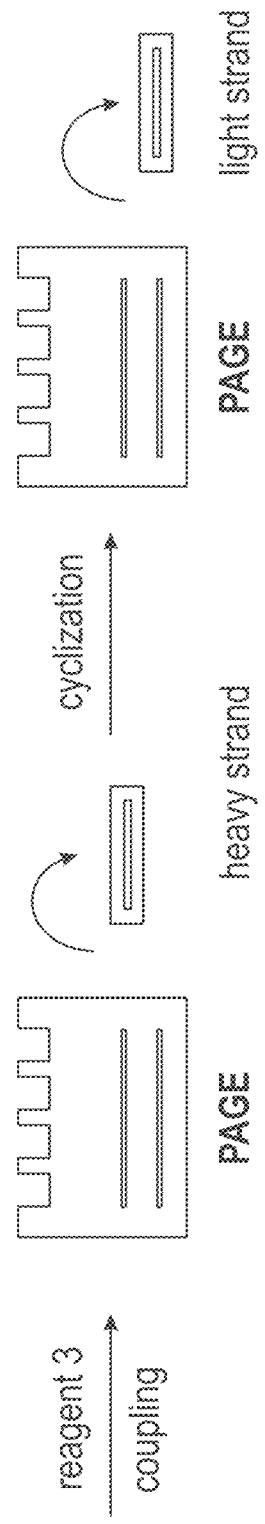

The present invention provides methods for preparing compounds of Formula (I) described herein. The present invention further provides methods for preparing macrocyclic IDE inhibitors of the present invention, e.g., following the synthetic steps depicted in FIG. 1 and/or FIG. 3A (e.g., according to a synthetic scheme described in Example 1 below). In one aspect, provided are methods of synthesizing a DNA-templated compound library, wherein each compound is encoded by a covalently associated DNA tag, comprising: creating a template of a combination of orthogonal codons interspaced by constant regions wherein the template is based on codons from the orthogonal codon sets depicted in FIG. 5 or 7; and running templated coupling reactions to assemble a compound based on the orthogonal codons. In certain embodiments, the method further comprises capping unreacted templates by acetylation. In certain embodiments, the method further comprises purifying the unreacted templates from the reacted templates. In certain embodiments, the purifying comprises capturing reacted templates with beads linked to a biotin-binder. In certain embodiments, the purifying comprises capturing reacted templates with streptavidin-linked beads. In certain embodiments, the purifying comprises using a solution-phase purification protocol. In certain embodiments, the purifying comprises using a PAGE purification protocol. In certain embodiments, the PAGE purification protocol is depicted in FIG. 26. In certain embodiments, the method further comprises macrocyclizing DNA-templated products from the reacted templates. In one aspect, provided are methods of identifying and/or selecting macrocyclic protease inhibitors (e.g., IDE inhibitors) from a DNA-templated compound library. In certain embodiments, the methods of identifying and/or selecting macrocyclic protease inhibitors comprise high thoroughput screening of a DNA-templated compound library using the DNA tags on the compounds in the library. In certain embodiments, the DNA-templated compound library is synthesized using a chaotropic buffer. In certain embodiments, the chaotropic buffer is used in the synthesis step. In certain embodiments, the chaotropic buffer is used in the screening step. In certain embodiments, the synthesized DNA-templated compound library is isolated from dilute solution using a chaotropic buffer. In certain embodiments, synthesized template-linked macrocycles and/or intermediates of the DNA-templated compound library are isolated from dilute solution using a chaotropic buffer. In certain embodiments, the chaotropic buffer comprises saturated aqueous guanidine hydrochloride (4:6 ratio with isopropanol). In certain embodiments, the chaotropic buffer is aqueous guanidine hydrochloride (4:6 ratio with isopropanol). In certain embodiments, the pH of the chaotropic buffer is between 5.0 and 8.0. In certain embodiments, the pH of the chaotropic buffer is between 6.0 and 7.0. In certain embodiments, the pH of the chaotropic buffer is 6.4.

Codon Set

The present invention provides nucleic acid templates (e.g., codons from orthogonal codon sets depicted in Tables 5 and/or 7), which one or more nucleic acid templates optionally have a reactive unit associated therewith; and 2) contacting the one or more nucleic acid templates with one or more transfer units designed to have a first moiety, an anti-codon which hybridizes to a sequence of the nucleic acid, and is associated with a second moiety, a reactive unit, which includes specific functionality, a building block, reactant, etc. for the compound to be synthesized. In certain embodiments, the transfer unit comprises one moiety incorporating the hybridization capability of the anti-codon unit and the chemical functionality of the reaction unit. In certain embodiments, the templates comprise orthogonal codon sets depicted in Tables 5 and/or 7.

The nucleic acid templates used in the present invention are made of DNA, RNA, a hybrid of DNA and RNA, or a derivative of DNA and RNA, and may be single- or double-stranded. The sequence of the template is used in the inventive method to encode the synthesis of a chemical compound, preferably a compound that is not, or does not resemble, a nucleic acid or nucleic acid analog (e.g., an unnatural polymer or a small molecule). In certain embodiments, the method described herein does not encode the synthesis of peptides or proteins.

In the case of certain unnatural polymers, the nucleic acid template is used to align the monomer units in the sequence they will appear in the polymer and to bring them in close proximity with adjacent monomer units along the template so that they will react and become joined by a covalent bond. In the case of a small molecule, the template is used to bring particular reactants within proximity of the small molecule scaffold in order that they may modify the scaffold in a particular way. In certain other embodiments, the template can be utilized to generate non-natural polymers by PCR amplification of a synthetic DNA template library consisting of a random region of nucleotides. In certain embodiments, the templates may be used to synthesize one molecule at a time or may be used to synthesize thousands to millions of compounds using combinatorial methods.

In certain embodiments, the template is 10 to 10,000 bases long. In certain embodiments, the template is between 10 and 1,000 bases long. The length of the template will of course depend on the length of the codons, complexity of the library, length of the unnatural polymer to be synthesized, complexity of the small molecule to be synthesized, use of constant regions, etc. The nucleic acid sequence may be prepared using any method known in the art to prepare nucleic acid sequences. These methods include both in vivo and in vitro methods including PCR, plasmid preparation, endonuclease digestion, solid phase synthesis, in vitro transcription, strand separation, etc. In certain embodiments, the nucleic acid template is synthesized using an automated DNA synthesizer.

In certain embodiments, a compound is a product synthesized based on a template using the orthogonal codon set depicted in Table 5 and/or Table 7. In certain embodiments, a compound is a product synthesized based on a template using the codons from the orthogonal codon sets depicted in Table 5 and/or Table 7. In certain embodiments, a compound is a product synthesized based on a template using the codons from the orthogonal codon sets depicted in Table 5 and/or Table 7 and anticodons and/or reagents depicted in Table 6. In certain embodiments, a compound is a product synthesized based on a template using the orthogonal codon set depicted in Table 5. In certain embodiments, a compound of Formula (I) is a product synthesized based on a template using the orthogonal codon set depicted in Table 5. In certain embodiments, the codons are interspaced with constant regions. In certain embodiments, the codons are not interspaced with constant regions.

In certain embodiments, a compound of Formula (I) is a product synthesized based on a template using the following orthogonal codon set (SEQ ID NO: 1):

In certain embodiments, the fourth building block codon is a codon selected from the group consisting of $4A_2$ through $4P_4$ depicted below. See Table 7.

In certain embodiments, a first one of the at least three building block codons is selected from the codons 1A-1T depicted below; a second one of the at least three building block codons is selected from the codons 2A-2T depicted below; and a third one of the at least three building block codons is selected from the codons 3A-3T depicted below. In certain embodiments, the first building block codon is a codon selected from the group consisting of 1A-1T, 2A-1T, 3A-1T, 4A through 4ZZ, and $4A_2$ through $4P_4$ depicted below. In certain embodiments, the second building block codon is a codon selected from the group consisting of 1A-1T, 2A-1T, 3A-1T, 4A through 4ZZ, and $4A_2$ through $4P_4$ depicted below. In certain embodiments, the third building block codon is a codon selected from the group consisting of 1A-1T, 2A-1T, 3A-1T, 4A through 4ZZ, and $4A_2$ through $4P_4$ depicted below. In certain embodiments, the fourth building block codon is a codon selected from the group consisting of 1A-1T, 2A-1T, 3A-1T, 4A through 4ZZ, and $4A_2$ through $4P_4$ depicted below.

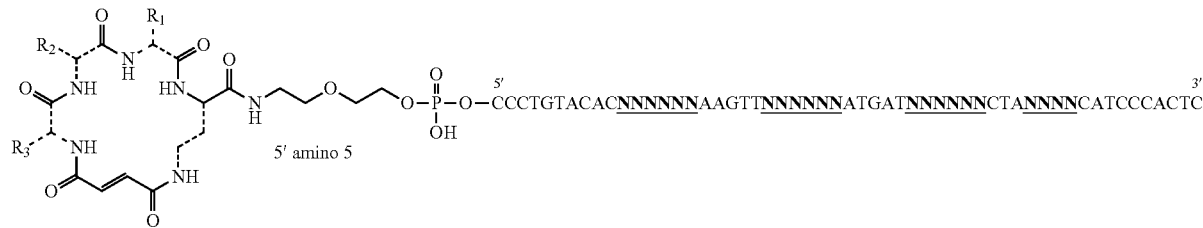

```
left primer                                                              right primer
(SEQ ID             constant            constant           constant codon 4    (SEQ ID
NO: 2)     codon 3  region 3  codon 2   region 2  codon 1  region 1 (scaffold) NO: 3)

CCCTGTACAC NNNNNN   AAGTT     NNNNNN    ATGAT     NNNNNN   CTA       NNNN      CATCCCACTC
```

In certain embodiments, the template comprises a fourth building block codon that identifies a scaffold at the 5' end of the template. In certain embodiments, the template comprises a fourth building block codon that identifies a bis-amino acid scaffold at the 5' end of the template. In certain embodiments, the fourth building block codon is a codon selected from the group consisting of 1 A-1T, 2A-1T, 3A-1T, and 4A through 4ZZ depicted below. In certain embodiments, the fourth building block codon is a codon selected from the group consisting of 4A through 4ZZ depicted below. In certain embodiments, the fourth building block codon is not a codon in the group consisting of 4A through 4H depicted below.

In certain embodiments, the fourth building block codon is a codon selected from the group consisting of 4U through 4ZZ depicted below. See Table 5.

In certain embodiments, a compound of Formula (I) is synthesized based on a template using the orthogonal codon set depicted in Table 7. In certain embodiments, the template comprises a fourth building block codon that identifies a bis-amino acid scaffold at the 5' end of the template. In

| | codon |
|---|---|
| 1A | GGCTTT |
| 1B | AGGCTT |
| 1C | GCCAAA |
| 1D | AGGAAC |
| 1E | CGTATG |
| 1F | CATGAG |
| 1G | GAGACA |
| 1H | CTGTAG |
| 1I | TAGCTG |
| 1J | TCTCAG |
| 1K | AGAGCT |

| codon | |
|---|---|
| 1L | CGAACA |
| 1M | GCTCTT |
| 1N | TCTGCT |
| 1O | TCGATC |
| 1P | GACTGA |
| 1Q | GCAGTA |
| 1R | GCGTAT |
| 1S | GGAATC |
| 1T | GCTTCA |
| 2A | GCTGAA |
| 2B | GTCGAT |
| 2C | GATTGC |
| 2D | GGACTT |
| 2E | ACGGAT |
| 2F | TCGAGT |
| 2G | GCAAGA |
| 2H | CTTGTG |
| 2I | GGCTAA |
| 2J | AGGACT |
| 2K | TCATGC |
| 2L | AGTCTG |
| 2M | CTGGAA |
| 2N | ATTGCC |
| 2O | TCTCGA |
| 2P | CCTTAG |
| 2Q | TAGCCT |
| 2R | CAGTGA |
| 2S | GAGCAA |
| 2T | GAAGCT |
| 3A | ATCGGA |
| 3B | TGTGCA |
| 3C | AGACTC |
| 3D | CTTCAG |
| 3E | AGTCGA |
| 3F | ATGACG |
| 3G | CAACCT |
| 3H | TCCGTA |
| 3I | GCTTAC |
| 3J | TCTACG |

| codon | |
|---|---|
| 3K | GTGTCA |
| 3L | CACTAC |
| 3M | CTGAAC |
| 3N | CTAGTC |
| 3O | CGGTTT |
| 3P | CCCATT |
| 3Q | CTCTCT |
| 3R | TTACCG |
| 3S | TGCTGT |
| 3T | CCTTGT |
| 4A | TCCA |
| 4B | GTTG |
| 4C | TTAA |
| 4D | TTGT |
| 4E | CTCA |
| 4F | GGAA |
| 4G | TATA |
| 4H | ATTT |
| 4I | GTAG |
| 4J | TAGA |
| 4K | GTTT |
| 4L | TTTT |
| 4M | TTTG |
| 4N | AGGT |
| 4O | AGGA |
| 4P | GTAA |
| 4Q | ATTA |
| 4R | GTTA |
| 4S | GATT |
| 4T | ATAG |
| 4U | ATCA |
| 4V | AAAA |
| 4W | AAAG |
| 4X | AATT |
| 4Y | GATA |
| 4Z | GGTT |
| 4UU | GTGA |
| 4VV | TGTG |

| codon | |
|---|---|
| 4WW | AATG |
| 4XX | AAGT |
| 4YY | AATA |
| 4ZZ | AAGA |
| 4A$_2$ | AAAT |
| 4B$_2$ | ACCA |
| 4C$_2$ | AGCT |
| 4D$_2$ | ACGA |
| 4E$_2$ | ACGT |
| 4F$_2$ | ACTA |
| 4G$_2$ | ACTT |
| 4H$_2$ | AGTA |
| 4I$_2$ | AGTT |
| 4J$_2$ | ATAA |
| 4K$_2$ | ATAT |
| 4L$_2$ | ATGA |
| 4M$_2$ | ATGT |
| 4N$_2$ | CACA |
| 4O$_2$ | CAGA |
| 4P$_2$ | CATA |
| 4A$_3$ | CATT |
| 4B$_3$ | CCAA |
| 4C$_3$ | CCTA |
| 4D$_3$ | CCTT |
| 4E$_3$ | CGAA |
| 4F$_3$ | CGTA |
| 4G$_3$ | CGTT |
| 4H$_3$ | CTGA |
| 4I$_3$ | CTGT |
| 4J$_3$ | CTTA |
| 4K$_3$ | CTTT |
| 4L$_3$ | GACA |
| 4M$_3$ | GAGA |
| 4N$_3$ | GCTA |
| 4O$_3$ | GGTA |
| 4P$_3$ | TAAA |
| 4A$_4$ | TAAT |
| 4B$_4$ | TATT |
| 4C$_4$ | TCAA |
| 4D$_4$ | TCCT |
| 4E$_4$ | TCGA |
| 4F$_4$ | TCGT |
| 4G$_4$ | TCTA |
| 4H$_4$ | TCTT |
| 4I$_4$ | TGCA |
| 4J$_4$ | TGGA |
| 4K$_4$ | TGTA |
| 4L$_4$ | TGTT |
| 4M$_4$ | TTAT |
| 4N$_4$ | TTCA |
| 4O$_4$ | TTGA |
| 4P$_4$ | TTTA |

In certain embodiments, the template of the combination of orthogonal codons comprises: multiple-residue primer-binding sites; at least three building block codons that determine the identity of three building blocks; and at least a fourth building block codon that identifies a compound scaffold at the 5' end of the template. In certain embodiments, the template comprises two or more building block codons that determine the identity of two compound building blocks. In certain embodiments, the template comprises two building block codons that determine the identity of two macrocycle building blocks. In certain embodiments, the template comprises three building block codons that determine the identity of three compound building blocks. In certain embodiments, the template comprises three building block codons that determine the identity of three macrocycle building blocks. In certain embodiments, the template comprises a fourth building block codon that identifies a compound scaffold at the 5' end of the template. In certain embodiments, the template comprises a fourth building block codon that identifies a bis-amino acid scaffold at the 5' end of the template.

In certain embodiments, a compound of Formula (I) is a product synthesized based on a template using one or more anticodons and/or reagents depicted in Table 6. In certain embodiments, the template comprises reagents 1, 2, and 3 depicted below. In certain embodiments, the template comprises reagents 1, 2, and 3 depicted in Table 6. In certain embodiments, the template comprises reagents 1-3 depicted below. In certain embodiments, the template comprises reagents 1-3 depicted in Table 6. In certain embodiments, the template comprises anticodons 1A-1T for DTS reagent 5'-3' depicted below. In certain embodiments, the template comprises anticodons 1A-1T for DTS reagent 5'-3' depicted in Table 6. In certain embodiments, the template comprises anticodons 2A-2T for DTS reagent 5'-3' depicted below. In certain embodiments, the template comprises anticodons 2A-2T for DTS reagent 5'-3' depicted in Table 6. In certain embodiments, the template comprises anticodons 3A-3T for DTS reagent 5'-3' depicted below. In certain embodiments, the template comprises anticodons 3A-3T for DTS reagent 5'-3' depicted in Table 6.

Reagents 1 and 2

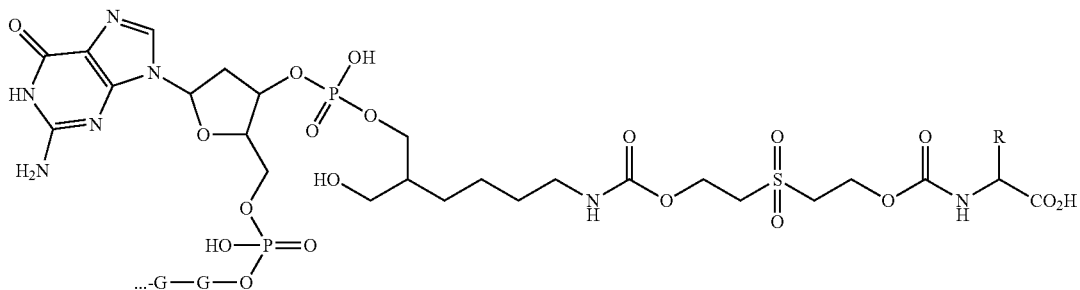

3' C7 Amino modifier

| | DTS reagent 5'-3' (SEQ ID NOs: 4-23) | | DTS reagent 5'-3' (SEQ ID NOs: 24-43) |
|---|---|---|---|
| 1A | TAGAAAGCCATAGGG7 | 2A | CATTTCAGCAAAGGG7 |
| 1B | TAGAAGCCTATAGGG7 | 2B | CATATCGACAAAGGG7 |
| 1C | TAGTTTGGCATAGGG7 | 2C | CATGCAATCAAAGGG7 |
| 1D | TAGGTTCCTATAGGG7 | 2D | CATAAGTCCAAAGGG7 |
| 1E | TAGCATACGATAGGG7 | 2E | CATATCCGTAAAGGG7 |
| 1F | TAGCTCATGATAGGG7 | 2F | CATACTCGAAAAGGG7 |
| 1G | TAGTGTCTCATAGGG7 | 2G | CATTCTTGCAAAGGG7 |
| 1H | TAGCTACAGATAGGG7 | 2H | CATCACAAGAAAGGG7 |
| 1I | TAGCAGCTAATAGGG7 | 2I | CATTTAGCCAAAGGG7 |
| 1J | TAGCTGAGAATAGGG7 | 2J | CATAGTCCTAAAGGG7 |
| 1K | TAGAGCTCTATAGGG7 | 2K | CATGCATGAAAAGGG7 |
| 1L | TAGTGTTCGATAGGG7 | 2L | CATCAGACTAAAGGG7 |
| 1M | TAGAAGAGCATAGGG7 | 2M | CATTTCCAGAAAGGG7 |
| 1N | TAGAGCAGAATAGGG7 | 2N | CATGGCAATAAAGGG7 |
| 1O | TAGGATCGAATAGGG7 | 2O | CATTCGAGAAAAGGG7 |
| 1P | TAGTCAGTCATAGGG7 | 2P | CATCTAAGGAAAGGG7 |
| 1Q | TAGTACTGCATAGGG7 | 2Q | CATAGGCTAAAAGGG7 |
| 1R | TAGATACGCATAGGG7 | 2R | CATTCACTGAAAGGG7 |
| 1S | TAGGATTCCATAGGG7 | 2S | CATTTGCTCAAAGGG7 |
| 1T | TAGTGAAGCATAGGG7 | 2T | CATAGCTTCAAAGGG7 |

Reagents 3

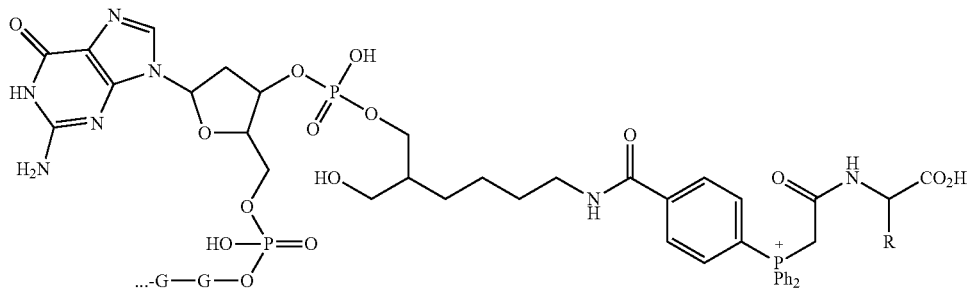

3' C7 Amino modifier

| | DTS reagent 5'-3' (SEQ ID NOs: 44-63) |
|---|---|
| 3A | 888CTTTCCGATGTAGGG7 |
| 3B | 888CTTTGCACAGTAGGG7 |
| 3C | 888CTTGAGTCTGTAGGG7 |
| 3D | 888CTTCTGAAGGTAGGG7 |
| 3E | 888CTTTCGACTGTAGGG7 |
| 3F | 888CTTCGTCATGTAGGG7 |
| 3G | 888CTTAGGTTGGTAGGG7 |
| 3H | 888CTTTACGGAGTAGGG7 |
| 3I | 888CTTGTAAGCGTAGGG7 |
| 3J | 888CTTCGTAGAGTAGGG7 |
| 3K | 888CTTTGACACGTAGGG7 |
| 3L | 888CTTGTAGTGGTAGGG7 |
| 3M | 888CTTGTTCAGGTAGGG7 |

| | |
|---|---|
| 3N | 888CTTGACTAGGTAGGG7 |
| 3O | 888CTTAAACCGGTAGGG7 |
| 3P | 888CTTAATGGGGTAGGG7 |
| 3Q | 888CTTAGAGAGGTAGGG7 |
| 3R | 888CTTCGGTAAGTAGGG7 |
| 3S | 888CTTACAGCAGTAGGG7 |
| 3T | 888CTTACAAGGGTAGGG7 |

7 = 3' amino C7 (Glen Research);
8 = spacer-18 (Glen Research, 6 PEG units)

The present invention provides templates for DNA-templated synthesis of products described herein comprising a combination of orthogonal codons interspaced by constant regions comprising: multiple-residue primer-binding sites; at least three building block codons that determine the identity of three building blocks; and at least a fourth building block codon that identifies a compound scaffold at the 5' end of the template. In certain embodiments, the templates for DNA-templated synthesis of products described herein comprise a combination of orthogonal codons interspaced by constant regions comprising: multiple-residue primer-binding sites; at least three building block codons that determine the identity of three macrocycle building blocks; and at least a fourth building block codon that identifies a bis-amino acid scaffold at the 5' end of the template.

In certain embodiments, the template of the combination of orthogonal codons comprises: multiple-residue primer-binding sites; at least three building block codons that determine the identity of three macrocycle building blocks; and at least a fourth building block codon that identifies a bis-amino acid scaffold at the 5'-end of the template. In certain embodiments, the template of the combination of orthogonal codons comprises 10-mer to 100-mer primer-binding sites. In certain embodiments, the template of the combination of orthogonal codons comprises 50-mer, 40-mer, 30-mer, 25-mer, 20-mer, 15-mer, or 10-mer primer-binding sites. In certain embodiments, the template of the combination of orthogonal codons comprises 10-mer primer-binding sites. In certain embodiments, the template comprises three building block codons that determine the identity of three macrocycle building blocks. In certain embodiments, the template comprises a fourth building block codon that identifies a bis-amino acid scaffold at the 5' end of the template. In certain embodiments, the fourth building block codon is a codon that determines the identity of a building block selected from the group consisting of 4A through 4ZZ depicted in FIG. 3B. In certain embodiments, the fourth building block codon is not a codon in the group that determines the identity of a building block selected from the group consisting of 4A through 4H depicted in FIG. 3B. In certain embodiments, the fourth building block codon is a codon that determines the identity of a building block selected from the group consisting of 4I through 4T depicted in FIG. 3B. In certain embodiments, the fourth building block codon is a codon that determines the identity of a building block selected from the group consisting of 4I through 4ZZ depicted in FIG. 3B. In certain embodiments, the fourth building block codon is a codon that determines the identity of a building block selected from the group consisting of 4U through 4ZZ depicted in FIG. 3B. In certain embodiments, a first one of the at least three building block codons is selected from the codons that determine the identity of building blocks 1A-1T depicted in FIG. 3C; a second one of the at least three building block codons is selected from the codons that determine the identity of building blocks 2A-2T depicted in FIG. 3C; and a third one of the at least three building block codons is selected from the codons that determine the identity of building blocks 3A-3T depicted in FIG. 3C.

In certain embodiments, a first one of the at least three building block codons is selected from the codons that determine the identity of building blocks 1A-1T depicted in FIG. 3C. In certain embodiments, a second one of the at least three building block codons is selected from the codons that determine the identity of building blocks 2A-2T depicted in FIG. 3C. In certain embodiments, a third one of the at least three building block codons is selected from the codons that determine the identity of building blocks 3A-3T depicted in FIG. 3C.

In certain embodiments, the template of the combination of orthogonal codons comprises: 10-mer primer-binding sites; three building block codons that determine the identity of three macrocycle building blocks; and a fourth building block codon that identifies a bis-amino acid scaffold at the 5' end of the template.

In certain embodiments, the template is an orthogonal codon set depicted in Table 5. In certain embodiments, the template is synthesized using one or more anticodons and/or reagents depicted in Table 6. In certain embodiments, the template is synthesized using one or more anticodons attached to reagents depicted in Table 6. In certain embodiments, the template is an orthogonal codon set including one or more codons depicted in Table 7. In certain embodiments, the template is an orthogonal codon set including one or more codons depicted in Tables 5 and/or 7. In certain embodiments, the template is an orthogonal codon set including one or more codons and/or anticodons depicted in Tables 5, 6, and/or 7.

Methods of Using Compounds of Formula (I)

In one aspect, this invention provides methods of using compounds described herein. In one aspect, this invention provides methods of using compounds described herein (e.g., compounds of Formula (I)). In another aspect, this invention provides methods of treating a disease (e.g., a disease associated with aberrant enzyme activity (e.g., aberrant protease and/or kinase activity (e.g., aberrant activity of an insulin degrading enzyme (IDE)), impaired insulin signaling, or insulin resistance, the method comprising administering to a subject in need thereof a therapeutically effective amount of a compound described herein. In certain embodiments, the aberrant protease activity is aberrant IDE activity. In another aspect, this invention provides in vitro or in vivo methods of inhibiting the activity of an insulin degrading enzyme (IDE). Such methods are useful for inhibiting IDE, for example, in cell culture or in a subject. In some embodiments, inhibition of IDE results in a stabilization (e.g., greater half-life) of insulin and in improved (e.g., increased) insulin signaling. Accordingly, the in vivo methods of using the macrocyclic IDE inhibitors provided herein are useful in improving insulin signaling in subjects having a disease associated with IDE activity, or impaired insulin signaling, for example, in patients exhibiting metabolic syndrome or diabetes (e.g., Type I or Type II diabetes). In certain embodiments, the subject exhibits impaired insulin signaling or insulin resistance. In some embodiments, the disease treated is diabetes. In some embodiments, the disease treated is metabolic syndrome.

In some embodiments, the in vitro or in vivo methods of inhibiting the activity of IDE comprise contacting an IDE with an IDE inhibitor provided herein in an amount effective to inhibit the activity of the IDE. In some embodiments, an amount of an IDE inhibitor effective to inhibit the activity of IDE comprises an amount that effects a significant decrease, for example, a statistically significant decrease, in IDE activity as compared to IDE activity in the absence of the IDE inhibitor. In some embodiments, an amount of an IDE inhibitor effective to inhibit the activity of IDE comprises an amount that results in an inhibition of IDE activity to less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the activity in the absence of the compound. In some embodiments, an amount of an IDE inhibitor effective to inhibit the activity of IDE comprises an amount that results in an inhibition of IDE activity to less than about 50% of the IDE activity as compared to the activity in the absence of the compound.

In some embodiments, an IDE inhibitory macrocyclic compound provided herein is used to inhibit IDE activity in vivo. In such embodiments, the IDE inhibitor is administered to a subject, for example, in the form of a pharmaceutically acceptable salt or as part of a pharmaceutical composition. In some embodiments, the subject is human. In some embodiments, the subject is an animal, for example, an experimental animal, e.g., an animal model of diabetes. In some embodiments, the animal is a mammal, for example, a rodent (e.g., a mouse, a rat, a hamster), a dog, a cat, a cattle, a goat, a sheep, or a horse.

In some embodiments, an in vivo method of inhibiting IDE is provided that comprises administering an IDE inhibitor provided herein, or a pharmaceutically acceptable composition thereof, to a subject in an amount effective to reduce IDE activity in the subject to less than about 75%, less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the IDE activity in the absence of the compound.

The present disclosure also provides pharmaceutical compositions comprising a compound described herein and optionally a pharmaceutically acceptable excipient. In certain embodiments, a compound described herein is a compound of Formula (I), or a pharmaceutically acceptable salt thereof, and a pharmaceutically acceptable excipient.

Other aspects of this invention provide methods of using a macrocyclic IDE inhibitor as described herein in the production of pharmaceutical compositions, or in the manufacture of a medicament, for the reduction of IDE activity. Some aspects of this invention provide methods of using a macrocyclic IDE inhibitor as described herein in the production of a pharmaceutical composition, or in the manufacture of a medicament, for the treatment, prophylaxis, and/or amelioration of a disease or disorder associated with aberrant IDE activity, impaired insulin signaling, or insulin resistance, for example, diabetes, or metabolic syndrome. In some embodiments, the pharmaceutical composition or the medicament is for the treatment, prophylaxis, and/or amelioration of a disease or disorder associated with aberrant IDE activity, impaired insulin signaling, or insulin resistance, for example, diabetes, or metabolic syndrome, wherein the disease or disorder is exhibited by a subject also exhibiting one or more symptoms of a neurological disease (e.g., Alzheimer's disease). Some aspects of this invention relate to the use of a macrocyclic IDE inhibitor as described herein for the production of pharmaceutical compositions which can be used for treating, preventing, or ameliorating diseases responsive to the inhibition of IDE activity, for example, diabetes or metabolic syndrome.

The amount of a macrocyclic IDE inhibitor as described herein that is required for effective inhibition of IDE in a subject or in vitro, or for the treatment or amelioration of a disease associated with IDE activity will vary from subject to subject, depending on a variety of factors, including, for example, the disorder being treated and the severity of the disorder, or the level of IDE activity in the subject, the activity of the specific macrocyclic IDE inhibitor administered, the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well known in the medical arts. The macrocyclic IDE inhibitor described herein are preferably formulated in dosage unit form for ease of administration and uniformity of dosage. It will be understood that in some embodiments involving administration of a macrocyclic IDE inhibitor described herein to a human patient, the total daily dose may be determined by the attending physician based on sound medical judgment.

In some embodiments, a macrocyclic IDE inhibitor described herein is formulated into a pharmaceutically acceptable composition comprising the IDE inhibitor, or a pharmaceutically acceptable salt thereof, and optionally a pharmaceutically acceptable carrier. In some embodiments, after formulation with an appropriate pharmaceutically acceptable carrier of a desired dosage, the pharmaceutical composition can be administered to a subject, for example, a human subject via any suitable route, for example, orally, rectally, parenterally, intracisternally, intravaginally, intraperitoneally, topically (as by powders, ointments, or drops), bucally, as an oral or nasal spray, or the like.

In certain embodiments, a macrocyclic IDE inhibitor described herein, for example, in Formula (I), is administered to a subject, for example, orally or parenterally, at a dosage level of about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg of the subject's body weight per day, one or more times a day, to obtain the desired therapeutic effect or the desired level of IDE inhibition. In some embodiments, the daily dosage is delivered in three separate doses per day, two separate doses per day, or in a single dose per day. In other embodiments, a macrocyclic IDE inhibitor described herein is administered every other day, every third day, every week, every two weeks, every three weeks, or every four weeks. In certain embodiments, the desired dosage is delivered using multiple administrations (e.g., two, three, four, five, six, seven, eight, nine, ten, or more than ten administrations).

Liquid dosage forms of the macrocyclic IDE inhibitor described herein, for example, for oral and parenteral administration include, but are not limited to, pharmaceutically acceptable emulsions, microemulsions, solutions, suspensions, syrups, and elixirs. In addition to the active compounds, the liquid dosage forms may contain inert diluents commonly used in the art, such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such polyethoxylated castor oil, alcohols, oils, modified oils, glycols, polysorbates, cyclodextrins, polymers, and combinations thereof.

Injectable preparations of the macrocyclic IDE inhibitor described herein, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the macrocyclic IDE inhibitor described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, a macrocyclic IDE inhibitor described herein is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The macrocyclic IDE inhibitor described herein can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations of the a macrocyclic IDE inhibitor described herein suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the macrocyclic IDE inhibitors described herein and pharmaceutical compositions thereof can be employed in combination therapies, that is, the IDE inhibitors and pharmaceutical compositions provided herein can be administered concurrently with, prior to, or subsequent to, one or more other desired therapeutics or medical procedures. For example, in the context of metabolic syndrome or diabetes, a patient may receive a macrocyclic IDE inhibitor described herein and, additionally, a drug or pharmaceutical composition approved for the treatment of or commonly used to ameliorate a symptom associated with metabolic syndrome or diabetes. Similarly, if an IDE inhibitor or a pharmaceutical composition as provided herein is administered to a subject suffering from another disease, for example, from a neurological disease (e.g., Alzheimer's Disease), the subject may receive a macrocyclic IDE inhibitor described herein and, additionally, a drug or pharmaceutical composition approved for the treatment of or commonly used to ameliorate a symptom associated with a neurological disease (e.g., Alzheimer's disease). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a macrocyclic IDE inhibitor may be administered concurrently with another agent), or they may achieve different effects (e.g., control of any adverse effects).

In still another aspect, the present invention also provides a pharmaceutical pack or kit comprising one or more containers filled with one or more macrocyclic IDE inhibitor described herein, salts thereof, or with a pharmaceutical composition comprising a macrocyclic IDE inhibitor described herein. In certain embodiments, the pack or kit may also include an additional approved therapeutic agent for use as a combination therapy. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., a disease associated with aberrant enzyme activity (e.g., aberrant protease and/or kinase activity (e.g., aberrant IDE activity)). Optionally associated with such container(s) can be a notice in the form prescribed by a governmental agency regulating the manufacture, use, or sale of pharmaceutical products, which notice reflects approval by the agency of manufacture, use, or sale for human or veterinary administration. Provided herein are kits comprising the compounds described herein, or a pharmaceutical composition thereof, and instructions for administering to a subject or contacting a biological sample with the compound or pharmaceutical composition.

The present invention also provides uses of the compounds described herein, or a pharmaceutical composition thereof, for treating a disease in a subject in need thereof (e.g., a disease (e.g., a disease associated with aberrant enzyme activity (e.g., aberrant protease and/or kinase activity (e.g., aberrant IDE activity)).

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1

DNA-encoded libraries have emerged as a widely used resource for discovery of bioactive small molecules and offer substantial advantages compared to conventional small-molecule libraries, including their ability to be evaluated en masse in a single experiment and the minute amounts of library and biological target required for their use. Unfortunately, few research groups have access to these resources and the vast majority of DNA-encoded libraries remain in the private sector. Here, multiple fundamental aspects of DNA-encoded and DNA-templated library synthesis methodology was developed and streamlined, including computational identification and experimental validation of a 20×20×20×80 set of orthogonal codons, chemical and computational tools for enhancing the structural diversity and drug-likeness of library members, a highly efficient polymerase-mediated template library assembly strategy, and library isolation and purification methods. These improvements together enable much more robust, scalable, high-yielding, streamlined, and cost-effective preparation of DNA-encoded libraries. These improved methods were integrated to produce a second-generation DNA-templated library of 256,000 small-molecule macrocycles with improved drug-like physical properties. In vitro selection of this library for insulin-degrading enzyme (IDE) affinity resulted in novel IDE inhibitors including one of unusual potency and novel macrocycle stereochemistry ($IC_{50}$=40 nM), demonstrating the ability of this library to support the discovery of inhibitors of proteins of biomedical interest. These developments enable DNA-templated small-molecule libraries to serve as more powerful, accessible, cost-effective, and convenient tools for bioactive small-molecule discovery.

Results

General Design of the DNA-Templated Library Architecture

Figures 2A, 2B:
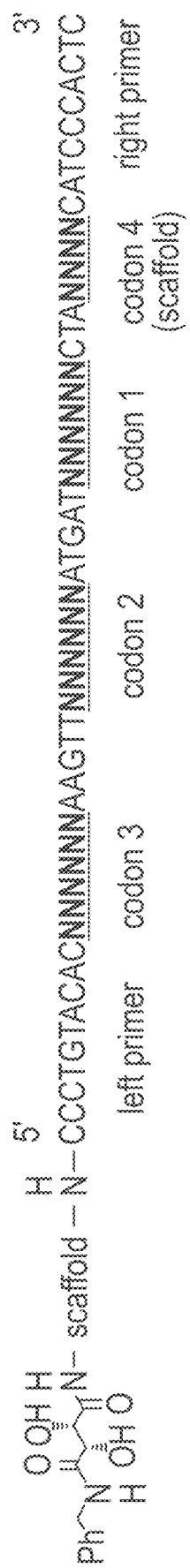

The DNA-templated library synthesis is summarized in FIG. 1, with changes compared to the first-generation library shown in grey[38]. The template architecture of the library is shown in FIG. 2A. The coding region is flanked with 10-mer primer-binding sites and consists of three building block codons and a scaffold codon interspaced with three constant regions. Codons 1, 2, and 3 determine the identity of three macrocycle building blocks introduced by DTS, while codon 4 identifies the bis-amino acid scaffold at the 5' end of the template. After each templated coupling reaction, unreacted templates are capped by acetylation (FIG. 1). Capture with streptavidin-linked beads separates templates that successfully reacted at all three steps from those that failed to react at any step. During macrocyclization, the library is purified again by a capture-and-release strategy that causes successfully macrocyclized DNA-linked library members to self-elute from beads, whereas uncyclized material remains bound. This capping and macrocycle purification strategy furnishes material of sufficiently high purity to support DNA-encoded library selections and accurate post-selection decoding[9].

Identification of an Orthogonal Codon Set

One factor that limits the size of DNA-templated libraries is this requirement of codon orthogonality. A DTS reagent's anticodon must efficiently anneal only with the corresponding complimentary codon of the template. Moreover, the template requires a certain degree of secondary structure in order for the hybridized reacting groups to experience optimal effective molarity[44]. To design the codon set for the second-generation DNA-templated macrocycle library, a set of 30×30×30 putatively orthogonal codons was used that was previously derived[38] computationally to impart template folding energies in the range found to be optimal for DNA-templated synthesis[44]. The Visual OMP platform (DNA Software, Inc.) was used to identify a set of 30 scaffold codon candidates out of 256 possible sequences of the form NNNN that avoided hairpin formation with the adjacent codons and minimized predicted off-target hybridization to reagent anticodons (FIGS. 2A, 2B). The resulting building block and scaffold codons were arbitrarily assigned number and letter codes (2). Codons involved in DTS steps 1, 2, and 3 were designated codons 1, 2, and 3 respectively, while the scaffold codon was defined as codon 4 (FIG. 2A).

Figure 7A:
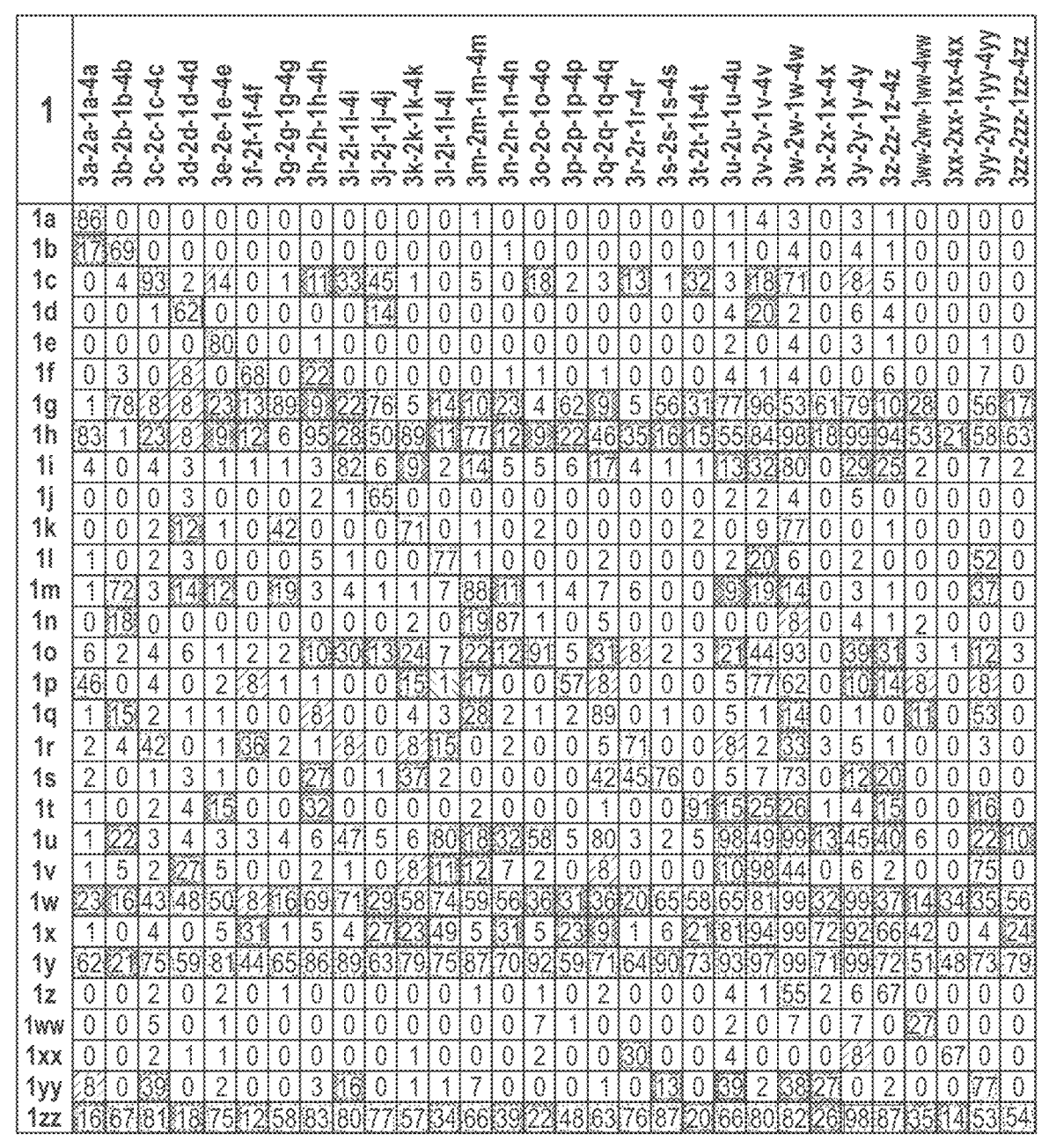

90 DNA-linked phenylalanine model reagents were synthesized and purified, each containing one of the 90 different anticodon oligonucleotides (1a . . . 1z, 1ww . . . 1zz, 2a . . . 2z, 2ww . . . 2zz, and 3a . . . 3z, 3ww . . . 3zz), and 30 DNA templates (3a-2a-1a-4a . . . 3zz-2zz-1zz-4zz) that collectively contain codons for all 90 reagents in order to validate all possible codon-anticodon combinations for their ability to support efficient and sequence-specific DTS. 2,700 individual DNA-templated amine acylation reactions were performed between each of the 90 DNA-linked model reagents and each of the 30 test templates that collectively contain all 90 possible building block codons and all 30 possible scaffold codons. Based on previous work[38], a threshold of 7% or greater conversion of non-complementary reagent and template was chosen as being unacceptable. The DTS reactivity tables for codons 1 and 2 obtained at the previously used temperature regimes (25° C. for steps 1 and 2, and 37° C. for step 3)[38] resulted in prohibitively high levels of mismatched cross-reactivity, with 31% of mismatched step 1 reagent-template combinations and 22% of mismatched step 2 combinations yielding apparent DTS conversions above the 7% threshold at 25° C. (FIGS. 7A to 7C).

Figure 8A:
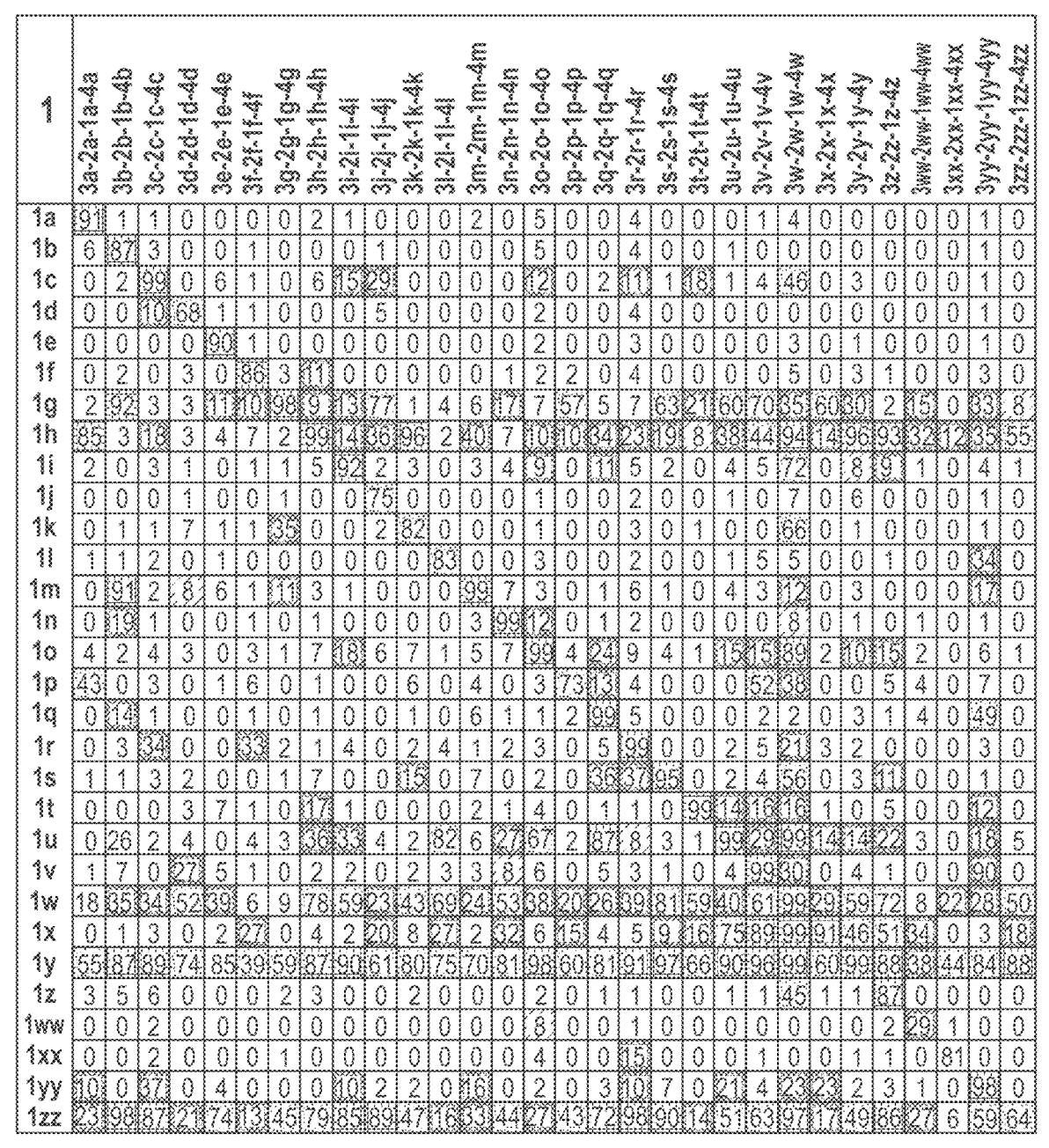
Figure 8C:
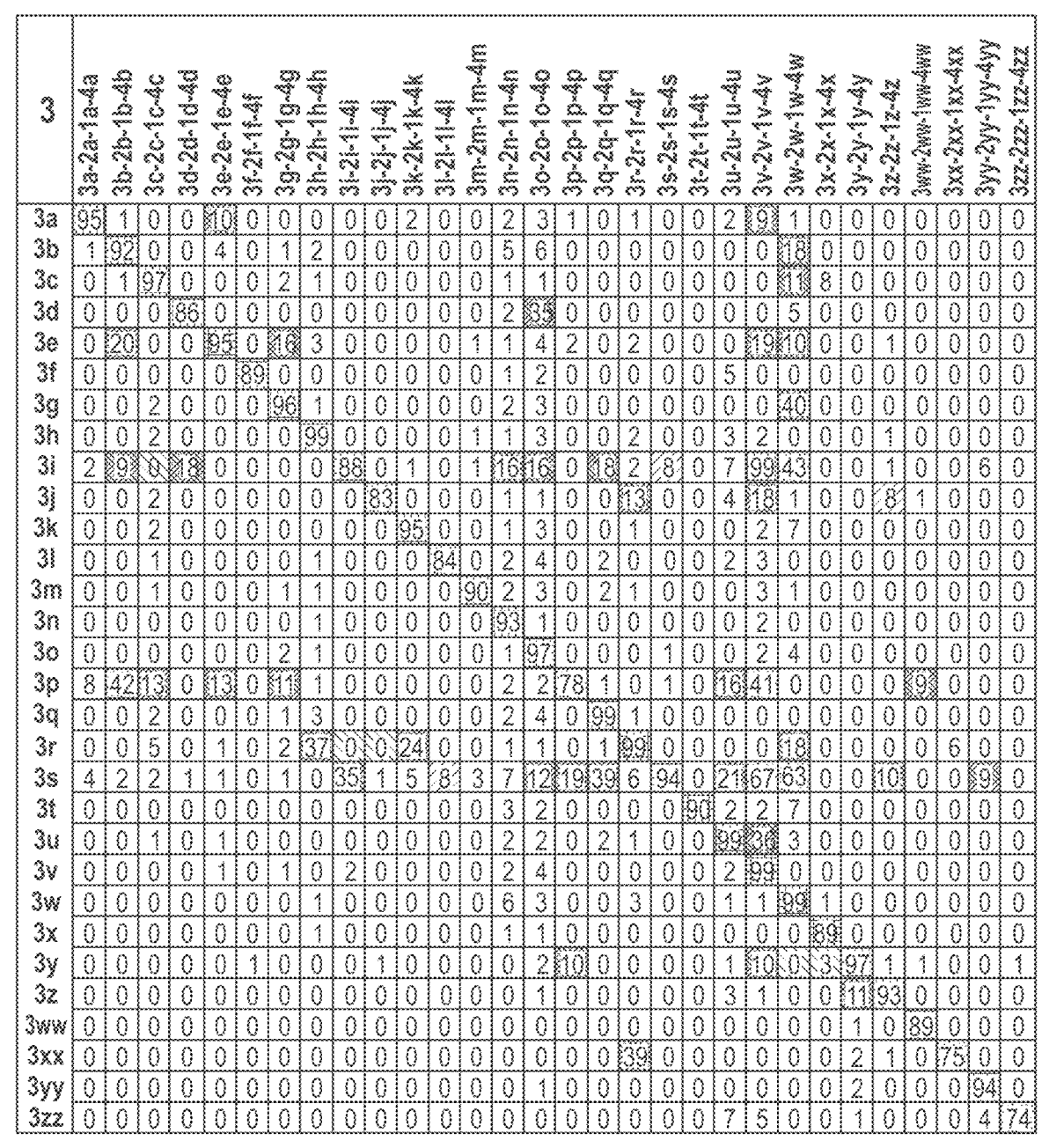

Therefore, the set of reactions was repeated at elevated temperatures (30° C. for steps 1 and 2), resulting in a substantial reduction in cross-reactive mismatched reagent-template combinations for DTS steps 1 and 2 (23% and 16%, respectively) (FIGS. 8A to 8C). While elevating the temperature of step 3 to 43° C. dramatically reduced the frequency of unacceptable mismatched product formation from 5.3% to 0.1%, the yields of matched reactions also decreased substantially from 92% to 53% average apparent conversion (FIG. 8C). As a result, temperatures of 30° C., 30° C. and 37° C. were chosen for DTS reactions 1, 2, and 3, respectively. Despite these sequence specificity improvements, the remaining number of templates not involved any mismatched conversions provided an insufficient number of codons to support the DTS of 256,000 macrocycles (FIGS. 7A to 7C and 8A to 8C).

Figure 2E:
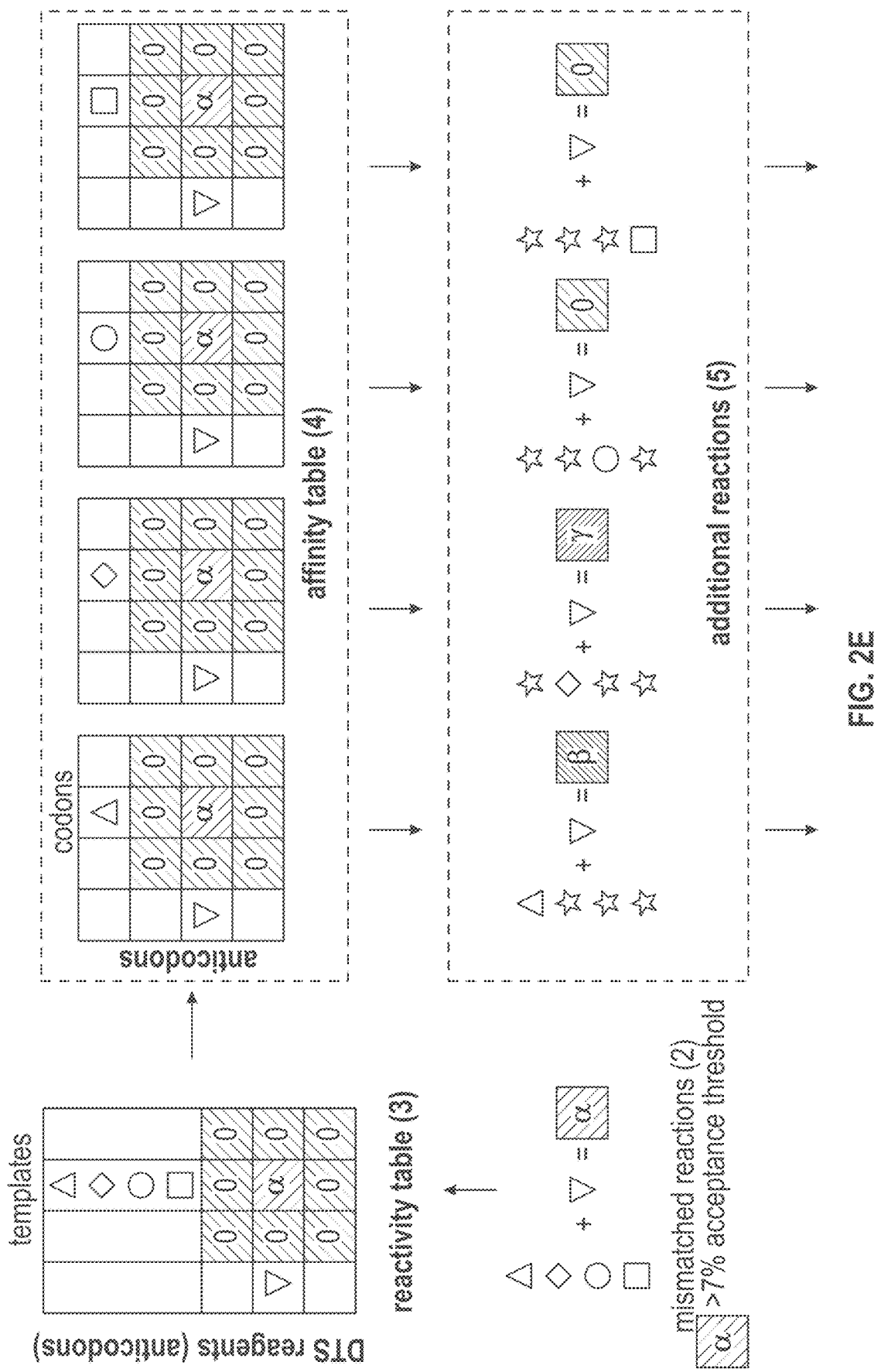
Figure 2E:
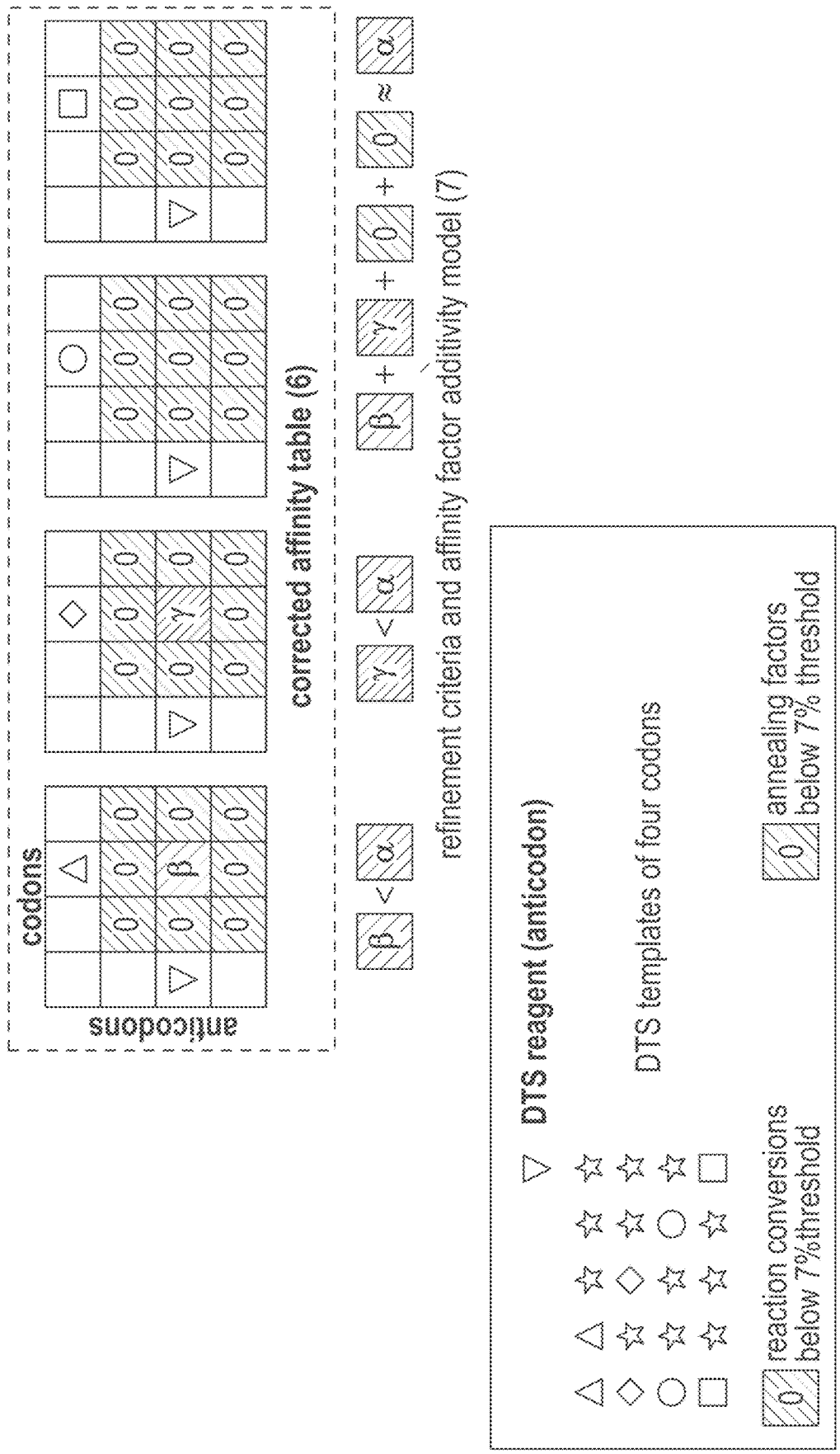
Figure 9:
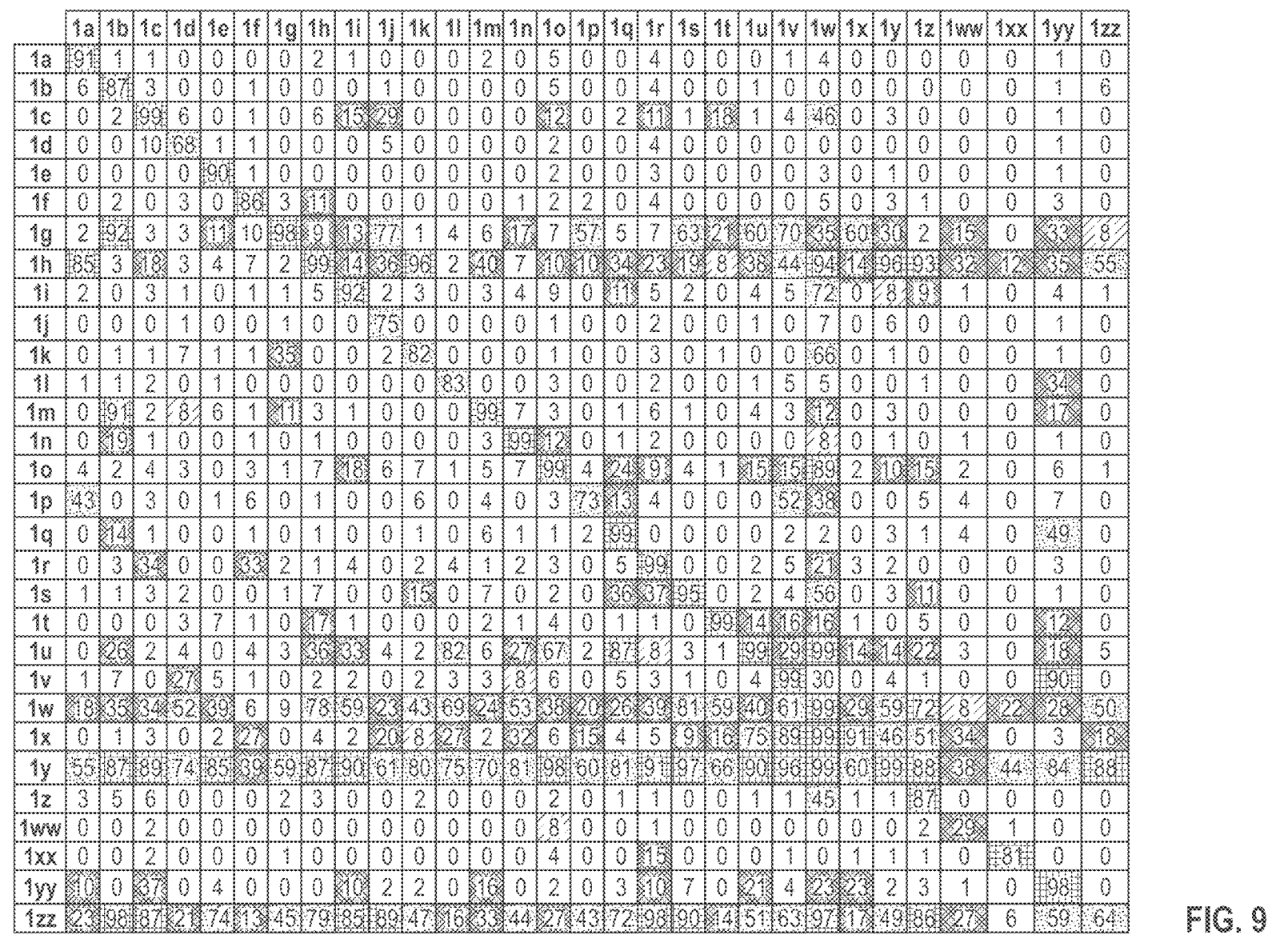
Figure 9:
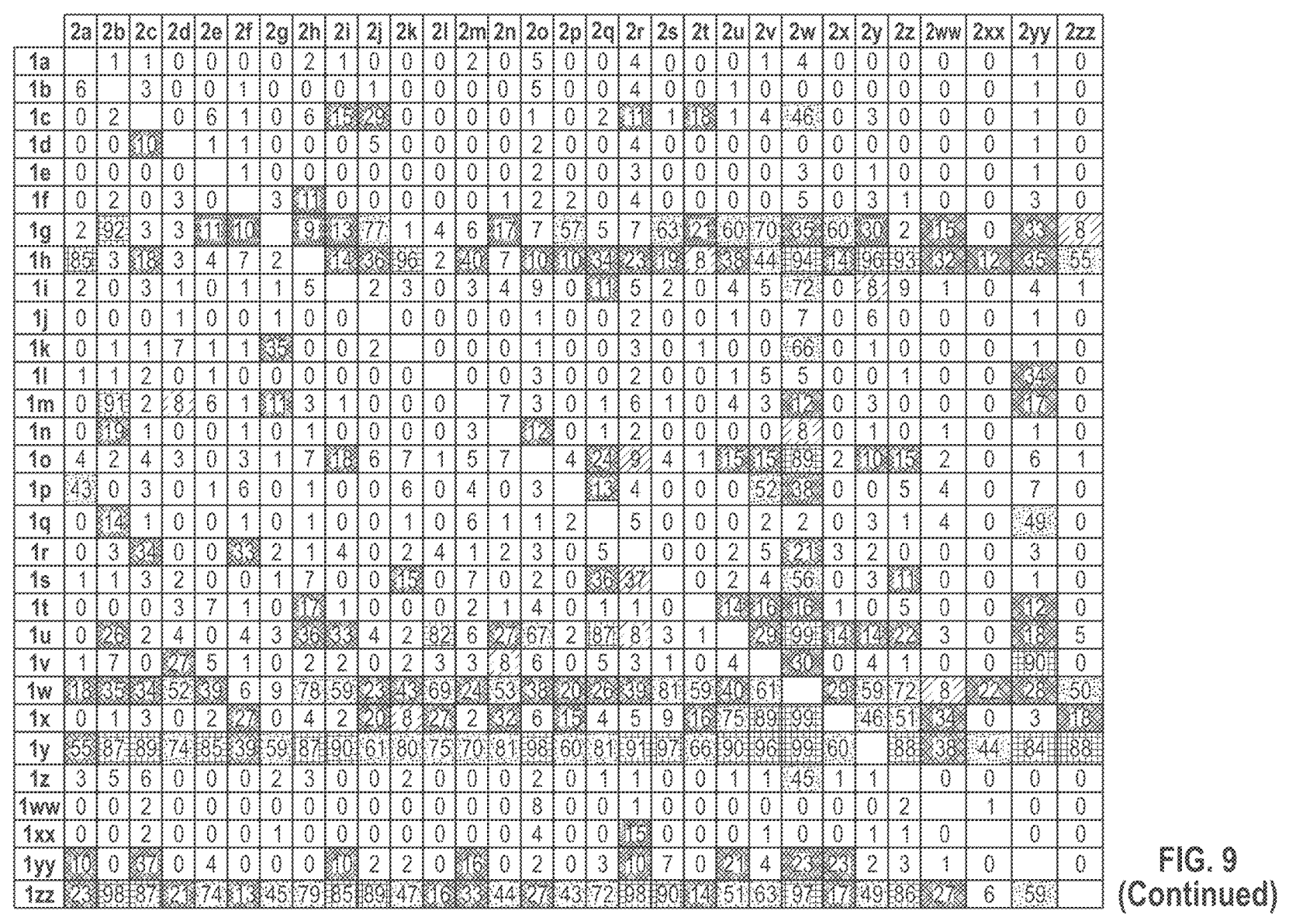
Figure 9:
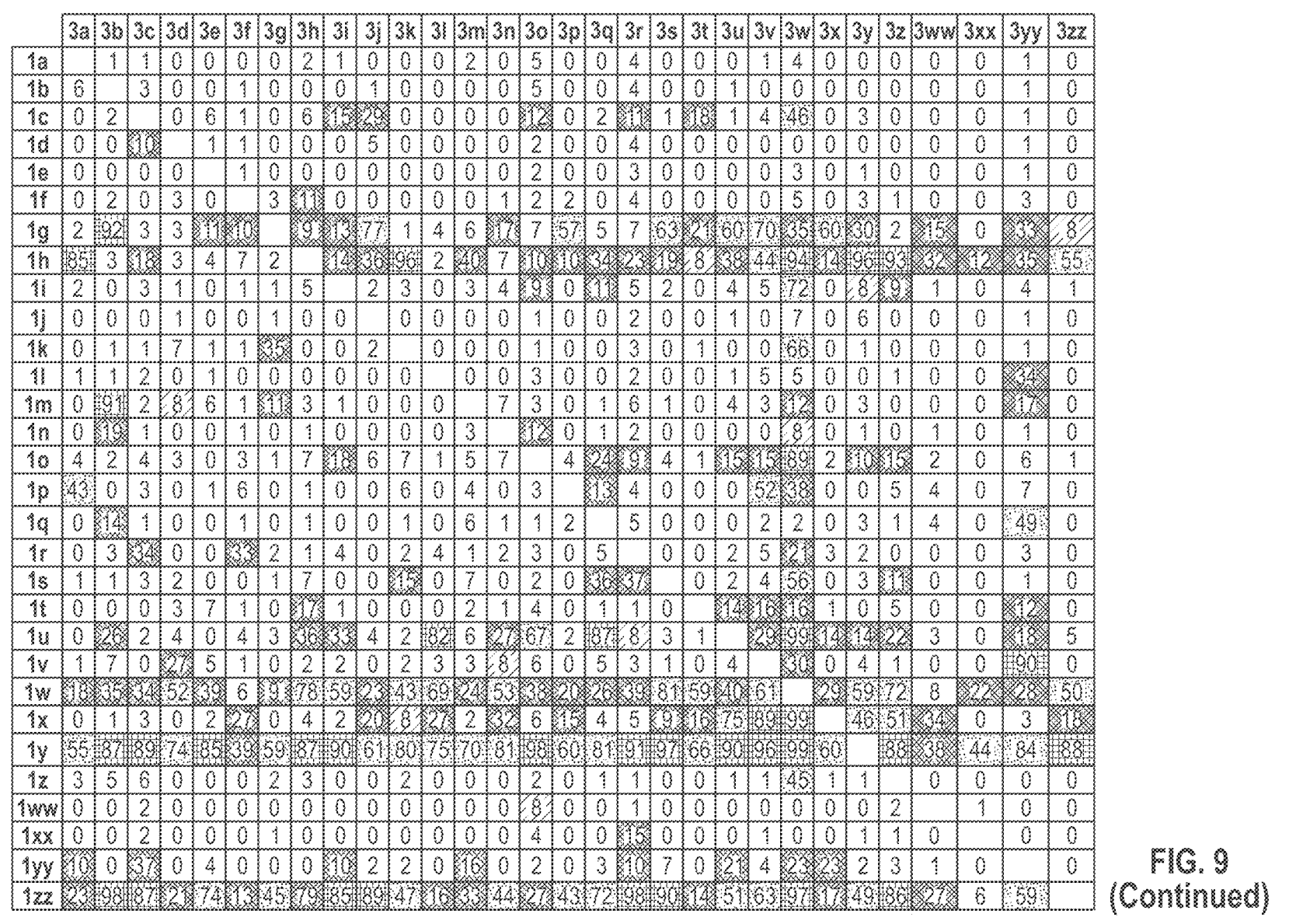
Figure 9:
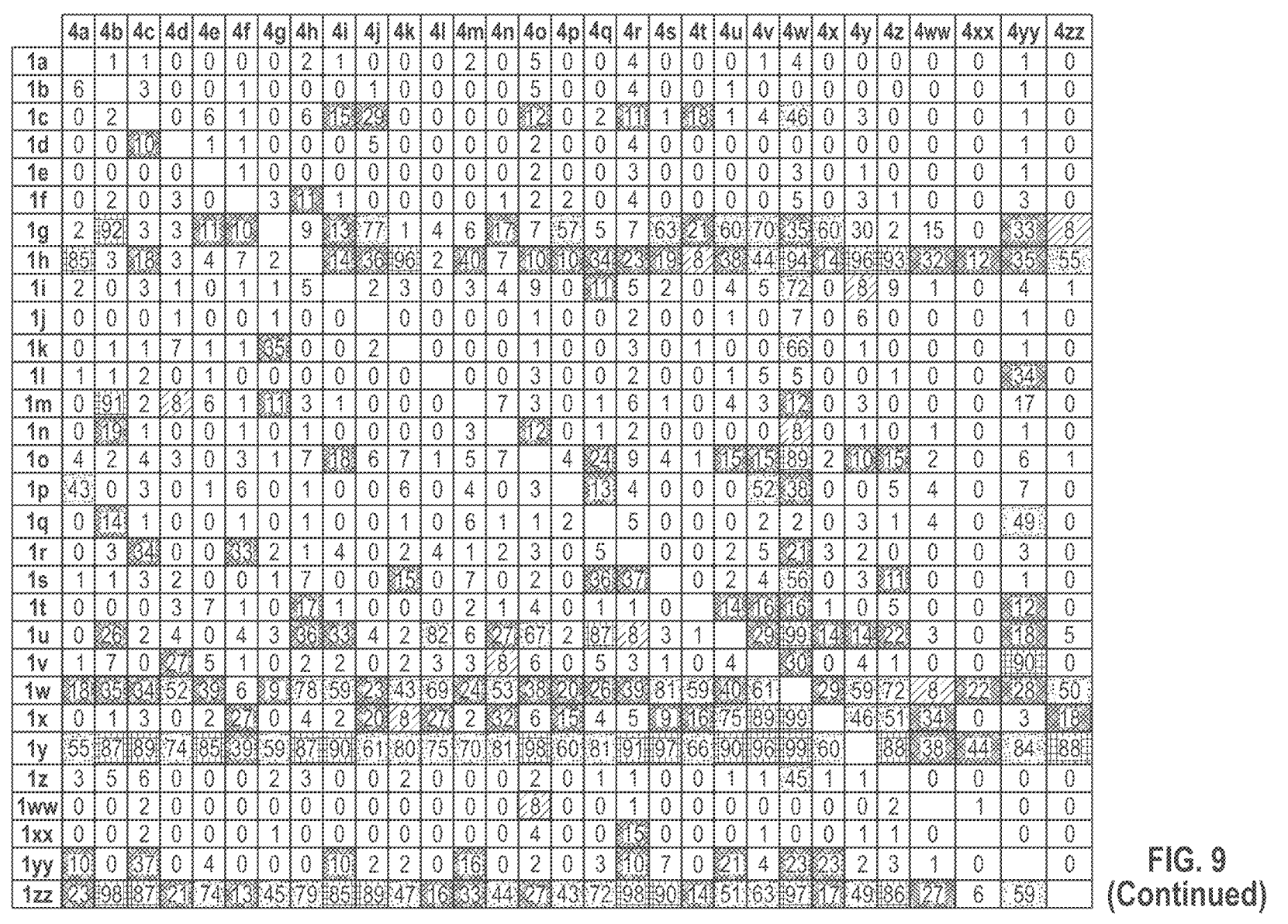
Figure 9:
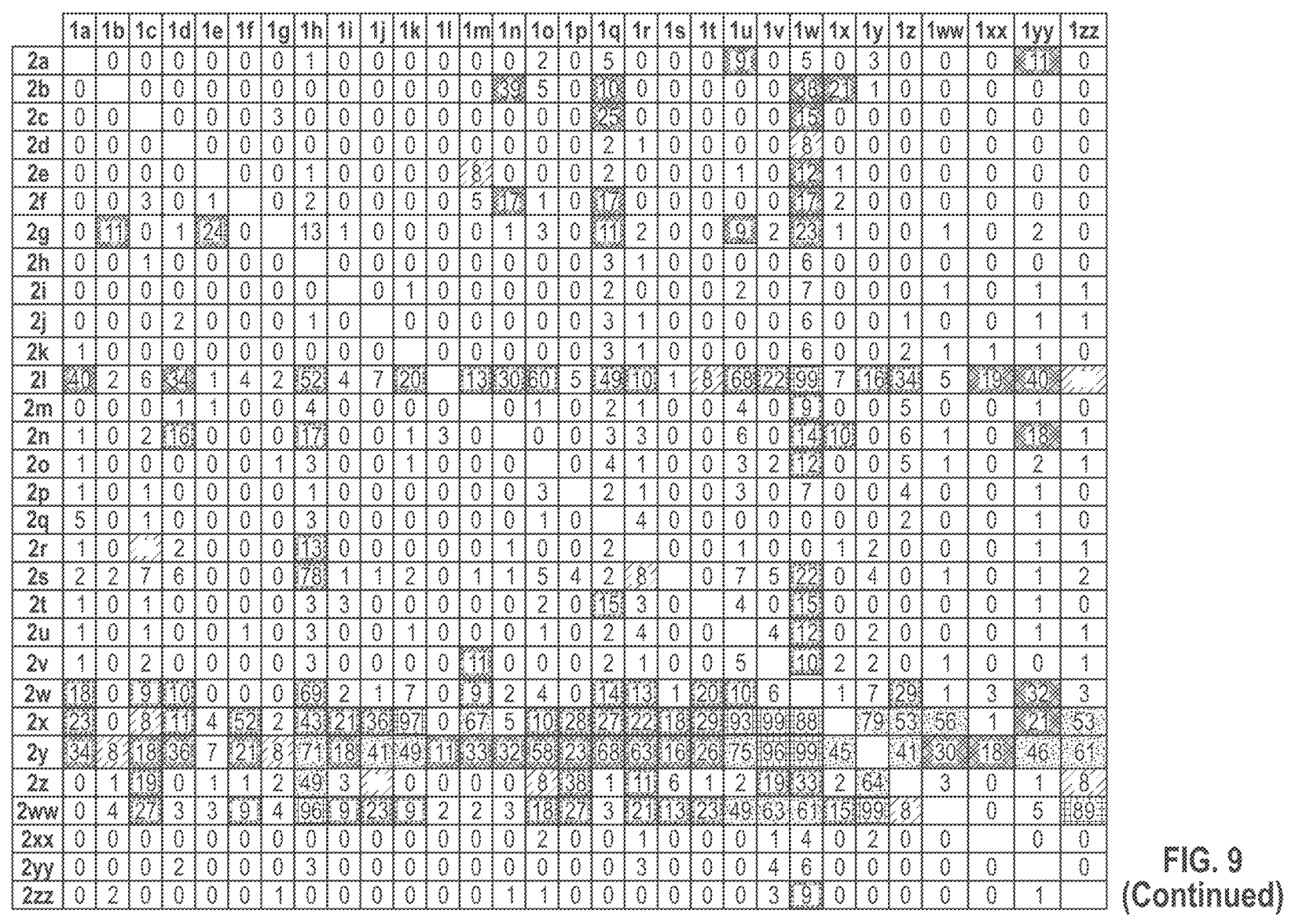
Figure 9:
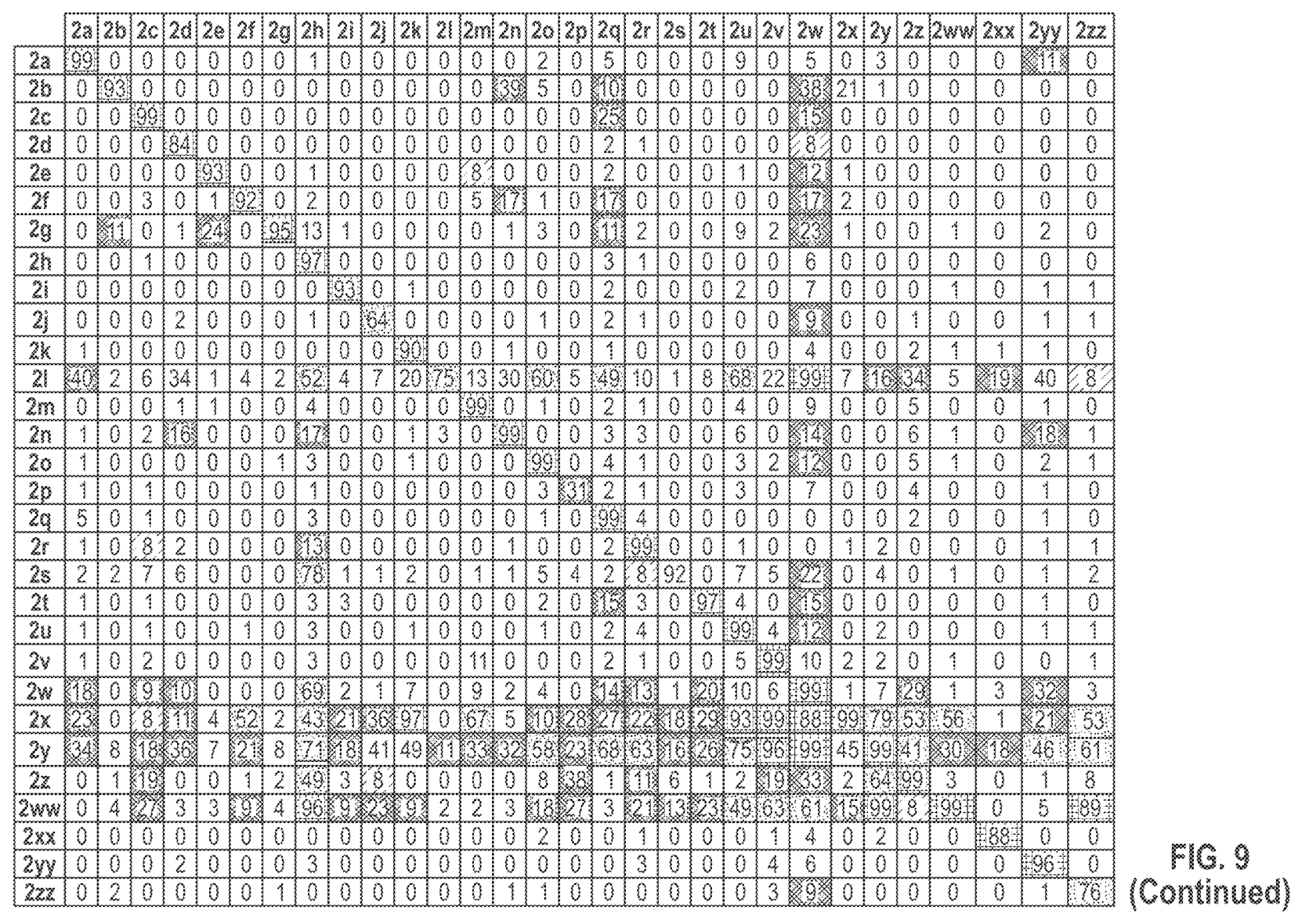
Figure 9:
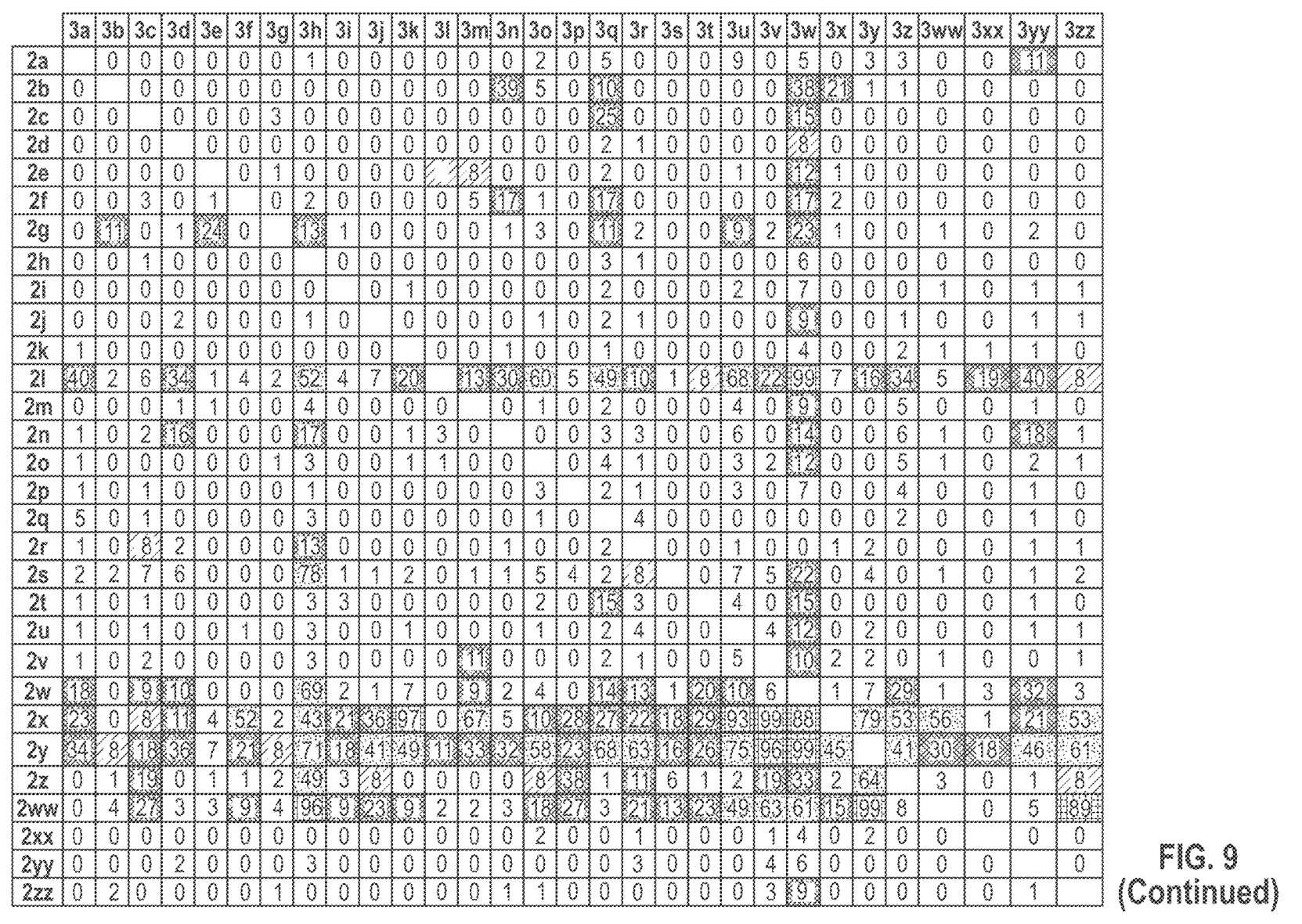
Figure 9:
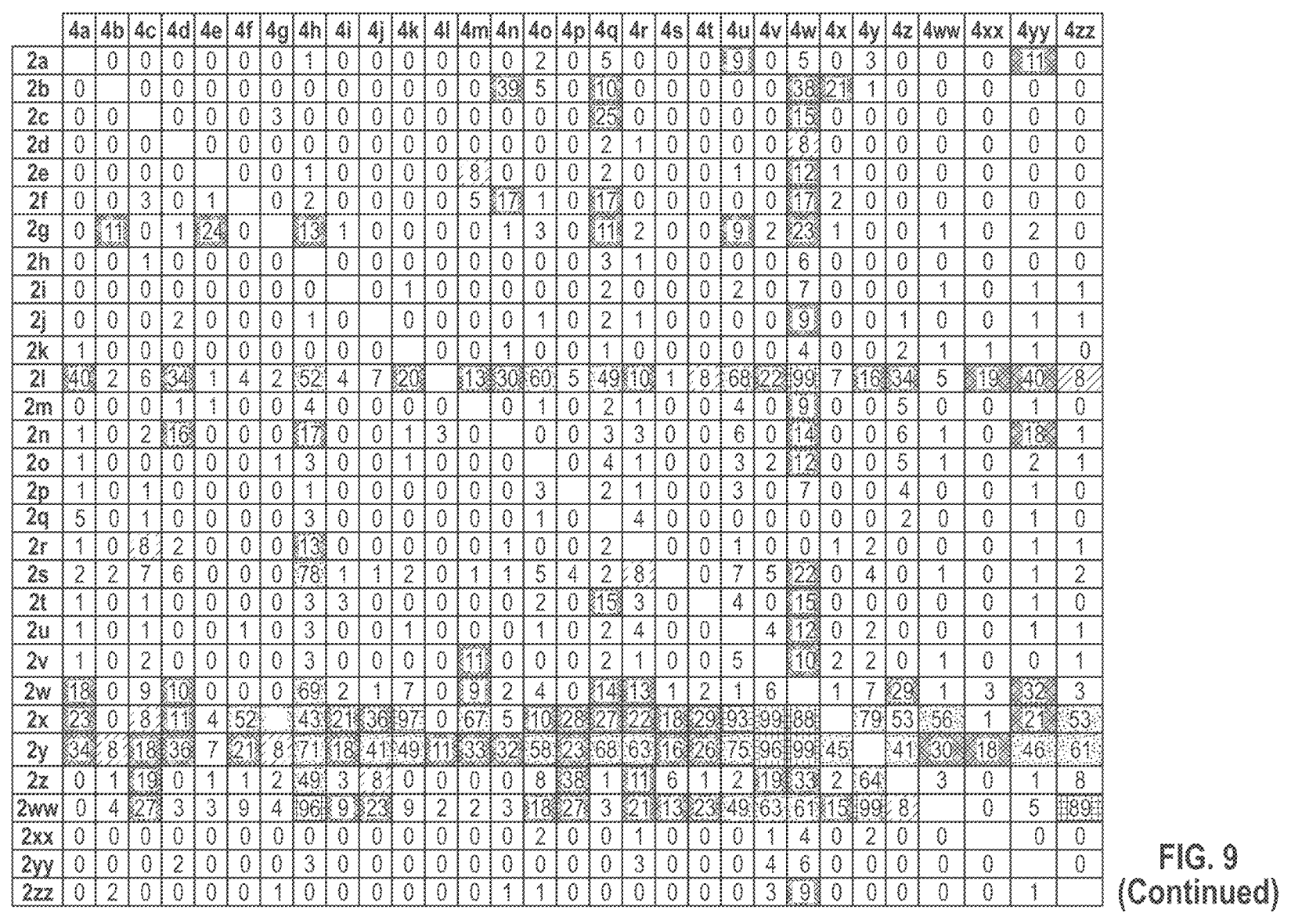
Figure 9:
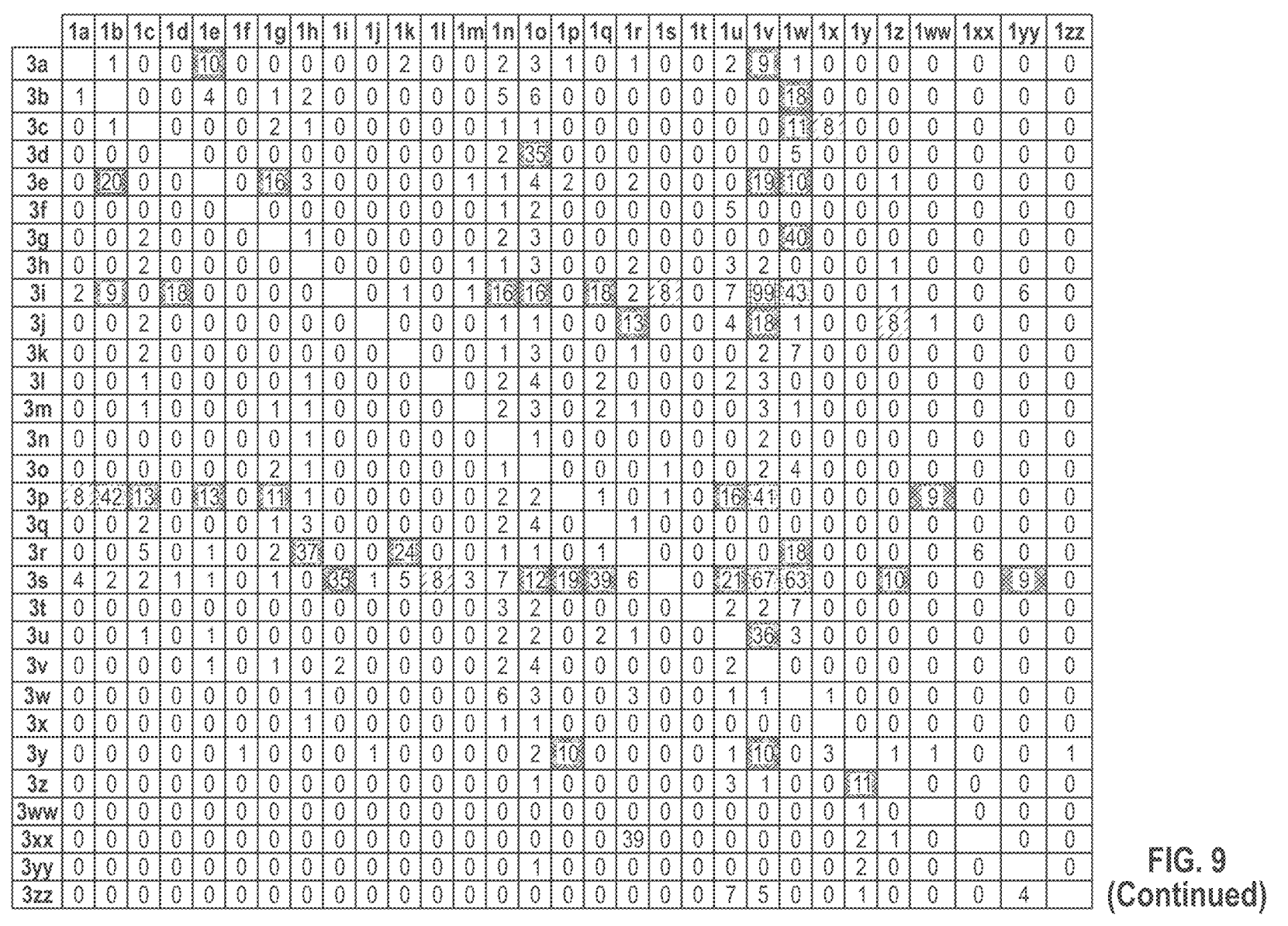
Figure 9:
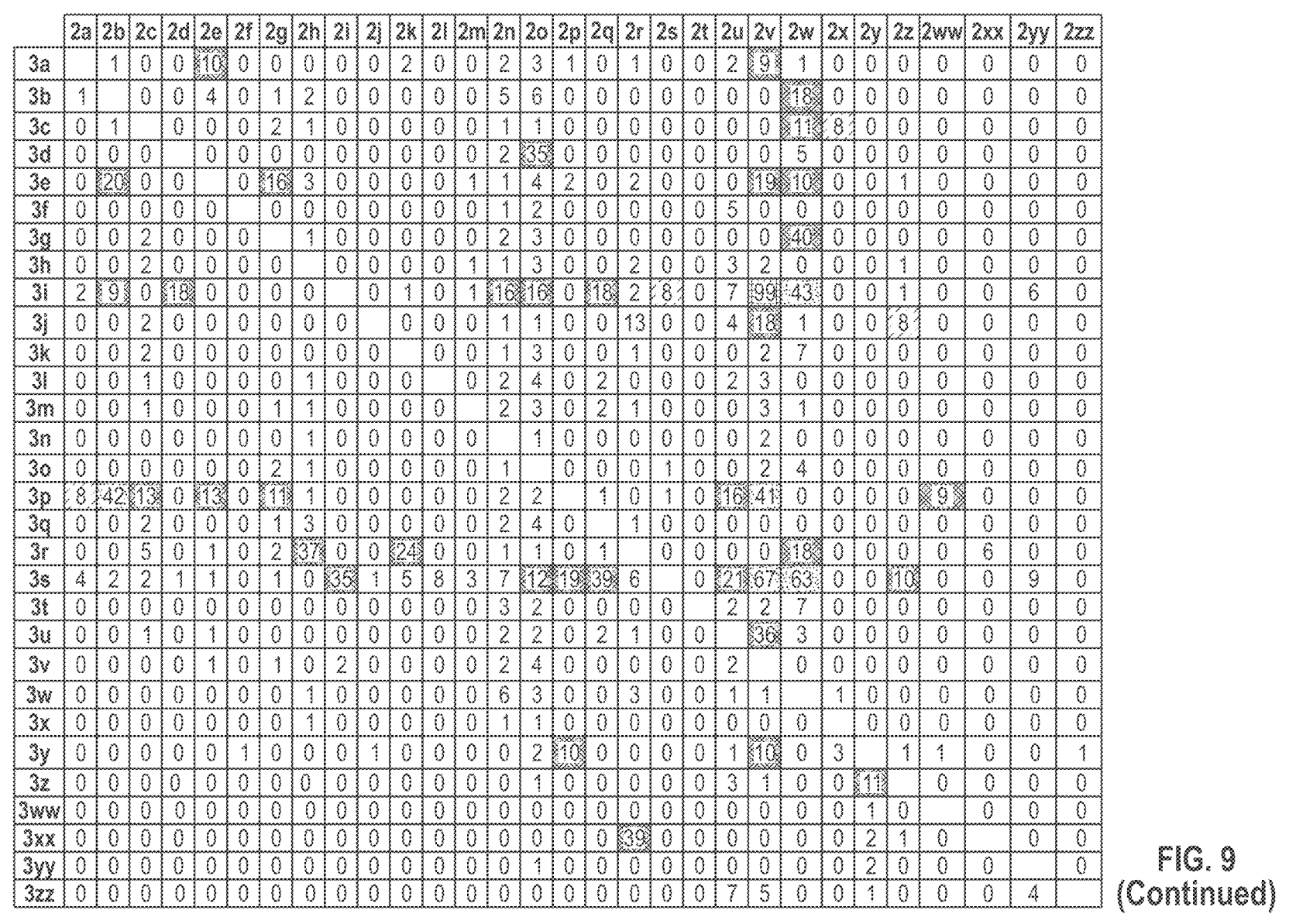
Figure 9:
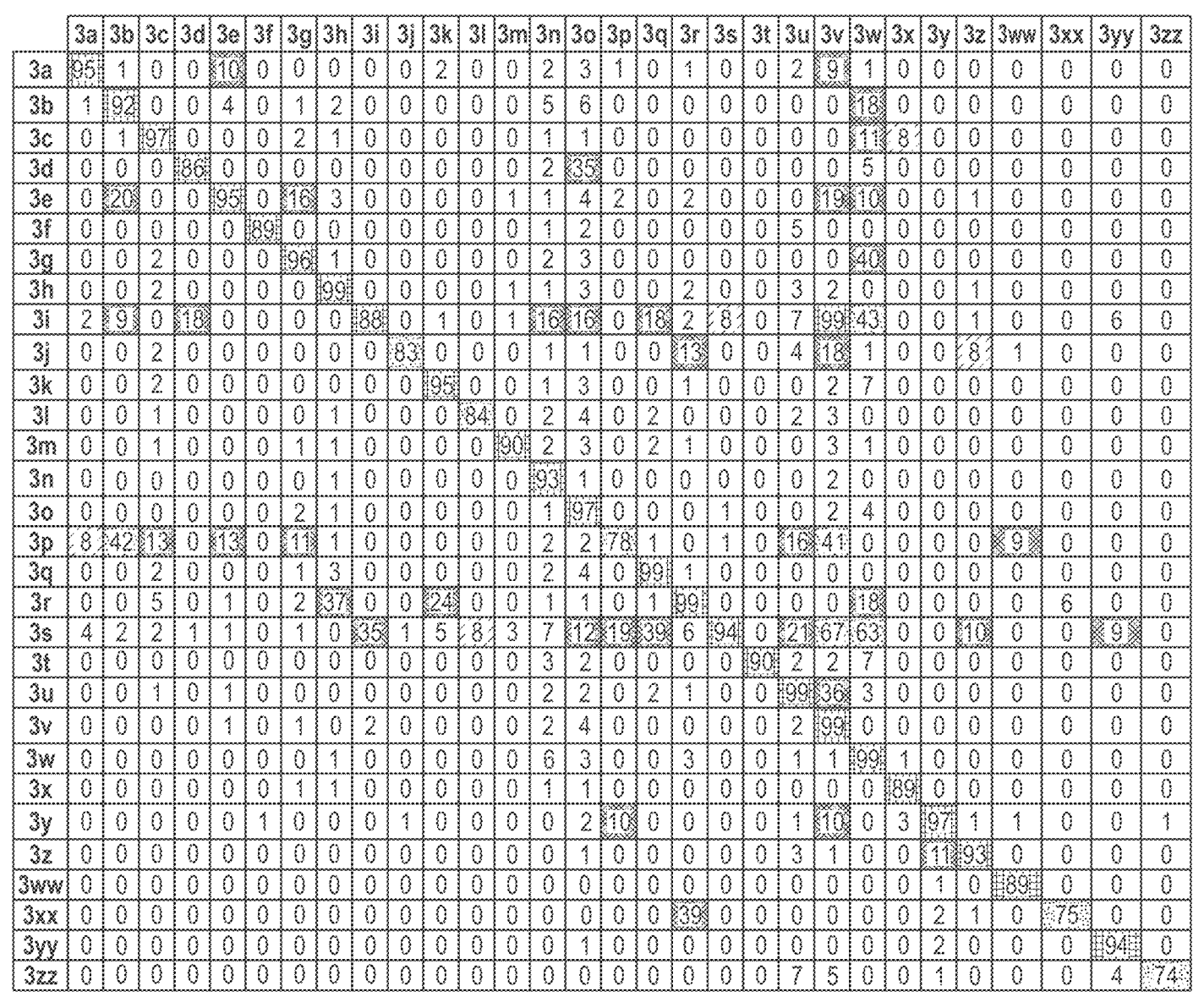
Figure 9:
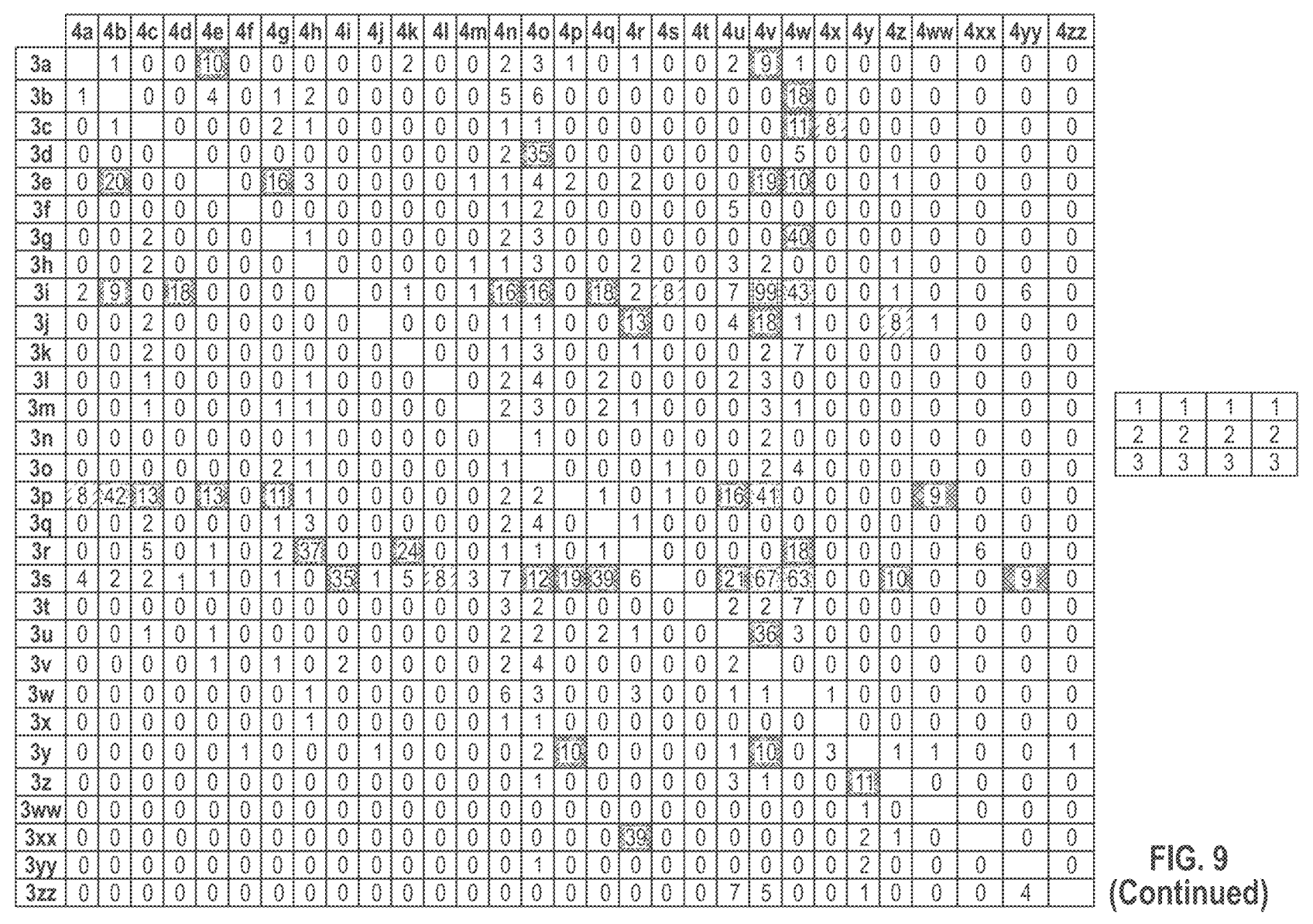
Figure 11:
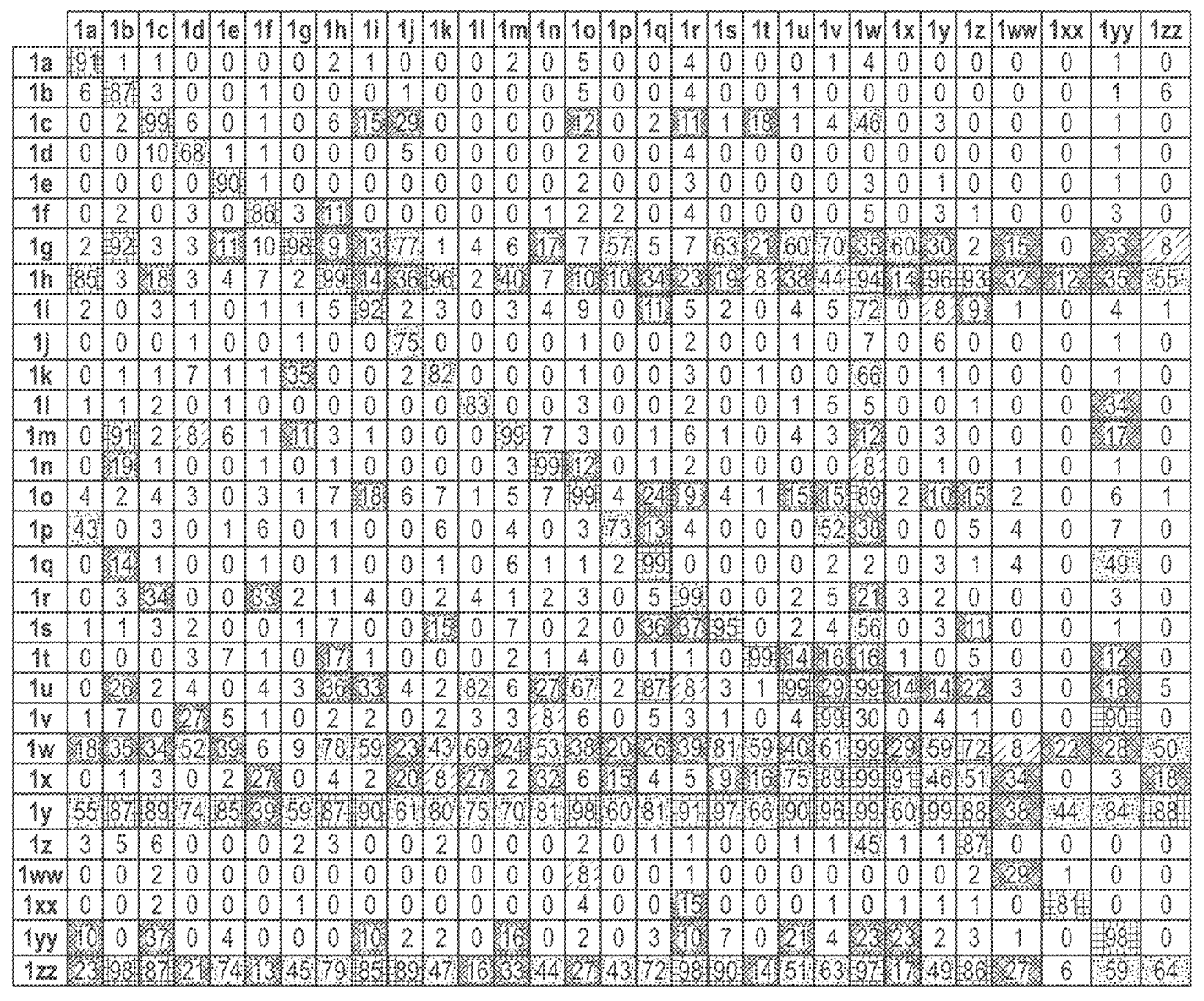
Figure 11:
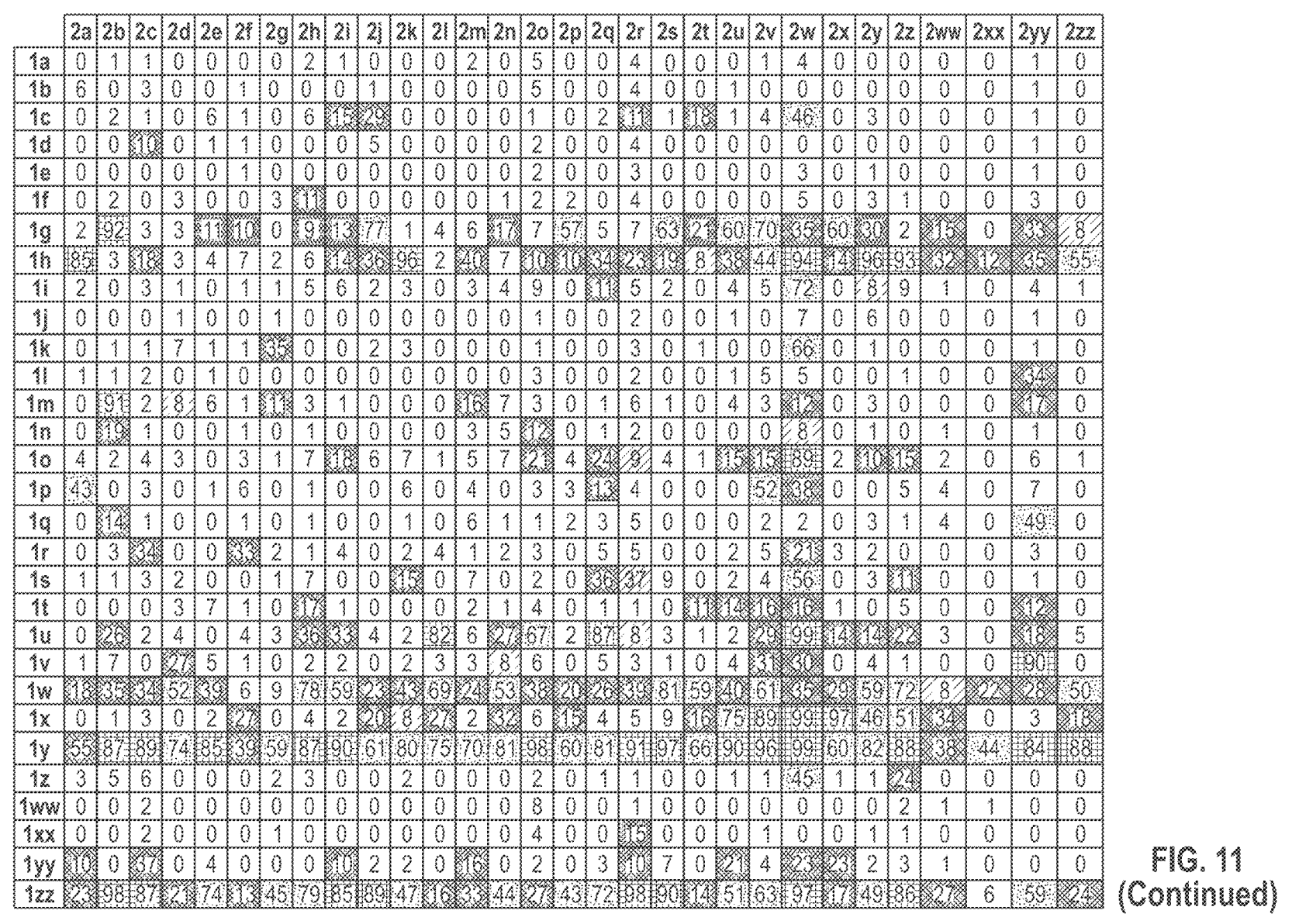
Figure 11:
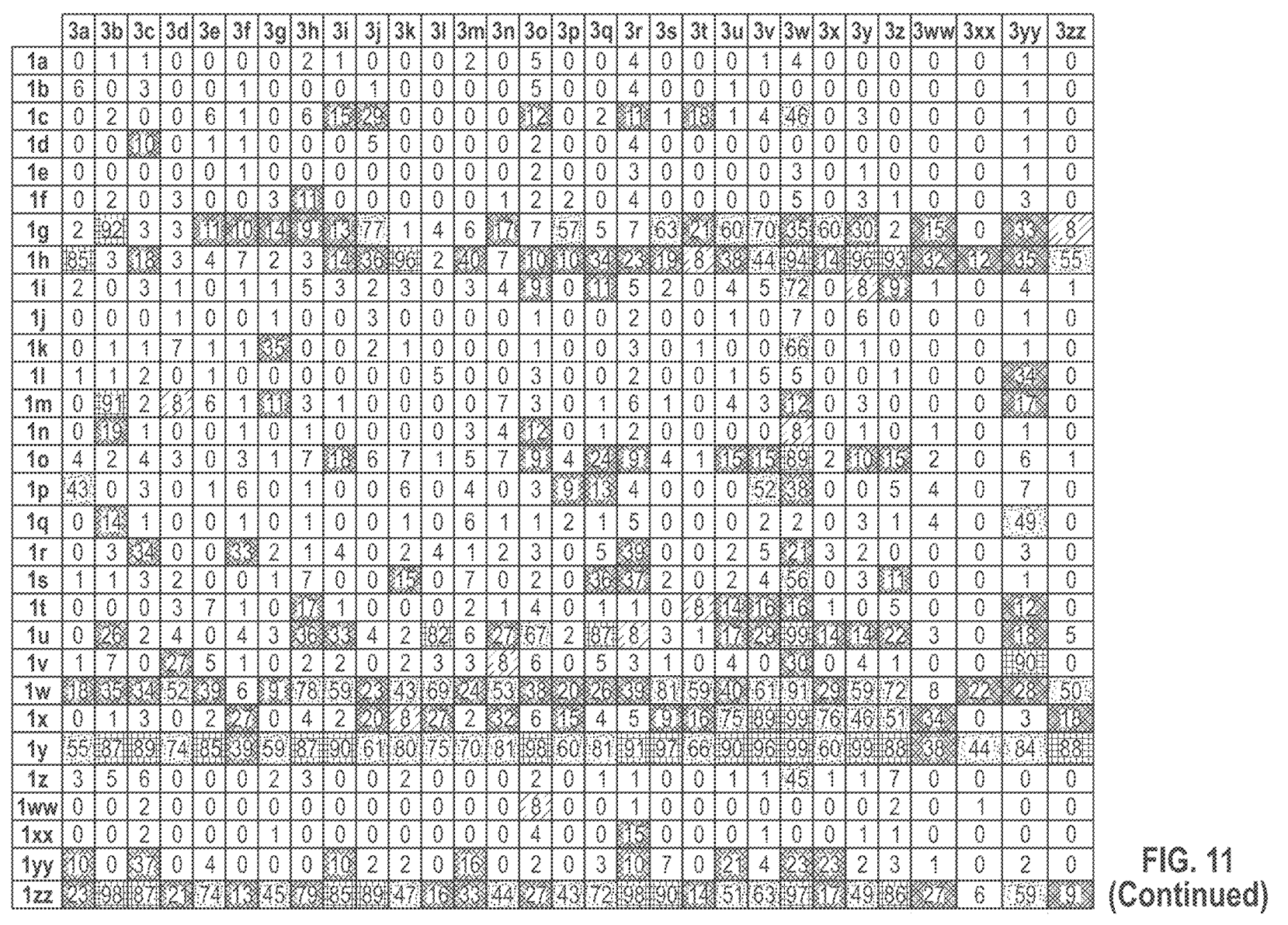
Figure 11:
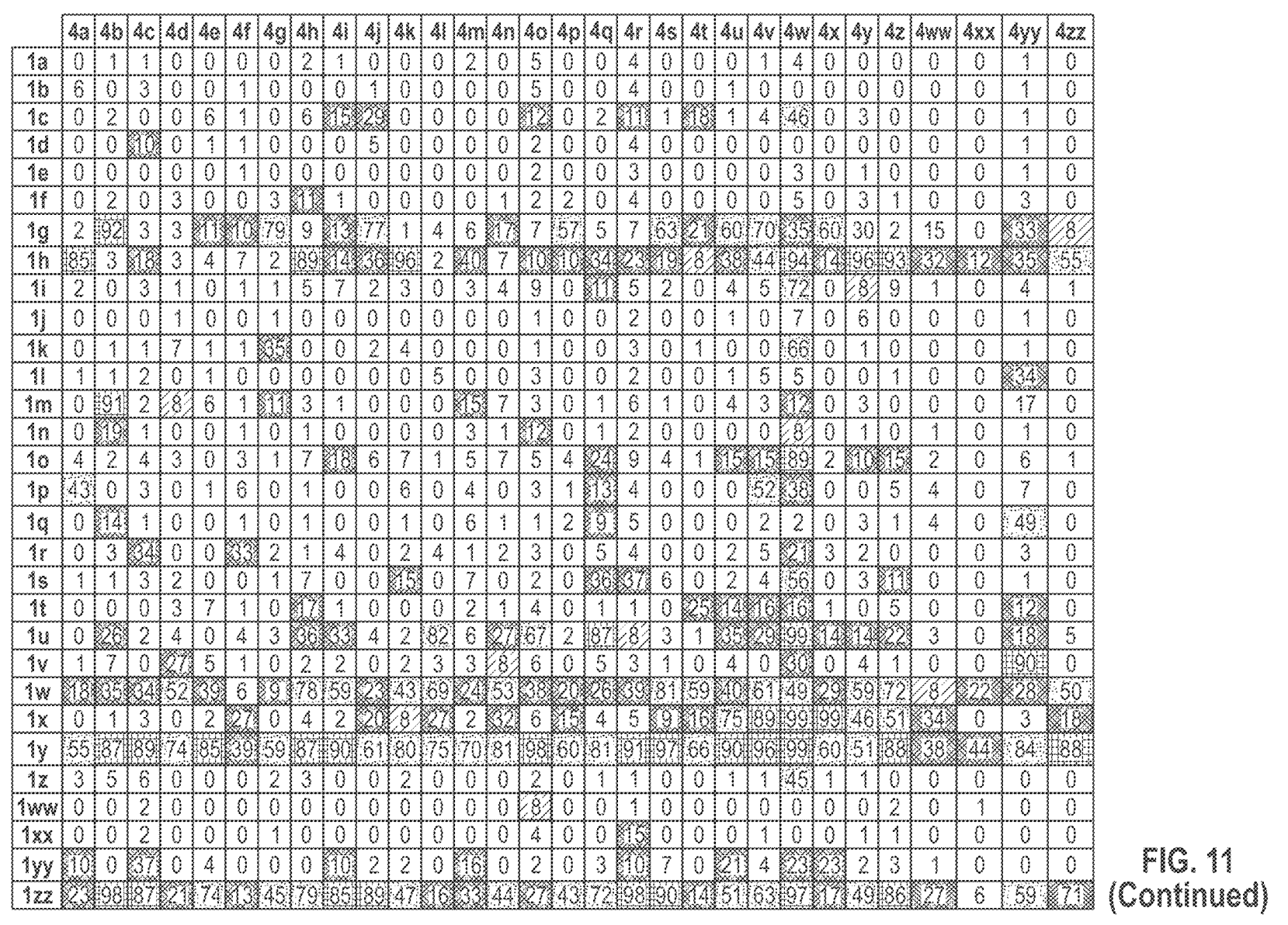
Figure 11:
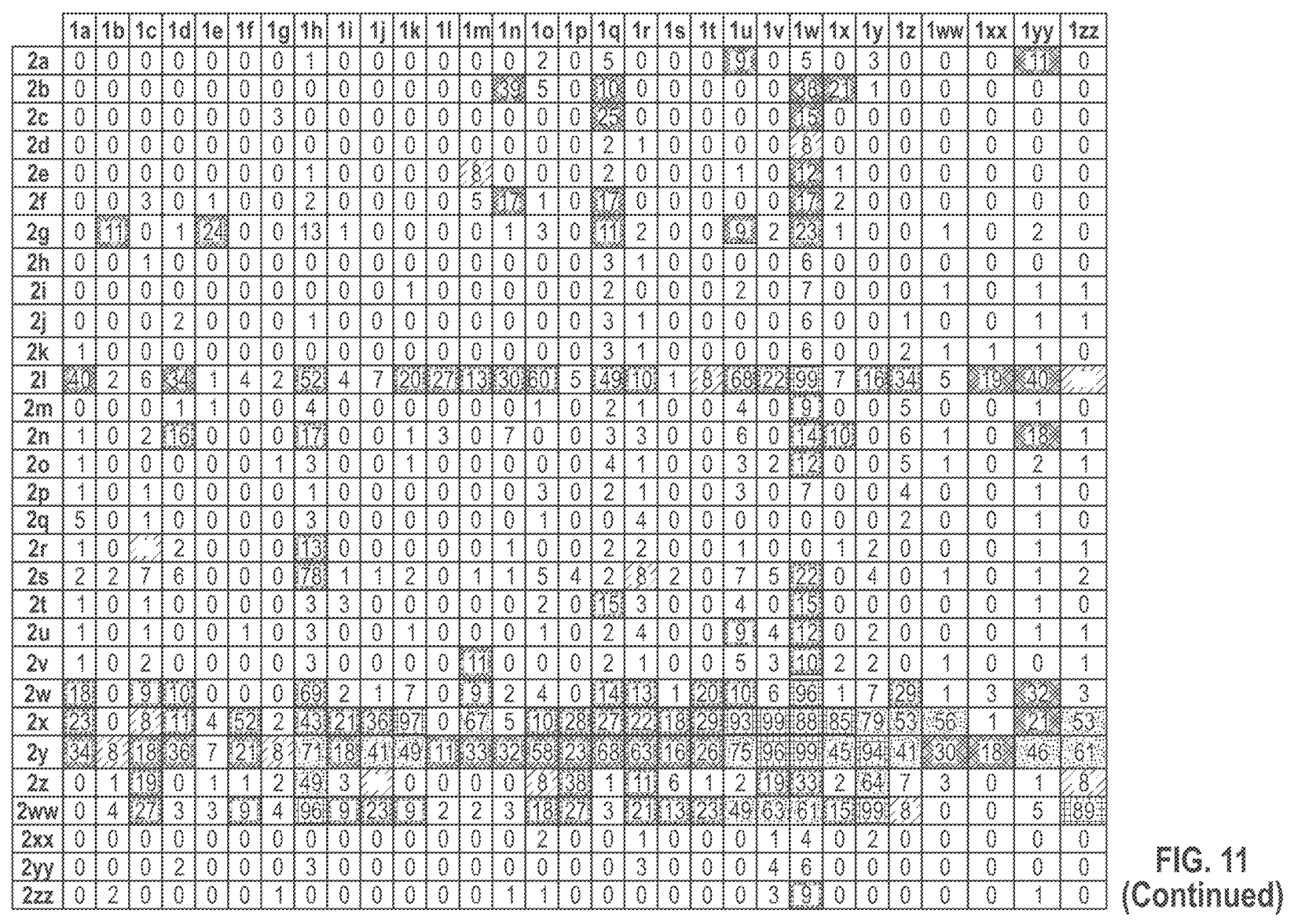
Figure 11:
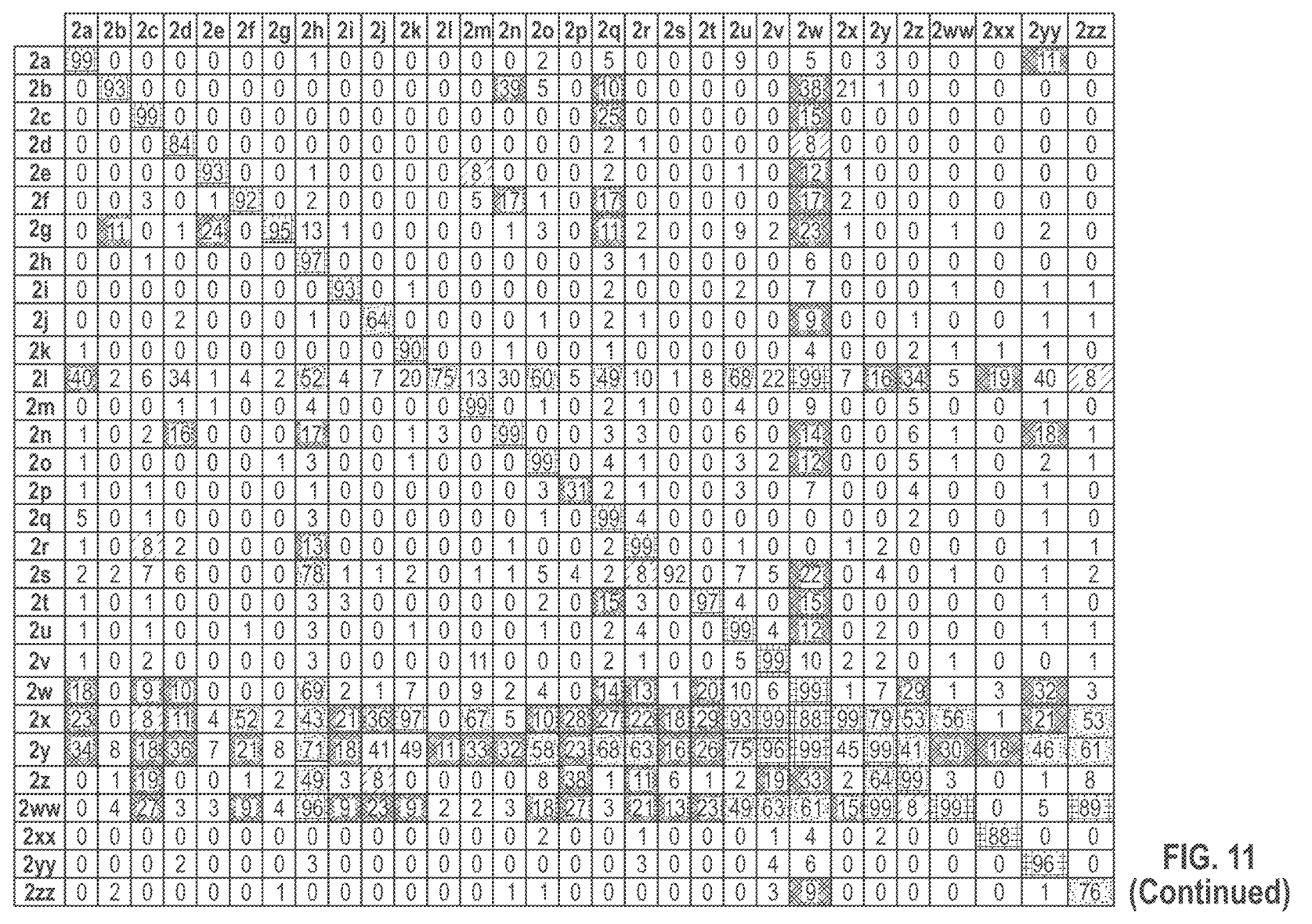
Figure 11:
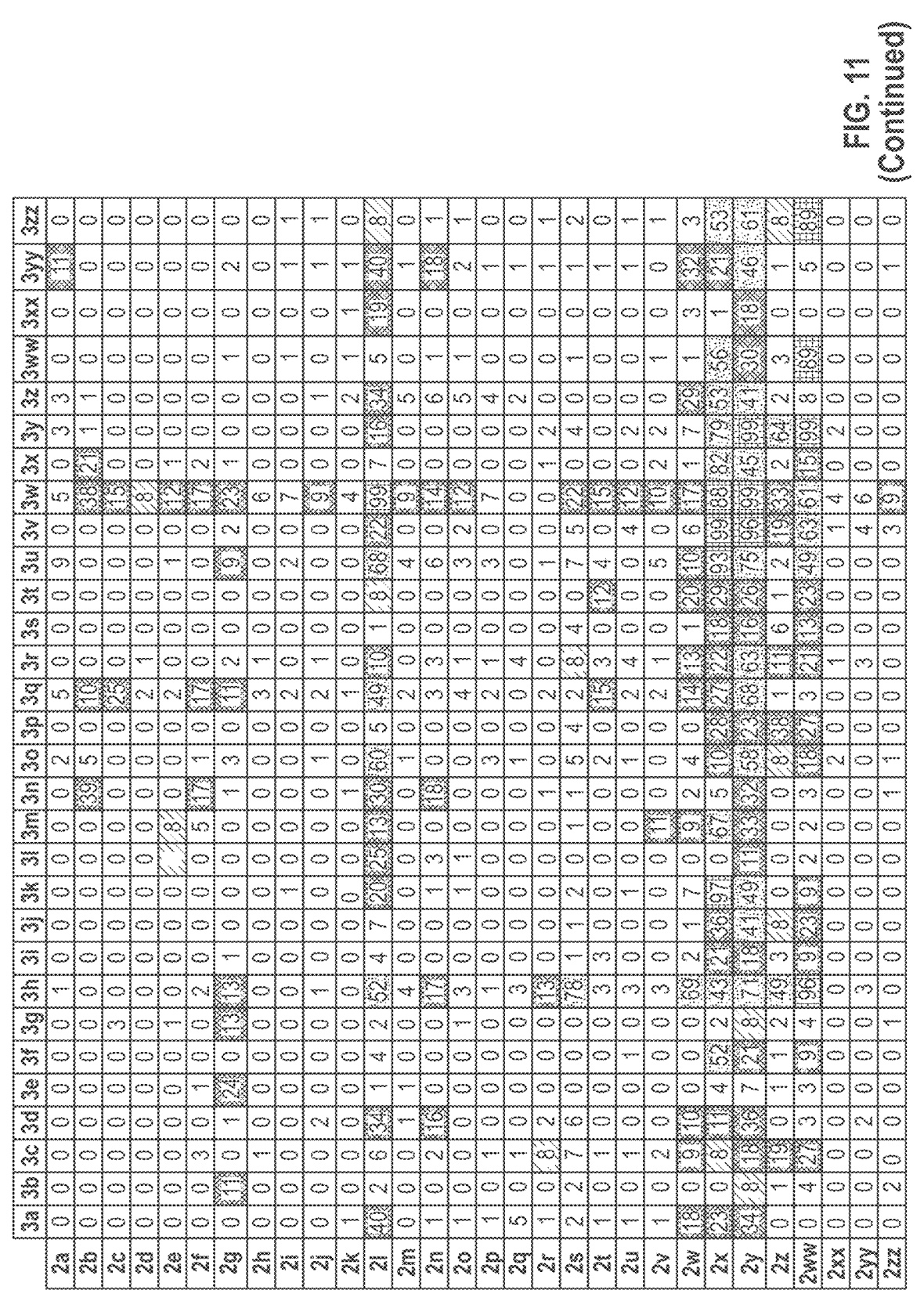
Figure 11:
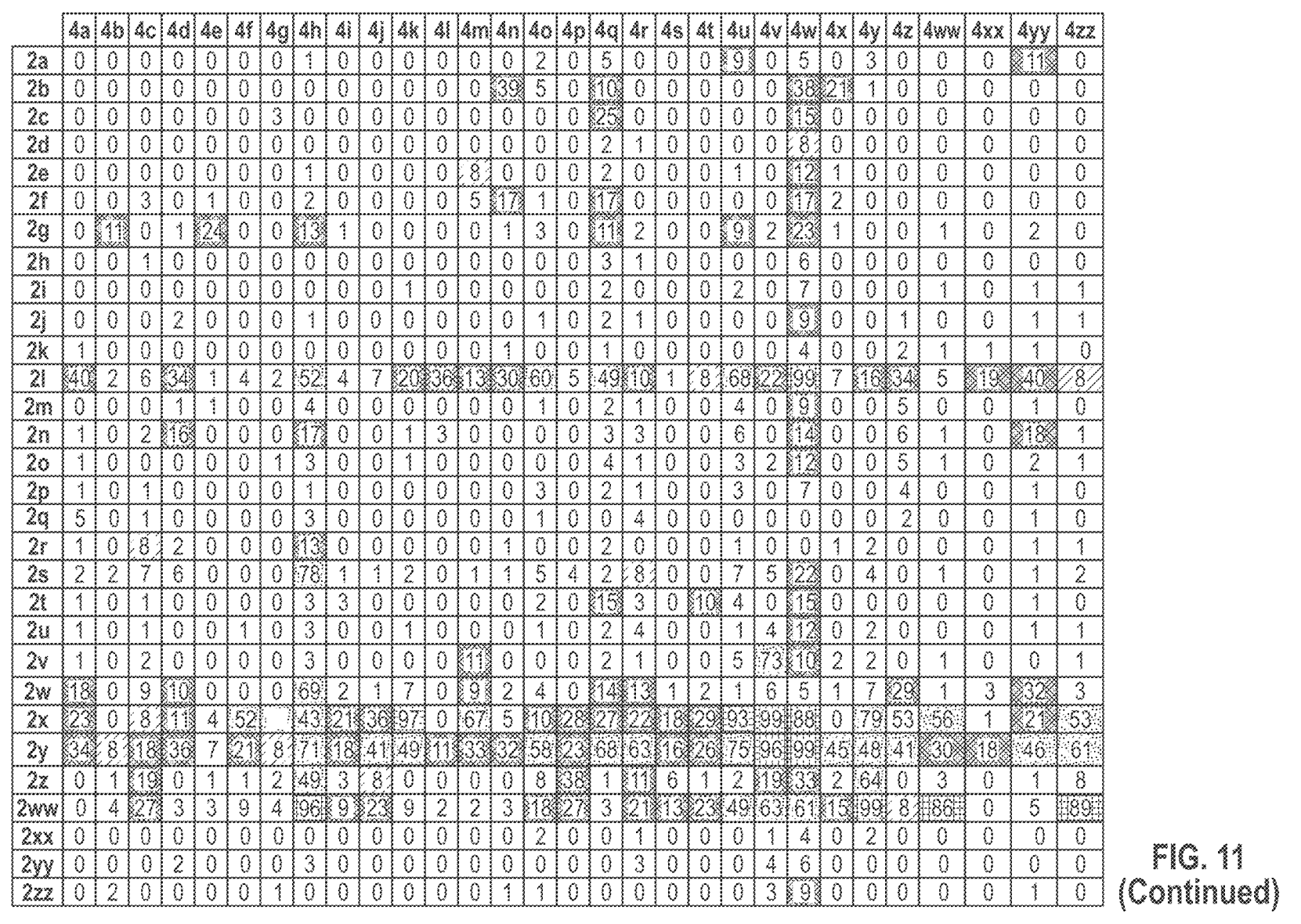
Figure 11:
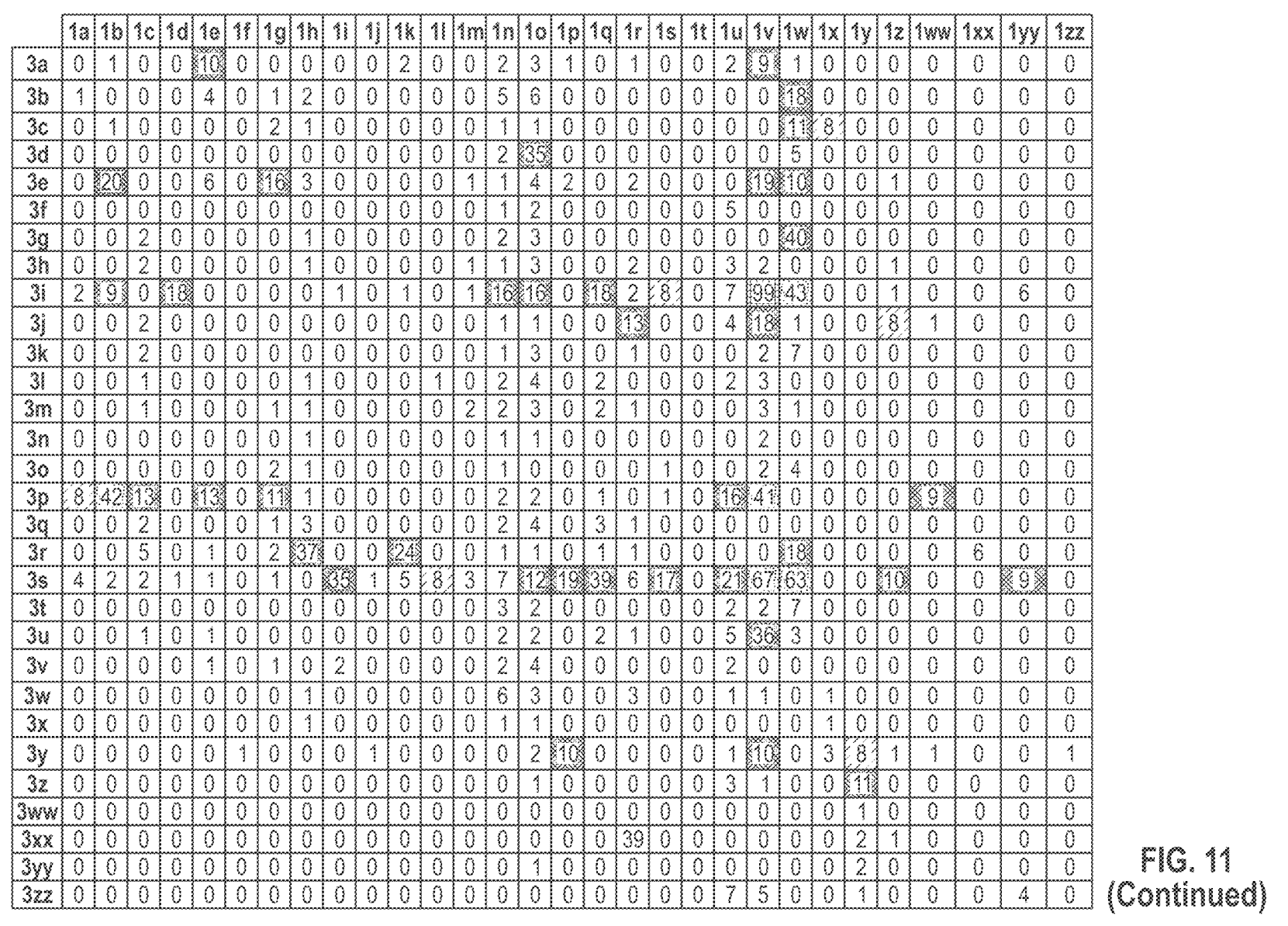
Figure 11:
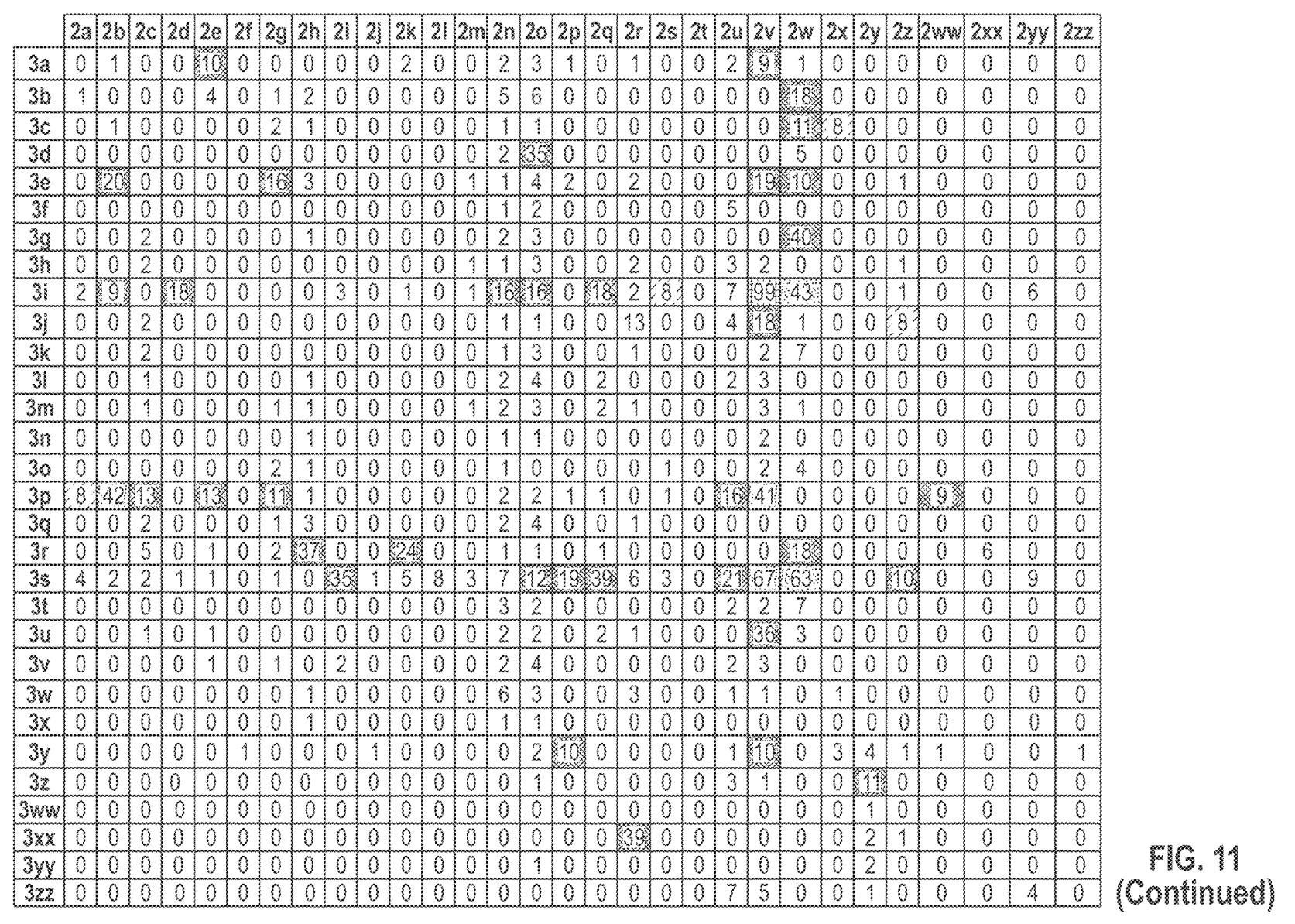
Figure 11:
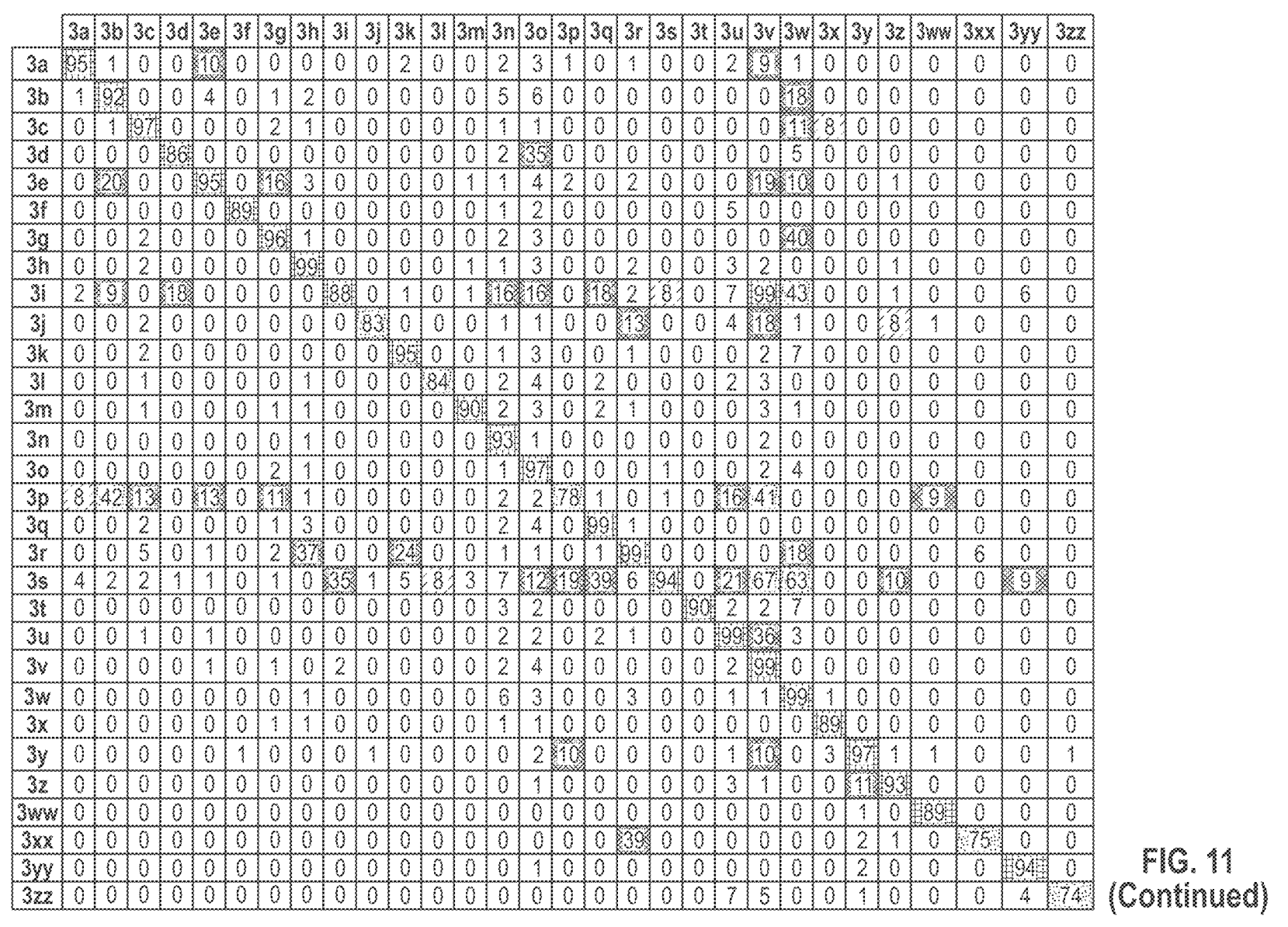
Figure 11:
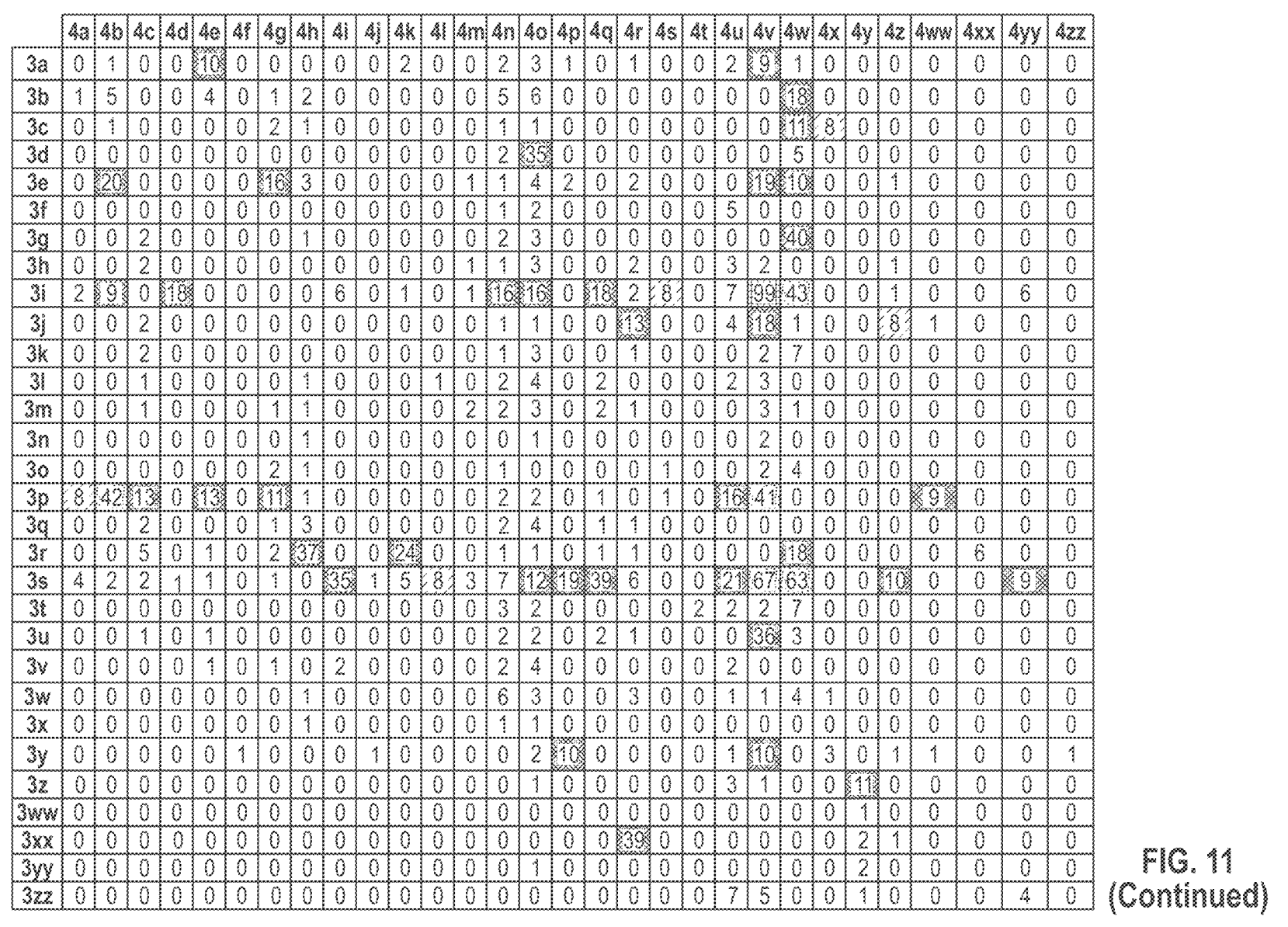
Figure 12:
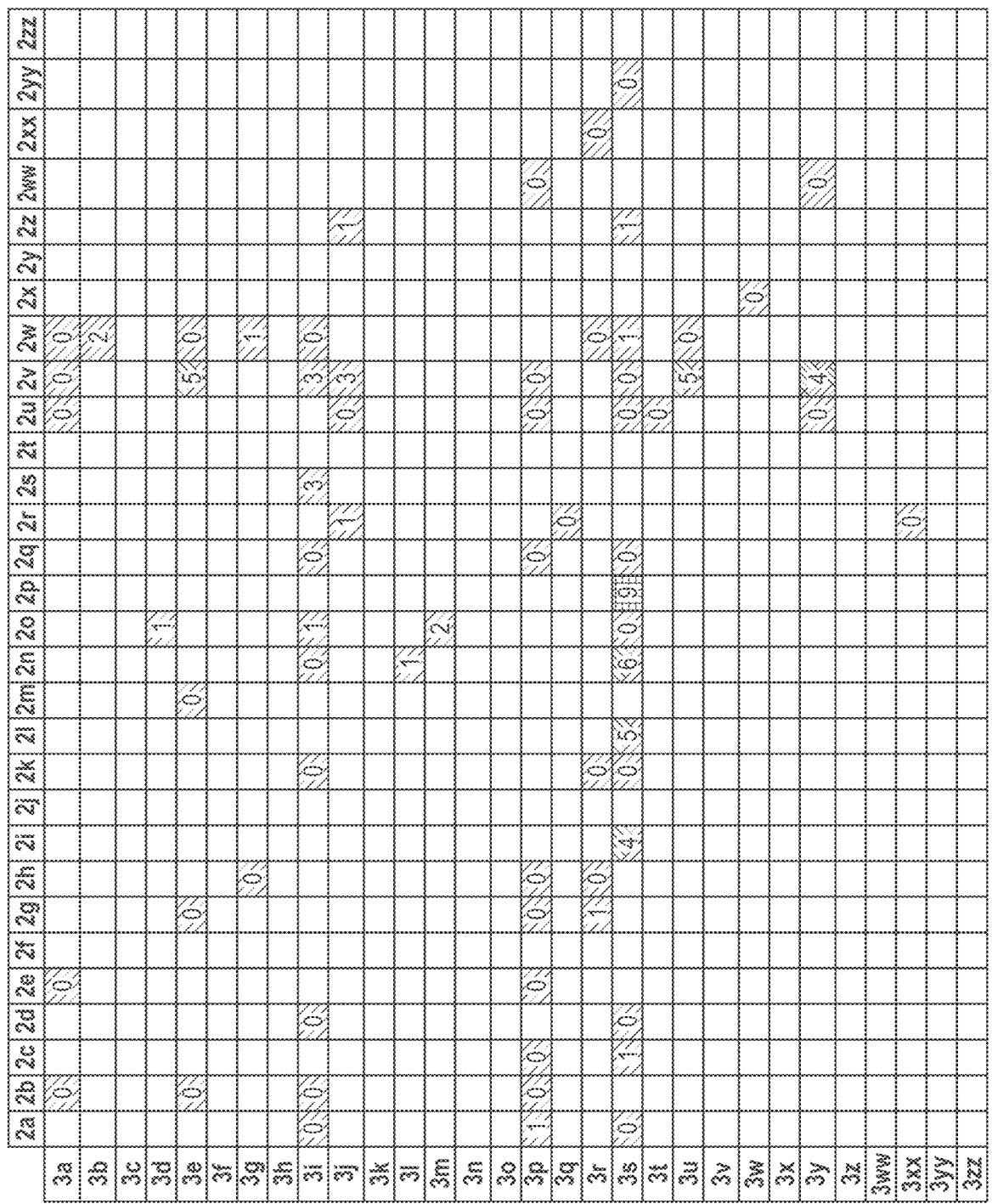
FIG. 12. Corrected values of the concatenated FIG. 11 obtained via deconvolution with additional DTS reactions.

Mismatched product formation likely arises from a single problematic codon:anticodon combination, and thus some codons in excluded templates were likely innocent bystanders that did not contribute to mismatched product formation. It was sought to identify the smallest possible set of problematic codons that, once removed from the codon pool, would enable all remaining reagent-template combinations to satisfy the above orthogonality criteria. To identify the problematic codons, a model in which each template behaves as a chain of four independent codons was assumed (FIG. 2C) and that contributions of DNA hybridization between a given anticodon and each of the four codons to reaction conversion were additive. These assumptions allowed the conversion of experimental reactivity tables (FIGS. 7A to 7C and 8A to 8C) into an anticipated "annealing factor" table that assigns the expected contribution of each individual codon-anticodon hybridization to overall conversion (FIG. 9). This process is summarized in FIG. 2E. For each case of a template-reagent combination that resulted in unacceptable mismatched product formation, new templates were designed and synthesized containing each of the four original codons in a different surrounding codon context and performed new DTS reactions with the original reagent. The resulting iterative deconvolution used 80 templates and 1,890 additional DTS reactions (FIGS. 11-13), and resulted in the refinement of annealing factors for 1,372 codon-anticodon pairs initially identified as potentially problematic. The refined annealing factors confirmed that 813 of these codon-anticodon pairs do not cause≥7% mismatched product formation, which substantially contributed to the identification of a maximum set of orthogonal codons (FIG. 12).

Figure 16:
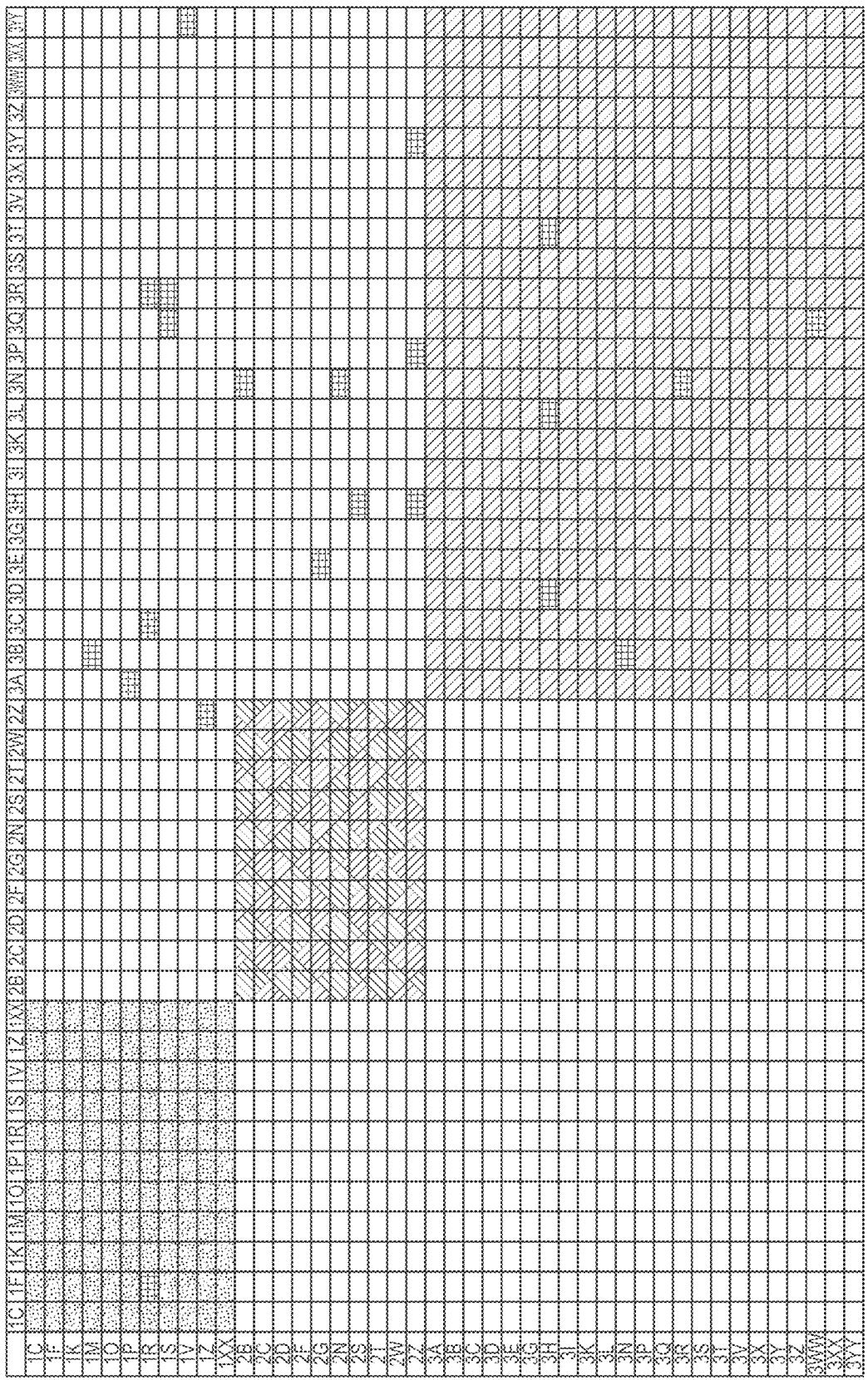
FIG. 16. Brute-force identification of the orthogonal codon subset.
Figure 17:
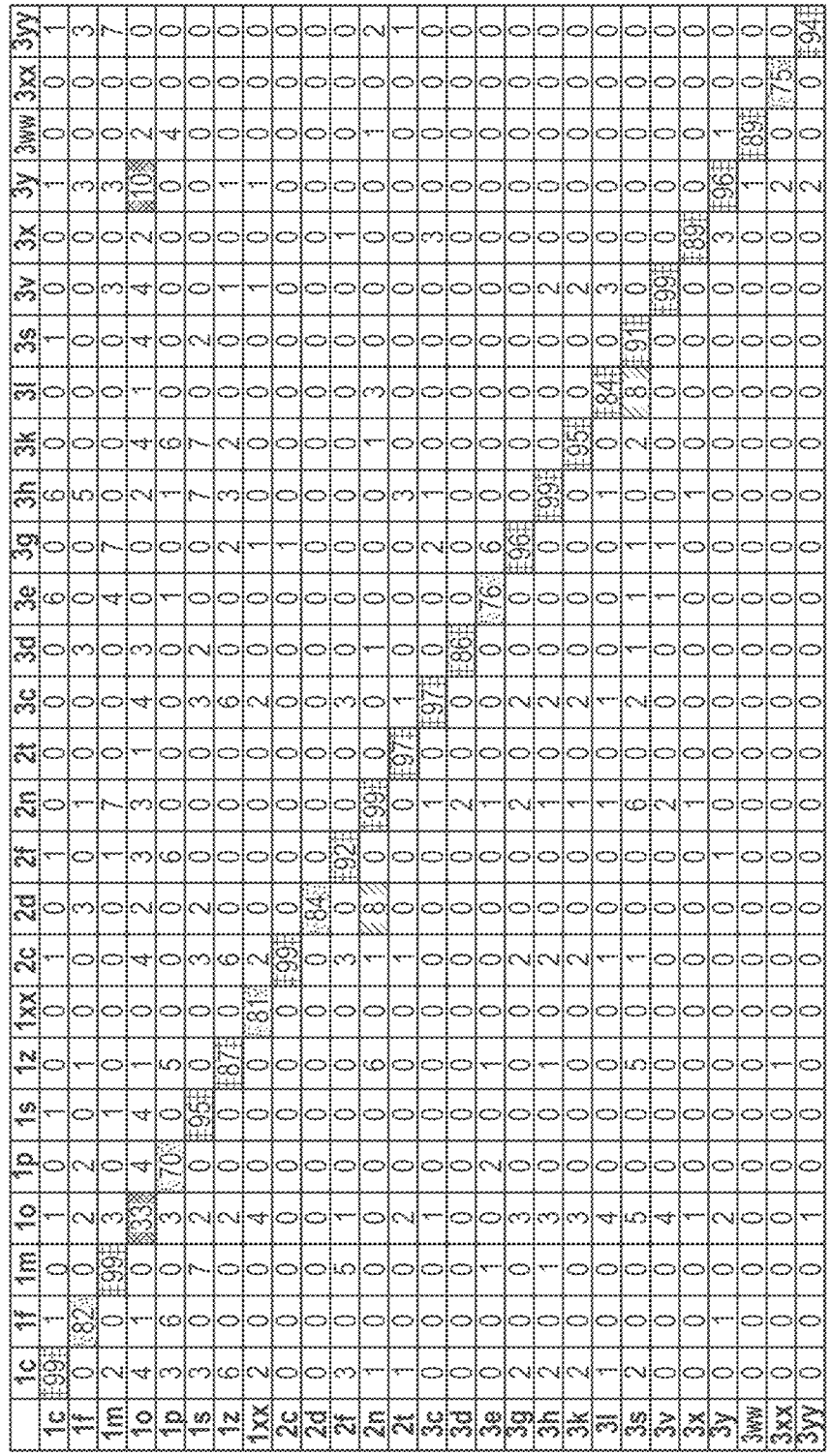
FIG. 17. The maximum subset of the problematic codon set found via brute-force calculation.

The most promiscuous codons were excluded by inspection from further consideration, resulting in the removal of 7, 5, and 1 codons from reactions 1, 2, and 3, respectively. The least promiscuous codons (12, 15, and 6 codons from reactions 1, 2, and 3, respectively, and all 30 scaffold codons), showing no mismatched reactivity were directly included into the final orthogonal codon set. The remaining 44 "grey-area" codons (FIG. 15) could not be excluded or included by inspection because their suitability was mutually dependent on the inclusion or exclusion of other grey-area codons and instead were further analyzed by a computational approach. A mathematical model was developed in which the presence (1) or absence (0) of each of the remaining 44 codons was represented by a binary digit in a 44-digit binary string. Each of the $2^{44}$ possible binary strings representing a candidate set of viable codons was scored computationally using the annealing factor table to identify the number of incompatible sequence pairs contained within each codon set (see FIG. 16 for details). The codon set containing the minimum number of problematic reagent-template combinations (those predicted to result in ≥7% conversion) contained 27 of the 44 grey zone codons (FIG. 17) and was added to the previously accepted subset of 12, 15, and 6 codons for reactions 1, 2, and 3, respectively. The resulting orthogonal codon set contained 20×20×20×30 codons for reactions 1, 2, 3, and the scaffold, respectively. After separate validation of additional two scaffold codons with 2×60 DTS reactions, a final orthogonal 20×20×20×32 codon set was obtained (FIG. 18 and Table 4) capable of encoding 256,000 unique DNA-templated reaction products. This final codon set was renamed as 1A . . . 1T; 2A . . . 2T; 3A . . . 3T; and 4A . . . 4Z, 4UU . . . 4ZZ (FIGS. 3A to 3C, FIG. 18, and Table 4).

To validate the final orthogonal codon set, the results of 4,068 DNA-templated reactions were re-analyzed, performed at the optimized temperatures collectively involving all of these codons and it was tested if the empirical conversion data matched the result predicted by the final annealing factor table. The predicted apparent conversions of only 178 of the 3,929 mismatched reactions (4.5%) were substantially (>50%) different from the observed experimental values, out of which only 108 (2.7%) corresponded to selected codons, suggesting the validity of the codon set and the codon derivation methodology (FIG. 2C). Finally, it was noticed that the scaffold codon is rarely problematic in our DTS architecture due to its distal location. Therefore, the in silico codon analysis described above was repeated including only the 20+20+20 final codons encoding reagents for steps 1, 2, and 3 resulted in the identification of an additional 48 scaffold codons predicted to not interfere with codon orthogonality (Table 4). These additional scaffold codons expand the theoretical capacity of future DNA-templated libraries of this format to 640,000 members.

Expanding the Diversity of Macrocycle Scaffolds

Figure 19:
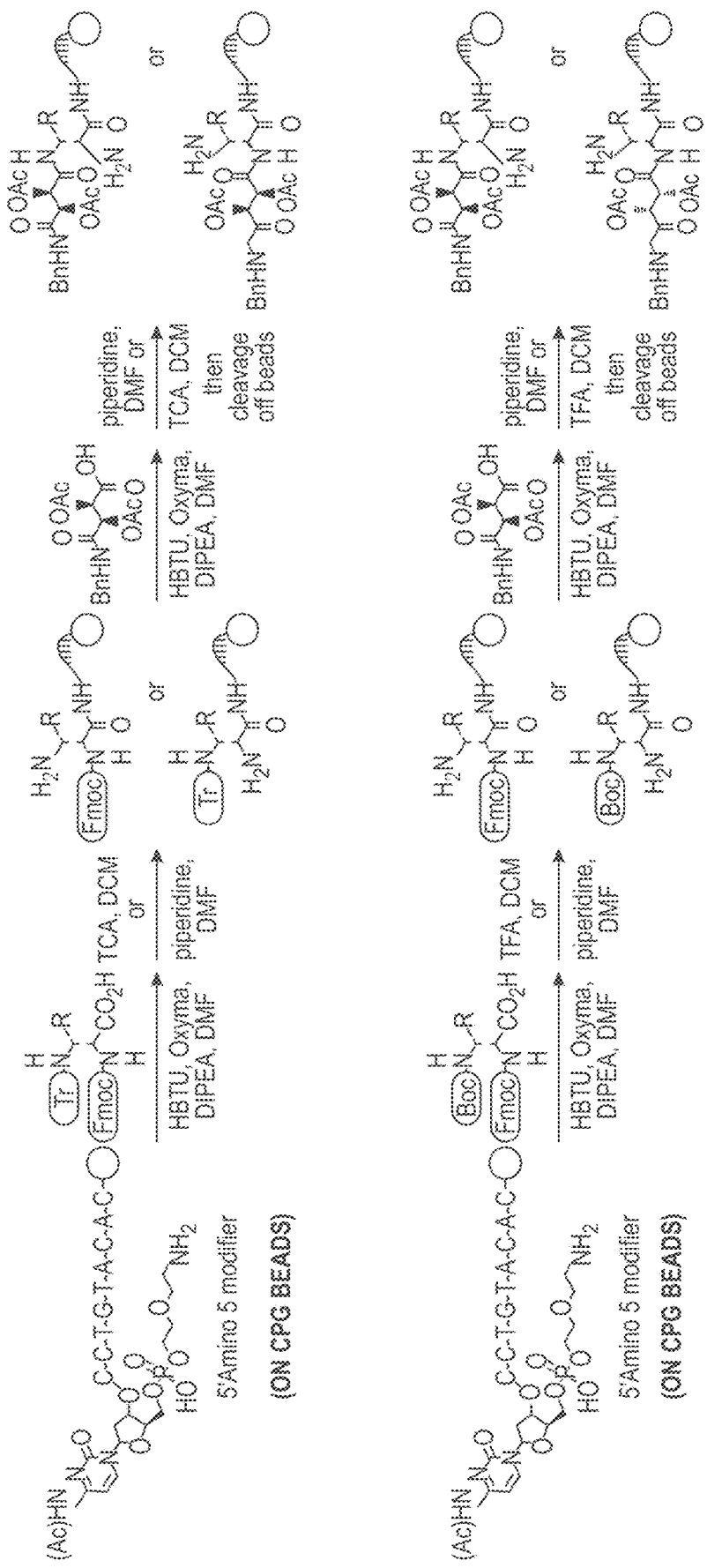
FIG. 19. Standard (Fmoc/Tr) and novel (Fmoc/Boc) approaches to attachment of scaffold to DNA.

It was sought to expand the functional and stereochemical diversity of simple bis-amino acid scaffolds[38], which were previously chosen based on the commercial availability of Fmoc- and trityl-protected derivatives suitable for on-bead DNA conjugation. Previously, Boc-protected bis-amino acids could not be used as scaffolds due to DNA-incompatible deprotection conditions. It was found that DNA-coupled Boc-functionalized scaffolds could be successfully deprotected on-beads upon 1-minute exposure to 50% trifluoroacetic acid in dichloromethane; analysis of the purified products showed no significant decomposition or detectable depurination of DNA (FIGS. 3A and 19). It was confirmed that these conditions did not isomerize a variety of candidate new scaffolds (Table 15), allowing the addition of 12 aminomethyl phenylalanine scaffolds and four aminoprolines in addition to 8 stereoisomers of previously used scaffolds. These additions expanded the set of scaffolds from 8 used in our original library[38] to 32 (FIGS. 3B and Table 8) and also substantially increased the structural diversity of the resulting library.

Selection of Building Blocks to Improve Cell Permeability

Lipinski and coworkers developed guidelines commonly known as "the rule of 5," which postulates that a molecule is more likely to be orally active (and, by inference, cell-permeable) if molecular weight, octanol/water partition coefficient (Log P), numbers of hydrogen bond donors, and number of hydrogen bond acceptors lie within the ranges listed in Table 1A.[45] Additional limitations for the number of rotatable bonds and polar surface area were subsequently introduced[46]. Multiple examples of orally bioavailable molecules violating rule-of-5 principles, especially including macrocycles[33,47-51], have led researchers including Kihlberg and co-workers to develop alternative, expanded guidelines (MW≤1,000 Da, # of H-bond donors below 6; # of H-bond acceptors below 15, c Log P from −2 to 10, # of rotatable bonds below 20, polar surface area below 250 Å2) that are especially relevant to macrocyclic molecules such as those in our DNA-templated libraries[33,50-54] (Table 1A).

TABLE 1A

Desirable chemical spaces described by Lipinski[45] and Kihlberg[52, 54].

| Parameter | Lipinski | Kihlberg |
|---|---|---|
| molecular weight | <500 Da | <1000 Da |
| cLogP | 0 < x < 5 | −2 < x < 10 |
| # hydrogen bond donors | <5 | <6 |
| # hydrogen bond acceptors | <10 | <15 |
| # rotatable bonds | <10 | <20 |
| polar surface area | <140 Å$^2$ | <250 Å$^2$ |

Building blocks were chosen for the second-generation library such that the resulting macrocycles are consistent with Kihlberg rules[52] in order to increase the likelihood of compatibility with cell-based assays and to facilitate subsequent hit-to-lead optimization. A method was developed to calculate the influence of any building block candidate on the predicted Kihlberg conformity of the resulting library using widely available chemistry software (ChemBioOffice from CambridgeSoft). Code was designed for the VBA platform (an integrated part of Microsoft Office) that generates SDF files, a widely used structure-data file format, containing the building block connectivities of all 256,000 macrocycles. ChemBioDraw was programmed to recognize the letter codes of a given selection of building block candidates and used this software to convert SDF files into drawn chemical structures. A VBA program then exported the resulting files into ChemFinder, which calculated the Kihlberg parameters. The set of building blocks were iteratively optimized to comply with Kihlberg's guidelines through minimization of the number of highly polar functional groups and hydrogen bond donors, as well as liberal use of N-alkylated amino acids (FIG. 3C and Table 9).

In order to access underexplored macrocycle chemical space, sterically and conformationally challenged structures were also introduced, including fused alicyclic (1O, 1R, 1S, 2K, 2N, 2P, 3B, 3C, 3D, 3F, 3G, 3J, 3K, 3M), fused aromatic (1J, 1L, 1M, 1N, 1T, 3E, 3H, 3L, 3R) and spirogenic (1I, 2E, 2Q, 2S, 3N, 3O, 3Q) building blocks. Amino acids with less nucleophilic nitrogen centers were mostly used in reaction 3, since the corresponding amide bond is not formed through DNA-templated amine acylations requiring nucleophilic amines (FIG. 1). To maximize library diversity and take full advantage of DNA-templated macrocyclization, building blocks were chosen that include α (29 building blocks), β (12), γ (8), δ (7) and ε+(4) amino acids. Likewise, a comparable number of building blocks were incorporated from both L- and D-amino acid pools for each structural type (13 and 12 amino acids, respectively).

To maximize the quality of the resulting library, all candidate building blocks not previously tested were validated in model single-macrocycle DNA-templated syntheses and only those that provided at least 30% yield of coupling product (typically 50-80%) and at least 45% yield of cyclization (typically 80-90%) were considered further. The final sets of selected scaffolds and building blocks are shown in FIGS. 3B and 3C.

Figure 4:
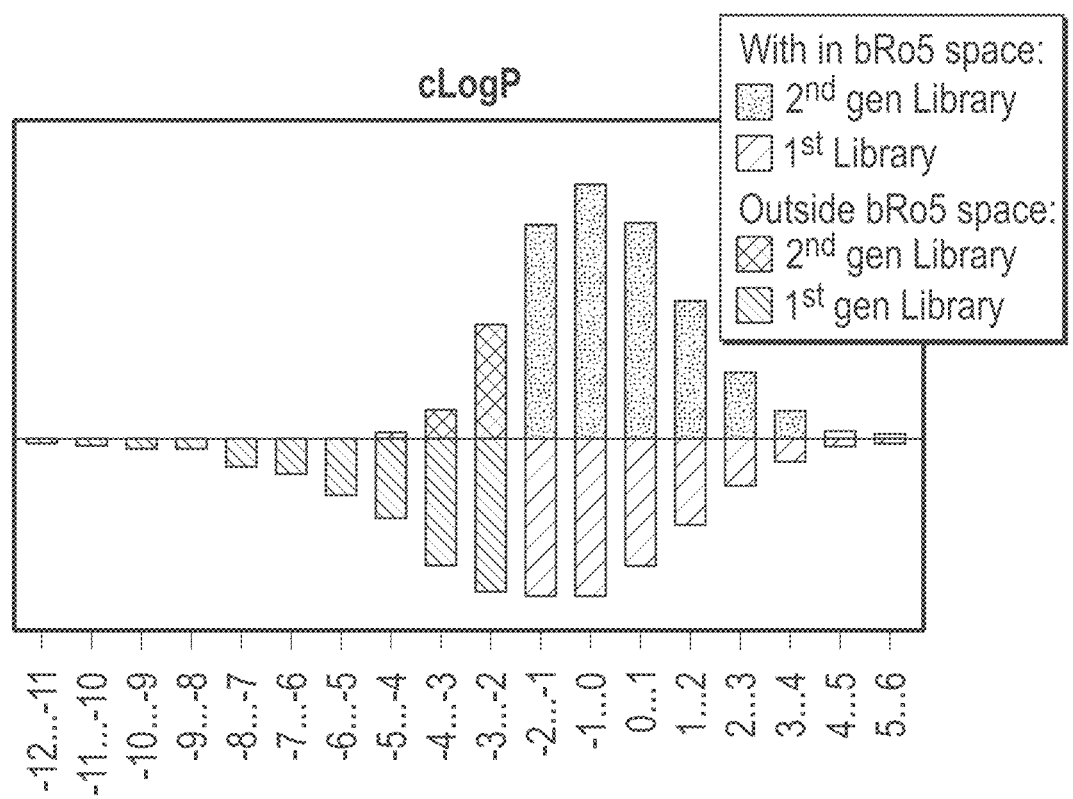
FIG. 4. Distribution of physical parameters among library members from the second-generation macrocycle library (above the X-axis) and the first-generation library (below the X-axis) Colors represents values that lie within (patterned) or outside (gray shaded) desirable "beyond rule-of-five" (bRo5) parameter space described by Kihlberg and coworkers.[52,54]
Figure 4:
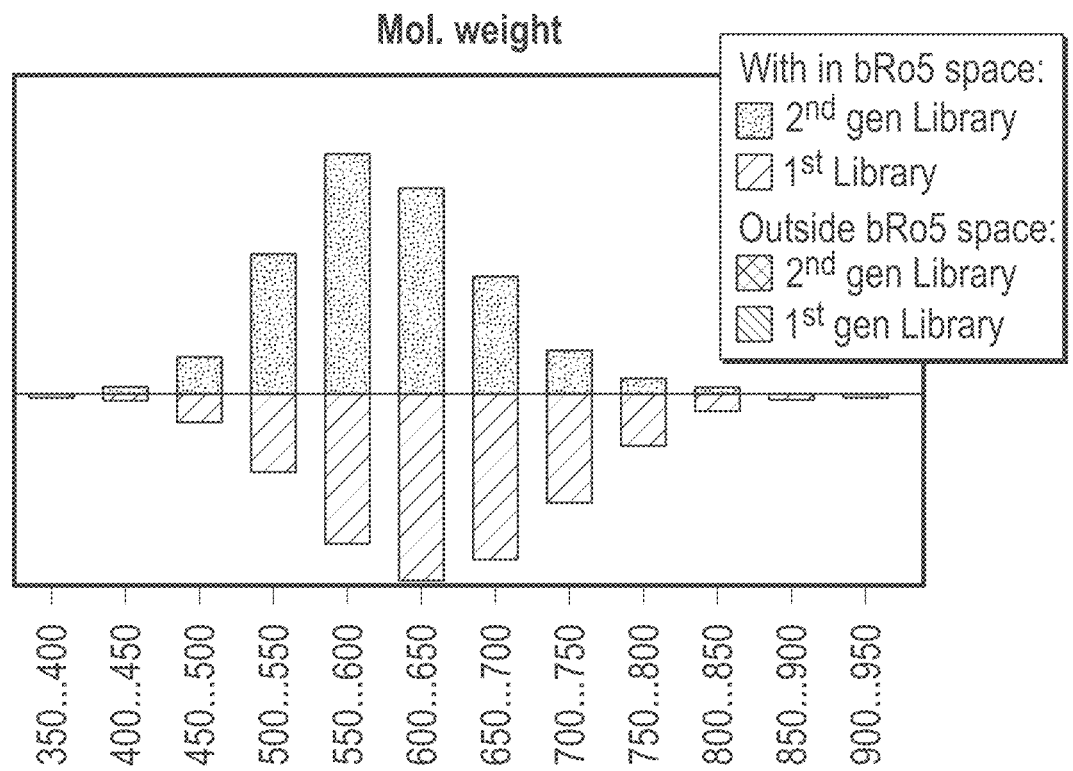
Figure 4:
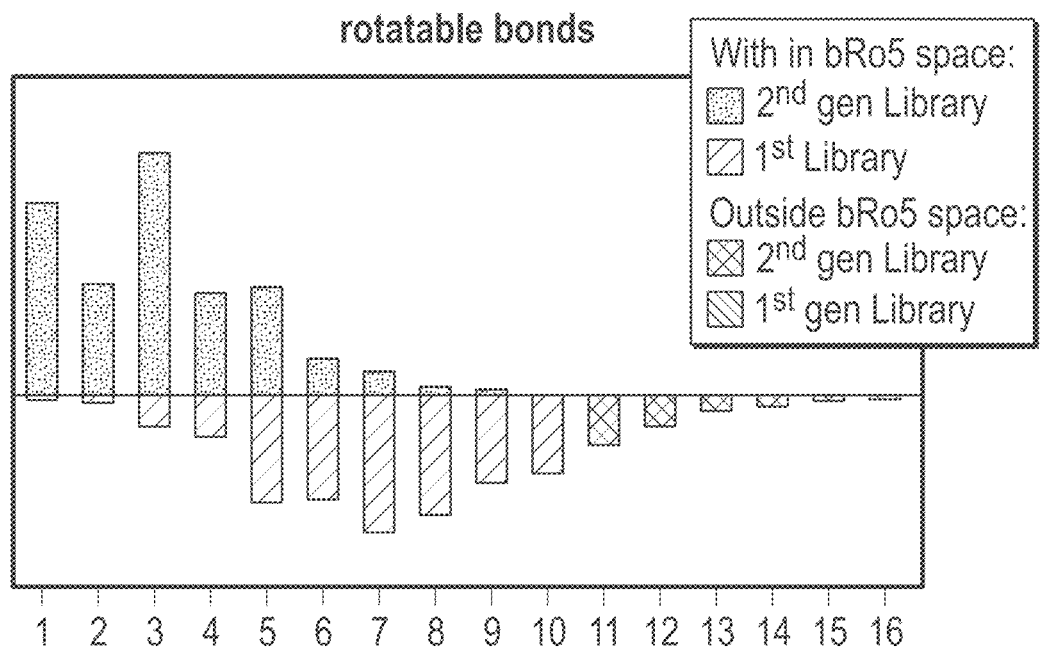
Figure 4:
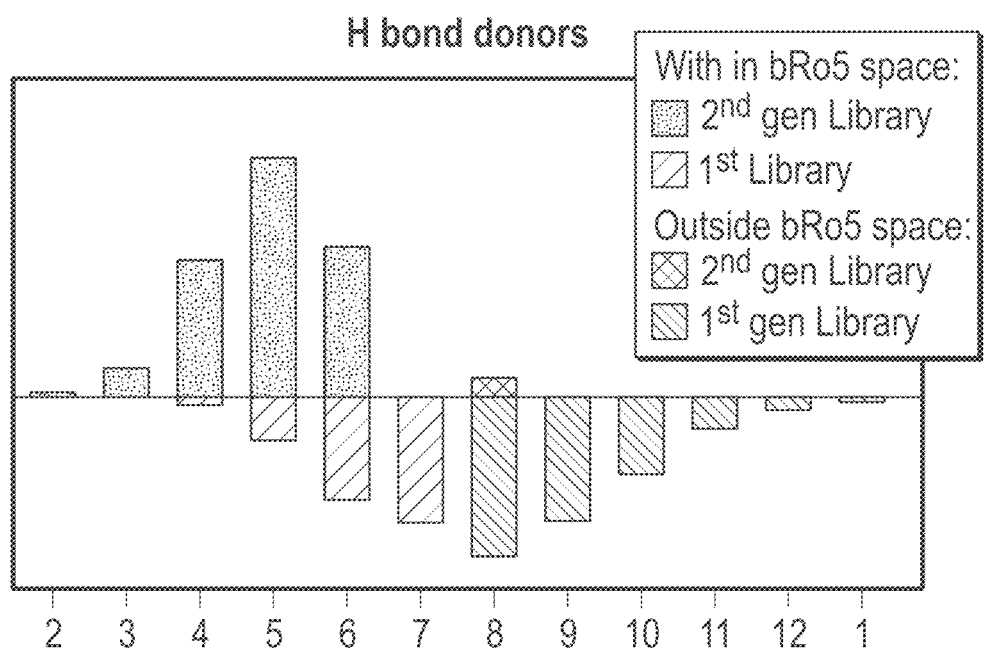
Figure 4:
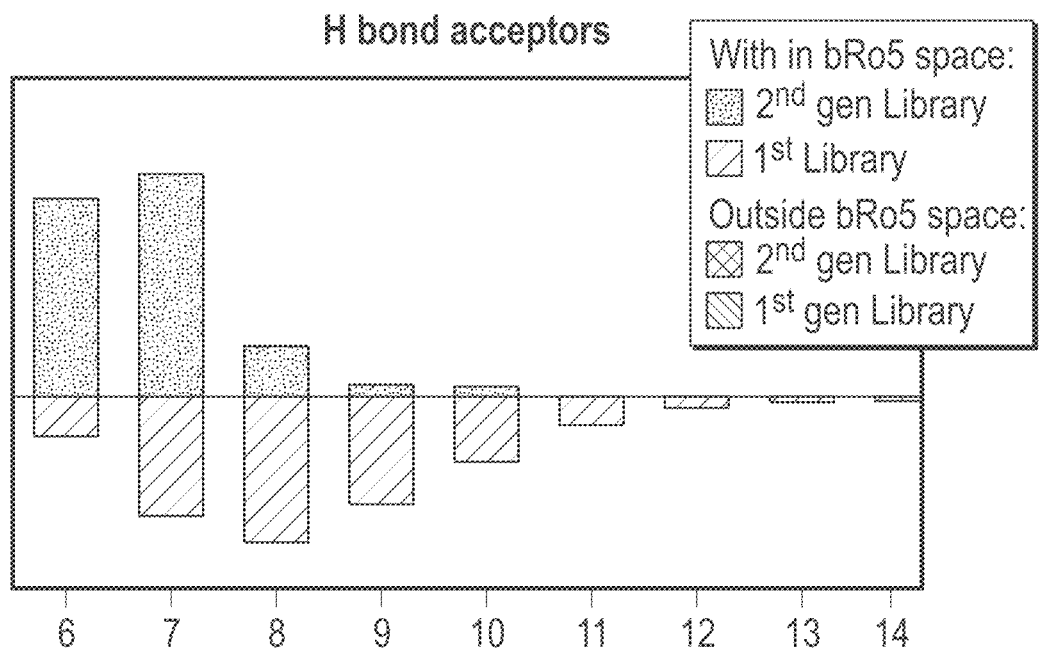
Figure 4:
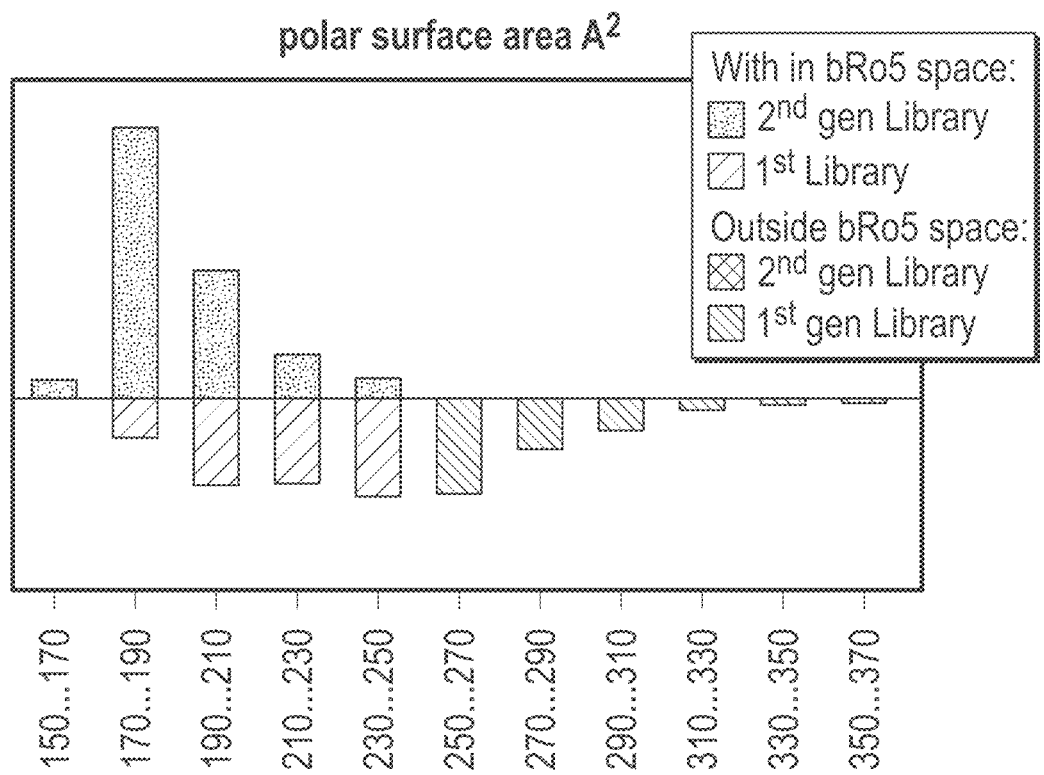

The resulting final macrocyclic products were calculated to possess bioavailability-correlated parameters that are greatly improved compared to our first-generation DNA-templated macrocycle library (FIG. 4). The difference is particularly striking for c Log P, polar surface area, and the number of hydrogen bond donors. In addition, the methodology developed here enables rapid generation of large virtual libraries using widely available, economical software and thus could assist the broader small-molecule library research community (see Supporting Information for programming code and detailed protocols).

Novel DNA Template Assembly Methodology

Figure 5A:
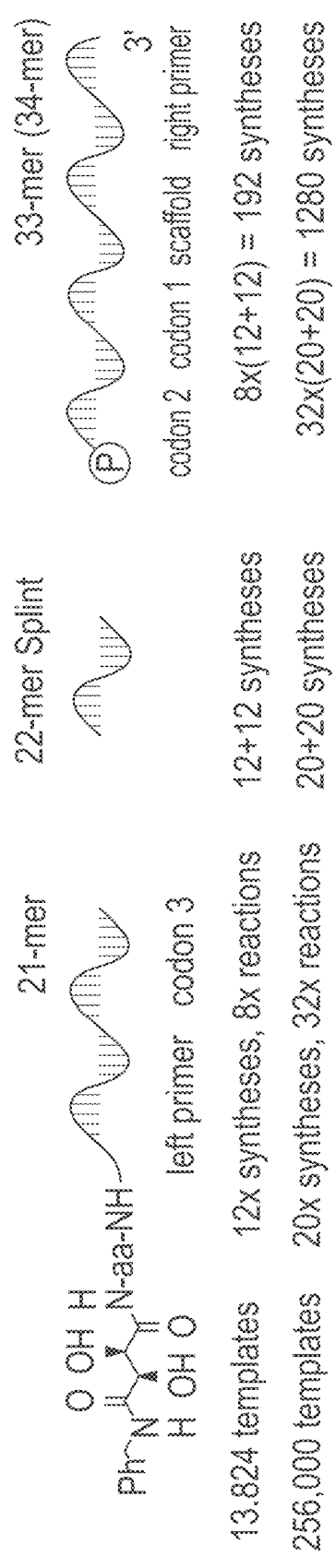
FIGS. 5A to 5C. Approaches to the assembly of DNA template libraries.

The previously established strategy of assembling the library of DNA templates used split-pool oligonucleotide synthesis of phosphorylated 3' fragments, followed by enzymatic splint-assisted ligation with chemically modified 5' fragments[38]. Applying the same approach to the preparation of a 256,000-membered library would require many more oligonucleotide syntheses and split-pool events; for example, 1,280 vs. 192 oligonucleotide syntheses alone would be required for the preparation of the 3' fragment (FIG. 5A). Splitting the template into three parts rather than two (FIG. 5B) could mitigate the problem, however, it was sought to provide a more convenient template library assembly to popularize application of DNA-templated libraries. It was sought to reduce the number of required manipulations, enable quality control before the final stages of the library assembly, avoid the use of splint ligations, which are inconvenient on preparative scale, and enable template library synthesis components to be reused wherever possible for subsequent library preparation efforts.

Furthermore, it was sought to eliminate the need to isolate and characterize complex mixtures of chemically modified oligonucleotides, which is problematic in the case of low-yielding reactions with multiple by-products (such as those involving some of the novel scaffolds). Therefore, a novel approach to template library assembly was developed based on polymerase-mediated extension of chemically modified primers.

Figure 5B:
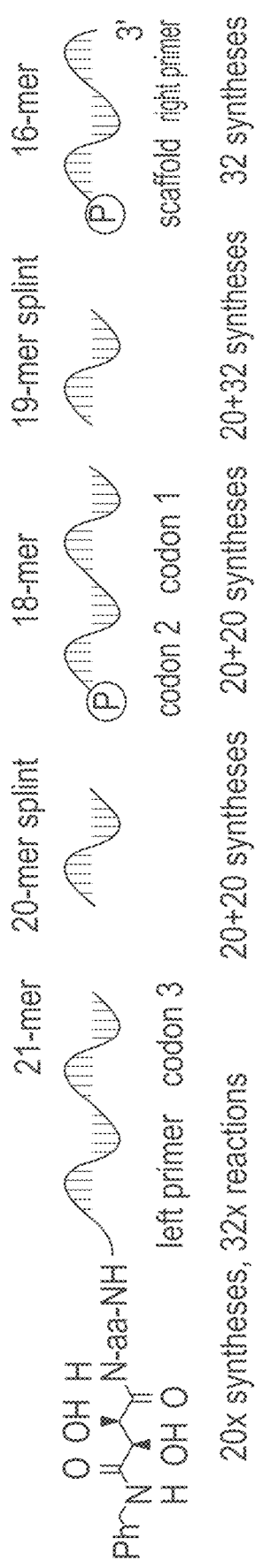
Figure 5C:
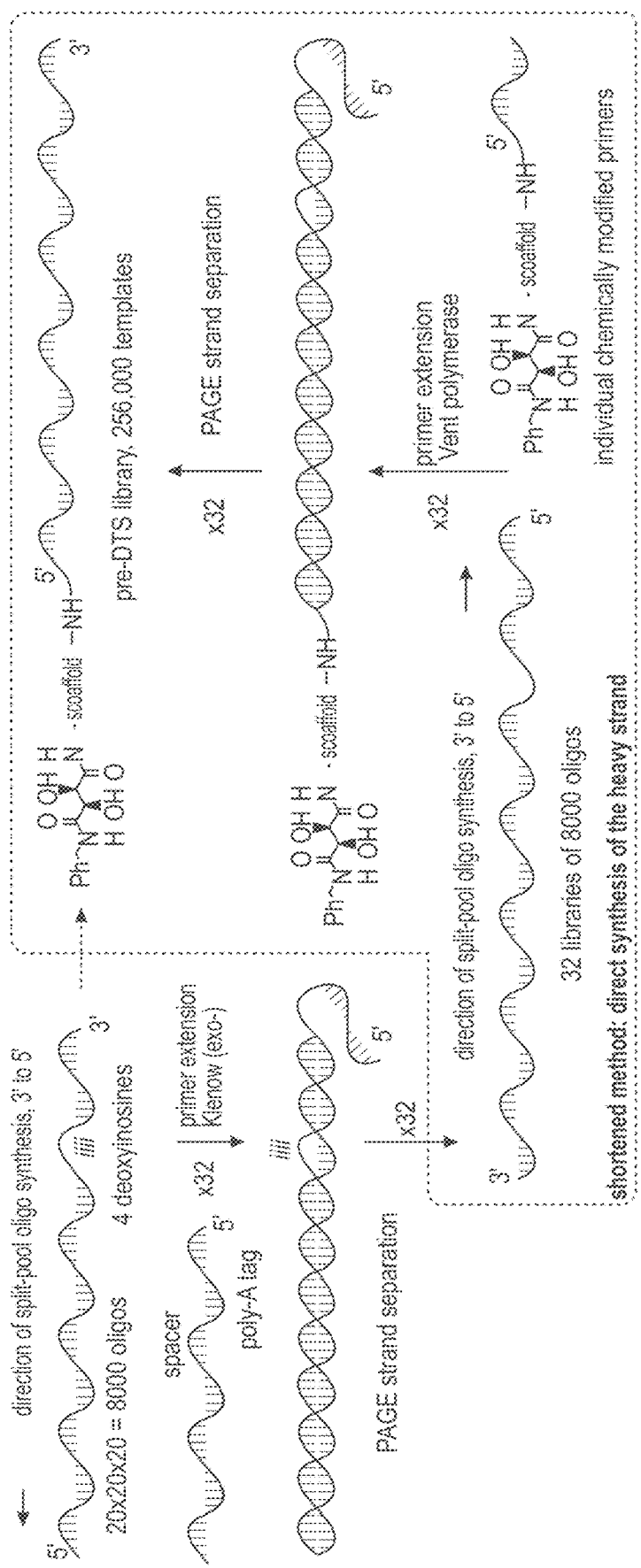
Figure 20A:
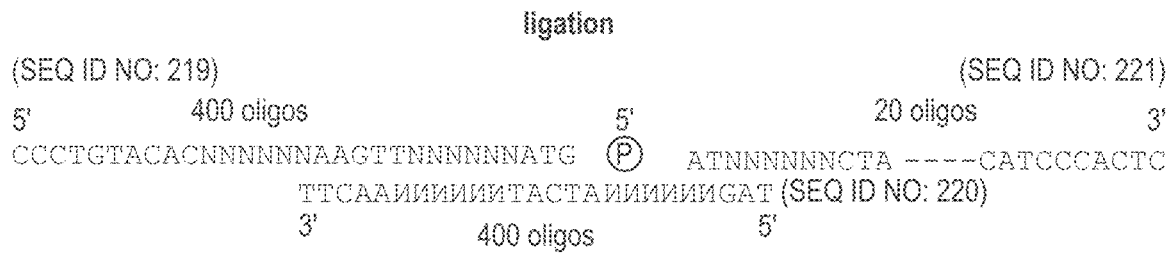
FIG. 20. Assembly strategies for 8,000-membered I$_4$ libraries.
Figure 20B:
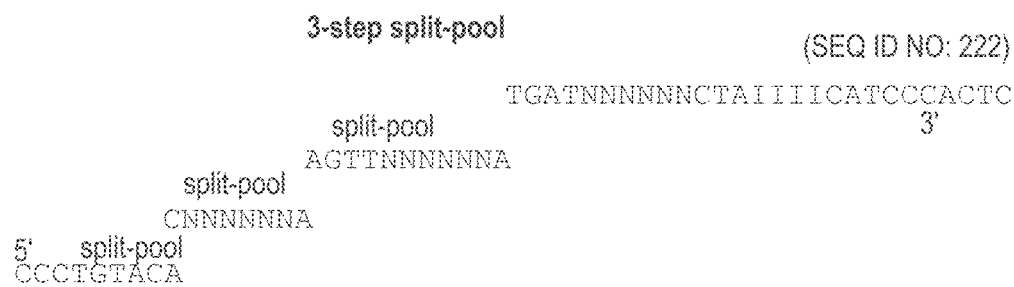
Figure 20C:
Figure 21:
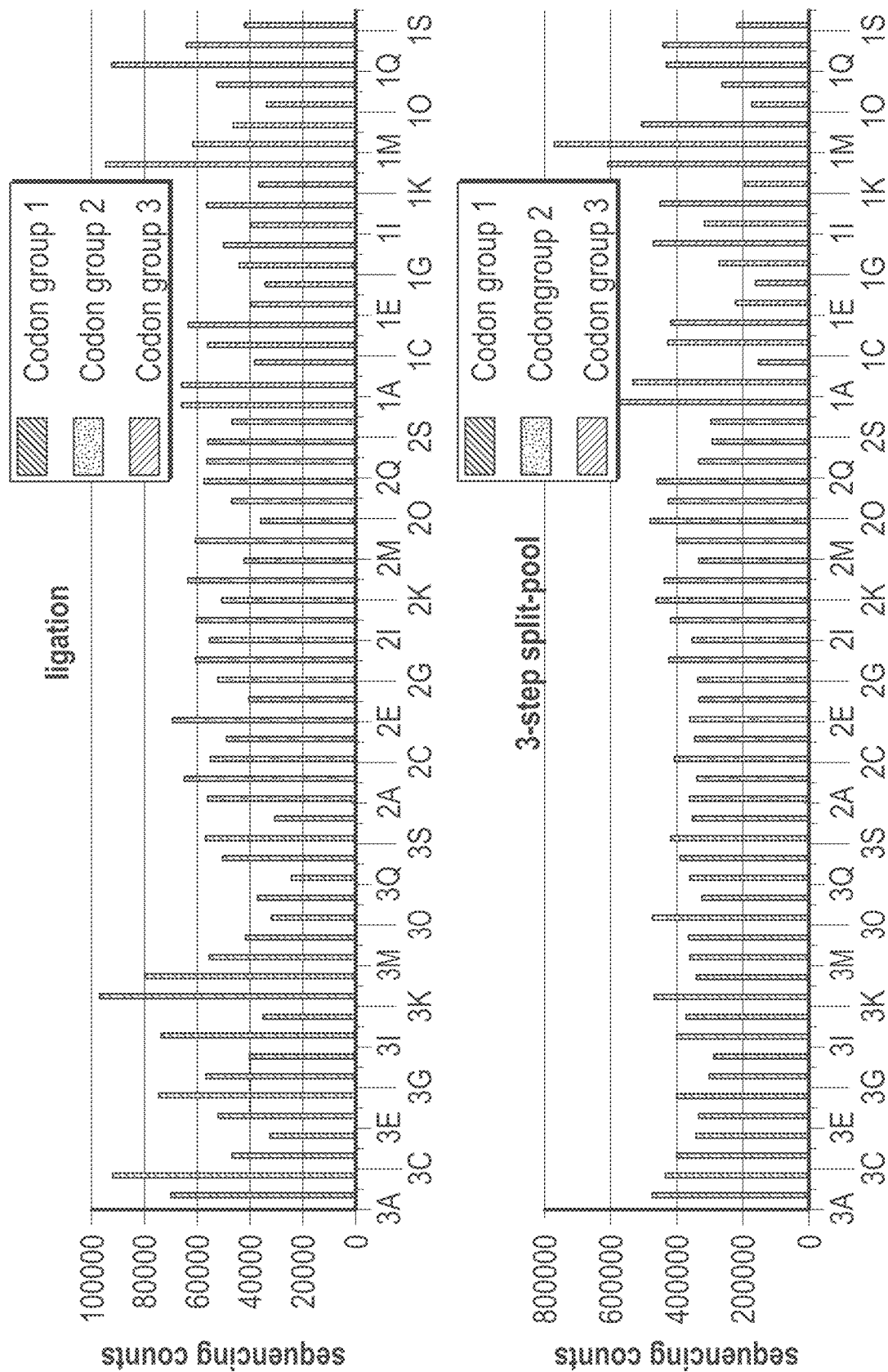
FIG. 21. Codon distributions of 8,000-membered I$_4$ libraries prepared via different routes.
Figure 21:
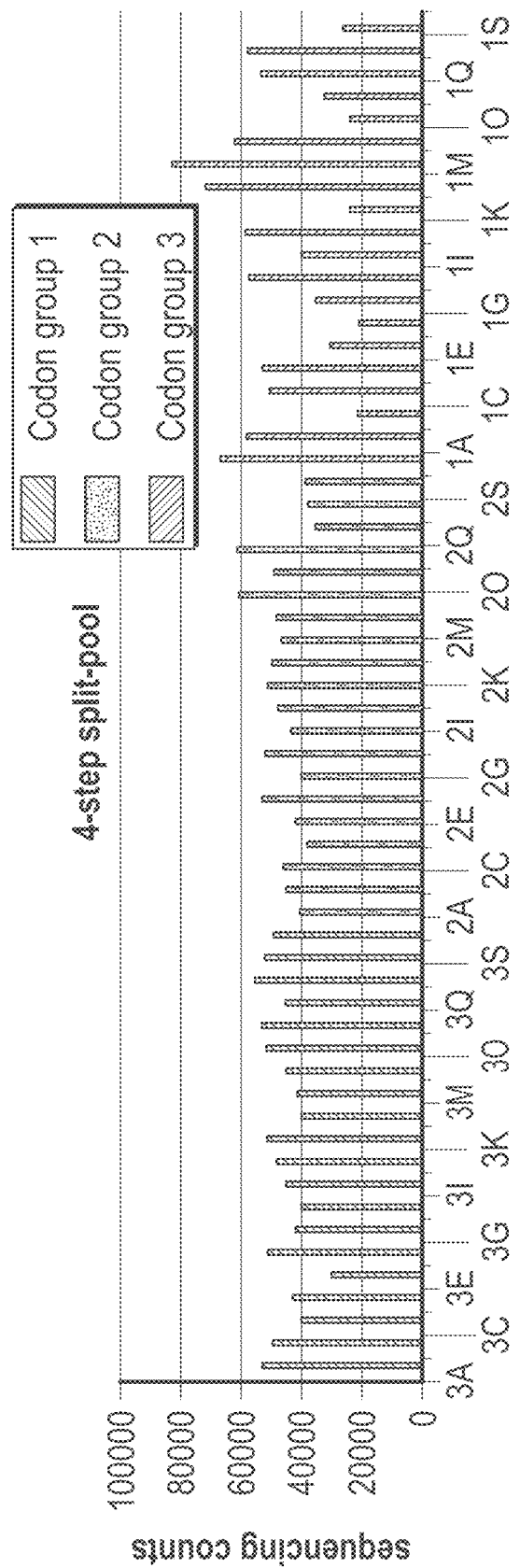
Figure 22A:
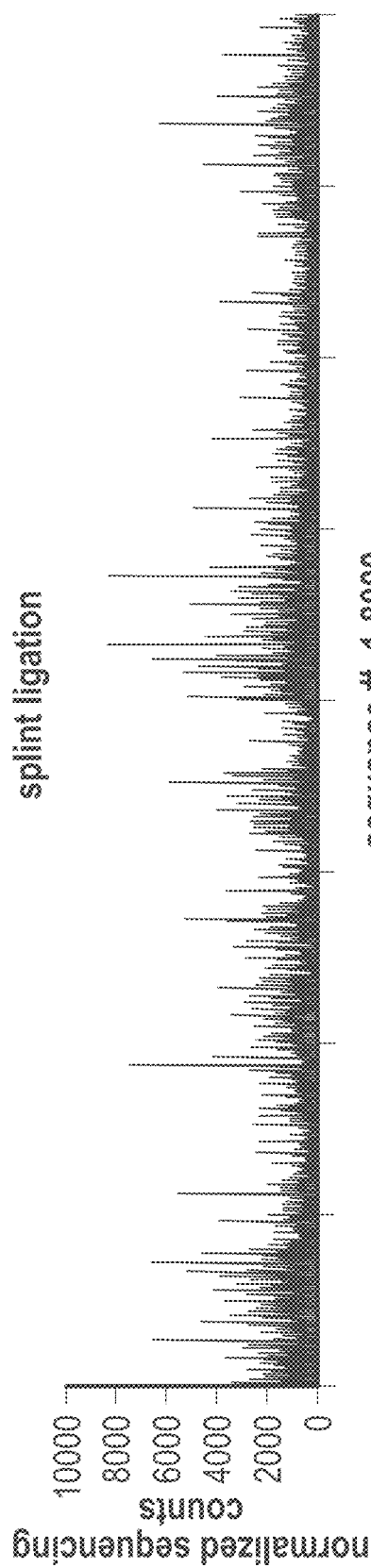
FIG. 22. Library member distributions for 8,000-membered I$_4$ libraries prepared via different routes.
Figure 22:
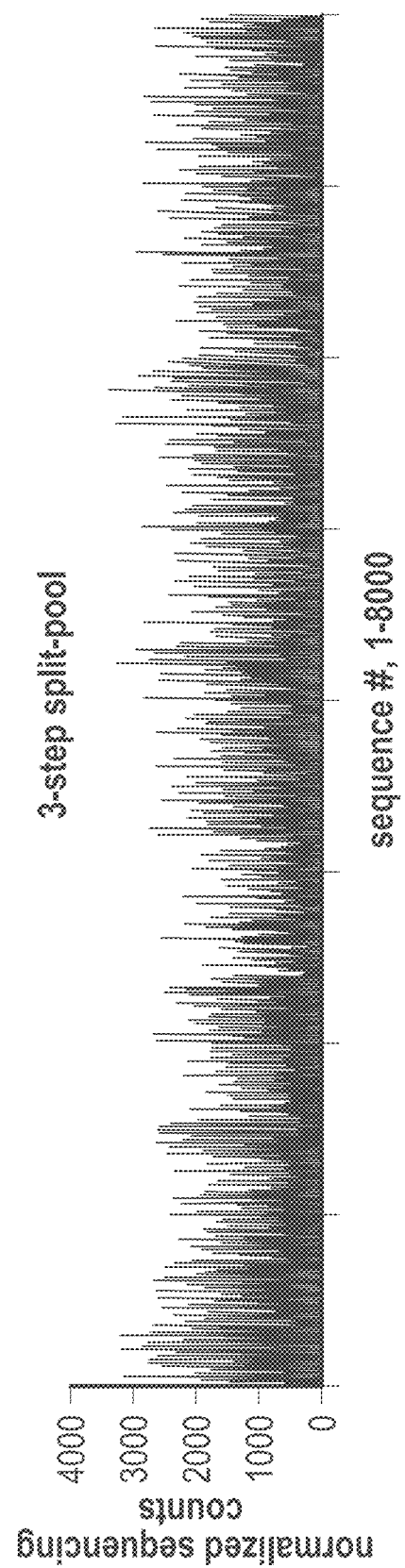

For a 32×20×20×20 library this route would involve separate primer extensions of thirty-two 8,000-membered libraries with different scaffold codons. To avoid synthesizing multiple initial libraries, the ability of deoxyinosine to pair in vitro with all four natural nucleobases[55] was exploited. It was reasoned that a 256,000-membered template library could be generated from a single universal 8,000-membered starting library (tetradeoxyinosine library or $I_4$ library, FIGS. 20-22) by allowing the 32 scaffold codons to each hybridize to the $I_4$ region of a DNA template containing codons 1, 2, and 3 in a primer extension reaction (FIG. 5C). For each of the 32 primer extensions, the identity of the scaffold on the 5'-scaffold-linked primer is encoded by the sequence information introduced by the other primer (FIG. 5C). After extensive experimentation, it was found that the $I_4$ template could be successfully converted to the desired library by consecutive primer extensions with Klenow(exo-) fragment of DNA polymerase I and Vent polymerase. It was also found that appending a sufficiently long oligonucleotide tail (e.g. $A_{30}$) on one primer allows separation of the two product strands (55-mer light strand and 55-mer+30-mer tail heavy strand) in a library format using denaturing PAGE. These results together provide streamlined access to libraries of single-stranded DNA templates suitable for DTS (FIG. 5C and FIG. 23B).

Improved Synthesis and Recovery of DNA-Templated Libraries

A solution-phase alternative to the on-bead macrocyclization of immobilized DTS intermediates was developed FIG. 1). Instead of using a biotin group to capture intermediates prior to macrocyclization, each reagent 3 oligonucleotide was equipped with 18 ethylene glycol units and developed an efficient PAGE purification protocol for intermediates that successfully reacted in all three DTS steps (FIG. 26). The macrocyclization step occurs in solution, and macrocyclized products are separated from uncyclized intermediates by PAGE isolation. This strategy allowed more accurate control over library preparation and avoided uncertainties associated with solid-phase capture and heterogeneous on-bead reactions. Moreover, this solution-phase approach enables library syntheses on nmol to μmol scales, which would previously have required prohibitive quantities of expensive streptavidin-conjugated magnetic beads.

Figure 35:
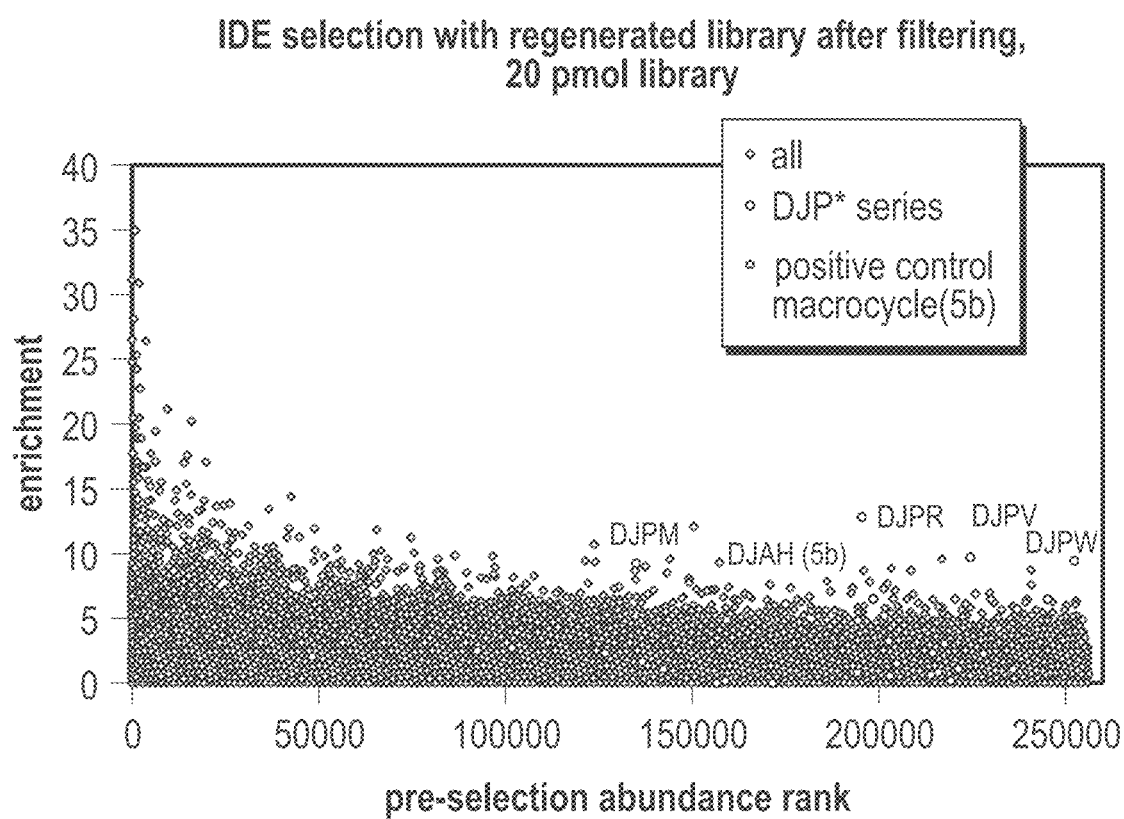
FIG. 35. Refined selection of recycled library against insulin-degrading enzyme.

To isolate template-linked macrocycles or intermediates from dilute solutions with minimal losses a simple chaotropic buffer (4 vol. saturated aqueous guanidine hydrochloride+6 vol. isopropanol) was developed that efficiently promotes the association of DNA-linked species with commercially available silica membranes such as Omega HiBind or Qiagen Qiaquick columns. For example, 99% recovery and 50-fold concentration of 4.8 nmol of single-stranded 55-mer oligonucleotide from a dilute (120 nM) solution was achieved. This methodology has proven instrumental for DTS, which requires multiple isolations of dilute short oligonucleotide-linked products that were previously recovered by less reliable alcohol precipitation[38]. Importantly, this approach also enables efficient recycling of DNA-templated libraries from in vitro selections, as the vast majority of library members (both target binders and non-binders) end up in dilute flowthrough and wash solutions, from which they can be salvaged using the chaotropic buffer and silica membranes. For example, 867 pmol (51%) of the final DNA-templated macrocycle library described below was recovered from the combined flowthrough volumes of 98 selections (averaging 17 pmol library each). The quality of the recovered material as evaluated by PAGE was very similar to that of freshly made library, and selections for target protein binding described below yielded similar selection results using freshly synthesized or recovered library (FIG. 35). This recycling capability greatly reduces the resources expended in each DNA-templated library selection and should also facilitate the recycling of other DNA-encoded libraries.

DNA-Templated Synthesis of a Library of 256,000 Macrocycles

Figure 29:
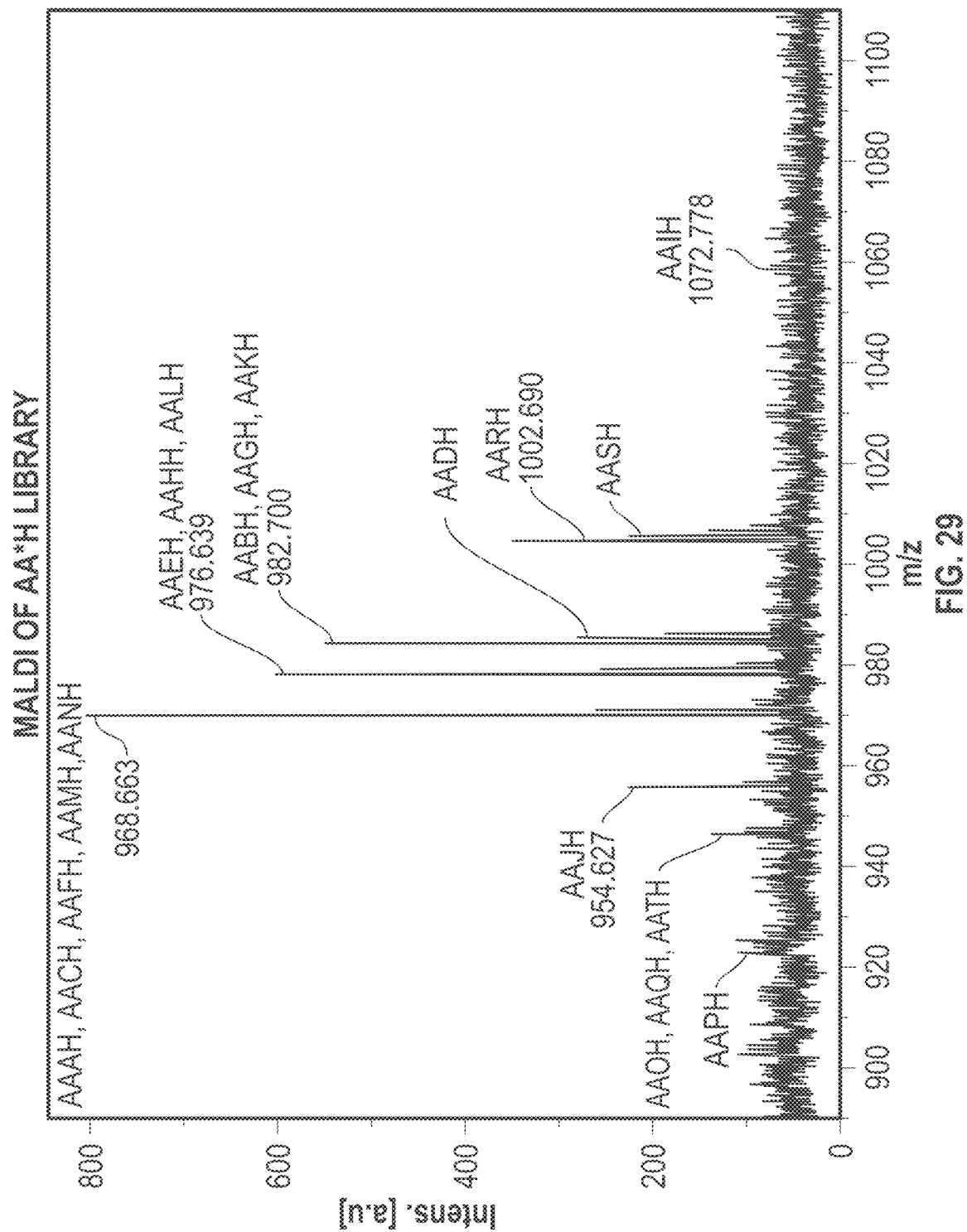
FIG. 29. MALDI spectra of S1 nuclease-digested 20×1×1 libraries of macrocycles.
Figure 29:
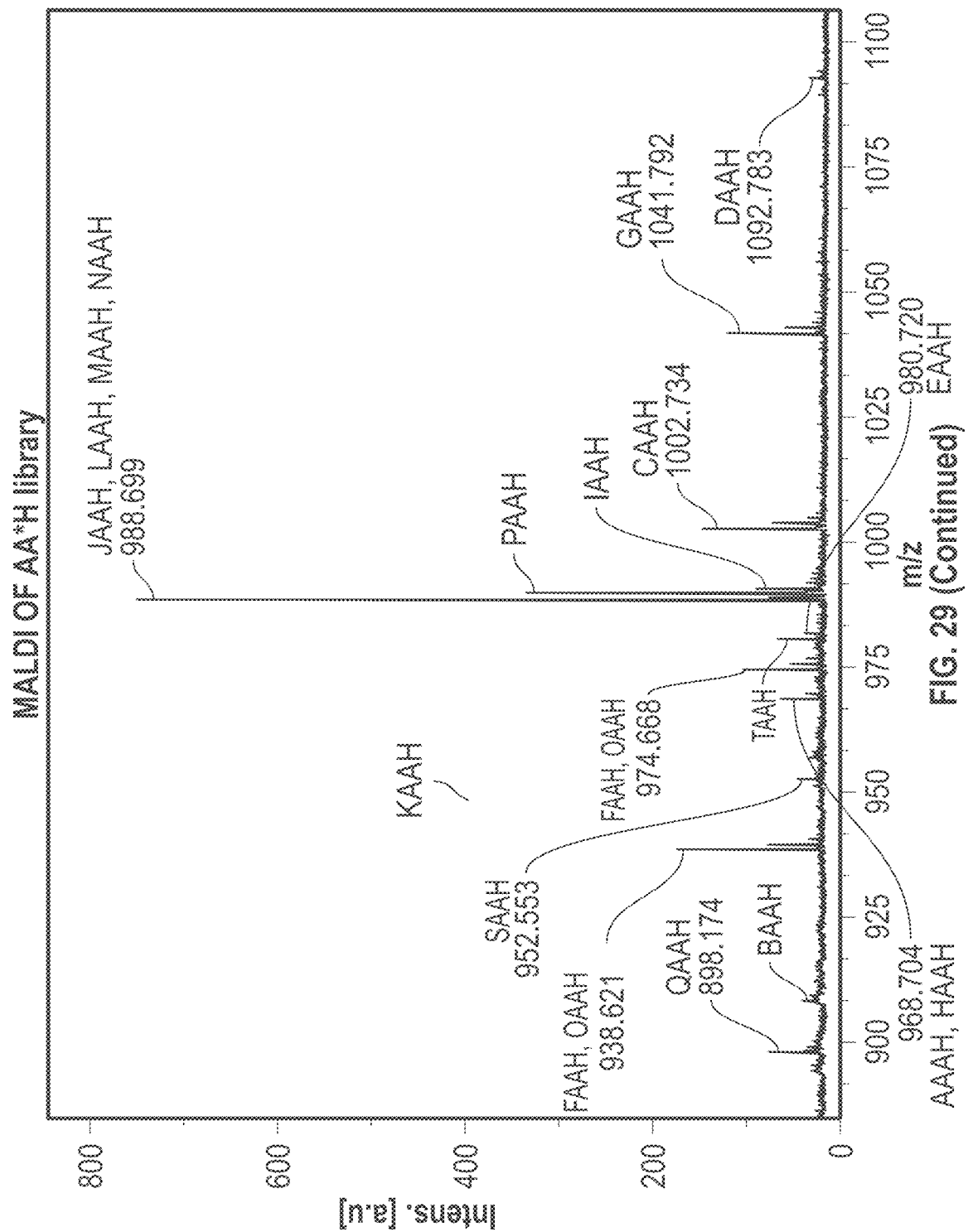

To confirm that the second-generation DNA-templated library synthesis methodology and materials generate compounds consistent with the target macrocycles, 20×1×1×1 and a 1×1×20×1 template subsets of the library were subjected to the DNA-templated library synthesis methodology, followed by removal of DNA templates with S1 nuclease to afford macrocycles made conjugates to a guanine nucleotide. MALDI mass spectrometry revealed product masses consistent with the presence of 32/40 expected macrocycles (FIG. 29). These results confirmed the ability of the DNA-templated library synthesis methodology to generate expected macrocycles, as previously shown.[38,40,42]

The second-generation DTS library of macrocycles was prepared by integrating the above methodologies. The DNA template library was generated by two sequential series of 32 primer extensions/PAGE purifications (FIG. 5C) starting with 32×50 nmol of 8,000-membered universal library of $I_4$ templates and yielding 250 nmol of the 5′-scaffold modified template library. The improved DNA-templated synthesis protocol with two sequential PAGE purifications allowed isolation of the final macrocycle library in a total yield of 1.5% relative to the DNA template library entering the process. Assuming two regeneration cycles per library member, this library synthesis (2×1.83 nmol) is sufficient to conduct >300 selections using a validated quantity of 20 pmol library per selection (see below). Importantly, the developed methodology enables facile scale-up of the library synthesis, as well as swapping of building blocks or scaffolds in subsequent library syntheses.

Figure 27:
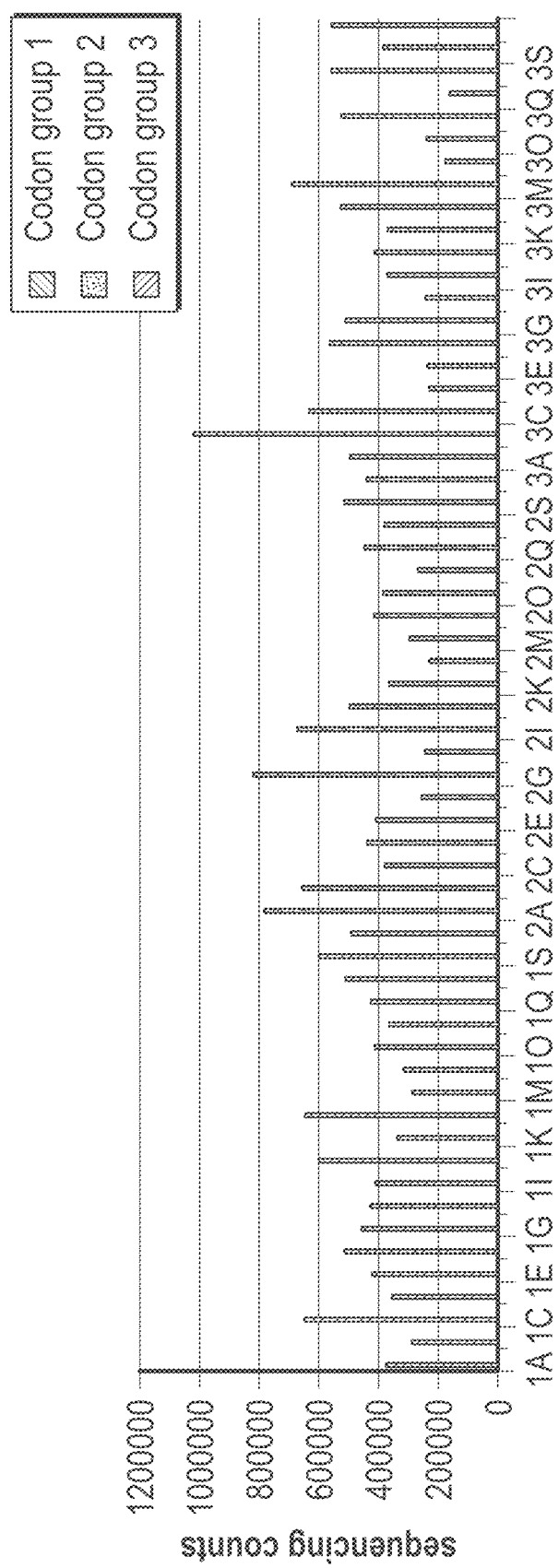
FIG. 27. Codon distribution of the second-generation DNA-templated library of macrocycles.
Figure 28:
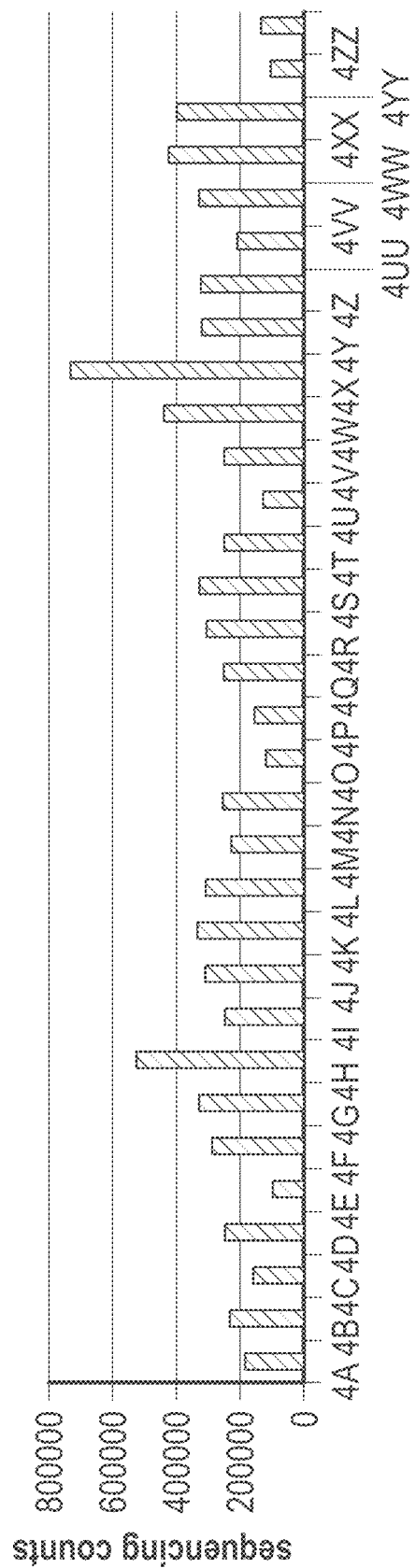
FIG. 28. Scaffold distribution of the second-generation DNA-templated library of macrocycles.

High-throughput DNA sequencing of the final library revealed the presence of 255,954 (>99%) library member templates. A distribution of DNA sequences were observed in the final library that was consistent with the anticipated reactivities of individual building blocks and the expected efficiency of macrocyclization. For example, large and flexible scaffolds, which are expected to result in the most facile cyclizations (α-Lys, 4H, 4X) were more highly represented than structures expected to macrocyclize less efficiently (α-Dap, 4E, 4U; aminoprolines 4O, 4P, 4YY, 4ZZ). Likewise, N-alkylated amino acids and other building blocks predicted to be less reactive also were found in lower representation of the library (FIGS. 27 and 28).

In Vitro Selection and Validation of the Library of 256,000 Macrocycles

Insulin-degrading enzyme (IDE) was chosen as a protein target for library selection and validation. From our first-generation DNA-encoded macrocycle library[38], macrocycles 6b and 5b were previously identified containing D-4-benzoylphenylalanine and L-3-cyclohexylalanine as potent ligands and inhibitors of IDE (FIGS. 6A to 6D)[42]. In vitro selections for IDE binding were performed using the 256,000-membered macrocycle library. His-tagged IDE (10 μg) was immobilized on 25 μL of magnetic Dynabeads, treated with yeast total RNA to minimize non-specific binding to DNA templates, and incubated with 1 to 20 pmol macrocycle library in TBST buffer (50 mM Tris-HCl pH 8, 150 mM NaCl, 0.05% Tween-20) for 1 h. Three washes with TBST were followed by elution with 300 mM imidazole in TBST. The eluate was directly used in PCR reactions introducing adapter sequences and barcodes for high-throughput sequencing (Illumina MiSeq and NextSeq). Selections were highly reproducible using 20 pmol of library (FIG. 35), which corresponds to an amount of each library member less than or similar to our previously reported selections using 5 pmol of the 13,824-membered DNA-templated macrocycle library[40,42].

Figure 6B:
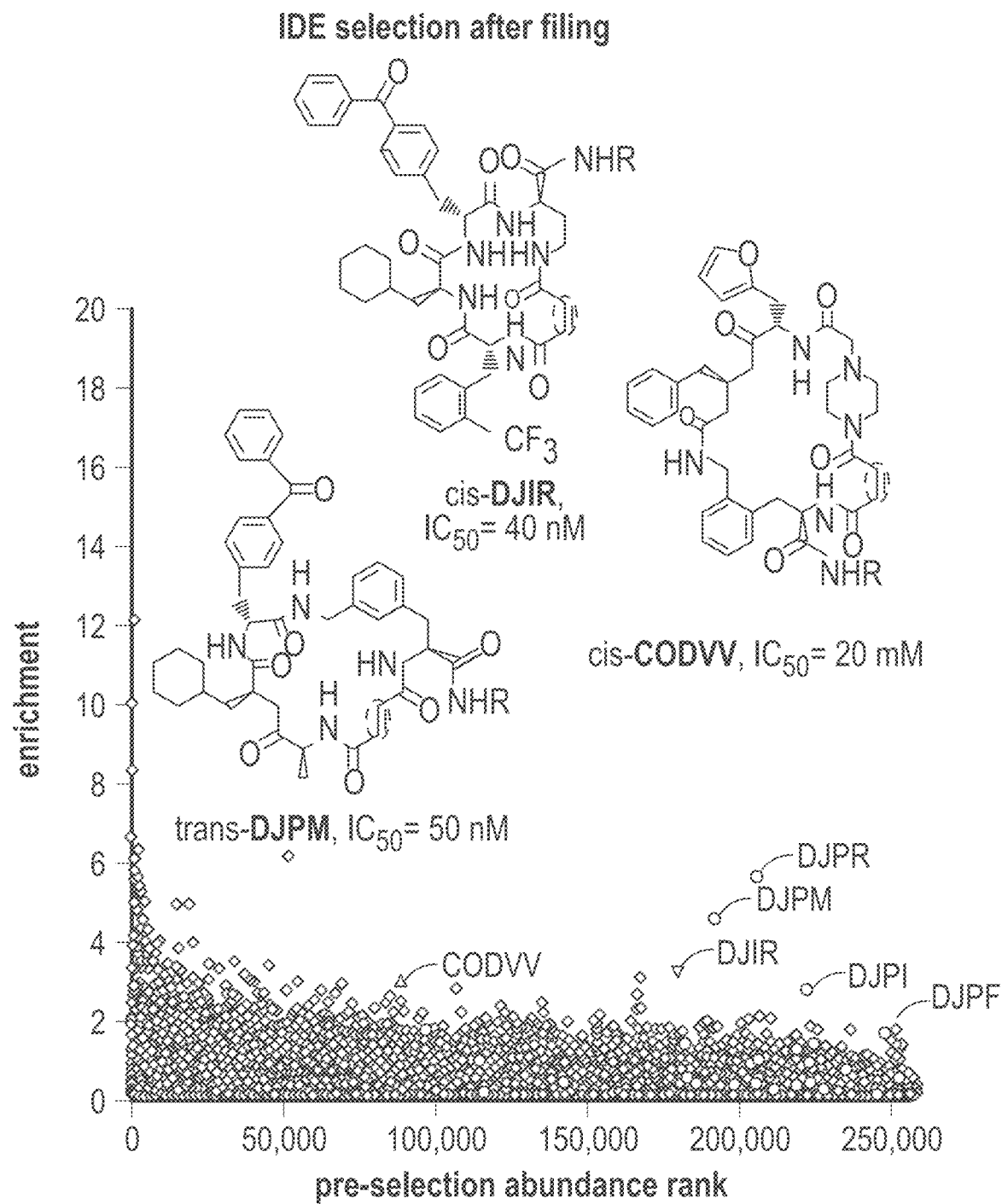
Figure 30:
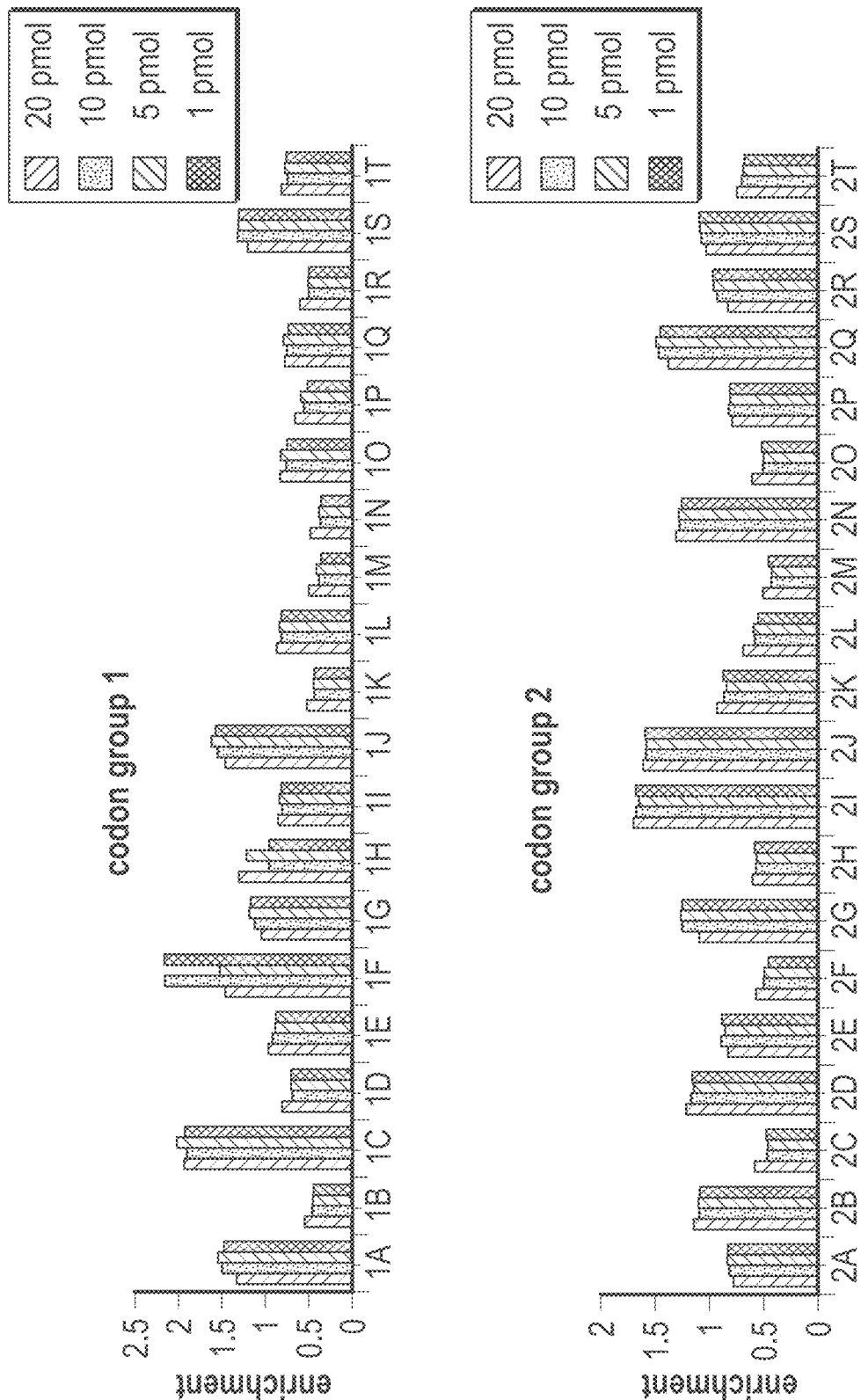
FIG. 30. Enrichments per codon for the selection of the second-generation DTL against insulin-degrading enzyme.
Figure 30:
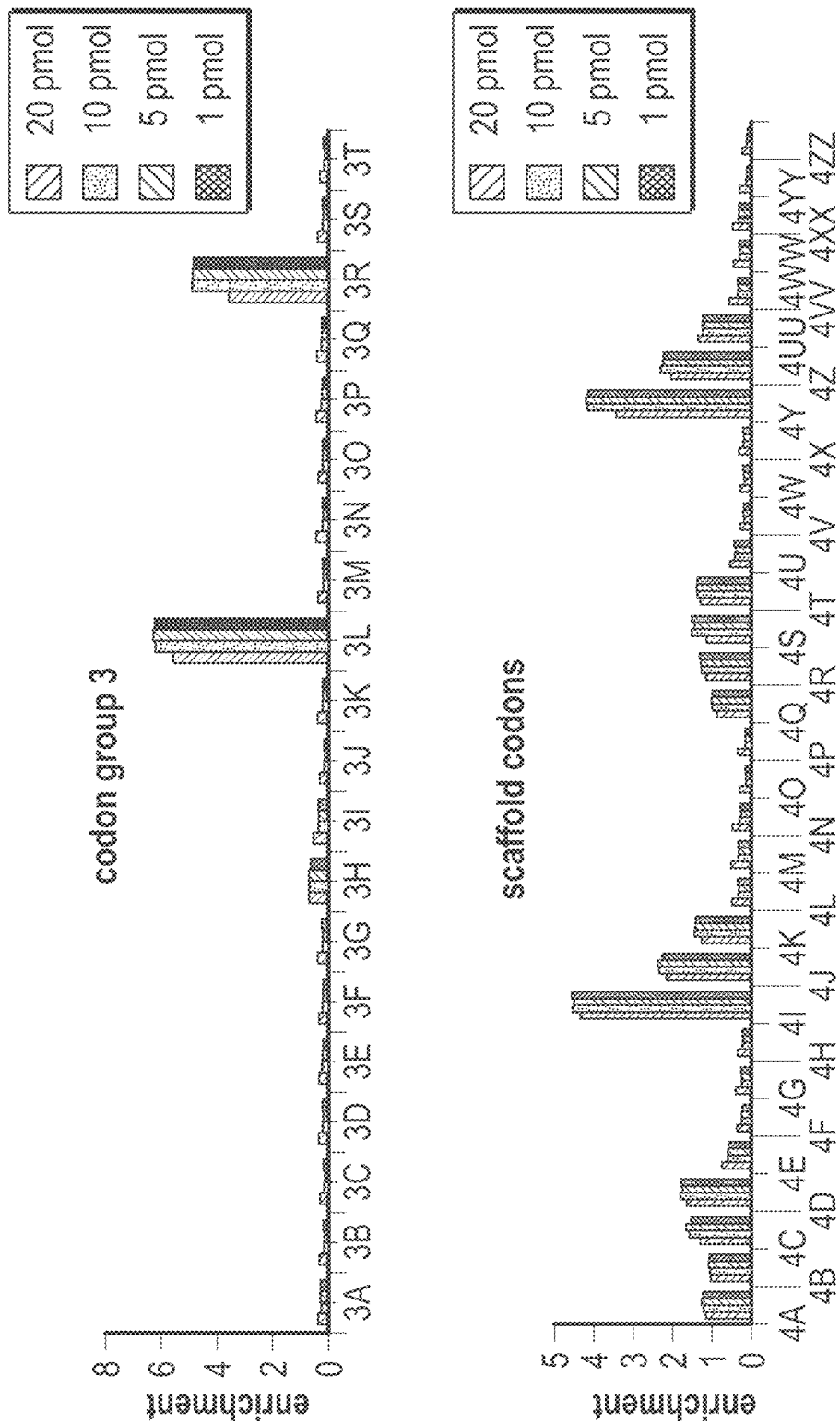
Figure 31:
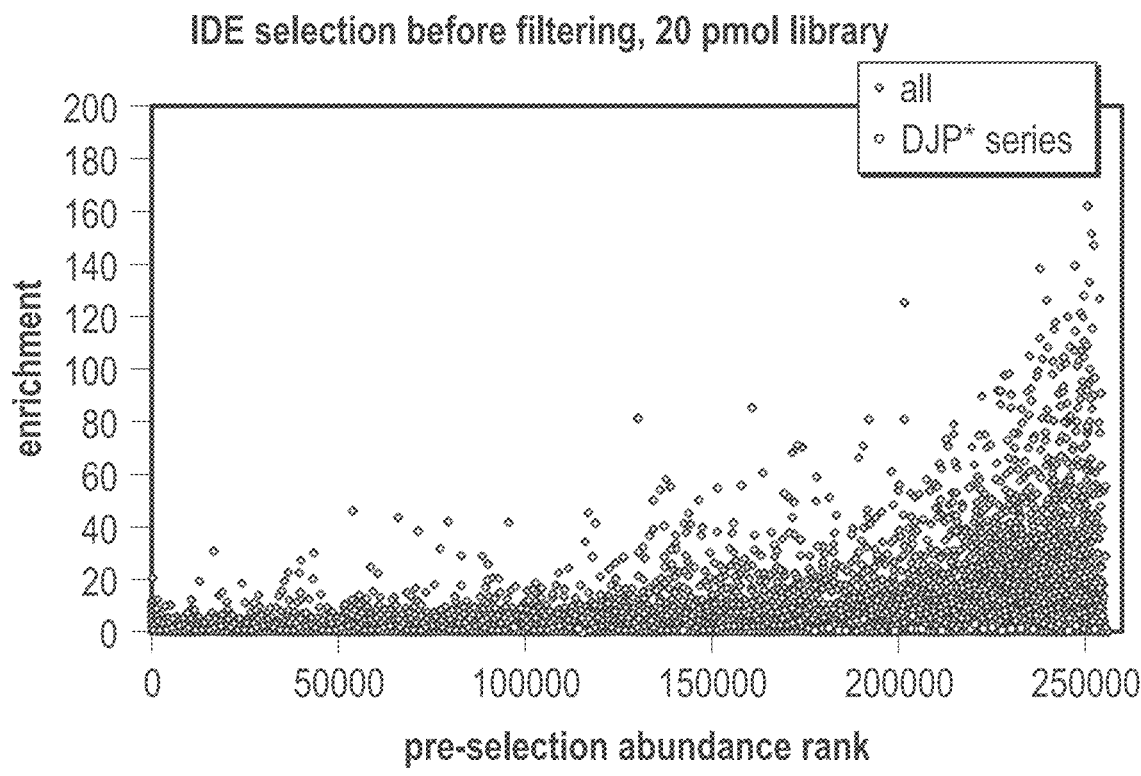
FIG. 31. Selection of the second-generation DNA-templated library against insulin-degrading enzyme.
Figure 32:
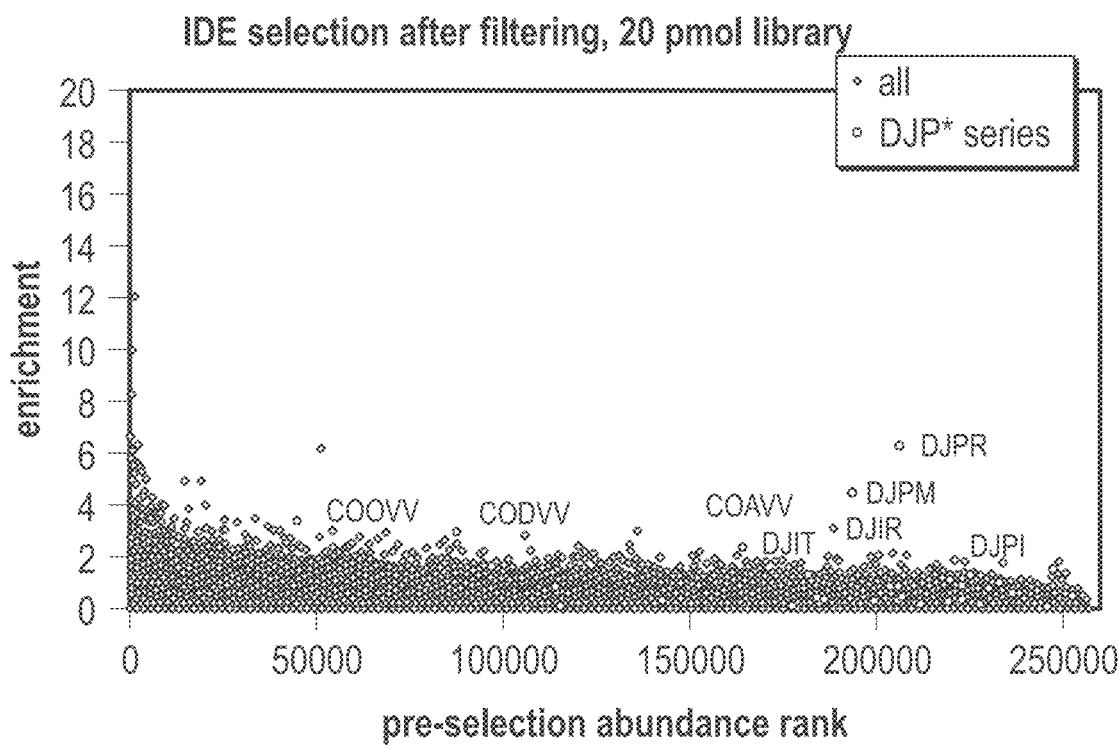
FIG. 32. Computationally refined selection of the second-generation DTL against insulin-degrading enzyme after the removal of promiscuous building blocks. Removed building blocks: 1J, 1L, 1M, 1N, 1T, 3E, 3H, 3L, 3R. Promiscuous BQ** series was also eliminated.
Figure 33:
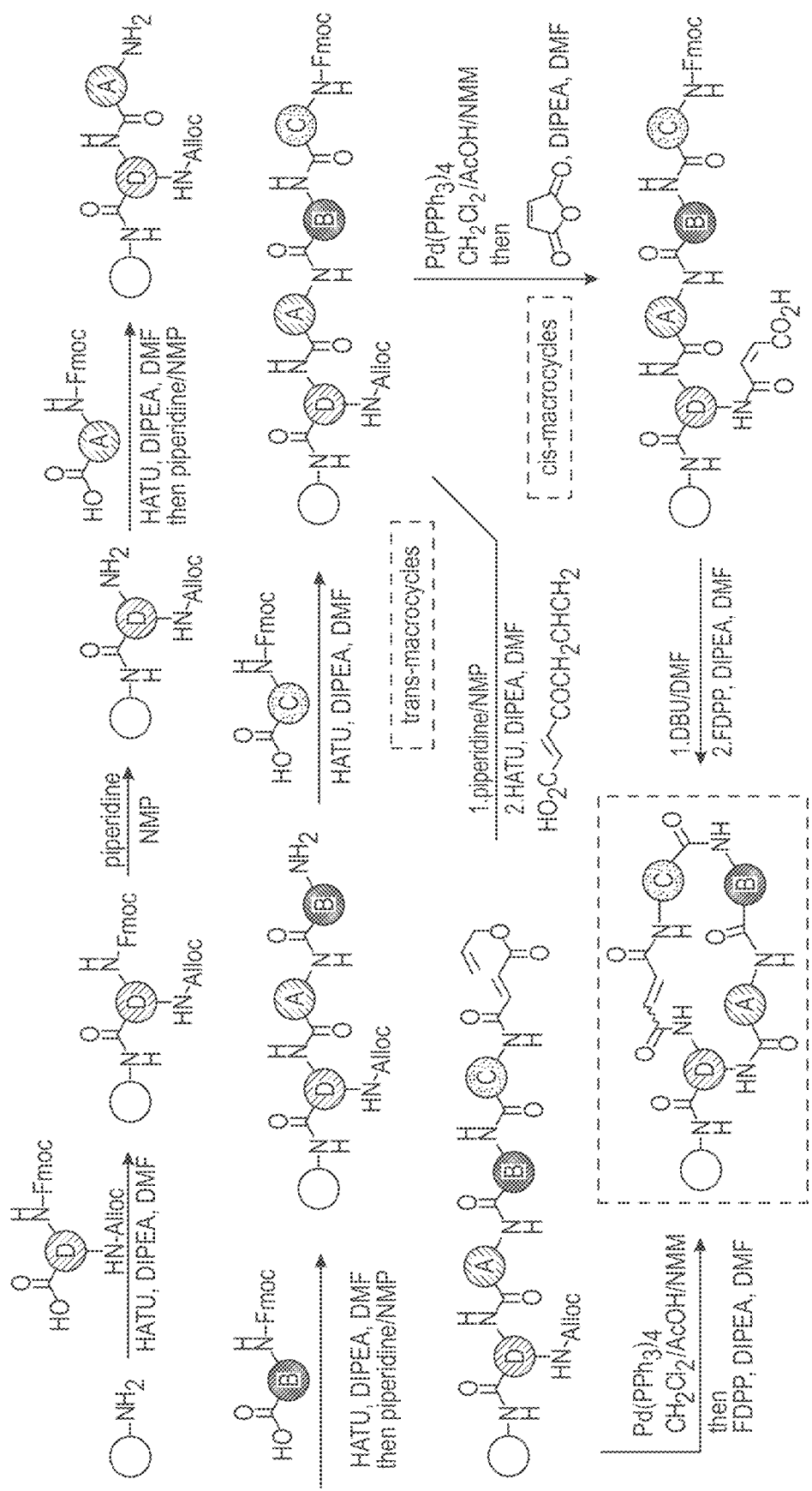
FIG. 33. General scheme of solid-phase synthesis of macrocycles.
Figure 38:
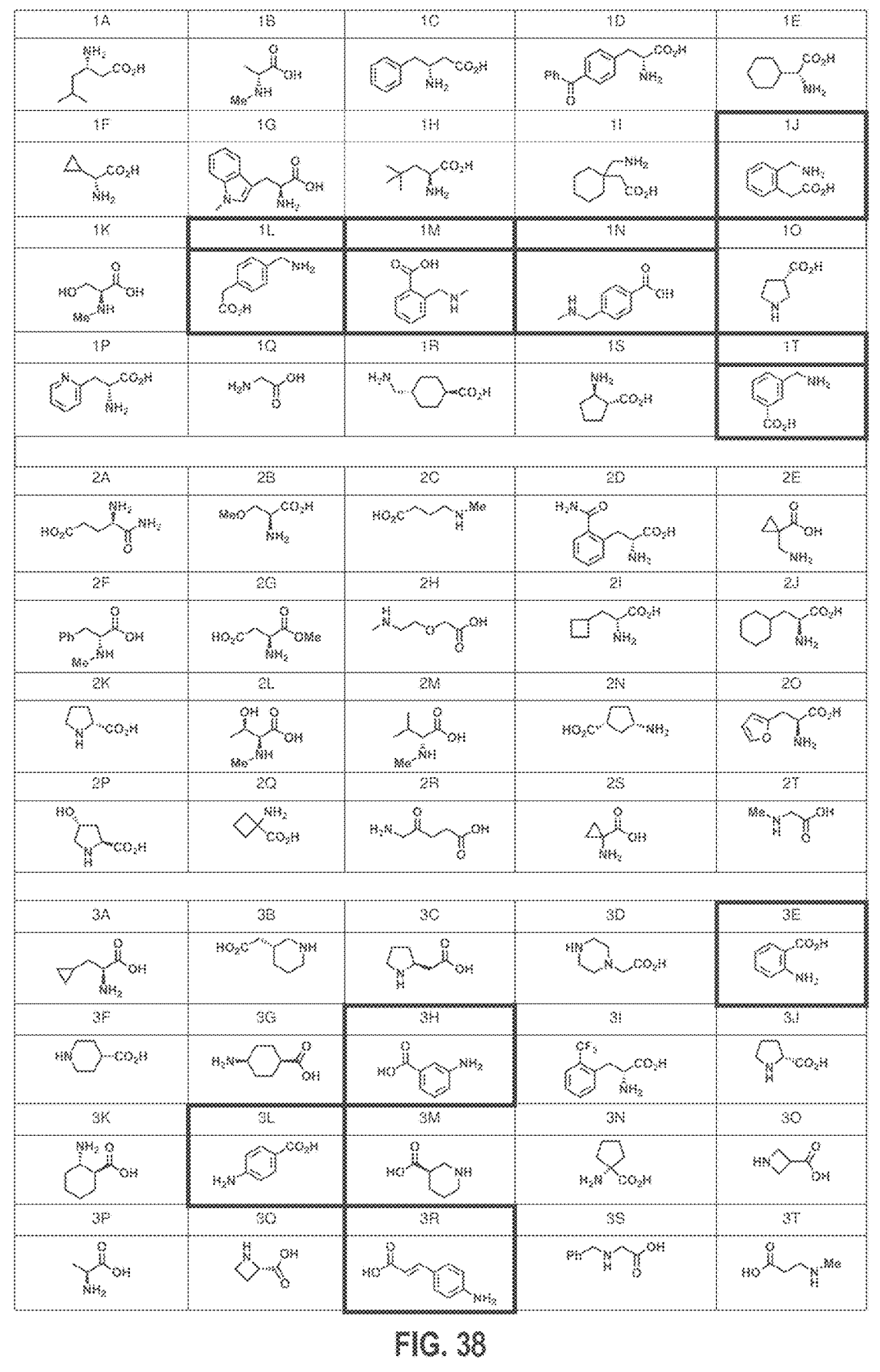

The initial raw IDE selection results revealed several building blocks (1J, 1L, 1M, 1N, 1T, 3E, 3H, 3L, 3R) that consistently demonstrated unusually high enrichments across all amounts of library tested (FIGS. 30 and 31). It was hypothesized that these building blocks formed excessively hydrophobic macrocycles prone to IDE binding, possibly as promiscuous aggregators[56]. Indeed, analysis of multiple in vitro selections of the 256,000-membered library on unrelated proteins revealed that those building blocks introducing fused aromatic rings into the macrocycle backbone were unusually represented among non-specific hits. Plotting the selections results after computational filtering of the nine building blocks highlighted in FIG. 38 (1J, 1L, 1M, 1N, 1T, 3E, 3H, 3L, 3R) greatly reduced background binding and restored the normal enrichment range and distribution (FIG. 6B). The most strongly enriched macrocycles after this filtering step shared the codon combination of the form DJP(*), which encode structures closely resembling a previously discovered family of IDE-inhibiting macrocycles including 6b and 5b (FIG. 6B).

Figure 6C:
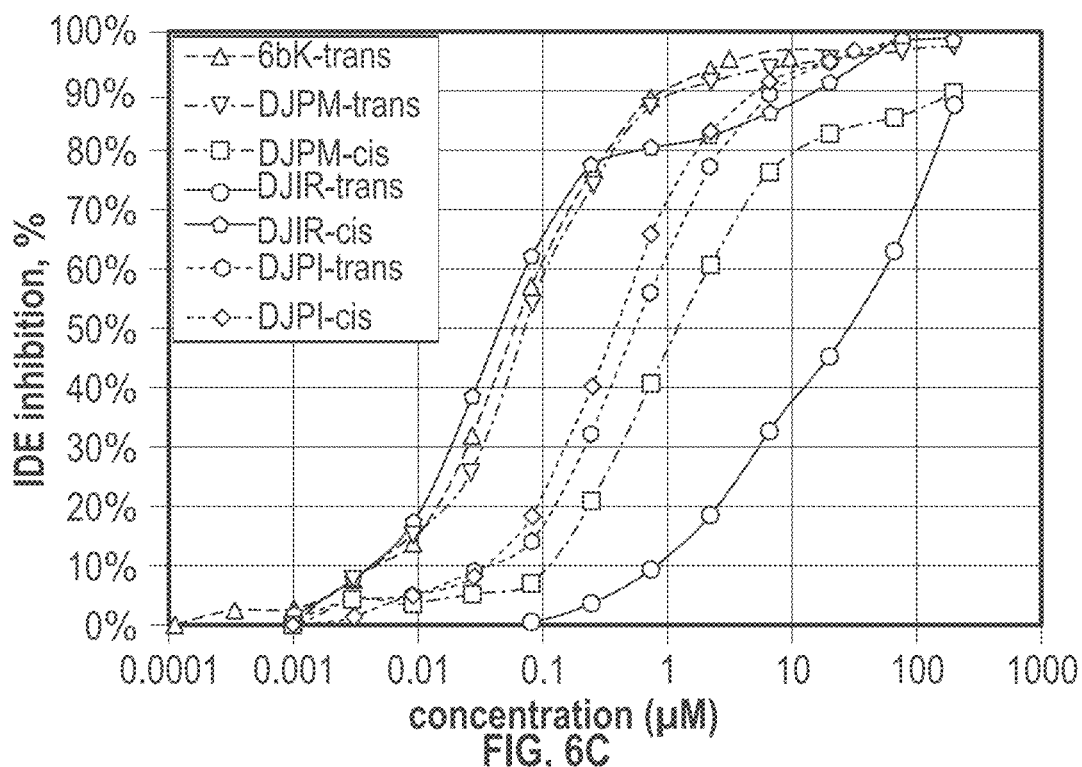
Figure 6D:
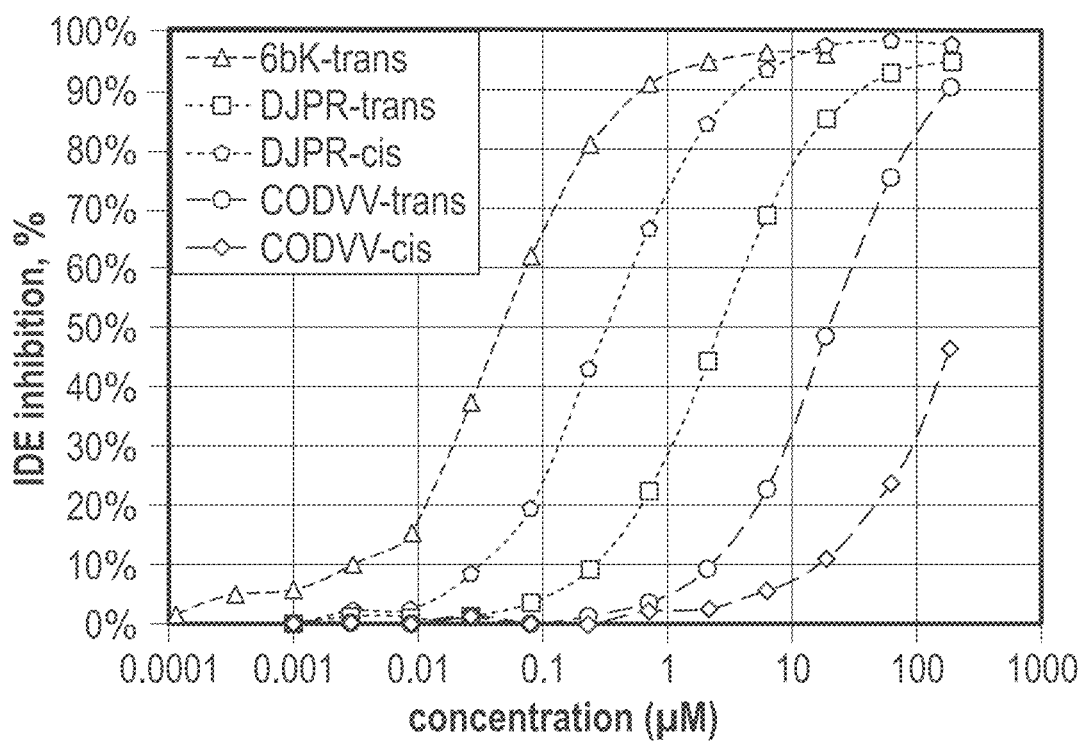
Figure 34:
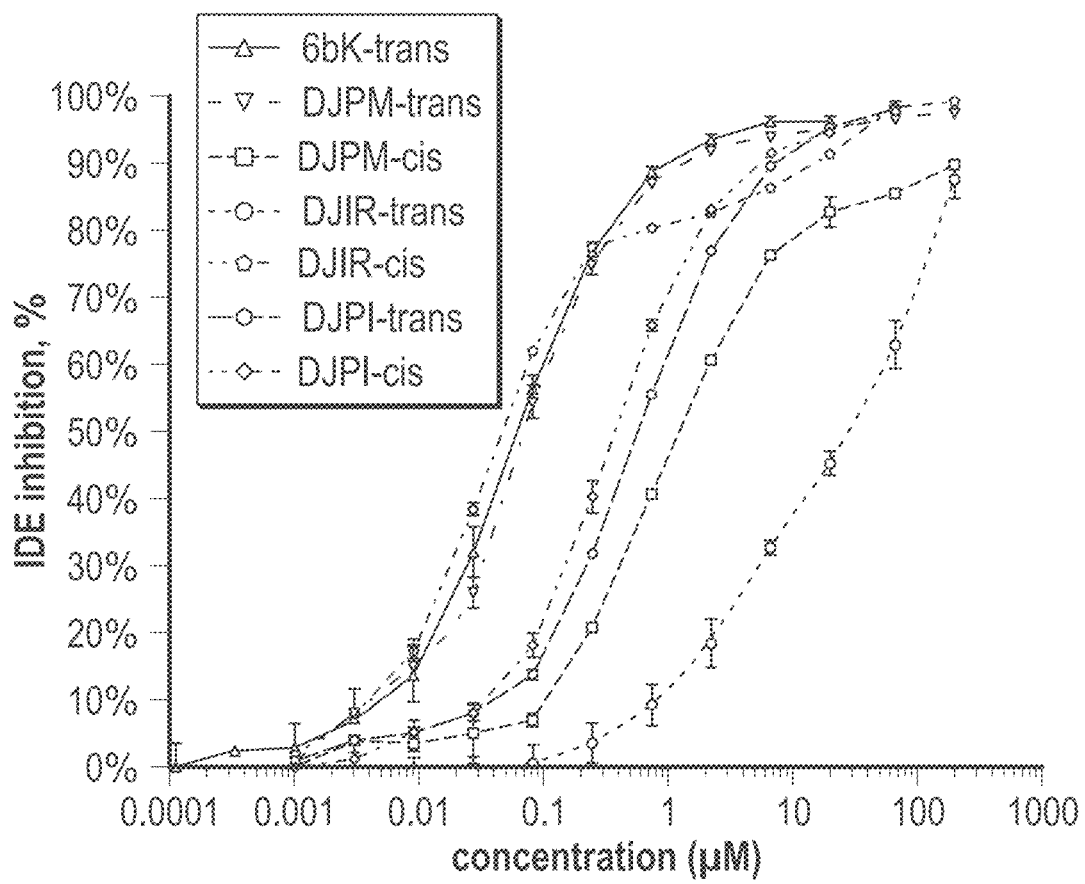
FIG. 34. Inhibition assays of insulin-degrading enzyme.
Figure 34:
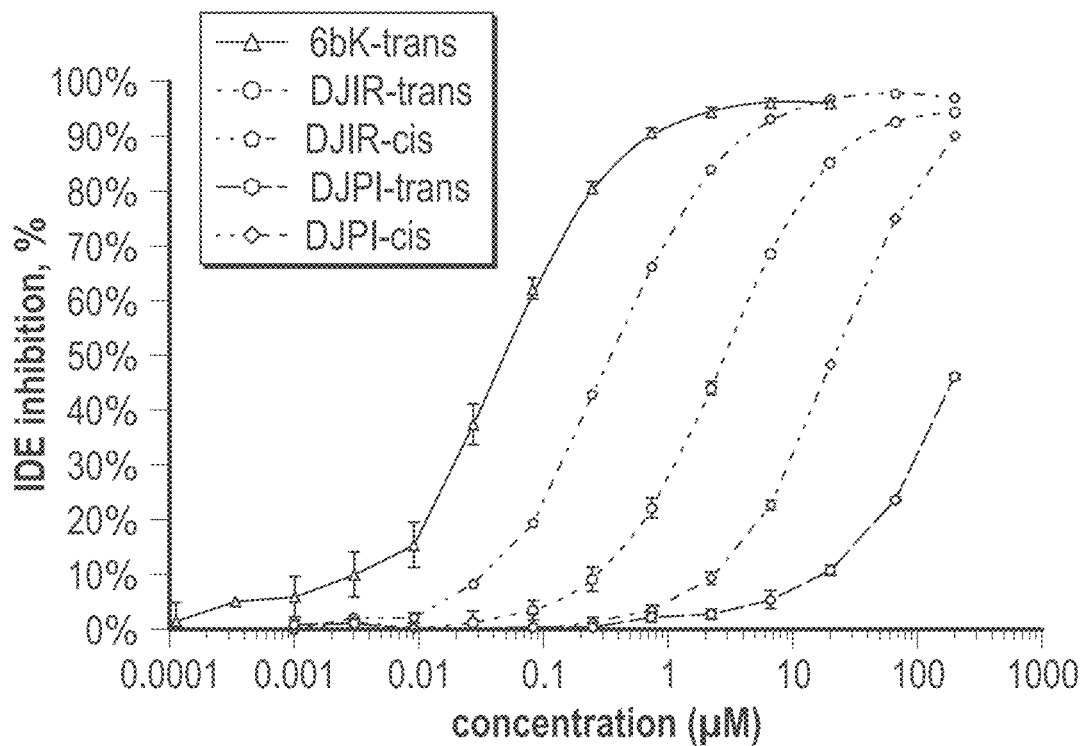

To test if these new hits from the in vitro selection of the 256,000-membered library represent bonafide IDE inhibitors, several of the corresponding cis- and trans-macrocycles (DJPR, DJPM, DJPI, DJIR, CODVV) were synthesized in a DNA-free format and assayed their ability to inhibit IDE activity. All tested hits demonstrated inhibition of IDE over a range of concentrations using a fluorogenic decapeptide cleavage assay (FIGS. 6B, 6C and 34). Notably, the 21-membered trans-DJPM macrocycle (FIG. 6B) is comparable in potency to our previously optimized 20-membered inhibitor 6bK[42] ($IC_{50}$=50 nM, FIG. 6C) and is more potent than the original lead compound 6b[42]. Enrichment of the related macrocycle DJPI was also observed, which features an unusual ortho-substituted backbone (cis/trans IDE $IC_{50}$=400 nM/600 nM). Smaller, 18-membered DJPR macrocycles were also less potent (cis/trans $IC_{50}$=400 nM/2 μM) than DJPM, consistent with our previous characterization of the crystal structure of IDE bound to related DNA-templated macrocycles[42]. Weak inhibition was observed for unrelated 24-membered CODVV macrocycles encoding a new structural family (cis/trans $IC_{50}$=30 μM/>100 μM).

Interestingly, whereas trans-isomers of all previously screened IDE inhibitors[42] were much more potent than their cis-analogs, CODVV and DJ*R families demonstrated the opposite stereochemistry-activity relationship. For the DJIR compounds, changing L-alanine in position 3 to 2-trifluoromethyl-D-phenylalanine preserved the feature of superior inhibitory activity of the cis-isomer but greatly increased potency: in contrast to weakly active trans-DJIR ($IC_{50}$=20 μM), cis-DJIR ($IC_{50}$=40 nM) was found to be at least as potent that 6bK and thereby serves as the first example of a highly potent macrocyclic IDE inhibitor containing a backbone alkene with cis configuration. Together these results validate the new library and demonstrated the ability of the DTS library of macrocycles to identify new ligands for targets of biomedical interest, as well as to provide new structure-activity insights that facilitate medicinal chemistry efforts.

Discussion

A second-generation DNA-templated and DNA-encoded library of 256,000 macrocycles suitable for in vitro selection and high-throughput DNA sequencing was developed and synthesized. During the course of this library's synthesis, many fundamental aspects of DNA-encoded and DNA-templated library technology were developed and extensively optimized. These advances include: (1) A new model for identifying orthogonal codons for DTS library syntheses was proposed and experimentally validated, which resulted in a 20×20×20×80 codon set sufficient to support up to 640,000 membered libraries. (2) New chemical tools were developed that substantially expand scaffold and building block diversity of DNA-templated macrocycles. (3) Programs were developed to generate in silico databases of compound libraries and to select building blocks that enhance the predicted bioavailability of the resulting molecules. (4) New isolation and purification methods were developed for DNA-linked small molecules that allow more reliable, scalable, high-yielding, and cost-effective preparation of DTS libraries and also enable the recovery and recycling of libraries after selection. (5) New polymerase-assisted methods were developed to synthesize libraries of DNA templates with 5' chemical modifications. These methods provide more precise control of the library quality, eliminate the necessity of conducting reactions with oligonucleotide mixtures, and minimize material losses through unreliable immobilization on streptavidin-linked beads and poor recovery from standard precipitation methods. (6) Finally, the new library synthesis protocols were validated by in vitro selection against insulin-degrading enzyme (IDE), resulting in the discovery of macrocycle trans-DJPM, which is equipotent to the previously optimized IDE inhibitor 6bK ($IC_{50}$=50 nM), and the discovery of cis-DJIR ($IC_{50}$=40 nM), an unexpectedly potent IDE inhibitor of cis macrocycle backbone configuration that represents a new class of macrocycles that bind IDE.

The successful application of DNA-encoded libraries and the development of macrocycles emerging from our first-generation library has already resulted in highly potent and selective macrocycles that modulate the activity of a variety of targets of biomedical interest, in some cases with activity in mammalian cells and in mice[40-42]. It is anticipated that this second-generation macrocycle library will prove a fertile source of new bioactive small molecules. An extensive selection campaign against biomedically important targets is underway, and the results will be reported in due course as separate studies focused on the corresponding biological investigations. In addition, it is believed that the comprehensively improved methodology of DNA-templated libraries reported in this work will stimulate the use of this unique, accessible, and convenient tool for molecular discovery.

General Methods

TABLE 30

Acronyms

| acronym | definition | acronym | definition |
|---|---|---|---|
| AMA | 1:1 mixture of 28% aq. $NH_3$ and 40% aq. $MeNH_2$ | HTS | high-throughput sequencing |
| Boc | tert-butyloxycarbonyl | IDE | insulin-degrading enzyme |
| BSA | bovine serum albumin | IPA | isopropanol |
| BSOCOES | bis(2-(succinimidooxy-carbonyloxy)ethyl)sulfone | MES | 2-(N-morpholino)ethanesulfonic acid |
| CPG | controlled-pore glass | Mmt | 4-methoxytrityl |
| Cy3 | Cyanine 3 | Ms | methanesulfonyl |
| Dab | diaminobutyric acid | Mtt | 4-methyltrityl |
| Dap | diaminopropionic acid | NEB | New England Biolabs (Ipswich, MA) |
| DCC | N,N'-Dicyclohexylcarbodiimide | Oxyma Pure | ethyl (hydroxyimino)cyanoacetate 3849-21-6 |
| DCI | 4,5-dicyanoimidazole | PAGE | polyacrylamide gel electrophoresis |
| DEL | DNA-encoded library | PBST | 50 mM sodium phosphate pH 8.0, 300 mM NaCl, 0.01% Tween-20, ±5 mM DTT |
| DIPEA | N,N-diisopropylethylamine | PCR | polymerase chain reaction |
| DMF | N,N-dimethylformamide | PEG | polyethylene glycol |
| DMT | 4,4'-dimethoxytrityl | qPCR | quantitative polymerase chain reaction |
| dNTP | deoxynucleotide triphosphate | SIA | succinimidyl iodoacetate |
| DTL | DNA-templated library | sNHS | N-hydroxysulfosuccinimide sodium salt |
| DTS | DNA-templated synthesis | SPPS | solid-phase peptide synthesis |
| DTT | 1,4-dithiothreitol | TBE | Tris/Borate/EDTA buffer |
| EDC | N-(3-Dimethylaminopropyl)-N'-ethylcarbodiimide hydrochloride, 25952-53-8 | TBST | 50 mM Tris-HCl pH 8, 150 mM NaCl, 0.05% Tween-20, ±5 mM DTT |
| Fmoc | fluorenylmethyloxycarbonyl | TCA | trichloroacetic acid |
| GuHCl | Guanidinium chloride, guanidine hydrochloride | TCEP | tris(2-carboxyethyl)phosphine |
| HATU | O-(7-azabenzotriazol-1-yl)-N,N,N',N'-tetramethyluronium hexafluorophosphate, 148893-10-1 | TEAA | triethylammonium acetate |
| HBTU | 2-(1H-benzotriazole-1-yl)-1,1,3,3-tetramethyluronium hexafluorophosphate, 94790-37-1 | TFA | trifluoroacetic acid |
| HEPES | 4-(2-hydroxyethyl)-1-piperazineethanesulfonic acid | Tris | tris(hydroxymethyl)aminomethane |

General Techniques and Conventions

Throughout this work the use of common equipment was avoided for any sample containing templates with both primer binding sites to avoid cross-contamination of DNA capable of PCR amplification. A number of procedures described below were designed with this principle in mind.

All DNA sequences are provided in 5' to 3' representation unless otherwise noted. MilliQ-grade water was used in all experiments. Oxyma Pure (26426) was obtained from Chem-Impex. HBTU (2-(1H-benzotriazole-1-yl)-1,1,3,3-tetramethyluronium hexafluorophosphate) was purchased from EMD Millipore (8510060100). BSOCOES (bis[2-(succinimidooxycarbonyloxy)ethyl] sulfone) was purchased from Toronto Research Chemicals (B585000) or G-Biosciences (BC01). EDC (N-(3-Dimethylaminopropyl)-N'-ethylcarbodiimide hydrochloride) was obtained from Sigma-Aldrich (E1769-10G, BioXtra). sNHS (N-hydroxysulfosuccinimide Sodium Salt) was obtained from Toronto Research Chemicals (H954000). 2 M TEAA pH 7 solution was prepared from acetic acid and triethylamine (see below).

Functionalized oligonucleotides were purified on an xBridge prep C18 5 μm column (10×250 mm) in the gradient of acetonitrile in 0.1 M triethylammonium acetate pH 7 buffer using an Agilent Technologies 1200 Series HPLC purification system with an automatic fraction collector. Purified fractions were desalted using Nap-5, Nap-10, or Nap-25 size-exclusion columns (GE Life Sciences), frozen at −78° C. and lyophilized on a Labconco FreeZone Cascade Console Freeze Dry System. Mass spectrometry analysis of all modified and unmodified oligonucleotides was conducted on a Waters Q-Tof Premier LC-MS mass spectrometer (10-20 pmol injection, ESI, negative mode, 6 mM triethylammonium bicarbonate pH 8.5/acetonitrile).

Spin-Column Isolation of Nucleic Acids

Buffer UM: 1 volume of the DNA solution is combined with a mixture of 4 volumes of aqueous guanidinium chloride solution (saturated at room temperature, natural pH −6.4) and 6 volumes of isopropanol. The buffer enables isolation of at least 55-mer (and longer) single- and double-stranded oligonucleotides from very dilute solutions with minimal losses. For instance, 99% recovery of 4.8 nmol of a single-stranded 55-mer oligonucleotide was achieved from 40 mL of 120 nM solution (400 mL of Buffer UM was used, Omega HiBind Midi column). Guanidinium chloride solution should be mixed with isopropanol immediately before addition to the sample. Prolonged storage (months) of saturated solution of guanidinium chloride should be avoided due to a slight decrease of oligonucleotide recovery efficiency. Retention of single-stranded oligonucleotides shorter than 55-mers decreases with oligonucleotide length (to 5% for a 10-mer).

Experimentally determined capacities of commercially available silica membrane spin columns: QIAquick (Qiagen): 800 pmol of a single-stranded 85-mer; HiBind DNA Midi columns (Omega): 4.5 nmol of a double-stranded 55-mer or 10 nmol of single-stranded 48-mer; HiBind DNA Maxi columns (Omega): 40 nmol of single-stranded 48-mer.

Oligonucleotide Synthesis

Oligonucleotides were synthesized on Expedite 8909 DNA synthesizers with helium as a working gas. All synthesis supplies were purchased from Glen Research (Sterling, Va.). Modified methods with prolonged capping times were used and special modifiers were double-coupled (30-min overall exposure to the beads). DNA syntheses were carried out on 1000 Å CPG beads except for the preparation of DTS reagents 3, where only 500 Å CPG beads can be used (3'-Amino-Modifier C7 CPG 500, 20-2957-10, discontinued, special order from Glen Research). Standard tetrazole was used as the activator, and Ac-dC-CE (10-1015-1C), dT-CE (10-1030-1C), dG-CE (10-1020-1C)/dmf-dG-CE (10-1029-1C), dA-CE (10-1000-1C), and dI-CE (10-1040-90) were used as monomers. 100 μmol modifiers were dissolved in 1.8 mL of dry acetonitrile: 5' amino modifier 5 (10-1905-90), spacer-18 (10-1918-90), Cyanine 3 (10-5913-95), and chemical phosphorylation reagent II (10-1901-90). For split-pool synthesis of the heavy strand the following modifications were introduced: DCI was used instead of tetrazole, def-dA-CE (10-1504-10), and 2000 Å CPG beads.

Cleavage of oligonucleotides off CPG beads was conducted by heating 1 μmol of the beads with 0.4 mL of AMA solution (1:1 mixture of 28% aqueous ammonia and 40% aqueous methylamine) at 65° C. for 15-20 min in sealed 1.5 mL microcentrifuge tubes. The samples were used directly in Glen-Pak cartridge purification (diluted 1:1 with 100 mg/mL NaCl solution for loading) or concentrated on a speedvac until removal of volatile material (~20 min at room temperature) for HPLC purification. In the latter case, samples were diluted with 0.1 M TEAA pH 7 buffer and filtered using EMD Ultrafree-MC GV 0.22 μm filter units prior to HPLC.

5'-phosphorylated oligonucleotides were prepared with CPRII modifier (Glen Research, 10-1901-90). Lyophilized Glen-Pak cartridge-purified products were dissolved in 0.5 mL of 28% aqueous ammonia, left at room temperature for 2.5 h, loaded on Nap-5 columns equilibrated in water (GE Life Sciences) and eluted with 1 mL of water to afford deprotected oligonucleotides ready for enzymatic ligations.

Analytical and Preparative Polyacrylamide Gel Electrophoresis (PAGE)

PAGE gels for Criterion cells were purchased from Bio-Rad Laboratories and were typically run in 0.5×TBE buffer at 200V. Unless otherwise noted, samples were loaded as 1:1 mixture with formamide solution of Qiagen GelPilot 5× loading dye (50 μL of dye per 1 mL of formamide; Orange G+bromophenol blue+xylene cyanol dyes, less than recommended 5×). Gels requiring 55° C. temperature were pre-run in the oven for 30 minutes before loading the samples with adjustable Viaflo electronic pipettes.

Gel extraction. DNA bands were visualized either with a UV lamp or using a transilluminator after exposure to SYBR Gold. In a typical protocol, the bands are excised and placed in 0.5-mL Eppendorf tubes with an orifice at the bottom made with a 27-gauge needle. The tube is placed into a 2-mL centrifuge tube and centrifuged at 20,000 rcf to homogenize the gel. The gel is then subject to three dry ice freeze/thaw cycles followed by the addition of the extraction buffer (usually 1× TE pH 7.5). The tubes are rotated on a rotary wheel at 4° C. overnight, then centrifuged at 20,000 rcf. The supernatant is manually removed and the residue is washed with additional amounts of the buffer. For fast extraction of sequencing amplicons the process is conducted in Eppendorf LoBind tubes (022431021) at 40° C. using Eppendorf Thermomixer (2,000 rpm).

On-Bead Chemical Functionalization of Oligonucleotides

Chemical functionalization of CPG beads was conducted in eppendorf tubes. Washing of the beads in between reactions was achieved by the following sequence (1-mL disposable pipette tips used): 1) air is pumped into the mixture until the pipette tip reaches the bottom of the tube; 2) The tip is held tightly next to the tube bottom; gentle swirling/suction enables removal of most of the solution; 3) the tube is placed on a rack and a second pipette is used to wash down the beads on the outside of the pipette tip with a fresh portion of the solution. After vortexing, the beads can be concentrated at the bottom of the tube by repeated washing/centrifugation.

Standard peptide coupling reaction vessels with nitrogen bubbling can also be used, however, they are impractical for small loadings (1-4 μmol) of CPG beads. If the reaction sequence has to be interrupted, the beads can be washed with acetonitrile and left in the freezer in eppendorf tubes overnight without any adverse effect on the downstream reactions.

Preparation of Auxiliary Chemical Reagents.

2M TEAA pH 7 Buffer.

Acetic acid (458 mL) and water (2.427 L) were mixed in a 4-L bottle with a rod-shaped stir bar (~8 cm). Triethylamine (1.115 L) was added at ~1 drop/s with vigorous stirring over ~8-12 h. pH of the resulting solution was adjusted to 7.0 by the addition of acetic acid in 1-mL portions and the resulting buffer was diluted with water to the 4-L rim. The buffer was kept at 4° C. and was freshly diluted to 0.1 M concentration for the use in HPLC purifications. It is recommended to desalt lyophilized HPLC-purified DTS components since residual acetic acid can largely affect the yields of DNA-templated reactions. Triethylammonium bicarbonate-based buffer can be considered as an alternative to TEAA.

(2R,3R)-2,3-diacetoxy-4-(benzylamino)-4-oxobutanoic acid (S1)[38]

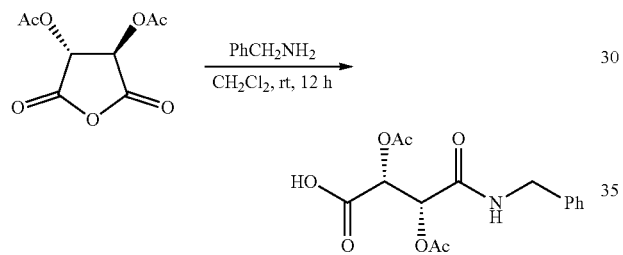

10 g (46.2 mmol) of (+)-O,O'-Diacetyl-L-tartaric anhydride was dissolved in 125 mL of dichloromethane in a 250 mL flask sealed with a sleeve stopper and equipped with a powerful stir bar and a balloon as a pressure compensator. 5.05 mL (4.95 g, 46.2 mmol) of benzylamine was added dropwise on stirring (cooling with an ice bath was useful during the addition). The reaction was left at room temperature overnight, the precipitate was filtered, washed three times with 25 mL of dichloromethane and dried to give the pure product as white crystals (12.1 g, 81%). The compound is indefinitely stable at −20° C. and should be stored at this temperature. $^1$H NMR (500 MHz, DMSO-d$_6$) δ 8.77 (t, J=6.1 Hz, 1H), 7.35-7.28 (m, 2H), 7.28-7.17 (m, 3H), 5.54 (qd, J=2.6, 0.9 Hz, 2H), 4.39 (dd, J=15.2, 6.5 Hz, 1H), 4.22 (dd, J=15.2, 5.6 Hz, 1H), 2.50 (q, J=1.9 Hz, 1H), 2.12 (d, J=1.0 Hz, 3H), 2.00 (d, J=1.0 Hz, 3H). $^{13}$C NMR (126 MHz, DMSO-d$_6$) δ 170.03, 169.81, 168.10, 165.79, 139.49, 128.71, 127.35, 127.30, 72.24, 71.67, 42.48, 21.10, 20.66.

Succinimidyl Iodoacetate (S2)[57]

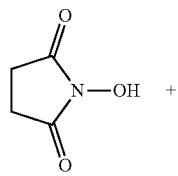

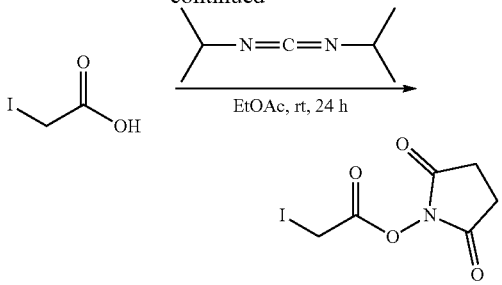

The compound is available from ThermoFisher (22349).

A 100-mL flask sealed with a sleeve stopper was charged with N-hydroxysuccinimide (1.15 g, 10 mmol) and iodoacetic acid (1.86 g, 10 mmol). 50 mL of ethyl acetate was added and diisopropylcarbodiimide (1.55 mL, 10 mmol) was added dropwise. The reaction was left stirring at room temperature for 24 h. The mixture was then filtered, the precipitate was washed with a minimum amount of ethyl acetate and dried in vacuo. The solids were dissolved in ~50 mL of boiling isopropanol and the solution was transferred into a beaker to initiate crystallization. The crystals were filtered, washed with isopropanol and dried in vacuo to give 1.72 g (60%) of pure product as white crystals. The compound is indefinitely stable at −20° C. and should be stored at this temperature. $^1$H NMR (500 MHz, CDCl$_3$) δ 4.02 (s, 2H), 2.95-2.85 (m, 4H).

(E)-4-(allyloxy)-4-oxobut-2-enoic acid/monoallyl fumarate (S3)

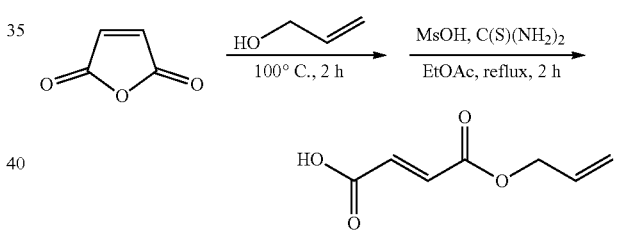

Maleic anhydride (20 g, 0.2 mol) and allyl alcohol (13.8 mL, 0.2 mol) were mixed in a 500-mL flask and were heated on intensive stirring for 2 h. Then ethyl acetate (200 mL), thiourea (1.24 g, 0.016 mol) and methanesulfonic acid (0.92 mL, 0.014 mol) were added and the mixture was stirred under reflux for 2 h. The mixture was cooled, washed with brine, dried over anhydrous sodium sulfate and concentrated to dryness on a rotovap. Most part of the residue was dissolved in boiling hexanes and the insoluble solid was filtered off. The solvent of the filtrate was removed on a rotovap. The residue was dissolved in a minimum amount of boiling hexanes (~50 mL), the solution was cooled down to room temperature and left to crystallize for 1.5 h. The crystals were filtered off, washed with hexanes and dried in vacuo. 11 g of the pure product was isolated, which was sufficient for the downstream applications. The compound should be stored at −20° C. (freezer). $^1$H NMR (500 MHz, DMSO-d$_6$) δ 6.72 (d, J=0.5 Hz, 2H), 5.95 (ddtd, J=17.2, 10.5, 5.5, 0.5 Hz, 1H), 5.35 (dqd, J=17.2, 1.6, 0.5 Hz, 1H), 5.25 (dqd, J=10.6, 1.4, 0.5 Hz, 1H), 4.71-4.65 (m, 2H). $^{13}$C NMR (126 MHz, DMSO-d$_6$) δ 166.09, 164.66, 135.32, 132.75, 132.56, 118.72, 65.74, 40.45, 40.28, 40.12, 39.95, 39.78, 39.62, 39.45.

Identification of the Orthogonal Codon Set

The architecture of the model templates was simplified with respect to the actual library assembly: no scaffold amino acid or tartaramide groups were installed on the 5' amino 5 linker; the amino group of the linker was itself reacting in DTS (compare FIG. 2A and the graphic part of Table 2A). All the model DTS reagents contained D-phenylalanine attached to the 3' amino modification of the oligonucleotide via BSOCOES linker. The reactions were carried out under the conditions identical to those of the actual DTS library assembly with the exception of prolonged reaction times for higher assay stringency (8 hours). The reactions were analyzed by polyacrylamide gel electrophoresis (PAGE, ethidium bromide in the linear range).

Figure 10:
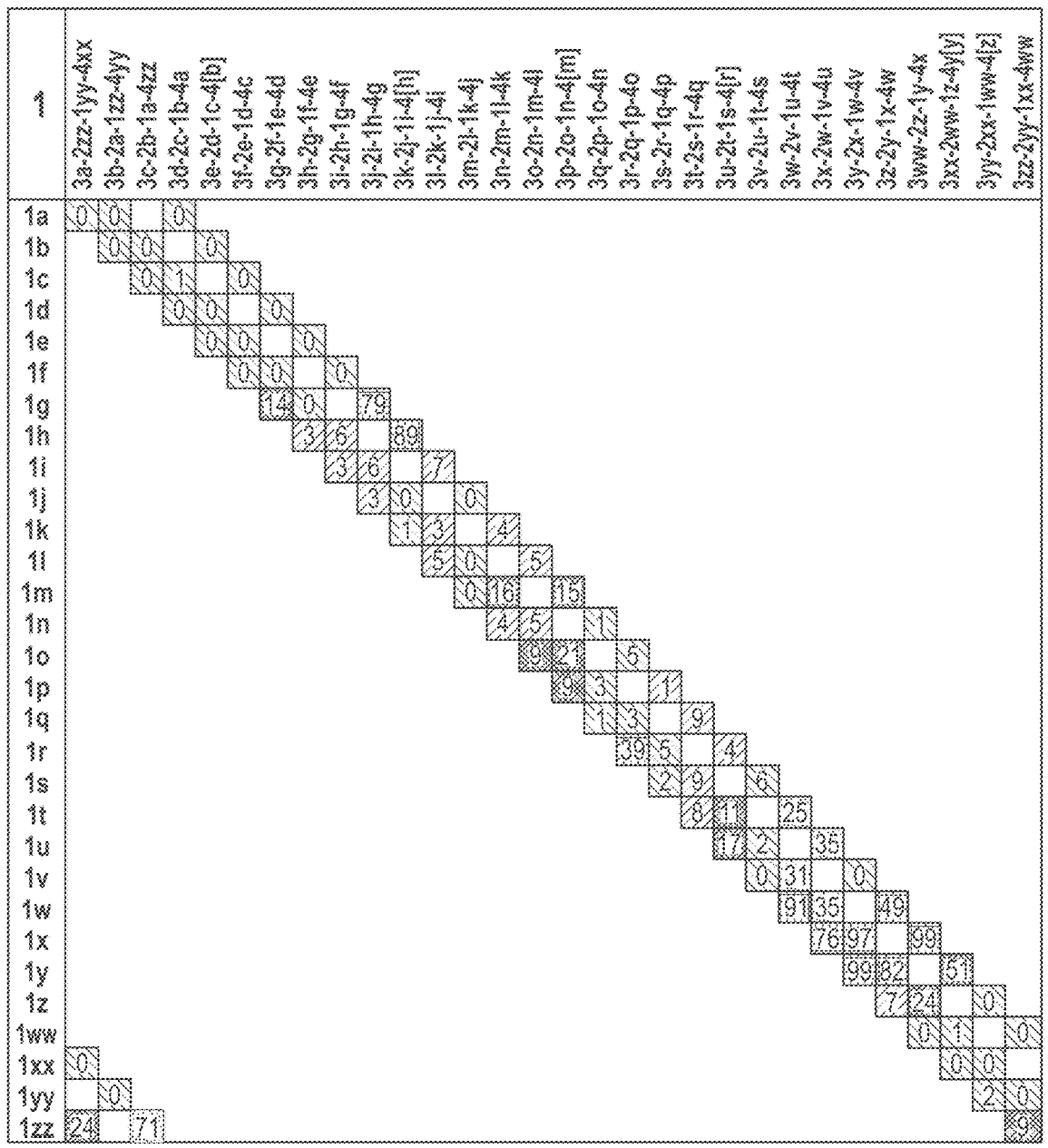
FIG. 10. DTS reactions conducted for the identification of "hidden" interactions (at the improved temperature regime, 30, 30, 37° C. for reagents 1, 2 and 3 respectively).

Importantly, for each matched template-anticodon pair, three out of four annealing factors are naturally screened by efficient DNA-templated interaction of matched sequences. In order to obtain the missing data, 30 additional templates were prepared and 270 extra reactions were conducted (FIG. 10) to yield the full affinity map (FIG. 11).

As a general rule of the proposed refinement procedure, each cell of the integral affinity table contains the minimum DTS reaction conversion value among all the DTS reactions conducted between the corresponding DTS reagent (anticodon) and all the templates containing the corresponding codon.

In order to enable alignment of the scaffold space of the $1^{st}$ generation DTS library (8 scaffolds) with the new codon set, two additional scaffold codons (4UU, 4VV) were validated, thus bringing the number of available scaffolds to 32.

TABLE 2A

Initially calculated set used for experimental identification of the orthogonal codon set. (SEQ ID NO: 1)

```
                                        constant   constant   constant
                                    5'     3          2          1                    3'
  H2N~O~O-P(=O)(OH)-O—CCCTGTACAC NNNNNN AAGTT NNNNNN ATGAT NNNNNN CTA NNNNN CATCCCACTC
                                 left    codon     codon     codon  scaffold   right primer
                                 primer    3         2         1     codon
  5' amino 5 modifier
```

| name | codon (templates) 5'-3' | anti-codon (reagents) 5'-3' | name | codon (templates) 5'-3' | anti-codon (reagents) 5'-3' | name | codon (templates) 5'-3' | anti-codon (reagents) 5'-3' |
|---|---|---|---|---|---|---|---|---|
| 1a | GGCTTT | AAAGCC | 2a | GCTGAA | TTCAGC | 3a | TTCCTC | GAGGAA |
| 1b | AGGCTT | AAGCCT | 2b | AACGGT | ACCGTT | 3b | AGCTCA | TGAGCT |
| 1c | GCCAAA | TTTGGC | 2c | GTCGAT | ATCGAC | 3c | ATCGGA | TCCGAT |
| 1d | AGGAAC | GTTCCT | 2d | GATTGC | GCAATC | 3d | TGTGCA | TGCACA |
| 1e | CGTATG | CATACG | 2e | GGACTT | AAGTCC | 3e | AGACTC | GAGTCT |
| 1f | CATGAG | CTCATG | 2f | ACGGAT | ATCCGT | 3f | CTTCAG | CTGAAG |
| 1g | AACCAG | CTGGTT | 2g | CAACAG | CTGTTG | 3g | AGTCGA | TCGACT |
| 1h | AACTCC | GGAGTT | 2h | TCGAGT | ACTCGA | 3h | ATGACG | CGTCAT |
| 1i | GAGACA | TGTCTC | 2i | GCAAGA | TCTTGC | 3i | ACTAGC | GCTAGT |
| 1j | CTGTAG | CTACAG | 2j | CTTGTG | CACAAG | 3j | CAACCT | AGGTTG |
| 1k | GTCAGT | ACTGAC | 2k | GGCTAA | TTAGCC | 3k | TCCGTA | TACGGA |
| 1l | TAGCTG | CAGCTA | 2l | CACTTG | CAAGTG | 3l | GCTTAC | GTAAGC |
| 1m | TCTCAG | CTGAGA | 2m | AGGACT | AGTCCT | 3m | TCTACG | CGTAGA |
| 1n | AGAGCT | AGCTCT | 2n | TCATGC | GCATGA | 3n | GGCATA | TATGCC |
| 1o | CGAACA | TGTTCG | 2o | AGTCTG | CAGACT | 3o | GTGTCA | TGACAC |
| 1p | GCTCTT | AAGAGC | 2p | CTATGG | CCATAG | 3p | CATCTC | GAGATG |
| 1q | TCTGCT | AGCAGA | 2q | CTGGAA | TTCCAG | 3q | GATACC | GGTATC |
| 1r | CAATCG | CGATTG | 2r | ATTGCC | GGCAAT | 3r | AATCCG | CGGATT |
| 1s | TCGATC | GATCGA | 2s | GTATCC | GGATAC | 3s | CACTAC | GTAGTG |
| 1t | GACTGA | TCAGTC | 2t | TCTCGA | TCGAGA | 3t | CGAGAT | ATCTCG |
| 1u | TTCACG | CGTGAA | 2u | CCTTAG | CTAAGG | 3u | CTGAAC | GTTCAG |
| 1v | CTACTG | CAGTAG | 2v | TAGCCT | AGGCTA | 3v | CTAGTC | GACTAG |
| 1w | CATCCA | TGGATG | 2w | CCAATG | CATTGG | 3w | GTCCAA | TTGGAC |
| 1x | TTACGC | GCGTAA | 2x | ACTCCT | AGGAGT | 3x | CGGTTT | AAACCG |
| 1y | ATCCCA | TGGGAT | 2y | ACCCTA | TAGGGT | 3y | CCCATT | AATGGG |
| 1z | GCAGTA | TACTGC | 2z | TCCCAT | ATGGGA | 3z | GACCTT | AAGGTC |
| 1ww | GCGTAT | ATACGC | 2ww | AAACCC | GGGTTT | 3ww | CTCTCT | AGAGAG |
| 1xx | GGAATC | GATTCC | 2xx | CAGTGA | TCACTG | 3xx | TTACCG | CGGTAA |
| 1yy | GCTTCA | TGAAGC | 2yy | GAGCAA | TTGCTC | 3yy | TGCTGT | ACAGCA |
| 1zz | ACGCAA | TTGCGT | 2zz | GAAGCT | AGCTTC | 3zz | CCTTGT | ACAAGG |

Note: this is not an orthogonal codon set; for an orthogonal set see Table 2B.

| name | codon 5'-3' | name | codon 5'-3' | name | codon 5'-3' | name | codon 5'-3' |
|---|---|---|---|---|---|---|---|
| 4a | TCCA | 4f | GGAA | 4k | GTTT | 4p | GTAA |
| 4b | GTTG | 4g | TATA | 4l | TTTT | 4q | ATTA |
| 4c | TTAA | 4h | ATTT | 4m | TTTG | 4r | GTTA |
| 4d | TTGT | 4i | GTAG | 4n | AGGT | 4s | GATT |
| 4e | CTCA | 4j | TAGA | 4o | AGGA | 4t | ATAG |

TABLE 2A-continued

| name | codon 5'-3' | name | codon 5'-3' | name | codon 5'-3' |
|---|---|---|---|---|---|
| 4u | ATCA | 4z | GGTT | 4yy | AATA |
| 4v | AAAA | 4uu | GTGA | 4zz | AAGA |
| 4w | AAAG | 4vv | TGTG | | |
| 4x | AATT | 4ww | AATG | | |
| 4y | GATA | 4xx | AAGT | | |

TABLE 3A

Synthesized templates used for the identification of an orthogonal codon set. (SEQ ID NO: 1)

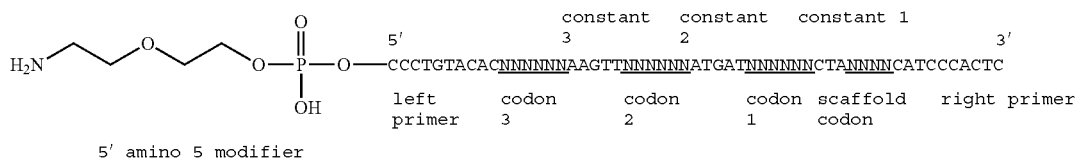

5' amino 5 modifier

| name | sequence (SEQ ID NOs: 107-143) | name | sequence (SEQ ID NOs: 144-180) | name | sequence (SEQ ID NOs: 181-217) |
|---|---|---|---|---|---|
| TM1 | 3a-2a-1a-4a | TM38 | 3j-2k-1q-4z | TM75 | 3xx-2ww-1z-4y |
| TM2 | 3b-2b-1b-4b | TM39 | 3h-2d-1v-4l | TM76 | 3yy-2xx-1ww-4z |
| TM3 | 3c-2c-1c-4c | TM40 | 3y-2o-1j-4e | TM77 | 3zz-2yy-1xx-4ww |
| TM4 | 3d-2d-1d-4d | TM41 | 3c-2h-1d-4j | TM78 | 3c-2xx-1n-4zz |
| TM5 | 3e-2e-1e-4e | TM42 | 3g-2j-1e-4q | TM79 | 3d-2t-1j-4zz |
| TM6 | 3f-2f-1f-4f | TM43 | 3e-2a-1n-4k | TM80 | 3g-2xx-1j-4t |
| TM7 | 3g-2g-1g-4g | TM44 | 3u-2yy-1ww-4i | TM81 | 3o-2xx-1j-4zz |
| TM8 | 3h-2h-1h-4h | TM45 | 3x-2i-1yy-4b | TM82 | 3p-2xx-1c-4zz |
| TM9 | 3i-2i-1i-4i | TM46 | 3v-2zz-1f-4y | TM83 | 3q-2xx-1j-4zz |
| TM10 | 3j-2j-1j-4j | TM47 | 3ww-2t-1p-4v | TM84 | 3t-2xx-1v-4zz |
| TM11 | 3k-2k-1k-4k | TM48 | 3a-2zz-1yy-4xx | TM85 | 3u-2xx-1j-4m |
| TM12 | 3l-2l-1l-4l | TM49 | 3b-2a-1zz-4yy | TM86 | 3z-2d-1j-4zz |
| TM13 | 3m-2m-1m-4m | TM50 | 3c-2b-1a-4zz | TM87 | 3ww-2n-1j-4zz |
| TM14 | 3n-2n-1n-4n | TM51 | 3d-2c-1b-4a | TM88 | 3a-2m-1o-4b |
| TM15 | 3o-2o-1o-4o | TM52 | 3e-2d-1c-4b | TM89 | 3b-2o-1f-4c |
| TM16 | 3p-2p-1p-4p | TM53 | 3f-2e-1d-4c | TM90 | 3e-2u-1j-4p |
| TM17 | 3q-2q-1q-4q | TM54 | 3g-2f-1e-4d | TM91 | 3h-2xx-1b-4g |
| TM18 | 3r-2r-1r-4r | TM55 | 3h-2g-1f-4e | TM92 | 3i-2g-1j-4h |
| TM19 | 3s-2s-1s-4s | TM56 | 3i-2h-1g-4f | TM93 | 3k-2a-1e-4i |
| TM20 | 3t-2t-1t-4t | TM57 | 3j-2i-1h-4g | TM94 | 3l-2s-1q-4k |
| TM21 | 3u-2u-1u-4u | TM58 | 3k-2j-1i-4h | TM95 | 3n-2xx-1r-4o |
| TM22 | 3v-2v-1v-4v | TM59 | 3l-2k-1j-4i | TM96 | 3r-2xx-1j-4s |
| TM23 | 3w-2w-1w-4w | TM60 | 3m-2l-1k-4j | TM97 | 3s-2xx-1p-4d |
| TM24 | 3x-2x-1x-4x | TM61 | 3n-2m-1l-4k | TM98 | 3v-2xx-1j-4r |
| TM25 | 3y-2y-1y-4y | TM62 | 3o-2n-1m-4l | TM99 | 3x-2xx-1s-4q |
| TM26 | 3z-2z-1z-4z | TM63 | 3p-2o-1n-4m | TM100 | 3y-2q-1j-4u |
| TM27 | 3ww-2ww-1ww-4ww | TM64 | 3q-2p-1o-4n | TM101 | 3yy-2xx-1m-4v |
| TM28 | 3xx-2xx-1xx-4xx | TM65 | 3r-2q-1p-4o | TM102 | 3zz-2r-1j-4x |
| TM29 | 3yy-2yy-1yy-4yy | TM66 | 3s-2r-1q-4p | TM103 | 3zz-2v-1j-4yy |
| TM30 | 3zz-2zz-1zz-4zz | TM67 | 3t-2s-1r-4q | TM104 | 3zz-2w-1j-4zz |
| TM31 | 3k-2b-1l-4yy | TM68 | 3u-2t-1s-4r | TM105 | 3zz-2z-1j-4zz |
| TM32 | 3r-2q-1b-4n | TM69 | 3v-2u-1t-4s | TM106 | 3zz-2xx-1j-4w |
| TM33 | 3l-2m-1z-4g | TM70 | 3w-2v-1u-4t | TM107 | 3z-2xx-1ww-4zz |
| TM34 | 3l-2u-1m-4o | TM71 | 3x-2w-1v-4u | TM108 | 3zz-2xx-1j-4uu |
| TM35 | 3z-2r-1k-4a | TM72 | 3y-2x-1w-4v | TM109 | 3zz-2xx-1j-4vv |
| TM36 | 3o-2c-1a-4m | TM73 | 3z-2y-1x-4w | TM110 | 3m-2a-1p-4uu |
| TM37 | 3s-2e-1i-4x | TM74 | 3ww-2z-1y-4x | TM111 | 3h-2c-1z-4vv |

Note that 5' end of the templates was simplified for the codon optimization model reactions.
Neither tartaramide S1 nor scaffold fragments were introduced; rather, 5' amino 5 linker served as a reactive group itself.

TABLE 1B

New codon designations and the list of removed codons.

| old | new |
|---|---|
| 3c | 3A |
| 3d | 3B |
| 3e | 3C |
| 3f | 3D |
| 3g | 3E |
| 3h | 3F |
| 3j | 3G |
| 3k | 3H |
| 3l | 3I |
| 3m | 3J |
| 3o | 3K |
| 3s | 3L |
| 3u | 3M |
| 3v | 3N |
| 3x | 3O |
| 3y | 3P |
| 3ww | 3Q |
| 3xx | 3R |
| 3yy | 3S |
| 3zz | 3T |
| 2a | 2A |
| 2c | 2B |
| 2d | 2C |
| 2e | 2D |
| 2f | 2E |
| 2h | 2F |
| 2i | 2G |
| 2j | 2H |
| 2k | 2I |
| 2m | 2J |
| 2n | 2K |
| 2o | 2L |
| 2q | 2M |
| 2r | 2N |
| 2t | 2O |
| 2u | 2P |
| 2v | 2Q |
| 2xx | 2R |
| 2yy | 2S |
| 2zz | 2T |
| 1a | 1A |
| 1b | 1B |
| 1c | 1C |
| 1d | 1D |
| 1e | 1E |
| 1f | 1F |
| 1i | 1G |
| 1j | 1H |
| 1l | 1I |
| 1m | 1J |
| 1n | 1K |
| 1o | 1L |
| 1p | 1M |
| 1q | 1N |
| 1s | 1O |
| 1t | 1P |
| 1z | 1Q |
| 1ww | 1R |
| 1xx | 1S |
| 1yy | 1T |

Removed codons: 1g, 1h, 1k, 1r, 1u, 1v, 1w, 1x, 1y, 1zz, 2b, 2g, 2l, 2p, 2s, 2w, 2x, 2y, 2z, 2ww, 3a, 3b, 3i, 3n, 3p, 3q, 3r, 3t, 3w, 3z Final Orthogonal Codon Set

TABLE 2B

The orthogonal codon set for a 256,000-membered DTS library (SEQ ID NO: 1).

| Left primer (SEQ ID NO: 2) | codon 3 | constant region 3 | codon 2 | constant region 2 | codon 1 | constant region 1 | codon 4 (scaffold) | right primer (SEQ ID NO: 3) |
|---|---|---|---|---|---|---|---|---|
| CCCTGTACAC | NNNNNN | AAGTT | NNNNNN | ATGAT | NNNNNN | CTA | NNNN | CATCCCACTC |
| | codon | | codon | | codon | | codon | |
| 1A | | GGCTTT | 2A | GCTGAA | 3A | | ATCGGA | |
| 1B | | AGGCTT | 2B | GTCGAT | 3B | | TGTGCA | |
| 1C | | GCCAAA | 2C | GATTGC | 3C | | AGACTC | |
| 1D | | AGGAAC | 2D | GGACTT | 3D | | CTTCAG | |
| 1E | | CGTATG | 2E | ACGAGT | 3E | | AGTGGA | |
| 1F | | CATGAG | 2F | TCGAGT | 3F | | ATGACG | |
| 1G | | GAGACA | 2G | GCAAGA | 3G | | CAACCT | |
| 1H | | CTGTAG | 2H | CTTGTG | 3H | | TCCGTA | |
| 1I | | TAGCTG | 2I | GGCTAA | 3I | | GCTTAC | |
| 1J | | TCTCAG | 2J | AGGACT | 3J | | TCTACG | |
| 1K | | AGAGCT | 2K | TCATGC | 3K | | GTGTCA | |
| 1L | | CGAACA | 2L | AGTCTG | 3L | | CACTAC | |
| 1M | | GCTCTT | 2M | CTGAAC | 3M | | CTGAAC | |
| 1N | | TCTGCT | 2N | ATTGCC | 3N | | CTAGTC | |
| 1O | | TCGAGT | 2O | TCTCGA | 3O | | CGGTTT | |
| 1P | | GACTGA | 2P | CCTTAG | 3P | | CCCATT | |
| 1Q | | GCAGTA | 2Q | TAGCCT | 3Q | | CTCTCT | |
| 1R | | GCGTAT | 2R | CAGTGA | 3R | | TTACCG | |
| 1S | | GGAATC | 2S | GAGCAA | 3S | | TGCTGT | |
| 1T | | GCTTCA | 2T | GAAGCT | 3T | | CCTTGT | |
| | codon | | codon | | codon | | codon | |
| 4A | TCCA | 4I | | GTAG | 4Q | | ATTA | 4Y | GATA |
| 4B | GTTG | 4J | | TAGA | 4R | | GTTA | 4Z | GGTT |

TABLE 2B-continued

| | | | | | |
|---|---|---|---|---|---|
| 4C | TTAA | 4K | GTTT | 4S | GATT | 4UU | GTGA |
| 4D | TTGT | 4L | TTTT | 4T | ATAG | 4VV | TGTG |
| 4E | CTCA | 4M | TTTG | 4U | ATCA | 4WW | AATG |
| 4F | GGAA | 4N | AGGT | 4V | AAAA | 4XX | AAGT |
| 4G | TATA | 4O | AGGA | 4W | AAAG | 4YY | AATA |
| 4H | ATTT | 4P | GTAA | 4X | AATT | 4ZZ | AAGA |

TABLE 3B

Anticodons/reagents for the orthogonal codon set.

Reagents 1 and 2

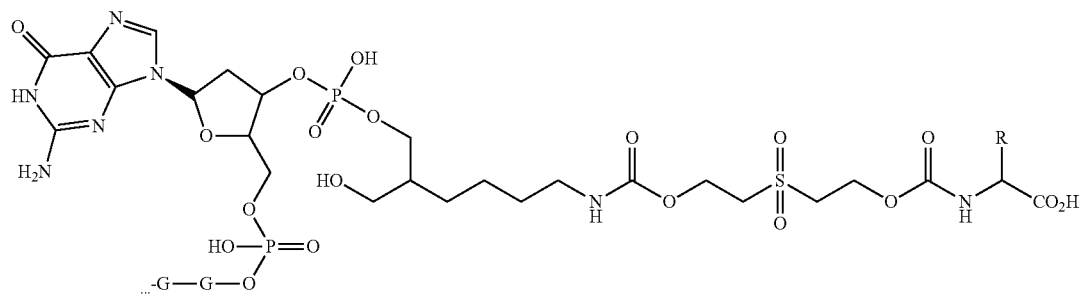

3′ C7 Amino modifier

| | DTS reagent 5'-3'<br>(SEQ ID NOs: 4-23) | | DTS reagent 5'-3'<br>(SEQ ID NOs: 24-43) |
|---|---|---|---|
| 1A | TAGAAAGCCATAGGG7 | 2A | CATTTCAGCAAAGGG7 |
| 1B | TAGAAGCCTATAGGG7 | 2B | CATATCGACAAAGGG7 |
| 1C | TAGTTTGGCATAGGG7 | 2C | CATGCAATCAAAGGG7 |
| 1D | TAGGTTCCTATAGGG7 | 2D | CATAAGTCCAAAGGG7 |
| 1E | TAGCATACGATAGGG7 | 2E | CATATCCGTAAAGGG7 |
| 1F | TAGCTCATGATAGGG7 | 2F | CATACTCGAAAAGGG7 |
| 1G | TAGTGTCTCATAGGG7 | 2G | CATTCTTGCAAAGGG7 |
| 1H | TAGCTACAGATAGGG7 | 2H | CATCACAAGAAAGGG7 |
| 1I | TAGCAGCTAATAGGG7 | 2I | CATTTAGCCAAAGGG7 |
| 1J | TAGCTGAGAATAGGG7 | 2J | CATAGTCCTAAAGGG7 |
| 1K | TAGAGCTCTATAGGG7 | 2K | CATGCATGAAAAGGG7 |
| 1L | TAGTGTTCGATAGGG7 | 2L | CATCAGACTAAAGGG7 |
| 1M | TAGAAGAGCATAGGG7 | 2M | CATTTCCAGAAAGGG7 |
| 1N | TAGAGCAGAATAGGG7 | 2N | CATGGCAATAAAGGG7 |
| 1O | TAGGATCGAATAGGG7 | 2O | CATTCGAGAAAAGGG7 |
| 1P | TAGTCAGTCATAGGG7 | 2P | CATCTAAGGAAAGGG7 |
| 1Q | TAGTACTGCATAGGG7 | 2Q | CATAGGCTAAAAGGG7 |
| 1R | TAGATACGCATAGGG7 | 2R | CATTCACTGAAAGGG7 |
| 1S | TAGGATTCCATAGGG7 | 2S | CATTTGCTCAAAGGG7 |
| 1T | TAGTGAAGCATAGGG7 | 2T | CATAGCTTCAAAGGG7 |

Reagents 3

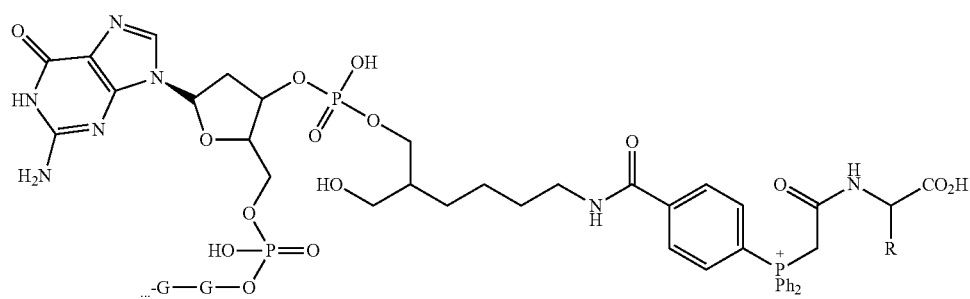

3′ C7 Amino modifier

| | DTS reagent 5'-3'<br>(SEQ ID NOs: 44-63) |
|---|---|
| 3A | 888CTTTCCGATGTAGGG7 |
| 3B | 888CTTTGCACAGTAGGG7 |
| 3C | 888CTTGAGTCTGTAGGG7 |
| 3D | 888CTTCTGAAGGTAGGG7 |
| 3E | 888CTTTCGACTGTAGGG7 |
| 3F | 888CTTCGTCATGTAGGG7 |
| 3G | 888CTTAGGTTGGTAGGG7 |
| 3H | 888CTTTACGGAGTAGGG7 |
| 3I | 888CTTGTAAGCGTAGGG7 |
| 3J | 888CTTCGTAGAGTAGGG7 |

TABLE 3B-continued

| | |
|---|---|
| 3K | 888CTTTGACACGTAGGG7 |
| 3L | 888CTTGTAGTGGTAGGG7 |
| 3M | 888CTTGTTCAGGTAGGG7 |
| 3N | 888CTTGACTAGGTAGGG7 |
| 3O | 888CTTAAACCGGTAGGG7 |
| 3P | 888CTTAATGGGGTAGGG7 |
| 3Q | 888CTTAGAGAGGTAGGG7 |
| 3R | 888CTTCGGTAAGTAGGG7 |
| 3S | 888CTTACAGCAGTAGGG7 |
| 3T | 888CTTACAAGGGTAGGG7 |

7 = 3' amino C7 (Glen Research);
8 = spacer-18 (Glen Research, 6 PEG units)

TABLE 4

Additional calculated scaffold codons
The suggested macrocycle nomenclature for larger libraries is ABCD1, ABCD2 etc.
The number defines the group of scaffold codons (which determines the other 60 building blocks)

| | codon |
|---|---|
| $4A_2$ | AAAT |
| $4B_2$ | ACCA |
| $4C_2$ | ACCT |
| $4D_2$ | ACGA |
| $4E_2$ | ACGT |
| $4F_2$ | ACTA |
| $4G_2$ | ACTT |
| $4H_2$ | AGTA |
| $4I_2$ | AGTT |
| $4J_2$ | ATAA |
| $4K_2$ | ATAT |
| $4L_2$ | ATGA |
| $4M_2$ | ATGT |
| $4N_2$ | CACA |
| $4O_2$ | CAGA |
| $4P_2$ | CATA |
| $4A_3$ | CATT |
| $4B_3$ | CCAA |
| $4C_3$ | CCTA |
| $4D_3$ | CCTT |
| $4E_3$ | CGAA |
| $4F_3$ | CGTA |
| $4G_3$ | CGTT |
| $4H_3$ | CTGA |
| $4I_3$ | CTGT |
| $4J_3$ | CTTA |
| $4K_3$ | CTTT |
| $4L_3$ | GACA |
| $4M_3$ | GAGA |
| $4N_3$ | GCTA |
| $4O_3$ | GGTA |
| $4P_3$ | TAAA |
| $4A_4$ | TAAT |
| $4B_4$ | TATT |
| $4C_4$ | TCAA |
| $4D_4$ | TCCT |
| $4E_4$ | TCGA |
| $4F_4$ | TCGT |
| $4G_4$ | TCTA |
| $4H_4$ | TCTT |
| $4I_4$ | TGCA |
| $4J_4$ | TGGA |
| $4K_4$ | TGTA |
| $4L_4$ | TGTT |
| $4M_4$ | TTAT |
| $4N_4$ | TTCA |
| $4O_4$ | TTGA |
| $4P_4$ | TTTA |

Building Blocks Selected for the Second-Generation Library of Macrocycles

TABLE 5

Scaffolds for the second-generation DNA-templated libraries of macrocycles

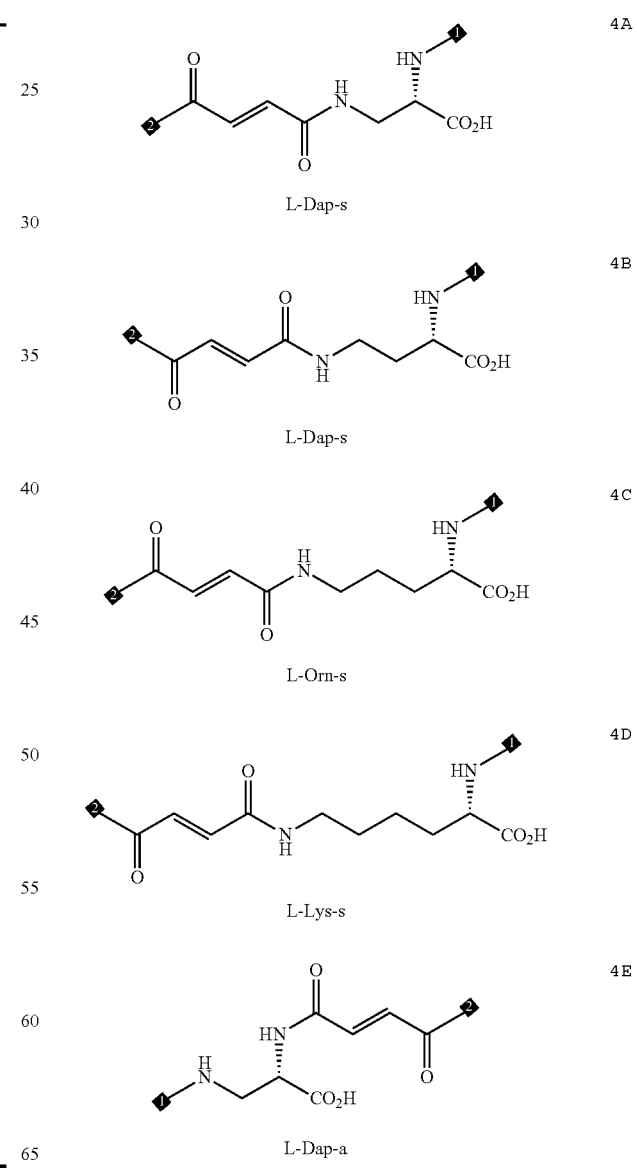

TABLE 5-continued
Scaffolds for the second-generation DNA-templated libraries of macrocycles
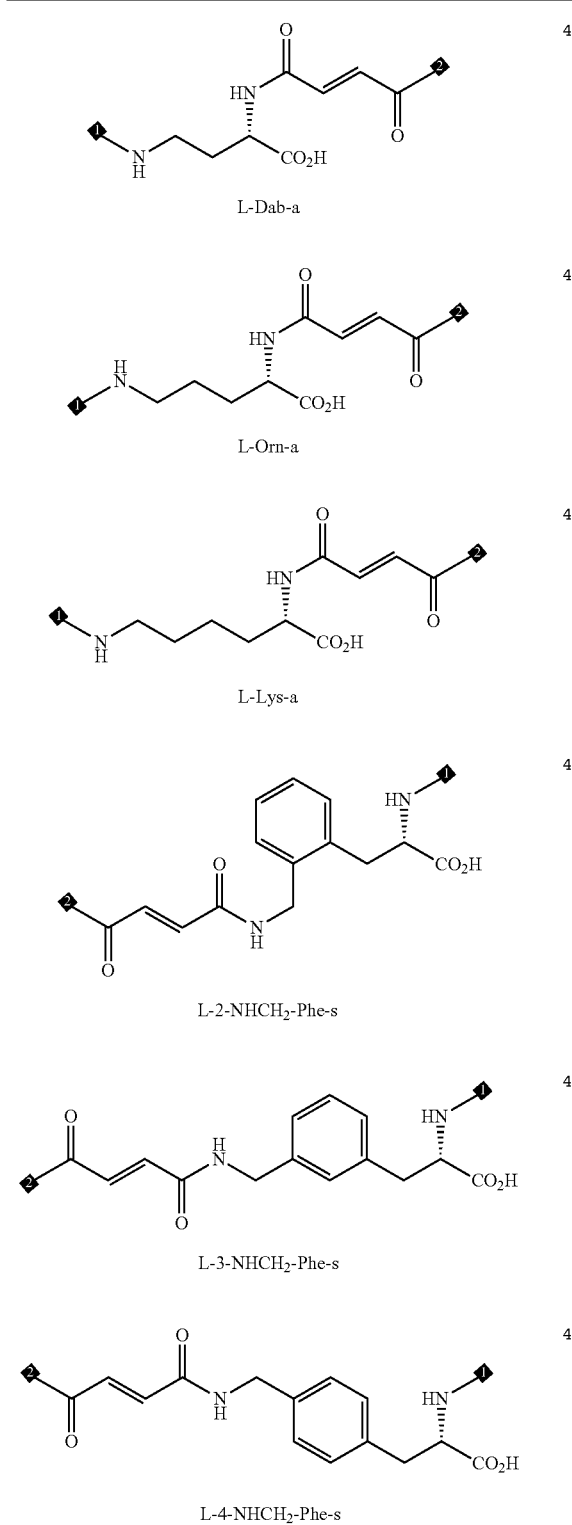
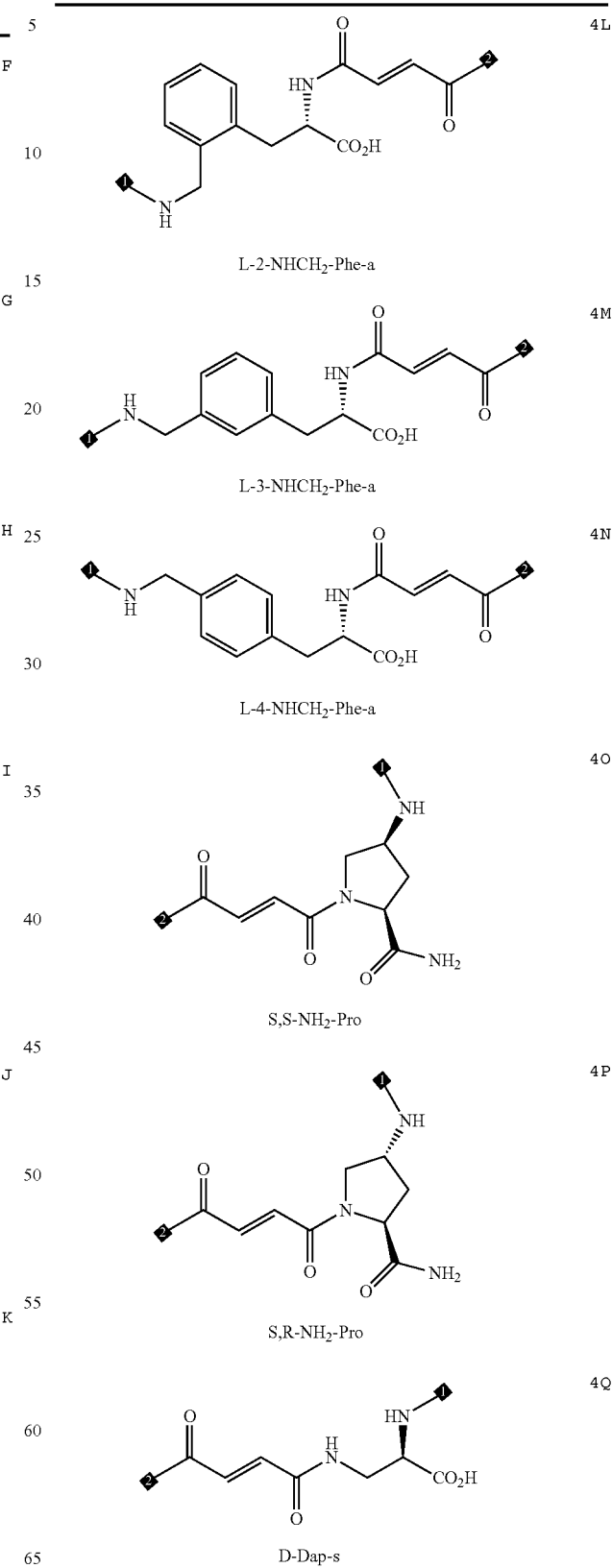

TABLE 5-continued
Scaffolds for the second-generation DNA-templated libraries of macrocycles
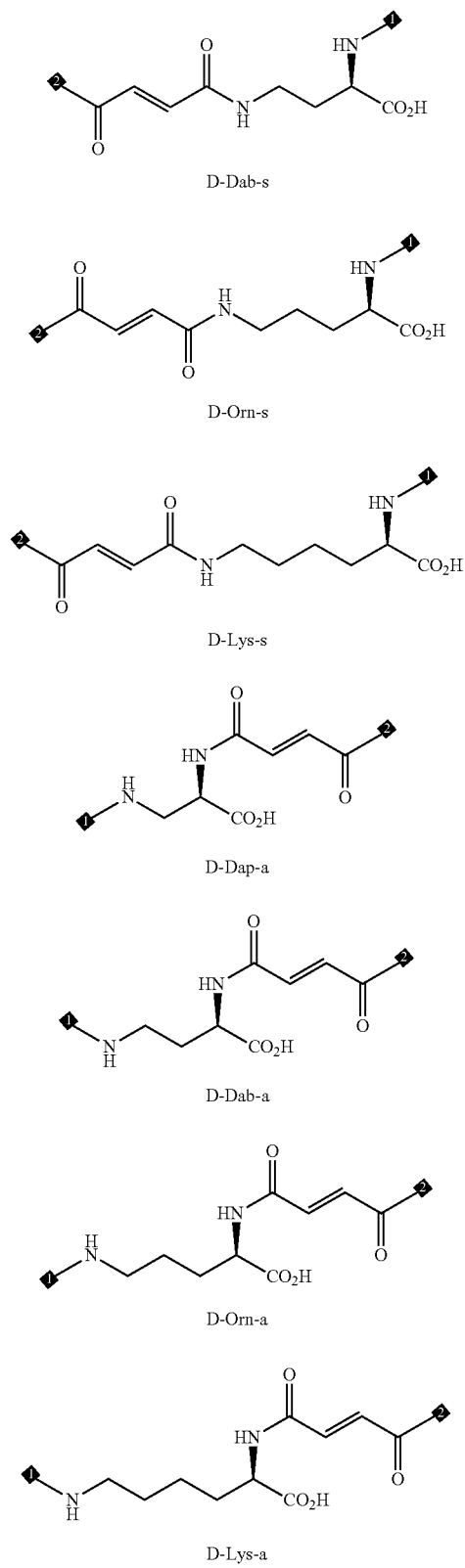
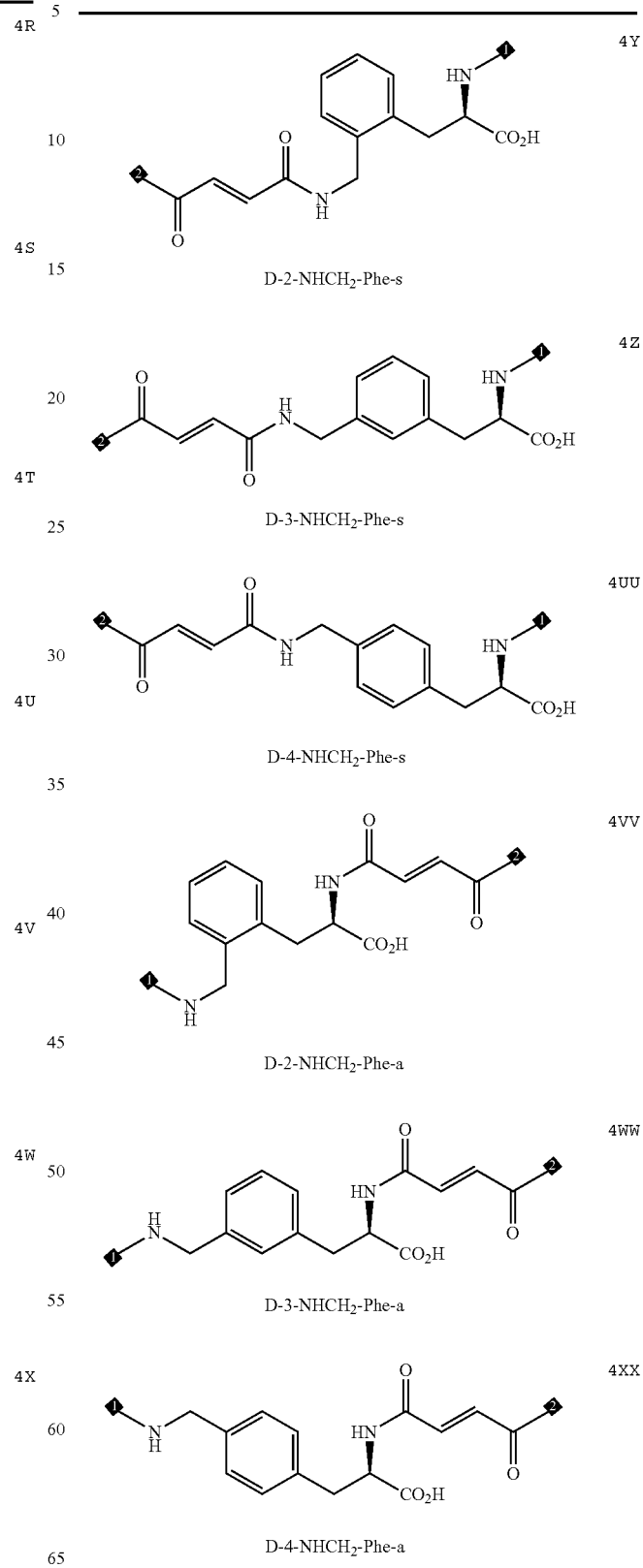

TABLE 5-continued
Scaffolds for the second-generation DNA-templated libraries of macrocycles
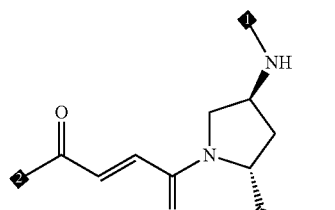
R,S-NH₂-Pro
4YY
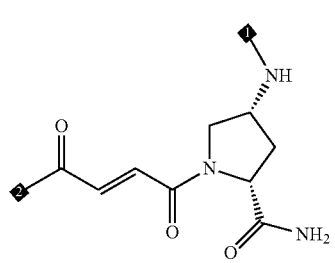
R,R-NH₂-Pro
4ZZ
TABLE 6
Building blocks 1-3 for the second-generation DNA-templated library of macrocycles
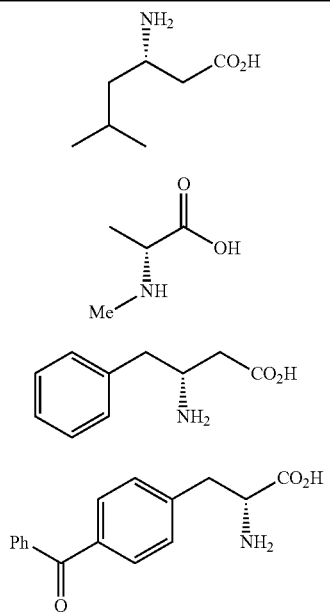
1A
1B
1C
1D
1E
TABLE 6-continued
Building blocks 1-3 for the second-generation DNA-templated library of macrocycles
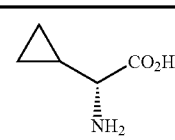 1F
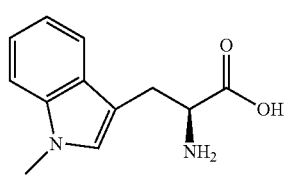 [SMILES: Cn1cc(C[C@H](N)C(=O)O)c2ccccc21] 1G
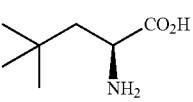 1H
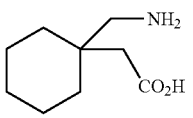 1I
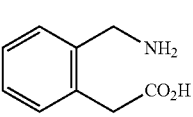 1J
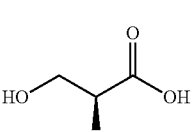 1K
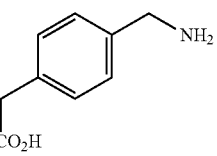 1L
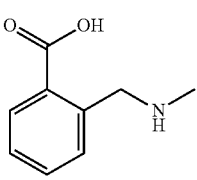 1M
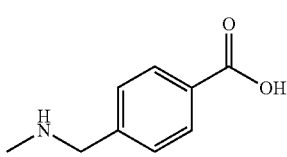 1N
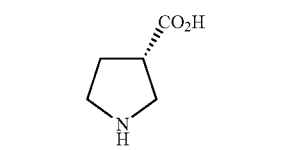 1O TABLE 6-continued
Building blocks 1-3 for the second-generation DNA-templated library of macrocycles
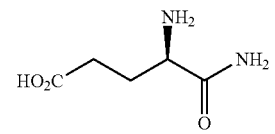 2A
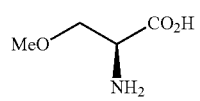 2B
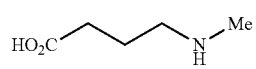 2C
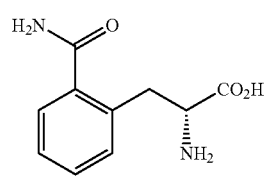 2D
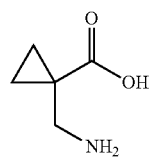 2E
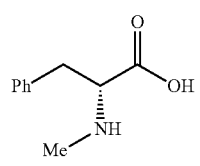 [SMILES: CN[C@H](Cc1ccccc1)C(=O)O] 2F
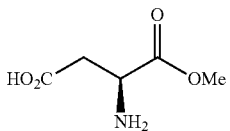 2G
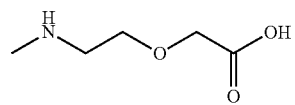 2H
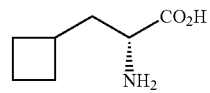 2I
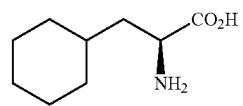 [SMILES: N[C@@H](CC1CCCCC1)C(=O)O] 2J
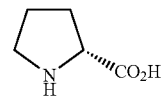 2K
TABLE 6-continued
Building blocks 1-3 for the second-generation DNA-templated library of macrocycles
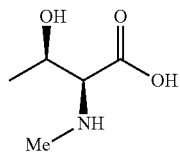 2L
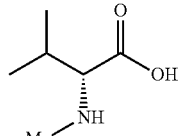 2M
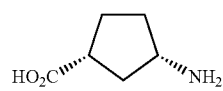 2N
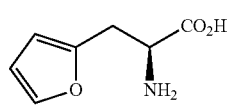 [SMILES: N[C@@H](Cc1ccco1)C(=O)O] 2O
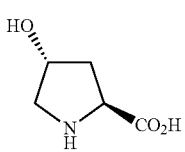 2P
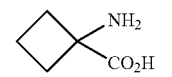 2Q
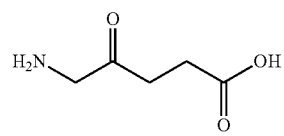 2R
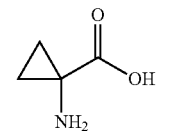 2S
 2T
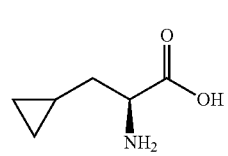 3A
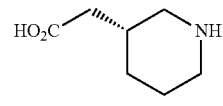 3B
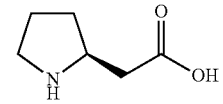 3C TABLE 6-continued
Building blocks 1-3 for the second-generation DNA-templated library of macrocycles
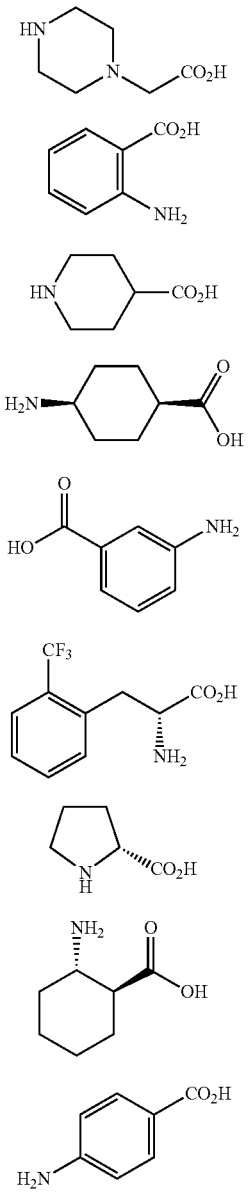
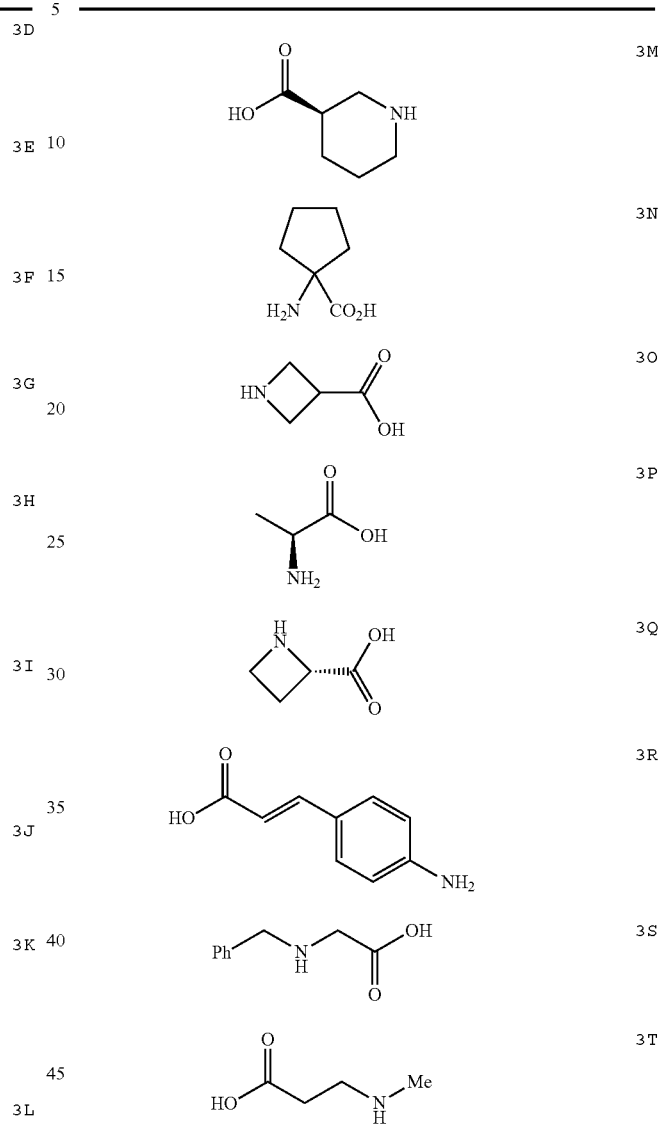
Preparation of DNA-Tagged Library Components
Preparation of DTS Reagents, Groups 1 and 2
Scheme 1: Preparation of DTS reagents 1 and 2.
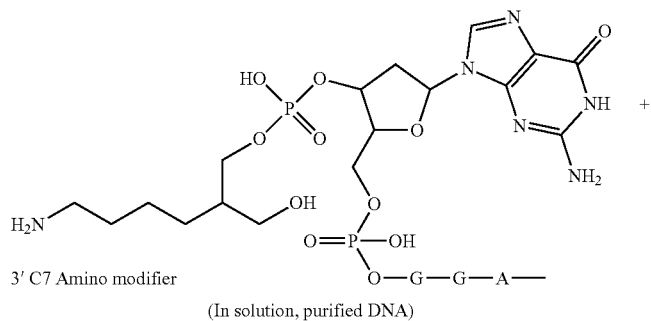

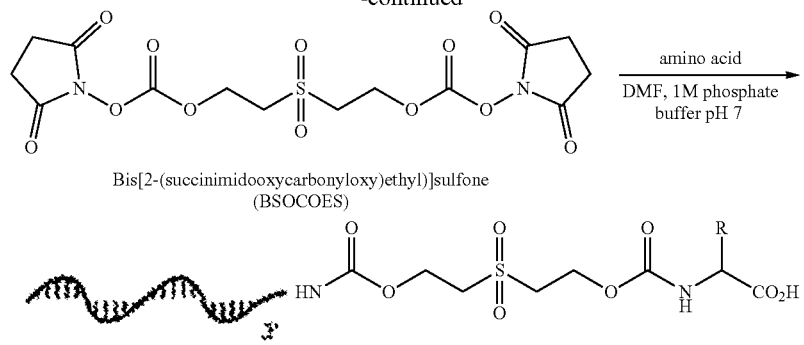

Bis[2-(succinimidooxycarbonyloxy)ethyl)]sulfone
(BSOCOES)

Oligonucleotides were synthesized trityl-on and purified on Glen-pak cartridges (Glen Research) according to the standard procedure for amino-modified oligonucleotides (4% TFA, vide supra). 100 μL of ~2 mM DNA solution in water was mixed with 100 μL of 100 mM amino acid solution (see Table 4) in 1 M sodium phosphate pH 7 buffer (for hydrophilic acids—250 mM: 1B, 1F, 1K, 1M, 1N, 1Q, 2B, 2C, 2E, 2F, 2H, 2L, 2M, 2Q, 2S, 2T). 50 μL of 100 mg/mL BSOCOES (G-Biosciences, Pierce or Toronto Research Chemicals) solution in DMF was added. The mixtures were sonicated until clear (1D, 1E, 1G, 1J, 2D, 2F, 2I, 2J never cleared, and reactions with them were carried out in a heterogeneous mode) and were agitated at room temperature for 1 h. Each mixture was loaded on a Nap-5 column (GE Life Sciences) equilibrated in 0.1 M triethylammonium acetate (TEAA) pH 7, equilibrated with 250 μL of 0.1M TEAA and eluted with 700 μL of the same buffer. The eluate was filtered using EMD Ultrafree-MC GV 0.22 μm filter units and purified by HPLC (3-30 min: 5-32% acetonitrile in 0.1 M TEAA, pH 7). Lyophilized fractions were redissolved in 500 μL of 5 mM phosphate buffer pH 7 and used for DTS reactions.

TABLE 4

Chemical building blocks (1) used for the second-generation library

| parent amino acid | CAS number | commercial source |
| --- | --- | --- |
| 1A hexanoic acid, 3-amino-5-methyl-,(3S)- | 22818-43-5 | Astatech 52006 |

TABLE 4-continued

Chemical building blocks (1) used for the second-generation library

| parent amino acid | CAS number | commercial source |
| --- | --- | --- |
| 1B N-methyl-D-alanine (HCl) | 29475-64-7 | Chem-Impex 04405 |
| 1C D-beta-homophenylalanine (HCl) | 131270-08-1 | Peptech BD733-1 |
| 1D D-4-benzoylphenylalanine | 201466-03-7 | Chem-Impex 05111 |
| 1E 2-cyclohexyl-D-glycine | 14328-52-0 | Oakwood 040199-1g |
| 1F D-cyclopropylglycine | 49607-01-4 | Chem-Impex 16797 |
| 1G 1-methyl-L-tryptophan | 21339-55-9 | Sigma 447439-1G |
| 1H L-neopentylglycine | 57224-50-7 | Chem-Impex 06234 |
| 1I gabapentin | 60142-96-3 | Chem-Impex 16983 |
| 1J 2-aminomethylphenylacetic Acid | 40851-65-8 | TCI America A2199 |
| 1K N-methyl-L-serine (HCl) | 2480-26-4 | Chem-Impex 06357 |
| 1L 4-(aminomethyl)benzeneacetic acid | 1200-05-1 | Astatech 75935 |
| 1M 2-[(methylamino)methyl]benzoic acid | 527705-23-3 | Matrix Scientific 077672 |
| 1N 4-[(methylamino)methyl]benzoic acid | 96084-38-7 | Matrix Scientific 065416 |
| 1O L-beta-Proline | 72580-53-1 | Alfa Aesar H57895 |
| 1P 3-(2-pyridyl)-D-alanine | 37535-52-7 | Peptech AD185-1 |
| 1Q glycine | 56-40-6 | Sigma-Aldrich |
| 1R tranexamic acid | 1197-18-8 | Chem-Impex 06911 |
| 1S (1R,2R)-boc-2-aminocyclopentane carboxylic acid | 245115-25-7 | Chem-Impex 14468 |
| 1T 3-aminomethylbenzoic acid | 2393-20-6 | Chem-Impex 28733 |

TABLE 8

Chemical building blocks (2) used for the second-generation library

| parent amino acid | CAS number | commercial source |
| --- | --- | --- |
| 2A D-isoglutamine (HCl) | 19522-40-8 | Chem-Impex 05966 |
| 2B O-methyl-L-serine | 32620-11-4 | Astatech F10843 |
| 2C 4-(methylamino)butanoic acid | 1119-48-8 | Astatech AB7427 |
| 2D D-2-carbamoylphenylalanine | 1217613-52-9 | Chem-Impex 16773 |
| 2E 1-(aminomethyl)cyclopropanecarboxylic acid | 139126-45-7 | AldrichCPR CDS015451-100MG |
| 2F N-methyl-D-phenylalanine | 56564-52-4 | Alfa Aesar H65675 |
| 2G L-aspartic acid α-methyl ester | 17812-32-7 | Chem-Impex 02695 |
| 2H (2-methylamino-ethoxy)-acetic acid | 98137-58-7 | Oakwood 095219-1g |
| 2I D-3-cyclobutylalanine | 174266-00-3 | Astatech 59421 |
| 2J 3-cyclohexyl-L-alanine | 27527-05-5 | Chem-Impex 02560 |
| 2K D-proline | 344-25-2 | Sigma-Aldrich 858919 |
| 2L N-methyl-L-threonine (HCl) | 2812-28-4 | Chem-Impex 09616 |
| 2M N-methyl-D-Valine (HCl) | 88930-14-7 | Chem-Impex 04461 |
| 2N (1R,3S)-3-aminocyclopentane carboxylic acid | 71830-08-5 | Chem-Impex 15488 |
| 2O L-2-furylalanine | 121786-31-0 | Chem-Impex 07442 |

TABLE 8-continued

Chemical building blocks (2) used for the second-generation library

| parent amino acid | CAS number | commercial source |
|---|---|---|
| 2P trans-L-4-hydroxyproline | 51-35-4 | Chem-Impex 00185 |
| 2Q 1-aminocyclobutanecarboxylic acid | 22264-50-2 | Oakwood 066472-1g |
| 2R 5-amino-4-oxopentanoic acid | 106-60-5 | Astatech 27973 |
| 2S 1-aminocyclopropane-1-carboxylic acid | 22059-21-8 | Chem-Impex 07075 |
| 2T N-methylglycine | 107-97-1 | Chem-Impex 01319 |

TABLE 9

Analytical data of DTS reagents 1.

| | sequence 5'-3' (SEQ ID NOs: 4-23) | HPLC ret. time | yield | formula | calc. (z = 3) | found (z = 3) |
|---|---|---|---|---|---|---|
| 1A | TAGAAAGCCATAGGG7 | 17.9 min | 12% | $C_{168}H_{220}N_{67}O_{96}P_{15}S$ | 1735.0 | 1735.2 |
| 1B | TAGAAGCCTATAGGG7 | 12.3 min | 15% | $C_{165}H_{215}N_{64}O_{98}P_{15}S$ | 1718.0 | 1718.2 |
| 1C | TAGTTTGGCATAGGG7 | 18.5 min | 15% | $C_{172}H_{221}N_{60}O_{102}P_{15}S$ | 1750.7 | 1750.8 |
| 1D | TAGGTTCCTATAGGG7 | 22.5 min | 12% | $C_{177}H_{223}N_{58}O_{103}P_{15}S$ | 1767.3 | 1767.5 |
| 1E | TAGCATACGATAGGG7 | 18.8 min | 12% | $C_{169}H_{221}N_{64}O_{98}P_{15}S$ | 1736.0 | 1736.2 |
| 1F | TAGCTCATGATAGGG7 | 14.9 min | 14% | $C_{166}H_{216}N_{61}O_{100}P_{15}S$ | 1719.0 | 1719.2 |
| 1G | TAGTGTCTCATAGGG7 | 20.2 min | 13% | $C_{173}H_{222}N_{59}O_{102}P_{15}S$ | 1750.3 | 1750.5 |
| 1H | TAGCTACAGATAGGG7 | 18.6 min | 17% | $C_{168}H_{221}N_{64}O_{98}P_{15}S$ | 1732.0 | 1732.2 |
| 1I | TAGCAGCTAATAGGG7 | 19 min | 16% | $C_{170}H_{223}N_{64}O_{98}P_{15}S$ | 1740.7 | 1740.9 |
| 1J | TAGCTGAGAATAGGG7 | 16.8 min | 15% | $C_{171}H_{217}N_{66}O_{98}P_{15}S$ | 1752.0 | 1752.2 |
| 1K | TAGAGCTCTATAGGG7 | 13.4 min | 15% | $C_{165}H_{216}N_{61}O_{101}P_{15}S$ | 1720.3 | 1720.6 |
| 1L | TAGTGTTCGATAGGG7 | 15.9 min | 7% | $C_{171}H_{219}N_{60}O_{102}P_{15}S$ | 1746.0 | 1746.2 |
| 1M | TAGAAGAGCATAGGG7 | 16.8 min | 17% | $C_{171}H_{216}N_{69}O_{96}P_{15}S$ | 1755.0 | 1755.2 |
| 1N | TAGAGCAGAATAGGG7 | 16.3 min | 17% | $C_{171}H_{216}N_{69}O_{96}P_{15}S$ | 1755.0 | 1755.2 |
| 1O | TAGGATCGAATAGGG7 | 14.1 min | 8% | $C_{167}H_{215}N_{66}O_{98}P_{15}S$ | 1735.3 | 1735.6 |
| 1P | TAGTCAGTCATAGGG7 | 15.3 min | 17% | $C_{169}H_{217}N_{62}O_{100}P_{15}S$ | 1736.0 | 1736.3 |
| 1Q | TAGTACTGCATAGGG7 | 13.7 min | 9% | $C_{163}H_{212}N_{61}O_{100}P_{15}S$ | 1705.6 | 1705.9 |
| 1R | TAGATACGCATAGGG7 | 15.5 min | 16% | $C_{169}H_{221}N_{64}O_{98}P_{15}S$ | 1736.0 | 1736.2 |
| 1S | TAGGATTCCATAGGG7 | 15.15 min | 14% | $C_{167}H_{218}N_{61}O_{100}P_{15}S$ | 1723.6 | 1723.9 |
| 1T | TAGTGAAGCATAGGG7 | 15.9 min | 13% | $C_{170}H_{215}N_{66}O_{98}P_{15}S$ | 1747.3 | 1747.6 |

TABLE 10

Analytical data of DTS reagents 2

| | sequence 5'-3' (SEQ ID NOs: 24-43) | HPLC ret. time | yield | formula | calc. (z = 2) | found (z = 2) |
|---|---|---|---|---|---|---|
| 2A | CATTTCAGCAAAGGG7 | 12.9 min | 16% | $C_{165}H_{216}N_{63}O_{99}P_{15}S$ | 1719.0 | 1719.2 |
| 2B | CATATCGACAAAGGG7 | 13.8 min | 11% | $C_{164}H_{214}N_{65}O_{97}P_{15}S$ | 1713.0 | 1713.3 |
| 2C | CATGCAATCAAAGGG7 | 14.4 min | 23% | $C_{165}H_{216}N_{65}O_{96}P_{15}S$ | 1712.3 | 1712.6 |
| 2D | CATAAGTCCAAAGGG7 | 15.2 min | 11% | $C_{170}H_{217}N_{66}O_{97}P_{15}S$ | 1742.7 | 1742.9 |

TABLE 10-continued

Analytical data of DTS reagents 2

| sequence 5'-3' (SEQ ID NOs: 24-43) | HPLC ret. time | yield | formula | calc. (z = 2) | found (z = 2) |
|---|---|---|---|---|---|
| 2E CATATCCGTAAAGGG7 | 14.6 min | 7% | $C_{165}H_{215}N_{62}O_{98}P_{15}S$ | 1708.6 | 1708.9 |
| 2F CATACTCGAAAAGGG7 | 18.7 min | 13% | $C_{170}H_{218}N_{65}O_{96}P_{15}S$ | 1733.0 | 1733.2 |
| 2G CATTCTTGCAAAGGG7 | 14.2 min | 11% | $C_{165}H_{216}N_{59}O_{102}P_{15}S$ | 1716.3 | 1716.6 |
| 2H CATCACAAGAAAGGG7 | 14.1 min | 10% | $C_{165}H_{215}N_{68}O_{95}P_{15}S$ | 1720.7 | 1720.9 |
| 2I CATTTAGCCAAAGGG7 | 17.8 min | 16% | $C_{167}H_{219}N_{62}O_{98}P_{15}S$ | 1718.0 | 1718.2 |
| 2J CATAGTCCTAAAGGG7 | 21.0 min | 12% | $C_{169}H_{223}N_{62}O_{98}P_{15}S$ | 1727.3 | 1727.6 |
| 2K CATGCATGAAAAGGG7 | 13.9 min | 16% | $C_{166}H_{214}N_{67}O_{96}P_{15}S$ | 1725.0 | 1725.2 |
| 2L CATCAGACTAAAGGG7 | 13.5 min (middle peak) | 12% | $C_{165}H_{216}N_{65}O_{97}P_{15}S$ | 1717.7 | 1717.9 |
| 2M CATTTCCAGAAAGGG7 | 16.5 min | 3% | $C_{166}H_{219}N_{62}O_{98}P_{15}S$ | 1714.0 | 1714.3 |
| 2N CATGGCAATAAAGGG7 | 14.5 min | 14% | $C_{167}H_{216}N_{67}O_{96}P_{15}S$ | 1729.7 | 1729.9 |
| 2O CATTCGAGAAAAGGG7 | 16.1 min | 16% | $C_{168}H_{214}N_{67}O_{97}P_{15}S$ | 1738.3 | 1738.6 |
| 2P CATCTAAGGAAAGGG7 | 12.8 min | 15% | $C_{166}H_{214}N_{67}O_{97}P_{15}S$ | 1730.3 | 1730.6 |
| 2Q CATAGGCTAAAAGGG7 | 14.7 min | 22% | $C_{166}H_{214}N_{67}O_{96}P_{15}S$ | 1725.0 | 1725.2 |
| 2R CATTCACTGAAAGGG7 | 13.7 min | 15% | $C_{165}H_{215}N_{62}O_{99}P_{15}S$ | 1714.0 | 1714.2 |
| 2S CATTTGCTCAAAGGG7 | 14 min | 19% | $C_{164}H_{214}N_{59}O_{100}P_{15}S$ | 1701.0 | 1701.2 |
| 2T CATAGCTTCAAAGGG7 | 13.7 min | 9% | $C_{163}H_{213}N_{62}O_{98}P_{15}S$ | 1700.0 | 1700.2 |

Preparation of DTS Reagents 3

Each product was prepared from 2 µmol of CPG-bound oligonucleotide. Importantly, only 500 Å 3' amino C7 CPG beads can be used (Glen Research cat. no. 20-2957-10, discontinued item, custom order needed), very low yields were observed with a 1000 Å analog. The products are prone to oxidation, and the corresponding solutions should be immediately frozen on dry ice until needed.

Scheme 2. Preparation of DTS reagents 3.

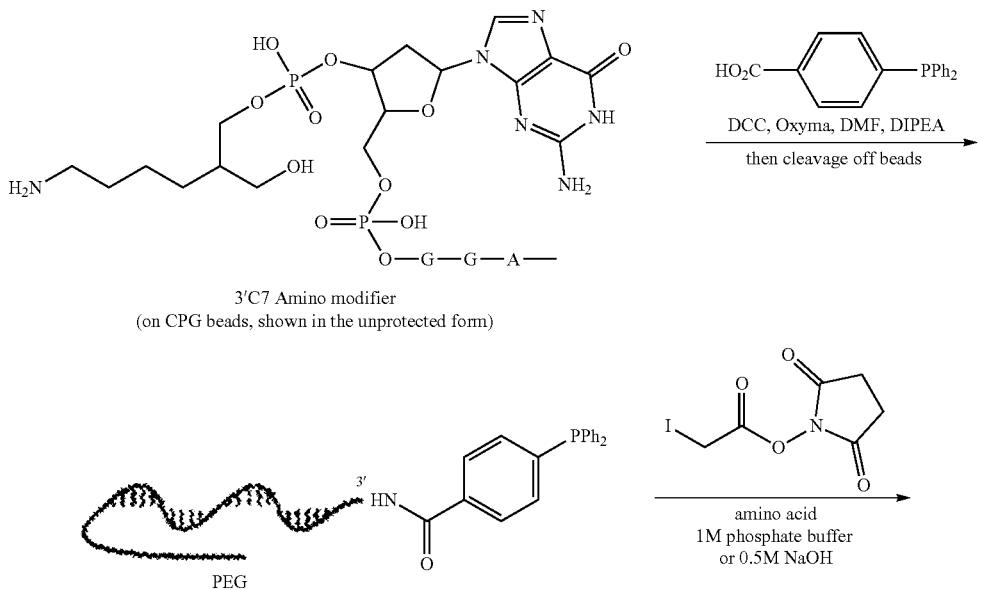

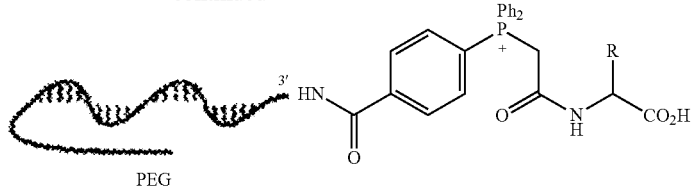

Final Orthogonal Codon Set

After 5'-detritylation on the DNA synthesizer, CPG beads were washed with 20% piperidine in DMF (3×1 mL, 5 minutes agitation on a rotary each time), then 2×0.7 mL of DMF and 2×0.7 mL of MeCN.

4-(diphenylphosphino)benzoic acid (61 mg, 200 µmol), dicyclohexylcarbodiimide (41 mg, 200 µmol) and Oxyma Pure (28 mg, 200 µmol) were dissolved in 0.8 mL of dry DMF and 35 µL (200 µmol) of diisopropylethylamine was added. The mixture was left at room temperature without agitation for 2 h. The crystals were filtered off using EMD Ultrafree-MC GV 0.22 µm filter units and the solution was added to CPG beads in a 1.5 mL eppendorf tube. The reaction was agitated on a rotary for 3 h. The liquid phase was removed and the beads were washed with 3×0.7 mL of DMF and 2×0.7 mL of MeCN. 400 µL of AMA solution containing 1 mg of TCEP was added and the mixture was heated to 65° C. for precisely 10 min. The samples were concentrated for 10-15 min using a speedvac to remove ammonia and methylamine and were diluted with 0.1 M TEAA pH 7 to the 600 µL mark. The beads were filtered off using EMD Ultrafree-MC GV 0.22 µm filter units and the filtrate was immediately frozen on dry ice. The samples were stored at −20° C. until HPLC purification in 0.1 M TEAA pH 7/acetonitrile (0-3 min: 5% MeCN; 3-25 min: 5-40%; 25-25.5 min: 40-100%; 25.5-27 min: 100%; 27-27.1 min: 100-10%; 27.1-30 min: 10%). Fractions containing peaks at ~26 min were frozen on dry ice immediately after each chromatography run. After lyophilization, the residue was dissolved in 400 µL of 10 mM sodium phosphate buffer pH 7 and immediately frozen until the follow-up reaction. 13-29% yields.

TABLE 11

Chemical building blocks (3) used for the second-generation library

| | parent amino acid | used in | CAS number | commercial source |
|---|---|---|---|---|
| 3A | L-cyclopropylalanine | 1M phosphate pH 7 | 102735-53-5 | Chem-Impex 07175 |
| 3B | (R)-2-(piperidin-3-yl)acetic acid (HCl) | 1M phosphate pH 7 | 1334509-89-5 | Astatech 56293 |
| 3C | L-beta-homoproline (HCl) | 1M phosphate pH 7 | 53912-85-9 | Peptech BL712-1 |
| 3D | 1-piperazineacetic acid | 1M phosphate pH 7 | 37478-58-3 | Sigma, 728144 |
| 3E | anthranilic acid | 500 mM NaOH | 118-92-3 | Sigma A89855-25G |
| 3F | isonipecotic acic | 1M phosphate pH 7 | 498-94-2 | Chem-Impex 06897 |
| 3G | cis-4-aminocyclohexanecarboxylic acid | 1M phosphate pH 7 | 3685-23-2 | Oakwood 047831-1g |
| 3H | 3-aminobenzoic acid | 500 mM NaOH | 99-05-8 | Oakwood 078487-10 g |
| 3I | 2-(trifluoromethyl)-D-phenylalanine | 500 mM NaOH | 130930-49-3 | Chem-Impex 07435 |
| 3J | D-proline | 1M phosphate pH 7 | 344-25-2 | Chem-Impex 00355 |
| 3K | (1S,2S)-2-aminocyclohexanecarboxylic acid | 1M phosphate pH 7 | 24716-93-6 | Alfa Aesar H52779 |
| 3L | 4-aminobenzoic acid | 500 mM NaOH | 150-13-0 | Sigma A9878-5G |
| 3M | (R)-nipecotic acid | 1M phosphate pH 7 | 25137-00-2 | Chem-Impex 28509 |
| 3N | cycloleucine | 1M phosphate pH 7 | 52-52-8 | Chem-Impex 03534 |
| 3O | 3-azetidinecarboxylic acid | 1M phosphate pH 7 | 36476-78-5 | Oakwood 035210-1g |
| 3P | L-alanine | 1M phosphate pH 7 | 56-41-7 | |
| 3Q | L-azetidine-2-carboxylic acid | 1M phosphate pH 7 | 2133-34-8 | Chem-Impex 04462 |
| 3R | (2E)-3-(4-aminophenyl)-2-propenoic acid | 500 mM NaOH | 17570-30-8 | AldrichCPR CD5000175-250MG |
| 3S | N-benzylglycine | 1M phosphate pH 7 | 17136-36-6 | Chem-Impex 17126 |
| 3T | N-methyl-β-Alanine | 1M phosphate pH 7 | 2679-14-3 | Astatech 29150 |

Each amino acid was dissolved in 100 µL of either 1 M sodium phosphate buffer pH 7 or 0.5 M NaOH (see Table). In a few cases some sonication was needed. 100 µL of 50 mg/mL SIA (succinimidyl iodoacetate, S2) was added and the mixture was agitated for 30 minutes for the phosphate buffer solutions and for 5 minutes for alkaline solutions. Alkaline solutions were diluted with 100 μL of 1 M sodium phosphate buffer pH 7. The corresponding 3'-4-(diphenylphosphino)benzoic acid amide-linked oligonucleotide solution was added to each solution, the mixtures were agitated at room temperature for 2 h and then desalted using Nap-5 columns (GE Life Sciences, elution with 1 mL of water). 50 μL of 2 M TEAA buffer pH 7 was added to each sample followed by filtration with EMD Ultrafree-MC GV 0.22 μm filter units. The samples were purified by HPLC (3-25 min: 5-40% MeCN in 0.1M TEAA pH 7 unless otherwise noted, see Table 15), pure fractions were lyophilized and the residues were dissolved in 500 μL of 5 mM sodium phosphate buffer pH 7 to be used in DNA-templated reactions.

TABLE 12

Analytical data for DTS reagents 3

| | HPLC ret. time | yield | formula | calc. (z = 3) | found (z = 3) |
|---|---|---|---|---|---|
| 3A | 16.1 min | 32% | $C_{217}H_{302}N_{56}O_{126}P_{19}$ | 2097.8 | 2097.7 |
| 3B | 15.8 min | 30% | $C_{218}H_{303}N_{59}O_{124}P_{19}$ | 2105.5 | 2105.4 |
| 3C | 6 min, 1$^{st}$ peak[1] | 29% | $C_{218}H_{302}N_{58}O_{126}P_{19}$ | 2111.1 | 2111.0 |
| 3D | 15.1 min | 41% | $C_{218}H_{302}N_{62}O_{124}P_{19}$ | 2119.1 | 2119.1 |
| 3E | 18.1 min | 59% | $C_{218}H_{298}N_{56}O_{126}P_{19}$ | 2100.4 | 2100.3 |
| 3F | 15.3 min | 44% | $C_{217}H_{302}N_{56}O_{126}P_{19}$ | 2097.8 | 2097.7 |
| 3G | 15.6 min | 20% | $C_{220}H_{304}N_{60}O_{126}P_{19}$ | 2129.1 | 2129.0 |
| 3H | 16.0 min | 49% | $C_{219}H_{297}N_{61}O_{124}P_{19}$ | 2116.8 | 2116.7 |
| 3I | 19.1 min | 45% | $C_{222}H_{300}F_3N_{61}O_{124}P_{19}$ | 2148.8 | 2148.7 |
| 3J | 15.2 min[2] | 18% | $C_{217}H_{299}N_{61}O_{124}P_{19}$ | 2109.5 | 2109.3 |
| 3K | 16.3 min | 24% | $C_{218}H_{303}N_{59}O_{124}P_{19}$ | 2105.5 | 2105.4 |
| 3L | 55.8-56.7 min[3] | 14% | $C_{220}H_{298}N_{60}O_{126}P_{19}$ | 2127.1 | 2127.0 |
| 3M | 15.6 min | 44% | $C_{218}H_{302}N_{58}O_{126}P_{19}$ | 2111.1 | 2111.0 |
| 3N | 18.4 min | 20% | $C_{218}H_{301}N_{61}O_{124}P_{19}$ | 2114.1 | 2114.0 |
| 3O | 14.7 min | 56% | $C_{215}H_{296}N_{62}O_{122}P_{19}$ | 2094.5 | 2094.4 |
| 3P | 15.0 min | 59% | $C_{216}H_{297}N_{63}O_{124}P_{19}$ | 2114.1 | 2114.0 |
| 3Q | 15 min[2] | 40% | $C_{217}H_{296}N_{66}O_{122}P_{19}$ | 2121.1 | 2121.0 |
| 3R | 15.8 min | 48% | $C_{221}H_{299}N_{61}O_{124}P_{19}$ | 2125.5 | 2125.4 |
| 3S | 67.6 min[4] | 12% | $C_{220}H_{300}N_{62}O_{122}P_{19}$ | 2115.8 | 2115.7 |
| 3T | 15.1 min | 33% | $C_{216}H_{298}N_{64}O_{122}P_{19}$ | 2108.5 | 2108.4 |

Acetonitrile in 0.1 M TEAA pH 7;
[1] 3-80 min: 5-32% MeCN.
[2] 3-60 min: 5-40% MeCN.
[3] 3-80 min: 5-22% MeCN, 0.1 min fractions.
[4] 3-120 min; 5-32% MeCN.

Preparation of Chemically Modified Primers

TABLE 13

Sources of scaffold building blocks

| | code | parent amino acid | CAS number | commercial source |
|---|---|---|---|---|
| A | L-Dap-s | Fmoc-L-Dap(Mtt)-OH | 654670-89-0 | EMD Millipore 04121204 |
| B | L-Dab-s | Boc-L-Dab(Fmoc)-OH | 117106-21-5 | Chem-Impex 04963 |
| C | L-Orn-s | Fmoc-L-Orn(Mtt)-OH | 343770-23-0 | Chem-Impex 03729 |
| D | L-Lys-s | Fmoc-L-Lys(Mmt)-OH | 159857-60-0 | Chem-Impex 11187 |
| E | L-Dap-a | Fmoc-L-Dap(Mtt)-OH | 654670-89-0 | EMD Millipore 04121204 |
| F | L-Dab-a | Fmoc-L-Dab(Boc)-OH | 125238-99-5 | Chem-Impex 03762 |
| G | L-Orn-a | Fmoc-L-Orn(Mtt)-OH | 343770-23-0 | Chem-Impex 03729 |
| H | L-Lys-a | Fmoc-L-Lys(Mmt)-OH | 159857-60-0 | Chem-Impex 11187 |
| I | L-o-NHCH$_2$-Phe-s | Fmoc-2-(Boc-aminomethyl)-L-Phe-OH | 1217808-42-8 | Peptech FL552 |
| J | L-m-NHCH$_2$-Phe-s | Fmoc-3-(Boc-aminomethyl)-L-Phe-OH | 266999-24-0 | Chem-Impex 16862 |
| K | L-p-NHCH$_2$-Phe-s | Fmoc-4-(Boc-aminomethyl)-L-Phe-OH | 204715-91-3 | Chem-Impex 07408 |
| L | L-o-NHCH$_2$-Phe-a | Boc-2-(Fmoc-aminomethyl)-L-Phe-OH | 959573-16-1 | Peptech BL550 |
| M | L-m-NHCH$_2$-Phe-a | Boc-3-(Fmoc-aminomethyl)-L-Phe-OH | 959573-13-8 | Peptech BL554 |
| N | L-p-NHCH$_2$-Phe-a | Boc-4-(Fmoc-aminomethyl)-L-Phe-OH | 170157-61-6 | Peptech BL300 |
| O | S,S-NH$_2$-Pro | Boc-(2S,4S)-4-amino-1-Fmoc- | 221352-74-5 | Chem-Impex 07324 |

TABLE 13-continued

Sources of scaffold building blocks

| code | | parent amino acid | CAS number | commercial source |
|---|---|---|---|---|
| P | S,R-NH$_2$-Pro | pyrrolidine-2-carboxylic acid (2S,4R)-Boc-4-amino-1-Fmoc-pyrrolidine-2-carboxylic acid | 273222-06-3 | Chem-Impex 29660 |
| Q | D-Dap-s | Fmoc-D-Dap(Mtt)-OH | 1263046-35-0 | Chem-Impex 16190 |
| R | D-Dab-s | Boc-D-Dab(Fmoc)-OH | 131570-57-5 | Chem-Impex 06297 |
| S | D-Orn-s | Fmoc-D-Orn(Mtt)-OH | 198545-20-9 | Chem-Impex 03731 |
| T | D-Dys-s | Fmoc-D-Lys(Mtt)-OH | 198544-94-4 | Chem-Impex 03924 |
| U | D-Dap-a | Fmoc-D-Dap(Mtt)-OH | 1263046-35-0 | Chem-Impex 16190 |
| V | D-Dab-a | Fmoc-D-Dab(Mtt)-OH | 1217809-38-5 | Chem-Impex 16187 |
| W | D-Orn-a | Fmoc-D-Orn(Mtt)-OH | 198545-20-9 | Chem-Impex 03731 |
| X | D-Dys-a | Fmoc-D-Lys(Mtt)-OH | 198544-94-4 | Chem-Impex 03924 |
| Y | D-o-NHCH$_2$-Phe-s | Fmoc-2-(Boc-aminomethyl)-D-Phe-OH | 1217729-44-6 | Peptech FD553 |
| Z | D-m-NHCH$_2$-Phe-s | Fmoc-3-(Boc-aminomethyl)-D-Phe-OH | 1217665-54-7 | Peptech FD557 |
| UU | D-p-NHCH$_2$-Phe-s | Fmoc-4-(Boc-aminomethyl)-D-Phe-OH | 268731-06-2 | Peptech FD304 |
| VV | D-o-NHCH$_2$-Phe-a | Boc-2-(Fmoc-aminomethyl)-D-Phe-OH | 1212895-19-6 | Peptech BD551 |
| WW | D-m-NHCH$_2$-Phe-a | Boc-3-(Fmoc-aminomethyl)-D-Phe-OH | 1213080-68-2 | Peptech BD555 |
| XX | D-p-NHCH$_2$-Phe-a | Boc-4-(Fmoc-aminomethyl)-D-Phe-OH | 215302-77-5 | Peptech BD302 |
| YY | R,S-NH$_2$-Pro | (2R,4S)-Boc-4-amino-1-Fmoc-pyrrolidine-2-carboxylic acid | 1253791-18-2 | Chem-Impex 29664 |
| ZZ | R,R-NH$_2$-Pro | (2R,4R)-Boc-4-amino-1-Fmoc-pyrrolidine-2-carboxylic acid | 1253790-74-7 | Chem-Impex 29663 |

All primers were prepared on-beads from CCCTGTACAC (SEQ ID NO: 2) primer modified with 5' Amino Modifier 5 (Glen Research) synthesized on 1000 Å Ac-dC CPG beads.

Primers A, C, D, Q, S, T

4 µmol of CPG beads was detritylated on the DNA synthesizer, split between two 1.5 mL eppendorf tubes and each batch was washed with 0.6 mL of dry DMF. The corresponding amino acid (200 µmol), HBTU (68 mg, 180 µmol) and Oxyma Pure (29 mg, 200 µmol) were dissolved in 1.2 mL of dry DMF followed by the addition of 70 µL of DIPEA (400 µmol). The solution was split in two halves, which were added to the CPG beads. The reaction mixtures were agitated on a rotary for 3 h. The beads were washed with 3×0.6 mL of DMF and 2×0.6 mL of MeCN and moved into empty Expedite-type DNA synthesis columns for detritylation on a DNA synthesizer with 3% trichloroacetic acid in dichloromethane followed by washing with ample amounts of MeCN. Detritylation is slow, ample washing with TCA is needed; 4% TFA can be used instead; however, connectivity swapping verification should be conducted. The beads were split between two 1.5 mL eppendorf tubes and each batch was washed with 0.6 mL of dry DMF. Tartaramide S1 (65 mg, 200 µmol), HBTU (68 mg, 180 µmol) and Oxyma Pure (29 mg, 200 µmol) were dissolved in 1.2 mL of dry DMF followed by the addition of 70 µL of DIPEA (400 µmol), which led to the development of a dark-green color within few minutes. The solution was split in two halves which were added to the CPG beads. The reaction mixtures were agitated on a rotary for 3 h. Each batch of the beads was washed with 3×0.6 mL of DMF and 2×0.6 mL of MeCN followed by the addition of 400 µL of AMA solution. After heating to 65° C. for 15 min, the samples were concentrated for 30 min using a speedvac to remove ammonia/methylamine and were diluted with 300 µL of 0.1 M TEAA pH 7 buffer. The beads were filtered off using EMD Ultrafree-MC GV 0.22 µm filter units and the samples were purified by HPLC under conditions individual for each primer (see Table for conditions and retention times). Lyophilized HPLC fractions were redissolved in 500 µL of water and desalted with Nap-5 columns (GE Life Sciences, elution with 1 mL of water).

Primers G, H, W, X

4 µmol of CPG beads was detritylated on the DNA synthesizer, split between two 1.5 mL eppendorf tubes and each batch was washed with 0.6 mL of dry DMF. The corresponding amino acid (200 µmol), HBTU (68 mg, 180 µmol) and Oxyma Pure (29 mg, 200 µmol) were dissolved in 1.2 mL of dry DMF followed by the addition of 70 µL of DIPEA (400 µmol). The solution was split in two halves, which were added to the CPG beads. The reaction mixtures were agitated on a rotary for 3 h. Each batch of the beads was washed with 3×0.6 mL of DMF. Fmoc-protection was cleaved by 3×1 mL washes with 20% piperidine in DMF (5 min agitation on a rotary each time). Each batch was then washed with 2×0.6 mL of DMF and 2×0.6 mL of MeCN. Tartaramide S1 (65 mg, 200 µmol), HBTU (68 mg, 180 µmol) and Oxyma Pure (29 mg, 200 µmol) were dissolved in 1.2 mL of dry DMF followed by the addition of 70 µL of DIPEA (400 µmol), which led to the development of a dark-green color within few minutes. The solution was split in two halves, which were added to the CPG beads. The reaction mixtures were agitated on a rotary for 3 h. Each batch of the beads was washed with 3×0.6 mL of DMF and 2×0.6 mL of MeCN and then moved into empty Expedite-type DNA synthesis columns for detritylation on a DNA synthesizer with 3% trichloroacetic acid in dichloromethane followed by washing with ample amounts of MeCN. Each half of the beads was mixed with 400 µL of AMA solution. After heating to 65° C. for 15 min, the samples were concentrated for 30 min using a speedvac to remove ammonia/methylamine and were diluted with 300 µL of 0.1 M TEAA pH 7 buffer. The beads were filtered off using EMD Ultrafree-MC GV 0.22 µm filter units and the samples were purified by HPLC under conditions individual for each primer (see Table for conditions and retention times). Lyophilized HPLC fractions were redissolved in 500 µL of water and desalted with Nap-5 columns (GE Life Sciences, elution with 1 mL of water).

Primers E, U

Due to connectivity swapping issues (undesired partial conversion of α-functionalized products E and U into the corresponding isomers with side-chain tartaramide, primers A and Q), for primers E and U the trityl protection is kept throughout the synthesis. 4 μmol of CPG beads was detritylated on the DNA synthesizer, split between two 1.5 mL eppendorf tubes and each batch was washed with 0.6 mL of dry DMF. The corresponding amino acid (200 μmol), HBTU (68 mg, 180 μmol) and Oxyma Pure (29 mg, 200 μmol) were dissolved in 1.2 mL of dry DMF followed by the addition of 70 μL of DIPEA (400 μmol). The solution was split in two halves, which were added to the CPG beads. The reaction mixtures were agitated on a rotary for 3 h. Each batch of the beads was washed with 3×0.6 mL of DMF. Fmoc-protection was cleaved by 3×1 mL washes with 20% piperidine in DMF (5 min agitation on a rotary each time). Each batch was then washed with 2×0.6 mL of DMF and 2×0.6 mL of MeCN. Tartaramide S1 (65 mg, 200 μmol), HBTU (68 mg, 180 μmol) and Oxyma Pure (29 mg, 200 μmol) were dissolved in 1.2 mL of dry DMF followed by the addition of 70 μL of DIPEA (400 μmol), which led to the development of a dark-green color within few minutes. The solution was split in two halves which were added to the CPG beads. The reaction mixtures were agitated on a rotary for 3 h. Each batch of the beads was washed with 4×0.6 mL of DMF and 2×0.6 mL of MeCN. Each half of the beads was mixed with 400 μL of AMA solution. After heating to 65° C. for 15 min, the samples were concentrated for 30 min using a speedvac to remove ammonia/methylamine and were diluted with 300 μL of 0.1 M TEAA pH 7 buffer to bring the amount of the solvent to 500 μL. The beads were filtered off using EMD Ultrafree-MC GV 0.22 μm filter units and desalted (important!) with Nap-5 columns (GE Life Sciences) equilibrated in 0.1 M TEAA pH 7 (elution with 1 mL of 0.1 M TEAA pH 7). The resulting samples were combined and purified by HPLC (5-15% MeCN in 0.1 M TEAA pH 7 over 60 min, see Table 17 for retention times). Lyophilized fractions were redissolved in 500 μL of water and filtered using EMD Ultrafree-MC GV 0.22 μm filter units. 72 μL of 24% aqueous TFA was added; after 10 min, the reaction was carefully quenched with 72 μL of 28% ammonia and filtered again through a 0.22 μm frit. The filtrate was split between two Nap-5 columns, each column was equilibrated with 180 μL of water and the product was eluted with 0.7 mL of water. MS (ESI): Primer E, $C_{113}H_{150}N_{38}O_{67}P_{10}$ calc. 1709.8, found 1710.2. Primer U, $C_{113}H_{150}N_{38}O_{67}P_{10}$ calc. 1709.8, found 1710.1.

Primers B, F, R

5 μmol of CPG beads was detritylated on the DNA synthesizer, split between two 1.5 mL eppendorf tubes and each batch was washed with 0.6 mL of dry DMF. The corresponding amino acid (250 μmol), HBTU (85 mg, 225 μmol) and Oxyma Pure (35.5 mg, 250 μmol) were dissolved in 1 mL of dry DMF followed by the addition of 87 μL of DIPEA (500 μmol). The solution was split in two halves, which were added to the CPG beads. The reaction mixtures were agitated on a rotary for 3 h. Each batch of the beads was washed with 3×0.6 mL of DMF. Fmoc-protection was cleaved by washing with 3×1 mL of 20% piperidine in DMF (5 min agitation on a rotary each time). Each batch was then washed with 3×0.6 mL of DMF. Tartaramide S1 (81 mg, 250 μmol), HBTU (85 mg, 225 μmol) and Oxyma Pure (35.5 mg, 250 μmol) were dissolved in 1 mL of dry DMF followed by the addition of 87 μL of DIPEA (500 μmol), which led to the development of a dark-green color within few minutes. The solution was split in two halves, which were added to the CPG beads. The reaction mixtures were agitated on a rotary for 3 h. Each batch of the beads was washed with 3×0.6 mL of DMF and 2×0.6 mL of dichloromethane. Boc-protection was cleaved by washing with 500 μL of 50% TFA in dichloromethane (1 minute). Each batch was then washed with 1×0.6 mL of dichloromethane followed by the addition of 600 μL of AMA solution (small amounts of dichloromethane on the bottom of the tube were manually removed with a pipette). After heating to 65° C. for 15 min, the samples were concentrated for 30 min using a speedvac to remove ammonia/methylamine. The beads were washed with 0.1 M TEAA pH 7 buffer and filtered off using EMD Ultrafree-MC GV 0.22 μm filter units. The samples were purified by HPLC under conditions individualized for each primer (see Table 17 for conditions and retention times). Importantly, due to connectivity swapping, extra effort is needed in order to separate the isomeric product. Lyophilized HPLC fractions were redissolved in 500 μL of water and desalted with Nap-5 columns (GE Life Sciences, elution with 1 mL of water).

Primer V

The reaction was conducted using standard SPPS filter columns with vacuum suction. The oligonucleotide (20 μmol) was synthesized trityl-on; the CPG beads were detritylated with 3% trichloroacetic acid until the disappearance of the yellow color and washed with dry DMF. The beads were then transferred into two 5-mL eppendorf tubes. The corresponding amino acid (298 mg, 500 μmol), HBTU (171 mg, 450 μmol) and Oxyma Pure (71 mg, 500 μmol) were dissolved in 3 mL of dry DMF followed by the addition of 174 μL of DIPEA (1 mmol). The solution was split in two halves, which were added to the CPG beads. The reaction mixtures were agitated on a rotary for 3 h. Each half was then split between three 1.5 mL eppendorf tubes and each of six batches was washed with 3×0.6 mL of DMF. Fmoc-protection was cleaved by washing with 3×1 mL of 20% piperidine in DMF (5 min agitation on a rotary each time). The beads were combined in a filter column, washed with ample amount of DMF and split between two 5-mL eppendorf tubes. Tartaramide S1 (162 mg, 500 μmol), HBTU (171 mg, 450 μmol) and Oxyma Pure (71 mg, 500 μmol) were dissolved in 3 mL of dry DMF followed by the addition of 174 μL of DIPEA (1 mmol), which led to the development of dark-green color within few minutes. The solution was split in two halves which were added to the CPG beads. The reaction mixtures were agitated on a rotary for 2 h. The beads were combined in a filter column, and washed with DMF and MeCN and split between four 1.5 mL eppendorf tubes followed by the addition of 400 μL of AMA to each tube. After heating to 55° C. for 15 min, the samples were concentrated for 30 min using a speedvac to remove ammonia/methylamine and were diluted with 0.1 M TEAA pH 7 buffer to bring the amount of the solvent to 500 μL. The beads were filtered off using EMD Ultrafree-MC GV 0.22 μm filter units and desalted (important!) with Nap-5 columns (GE Life Sciences) equilibrated in 0.1 M TEAA pH 7 (elution with 1 mL of 0.1 M TEAA pH 7). The resulting samples were combined and purified by HPLC in 0.1 M TEAA pH 7/acetonitrile (0-3 min: 5% MeCN; 3-25 min: 5-40%; 25-25.5 min: 40-100%; 25.5-27 min: 100%; 27-27.1 min: 100-10%; 27.1-30 min: 10%). Fractions corresponding to the peak at 28.5 min were lyophilized, then resuspended in 500 μL of water. 72 μL of 24% TFA was added, the mixture was left for ~30 min and filtered using EMD Ultrafree-MC GV 0.22 μm filter units. The mixture was quenched with 72 μL of 28% aqueous ammonia, desalted on Nap-5 columns equilibrated in 0.1M TEAA pH 7 and purified by HPLC (9-11.5% MeCN in 0.1 M TEAA pH 7 over 35 min). The fractions corresponding to the peak at 30 min were lyophilized, the residue was dissolved in 500 μL of water and desalted using a Nap-5 column (elution with 1 mL of water).

Primers I, J, K, L, M, N, Y, Z, UU, VV, WW, XX

5 µmol of CPG beads was detritylated on the DNA synthesizer, split between two 1.5 mL eppendorf tubes and each batch was washed with 0.6 mL of dry DMF. The corresponding amino acid (250 µmol), HBTU (85 mg, 225 µmol) and Oxyma Pure (35.5 mg, 250 µmol) were dissolved in 1 mL of dry DMF followed by the addition of 87 µL of DIPEA (500 µmol). The solution was split in two halves which were added to the CPG beads. The reaction mixtures were agitated on a rotary for 3 h. Each batch of the beads was washed with 4×0.6 mL of DMF, 2×0.6 mL of MeCN and 0.6 mL of dichloromethane. Boc-protection was cleaved by washing with 500 µL of 50% TFA in dichloromethane (1 minute). Each batch was then washed with 2×0.6 mL of dichloromethane and 3×0.6 mL of DMF. Tartaramide S1 (81 mg, 250 µmol), HBTU (85 mg, 225 µmol) and Oxyma Pure (35.5 mg, 250 µmol) were dissolved in 1 mL of dry DMF followed by the addition of 87 µL of DIPEA (500 µmol), which led to the development of a dark-green color within few minutes. The solution was split in two halves, which were added to the CPG beads. The reaction mixtures were agitated on a rotary for 3 h. Each batch of the beads was washed with 4×0.6 mL of DMF and 2×0.6 mL of MeCN. The two batches were combined and mixed with 600 µL of AMA solution. After heating to 65° C. for 15 min, the samples were concentrated for 30 min using a speedvac to remove ammonia/methylamine and were diluted with 400 µL of 0.1 M TEAA pH 7 buffer. The beads were filtered off using EMD Ultrafree-MC GV 0.22 µm filter units and the samples were purified by HPLC under conditions individual for each primer (see Table for conditions and retention times). Lyophilized HPLC fractions were redissolved in 500 µL of water and desalted with Nap-5 columns (GE Life Sciences, elution with 1 mL of water).

Primers O, P, YY, ZZ

5 µmol of CPG beads was detritylated on the DNA synthesizer, split between two 1.5 mL eppendorf tubes and each batch was washed with 0.6 mL of dry DMF. The corresponding amino acid (250 µmol), HBTU (85 mg, 225 µmol) and Oxyma Pure (35.5 mg, 250 µmol) were dissolved in 1 mL of dry DMF followed by the addition of 87 µL of DIPEA (500 µmol). The solution was split in two halves, which were added to the CPG beads. The reaction mixtures were agitated on a rotary for 3 h. Each batch of the beads was washed with 3×0.6 mL of DMF. Fmoc-protection was cleaved by washing with 3×1 mL of 20% piperidine in DMF (5 min agitation on a rotary each time). Each batch was then washed with 3×0.6 mL of DMF. Tartaramide S1 (81 mg, 250 µmol), HBTU (85 mg, 225 µmol) and Oxyma Pure (35.5 mg, 250 µmol) were dissolved in 1 mL of dry DMF followed by the addition of 87 µL of DIPEA (500 µmol), which led to the development of a dark-green color within few minutes. The solution was split in two halves which were added to the CPG beads. The reaction mixtures were agitated on a rotary for 3 h. Each batch of the beads was washed with 3×0.6 mL of DMF and 2×0.6 mL of dichloromethane. Boc-protection was cleaved by washing with 500 µL of 50% TFA in dichloromethane (1 minute). Each batch was then washed with 1×0.6 mL of dichloromethane followed by the addition of 600 µL of AMA solution (small amount of dichloromethane on the bottom of the tube was manually removed with a pipette). After heating to 65° C. for 15 min, the samples were concentrated for 30 min using a speedvac to remove ammonia/methylamine. The beads were washed with 0.1 M TEAA pH 7 buffer and filtered off using EMD Ultrafree-MC GV 0.22 µm filter units. The samples were purified by HPLC, 5-11.5% MeCN in 0.1 M TEAA pH 7 over 35 min (see Table for retention times). Lyophilized HPLC fractions were redissolved in 500 µL of water and desalted with Nap-5 columns (elution with 1 mL of water). For better yields, it's recommended to conduct the second coupling at 40° C. (Eppendorf Thermomixer).

TABLE 14

Analytical data for chemically modified primers

| | ret. time | HPLC method$^a$ | yield | formula | calc. (z = 2) | found (z = 2) |
|---|---|---|---|---|---|---|
| A | 12 min | 0-3 min: 5%; 3-25 min: 5-40% | 12.4% | $C_{113} H_{150} N_{38} O_{67} P_{10}$ | 1709.3 | 1709.6 |
| B | 29.5 min | 0-35 min: 5-11.5% | 2.1% | $C_{114} H_{152} N_{38} O_{67} P_{10}$ | 1716.3 | 1716.6 |
| C | 12 min | 0-3 min: 5%; 3-25 min: 5-40% | 9.0% | $C_{115} H_{154} N_{38} O_{67} P_{10}$ | 1723.4 | 1723.6 |
| D | 21 min | 0-3 min: 5%; 3-40 min: 5-20% | 3.5% | $C_{116} H_{156} N_{38} O_{67} P_{10}$ | 1730.4 | 1730.6 |
| E* | 27.6 min | 0-60 min: 5-15% (pre-detr.) | 7.7% | $C_{133} H_{166} N_{38} O_{67} P_{10}$ | 1709.3 | 1709.6 |
| F | 31.0 min | 0-35 min: 5-11.5% | 2.4% | $C_{114} H_{152} N_{38} O_{67} P_{10}$ | 1716.3 | 1716.6 |
| G | 20 min | 0-3 min: 5%; 3-40 min: 5-20% | 9.1% | $C_{115} H_{154} N_{38} O_{67} P_{10}$ | 1723.4 | 1723.6 |
| H | 20 min | 0-3 min: 5%; 3-40 min: 5-20% | 10.5% | $C_{116} H_{156} N_{38} O_{67} P_{10}$ | 1730.4 | 1730.6 |
| I | 40 min | 0-42 min: 5-12% | 7.0% | $C_{120} H_{156} N_{38} O_{67} P_{10}$ | 1754.4 | 1754.6 |
| J | ~36 min | 0-42 min: 5-12% | 9.3% | $C_{120} H_{156} N_{38} O_{67} P_{10}$ | 1754.4 | 1754.6 |
| K | 34.5 min | 0-42 min: 5-12% | 6.8% | $C_{120} H_{156} N_{38} O_{67} P_{10}$ | 1754.4 | 1754.6 |
| L | 37 min | 0-42 min: 5-12% | 7.2% | $C_{120} H_{156} N_{38} O_{67} P_{10}$ | 1754.4 | 1754.6 |
| M | 35 min | 0-42 min: 5-12% | 7.5% | $C_{120} H_{156} N_{38} O_{67} P_{10}$ | 1754.4 | 1754.6 |
| N | 33 min | 0-42 min: 5-12% | 7.7% | $C_{120} H_{156} N_{38} O_{67} P_{10}$ | 1754.4 | 1754.7 |

TABLE 14-continued

Analytical data for chemically modified primers

| | ret. time | HPLC method[a] | yield | formula | calc. (z = 2) | found (z = 2) |
|---|---|---|---|---|---|---|
| O | 27.0 min | 0-35 min: 5-11.5% | 0.5% | $C_{115}H_{152}N_{38}O_{67}P_{10}$ | 1722.3 | 1722.6 |
| P | 29.0 min | 0-35 min: 5-11.5% | 1.6% | $C_{115}H_{152}N_{38}O_{67}P_{10}$ | 1722.3 | 1722.6 |
| Q | 19.5 min | 0-3 min: 5%; 3-60 min: 5-30% | 9.6% | $C_{113}H_{150}N_{38}O_{67}P10$ | 1709.3 | 1709.6 |
| R | 20.8 min | 0-3 min: 5%; 3-40 min: 5-20% | 3.0% | $C_{114}H_{152}N_{38}O_{67}P_{10}$ | 1716.3 | 1716.6 |
| S | 20 min | 0-3 min: 5%; 3-40 min: 5-20% | 9.5% | $C_{115}H_{154}N_{38}O_{67}P_{10}$ | 1723.4 | 1723.6 |
| T | 21 min | 0-3 min: 5%; 3-40 min: 5-20% | 10.9% | $C_{116}H_{156}N_{38}O_{67}P_{10}$ | 1730.4 | 1730.6 |
| U* | 28.4 min | 0-60 min: 5-15% (pre-detr.) | 6.6% | $C_{133}H_{166}N_{38}O_{67}P_{10}$ | 1709.3 | 1709.6 |
| V | 30 min | 0-35 min: 5-11.5% | 0.1% | $C_{114}H_{152}N_{38}O_{67}P_{10}$ | 1716.3 | 1716.6 |
| W | 20 min | 0-3 min: 5%; 3-40 min: 5-20% | 5.8% | $C_{115}H_{154}N_{38}O_{67}P_{10}$ | 1723.4 | 1723.6 |
| X | 20 min | 0-3 min: 5%; 3-40 min: 5-20% | 6.8% | $C_{116}H_{156}N_{38}O_{67}P_{10}$ | 1730.4 | 1730.6 |
| Y | 38 min | 0-42 min: 5-12% | 8.2% | $C_{120}H_{156}N_{38}O_{67}P_{10}$ | 1754.4 | 1754.6 |
| Z | 36 min | 0-42 min: 5-12% | 8.3% | $C_{120}H_{156}N_{38}O_{67}P_{10}$ | 1754.4 | 1754.7 |
| UU | 34 min | 0-42 min: 5-12% | 8.0% | $C_{120}H_{156}N_{38}O_{67}P_{10}$ | 1754.4 | 1754.6 |
| VV | 36.5 min | 0-42 min: 5-12% | 3.5% | $C_{120}H_{156}N_{38}O_{67}P_{10}$ | 1754.4 | 1754.6 |
| WW | 33.5 min | 0-42 min: 5-12% | 3.9% | $C_{120}H_{156}N_{38}O_{67}P_{10}$ | 1754.4 | 1754.6 |
| XX | 32.5 min | 0-42 min: 5-12% | 3.8% | $C_{120}H_{156}N_{38}O_{67}P_{10}$ | 1754.4 | 1754.6 |
| YY | 29.8 min | 0-35 min: 5-11.5% | 0.6% | $C_{115}H_{152}N_{38}O_{67}P_{10}$ | 1722.3 | 1722.6 |
| ZZ | 27.9 min | 0-35 min: 5-11.5% | 0.6% | $C_{115}H_{152}N_{38}O_{67}P_{10}$ | 1722.3 | 1722.6 |

[a]Acetonitrile percentage in 0.1M TEAA pH 7. Concentration ranges correspond to linear gradient.

TABLE 15

HPLC conditions for connectivity swapping verification of chemically modified primers

| primer pairs | HPLC conditions for 200 pmol[a] |
|---|---|
| 4A/4E, 4Q/4U | 0-45 mm: 9-12.5% |
| 4B/4F, 4R/4V | 0-35 mm: 5-11.5% |
| 4C/4G, 4S/4W | 0-30 mm: 9-11% |
| 4D/4H, 4T/4X | 0-30 mm: 9-11% |
| 4I/4L, 4Y/4VV | 0-40 mm: 9-12% |
| 4J/4M, 4Z/4WW | 0-30 mm: 9-11% |
| 4K/4N, 4UU/4XX | 0-30 mm: 9-11% |

[a]Acetonitrile percentage in 0.1 M TEAA pH 7. Concentration ranges correspond to linear gradient.

Assembly and Analysis of the Template Library
Assembly of 8,000-Membered $I_4$ Library Typical procedure of preparative split ligation. (See FIG. 5A). Desalted aqueous solutions (858 μL overall) of the Left Fragment (5' chemically modified, 21-mer, 100 nmol), the Right Fragment (5' chemically phosphorylated, 34-mer, 100 nmol) and the splint (22-mer, 100 nmol) were mixed together and heated to 55° C. for 10 min, then left at ambient temperature for 15 min. 2×T3 DNA ligase buffer (875 μL) was added followed by the addition of T3 DNA ligase (16.6 μL, NEB M0317S, 3,000,000 units/mL, 50,000 units). The mixture was left at room temperature in the absence of light for 90 hours and then split between five 2 mL eppendorf tubes. 35 μL of 3M NaOAc pH 5.2 solution was added to each tube followed by 1.05 mL of freezer-cold ethanol. After cooling at −20° C. for 1.5 hours, the tubes were centrifuged at 4° C. at 20,000 rcf for 45 min. The pellets were washed with 400 μL of 70% aqueous ethanol (centrifugation at 4° C. at 20,000 rcf for 30 min), dried in vacuo for 30 min and dissolved in 400 μL overall amount of water. 30-40% yields.

Large-scale preparative splint ligation. (FIG. 20), diluted twofold compared to the standard protocol). Desalted aqueous solutions (42 mL overall) of the Left Fragments (30-mer, 2 μmol combined), the Right Fragments (5' chemically phosphorylated, 25-mer, 2 μmol combined) and the splint (25-mer, 2 μmol combined) were mixed together and split between two 50 mL conical tubes. The solutions were heated to 55° C. for 30 min in a microhybridization incubator, then left to cool to ambient temperature over the course of several hours. 19 mL of 2×T3 DNA ligase buffer and 333 μL of T3 DNA ligase (2×standard amount) were added to each conical. The mixtures were left at room temperature in the absence of light for 5 days, after which they were split between eight 50 mL conicals (~9.5 mL each). 1 mL of 3 M NaOAc pH 5.2 solution was added to each tube followed by 30 mL of freezer-cold ethanol. After cooling at −20° C. for 1 hour, the tubes were centrifuged at 4° C. at 4,500 rcf for 30 min. Each pellet was washed with 15 mL of 70% aqueous ethanol and dried in vacuo. The pellets were dissolved in 4.5 mL overall amount of water, mixed with 4.5 mL of formamide containing GelPilot dye and purified using 30 TBE-Urea gels (5%, 200V, 0.5×TBE buffer, 55° C.). The samples were heated to 95° C. with rapid cooling on ice before loading on the gel. The gels were run for ~20 min until the bromophenol blue band reached the end of the gel. The upper bands were cut out, combined in two 50-mL conicals, centrifuged down at 4,400 rcf and subject to three dry ice freeze/thaw cycles. 20 mL of 1×TE buffer pH 7.5 was added to each conical, the mixtures were agitated on a rotary in the absence of light at room temperature for 3 days, after which they were spinned at 4,400 rcf, the supernatants were isolated and filtered using 0.22 µm sterile-filtration devices (VWR, Corning 430320 or 430314). The combined filtrates were desalted with 14 Nap-25 columns (GE Life Sciences, 2.5-mL loadings, 3.5-mL elutions). 49 mL of ~14.8 µM solution was obtained (~725 nmol, 36% yield).

Split-pool oligonucleotide synthesis. After the synthesis of the initial fragment, CPG beads in each Expedite-type column were moved towards one of the two frits by vacuum suction. The columns were cut with a razor blade on the other end and placed into 1.5-mL eppendorf tubes. After centrifugation, all the beads were quantitatively transferred with acetonitrile to a 50-mL conical, and the suspension of the beads in acetonitrile was mixed on a rotary for 30 min. The beads were then manually split between 200-µL PCR wells so that the bead level was as even as possible across all the wells. Each well was then loaded into an empty Expedite-type column with excess amount of acetonitrile/vacuum suction. The resulting columns were subject to the next step of oligonucleotide synthesis. This procedure enables highly consistent results for independently conducted split-pool campaigns. The $I_4$ library for the preparation of the DTS macrocycle library was synthesized via a 4-step split-pool process starting from 22 columns of 1 µmol Ac-dC CPG.

Different Enzymatic Methods for Template Library Assembly

For each of the methods, Cy3-labeled primers can be used, which enable unambiguous band identification after PAGE purifications. In PCR amplifications of $I_4$ library isolated yields of PAGE-purified amplicons above 3-6% could not be achieved even at a very high concentration of primers (5 µM). To address this challenge, we optimized a stoichiometric variant of the assembly scheme based on primer extensions without PCR amplification (FIG. 5C, 23B), which was used for the preparation of the second-generation DTS library of macrocycles. A further improved scheme for the library assembly was also proposed (FIG. 5C, 23C). Instead of primer extension of the amplifiable light strand, direct split-pool oligonucleotide synthesis of the complimentary heavy strand was considered, which would undergo primer extension to yield the desired library of templates. In the classical approach, the proximity of the scaffold codon to the 3' end required a separate split-pool campaign for each scaffold, which implied working with hundreds of oligonucleotide synthesis columns (FIGS. 5A, 5B). On the contrary, convenient location of the scaffold anticodon near 5' end of the heavy strand enables starting with merely 12 or 20 synthesis columns which are split into the number of scaffolds (8 or 32) at the very end of the split-pool campaign. Importantly, whereas precious chemically modified components previously had to be ligated with the split-pool material of unknown quality (FIGS. 5A, 5B), the novel protocol enables HTS analysis of the heavy strand prior to primer extension steps, which eliminates the problems associated with reliability of oligonucleotide synthesis.

Since the PCR method (FIG. 23A) was developed first, the poly-A-tagged primers used for the macrocycle library preparation were synthesized with a Cy3 label for better identification of the amplicon strand. The primers were synthesized and cleaved of CPG beads via standard procedures and were purified on Glen-Pak cartridges (Glen Research).

TABLE 16

Analytical data of Cy3-labeled poly-A-tagged primers

| | Sequence | SEQ ID NO: | formula | calc. (z = 5) | found (z = 5) |
|---|---|---|---|---|---|
| A | $(A)_6$-Cy3-$(A)_{25}$-sp18-GAGTGGGATGTGGATAG | 21864 | C511H630N225O263P48 | 3121.2 | 3121.2 |
| B | $(A)_6$-Cy3-$(A)_{25}$-sp18-GAGTGGGATGCAACTAG | 21865 | C509H629N224O261P48 | 3107.0 | 3107.0 |
| C | $(A)_6$-Cy3-$(A)_{25}$-sp18-GAGTGGGATGTTAATAG | 21866 | C511H631N222O263P48 | 3113.0 | 3113.0 |
| D | $(A)_6$-Cy3-$(A)_{25}$-sp18-GAGTGGGATGACAATAG | 21867 | C510H629N226O260P48 | 3111.8 | 3111.9 |
| E | $(A)_6$-Cy3-$(A)_{25}$-sp18-GAGTGGGATGTGAGTAG | 21868 | C511H630N225O263P48 | 3121.2 | 3121.2 |
| F | $(A)_6$-Cy3-$(A)_{25}$-sp18-GAGTGGGATGTTCCTAG | 21869 | C509H631N218O265P48 | 3103.4 | 3103.6 |
| G | $(A)_6$-Cy3-$(A)_{25}$-sp18-GAGTGGGATGTATATAG | 21870 | C511H631N222O263P48 | 3113.0 | 3113.1 |
| H | $(A)_6$-Cy3-$(A)_{25}$-sp18-GAGTGGGATGAAATTAG | 21871 | C511H630N225O261P48 | 3114.8 | 3114.9 |
| I | $(A)_6$-Cy3-$(A)_{25}$-sp18-GAGTGGGATGCTACTAG | 21872 | C509H630N221O263P48 | 3105.2 | 3105.4 |
| J | $(A)_6$-Cy3-$(A)_{25}$-sp18-GAGTGGGATGTCTATAG | 21873 | C510H631N220O264P48 | 3108.2 | 3108.4 |

TABLE 16-continued

Analytical data of Cy3-labeled poly-A-tagged primers

| | Sequence | SEQ ID NO: | formula | calc. (z = 5) | found (z = 5) |
|---|---|---|---|---|---|
| K | $(A)_6$-Cy3-$(A)_{25}$-sp18-GAGTGGGATGAAACTAG | 21874 | $C_{510}H_{629}N_{226}O_{260}P_{48}$ | 3111.8 | 3112.0 |
| L | $(A)_6$-Cy3-$(A)_{25}$-sp18-GAGTGGGATGAAAATAG | 21875 | $C_{511}H_{629}N_{228}O_{259}P_{48}$ | 3116.6 | 3116.7 |
| M | $(A)_6$-Cy3-$(A)_{25}$-sp18-GAGTGGGATGCAAATAG | 21876 | $C_{510}H_{629}N_{226}O_{260}P_{48}$ | 3111.8 | 3112.0 |
| N | $(A)_6$-Cy3-$(A)_{25}$-sp18-GAGTGGGATGACCTTAG | 21877 | $C_{509}H_{630}N_{221}O_{263}P_{48}$ | 3105.2 | 3105.3 |
| O | $(A)_6$-Cy3-$(A)_{25}$-sp18-GAGTGGGATGTCCTTAG | 21878 | $C_{509}H_{631}N_{218}O_{265}P_{48}$ | 3103.4 | 3103.6 |
| P | $(A)_6$-Cy3-$(A)_{25}$-sp18-GAGTGGGATGTTACTAG | 21879 | $C_{510}H_{631}N_{220}O_{264}P_{48}$ | 3108.2 | 3108.3 |
| Q | $(A)_6$-Cy3-$(A)_{25}$-sp18-GAGTGGGATGTAATTAG | 21880 | $C_{511}H_{631}N_{222}O_{263}P_{48}$ | 3113.0 | 3113.3 |
| R | $(A)_6$-Cy3-$(A)_{25}$-sp18-GAGTGGGATGTAACTAG | 21881 | $C_{510}H_{630}N_{223}O_{262}P_{48}$ | 3110.0 | 3110.0 |
| S | $(A)_6$-Cy3-$(A)_{25}$-sp18-GAGTGGGATGAATCTAG | 21882 | $C_{510}H_{630}N_{223}O_{262}P_{48}$ | 3110.0 | 3110.0 |
| T | $(A)_6$-Cy3-$(A)_{25}$-sp18-GAGTGGGATGCTATTAG | 21883 | $C_{510}H_{631}N_{220}O_{264}P_{48}$ | 3108.2 | 3108.3 |
| U | $(A)_6$-Cy3-$(A)_{25}$-sp18-GAGTGGGATGTGATTAG | 21884 | $C_{511}H_{631}N_{222}O_{264}P_{48}$ | 3116.2 | 3116.4 |
| V | $(A)_6$-Cy3-$(A)_{25}$-sp18-GAGTGGGATGTTTTTAG | 21885 | $C_{511}H_{633}N_{216}O_{267}P_{48}$ | 3109.4 | 3109.6 |
| W | $(A)_6$-Cy3-$(A)_{25}$-sp18-GAGTGGGATGCTTTTAG | 21886 | $C_{510}H_{632}N_{217}O_{266}P_{48}$ | 3106.4 | 3106.6 |
| X | $(A)_6$-Cy3-$(A)_{25}$-sp18-GAGTGGGATGAATTTAG | 21887 | $C_{511}H_{631}N_{222}O_{263}P_{48}$ | 3113.0 | 3113.0 |
| Y | $(A)_6$-Cy3-$(A)_{25}$-sp18-GAGTGGGATGTATCTAG | 21888 | $C_{510}H_{631}N_{220}O_{264}P_{48}$ | 3108.2 | 3108.3 |
| Z | $(A)_6$-Cy3-$(A)_{25}$-sp18-GAGTGGGATGAACCTAG | 21889 | $C_{509}H_{629}N_{224}O_{261}P_{48}$ | 3107.0 | 3107.2 |
| UU | $(A)_6$-Cy3-$(A)_{25}$-sp18-GAGTGGGATGTCACTAG | 21890 | $C_{509}H_{630}N_{221}O_{263}P_{48}$ | 3105.2 | 3105.3 |
| VV | $(A)_6$-Cy3-$(A)_{25}$-sp18-GAGTGGGATGCACATAG | 21891 | $C_{509}H_{629}N_{224}O_{261}P_{48}$ | 3107.0 | 3107.0 |
| WW | $(A)_6$-Cy3-$(A)_{25}$-sp18-GAGTGGGATGCATTTAG | 21892 | $C_{510}H_{631}N_{220}O_{264}P_{48}$ | 3108.2 | 3108.4 |
| XX | $(A)_6$-Cy3-$(A)_{25}$-sp18-GAGTGGGATGACTTTAG | 21893 | $C_{510}H_{631}N_{220}O_{264}P_{48}$ | 3108.2 | 3108.3 |
| YY | $(A)_6$-Cy3-$(A)_{25}$-sp18-GAGTGGGATGTATTTAG | 21894 | $C_{511}H_{632}N_{219}O_{265}P_{48}$ | 3111.2 | 3111.2 |
| ZZ | $(A)_6$-Cy3-$(A)_{25}$-sp18-GAGTGGGATGTCTTTAG | 21895 | $C_{510}H_{632}N_{217}O_{266}P_{48}$ | 3106.4 | 3106.6 |

Cy3 = cyanine 3 (Glen Research);
sp18 = spacer-18 (Glen Research)

TABLE 17

Figure 23A:
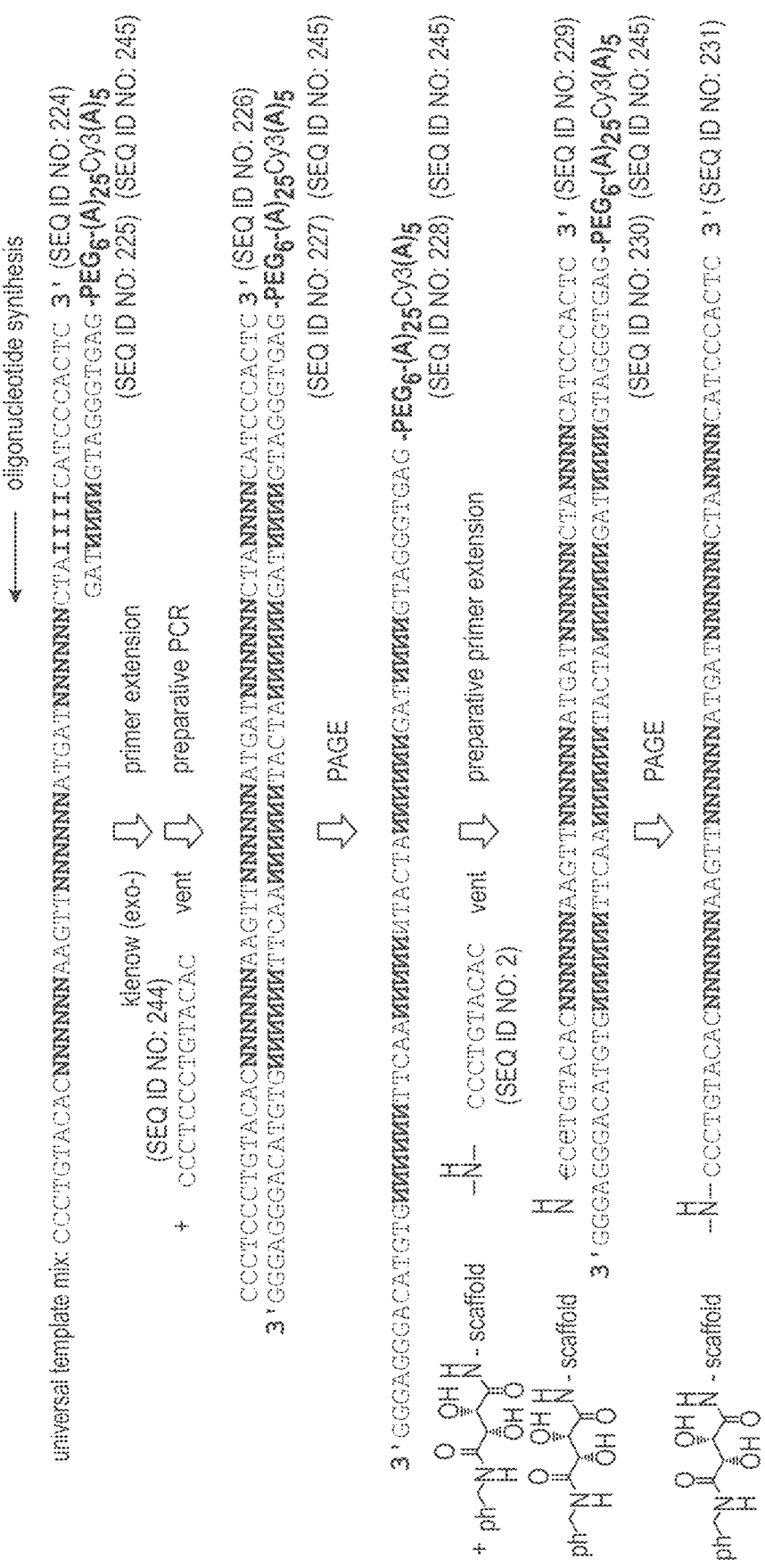
Figure 24:
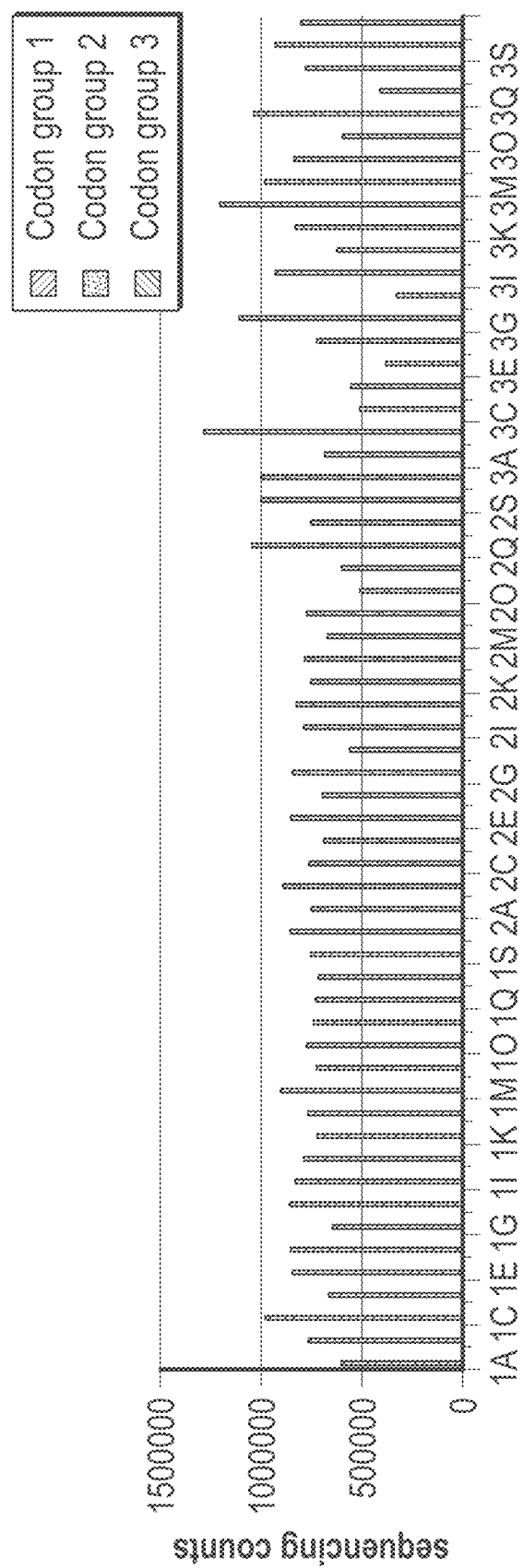
FIG. 24. Codon distribution of the template library.
Figure 25:
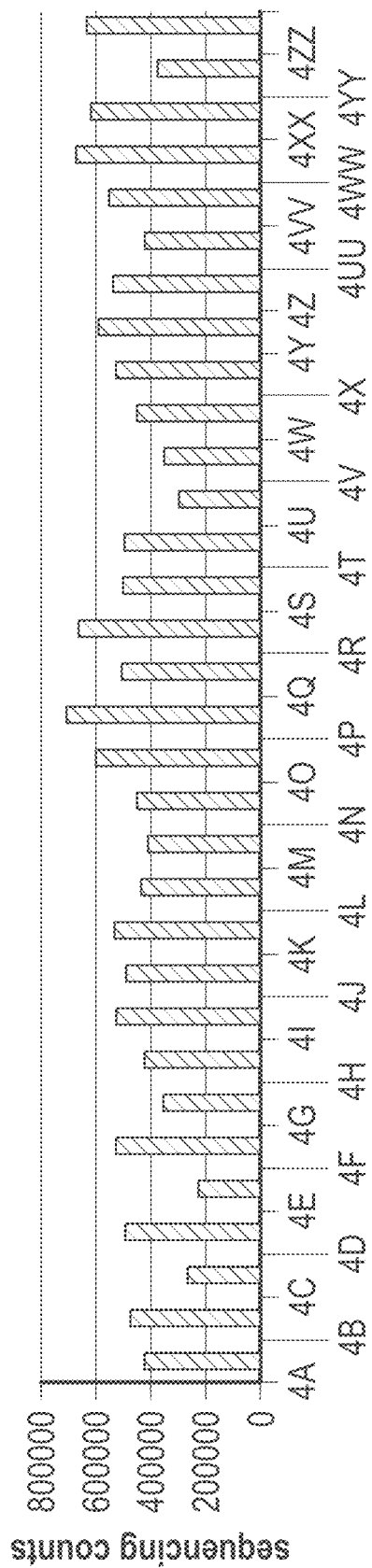
FIG. 25. Scaffold distributions of the template library.

Reaction compositions for the preparative PCR route towards the heavy strand of the template library (see FIGs. 23A to 23C, method A)

|  | [Stock] μM | [Final] μM | volume (μl) |
|---|---|---|---|
| polyA primer | 100 | 2 | 4.0 |
| dNTPs | 1000 | 1.33 | 6.65 |
| Water |  |  | 161.35 |
| 10× NEB buffer 2 | 10× | 1× | 20.0 |
| Klenow exo- 5000 U/mL | 5 U/μL | 0.1 U/μL | 4.0 |
| Template | 2.5 | 0.05 | 4.0 |
| Total |  |  | 200.00 |
| Thermopol buffer 10× | 10× | 1× | 480 |
| dNTPs | 10000 | 200 | 96 |
| Forward primer | 100 | 5 | 240 |
| Reverse primer | 100 | 5 | 240 |
| Water |  |  | 3504 |
| Vent 2000 U/mL | 2 U/μL | 0.02 U/μL | 48 |
| Template (from Klenow extension) | 0.05 | 0.002 | 192 |
| Total |  |  | 4800 |

Preparative PCR amplification

Water, I4 template, Cy3-labeled poly-A-tagged primer (for better identification of the amplicon band on a polyacrylamide gel), dNTPs and 10×NEB buffer 2 were mixed with Klenow(exo-) enzyme (New England Biolabs, M0212L, 5000 u/mL), the reaction mixture was split between PCR tube wells, heated at 37° C. for 30 min and at 75° C. for 20 min (for enzyme inactivation). The resulting solution was used as a template source for the mastermix for Vent-amplification, which was prepared at 0° C. The thermocycler was pre-heated to 95° C. prior to loading of the PCR tubes. After 18 cycles (determined by qPCR, end of exponential amplification phase), the reaction mixture was combined with 500 μL of 3 M NaOAc pH 5.3 buffer and split between two 50-mL conical tubes. 15 mL of saturated guanidinium chloride solution and 22.5 mL of isopropanol were added to each conical, and each mixture was passed through a separate Omega HiBind Midi spin column (maximum capacities of the columns were almost reached). Each column was washed with 3 mL of DNA wash buffer (Omega), centrifuged at 3,200 rcf for 10 min, hydrated with 1 mL of water for 10 min and eluted by centrifugation at 3,200 rcf for 10 min. The resulting combined solution (1.7 mL) was split evenly between four Amicon Ultra 0.5 mL 10K, UFC501096 regenerated cellulose filter units and centrifuged at 14,000 ref for 2 min. The resulting concentrated solution (560 μL) was combined with 520 μL of formamide containing GelPilot dye (Qiagen) and loaded on two 5% TBE-Urea gels, 30 μL/well without heating denaturation (which would be conducted in a library format). The gels were run at 200V at room temperature (55° C. would be needed for the library format to separate the bands) until the primer band, which runs almost synchronously with bromophenol blue, was at the very bottom of the gel. Faint pink bands of the amplicon between the bromophenol blue and xylene cyanol were cut out, split between eight 2-mL eppendorf tubes, gently crushed and subject to three dry ice freeze/thaw cycles prior to addition of 0.4 mL of 1×TE buffer pH 7.5 to each tube. After overnight extraction on a rotary at 4° C., the maximum possible volume of the solution was separated from the gel, filtered through EMD Ultrafree-MC GV 0.22 μm filter unit, mixed with 40 μL of 3M NaOAc pH 5.2 buffer and 1.2 mL of freezer-cold ethanol. After 1 h at −20° C., the tubes were centrifuged at 20,000 rcf at 4° C. for 40 min, the pellets were dried in vacuo for 0.5 h, dissolved in the overall amount of 200 μL of water and desalted on a Nap-5 column (GE Life Sciences). 792 pmol of the double-stranded amplicon was obtained, 3.3% yield.

Preparative Primer Extension with Klenow(Exo-) Polymerase

TABLE 18

Reaction composition for the first primer extension step of the template library assembly

|  | [Stock] μM | [Final] μM | volume (μl) |
|---|---|---|---|
| polyA primer | 100 | 2.5 | 500 |
| dNTPs | 10000 | 200 | 400 |
| Water |  |  | 16667 |
| 10× NEB buffer 2 | 10× | 1× | 2000 |
| Klenow exo- 5000 U/mL | 5 U/μL | 0.025 U/μL | 100 |
| Template | 150 | 2.5 | 333 |
| Total |  |  | 20000 |

For 50 nmol reactions: Water, the template, the primer, dNTPs and 10×NEB buffer 2 were mixed in a 50-mL conical tube and were left at 37° C. for 1 h. Klenow(exo-) enzyme (New England Biolabs, 5000 u/mL) was added, and the reaction was left at 37° C. for 2 days. The reaction was split between two 50-mL conical tubes. Each solution was mixed with 1 mL of 3 M NaOAc pH 5.2 buffer followed by 30 mL of freezer-cold absolute ethanol. The mixture was left at −20° C. for 6 hours. The tubes were spun at 15,000 g for 30 minutes, the supernatant was discarded and the pellets were dried in vacuo for a few hours. Each pellet was dissolved in 500 μL of water, the resulting solutions were desalted with a Nap-5 column (GE Life Sciences, elution with 1 mL of water). Combined solutions were concentrated to 540 μL using 10K Amicon Ultra 0.5 mL regenerated cellulose filter units. 540 μL of formamide containing GelPilot dye (Qiagen) was added. The mixture was moved into PCR strips (60 μl per well), heated to 95° C. for 3 minutes and then rapidly cooled on ice for 20-30 seconds. The samples were quickly loaded on the gel using Integra Viaflo electronic pipette to minimize cooling of the gel. Purification was conducted on two 10% TBE-Urea gels at 55° C. (the gel was pre-equilibrated at 55° C. for 30 minutes before loading the sample; 0.5x TBE, 200V, run until xylene cyanol band was right at the bottom, ~55 min). The product band of each of the two gels was cut out, split between three 2-mL tubes, manually crushed and subject to three dry ice freeze/thaw cycles. 1 mL of 10 mM Tris pH 8 buffer was added to each tube, followed by rotation at room temperature in the absence of light for 24 hours. The gel was centrifuged down, as much supernatant as possible was manually separated. The gels were washed with 0.5 mL of 10 mM Tris pH 8 buffer. Combined supernatants were centrifuged down, the clear supernatant was separated, the gel-containing residue was filtered through EMD Ultrafree-MC GV 0.22 μm filter units. The resulting solution (~8 mL) was moved to a 50 mL conical tube, followed by the addition of 800 μL of 3 M NaOAc pH 5.2 buffer and 24 mL of freezer-cold absolute ethanol. The mixture was left at −20° C. overnight and centrifuged at 15,000 g for 30 minutes. The supernatant was discarded and the pellet was dried in vacuo for a few hours. The product was dissolved in 500 μL of water and desalted with a Nap-5 column (GE Life Sciences, elution with 1 mL of water). Concentrations were determined based on UV absorption at 260 nm (calculated as equimolar mixtures of 8,000 oligonucleotides). The purity of the products was confirmed by analytical PAGE analysis (10% TBE-Urea gel).

TABLE 19

Yields of heavy strands of template sublibraries, Klenow(exo-) primer extension.

|  | nmol | % |
| --- | --- | --- |
| 4A | 23.9 | 48% |
| 4B | 21.2 | 42% |
| 4C | 25.2 | 50% |
| 4D | 23.4 | 47% |
| 4E | 18.2 | 36% |
| 4F | 25.4 | 51% |
| 4G | 21.9 | 44% |
| 4H | 22.2 | 44% |
| 4I | 21.7 | 43% |
| 4J | 25.8 | 52% |
| 4K | 21.4 | 43% |
| 4L | 21.6 | 43% |
| 4M | 22.5 | 45% |
| 4N | 23.4 | 47% |
| 4O | 23.5 | 47% |
| 4P | 22.2 | 44% |
| 4Q | 23.1 | 46% |
| 4R | 22.5 | 45% |
| 4S | 20.0 | 40% |
| 4T | 20.5 | 41% |
| 4U | 21.1 | 42% |
| 4V | 17.5 | 35% |
| 4W | 21.6 | 43% |
| 4X | 19.4 | 39% |
| 4Y | 20.7 | 41% |
| 4Z | 21.8 | 44% |
| 4UU | 22.3 | 45% |
| 4VV | 18.1 | 36% |
| 4WW | 22.3 | 45% |
| 4XX | 20.9 | 42% |
| 4YY | 19.6 | 39% |
| 4ZZ | 20.1 | 40% |

Preparative Primer Extension with Vent Polymerase

TABLE 20

Reaction composition for the second primer extension step of the template library assembly

|  | [Stock] μM | [Final] μM | volume (μl) |
| --- | --- | --- | --- |
| Thermopol buffer 10× | 10× | 1× | 240 |
| dNTPs | 10000 | 1000 | 240 |
| Modified primer | varied | varied | varied, 1.2 eq. |
| Water |  |  | 824-(primer) |
| Vent 2000 U/mL | 2 U/μL | 0.08 U/μL | 96 |
| Template | varied | varied | 1000 |
| Total |  |  | 2400 |

Klenow-extended product (1 mL, see above) was directly used for the next step. 1.2 equivalents of the chemically-modified primers were used. All the components except the enzyme were mixed in a 5-mL tube and the solution was heated to 46° C. for 30 min (Southwest Science SH1002 digital dry bath). After the addition of the enzyme, the reaction mixture was left at 46° C. for 24 hours and was then moved to a 50-mL conical tube containing 250 μL of 3M NaOAc pH 5.2 buffer. After the addition of 7.5 mL of freezer-cold absolute ethanol the mixture was left at −20° C. for 3 h and centrifuged at 15,000 g for 30 min. The supernatant was discarded and the pellet was dried in vacuo. The product was dissolved in 500 μL of water and desalted using a Nap-5 column (GE Life Sciences, elution with 1 mL of water). The eluate was concentrated to 450 μL using 10K Amicon Ultra 0.5 mL regenerated cellulose filter units. 450 μL of formamide containing GelPilot dye (Qiagen) was added. The mixture was moved into PCR strips (50 μl per well), heated to 95° C. for 3 minutes and then rapidly cooled on ice for 20-30 seconds. The samples were quickly loaded on the gel using Integra Viaflo electronic pipette to minimize cooling of the gel. Purification was conducted on two 10% TBE-Urea gels at 55° C. (the gel was pre-equilibrated at 55° C. for 30 minutes before loading the sample; 0.5×TBE, 200V, run until xylene cyanol band was ~1 cm away from the bottom of the gel, ~45 min). The product band of each of the two gels was cut out, split between three 2-mL tubes, manually crushed and subject to three dry ice freeze/thaw cycles. 1 mL of 10 mM Tris pH 8 buffer was added to each tube, followed by rotation at room temperature in the absence of light for 24 hours. The gel was centrifuged down and as much supernatant as possible was manually separated. The gels were washed with 0.5 mL of 10 mM Tris pH 8 buffer. Combined supernatants were centrifuged down, the clear supernatant was separated, the gel-containing residue was filtered through EMD Ultrafree-MC GV 0.22 μm filter units. The resulting solution (~9 mL) was split between two 50 mL conical tubes. 45 mL of Buffer UM (vide supra) was added to each conical and each of the resulting solutions was passed through a HiBind DNA Midi column (Omega Bio-tek). The columns were washed with 3×1 mL of Omega DNA Wash buffer (or Buffer PE, or 4:1 mixture of ethanol with 10 mM Tris-HCl pH 7.5) and centrifuged at 3,000 g for 10 minutes. After hydration with 1 mL of water for 10 min, the columns were centrifuged again at 3,000 g for 10 minutes. Combined eluates (1.7 mL) were mixed with 17 μL of 1M Tris pH 8 and stored at −20° C. Concentrations were determined based on UV absorption at 260 nm (calculated as equimolar mixtures of 8,000 oligonucleotides). The purity of the products was confirmed by analytical PAGE analysis (10% TBE-Urea gel).

TABLE 21

Yields of the template sublibraries, Vent primer extension.

|  | nmol | % |
| --- | --- | --- |
| 4A | 6.8 | 29% |
| 4B | 7.3 | 34% |
| 4C | 4.7 | 19% |
| 4D | 6.0 | 26% |
| 4E | 3.2 | 18% |
| 4F | 8.4 | 33% |
| 4G | 5.5 | 25% |
| 4H | 7.5 | 34% |
| 4I | 6.8 | 31% |
| 4J | 7.0 | 27% |
| 4K | 7.7 | 36% |
| 4L | 7.1 | 33% |
| 4M | 6.4 | 29% |
| 4N | 10.1 | 43% |
| 4O | 10.0 | 43% |
| 4P | 9.8 | 44% |
| 4Q | 8.2 | 35% |
| 4R | 8.5 | 38% |
| 4S | 8.8 | 44% |
| 4T | 8.7 | 42% |
| 4U | 4.8 | 23% |
| 4V | 5.7 | 32% |
| 4W | 8.3 | 38% |
| 4X | 9.0 | 46% |
| 4Y | 8.4 | 40% |
| 4Z | 10.6 | 48% |
| 4UU | 7.6 | 34% |
| 4VV | 9.6 | 53% |
| 4WW | 10.7 | 48% |
| 4XX | 10.4 | 50% |
| 4YY | 6.7 | 34% |
| 4ZZ | 9.7 | 48% |

DTS Library Assembly and Analysis
Library Assembly

All reagents were used in the amounts proportional to the relative ratios of the corresponding codons obtained from high-throughput sequencing data.

It was found that instead of using buffer UM (4:6 saturated aqueous guanidinium chloride-isopropanol, 10 volumes), isolation of DNA from the $3^{rd}$ step DTS reaction mixture on silica membranes (spin columns) is possible after simple dilution of the reaction mixture with isopropanol in 1:1 ratio. The observed recovery exceeded 95%, yet the remaining 5% could be isolated from the filtrate using buffer UM. Dilution of DTS reaction media with isopropanol can therefore be considered as a simpler alternative to buffer UM. For the DTS library preparation, this protocol was applied only to the more sensitive step 3; one can choose to use either buffer UM or isopropanol dilution after each of the three DTS steps. Therefore, steps 1 and 2 require the use of Buffer UM.

Each of two 50-mL conical tubes was charged with 13.6 mL of the template library solution (125 nmol combined), 2.6 mL of 1 M MES buffer pH 6.0, 5.2 mL of 5 M NaCl solution, DTS reagents (1.024 mL), sulfo-NHS solution (85 mg of 1 mL of water) and 2.076 mL of water (to bring the overall volume to 26 mL). The solutions were heated to 55° C. in a Southwest Science SH1002 digital dry bath for 1 h and then cooled in another identical dry bath at 30° C. over 1 h. EDC (100 mg) solution in 500 µL of water was added, and the reaction was left at 30° C. for 3 hours. 130 µL of acetic anhydride (1 µL per 200 µL) was added to each conical. After 2 h at 30° C., each batch was mixed with 6.5 mL (25% v/v) of 1 M NaOH solution, which was quenched with the same volume (6.5 mL) of 3 M NaOAc buffer pH 5.2. The reaction was poured into 800 mL of buffer UM (see General Methods) and passed through 14 HiBind DNA Midi columns (Omega Bio-tek). Each column was washed with 3×1 mL of Omega DNA Wash buffer (or Buffer PE, or 4:1 mixture of ethanol with 10 mM Tris-HCl pH 7.5) and centrifuged at 3,000 g for 10 minutes. After hydration with 1 mL of water for 10 min, the columns were centrifuged again at 3,000 g for 10 minutes. Combined eluates (11.9 mL) were split between two 50 mL conical tubes. The second DTS step was conducted in an identical manner (keep in mind different volumes).

For the third step, the combined spin-column eluates (11.9 mL) were split between two 50-mL conical tubes. Each of two tubes was charged with 2.6 mL of 1 M MES buffer pH 6.0, 5.2 mL of 5 M NaCl solution, DTS reagents (0.64 mL), sulfo-NHS solution (85 mg of 1 mL of water) and 10.11 mL of water (to bring the overall volume to 26 mL). The solutions were heated to 55° C. in a Southwest Science SH1002 digital dry bath for 1 h and then cooled in another identical dry bath at 37° C. over 1 h. EDC (100 mg) solution in 500 µL of water was added, and the reaction was left at 37° C. for 3 hours. The solution in each conical was diluted just with 25 mL of isopropanol and passed through 14 HiBind DNA Midi columns (Omega Bio-tek). Each column was washed with 3×1 mL of Omega DNA Wash buffer (or Buffer PE, or 4:1 mixture of ethanol with 10 mM Tris-HCl pH 7.5) and centrifuged at 3,000 g for 10 minutes. After hydration with 1 mL of water for 10 min, the columns were centrifuged again at 3,000 g for 10 minutes. Combined eluates were concentrated to 900 µL (combined) in four 10K Amicon Ultra 0.5 mL regenerated cellulose filter units.

360 µL of formamide containing GelPilot dye (Qiagen) was added. The sample was loaded on two 10% TBE-Urea gels without heating (35 µL/well, 0.5×TBE, 200V, run until xylene cyanol band was 0.5 cm away from the end of the gel). The upper band of each of the two gels was cut out, split between four 0.5 mL tubes and centrifuged down into 2-mL tubes through 27-gauge holes. 1 mL of 10 mM phosphate buffer pH 7 was added to each tube, followed by rotation at 4° C. in the absence of light for 15 hours (important: extraction at room temperature leads to some degree of product decomposition). The gel was centrifuged down to separate the supernatant. Each gel residue was washed with 2×1 mL of cold 10 mM phosphate buffer (all solutions from this point on were kept on ice). Combined solutions were filtered through a 50-mL tube sterile filtration unit and the membrane was washed with ample amount of the buffer to give 36 mL of the filtrate.

150 mL of saturated GuHCl and 225 mL of isopropanol were added and the resulting solution was passed through a single Omega HiBind Midi column, which was then washed with 3 mL of Omega DNA Wash Buffer, centrifuged for 10 min at 3,200 rcf, hydrated for 10 min with 10 mM phosphate buffer pH 7.4 and centrifuged again for 10 min at 3200 rcf. Eppendorf DNA Lobind tubes were used from this point on.

The solution was diluted with 0.15 µL of water to 1 mL and split into two portions. Each portion was mixed with 500 µL of 100 mM sodium periodate in 1 M NaOAc pH 3.5. After 5 minutes, the combined reaction mixture was passed through four Nap-5 columns (GE Life Sciences) equilibrated in water (loading in 500 µL, elution with 1 mL of water). 111 µL of 1 M HEPES pH 8.5 was added to each of the four eluates, and the reactions were left for 4 hours at room temperature in the absence of light. Combined solutions were mixed with 16 mL of saturated GuHCl and 24 mL of isopropanol and passed through an Omega HiBind Midi column, which was washed with 3 mL of Omega DNA wash buffer, centrifuged for 10 min at 3,200 rcf, hydrated with 1 mL of water for 10 min and centrifuged again for 10 min at 3,200 rcf. The eluate was concentrated in a 10K Amicon filter unit to 100 µL. 50 µL of formamide/GelPilot dye solution was added and the sample was loaded without heating on a 5% TBE-Urea gel (5 wells), 200 V, room temperature. The gel was run until bromophenol blue was at the very end of the gel. The lower band was cut out, split between two 0.5 mL microcentrifuge tubes and centrifuged down to 2 mL tubes through a 27-gauge orifice (20,000 rcf). The gel was subject to three dry ice freeze-thaw cycles, then 1 mL of 1×TE pH 7.5 was added and the product was extracted with rotation at room temperature in the absence of light for 24 h. The supernatant was separated, and filtered through a 0.22 µm frit. The gel was extracted again in the same manner. The extracts (6 mL) were combined in two 50 conicals. Each half was mixed with 15 mL of sat. GuHCl and 22.5 mL of IPA and the combined solution was passed through a single Omega HiBind Midi column, which was washed with 5 mL of Omega DNA wash buffer, centrifuged at 3,200 rcf for 10 min, hydrated with 1 mL of 10 mM phosphate buffer pH 7.4 for 10 min and centrifuged again at 3,200 rcf for 10 min. After determination of the concentration the solution was aliquoted in 60 µmol portions and stored at −80° C.

Library Characterization

MALDI analysis of DTS-prepared macrocycles. 100 µL of ~1 µM sample of the library in water was mixed with 5 µL of 1 M ammonium acetate pH 4.5, 200 units of S1 nuclease (Thermo, in 2 µL) and was incubated at 37° C. for 30 min. The sample was lyophilized, redissolved in 0.1% formic acid solution and desalted with a Millipore ZipTip (the tip was washed with 2×10 µL of 0.1% TFA in 50% aqueous acetonitrile, then 2×10 µL of 0.1% aqueous formic acid, the sample was loaded with multiple cycles of aspiration/dispensing followed by elution into 3 μL of 0.1% TFA in 50% aqueous acetonitrile with multiple cycles of aspiration/dispensing). 0.5 μL of the sample was mixed with 0.5 μL of CHCA matrix/0.1% TFA in 50% aqueous acetonitrile, dried on a MALDI plate and analyzed in a standard negative mode on a ultrafleXtreme MALDI-TOF/TOF Mass Spectrometer (Bruker) with 60-80% laser power.

gives cleaner results. For targets prone to covalently bind macrocycles, much shorter incubation with the library (5 min) can be recommended. The eluate is directly used for qPCR with adaptor primers for HTS barcoding in order to find the maximum number of cycles within the exponential amplification range. Preparative PCR is then run with the identified number of cycles without addition of SYBR Green.

TABLE 22

Primers used for the DTS library amplification

| Primer | Primer sequence 5'-3' |
|---|---|
| Re_DTL_primer2 | TGG AGT TCA GAC GTG TGC TCT TCC GAT CTC CCT GTA CAC (SEQ ID NO: 96) |
| Fw_DTL_primer2 | ACA CTC TTT CCC TAC ACG ACG CTC TTC CGA TCT GAG TGG GAT G (SEQ ID NO: 97) |
| Fw_DTL_T_primer2 | ACA CTC TTT CCC TAC ACG ACG CTC TTC CGA TCT TGA GTG GGA TG (SEQ ID NO: 98) |
| Fw_DTL_CT_primer2 | ACA CTC TTT CCC TAC ACG ACG CTC TTC CGA TCT CTG AGT GGG ATG (SEQ ID NO: 99) |
| Fw DTL_ACT_primer2 | ACA CTC TTT CCC TAC ACG ACG CTC TTC CGA TCT ACT GAG TGG GAT G (SEQ ID NO: 100) |
| Fw_DTL_CACT_primer2 | ACA CTC TTT CCC TAC ACG ACG CTC TTC CGA TCT CAC TGA GTG GGA TG (SEQ ID NO: 101) |
| Fw_DTL_TCACT_primer2 | ACA CTC TTT CCC TAC ACG ACG CTC TTC CGA TCT TCA CTG AGT GGG ATG (SEQ ID NO: 102) |

Selections and High-Throughput Sequencing
General Procedure for Selections and High-Throughput Sequencing Eppendorf LoBind microcentrifuge tubes (1.5 mL, 022431021) and MagJet magnetic rack (ThermoFisher, MR02) were used for all the operations with magnetic beads. All solutions were cooled to 0° C. All incubations were conducted via sideways rotation on a tiltable tube rotator, so that the top of the microcentrifuge tube never touches the solution). For the bead washing/elution steps, after each removal of the supernatant on the magnetic rack the beads were resuspended in the next portion of washing/eluting solution and transferred to a new microcentrifuge tube (to minimize contamination). All flow-throughs are usually saved and kept at −80° C.

For a His-tagged protein, 25 μL of Dynabeads (His-Tag Isolation and Pulldown, 10103D) were washed with 2×300 μL PBST (50 mM sodium phosphate pH 8.0, 300 mM NaCl, 0.01% Tween-20, ±5 mM DTT depending on whether the target needs reductive media). 5-40 μg of the protein was diluted into 300 μL PBST and incubated with the beads at 4° C. for 30 min. The flow-through was immediately frozen at −78° C. The beads were washed with 2×200 μL TBST (50 mM Tris-HCl pH 8, 150 mM NaCl, 0.05% Tween-20, ±5 mM DTT) followed by a 15-minute incubation with the blocking solution at 4° C. (100 μL TBST, 0.6 mg/mL yeast total RNA). The required amount of the DNA-encoded library (e.g. 20 μmol) was then incubated with the beads in 50 μL TBST w/RNA for 60 min at 4° C. The flow-throughs from this point on are saved for the library regeneration. The beads are washed with 3×200 μL TBST. Elution was accomplished by exposure of the beads to 50 μL of TBST containing 300 mM imidazole (5 min). Note: whereas BSA was previously used as a blocking agent in addition to yeast RNA, it was found that conducting selections without BSA

TABLE 23

Reaction composition for the first post-selection qPCR amplification

| | [Stock] μM | [Final] μM | volume (μl) |
|---|---|---|---|
| 2× Q5 mastermix NEB M0494L | 2× | 1× | 12.5 |
| Forward primer | 10 | 0.5 | 1.25 |
| Reverse primer | 10 | 0.5 | 1.25 |
| SYBR Green I | 10 | 1 | 2.5 |
| Water | | | 6.5 |
| Selection eluate | | | 1.0 |
| Total | | | 25.0 |

The PCR reaction is then diluted with 75 μL of water and 500 μL of PB buffer (Qiagen, 5 M GuHCl, 30% 2-propanol) and passed through a Qiaquick spin column (1 min at 6,000 rcf). The column was washed with 0.7 mL of Omega DNA wash buffer (or Qiagen buffer PE, 10 mM Tris-HC pH 7.5, 80% ethanol, 1 min, 17900 rcf). After removal of the flow-through the column was centrifuged at 17,900 ref for 1 min, hydrated with 50 μL of water for 1 min, then centrifuged again for 1 min at 17,900 rcf. The resulting sample was diluted 100 times for the next amplification. The second amplification is carried out in an identical manner with standard Illumina barcoding primers.

Selections Against Insulin-Degrading Enzyme
Macrocycle Synthesis
General Procedures of Solid-Phase Macrocycle Synthesis Boc/Alloc protecting group exchange.[58,59] A number of scaffold building blocks (4E,4F,4G,4I-4P,4U-4ZZ) are not commercially available in Fmoc,Alloc-protected form. Typically, 2.5-3.0 g of N-Boc,N-Fmoc amino acid were dissolved in trifluoroacetic acid (15 mL). After stirring for one hour at room temperature the solvent was removed by rotary evaporation. The resulting product was dissolved in THF and water (1:1, 200 mL) with sodium carbonate (3 eq.) at 0° C. Diallyl dicarbonate (TCI America P1277, 1.5 eq.) was added dropwise and the solution stirred for 2 hours at room temperature. THF was removed by rotary evaporation. The aqueous solution was washed with diethyl ether (100 mL), then acidified (10% HCl, ~15 mL) and extracted with ethyl acetate (3×100 mL). The combined organic layers were extracted with brine, dried with anhydrous sodium sulfate, and concentrated by rotary evaporation to yield the N-Alloc,N-Fmoc product as either a white solid or pale viscous oil, in 90-99% yield.

Installation of the scaffold and building blocks. Bis-(2-aminoethyl)-ether trityl resin (EMD Millipore, ~0.3 mmol/g loading, typically ~0.10 mmol scale per macrocycle for initial selections follow-up) was placed into a peptide synthesis vessel and swollen in ~5 mL of dry DMF for 30 m. Constant bubbling of dry nitrogen was maintained throughout the synthesis. In a separate flask, scaffold building block D (Fmoc,Alloc-protected, 5 equiv.) and 2-(1H-7-azabenzotriazol-1-yl)-1,1,3,3-tetramethyl uronium hexafluorophosphate (HATU, 4.75 equiv.) were dissolved in anhydrous DMF (~4 mL) followed by the addition of N,N'-diisopropylethylamine (DIPEA, 10 equiv.). After 5 min at room temperature the resulting solution was combined with the pre-swollen resin and mixed with nitrogen bubbling for 30-60 min. The vessel was then eluted and the resin washed three times with N-methyl-2-pyrrolidone (NMP, ~10 vol. each time). Following each coupling step, Fmoc deprotection was effected with 20% piperidine in NMP (~10 vol.) for 5 min, repeated three times, followed by washing three times with NMP (~10 vol.) and twice with DMF (~10 vol.).

The general procedure for amide coupling of building blocks A, B and C involved treatment of the resin with DMF solutions of HATU-activated Nα-Fmoc amino acids (5 equiv.) at room temperature for 30-60 minutes, mixing with dry nitrogen bubbling. The general procedure for HATU-activation is treating a solution of Nα-Fmoc amino acid (5 equiv.) and HATU (4.75 equiv.) in anhydrous DMF (10 vol.) with DIPEA (10 equiv.) for 5 min at room temperature. For cis-alkene macrocycles, the Fmoc group is not cleaved immediately after C-amino acid coupling. If both cis- and trans-isomers are synthesized, the resin is split in two halves at this point.

Trans-alkene (fumarate) installation. Following the final Fmoc deprotection procedure, the α-amine of building block C is coupled with allyl fumarate monoester (10 equiv.) using activation conditions as previously described with HATU (9.5 equiv.) and DIPEA (20 equiv.) in anhydrous DMF (~10 vol.). N-hydroxysuccinimide (NHS) (10 equiv.) may also be added to this coupling. Allyl fumarate coupling is accomplished by 1 hr mixing with dry nitrogen bubbling, followed by washing five times with NMP (~10 vol.) and three times with CHCl$_3$ (~10 vol.).

Allyl deprotections for cis and trans macrocycles. Simultaneous allyl ester and N-allyloxycarbonyl group cleavage were effected with three consecutive treatments with a solution of tetrakis(triphenylphosphine)palladium(0) (0.5 equiv. per allyl/alloc group) dissolved in degassed CHCl$_3$ containing acetic acid and N-methylmorpholine (40:2:1 ratio, ~20 vol.), mixing by nitrogen bubbling for 1 hour. The resin was then washed twice with ~20 vol. of 5% DIPEA in DMF, twice with a 5% solution of sodium diethyldithiocarbamate trihydrate in DMF (~20 vol.), twice with a 5% solution of hydroxybenzotriazole monohydrate in DMF, and finally washed with 50% CH$_2$Cl$_2$ in DMF and re-equilibrated with anhydrous DMF (~10 vol.).

Cis-alkene (maleic anhydride) coupling. Maleic anhydride (10 equiv.) was mixed with DIPEA (20 eq) in DMF and added to the Alloc-deprotected resin to couple to the side-chain amine of the scaffold (D) amino acid. After 1 hour, the resin is washed with DMF three times. The C-amino acid Fmoc group was then removed using 1% DBU in DMF (1,8-diazabicyclo[5.4.0]undec-7-ene), three washes of 1 min (it is necessary to use a non-nucleophilic base at this step, to prevent coupling to the free acid). The resin was then washed three times with 20% DIPEA/DMF for salt exchange.

Cyclization. The resin was treated with pentafluorophenyl diphenylphosphinate (FDPP, 5 equiv.) and DIPEA (10 equiv.) in anhydrous DMF (~10 vol.), mixing by nitrogen bubbling (3 hrs—overnight). The resin was then washed with NMP (~20 vol.), CH$_2$Cl$_2$ (~20 vol.) and dried.

Cleavage. The macrocyclized product was cleaved from the resin by two 5-minute treatments of the macrocycle-bound resin with 95% TFA containing 2.5% water and 2.5% triisopropylsilane (~20 vol.), followed by TFA washes (~5 vol.) until the solvent runs clear (~2-4 washes). The TFA solution was dried on a rotary evaporator, and the peptide was precipitated into cold (−80° C.), dry Et$_2$O. The ethereal supernatant as decanted, the remaining solid dried and dissolved in a minimum volume of 3:1 DMF-water prior (~1 mL) to filtration and purification. HPLC purification was performed on an Agilent 1260 Infinity LC system with a C18 column (Kinetex, 150×30 mm, 5 μm particle, 100 Å pore size) using a gradient of 10-60% acetonitrile/water (0.1% TFA) over 27 minutes (15 mL/min). Fractions containing the desired macrocyclic peptide were freeze-dried to produce a white powder. Typical yields were 5-10% based on theoretical resin loading.

IDE Selection Hits

TABLE 5

High-resolution mass spectrometry data for the prepared macrocycles.

| compound | calculated | observed |
|---|---|---|
| cis-DJPM | 836.4341 | 836.4372 |
| trans-DJPM | 836.4341 | 836.4372 |
| trans-DJPM-amide | 749.3657 | 749.3664 |
| cis-DJPR | 760.4028 | 760.4054 |
| trans-DJPR | 760.4028 | 760.4067 |
| trans-DJLysM | 806.4236 | 806.4258 |
| cis-DJQR | 772.4028 | 772.4033 |
| trans-DJQR | 772.4028 | 772.4058 |
| cis-DJIR | 904.4215 | 904.4231 |
| trans-DJIR | 904.4215 | 904.4254 |
| cis-CODVV | 785.3981 | 785.3973 |
| trans-CODVV | 785.3981 | 785.4003 |
| cis-DJPI | 836.4341 | 836.4368 |
| trans-DJPI | 836.4341 | 836.4356 | trans-DJPM (IDE IC$_{50}$=50 nM)
ESI-Tof HRMS calculated for[MH]$^+$ 836.4341, found 836.4372. $^1$H NMR (500 MHz, DMSO-d$_6$) δ 8.85 (d, J=5.0 Hz, 1H), 8.42 (d, J=7.3 Hz, 1H), 8.22 (t, J=6.0 Hz, 1H), 8.04-7.89 (m, 2H), 7.89-7.75 (m, 4H), 7.75-7.60 (m, 5H), 7.56 (t, J=8.0 Hz, 2H), 7.47 (d, J=7.1 Hz, 2H), 7.24 (t, J=7.4 Hz, 1H), 7.17 (t, J=8.6 Hz, 2H), 6.92 (d, J=15.5 Hz, 1H), 6.89-6.79 (m, 1H), 6.67 (d, J=15.5 Hz, 1H), 4.47-3.74 (m+water signal), 3.59 (t, J=5.1 Hz, 2H), 3.48 (t, J=6.0 Hz, 2H), 3.39-3.23 (m, 2H), 3.23-3.07 (m, 2H), 3.07-2.87 (m, 3H), 1.73-1.44 (m, 5H), 1.34 (d, J=7.3 Hz, 4H). $^{13}$C NMR (126 MHz, DMSO-d$_6$) δ 195.85, 172.69, 172.52, 171.73, 170.65, 166.54, 164.68, 144.37, 139.41, 139.11, 137.73, 135.38, 133.39, 132.93, 132.29, 130.20, 130.14, 129.87, 129.64, 128.97, 128.56, 128.03, 127.28, 69.30, 66.75, 56.90, 55.72, 51.42, 50.53, 43.48, 40.46, 40.29, 40.12, 39.96, 39.79, 39.62, 39.46, 39.16, 38.90, 38.15, 37.47, 34.84, 33.88, 33.41, 32.01, 26.42, 26.10, 25.94, 17.38.

cis-DJIR (IDE $IC_{50}$=40 nM)

ESI-Tof HRMS calculated for $[MH]^+$ 836.4341, found 836.4368. $^1$H NMR (500 MHz, DMSO-$d_6$) δ 8.87 (d, J=8.3 Hz, 1H), 8.46 (d, J=8.7 Hz, 1H), 8.41-8.30 (m, 1H), 7.90 (d, J=8.1 Hz, 1H), 7.86 (d, J=8.6 Hz, 1H), 7.81-7.61 (m, 8H), 7.61-7.50 (m, 2H), 7.49-7.42 (m, 1H), 7.40 (d, J=8.0 Hz, 2H), 6.29 (d, J=12.0 Hz, 1H), 6.08 (d, J=12.0 Hz, JH), 4.71-4.60 (m, 1H), 4.60-4.48 (m, 1H), 4.36-4.22 (m, 2H), 3.9-1.3 (mm, 27H+water signal). $^{13}$C NMR (126 MHz, DMSO-$d_6$) δ 195.91, 172.15, 171.67, 170.96, 170.56, 166.90, 164.79, 164.79, 158.71 (q, J=32.3 Hz, trifluoroacetate), 143.90, 137.8-137.6 (m), 137.26, 135.41, 135.32, 133.52, 132.97, 132.68, 131.78, 130.22, 130.04, 129.94, 129.90, 129.85, 129.31, 129.0-128.9 (m), 128.34, 127.99, 127.75, 127.36, 126.5-126.2 (m), 126.13, 123.95, (118.49, 116.12—part of trifluoroacetate q), 69.25, 66.79, 53.83, 53.23, 50.72, 50.41, 39.09, 38.74, 36.67, 34.60, 33.81, 33.63, 32.69, 32.07, 31.04, 26.45, 26.10, 25.90.

Biological Activity Assays

IDE Assays with Fluorogenic Decapeptide Substrate.

Recombinant human N-His$_6$-IDE$_{42-1019}$(R&D Systems) was assayed using the fluorophore/quencher-tagged peptide substrate Mca-RPPGFSAFK(Dnp)-OH (R&D) according to the manufacturer's instructions and using the recommended buffer 50 mM Tris, pH 7.5, 1 M NaCl (fluorophore Mca=(7-methoxycourmarin-4-yl)acetyl and quencher Dnp=2,4-dinitrophenyl). The enzyme mixture (48 μL) was transferred to a 96-well plate and combined with 2 μL of inhibitor in DMSO solutions, as 3-fold dilution series. The mixtures were allowed to equilibrate for 5 minutes and the enzymatic reaction was started by addition of substrate peptide in assay buffer (50 μL), immediately mixed by orbital shaking, and monitored on a fluorescence plate reader (excitation at 320 nm, emission at 405 nm). Concentration-dependent IDE inhibition profiles were obtained in triplicate for DJPM and DJIR analogs, and in duplicate for less active hits. Inhibitor 6bK was used as a positive control in each assay, and error bars correspond to the standard error.

TABLE 6

Sources of scaffold amino acids for solid-phase macrocycle synthesis.

| code | amino acid | | CAS number | Chem-Impex # |
|---|---|---|---|---|
| A | L-Dap-s | Fmoc-L-Dap(Alloc)-OH | 188970-92-5 | 04973 |
| B | L-Dab-s | Fmoc-L-Dab(Alloc)-OH | 204316-32-5 | 04964 |
| C | L-Orn-s | Fmoc-L-Orn(Alloc)-OH | 147290-11-7 | 04994 |
| D | L-Lys-s | Fmoc-L-Lys(Alloc)-OH | 146982-27-6 | 03616 |
| E | L-Dap-a | Boc-L-Dap(Fmoc)-OH | 122235-70-5 | 06305 |
| F | L-Dab-a | Boc-L-Dab(Fmoc)-OH | 117106-21-5 | 04963 |
| G | L-Orn-a | Boc-L-Orn(Fmoc)-OH | 150828-96-9 | 02719 |
| H | L-Lys-a | Aloc-L-Lys(Fmoc)-OH | 186350-56-1 | 14363 |
| I | L-o-NHCH$_2$-Phe-s | Fmoc-2-(Boc-aminomethyl)-L-Phe-OH | 1217808-42-8 | 16861 |
| J | L-m-NHCH$_2$-Phe-s | Fmoc-3-(Boc-aminomethyl)-L-Phe-OH | 266999-24-0 | 16862 |
| K | L-p-NHCH$_2$-Phe-s | Fmoc-4-(Boc-aminomethyl)-L-Phe-OH | 204715-91-3 | 07408 |
| L | L-o-NHCH$_2$-Phe-a | Boc-2-(Fmoc-aminomethyl)-L-Phe-OH | 959573-16-1 | 16857 |
| M | L-m-NHCH$_2$-Phe-a | Boc-3-(Fmoc-aminomethyl)-L-Phe-OH | 959573-13-8 | 16858 |
| N | L-p-NHCH$_2$-Phe-a | Boc-4-(Fmoc-aminomethyl)-L-Phe-OH | 170157-61-6 | 07406 |
| O | S,S-NH$_2$-Pro | Fmoc-ABPC(2S,4S)-OH | 174148-03-9 | 04942 |
| P | S,R-NH$_2$-Pro | Fmoc-ABPC(2S,4R)-OH | 176486-63-8 | 04941 |
| Q | D-Dap-s | Fmoc-D-Dap(Alloc)-OH | 178924-05-5 | 12403 |
| R | D-Dab-s | Fmoc-D-Dab(Alloc)-OH | 387824-78-4 | 12402 |
| S | D-Orn-s | Fmoc-D-Orn(Alloc)-OH | 214750-74-0 | 05704 |
| T | D-Lys-s | Fmoc-D-Lys(Alloc)-OH | 214750-75-1 | 05702 |
| U | D-Dap-a | Boc-D-Dap(Fmoc)-OH | 131570-56-4 | 06304 |
| V | D-Dab-a | Boc-D-Dab(Fmoc)-OH | 131570-57-5 | 06297 |
| W | D-Orn-a | Boc-D-Orn(Fmoc)-OH | 163336-15-0 | 05511 |
| X | D-Lys-a | Boc-D-Lys(Fmoc)-OH | 115186-31-7 | 05505 |
| Y | D-o-NHCH$_2$-Phe-s | Fmoc-2-(Boc-aminomethyl)-D-Phe-OH | 1217729-44-6 | 16863 |
| Z | D-m-NHCH$_2$-Phe-s | Fmoc-3-(Boc-aminomethyl)-D-Phe-OH | 1217665-54-7 | 16864 |
| UU | D-p-NHCH$_2$-Phe-s | Fmoc-4-(Boc-aminomethyl)-D-Phe-OH | 268731-06-2 | 07409 |
| VV | D-o-NHCH$_2$-Phe-a | Boc-2-(Fmoc-aminomethyl)-D-Phe-OH | 1212895-19-6 | 16859 |
| WW | D-m-NHCH$_2$-Phe-a | Boc-3-(Fmoc-aminomethyl)-D-Phe-OH | 1213080-68-2 | 16860 |
| XX | D-p-NHCH$_2$-Phe-a | Boc-4-(Fmoc-aminomethyl)-D-Phe-OH | 215302-77-5 | 07407 |
| YY | R,S-NH$_2$-Pro | (2R,4S)-Fmoc-4-amino-1-Boc-pyrrolidine-2-carboxylic acid | 1018332-23-4 | 29662 |
| ZZ | R,R-NH$_2$-Pro | (2R,4R)-Fmoc-4-amino-1-Boc-pyrrolidine-2-carboxylic acid | 1018332-24-5 | 29661 |

Regeneration of DNA-Encoded and DNA-Templated Libraries

Figure 37:
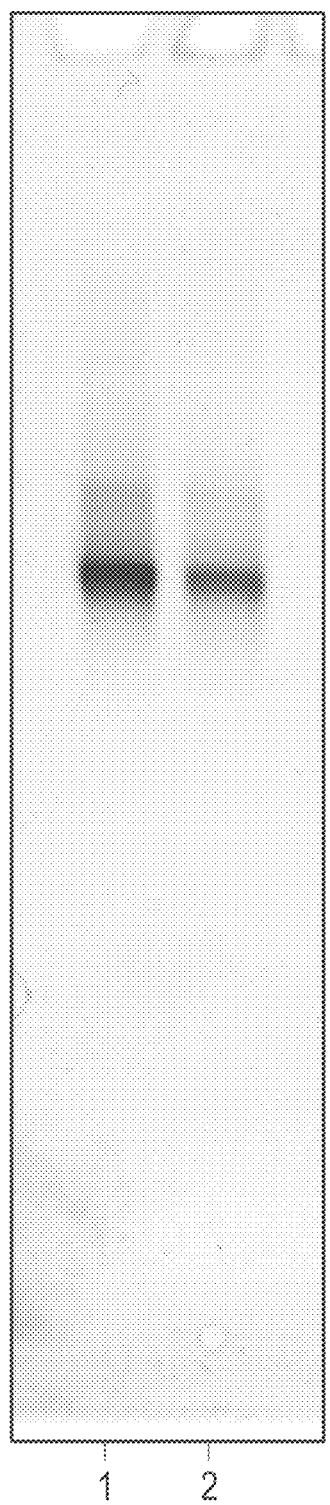
FIG. 37. 10% TBE-urea gel showing regeneration of DNA-encoded and DNA-templated libraries. Lanes 1 and 2 correspond to original and regenerated libraries, respectively.

Regeneration of DNA-encoded libraries can be achieved by using Buffer UM (vide supra). See FIG. 37. First flow-throughs of 98 selections (corresponding to 1.706 nmol of the library) were combined and filtered through EMD Ultrafree-MC GV 0.22 μm filter units. 4.75 mL of the resulting solution was concentrated with three 10K Amicon Ultra 0.5 mL regenerated cellulose filter units to 3×50 μL. RNAse A (Qiagen, 10 mg/mL) was diluted with P1 buffer (Qiagen). Each filter unit was exposed to 450 μL of the RNAse solution for 5 min at room temperature, then concentrated to 50 μL. 400 μL of P1 buffer was added to each filter unit, the solutions were combined and added to the mixture of 15 mL of saturated guanidinium chloride and 22.5 mL of isopropanol (Buffer UM). The solution was passed through a single Omega HiBind Midi spin column with vacuum suction. The column was washed with 5×1 mL of Omega DNA wash buffer, centrifuged at 3,200 rcf for 10 min, hydrated with 1 mL of 10 mM phosphate buffer pH 7 for 10 min and centrifuged into a clean tube at 3,200 rcf for 10 min. Concentration of the regenerated library was determined by comparison with the original library sample PAGE/densitometry, SYBR Gold with calibration curve). 867 μmol (51% recovery). The library was aliquoted and stored at −80° C. On the 10% TBE-urea gel shown, lanes 1 and 2 correspond to original and regenerated libraries, respectively. See FIG. 37.

Note: the precise yield of the regeneration protocol is higher than the apparent one, since the initial flow-throughs did not contain 100% of the library used for each selection.

Computer Scripts

All the computer programs developed for this project were written and executed in the Visual Basic for Applications framework (Microsoft).

Generation of Electronic Databases of Compounds

The sequence for generation of a ChemFinder library of macrocycles is as follows:

1) VBA generation of sdf files (sub sdf_file_generator) in MS Excel.
2) Saving of each spreadsheet as an individual sdf file (tab-delimited text).
3) Creation of ChemDraw nicknames for building blocks (1 Å to 4ZZ).
4) Opening and saving of each sdf file in CambridgeSoft ChemDraw (works well in no later than v.14).
5) Processing of each sdf file with the script which restores names of macrocycles.
6) Import of the files to ChemFinder (works well in no later than v.14). A MolfileName field has to be created before import.
7) Automatic cleanup of imported structures: call a .cfs file with a four-line script:
    LOOP
    RECORD NEXT
    CLEAN DENOVO
    ENDLOOP
8) Calculation & export of parameters to a spreadsheet Generation of SDF Files:

```
Sub sdf_file_generator( )
'by Usanov
For dd=1 To 16 'Two files are generated for each scaffold codons, each defined by variables dd and ch. Each file is written in a new Excel spreadsheet and is supposed to be manually saved with. sdf extension thereafter. Only first 16 scaffolds were used for bulk calculation of parameters (the other half contains epimeric analogues, which are identical to the first half for these calculations)
For ch=1 To 2
n=0 'Line #
If ch=1 Then iii=1 'definition of which half of codons 3 is included in a given spreadsheet.
If ch=1 Then jjj=10
If ch=2 Then iii=11
If ch=2 Then jjj=20
If dd=1 Then ddd="4A"
If dd=2 Then ddd="4B"
'[and so on—fill the lines]
If dd=26 Then ddd="4Z"
If dd=27 Then ddd="4UU"
If dd=28 Then ddd="4VV"
If dd=29 Then ddd="4WW"
If dd=30 Then ddd="4XX"
If dd=31 Then ddd="4YY"
If dd=32 Then ddd="4ZZ"
Sheets.Add after:=Sheets(Sheets.Count)
Sheets(ActiveSheet.Name).Name=Mid(ddd, 2, 2) & ch
For aa=1 To 20
For bb=1 To 20
For cc=iii To jjj
If aa=1 Then aaa="1 A"
If aa=2 Then aaa="1B"
'[and so on—fill the lines]
If aa=20 Then aaa="1T"
If bb=1 Then bbb="2A"
If bb=2 Then bbb="2B"
'[and so on—fill the lines]
If bb=20 Then bbb="2T"
If cc=1 Then ccc="3A"
If cc=2 Then ccc="B"
'[and so on—fill the lines]
If cc=20 Then ccc="3T"
'writing the SDF code
n=n+1
ActiveSheet.Range("a" & n).Value=aaa & "-" & bbb & "-" & ccc & "-" & ddd
n=n+1
ActiveSheet.Range("a" & n).Value="name"
n=n+2
ActiveSheet.Range("a" & n).Value="10 10 0 0 0 0 0 0 0 0999 V2000"
n=n+1
ActiveSheet.Range("a" & n).Value="−1.4475  0.1141  0.0000 C 0 0 0 0 0 0 0 0 0 0 0 0"
n=n+1
ActiveSheet.Range("a" & n).Value="−1.4681-0.5871  0.0000 C 0 0 0 0 0 0 0 0 0 0 0 0"
n=n+1
ActiveSheet.Range("a" & n).Value="−0.7875  0.6504  0.0000 C 0 0 0 0 0 0 0 0 0 0 0 0"
n=n+1
ActiveSheet.Range("a" & n).Value="−0.7296  1.2544  0.0000 0 0 0 0 0 0 0 0 0 0 0 0"
n=n+1
ActiveSheet.Range("a" & n).Value="0.0953 0.4294 0.0000" & ccc & "0 0 0 0 0 0 0 0 0 0 0"
n=n+1
ActiveSheet.Range("a" & n).Value="−2.1281-1.0409  0.0000 C 0 0 0 0 0 0 0 0 0 0 0 0"
n=n+1
ActiveSheet.Range("a" & n).Value="−2.9250-1.2544  0.0000 0 0 0 0 0 0 0 0 0 0 0 0"
```

```
n=n+1
ActiveSheet.Range("a" & n).Value="1.9969 0.6504 0.0000"
& bbb & "0 0 0 0 0 0 0 0 0 0 0"
n=n+1
ActiveSheet.Range("a" & n).Value="0.3056-1.1027
0.0000" & ddd & "0 0 0 0 0 0 0 0 0 0 0"
n=n+1
ActiveSheet.Range("a" & n).Value="2.9250-0.8140
0.0000" & aaa & "0 0 0 0 0 0 0 0 0 0 0"
n=n+1
ActiveSheet.Range("a" & n).Value="1 2 2 0"
n=n+1
ActiveSheet.Range("a" & n).Value="1 3 1 0"
n=n+1
ActiveSheet.Range("a" & n).Value="3 4 2 0"
n=n+1
ActiveSheet.Range("a" & n).Value="3 5 1 0"
n=n+1
ActiveSheet.Range("a" & n).Value="2 6 1 0"
n=n+1
ActiveSheet.Range("a" & n).Value="6 7 2 0"
n=n+1
ActiveSheet.Range("a" & n).Value="6 9 1 0"
n=n+1
ActiveSheet.Range("a" & n).Value="5 8 1 0"
n=n+1
ActiveSheet.Range("a" & n).Value="8 10 1 0"
n=n+1
ActiveSheet.Range("a" & n).Value="10 9 1 0"
n=n+1
ActiveSheet.Range("a" & n).Value="M END"
n=n+1
ActiveSheet.Range("a" & n).Value="$$$$"
Next cc
Next bb
Next aa
Next ch
Next dd
End Sub
Restoring Names in the SDF File:
Sub InsertMacrocycleName( )
'by Usanov
nachalo=1 'line # of the file, beginning of each sdf file record
Dim per(4) 'macrocycle building blocks, extracted in random order
Dim perr(4) 'renumbered building blocks in the right order
Do
If ActiveSheet.Range("a" & nachalo).Value=" " Then Exit Sub 'checks if the end of the file is reached
aa=nachalo 'current cell no, the beginning line # of the record
x=1 'to be used with per( )
cc=0 'exit while auxiliary variable
Do While cc=0 'scans each record for lines containing information of the library member
building blocks
curr=ActiveSheet.Range("a" & aa).Value
If curr="$$$$" Then cc=1 'exits loop if the end of a record is reached
If InStr(1, curr, "SMT") < > 0 Then per(x)=Right(curr, 3) 'extraction of building block names, not ordered in any record
If InStr(1, curr, "SMT") < > 0 Then x=x+1
aa=aa+1
Loop
konec=aa-1 'the end line # of the record
For k=1 To 4 'trimming the macrocycle elements
per(k)=Replace(per(k), " ", " ")
per(k)=Replace(per(k), " ", " ")
Next k
For k=1 To 4 'reordering and reformatting building blocks
If InStr(1, per(k), "1") < > 0 Then per(k)=Mid(per(k), InStr(1, per(k), "1"), Len(per(k))-InStr(1, per(k), "1")+1)
If InStr(1, per(k), "1") < > 0 Then perr(1)=per(k)
If InStr(1, per(k), "2") < > 0 Then per(k)=Mid(per(k), InStr(1, per(k), "2"), Len(per(k))-InStr(1, per(k), "2")+1)
If InStr(1, per(k), "2") < > 0 Then perr(2)=per(k)
If InStr(1, per(k), "3") < > 0 Then per(k)=Mid(per(k), InStr(1, per(k), "3"), Len(per(k))-InStr(1, per(k), "3")+1)
If InStr(1, per(k), "3") < > 0 Then perr(3)=per(k)
If InStr(1, per(k), "4") < > 0 Then per(k)=Mid(per(k), InStr(1, per(k), "4"), Len(per(k))-InStr(1, per(k), "4")+1)
If InStr(1, per(k), "4")< >0 Then perr(4)=per(k)
Next k
ActiveSheet.Range("a" & nachalo).Value=perr(1) & perr(2) & perr(3) & perr(4) 'name in the right format
nachalo=konec+1 'beginning line for the next record
For k=1 To 4 'clearing variables
per(k)=" "
perr(k)=" "
Next k
Loop
End Sub
Analysis of Selections
The array and auxiliary variable are declared as follows:
Dim r(256000) As Double 'an array of values where values correspond to the number of counts and each index reflext a unique number assigned to each macrocycle (vide infra)
Dim ReadData As String
For each of the files the initial fastq file is split in, the following subroutine:
Do Until EOF(1)
Line Input #1, ReadData
pp=WTMrev(ReadData) 'checking the reverse (complementary) sequence
If pp < > 0 And pp < > " " Then r(pp)=r(pp)+1 'r(pp)
If pp=0 Or pp=" " Then qq=WTMforw(ReadData) 'checking the direct sequence
If pp=0 And qq < > 0 And qq < > " " Then r(qq)=r(qq)+1
If pp=" " And qq < > 0 And qq < > " " Then r(qq)=r(qq)+1
Loop
Close #1
Called Functions are defined as follows:
Function WTMrev(f As String) As String 'checking the reverse (complementary) sequence 'the selection is very stringent, only perfect sequences are counted, no mutations allowed
RP=InStr(1, f, "GAGTGGGATG" (SEQ ID NO: 103))
If RP=0 Then Exit Function
ff=Mid(f, RP, 55)
RP=1
LP=InStr(1, ff, "GTGTACAGGG" (SEQ ID NO: 104))
If LP=0 Then Exit Function
const1=InStr(1, ff, "AACTT")
If const1=0 Then Exit Function
const2=InStr(1, ff, "ATCAT")
If const2=0 Then Exit Function
const3=InStr(1, ff, "TAG")
If const3=0 Then Exit Function
codon3=Mid(ff, const1+5, 6)
If codon3="TCCGAT" Then sc3=1
If codon3="TGCACA" Then sc3=2
'[and so on—fill the lines]
If codon3="ACAAGG" Then sc3=20
```

```
If sc3=0 Then Exit Function
codon2=Mid(ff, const2+5, 6)
If codon2="TTCAGC" Then sc2=1
If codon2="ATCGAC" Then sc2=2
'[and so on—fill the lines]
If codon2="AGCTTC" Then sc2=20
If sc2=0 Then Exit Function
codon1=Mid(ff, RP+17, 6)
If codon1="AAAGCC" Then sc1=1
If codon1="AAGCCT" Then sc1=2
'[and so on—fill the lines]
If codon1="TGAAGC" Then sc1=20
If sc1=0 Then Exit Function
codon4=Mid(ff, RP+10, 4)
If codon4="TGGA" Then sc4=1
If codon4="CAAC" Then sc4=2
'[and so on—fill the lines]
If codon4="TATC" Then sc4=25
If codon4="AACC" Then sc4=26
If codon4="TCAC" Then sc4=27
If codon4="CACA" Then sc4=28
If codon4="CATT" Then sc4=29
If codon4="ACTT" Then sc4=30
If codon4="TATT" Then sc4=31
If codon4="TCTT" Then sc4=32
If sc4=0 Then Exit Function
WTMrev=8000*(sc4−1)+400*(sc3−1)+20*(sc2−1)+sc1
'generation of the unique number # of the macrocycle
End Function
Function WTMforw(f As String) As String 'checking the direct sequence
LP=InStr(1, f, "CCCTGTACAC" (SEQ ID NO: 105))
If LP=0 Then Exit Function
ff=Mid(f, LP, 55)
LP=1
const1=InStr(1, ff, "AAGTT")
If const1=0 Then Exit Function
const2=InStr(1, ff, "ATGAT")
If const2=0 Then Exit Function
const3=InStr(1, ff, "CTA")
If const3=0 Then Exit Function
RP=InStr(1, ff, "CATCCCACTC" (SEQ ID NO: 106))
If RP=0 Then Exit Function
codon3=Mid(ff, LP+10, 6)
If codon3="ATCGGA" Then sc3=1
If codon3="TGTGCA" Then sc3=2
'[and so on—fill the lines]
If codon3="CCTTGT" Then sc3=20
If sc3=0 Then Exit Function
codon2=Mid(ff, const1+5, 6)
If codon2="GCTGAA" Then sc2=1
If codon2="GTCGAT" Then sc2=2
'[and so on—fill the lines]
If codon2="GAAGCT" Then sc2=20
If sc2=0 Then Exit Function
codon1=Mid(ff, const2+5, 6)
If codon1="GGCTTT" Then sc1=1
If codon1="AGGCTT" Then sc1=2
'[and so on—fill the lines]
If codon1="GCTTCA" Then sc1=20
If sc1=0 Then Exit Function
codon4=Mid(ff, RP−4, 4)
If codon4="TCCA" Then sc4=1
If codon4="GTTG" Then sc4=2
'[and so on—fill the lines]
If codon4="GATA" Then sc4=25
If codon4="GGTT" Then sc4=26
If codon4="GTGA" Then sc4=27
If codon4="TGTG" Then sc4=28
If codon4="AATG" Then sc4=29
If codon4="AAGT" Then sc4=30
If codon4="AATA" Then sc4=31
If codon4="AAGA" Then sc4=32
If sc4=0 Then Exit Function
WTMforw=8000*(sc4−1)+400*(sc3−1)+20*(sc2−1)+sc1
'generation of the unique number # of the macrocycle
End Function
The results are then exported to a ".csv" file:
Open fpathway & fname & ".csv" For Output As #
For n=1 To 256000
Print #7, r(n)
Next n
Close #7
```

REFERENCES

1. Hüser, J., Mannhold, R., Kubinyi, H. & Folkers, G. High-throughput screening in drug discovery. (Wiley, 2006).
2. Macarron, R. et al. Impact of high-throughput screening in biomedical research. *Nat. Rev. Drug Discov.* 10, 188-195 (2011).
3. Dandapani, S. & Marcaurelle, L. A. Grand Challenge commentary: accessing new chemical space for 'undruggable' targets. *Nat. Chem. Biol.* 6, 861-863 (2010).
4. Brenner, S. & Lerner, R. A. Encoded combinatorial chemistry. *Proc. Natl. Acad. Sci. U.S.A.* 89, 5381-5383 (1992).
5. Gartner, Z. J. & Liu, D. R. The generality of DNA-templated synthesis as a basis for evolving non-natural small molecules. *J. Am. Chem. Soc.* 123, 6961-6963 (2001).
6. Gartner, Z. J. et al. DNA-templated organic synthesis and selection of a library of macrocycles. *Science* 305, 1601-1605 (2004).
7. Zimmermann, G. & Neri, D. DNA-encoded chemical libraries: foundations and applications in lead discovery. *Drug Discov. Today* 21, 1828-1834 (2016).
8. Goodnow, R. A. A handbook for DNA-encoded chemistry: theory and applications for exploring chemical space and drug discovery. (Wiley, 2014).
9. Franzini, R. M., Neri, D. & Scheuermann, J. DNA-encoded chemical libraries: advancing beyond conventional small-molecule libraries. *Acc. Chem. Res.* 47, 1247-1255 (2014).
10. Krall, N., Scheuermann, J. & Neri, D. Small targeted cytotoxics: current state and promises from DNA-encoded chemical libraries. *Angew. Chem. Int. Ed.* 52, 1384-1402 (2013).
11. Mannocci, L., Leimbacher, M., Wichert, M., Scheuermann, J. & Neri, D. 20 Years of DNA-encoded chemical libraries. *Chem. Commun.* 47, 12747-12753 (2011).
12. Kleiner, R. E., Dumelin, C. E. & Liu, D. R. Small-molecule discovery from DNA-encoded chemical libraries. *Chem. Soc. Rev.* 40, 5707-5717 (2011).
13. Scheuermann, J. & Neri, D. DNA-encoded chemical libraries: a tool for drug discovery and for chemical biology. *ChemBioChem* 11, 931-937 (2010).
14. Clark, M. A. Selecting chemicals: the emerging utility of DNA-encoded libraries. *Curr. Opin. Chem. Biol.* 14, 396-403 (2010).
15. Buller, F., Mannocci, L., Scheuermann, J. & Neri, D. Drug discovery with DNA-encoded chemical libraries. *Bioconjugate Chem.* 21, 1571-1580 (2010).

16. Clark, M. A. et al. Design, synthesis and selection of DNA-encoded small-molecule libraries. *Nat. Chem. Biol.* 5, 647-654 (2009).
17. Doyon, J. B., Snyder, T. M. & Liu, D. R. Highly Sensitive in Vitro Selections for DNA-Linked Synthetic Small Molecules with Protein Binding Affinity and Specificity. *J. Am. Chem. Soc.* 125, 12372-12373 (2003).
18. Scheuermann, J. & Neri, D. Dual-pharmacophore DNA-encoded chemical libraries. *Curr. Opin. Chem. Biol.* 26, 99-103 (2015).
19. Wrenn, S. J., Weisinger, R. M., Halpin, D. R. & Harbury, P. B. Synthetic ligands discovered by in vitro selection. *J. Am. Chem. Soc.* 129, 13137-13143 (2007).
20. Li, Y., Zhao, P., Zhang, M., Zhao, X. & Li, X. Multistep DNA-templated synthesis using a universal template. *J. Am. Chem. Soc.* 135, 17727-17730 (2013).
21. Hansen, M. H. et al. A yoctoliter-scale DNA reactor for small-molecule evolution. *J. Am. Chem. Soc.* 131, 1322-1327 (2009).
22. Chan, A. I., McGregor, L. M. & Liu, D. R. Novel selection methods for DNA-encoded chemical libraries. *Curr. Opin. Chem. Biol.* 26, 55-61 (2015).
23. Satz, A. L. DNA encoded library selections and insights provided by computational simulations. *ACS Chem. Biol.* 10, 2237-2245 (2015).
24. Satz, A. L. Simulated screens of DNA encoded libraries: the potential influence of chemical synthesis fidelity on interpretation of structure-activity relationships. *ACS Comb. Sci.* 18, 415-424 (2016).
25. Connors, W. H., Hale, S. P. & Terrett, N. K. DNA-encoded chemical libraries of macrocycles. *Curr. Opin. Chem. Biol.* 26, 42-47 (2015).
26. Levin, J. I. Macrocycles in drug discovery. (Royal Society of Chemistry, 2014).
27. Driggers, E. M., Hale, S. P., Lee, J. & Terrett, N. K. The exploration of macrocycles for drug discovery—an underexploited structural class. *Nat. Rev. Drug. Discov.* 7, 608-624 (2008).
28. Marsault, E. & Peterson, M. L. Macrocycles are great cycles: applications, opportunities, and challenges of synthetic macrocycles in drug discovery. *J. Med. Chem.* 54, 1961-2004 (2011).
29. White, C. J. & Yudin, A. K. Contemporary strategies for peptide macrocyclization. *Nat. Chem.* 3, 509-524 (2011).
30. Yudin, A. K. Macrocycles: lessons from the distant past, recent developments, and future directions. *Chem. Sci.* 6, 30-49 (2015).
31. Villar, E. A. et al. How proteins bind macrocycles. *Nat. Chem. Biol.* 10, 723-731 (2014).
32. Dougherty, P. G., Qian, Z. & Pei, D. Macrocycles as protein-protein interaction inhibitors. *Biochem. J.* 474, 1109 (2017).
33. Giordanetto, F. & Kihlberg, J. Macrocyclic drugs and clinical candidates: what can medicinal chemists learn from their properties? *J. Med. Chem.* 57, 278-295 (2014).
34. Gartner, Z. J., Kanan, M. W. & Liu, D. R. Expanding the reaction scope of DNA-templated synthesis. *Angew. Chem. Int. Ed.* 41, 1796-1800 (2002).
35. Gartner, Z. J., Kanan, M. W. & Liu, D. R. Multistep small-molecule synthesis programmed by DNA templates. *J. Am. Chem. Soc.* 124, 10304-10306 (2002).
36. Li, X. & Liu, D. R. DNA-templated organic synthesis: Nature's strategy for controlling chemical reactivity applied to synthetic molecules. *Angew. Chem. Int. Ed.* 43, 4848-4870 (2004).
37. Calderone, C. T., Puckett, J. W., Gartner, Z. J. & Liu, D. R. Directing otherwise incompatible reactions in a single solution by using DNA-templated organic synthesis. *Angew. Chem. Int. Ed.* 41, 4104-4108 (2002).
38. Tse, B. N., Snyder, T. M., Shen, Y. & Liu, D. R. Translation of DNA into a library of 13 000 synthetic small-molecule macrocycles suitable for in vitro selection. *J. Am. Chem. Soc.* 130, 15611-15626 (2008).
39. Mullard, A. DNA tags help the hunt for drugs. *Nature* 530, 367-369 (2016).
40. Kleiner, R. E., Dumelin, C. E., Tiu, G. C., Sakurai, K. & Liu, D. R. In vitro selection of a DNA-templated small-molecule library reveals a class of macrocyclic kinase inhibitors. *J. Am. Chem. Soc.* 132, 11779-11791 (2010).
41. Georghiou, G., Kleiner, R. E., Pulkoski-Gross, M., Liu, D. R. & Seeliger, M. A. Highly specific, bisubstrate-competitive Src inhibitors from DNA-templated macrocycles. *Nat. Chem. Biol.* 8, 366-374 (2012).
42. Maianti, J. P. et al. Anti-diabetic activity of insulin-degrading enzyme inhibitors mediated by multiple hormones. *Nature* 511, 94-98 (2014).
43. Aleem, Saadat U. et al. Structural and Biochemical Basis for Intracellular Kinase Inhibition by Src-specific Peptidic Macrocycles. *Cell Chem. Biol.* 23, 1103-1112 (2016).
44. Snyder, T. M., Tse, B. N. & Liu, D. R. Effects of template sequence and secondary structure on DNA-templated reactivity. *J. Am. Chem. Soc.* 130, 1392-1401 (2008).
45. Lipinski, C. A., Lombardo, F., Dominy, B. W. & Feeney, P. J. Experimental and computational approaches to estimate solubility and permeability in drug discovery and development settings. *Adv. Drug Deliv. Rev.* 23, 3-25 (1997).
46. Veber, D. F. et al. Molecular properties that influence the oral bioavailability of drug candidates. *J. Med. Chem.* 45, 2615-2623 (2002).
47. Pye, C. R. et al. Nonclassical size dependence of permeation defines bounds for passive adsorption of large drug molecules. *J. Med. Chem.* 60, 1665-1672 (2017).
48. Bockus, A. T. et al. Probing the physicochemical boundaries of cell permeability and oral bioavailability in lipophilic macrocycles inspired by natural products. *J. Med. Chem.* 58, 4581-4589 (2015).
49. Hewitt, W. M. et al. Cell-permeable cyclic peptides from synthetic libraries inspired by natural products. *J. Am. Chem. Soc.* 137, 715-721 (2015).
50. Matsson, P. & Kihlberg, J. How big is too big for cell permeability? *J. Med. Chem.* 60, 1662-1664 (2017).
51. Over, B. et al. Structural and conformational determinants of macrocycle cell permeability. *Nat. Chem. Biol.* 12, 1065-1074 (2016).
52. Doak, B. C., Over, B., Giordanetto, F. & Kihlberg, J. Oral druggable space beyond the rule of 5: insights from drugs and clinical candidates. *Chem. Biol.* 21, 1115-1142 (2014).
53. Doak, B. C., Zheng, J., Dobritzsch, D. & Kihlberg, J. How beyond rule of 5 drugs and clinical candidates bind to their targets. *J. Med. Chem.* 59, 2312-2327 (2016).
54. Matsson, P., Doak, B. C., Over, B. & Kihlberg, J. Cell permeability beyond the rule of 5. *Adv. Drug Deliv. Rev.* 101, 42-61 (2016).
55. Watkins, J. N. E. & SantaLucia, J. J. Nearest-neighbor thermodynamics of deoxyinosine pairs in DNA duplexes. *Nucleic Acids Res.* 33, 6258-6267 (2005).
56. Irwin, J. J. et al. An Aggregation Advisor for Ligand Discovery. *J. Med. Chem.* 58, 7076-7087 (2015).
57. Berti, L., D'Agostino, P. S., Boeneman, K. & Medintz, I. L. Improved peptidyl linkers for self-assembly of semiconductor quantum dot bioconjugates. *Nano Res.* 2, 121-129 (2009).

58. Ahmed, S., Beleid, R., Sprules, T. & Kaur, K. Solid-Phase Synthesis and CD Spectroscopic Investigations of Novel β-Peptides from 1-Aspartic Acid and β-Amino-1-alanine. *Org. Lett.* 9, 25-28 (2007).
59. Demmer, O., Dijkgraaf, I., Schottelius, M., Wester, H. J. & Kessler, H. Introduction of Functional Groups into Peptides via N-Alkylation. *Org. Lett.* 10, 2015-2018 (2008).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of the formula:

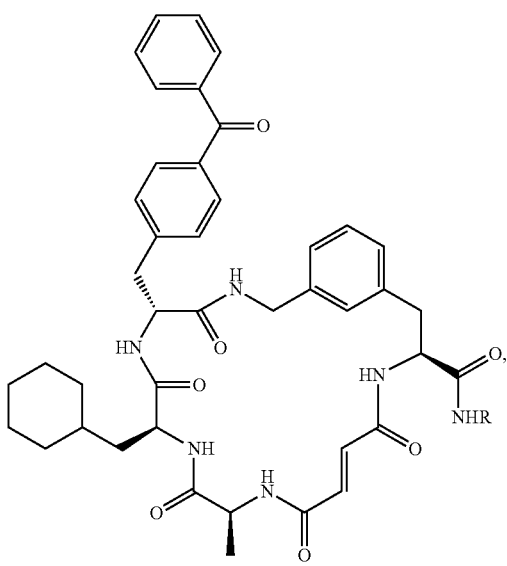

or a pharmaceutically acceptable salt, solvate, hydrate, stereoisomer, polymorph, tautomer, isotopically enriched form, or prodrug thereof,
wherein R is —(CH$_2$)$_2$O(CH$_2$)$_2$NH$_2$.

2. The compound of claim 1, or a pharmaceutically acceptable salt, solvate, hydrate, stereoisomer, polymorph, tautomer, or isotopically enriched form thereof.

3. The compound of claim 1, or a pharmaceutically acceptable salt, stereoisomer, tautomer, or isotopically enriched form thereof.

4. The compound of claim 1, or a pharmaceutically acceptable salt, stereoisomer, or tautomer thereof.

5. The compound of claim 1, or a pharmaceutically acceptable salt thereof.

6. The compound of claim 1.

7. A compound of the formula:

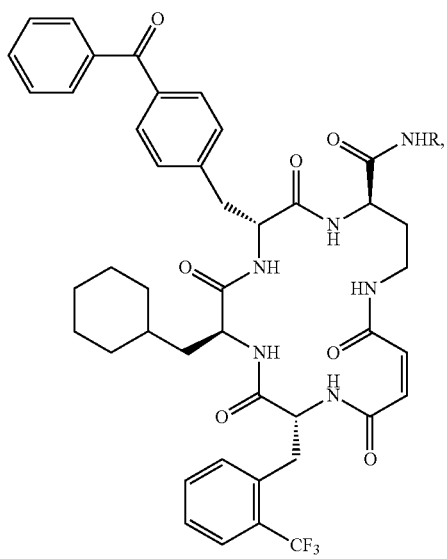

or a pharmaceutically acceptable salt, solvate, hydrate, stereoisomer, polymorph, tautomer, isotopically enriched form, or prodrug thereof,
wherein R is —(CH$_2$)$_2$O(CH$_2$)$_2$NH$_2$.

8. The compound of claim 7, or a pharmaceutically acceptable salt, solvate, hydrate, stereoisomer, polymorph, tautomer, or isotopically enriched form thereof.

9. The compound of claim 7, or a pharmaceutically acceptable salt, stereoisomer, tautomer, or isotopically enriched form thereof.

10. The compound of claim 7, or a pharmaceutically acceptable salt, stereoisomer, or tautomer thereof.

11. The compound of claim 7, or a pharmaceutically acceptable salt thereof.

12. The compound of claim 7.

13. A compound of the formula:

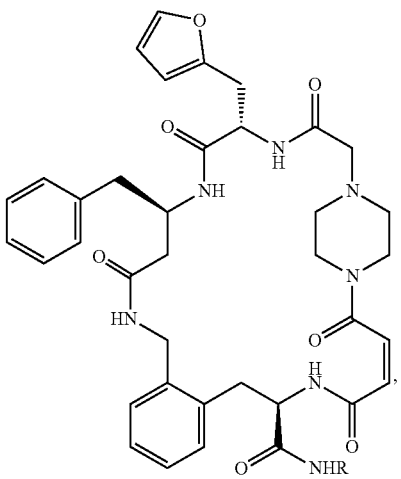

or a pharmaceutically acceptable salt, solvate, hydrate, stereoisomer, polymorph, tautomer, isotopically enriched form, or prodrug thereof,
wherein R is —(CH$_2$)$_2$O(CH$_2$)$_2$NH$_2$.

14. The compound of claim 13, or a pharmaceutically acceptable salt, solvate, hydrate, stereoisomer, polymorph, tautomer, or isotopically enriched form thereof.

15. The compound of claim 13, or a pharmaceutically acceptable salt, stereoisomer, tautomer, or isotopically enriched form thereof.

16. The compound of claim 13, or a pharmaceutically acceptable salt, stereoisomer, or tautomer thereof.

17. The compound of claim 13, or a pharmaceutically acceptable salt thereof.

18. The compound of claim 13.

* * * * *

SEQUENCE LISTING

```
<160> NUMBER OF SEQ ID NOS: 245

<210> SEQ ID NO 1
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 1
ccctgtacac nnnnnnaagt tnnnnnnatg atnnnnnnct annnncatcc cactc          55
```

```
<210> SEQ ID NO 2
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 2
ccctgtacac                                                          10

<210> SEQ ID NO 3
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 3
catcccactc                                                          10

<210> SEQ ID NO 4
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 4
tagaaagcca taggg                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 5
tagaagccta taggg                                                    15

<210> SEQ ID NO 6
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 6
tagtttggca taggg                                                    15

<210> SEQ ID NO 7
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (15)..(15)
<223> OTHER INFORMATION: may be modified by a 3' c7 amino modifier

<400> SEQUENCE: 7
taggttccta taggg                                                          15

<210> SEQ ID NO 8
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 8
tagcatacga taggg                                                          15

<210> SEQ ID NO 9
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 9
tagctcatga taggg                                                          15

<210> SEQ ID NO 10
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 10
tagtgtctca taggg                                                          15

<210> SEQ ID NO 11
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 11
tagctacaga taggg                                                          15

<210> SEQ ID NO 12
<211> LENGTH: 15
<212> TYPE: DNA
<213> ORGANISM: Artificial Sequence
<220> FEATURE:
<223> OTHER INFORMATION: Synthetic polynucleotide
```

-continued

```
<220> FEATURE:
<221> NAME/KEY: misc_feature
<222> LOCATION: (15)..(15)
<223> OTHER INFORMATION: may be modified by a 3' c7 amino modifier

<400> SEQUENCE: 12
tagcagctaa taggg                                                          15

<210> SEQ ID NO 13
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 13
tagctgagaa taggg                                                          15

<210> SEQ ID NO 14
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 14
tagagctcta taggg                                                          15

<210> SEQ ID NO 15
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 15
tagtgttcga taggg                                                          15

<210> SEQ ID NO 16
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 16
tagaagagca taggg                                                          15

<210> SEQ ID NO 17
<211> LENGTH: 15
<212> TYPE: DNA
<213> ORGANISM: Artificial Sequence
<220> FEATURE:
```

<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 17
tagagcagaa taggg                                                         15

<210> SEQ ID NO 18
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 18
taggatcgaa taggg                                                         15

<210> SEQ ID NO 19
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 19
tagtcagtca taggg                                                         15

<210> SEQ ID NO 20
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 20
tagtactgca taggg                                                         15

<210> SEQ ID NO 21
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 21
tagatacgca taggg                                                         15

<210> SEQ ID NO 22
<211> LENGTH: 15
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 22
taggattcca taggg                                                          15

<210> SEQ ID NO 23
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 23
tagtgaagca taggg                                                          15

<210> SEQ ID NO 24
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 24
catttcagca aaggg                                                          15

<210> SEQ ID NO 25
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 25
catatcgaca aaggg                                                          15

<210> SEQ ID NO 26
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 26
catgcaatca aaggg                                                          15

<210> SEQ ID NO 27
<211> LENGTH: 15
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 27
cataagtcca aaggg                                                    15

<210> SEQ ID NO 28
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 28
catatccgta aaggg                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 29
catactcgaa aaggg                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 30
cattcttgca aaggg                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 31
catcacaaga aaggg                                                    15

<210> SEQ ID NO 32
<211> LENGTH: 15
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 32
catttagcca aaggg                                                        15

<210> SEQ ID NO 33
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 33
catagtccta aaggg                                                        15

<210> SEQ ID NO 34
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 34
catgcatgaa aaggg                                                        15

<210> SEQ ID NO 35
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 35
catcagacta aaggg                                                        15

<210> SEQ ID NO 36
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 36
catttccaga aaggg                                                        15

<210> SEQ ID NO 37
```

```
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 37
catggcaata aaggg                                                     15

<210> SEQ ID NO 38
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 38
cattcgagaa aaggg                                                     15

<210> SEQ ID NO 39
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 39
catctaagga aaggg                                                     15

<210> SEQ ID NO 40
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 40
cataggctaa aaggg                                                     15

<210> SEQ ID NO 41
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 41
cattcactga aaggg                                                     15
```

```
<210> SEQ ID NO 42
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 42
catttgctca aaggg                                                    15

<210> SEQ ID NO 43
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 43
catagcttca aaggg                                                    15

<210> SEQ ID NO 44
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 44
ctttccgatg taggg                                                    15

<210> SEQ ID NO 45
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 45
ctttgcacag taggg                                                    15

<210> SEQ ID NO 46
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 46
cttgagtctg taggg                                                    15
```

```
<210> SEQ ID NO 47
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 47
cttctgaagg taggg                                                   15

<210> SEQ ID NO 48
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 48
ctttcgactg taggg                                                   15

<210> SEQ ID NO 49
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 49
cttcgtcatg taggg                                                   15

<210> SEQ ID NO 50
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 50
cttaggttgg taggg                                                   15

<210> SEQ ID NO 51
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 51
ctttacggag taggg                                                   15
```

```
<210> SEQ ID NO 52
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 52
cttgtaagcg taggg                                                    15

<210> SEQ ID NO 53
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 53
cttcgtagag taggg                                                    15

<210> SEQ ID NO 54
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 54
ctttgacacg taggg                                                    15

<210> SEQ ID NO 55
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 55
cttgtagtgg taggg                                                    15

<210> SEQ ID NO 56
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 56
```
cttgttcagg taggg                                                        15

<210> SEQ ID NO 57
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 57
cttgactagg taggg                                                        15

<210> SEQ ID NO 58
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 58
cttaaaccgg taggg                                                        15

<210> SEQ ID NO 59
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 59
cttaatgggg taggg                                                        15

<210> SEQ ID NO 60
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 60
cttagagagg taggg                                                        15

<210> SEQ ID NO 61
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 61

-continued

```
cttcggtaag taggg                                               15

<210> SEQ ID NO 62
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 62
cttacagcag taggg                                               15

<210> SEQ ID NO 63
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(15)
<223> OTHER INFORMATION: may be modified by a 3' c7 amino modifier

<400> SEQUENCE: 63
cttacaaggg taggg                                               15

<210> SEQ ID NO 64
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 64
gagtgggatg tggatag                                             17

<210> SEQ ID NO 65
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 65
gagtgggatg caactag                                             17

<210> SEQ ID NO 66
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3
```

```
<400> SEQUENCE: 66
gagtgggatg ttaatag                                                    17

<210> SEQ ID NO 67
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 67
gagtgggatg acaatag                                                    17

<210> SEQ ID NO 68
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 68
gagtgggatg tgagtag                                                    17

<210> SEQ ID NO 69
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 69
gagtgggatg ttcctag                                                    17

<210> SEQ ID NO 70
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 70
gagtgggatg tatatag                                                    17

<210> SEQ ID NO 71
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3
```

<400> SEQUENCE: 71
gagtgggatg aaattag                                                     17

<210> SEQ ID NO 72
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 72
gagtgggatg ctactag                                                     17

<210> SEQ ID NO 73
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 73
gagtgggatg tctatag                                                     17

<210> SEQ ID NO 74
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 74
gagtgggatg aaactag                                                     17

<210> SEQ ID NO 75
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 75
gagtgggatg aaaatag                                                     17

<210> SEQ ID NO 76
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)

```
<223> OTHER INFORMATION: may be modified by cyanine 3

<400> SEQUENCE: 76
gagtgggatg caaatag                                                        17

<210> SEQ ID NO 77
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 77
gagtgggatg accttag                                                        17

<210> SEQ ID NO 78
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 78
gagtgggatg tccttag                                                        17

<210> SEQ ID NO 79
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 79
gagtgggatg ttactag                                                        17

<210> SEQ ID NO 80
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 80
gagtgggatg taattag                                                        17

<210> SEQ ID NO 81
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

```
<222> LOCATION: (6)..(7)
<223> OTHER INFORMATION: may be modified by cyanine 3

<400> SEQUENCE: 81
gagtgggatg taactag                                                17

<210> SEQ ID NO 82
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 82
gagtgggatg aatctag                                                17

<210> SEQ ID NO 83
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 83
gagtgggatg ctattag                                                17

<210> SEQ ID NO 84
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 84
gagtgggatg tgattag                                                17

<210> SEQ ID NO 85
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 85
gagtgggatg tttttag                                                17

<210> SEQ ID NO 86
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
```

```
<221> NAME/KEY: misc_feature
<222> LOCATION: (6)..(7)
<223> OTHER INFORMATION: may be modified by cyanine 3

<400> SEQUENCE: 86
gagtgggatg cttttag                                                    17

<210> SEQ ID NO 87
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 87
gagtgggatg aatttag                                                    17

<210> SEQ ID NO 88
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 88
gagtgggatg tatctag                                                    17

<210> SEQ ID NO 89
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 89
gagtgggatg aacctag                                                    17

<210> SEQ ID NO 90
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 90
gagtgggatg tcactag                                                    17

<210> SEQ ID NO 91
<211> LENGTH: 17
<212> TYPE: DNA
<213> ORGANISM: Artificial Sequence
<220> FEATURE:
<223> OTHER INFORMATION: Synthetic polynucleotide
```

```
<220> FEATURE:
<221> NAME/KEY: misc_feature
<222> LOCATION: (6)..(7)
<223> OTHER INFORMATION: may be modified by cyanine 3

<400> SEQUENCE: 91
gagtgggatg cacatag                                                    17

<210> SEQ ID NO 92
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 92
gagtgggatg catttag                                                    17

<210> SEQ ID NO 93
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 93
gagtgggatg actttag                                                    17

<210> SEQ ID NO 94
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 94
gagtgggatg tatttag                                                    17

<210> SEQ ID NO 95
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 95
gagtgggatg tctttag                                                    17

<210> SEQ ID NO 96
<211> LENGTH: 39
<212> TYPE: DNA
<213> ORGANISM: Artificial Sequence
<220> FEATURE:
```

```
<223> OTHER INFORMATION: Synthetic polynucleotide

<400> SEQUENCE: 96
tggagttcag acgtgtgctc ttccgatctc cctgtacac                    39

<210> SEQ ID NO 97
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 97
acactctttc cctacacgac gctcttccga tctgagtggg at                42

<210> SEQ ID NO 98
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 98
acactctttc cctacacgac gctcttccga tcttgagtgg gatg              44

<210> SEQ ID NO 99
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 99
acactctttc cctacacgac gctcttccga tctctgagtg ggatg             45

<210> SEQ ID NO 100
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 100
acactctttc cctacacgac gctcttccga tctactgagt gggatg            46

<210> SEQ ID NO 101
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 101
acactctttc cctacacgac gctcttccga tctcactgag tgggatg           47

<210> SEQ ID NO 102
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 102
acactctttc cctacacgac gctcttccga tcttcactga gtgggatg          48
```

```
<210> SEQ ID NO 103
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 103
gagtgggatg                                                                10

<210> SEQ ID NO 104
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 104
gtgtacaggg                                                                10

<210> SEQ ID NO 105
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 105
ccctgtacac                                                                10

<210> SEQ ID NO 106
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 106
catcccactc                                                                10

<210> SEQ ID NO 107
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 107
ccctgtacac ttcctcaagt tgctgaaatg atggctttct atccacatcc cactc             55

<210> SEQ ID NO 108
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 108
ccctgtacac agctcaaagt taacggtatg ataggcttct agttgcatcc cactc             55

<210> SEQ ID NO 109
<211> LENGTH: 55
<212> TYPE: DNA
<213> ORGANISM: Artificial Sequence
<220> FEATURE:
<223> OTHER INFORMATION: Synthetic polynucleotide
```

<400> SEQUENCE: 109
ccctgtacac atcggaaagt tgtcgatatg atgccaaact attaacatcc cactc    55

<210> SEQ ID NO 110
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 110
ccctgtacac tgtgcaaagt tgattgcatg ataggaacct attgtcatcc cactc    55

<210> SEQ ID NO 111
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 111
ccctgtacac agactcaagt tggacttatg atcgtatgct actcacatcc cactc    55

<210> SEQ ID NO 112
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 112
ccctgtacac cttcagaagt tacggatatg atcatgagct aggaacatcc cactc    55

<210> SEQ ID NO 113
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 113
ccctgtacac agtcgaaagt tcaacagatg ataaccagct atatacatcc cactc    55

<210> SEQ ID NO 114
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 114
ccctgtacac atgacgaagt ttcgagtatg ataactccct aatttcatcc cactc    55

<210> SEQ ID NO 115
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 115
ccctgtacac actagcaagt tgcaagaatg atgagacact agtagcatcc cactc    55

<210> SEQ ID NO 116
<211> LENGTH: 55

```
<212> TYPE: DNA
<213> ORGANISM: Artificial Sequence
<220> FEATURE:
<223> OTHER INFORMATION: Synthetic polynucleotide

<400> SEQUENCE: 116
ccctgtacac caacctaagt tcttgtgatg atctgtagct atagacatcc cactc        55

<210> SEQ ID NO 117
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 117
ccctgtacac tccgtaaagt tggctaaatg atgtcagtct agtttcatcc cactc        55

<210> SEQ ID NO 118
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 118
ccctgtacac gcttacaagt tcacttgatg attagctgct attttcatcc cactc        55

<210> SEQ ID NO 119
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 119
ccctgtacac tctacgaagt taggactatg attctcagct atttgcatcc cactc        55

<210> SEQ ID NO 120
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 120
ccctgtacac ggcataaagt ttcatgcatg atagagctct aaggtcatcc cactc        55

<210> SEQ ID NO 121
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 121
ccctgtacac gtgtcaaagt tagtctgatg atcgaacact aaggacatcc cactc        55

<210> SEQ ID NO 122
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 122
```

```
ccctgtacac catctcaagt tctatggatg atgctcttct agtaacatcc cactc       55

<210> SEQ ID NO 123
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 123
ccctgtacac gataccaagt tctggaaatg attctgctct aattacatcc cactc       55

<210> SEQ ID NO 124
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 124
ccctgtacac aatccgaagt tattgccatg atcaatcgct agttacatcc cactc       55

<210> SEQ ID NO 125
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 125
ccctgtacac cactacaagt tgtatccatg attcgatcct agattcatcc cactc       55

<210> SEQ ID NO 126
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 126
ccctgtacac cgagataagt ttctcgaatg atgactgact aatagcatcc cactc       55

<210> SEQ ID NO 127
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 127
ccctgtacac ctgaacaagt tccttagatg atttcacgct aatcacatcc cactc       55

<210> SEQ ID NO 128
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 128
ccctgtacac ctagtcaagt ttagcctatg atctactgct aaaaacatcc cactc       55

<210> SEQ ID NO 129
<211> LENGTH: 55
<212> TYPE: DNA
<213> ORGANISM: Artificial Sequence
```

```
<220> FEATURE:
<223> OTHER INFORMATION: Synthetic polynucleotide

<400> SEQUENCE: 129
ccctgtacac gtccaaaagt tccaatgatg atcatccact aaaagcatcc cactc      55

<210> SEQ ID NO 130
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 130
ccctgtacac cggtttaagt tactcctatg atttacgcct aaattcatcc cactc      55

<210> SEQ ID NO 131
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 131
ccctgtacac cccattaagt taccctaatg atatcccact agatacatcc cactc      55

<210> SEQ ID NO 132
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 132
ccctgtacac gaccttaagt ttcccatatg atgcagtact aggttcatcc cactc      55

<210> SEQ ID NO 133
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 133
ccctgtacac ctctctaagt taaacccatg atgcgtatct aaatgcatcc cactc      55

<210> SEQ ID NO 134
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 134
ccctgtacac ttaccgaagt tcagtgaatg atggaatcct aaagtcatcc cactc      55

<210> SEQ ID NO 135
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 135
ccctgtacac tgctgtaagt tgagcaaatg atgcttcact aaatacatcc cactc      55
```

```
<210> SEQ ID NO 136
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 136
ccctgtacac ccttgtaagt tgaagctatg atacgcaact aaagacatcc cactc      55

<210> SEQ ID NO 137
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 137
ccctgtacac tccgtaaagt taacggtatg attagctgct aaatacatcc cactc      55

<210> SEQ ID NO 138
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 138
ccctgtacac aatccgaagt tctggaaatg ataggcttct aaggtcatcc cactc      55

<210> SEQ ID NO 139
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 139
ccctgtacac gcttacaagt taggactatg attcccatct atatacatcc cactc      55

<210> SEQ ID NO 140
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 140
ccctgtacac actagcaagt tccttagatg attctcagct aaggacatcc cactc      55

<210> SEQ ID NO 141
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 141
ccctgtacac gaccttaagt tattgccatg atgtcagtct atccacatcc cactc      55

<210> SEQ ID NO 142
<211> LENGTH: 55
<212> TYPE: DNA
<213> ORGANISM: Artificial Sequence
<220> FEATURE:
<223> OTHER INFORMATION: Synthetic polynucleotide
```

```
<400> SEQUENCE: 142
ccctgtacac gtgtcaaagt tgtcgatatg atggctttct atttgcatcc cactc        55

<210> SEQ ID NO 143
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 143
ccctgtacac cactacaagt tggacttatg atgagacact aaattcatcc cactc        55

<210> SEQ ID NO 144
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 144
ccctgtacac caacctaagt tggctaaatg attctgctct aggttcatcc cactc        55

<210> SEQ ID NO 145
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 145
ccctgtacac atgacgaagt tgattgcatg atctactgct attttcatcc cactc        55

<210> SEQ ID NO 146
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 146
ccctgtacac cccattaagt tagtctgatg atctgtagct actcacatcc cactc        55

<210> SEQ ID NO 147
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 147
ccctgtacac atcggaaagt ttcgagtatg ataggaacct atagacatcc cactc        55

<210> SEQ ID NO 148
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 148
ccctgtacac agtcgaaagt tcttgtgatg atcgtatgct aattacatcc cactc        55

<210> SEQ ID NO 149
```

```
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 149
ccctgtacac agactcaagt tgctgaaatg atagagctct agtttcatcc cactc        55

<210> SEQ ID NO 150
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 150
ccctgtacac ctgaacaagt tgagcaaatg atgcgtatct agtagcatcc cactc        55

<210> SEQ ID NO 151
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 151
ccctgtacac cggtttaagt tgcaagaatg atgcttcact agttgcatcc cactc        55

<210> SEQ ID NO 152
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 152
ccctgtacac ctagtcaagt tgaagctatg atcatgagct agatacatcc cactc        55

<210> SEQ ID NO 153
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 153
ccctgtacac ctctctaagt ttctcgaatg atgctcttct aaaaacatcc cactc        55

<210> SEQ ID NO 154
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 154
ccctgtacac ttcctcaagt tgaagctatg atgcttcact aaagtcatcc cactc        55

<210> SEQ ID NO 155
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 155
```

```
ccctgtacac agctcaaagt tgctgaaatg atacgcaact aaatacatcc cactc      55
```

<210> SEQ ID NO 156
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 156

```
ccctgtacac atcggaaagt taacggtatg atggctttct aaagacatcc cactc      55
```

<210> SEQ ID NO 157
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 157

```
ccctgtacac tgtgcaaagt tgtcgatatg ataggcttct atccacatcc cactc      55
```

<210> SEQ ID NO 158
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 158

```
ccctgtacac agactcaagt tgattgcatg atgccaaact agttgcatcc cactc      55
```

<210> SEQ ID NO 159
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 159

```
ccctgtacac cttcagaagt tggacttatg ataggaacct attaacatcc cactc      55
```

<210> SEQ ID NO 160
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 160

```
ccctgtacac agtcgaaagt tacggatatg atcgtatgct attgtcatcc cactc      55
```

<210> SEQ ID NO 161
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 161

```
ccctgtacac atgacgaagt tcaacagatg atcatgagct actcacatcc cactc      55
```

<210> SEQ ID NO 162
<211> LENGTH: 55
<212> TYPE: DNA

```
<213> ORGANISM: Artificial Sequence
<220> FEATURE:
<223> OTHER INFORMATION: Synthetic polynucleotide

<400> SEQUENCE: 162
ccctgtacac actagcaagt ttcgagtatg ataaccagct aggaacatcc cactc        55

<210> SEQ ID NO 163
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 163
ccctgtacac caacctaagt tgcaagaatg ataactccct atatacatcc cactc        55

<210> SEQ ID NO 164
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 164
ccctgtacac tccgtaaagt tcttgtgatg atgagacact aatttcatcc cactc        55

<210> SEQ ID NO 165
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 165
ccctgtacac gcttacaagt tggctaaatg atctgtagct agtagcatcc cactc        55

<210> SEQ ID NO 166
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 166
ccctgtacac tctacgaagt tcacttgatg atgtcagtct atagacatcc cactc        55

<210> SEQ ID NO 167
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 167
ccctgtacac ggcataaagt taggactatg attagctgct agtttcatcc cactc        55

<210> SEQ ID NO 168
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 168
ccctgtacac gtgtcaaagt ttcatgcatg attctcagct attttcatcc cactc        55
```

<210> SEQ ID NO 169
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 169
ccctgtacac catctcaagt tagtctgatg atagagctct atttgcatcc cactc    55

<210> SEQ ID NO 170
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 170
ccctgtacac gataccaagt tctatggatg atcgaacact aaggtcatcc cactc    55

<210> SEQ ID NO 171
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 171
ccctgtacac aatccgaagt tctggaaatg atgctcttct aaggacatcc cactc    55

<210> SEQ ID NO 172
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 172
ccctgtacac cactacaagt tattgccatg attctgctct agtaacatcc cactc    55

<210> SEQ ID NO 173
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 173
ccctgtacac cgagataagt tgtatccatg atcaatcgct aattacatcc cactc    55

<210> SEQ ID NO 174
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 174
ccctgtacac ctgaacaagt ttctcgaatg attcgatcct agttacatcc cactc    55

<210> SEQ ID NO 175
<211> LENGTH: 55
<212> TYPE: DNA
<213> ORGANISM: Artificial Sequence
<220> FEATURE:

<223> OTHER INFORMATION: Synthetic polynucleotide

<400> SEQUENCE: 175
ccctgtacac ctagtcaagt tccttagatg atgactgact agattcatcc cactc        55

<210> SEQ ID NO 176
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 176
ccctgtacac gtccaaaagt ttagcctatg atttcacgct aatagcatcc cactc        55

<210> SEQ ID NO 177
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 177
ccctgtacac cggtttaagt tccaatgatg atctactgct aatcacatcc cactc        55

<210> SEQ ID NO 178
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 178
ccctgtacac cccattaagt tactcctatg atcatccact aaaaacatcc cactc        55

<210> SEQ ID NO 179
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 179
ccctgtacac gaccttaagt taccctaatg atttacgcct aaaagcatcc cactc        55

<210> SEQ ID NO 180
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 180
ccctgtacac ctctctaagt ttcccatatg atatcccact aaattcatcc cactc        55

<210> SEQ ID NO 181
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 181
ccctgtacac ttaccgaagt taaacccatg atgcagtact agatacatcc cactc        55

<210> SEQ ID NO 182
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 182
ccctgtacac tgctgtaagt tcagtgaatg atgcgtatct aggttcatcc cactc    55

<210> SEQ ID NO 183
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 183
ccctgtacac ccttgtaagt tgagcaaatg atggaatcct aaatgcatcc cactc    55

<210> SEQ ID NO 184
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 184
ccctgtacac atcggaaagt tcagtgaatg atagagctct aaagacatcc cactc    55

<210> SEQ ID NO 185
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 185
ccctgtacac tgtgcaaagt ttctcgaatg atctgtagct aaagacatcc cactc    55

<210> SEQ ID NO 186
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 186
ccctgtacac agtcgaaagt tcagtgaatg atctgtagct aatagcatcc cactc    55

<210> SEQ ID NO 187
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 187
ccctgtacac gtgtcaaagt tcagtgaatg atctgtagct aaagacatcc cactc    55

<210> SEQ ID NO 188
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 188
ccctgtacac catctcaagt tcagtgaatg atgccaaact aaagacatcc cactc       55

<210> SEQ ID NO 189
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 189
ccctgtacac gataccaagt tcagtgaatg atctgtagct aaagacatcc cactc       55

<210> SEQ ID NO 190
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 190
ccctgtacac cgagataagt tcagtgaatg atctactgct aaagacatcc cactc       55

<210> SEQ ID NO 191
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 191
ccctgtacac ctgaacaagt tcagtgaatg atctgtagct atttgcatcc cactc       55

<210> SEQ ID NO 192
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 192
ccctgtacac gaccttaagt tgattgcatg atctgtagct aaagacatcc cactc       55

<210> SEQ ID NO 193
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 193
ccctgtacac ctctctaagt ttcatgcatg atctgtagct aaagacatcc cactc       55

<210> SEQ ID NO 194
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 194
ccctgtacac ttcctcaagt taggactatg atcgaacact agttgcatcc cactc       55

<210> SEQ ID NO 195
<211> LENGTH: 55

```
<212> TYPE: DNA
<213> ORGANISM: Artificial Sequence
<220> FEATURE:
<223> OTHER INFORMATION: Synthetic polynucleotide

<400> SEQUENCE: 195
ccctgtacac agctcaaagt tagtctgatg atcatgagct attaacatcc cactc      55

<210> SEQ ID NO 196
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 196
ccctgtacac agactcaagt tccttagatg atctgtagct agtaacatcc cactc      55

<210> SEQ ID NO 197
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 197
ccctgtacac atgacgaagt tcagtgaatg ataggcttct atatacatcc cactc      55

<210> SEQ ID NO 198
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 198
ccctgtacac actagcaagt tcaacagatg atctgtagct aatttcatcc cactc      55

<210> SEQ ID NO 199
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 199
ccctgtacac tccgtaaagt tgctgaaatg atcgtatgct agtagcatcc cactc      55

<210> SEQ ID NO 200
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 200
ccctgtacac gcttacaagt tgtatccatg attctgctct agtttcatcc cactc      55

<210> SEQ ID NO 201
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 201
```
ccctgtacac ggcataaagt tcagtgaatg atcaatcgct aaggacatcc cactc              55

<210> SEQ ID NO 202
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 202
ccctgtacac aatccgaagt tcagtgaatg atctgtagct agattcatcc cactc              55

<210> SEQ ID NO 203
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 203
ccctgtacac cactacaagt tcagtgaatg atgctcttct attgtcatcc cactc              55

<210> SEQ ID NO 204
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 204
ccctgtacac ctagtcaagt tcagtgaatg atctgtagct agttacatcc cactc              55

<210> SEQ ID NO 205
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 205
ccctgtacac cggtttaagt tcagtgaatg attcgatcct aattacatcc cactc              55

<210> SEQ ID NO 206
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 206
ccctgtacac cccattaagt tctggaaatg atctgtagct aatcacatcc cactc              55

<210> SEQ ID NO 207
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 207
ccctgtacac tgctgtaagt tcagtgaatg attctcagct aaaaacatcc cactc              55

<210> SEQ ID NO 208
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 208
ccctgtacac ccttgtaagt tattgccatg atctgtagct aaattcatcc cactc    55

<210> SEQ ID NO 209
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 209
ccctgtacac ccttgtaagt ttagcctatg atctgtagct aaatacatcc cactc    55

<210> SEQ ID NO 210
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 210
ccctgtacac ccttgtaagt tccaatgatg atctgtagct aaagacatcc cactc    55

<210> SEQ ID NO 211
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 211
ccctgtacac ccttgtaagt ttcccatatg atctgtagct aaagacatcc cactc    55

<210> SEQ ID NO 212
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 212
ccctgtacac ccttgtaagt tcagtgaatg atctgtagct aaaagcatcc cactc    55

<210> SEQ ID NO 213
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 213
ccctgtacac gaccttaagt tcagtgaatg atgcgtatct aaagacatcc cactc    55

<210> SEQ ID NO 214
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 214
ccctgtacac ccttgtaagt tcagtgaatg atctgtagct agtgacatcc cactc    55

<210> SEQ ID NO 215
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 215
ccctgtacac ccttgtaagt tcagtgaatg atctgtagct atgtgcatcc cactc    55

<210> SEQ ID NO 216
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 216
ccctgtacac tctacgaagt tgctgaaatg atgctcttct agtgacatcc cactc    55

<210> SEQ ID NO 217
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 217
ccctgtacac atgacgaagt tgtcgatatg atgcagtact atgtgcatcc cactc    55

<210> SEQ ID NO 218
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: may be modified by cyanine 3

<400> SEQUENCE: 218
aaaaaaaaaa aaaaaaaaaa aaaaaaaaaa a    31

<210> SEQ ID NO 219
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u

<400> SEQUENCE: 219
ccctgtacac nnnnnnaagt tnnnnnnatg    30

<210> SEQ ID NO 220
<211> LENGTH: 25
<212> TYPE: DNA
<213> ORGANISM: Artificial Sequence
<220> FEATURE:
<223> OTHER INFORMATION: Synthetic polynucleotide

```
<220> FEATURE:
<221> NAME/KEY: misc_feature
<222> LOCATION: (4)..(9)
<223> OTHER INFORMATION: n is a, c, g, t or u
<220> FEATURE:
<221> NAME/KEY: misc_feature
<222> LOCATION: (15)..(20)
<223> OTHER INFORMATION: n is a, c, g, t or u

<400> SEQUENCE: 220
tagnnnnnna tcatnnnnnn aactt                                       25

<210> SEQ ID NO 221
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(8)
<223> OTHER INFORMATION: n is a, c, g, t or u

<400> SEQUENCE: 221
atnnnnnnct acatcccact c                                           21

<210> SEQ ID NO 222
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: modified_base
<222> LOCATION: (42)..(45)
<223> OTHER INFORMATION: I

<400> SEQUENCE: 222
ccctgtacac nnnnnnaagt tnnnnnnatg atnnnnnnct annnncatcc cactc       55

<210> SEQ ID NO 223
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: modified_base
<222> LOCATION: (42)..(45)
```

<223> OTHER INFORMATION: I

<400> SEQUENCE: 223
ccctgtacac nnnnnnaagt tnnnnnnatg atnnnnnnct annnncatcc cactc     55

<210> SEQ ID NO 224
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: modified_base
<222> LOCATION: (42)..(45)
<223> OTHER INFORMATION: I

<400> SEQUENCE: 224
ccctgtacac nnnnnnaagt tnnnnnnatg atnnnnnnct annnncatcc cactc     55

<210> SEQ ID NO 225
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u

<400> SEQUENCE: 225
gagtgggatg nnnntag                                              17

<210> SEQ ID NO 226
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (15)..(20)
<223> OTHER INFORMATION: n is a, c, g, t or u
<220> FEATURE:
<221> NAME/KEY: misc_feature
<222> LOCATION: (26)..(31)
<223> OTHER INFORMATION: n is a, c, g, t or u
<220> FEATURE:
<221> NAME/KEY: misc_feature
<222> LOCATION: (37)..(42)
<223> OTHER INFORMATION: n is a, c, g, t or u
<220> FEATURE:
<221> NAME/KEY: misc_feature
<222> LOCATION: (46)..(49)
<223> OTHER INFORMATION: n is a, c, g, t or u

<400> SEQUENCE: 226
ccctccctgt acacnnnnnn aagttnnnnn natgatnnnn nnctannnnc atcccactc     59

-continued

```
<210> SEQ ID NO 227
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 227
gagtgggatg nnnntagnnn nnnatcatnn nnnnaacttn nnnngtgta cagggaggg      59

<210> SEQ ID NO 228
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 228
gagtgggatg nnnntagnnn nnnatcatnn nnnnaacttn nnnngtgta cagggaggg      59

<210> SEQ ID NO 229
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u
```

<400> SEQUENCE: 229
ccctgtacac nnnnnnaagt tnnnnnnatg atnnnnnnct annnncatcc cactc      55

<210> SEQ ID NO 230
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 230
gagtgggatg nnnntagnnn nnnatcatnn nnnnaacttn nnnnngtgta cagggaggg      59

<210> SEQ ID NO 231
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 231
ccctgtacac nnnnnnaagt tnnnnnnatg atnnnnnnct annnncatcc cactc      55

<210> SEQ ID NO 232
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u

```
<220> FEATURE:
<221> NAME/KEY: modified_base
<222> LOCATION: (42)..(45)
<223> OTHER INFORMATION: I

<400> SEQUENCE: 232
ccctgtacac nnnnnnaagt tnnnnnnatg atnnnnnnct annnncatcc cactc     55

<210> SEQ ID NO 233
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u

<400> SEQUENCE: 233
gagtgggatg nnnntag                                                17

<210> SEQ ID NO 234
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 234
ccctgtacac nnnnnnaagt tnnnnnnatg atnnnnnnct annnncatcc cactc     55

<210> SEQ ID NO 235
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 235
```
gagtgggatg nnnntagnnn nnnatcatnn nnnnaacttn nnnnngtgta caggg         55

<210> SEQ ID NO 236
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 236
gagtgggatg nnnntagnnn nnnatcatnn nnnnaacttn nnnnngtgta caggg         55

<210> SEQ ID NO 237
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 237
ccctgtacac nnnnnnaagt tnnnnnnatg atnnnnnnct annnncatcc cactc         55

<210> SEQ ID NO 238
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)

<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 238
gagtgggatg nnnntagnnn nnnatcatnn nnnnaacttn nnnnngtgta caggg      55

<210> SEQ ID NO 239
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 239
ccctgtacac nnnnnnaagt tnnnnnnatg atnnnnnnct annnncatcc cactc      55

<210> SEQ ID NO 240
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)

```
<223> OTHER INFORMATION: n is a, c, g, t or u
<220> FEATURE:
<221> NAME/KEY: misc_feature
<222> LOCATION: (40)..(45)
<223> OTHER INFORMATION: n is a, c, g, t or u

<400> SEQUENCE: 240
gagtgggatg nnnntagnnn nnnatcatnn nnnnaacttn nnnnngtgta caggg        55

<210> SEQ ID NO 241
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 241
ccctgtacac nnnnnnaagt tnnnnnnatg atnnnnnnct annnncatcc cactc        55

<210> SEQ ID NO 242
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, t or u
<220> FEATURE:
<221> NAME/KEY: misc_feature
<222> LOCATION: (18)..(23)
<223> OTHER INFORMATION: n is a, c, g, t or u
<220> FEATURE:
<221> NAME/KEY: misc_feature
<222> LOCATION: (29)..(34)
<223> OTHER INFORMATION: n is a, c, g, t or u
<220> FEATURE:
<221> NAME/KEY: misc_feature
<222> LOCATION: (40)..(45)
```

```
<223> OTHER INFORMATION: n is a, c, g, t or u

<400> SEQUENCE: 242
gagtgggatg nnnntagnnn nnnatcatnn nnnnaacttn nnnnngtgta caggg      55

<210> SEQ ID NO 243
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(16)
<223> OTHER INFORMATION: n is a, c, g, t or u
<220> FEATURE:
<221> NAME/KEY: misc_feature
<222> LOCATION: (22)..(27)
<223> OTHER INFORMATION: n is a, c, g, t or u
<220> FEATURE:
<221> NAME/KEY: misc_feature
<222> LOCATION: (33)..(38)
<223> OTHER INFORMATION: n is a, c, g, t or u
<220> FEATURE:
<221> NAME/KEY: misc_feature
<222> LOCATION: (42)..(45)
<223> OTHER INFORMATION: n is a, c, g, t or u

<400> SEQUENCE: 243
ccctgtacac nnnnnnaagt tnnnnnnatg atnnnnnnct annnncatcc cactc      55

<210> SEQ ID NO 244
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 244
ccctccctgt acac      14

<210> SEQ ID NO 245
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(26)
<223> OTHER INFORMATION: may be modified by cyanine 3

<400> SEQUENCE: 245
aaaaaaaaaa aaaaaaaaaa aaaaaaaaaa      30
```

UNITED STATES PATENT AND TRADEMARK OFFICE
CERTIFICATE OF CORRECTION

PATENT NO. : 11,674,136 B2
APPLICATION NO. : 16/968408
DATED : June 13, 2023
INVENTOR(S) : David R. Liu et al.

It is certified that error appears in the above-identified patent and that said Letters Patent is hereby corrected as shown below:

In the Specification

At Column 1, Lines 15-19, replace the paragraph immediately after the heading "GOVERNMENT SUPPORT" with the paragraph below:
-- This invention was made with government support under GM118062 awarded by the National Institutes of Health and under HR0011-17-2-0049 awarded by the Defense Advanced Research Projects Agency. The government has certain rights in the invention. --.

Signed and Sealed this
Third Day of October, 2023

Katherine Kelly Vidal
*Director of the United States Patent and Trademark Office*